United States Patent
Bach et al.

(10) Patent No.: US 6,713,645 B1
(45) Date of Patent: Mar. 30, 2004

(54) SUBSTITUTED TRICYCLICS

(75) Inventors: Nicholas James Bach, Indianapolis, IN (US); Susan Elizabeth Draheim, Indianapolis, IN (US); Robert Delane Dillard, Zionsville, IN (US); Edward David Mihelich, Carmel, IN (US); Jason Scott Sawyer, Indianapolis, IN (US); Douglas Wade Beight, Frankfort, IN (US); Michael LeRoy Phillips, Indianapolis, IN (US); Tulio Suarez, Greenwood, IN (US); Daniel Jon Sall, Greenwood, IN (US); Jolie Anne Bastian, Beech Grove, IN (US); Michael Lyle Denney, Franklin, IN (US); Gary Alan Hite, Indianapolis, IN (US); Michael Dean Kinnick, Indianapolis, IN (US); Robert Theodore Vasileff, Indianapolis, IN (US); John Michael Morin, Jr., Brownsburg, IN (US); Ho-Shen Lin, Indianapolis, IN (US); Michael Enrico Richett, Indianapolis, IN (US); Richard Waltz Harper, Indianapolis, IN (US); John McNeill McGill, III, Greenwood, IN (US); Benjamin Alan Anderson, Zionsville, IN (US); Nancy Kay Harn, Indianapolis, IN (US); Richard James Loncharich, Carmel, IN (US); Richard Walter Schevitz, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 398 days.

(21) Appl. No.: 09/688,106

(22) Filed: Oct. 13, 2000

Related U.S. Application Data

(60) Division of application No. 09/063,066, filed on Apr. 21, 1998, now Pat. No. 6,177,440, and a continuation-in-part of application No. 08/959,477, filed on Oct. 28, 1997, now abandoned

(60) Provisional application No. 60/029,849, filed on Oct. 30, 1996.

(51) Int. Cl.[7] .............................................. C07C 69/76
(52) U.S. Cl. ....................................................... 560/8
(58) Field of Search ............................................ 560/8

(56) References Cited

U.S. PATENT DOCUMENTS

| | | | |
|---|---|---|---|
| 3,752,823 A | * | 8/1973 | McManus et al. |
| 3,939,177 A | * | 2/1976 | Alexander et al. |
| 3,979,391 A | * | 9/1976 | Alexander et al. |
| 5,420,289 A | * | 5/1995 | Musser et al. |

FOREIGN PATENT DOCUMENTS

| | | | |
|---|---|---|---|
| DE | 2042280 | * | 3/1971 |
| EP | 496 237 | * | 7/1992 |
| EP | 0620 214 A1 | * | 4/1994 |
| EP | 0620 215 A1 | * | 4/1994 |
| EP | 0779 271 A1 | * | 4/1994 |
| WO | WO 96/3383 | * | 2/1996 |
| WO | WO 96/32379 | * | 10/1996 |

OTHER PUBLICATIONS

Garrett, et al., Bioorg. Med. Chem. Lett., (1994), 4(13), 1559–64.*
Chemical Abstracts 122:9757, Garratt, 1994.*
Chemical Abstracts 86:5313, Alexander 1976.*
Chemical Abstracts 85:21093, Alexander 1976.*

* cited by examiner

Primary Examiner—D. Margaret Seaman
(74) Attorney, Agent, or Firm—Francis O. Ginah; Arleen Palmberg

(57) ABSTRACT

A class of novel tricyclics is disclosed together with the use of such compounds for inhibiting sPLA$_2$ mediated release of fatty acids for treatment of conditions such as septic shock.

2 Claims, No Drawings

SUBSTITUTED TRICYCLICS

This application is a DIV of Ser. No. 09/063,066, filed Apr. 21, 1998 U.S. Pat. No. 6,177,440, which claims benefit of Provisional Application No. 60/029,849, filed Oct. 30, 1996, and a CIP of Ser. No. 08/959,477, filed Oct. 28, 1997, ABN.

FIELD OF THE INVENTION

This invention relates to novel substituted tricyclic organic compounds useful for inhibiting sPLA$_2$ mediated release of fatty acids for conditions such as septic shock.

BACKGROUND INFORMATION

The structure and physical properties of human non-pancreatic secretory phospholipase A$_2$ (hereinafter called, "sPLA$_2$") has been thoroughly described in two articles, namely, "Cloning and Recombinant Expression of Phospholipase A$_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of April 5, pp. 5335–5338, 1989; and "Structure and Properties of a Human Non-pancreatic Phospholipase A$_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of April 5, pp. 5768–5775, 1989; the disclosures of which are incorporated herein by reference.

It is believed that sPLA$_2$ is a rate limiting enzyme in the arachidonic acid cascade which hydrolyzes membrane phospholipids. Thus, it is important to develop compounds which inhibit sPLA$_2$ mediated release of fatty acids (e.g., arachidonic acid). Such compounds would be of value in general treatment of conditions induced and/or maintained by overproduction of sPLA$_2$ such as septic shock, adult respiratory distress syndrome, pancreatitis, trauma-induced shock, bronchial asthma, allergic rhinitis, rheumatoid arthritis, etc.

It is desirable to develop new compounds and treatments for sPLA$_2$ induced diseases.

Alexander, et al., U.S. Pat. Nos. 3,939,177 and 3,979,391, disclose 1,2,3,4-tetrahydrocarbazoles useful as antibacterial agents.

SUMMARY OF THE INVENTION

This invention provides tricyclic compounds as depicted in the general formula (I) below:

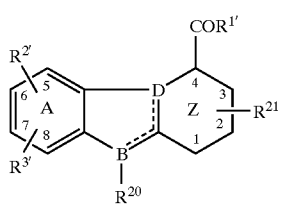

(I)

wherein;

A is phenyl or pyridyl wherein the nitrogen is at the 5-, 6-, 7- or 8-position;

one of B or D is nitrogen and the other is carbon;

Z is cyclohexenyl, phenyl, pyridyl, wherein the nitrogen is at the 1-, 2-, or 3-position, or a 6-membered heterocyclic ring having one heteroatom selected from the group consisting of sulfur or oxygen at the 1-, 2- or 3-position, and nitrogen at the 1-, 2-, 3- or 4-position;

----- is a double or single bond;

R$^{20}$ is selected from groups (a), (b) and (c) where;
(a) is —(C$_5$–C$_{20}$)alkyl, —(C$_5$–C$_{20}$)alkenyl, (C$_5$–C$_{20}$) alkynyl, carbocyclic radicals, or heterocyclic radicals, or
(b) is a member of (a) substituted with one or more independently selected non-interfering substituents; or
(c) is the group —(L)—R$^{80}$; where, —(L)— is a divalent linking group of 1 to 12 atoms selected from carbon, hydrogen, oxygen, nitrogen, and sulfur; wherein the combination of atoms in —(L)— are selected from the group consisting of (i) carbon and hydrogen only, (ii) one sulfur only, (iii) one oxygen only, (iv) one or two nitrogen and hydrogen only, (v) carbon, hydrogen, and one sulfur only, and (vi) and carbon, hydrogen, and oxygen only; and where R$^{80}$ is a group selected from (a) or (b);

R$^{21}$ is a non-interfering substituent;

R1' is —NHNH$_2$, —NH$_2$ or —CONH$_2$;

R2' is selected from the group consisting of —OH, and —O(CH$_2$)$_t$R$^{5'}$ where R$^{5'}$ is H, —CN, —NH$_2$, —CONH$_2$, —CONR$^9$R$^{10}$ —NHSO$_2$R$^{15}$; —CONHSO$_2$R$^{15}$, where R$^{15}$ is —(C$_1$–C$_6$)alkyl or —CF$_3$; phenyl or phenyl substituted with —CO$_2$H or —CO$_2$(C$_1$–C$_4$)alkyl; and —(L$_a$)— (acidic group), wherein —(L$_a$)— is an acid linker having an acid linker length of 1 to 7 and t is 1–5;

R$^{3'}$ is selected from non-interfering substituent, carbocyclic radicals, carbocyclic radicals substituted with non-interfering substituents, heterocyclic radicals, and heterocyclic radicals substituted with non-interfering substituents; or a pharmaceutically acceptable racemate, solvate, tautomer, optical isomer, prodrug derivative or salt thereof;

provided that; when R$^{3'}$ is H, R$^{20}$ is benzyl and m is 1 or 2; R$^{2'}$ cannot be —O(CH$_2$)$_m$H; and provided that when D is nitrogen, the heteroatom of Z is selected from the group consisting of sulfur or oxygen at the 1-, 2- or 3-position and nitrogen at the 1-, 2-, 3- or 4-position.

These substituted tricyclics are effective in inhibiting human sPLA$_2$ mediated release of fatty acids.

This invention is also a pharmaceutical formulation comprising a compound of formula I in association with one or more pharmaceutically acceptable diluents, carriers and excipients.

This invention is also a method of inhibiting sPLA$_2$ comprising administering to a mammal in need of such treatment a therapeutically effective amount of a compound of formula I.

According to a further aspect of the present invention, there is provided a method of selectively inhibiting sPLA$_2$ in a mammal in need of such treatment comprising administering to said mammal a therapeutically effective amount of a compound of formula I.

This invention, further provides a compound of formula I for use as a medicament in the treatment of inflammatory diseases such as, sepsis, septic shock, adult respiratory distress syndrome, pancreatitis, trauma-induced shock, bronchial asthma, allergic rhinitis, rheumatoid arthritis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enterapathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula I in an amount sufficient to inhibit $sPLA_2$ mediated release of fatty acid and to thereby inhibit or prevent the arachidonic acid cascade and its deleterious products.

This invention provides, in addition, a process for preparing compounds of formula II

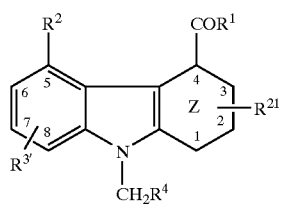

(II)

wherein;

Z is cyclohexenyl, or phenyl, $R^{21}$ is a non-interfering substituent;

$R^1$ is —NHNH$_2$ or —NH$_2$;

$R^2$ is selected from the group consisting of —OH and —O(CH$_2$)$_m$R$^5$ where $R^5$ is H, —CO$_2$H, —CONH$_2$, —CO$_2$(C$_1$–C$_4$ alkyl)

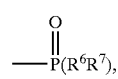

where $R^6$ and $R^7$ are each independently —OH or —O(C$_1$–C$_4$)alkyl; —SO$_3$H, —SO$_3$(C1–C4 alkyl), tetrazolyl, —CN, —NH$_2$, —NHSO$_2$R$^{15}$, —CONHSO$_2$R$^{15}$; where R$^{15}$ is —(C$_1$–C$_6$)alkyl or —CF$_3$; phenyl or phenyl substituted with —CO$_2$H or —CO$_2$(C$_1$–C$_4$)alkyl where m is 1–3;

$R^3$ is H, —O(C$_1$–C$_4$)alkyl, halo, —(C$_1$–C$_6$)alkyl, phenyl, —(C$_1$–C$_4$)alkylphenyl; phenyl substituted with —(C$_1$–C$_6$)alkyl, halo, or —CF$_3$; —CH$_2$OSi(C$_1$–C$_6$) alkyl, furyl, thiophenyl, —(C$_1$–C$_6$)hydroxyalkyl, —(C$_1$–C$_6$)alkoxy(C$_1$–C$_6$)alkyl, —(C$_1$–C$_6$)alkoxy (C$_1$–C$_6$)alkenyl; or —(CH$_2$)$_n$R$^8$ where R$^8$ is H, —CONH$_2$, —NR$^9$R$^{10}$, —CN or phenyl where R$^9$ and R$^{10}$ are independently hydrogen, —CF$_3$, phenyl, —(C$_1$–C$_4$)alkyl, —(C$_1$–C$_4$)alkylphenyl or -phenyl (C$_1$–C$_4$)alkyl and n is 1 to 8; and $R^4$ is H, —(C$_5$–C$_{14}$)alkyl, —(C$_3$–C$_4$)cycloalkyl, pyridyl, phenyl or phenyl substituted with from 1–5 substituents selected from the group consisting of —(C$_1$–C$_6$)alkyl, halo, —CF$_3$, —OCF$_3$, —(C$_1$–C$_4$)alkoxy, —CN, —(C$_1$–C$_4$)alkylthio, phenyl(C1–C$_4$)alkyl, —(C$_1$–C$_4$) alkylphenyl, phenyl, phenoxy, —OR$^9$; where R$^9$ and R$^{10}$ are independently hydrogen, —CF$_3$, phenyl, —(C$_1$–C$_4$)alkyl, (C$_1$–C$_4$)alkylphenyl or -phenyl (C$_1$–C$_4$)alkyl; tetrazole; tetrazole substituted with —(C$_1$–C$_4$)alkyl or —(C$_1$–C$_4$)alkylphenyl: or naphthyl;

or a pharmaceutically acceptable racemate, solvate, tautomer, optical isomer, prodrug derivative or salt, thereof;

a) esterifying a compound of formula XVI

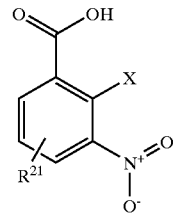

(XVI)

where X is halo;

to form a compound of formula XV

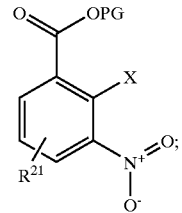

(XV)

where PG is an acid protecting group b) reducing a compound of formula XV to form a compound of formula XIV

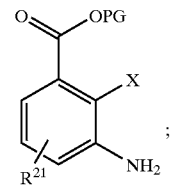

(XIV)

where PG is an acid protecting group c) condensing a compound of formula XIV with a compound of formula XIII

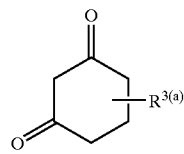
(XIII)

where R³(a) is H, —O(C₁–C₄)alkyl, halo, —(C₁–C₆)alkyl, phenyl, —(C₁–C₄)alkylphenyl; phenyl substituted with —(C₁–C₆)alkyl, halo or —CF₃; —CH₂OSi(C₁–C₆)alkyl, furyl, thiophenyl, —(C₁–C₆)hydroxyalkyl, —(C₁–C₆)alkoxy(C₁–C₆)alkyl, —(C₁–C₆)alkoxy(C₁–C₆)alkenyl; or —(CH₂)ₙR⁸ where R⁸ is H, —NR⁹R¹⁰, —CN or phenyl where R⁹ and R¹⁰ are independently hydrogen, —CF₃, phenyl, —(C₁–C₄)alkyl, —(C₁–C₄)alkylphenyl or -phenyl (C₁–C₄)alkyl and n is 1 to 8;

to form a compound of formula XII

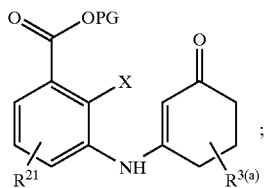
(XII)

d) cyclizing a compound of formula XII to form a compound of formula XI

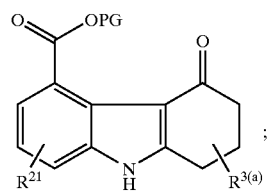
(XI)

e) alkylating a compound of formula XI with an alkylating agent of the formula XCH₂R⁴, where X is halo to form a compound of formula X

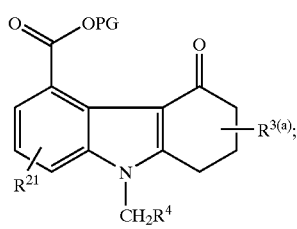
(X)

f) dehydrogenating a compound of formula X to form a compound of formula IX

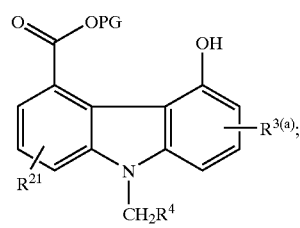
(IX)

g) aminating a compound of formula IX to form a compound of formula VIII

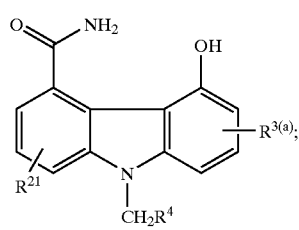
(VIII)

h) alkylating a compound of formula VIII with an alkylating agent of formula XCH₂R¹⁵ where X is halo and R¹⁵ is —CO₂R¹⁶, —SO₃R¹⁶, —P(O)(OR¹⁶)₂, or —P(O)(OR¹⁶)H, where R¹⁶ is an acid protecting group to form a compound of formula VII

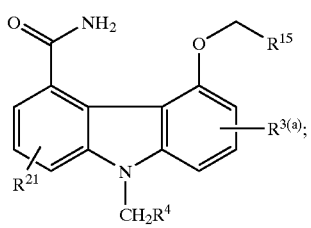
(VII)

i) optionally hydrolyzing a compound of formula VII to form a compound of formula I and optionally salifying a compound of formula I.

This invention provides, in addition, a process for preparing compounds of formula II or a pharmaceutically acceptable racemate, solvate, tautomer, optical isomer, prodrug derivative or salt, thereof;

which process comprises the steps of:

a) esterifying a compound of formula XVI

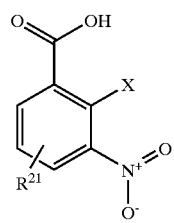
XVI where X is halo to form a compound of formula XV

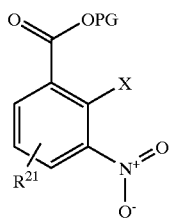

XV where PG is an acid protecting group;

b) condensing a compound of formula XV with a compound of formula XVII

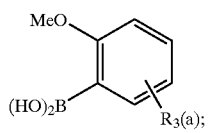

XVII to form a compound of formula XVIII

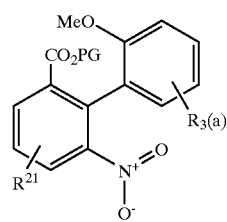

XVIII c) cyclizing a compound of formula XVIII to form a compound of formula XIX.

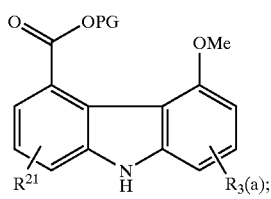

XIX d) alkylating a compound of formula XIX with an alkylating agent of the formula $XCH_2R^4$, where X is halo, to form a compound of formula XX

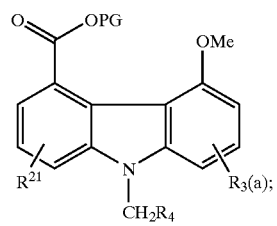

XX e) dealkylating a compound of formula XX to form a compound of formula IX

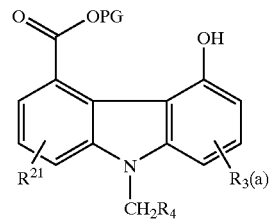

IX f) aminating compound of formula IX to form a compound of formula VIII

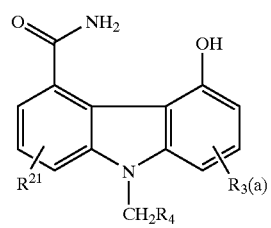

VIII g) alkylating a compound of formula VIII with an alkylating agent of formula $XCH_2R^{15}$, where X is halo and $R^{15}$ is $—CO_2R^{16}$, $—SO_3R^{16}$, $P(O)(OR^{16})_2$, or $—P(O)(OR^{16})H$, where $R^{16}$ is an acid protecting group to form a compound of formula VII

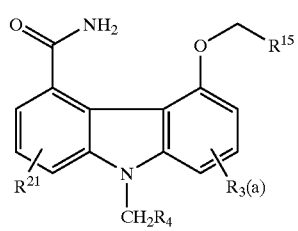

VII h) optionally hydroyzing a compound of formula VII to form a compound of formula I and optionally salifying a compound of formula I.

This invention provides, in addition, new intermediates of the formula III

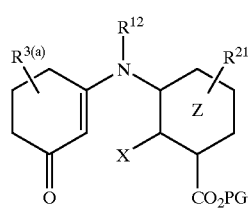

(III)

wherein;

PG is an acid protecting group $R^{21}$ is a non-interfering substituent;

$R^{12}$ is H or $CH_2R^4$ where $R^4$ is H, $—(C_5–C_{14})$alkyl, $—(C_3–C_{14})$cycloalkyl, pyridyl, phenyl or phenyl substituted with from 1–5 substituents selected from the group consisting of $—(C_1–C_6)$alkyl, halo, $—CF_3$, $—OCF_3$, $—(C_1–C_4)$alkoxy, $—CN$, $—(C_1–C_4)$alkylthio, phenyl(C1–$C_4$)alkyl, $—(C_1–C_4)$ alkylphenyl, phenyl, phenoxy, —OR$^9$; where R$^9$ and R$^{10}$ are independently hydrogen, —CF$_3$, phenyl, —(C$_1$–C$_4$)alkyl, —(C$_1$–C$_4$)alkylphenyl or -phenyl (C$_1$–C$_4$)alkyl; tetrazole; tetrazole substituted with —(C$_1$–C$_4$)alkyl or —(C$_1$–C$_4$)alkylphenyl: or naphthyl;

R$^3$(a) is H, —O(C$_1$–C$_4$)alkyl, halo, —(C$_1$–C$_6$)alkyl, phenyl, —(C$_1$–C$_4$)alkylphenyl; phenyl substituted with —(C$_1$–C$_6$)alkyl, halo or —CF$_3$; —CH$_2$OSi(C$_1$–C$_6$)alkyl, furyl, thiophenyl, —(C$_1$–C$_6$)hydroxyalkyl, —(C$_1$–C$_6$)alkoxy(C$_1$–C$_6$)alkyl, —(C$_1$–C$_6$)alkoxy(C$_1$–C$_6$)alkenyl; or —(CH$_2$)$_n$R$^8$ where R$^8$ is H, —NR$^9$R$^{10}$, —CN or phenyl where R$^9$ and R$^{10}$ are independently hydrogen, —CF$_3$, phenyl, —(C$_1$–C$_4$)alkyl, —(C$_1$–C$_4$)alkylphenyl or -phenyl(C$_1$–C$_4$)alkyl and n is 1 to 8:

Z is cyclohexenyl or phenyl; and

X is halo.

As another embodiment, this invention provides intermediates of the formula IV

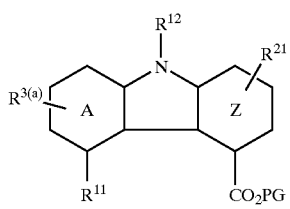

(IV)

wherein;

PG is an acid protecting group

R$^{21}$ is a non-interfering substituent

R$^{12}$ or CH$_2$R$^4$ where

R$^4$ is H, —(C$_5$–C$_{14}$)alkyl, —(C$_3$–C$_{14}$)cycloalkyl, pyridyl, phenyl or phenyl substituted with from 1–5 substituents selected from the group consisting of —(C$_1$–C$_6$)alkyl, halo, —CF$_3$, —OCF$_3$, —(C$_1$–C$_4$)alkoxy, —CN, —(C$_1$–C$_4$)alkylthio, phenyl(C1–C$_4$)alkyl, —(C$_1$–C$_4$)alkylphenyl, phenyl, phenoxy, —OR$^9$; where R$^9$and R$^{10}$ are independently hydrogen, —CF$_3$, phenyl, —(C$_1$–C$_4$)alkyl, —(C$_1$–C$_4$)alkylphenyl or -phenyl (C$_1$–C$_4$)alkyl; tetrazole; tetrazole substituted with —(C$_1$–C$_4$)alkyl or —(C$_1$–C$_4$)alkylphenyl: or naphthyl;

R$^3$(a) is H, —O(C$_1$–C$_4$)alkyl, halo, —(C$_1$–C$_6$)alkyl, phenyl, —(C$_1$–C$_4$)alkylphenyl; phenyl substituted with —(C$_1$–C$_6$)alkyl, halo or —CF$_3$, —CH$_2$OSi(C$_1$–C$_6$)alkyl, furyl, thiophenyl, —(C$_1$–C$_6$)hydroxyalkyl, —(C$_1$–C$_6$)alkoxy(C$_1$–C$_6$)alkyl, —(C$_1$–C$_6$)alkoxy(C$_1$–C$_6$)alkenyl; or —(CH$_2$)$_n$R$^8$ where R$^8$ is H, —NR$^9$R$^{10}$, —CN or phenyl where R$^9$ and R$^{10}$ are independently hydrogen, —CF$_3$, phenyl, —(C$_1$–C$_4$)alkyl, —(C$_1$–C$_4$)alkylphenyl or -phenyl(C$_1$–C$_4$)alkyl and n is 1 to 8;

R$^{11}$ is —OH, =O, —O(C$_1$–C$_4$)alkyl or —O(CH$_2$)R$^{15}$, where R$^{15}$ is —CO$_2$R$^{16}$, —SO$_3$R$^{16}$, P(O)(OR$^{16}$)$_2$, or —P(O)(OR$^{16}$)H, where R$^{16}$ is an acid protecting group; and A and Z are each independently phenyl or cyclohexenyl provided that A and Z cannot both be phenyl.

In a still further embodiment, this invention provides new intermediates of the formula

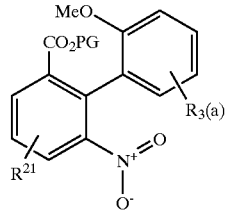

XVIII where

PG is an acid protecting group;

R$^{21}$ is a non-interfering substituent; and

R$^3$(a) is H, —O(C$_1$–C$_4$)alkyl, halo, —(C$_1$–C$_6$)alkyl, phenyl, —(C$_1$–C$_4$)alkylphenyl; phenyl substituted with —(C$_1$–C$_6$)alkyl, halo or —CF$_3$; —CH$_2$OSi(C$_1$–C$_6$)alkyl, furyl, thiophenyl, —(C$_1$–C$_6$)hydroxyalkyl, —(C$_1$–C$_6$)alkoxy(C$_1$–C$_6$)alkyl, —(C$_1$–C$_6$)alkoxy(C$_1$–C$_6$)alkenyl; or —(CH$_2$)$_n$R$^8$ where R$^8$ is H, —NR$^9$R$^{10}$, —CN or phenyl where R$^9$ and R$^{10}$ are independently hydrogen, —CF$_3$, phenyl, —(C$_1$–C$_4$)alkyl, —(C$_1$–C$_4$)alkylphenyl or -phenyl(C$_1$–C$_4$)alkyl and n is 1 to 8.

Other objects, features and advantages of the present invention will become apparent from the subsequent description and the appended claims.

DETAILED DESCRIPTION OF THE INVENTION

Definitions

As used herein, the term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl tert butyl, n-pentyl, isopentyl, neopentyl, heptyl, hexyl, octyl, nonyl, decyl, undecyl, dodecyl, tridecyl, tetradecyl and the like. The term "alkyl" includes —(C$_1$–C$_2$)alkyl, —(C$_1$–C$_4$)alkyl, —(C$_1$–C$_6$)alkyl, —(C$_5$–C$_{14}$)alkyl, and —(C$_1$–C$_{10}$)alkyl.

The term "alkenyl" as used herein represents an olefinically unsaturated branched or linear group having at least one double bond. Examples of such groups include radicals such as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl as well as dienes and trienes of straight and branched chains.

The term "alkynyl" denotes such radicals as ethynyl, propynyl, butynyl, pentynyl, hexynyl, heptynyl as well as di- and tri-ynes.

The term "halo" means chloro, fluoro, bromo or iodo.

The term "—(C$_1$–C$_4$)alkoxy", as used herein, denotes a group such as methoxy, ethoxy, n-propoxy, isopropoxy, n-butoxy, t-butoxy and like groups, attached to the remainder of the molecule by the oxygen atom.

The term "phenyl(C$_1$–C$_4$)alkyl" refers to a straight or branched chain alkyl group having from one to four carbon atoms attached to a phenyl ring which chain is attached to the remainder of the molecule. Typical phenylalkyl groups include benzyl, phenylethyl, phenylpropyl, phenylisopropyl, and phenylbutyl.

The term "—(C$_1$–C$_4$)alkylthio" defines a straight or branched alkyl chain having one to four carbon atoms attached to the remainder of the molecule by a sulfur atom. Typical —(C$_1$–C$_4$)alkylthio groups include methylthio, ethylthio, propylthio, butylthio and the like.

The term "—($C_3$–$C_{14}$)cycloalkyl" includes groups such as cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl and the like. The term "—($C_3$–$C_{14}$)cycloalkyl" includes and —($C_3$–$C_7$)cycloalkyl.

The term, "heterocyclic radical", refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyridyl, thienyl, fluorenyl, pyrrolyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, thianaphtheneyl, dibenzothiophenyl, indazolyl, imidazo (1.2-A)pyridinyl, benzotriazolyl, anthranilyl, 1,2-benzisoxazolyl, benzoxazolyl, benzothiazolyl, purinyl, pryidinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl, and quinoxalinyl.

The term "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are cycloalkyl, cycloalkenyl, phenyl, naphthyl, norbornanyl, bicycloheptadienyl, tolulyl, xylenyl, indenyl, stilbenyl, terphenylyl, diphenylethylenyl, phenylcyclohexeyl, acenaphthylenyl, and anthracenyl, biphenyl, bibenzylyl and related bibenzylyl homologues represented by the formula (bb),

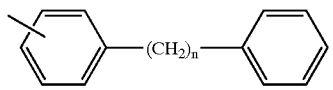

(bb)

where n is an integer from 1 to 8.

The term, "non-interfering substituent", refers to radicals suitable for substitution at positions 1, 2, 3, 7 and/or 8 on the tricyclic nucleus (as depicted in Formula III) and radical(s) suitable for substitution on the heterocyclic radical and carbocyclic radical as defined above. Illustrative non-interfering radicals are hydrogen, —($C_1$–$C_{14}$)alkyl, —($C_2$–$C_6$)alkenyl, —($C_2$–$C_6$)alkynyl, —($C_7$–$C_{12}$)aralkyl, —($C_7$–$C_{12}$)alkaryl, —($C_3$–$C_8$)cycloalkyl, —($C_3$–$C_8$)cycloalkenyl, phenyl, tolulyl, xylenyl, biphenyl, —($C_1$–$C_6$)alkoxy, —($C_2$–$C_6$)alkenyloxy, —($C_2$–$C_6$)alkynyloxy, —($C_1$–$C_{12}$)alkoxyalkyl, —($C_1$–$C_{12}$)alkoxyalkyloxy, —($C_1$–$C_{12}$)alkylcarbonyl, —($C_1$–$C_{12}$)alkylcarbonylamino, —($C_1$–$C_{12}$)alkoxyamino,—($C_1$–$C_{12}$)alkoxyaminocarbonyl, —($C_1$–$C_{12}$)alkylamino, —($C_1$–$C_6$)alkylthio, —($C_1$–$C_{12}$)alkylthiocarbonyl, —($C_1$–$C_6$)alkylsulfinyl, —($C_1$–$C_6$)alkylsulfonyl, —($C_1$–$C_6$)haloalkoxy, —($C_1$–$C_6$)haloalkylsulfonyl, —($C_1$–$C_6$)haloalkyl, —($C_1$–$C_6$)hydroxyalkyl, —$(CH_2)_n$CN, —$(CH_2)_n$$NR^9R^{10}$, —C(O)O ($C_1$–$C_6$alkyl), —$(CH_2)_n$O($C_1$–$C_6$ alkyl), benzyloxy, phenoxy, phenylthio; —(CONHSO_2)$R^{15}$, where $R^{15}$ is —($C_1$–$C_6$)alkyl; —$CF_3$, naphthyl or —$(CH_2)_s$phenyl where s is 0–5; —CHO, —$CF_3$, —$OCF_3$, pyridyl, amino, amidino, halo, carbamyl, carboxyl, carbalkoxy, —$(CH_2)_n$$CO_2H$, cyano, cyanoguanidinyl, guanidino, hydrazide, hydrazino, hydrazido, hydroxy, hydroxyamino, nitro, phosphono, —$SO_3H$, thioacetal, thiocarbonyl, furyl, thiophenyl —$COR^9$, —$CONR^9R^{10}$, —$NR^9R^{10}$, —$NCHCOR^9$, —$SO_2R^9$, —$OR^9$, —$SR^9$, $CH_2SO_2R^9$, tetrazolyl or tetrazolyl substituted with —($C_1$–$C_6$)alkyl, phenyl or —($C_1$–$C_4$)alkylphenyl, —$(CH_2)_n$OSi($C_1$–$C_6$)alkyl and ($C_1$–$C_6$)alkylcarbonyl; where n is from 1 to 8 and $R^9$ and $R^{10}$ are independently hydrogen, —$CF_3$, phenyl, —($C_1$–$C_4$)alkyl, —($C_1$–$C_4$)alkylphenyl or -phenyl ($C_1$–$C_4$)alkyl The term, "acidic group" means an organic group which when attached to a tricyclic nucleus, through suitable linking atoms (hereinafter defined as the "acid linker"), acts as a proton donor capable of hydrogen bonding. Illustrative of an acidic group are the following:

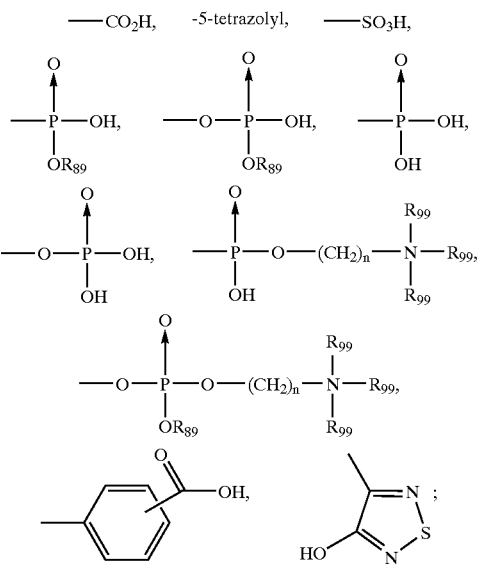

where n is 1 to 8, $R_{89}$ is a metal or —($C_1$–$C_{10}$)alkyl, and $R_{99}$ is hydrogen or —($C_1$–$C_{10}$)alkyl.

The words, "acid linker" refer to a divalent linking group symbolized as, —($L_a$)—, which has the function of joining the 5 or 6 position of the tricyclic nucleus to an acidic group in the general relationship:

(tricyclic nucleus) —($L_a$)— Acidic Group

The words, "acid linker length", refer to the number of atoms (excluding hydrogen) in the shortest chain of the linking group —($L_a$)— that connects the 5 or 6 position of the tricyclic nucleus with the acidic group. The presence of a carbocyclic ring in —($L_a$)— counts as the number of atoms approximately equivalent to the calculated diameter of the carbocyclic ring. Thus, a benzene or cyclohexane ring in the acid linker counts as 2 atoms in calculating the length of —($L_a$)—. Illustrative acid linker groups are;

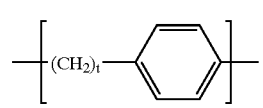

(a)

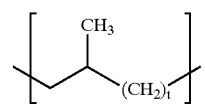

(b)

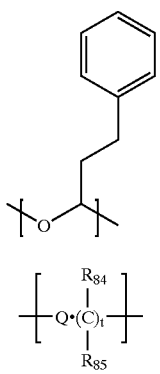

(c)

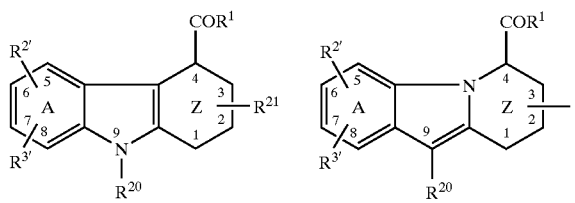

(d)

where t is 1 to 5, Q is selected from the group —(CH$_2$)—, —O—, —NH—, and —S—, and R$_{84}$ and R$_{85}$ are each independently selected from hydrogen, —(C$_1$–C$_{10}$)alkyl, aryl, —(C$_1$–C$_{10}$)alkaryl, —(C$_1$–C$_{10}$)aralkyl, carboxy, carbalkoxy, and halo, when t is one (1), groups (a), (b), (c) and (d) have acid linker lengths of 3, 3, 2, and 2, respectively.

The skilled artisan will appreciate that the position of the double bond in the center 5-membered ring depends on the position of the nitrogen atom as depicted below.

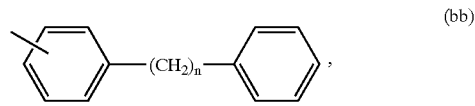

The salts of the above tricyclics are an additional aspect of the invention. In those instances where the compounds of the invention possess acidic functional groups various salts may be formed which are more water soluble and physiologically suitable than the parent compound. Representative pharmaceutically acceptable salts include but are not limited to the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1–19 (1977)).

Compounds of the invention may have chiral centers and exist in optically active forms. R- and S-isomers and racemic mixtures are contemplated by this invention. A particular stereoisomer may be prepared by known methods using stereospecific reactions with starting materials containing asymmetric centers already resolved or, alternatively, by subsequent resolution of mixtures of stereoisomers using known methods.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7–9, 21–24, Elsevier, Amsterdam 1985). Prodrugs include acid derivatives, such as, esters prepared by reaction of the parent acidic compound with a suitable alcohol, or amides prepared by reaction of the parent acid compound with a suitable amine. Simple aliphatic esters (e.g., methyl, ethyl, propyl, isopropyl, butyl, sec-butyl, tert-butyl) or aromatic esters derived from acidic groups pendent on the compounds of this invention are preferred prodrugs. Other preferred esters include morpholinoethyloxy, diethylglycolamide and diethylaminocarbonylmethoxy. In some cases it is desirable to prepare double ester type prodrugs such as (acyloxy) alkyl esters or ((alkoxycarbonyl)oxy)alkyl esters.

The term "acid protecting group" is used herein as it is frequently used in synthetic organic chemistry, to refer to a group which will prevent an acid group from participating in a reaction carried out on some other functional group in the molecule, but which can be removed when it is desired to do so. Such groups are discussed by T. W. Greene in chapter 5 of Protective Groups in Organic Synthesis, John Wiley and Sons, New York, 1981, incorporated herein by reference in its entirety. Examples of acid protecting groups include ester or amide derivatives of the acid group, such as, methyl, methoxymethyl, methyl-thiomethyl, tetrahydropyranyl, methoxyethoxymethyl, benzyloxymethyl, phenyl, aryl, ethyl, 2,2,2-trichloroethyl, 2-methylthioethyl, t-butyl, cyclopentyl, triphenylmethyl, diphenylmethyl, benzyl, trimethylsilyl, N,N-dimethyl, pyrrolidinyl, piperidinyl, or o-nitroanilide. A preferred acid-protecting group is methyl.

PREFERRED COMPOUNDS OF THE INVENTION

Preferred Subgroups of Compounds of Formula (I)

A preferred subclass of compounds of formula (I) are those wherein R$^{21}$ is selected from the group hydrogen, halo, —(C$_1$–C$_3$)alkyl, —(C$_3$–C$_4$)cycloalkyl, —(C$_3$–C$_4$)cycloalkenyl, —O(C$_1$–C$_2$)alkyl and —S(C$_1$–C$_2$)alkyl.

Another preferred subclass of compounds of formula (I) are those wherein for R$^{2'}$, —(L)— is an alkyl chain of 1 or 2 carbon atoms.

Another preferred subclass of compounds of formula (I) are those wherein for R$^{20}$, group R$^{80}$ is selected from the group consisting of cycloalkyl, cycloalkenyl, phenyl, naphthyl, norbornanyl, bicycloheptadienyl, tolulyl, xylenyl, indenyl, stilbenyl, terphenylyl, diphenylethylenyl, phenylcyclohexenyl, acenaphthylenyl, and anthracenyl, biphenyl, bibenzylyl and related bibenzylyl homologues represented by the formula bb, (bb)

where n is a number from 1 to 8. Particularly preferred are compounds wherein R$^{20}$ is selected from the group consisting of

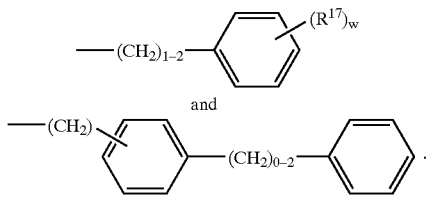

where $R^{17}$ is a radical independently selected from halo, —$(C_1-C_{10})$alkyl, —$(C_1-C_{10})$alkoxy, —S—$(C_1-C_{10}$ alkyl), and —$(C_1-C_{10})$haloalkyl, and w is a number from 0 to 5.

Another preferred subclass of compounds of formula (I) are those wherein $R^{2'}$ is a substituent having an acid linker with an acid linker length of 2 or 3. Most preferred are compounds where the acidic group is selected from

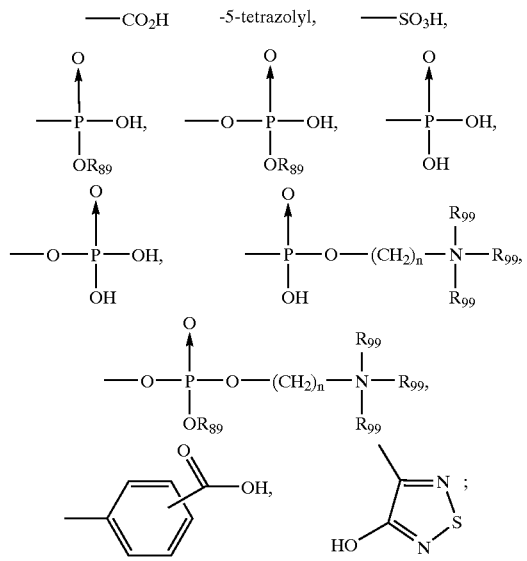

where n is 1 to 8, $R_{89}$ is a metal or —$(C_1-C_{10})$alkyl, and $R_{99}$ is hydrogen or —$(C_1-C_{10})$alkyl. Particularly preferred are compounds wherein the acidic group of $R^{2'}$ is selected from;

—CO$_2$H,   —SO$_3$H,   —P(O)(OH)$_2$, or salt, and prodrug (e.g., ester) derivatives thereof.

Another preferred subclass of compounds of formula (I) are those wherein $R^{2'}$ is a substituent having an acid linker with an acid linker length of 2 or 3 and the acid linker group, —$(L_a)$—, for $R^{2'}$ is selected from a group represented by the formula;

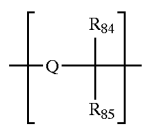

where Q is selected from the group —$(CH_2)$—, —O—, —NH—, and —S—, and $R_{84}$ and $R_{85}$ are each independently selected from hydrogen, —$(C_1-C_{10})$alkyl, aryl, —$(C_1-C_{10})$alkylaryl, -aryl$(C_1-C_{10})$alkyl, carboxy, carbalkoxy, and halo. Most preferred are compounds where the acid linker, —$(L_a)$—, for $R^{2'}$ is selected from the specific groups;

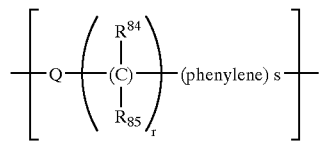

Another preferred subclass of compounds of formula (I) are those wherein $R^{2'}$ is a substituent having an acid linker with an acid linker length of 3 to 8 atoms and the acid linker group, —$(L_a)$—, for $R^{2'}$ is selected from;

$$\left[ Q \left( \underset{R^{85}}{\overset{R^{84}}{C}} \right)_r (\text{phenylene})_s \right]$$

where r is a number from 1 to 7, s is 0 or 1, and Q is selected from the group —$(CH_2)$—, —O—, —NH—, and —S—, and $R_{84}$ and $R_{85}$ are each independently selected from hydrogen, —$(C_1-C_{10})$alkyl, aryl, —$(C_1-C_{10})$alkylaryl, -aryl$(C_1-C_{10})$alkyl, carboxy, carbalkoxy, and halo.

Most preferred are compounds where the acid linker, —$(L_a)$—, for $R^{2'}$ is selected from the specific groups;

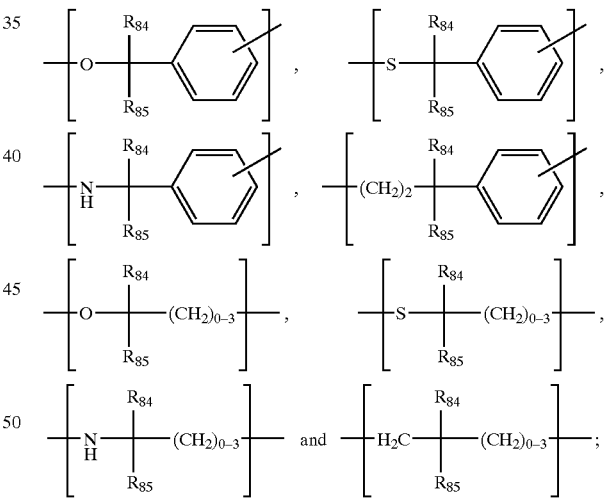

wherein $R_{84}$ and $R_{85}$ are each independently selected from hydrogen, —$(C_1-C_{10})$alkyl, aryl, —$(C_1-C_{10})$alkaryl, —$(C_1-C_{10})$aralkyl, carboxy, carbalkoxy, and halo.

Another preferred subclass of compounds of formula (I) are those wherein $R^{3'}$ is selected from hydrogen and non-interfering substituents, with the non-interfering substituents being selected from the group consisting of hydrogen, —$(C_1-C_6)$alkyl, —$(C_2-C_6)$alkenyl, —$(C_2-C_6)$alkynyl, —$(C_7-C_{12})$aralkyl, —$(C_7-C_{12})$alkaryl, —$(C_3-C_8)$cycloalkyl, —$(C_3-C_8)$cycloalkenyl, phenyl, tolulyl, xylenyl, biphenyl, —$(C_1-C_6)$alkoxy, —$(C_2-C_6)$alkenyloxy —$(C_2-C_6)$alkynyloxy, —$(C_1-C_{12})$alkoxyalkyl, —$(C_1-C_{12})$alkoxyalkyloxy, —$(C_1-C_{12})$alkylcarbonyl, —$(C_1-C_{12})$ alkylcarbonylamino, —$(C_1-C_{12})$alkoxyamino, —$(C_1-C_{12})$ alkoxyaminocarbonyl, —$(C_1-C_{12})$alkylamino, —$(C_1-C_6)$ alkylthio, —$(C_1-C_{12})$alkylthiocarbonyl, —$(C_1-C_6)$ alkylsulfinyl, —$(C_1-C_6)$alkylsulfonyl, —$(C_1-C_6)$ haloalkoxy, —$(C_1-C_6)$haloalkylsulfonyl, —$(C_1-C_6)$ haloalkyl, —$(C_1-C_6)$hydroxyalkyl, —$C(O)O(C_1-C_6$ alkyl), —$(CH_2)_nO(C_1-C_6$ alkyl), benzyloxy, halo, phenylthio; phenyl substituted with —$(C_1-C_6)$alkyl, halo, or —$CF_3$; furyl, thiophenyl, —$(CH_2)_n$CN, —$(CH_2)_nR^8$ where $R^8$ is H, —$CONH_2$, —$NR^9R^{10}$, —CN or phenyl where $R^9$ and $R^{10}$ are independently —$(C_1-C_4)$alkyl or -phenyl$(C_1-C_4)$; —CHO, amino, amidino, carbamyl, carboxyl, carbalkoxy, —$(CH_2)_nCO_2H$, cyano, cyanoguanidinyl, guanidino, hydrazide, hydrazino, hydrazido, hydroxy, hydroxyamino, nitro, phosphono, —$SO_3H$, thioacetal, thiocarbonyl, and —$(C_1-C_6)$alkylcarbonyl; where n is from 1 to 8.

Another preferred group of substituents for $R^{3'}$ include H, —$O(C_1-C_4)$alkyl, halo, —$(C_1-C_6)$alkyl, phenyl, —$(C_1-C_4)$ alkylphenyl; phenyl substituted with —$(C_1-C_6)$alkyl, halo, or —$CF_3$; —$CH_2OSi(C_1-C_6)$alkyl, furyl, thiophenyl, —$(C_1-C_6)$hydroxyalkyl; or —$(CH_2)_nR^8$ where $R^8$ is H, —$CONH_2$, —$NR^9R^{10}$, —CN or phenyl where $R^9$ and $R^{10}$ are independently —$(C_1-C_4)$alkyl or -phenyl$(C_1-C_4)$alkyl and n is 1 to 8;

Yet another preferred group include H, —$O(C_1-C_4)$alkyl, halo, —$(C_1-C_6)$alkyl, phenyl, —$(C_1-C_4)$alkylphenyl; phenyl substituted with —$(C_1-C_6)$alkyl, halo or —$CF_3$; —$CH_2OSi(C_1-C_6)$alkyl, furyl, thiophenyl, —$(C_1-C_6)$ hydroxyalkyl; or —$(CH_2)_nR^8$ where $R^8$ is H, —$NR^9R^{10}$, —CN or phenyl where $R^9$ and $R^{10}$ are independently —$(C_1-C_4)$alkyl or -phenyl$(C_1-C_4)$alkyl and n is 1 to 8.

Preferred compounds of the invention are those having the general formula (II)

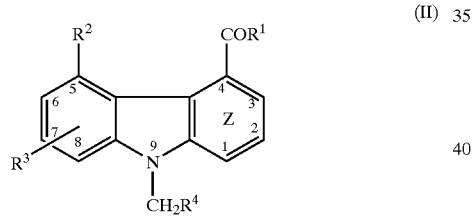

(II)

wherein;
$R^1$ is —$NHNH_2$, or —$NH_2$;
$R^2$ is selected from the group consisting of —OH and —$O(CH_2)_nR^5$ where
$R^5$ is H, —$CO_2H$, —$CO_2(C_1-C_4$ alkyl);

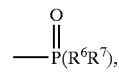

where $R^6$ and $R^7$ are each independently —OH or —$O(C_1-C_4)$alkyl; —$SO_3H$, —$SO_3(C1-C4$ alkyl), tetrazolyl, —CN, —$NH_2$, —$NHSO_2R^{15}$; —$CONHSO_2R^{15}$, where $R^{15}$ is —$(C_1-C_6)$alkyl or —$CF_3$, phenyl or phenyl substituted with —$CO_2H$ or —$CO_2(C_1-C_4)$alkyl where m is 1–3;

$R^3$ is H, —$O(C_1-C_4)$alkyl, halo, —$(C_1-C_6)$alkyl, phenyl, —$(C_1-C_4)$alkylphenyl; phenyl substituted with —$(C_1-C_6)$alkyl, halo, or —$CF_3$; —$CH_2OSi(C_1-C_6)$ alkyl, furyl, thiophenyl, —$(C_1-C_6)$hydroxyalkyl; or —$(CH_2)_nR^8$ where $R^8$ is H, —$CONH_2$, —$NR^9R^{10}$, —CN or phenyl where $R^9$ and $R^{10}$ are independently —$(C_1-C_4)$alkyl or -phenyl$(C_1-C_4)$alkyl and n is 1 to 8;

$R^4$ is H, —$(C_5-C_{14})$alkyl, —$(C_3-C_{14})$cycloalkyl, pyridyl, phenyl or phenyl substituted with —$(C_1-C_6)$alkyl, halo, —$CF_3$, —$OCF_3$, —$(C_1-C_4)$alkoxy, —CN, —$(C_1-C_4)$alkylthio, phenyl $(C1-C_4)$alkyl, —$(C_1-C_4)$ alkylphenyl, phenyl, phenoxy or naphthyl;

Z is cyclohexenyl, or phenyl;

or a pharmaceutically acceptable racemate, solvate, tautomer, optical isomer, prodrug derivative or salt, thereof.

Another preferred genus of compounds of the invention are those having the general formula (XXX)

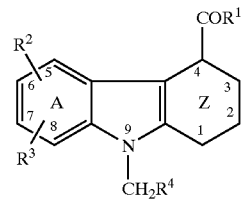

(XXX)

wherein:
$R^1$ is —$NHNH_2$, or —$NH_2$;
$R^2$ is selected from the group consisting of —OH and —$O(CH_2)_mR^5$ where
$R^5$ is H, —$CO_2H$, —$CO_2(C_1-C_4$ alkyl);

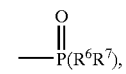

where $R^6$ and $R^7$ are each independently —OH or —$O(C_1-C_4)$alkyl; —$SO_3H$, —$SO_3(C1-C4$ alkyl), tetrazolyl, —CN, —$NH_2$, —$NHSO_2R^{15}$; —$CONHSO_2R^{15}$, where $R^{15}$ is —$(C_1-C_6)$alkyl or —$CF_3$, phenyl or phenyl substituted with —$CO_2H$ or —$CO_2(C_1-C_4)$alkyl where m is 1–3;

$R^3$ is H, —$O(C_1-C_4)$alkyl, halo, —$(C_1-C_6)$alkyl, phenyl, —$(C_1-C_4)$alkylphenyl; phenyl substituted with —$(C_1-C_6)$alkyl, halo, or —$CF_3$; —$CH_2OSi(C_1-C_6)$ alkyl, furyl, thiophenyl, —$(C_1-C_6)$hydroxyalkyl; or —$(CH_2)_nR^8$ where $R^8$ is H, —$CONH_2$, —$NR^9R^{10}$, —CN or phenyl where $R^9$ and $R^{10}$ are independently —$(C_1-C_4)$alkyl or -phenyl $(C_1-C_4)$alkyl and n is 1 to 8;

$R^4$ is H, —$(C_5-C_{14})$alkyl, —$(C_3-C_{14})$cycloalkyl, pyridyl, phenyl or phenyl substituted with —$(C_1-C_6)$alkyl, halo, —$CF_3$, —$OCF_3$, —$(C_1-C_4)$alkoxy, —CN, —$(C_1-C_4)$alkylthio, phenyl$(C1-C_4)$alkyl, —$(C_1-C_4)$ alkylphenyl, phenyl, phenoxy or naphthyl;

A is phenyl or pyridyl wherein the nitrogen is at the 5-, 6-, 7- or 8-position;

Z is cyclohexenyl, phenyl, pyridyl wherein the nitrogen is at the 1-, 2- or 3-position or a 6-membered heterocyclic ring having one heteroatom selected from the group consisting of sulfur or oxygen at the 1-, 2- or 3-position and nitrogen at the 1-, 2-, 3- or 4-position, or wherein one carbon on the heterocyclic ring is optionally substituted with =O or a pharmaceutically acceptable racemate, solvate, tautomer, optical isomer, prodrug derivative or salt thereof;

provided that one of A or Z is a heterocyclic ring.

Preferred substituents of compounds of formula I and II include the following:

(a) $R^1$ is —$NH_2$, —$NHNH_2$;
(b) $R^1$ is —$NH_2$;

(c) $R^2$ is —O(CH$_2$)$_m$R$^5$ where $R^5$ is —H, —CO$_2$H or

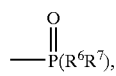

where $R^6$ and $R^7$ are —OH;

(d) $R^2$ is —OH;

(e) $R^2$ is —O(CH$_2$)$_m$R$^5$ where $R^5$ is —H, —CO$_2$(C$_1$–C$_4$ alkyl), phenyl or phenyl substituted with —CO$_2$H or —CO$_2$(C$_1$–C$_4$ alkyl);

(f) $R^2$ is —O(CH$_2$)$_m$R$^5$ where $R^5$ is

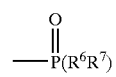

and $R^6$ and $R^7$ are —O(C$_1$–C$_4$ alkyl), or when one of $R^6$ and $R^7$ is —O(C$_1$–C$_4$ alkyl), the other is —OH;

(g) $R^3$ is —H, —O(C$_1$–C$_4$ alkyl) or —(CH$_2$)$_n$R$^8$ where n=2 and
$R^8$ is H or phenyl;

(h) $R^3$ is H, or —O(C$_1$–C$_4$ alkyl);

(i) $R^3$ is —(CH$_2$)$_n$R$^8$ where $R^8$ is —NR$^9$R$^{10}$,

or —CN where $R^9$ and $R^{10}$ are —(C$_1$–C$_4$)alkyl;

(j) $R^4$ is phenyl;

(k) $R^4$ is phenyl substituted at the 2- and 6-position of the phenyl ring with —(C$_1$–C$_4$)alkyl, (C$_1$–C$_4$)alkoxy, halo or phenyl;

(l) $R^4$ is phenyl substituted at the 2- or 6-position of the phenyl ring with —(C$_1$–C$_4$)alkyl, —(C$_1$–C$_4$)alkoxy, halo or phenyl;

(m) $R^4$ is phenyl substituted at the 3- or 5-position of the phenyl ring with —(C$_1$–C$_4$)alkyl, —(C$_1$–C$_4$)alkoxy, halo or phenyl;

(n) $R^4$ is —(C$_6$–C$_{14}$)alkyl or —(C$_6$–C$_{14}$)cycloalkyl;

(o) Z is cyclohexenyl;

(p) $R^5$ is H, —CO$_2$H, —CO$_2$(C$_1$–C$_4$ alkyl),

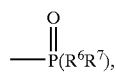

—NHSO$_2$(C$_1$–C$_6$)alkyl, —CONHSO$_2$(C$_1$–C$_6$)alkyl, tetrazolyl, phenyl, or phenyl substituted with —CO$_2$H or —CO$_2$(C$_1$–C$_4$ alkyl) where $R^6$ and $R^7$ are each independently —OH or —O(C$_1$–C$_4$ alkyl) and m is 1–3;

(q) $R^5$ is H, —CO$_2$H, —CO$_2$(C$_1$–C$_4$ alkyl),

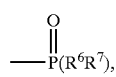

phenyl, or phenyl substituted with —CO$_2$H or —CO$_2$(C$_1$–C$_4$ alkyl) where $R^6$ and $R^7$ are each independently —OH or —O(C$_1$–C$_4$ alkyl) and m is 1–3;

(r) Z is cyclohexenyl;

(s) Z is phenyl;

(t) $R^5$ is H, —CO$_2$H, —CO$_2$(C$_1$–C$_4$ alkyl);

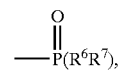

where $R^6$ and $R^7$ are each independently —OH or —O(C$_1$–C$_4$)alkyl; —SO$_3$H, —SO$_3$(C1–C4 alkyl), tetrazolyl, —CN, —NH$_2$, —NHSO$_2$R$^{15}$; —CONHSO$_2$R$^{15}$, where $R^{15}$ is —(C$_1$–C$_6$)alkyl or —CF$_3$, phenyl or phenyl substituted with —CO$_2$H or —CO$_2$(C$_1$–C$_4$)alkyl where m is 1–3;

(u) $R^3$ is H, —O(C$_1$–C$_4$)alkyl, halo, —(C$_1$–C$_6$)alkyl, phenyl, —(C$_1$–C$_4$)alkylphenyl; phenyl substituted with —(C$_1$–C$_6$)alkyl, halo, or —CF$_3$; —CH$_2$OSi(C$_1$–C$_6$) alkyl, furyl, thiophenyl, —(C$_1$–C$_6$)hydroxyalkyl —(C$_1$–C$_6$)alkoxy(C$_1$–C$_6$)alkyl, —(C$_1$–C$_6$)alkoxy (C$_1$–C$_6$)alkenyl, —(C$_1$–C$_6$)alkoxy(C$_1$–C$_6$)alkyl, —(C$_1$–C$_6$)alkoxy, —(C$_1$–C$_6$)alkenyl; or —(CH$_2$)$_n$R$^8$ where $R^8$ is H, —CONH$_2$, —NR$^9$R$^{10}$, —CN or phenyl where $R^9$ and $R^{10}$ are independently hydrogen, —CF$_3$, phenyl, —(C$_1$–C$_4$)alkyl, —(C$_1$–C$_4$)alkylphenyl or -phenyl (C$_1$–C$_4$)alkyl and n is 1 to 8.

(v) Z is cyclohexenyl, phenyl, pyridyl wherein the nitrogen is at the 1-, 2- or 3-position or a 6-membered heterocyclic ring having one heteroatom selected from the group consisting of sulfur or oxygen at the 1-, 2- or 3-position and nitrogen at the 1-, 2-, 3- or 4-position wherein one carbon on the heterocyclic ring is optionally substituted with

(w) Z is cyclohexenyl or phenyl; or a pharmaceutically acceptable salt, racemate or optical isomer thereof; provided that when $R^3$ is H, $R^4$ is phenyl, m is 1 or 2 and $R^2$ is substituted at the 6 position, $R^5$ cannot be H; and when $R^1$ is NHNH$_2$, $R^8$ cannot be

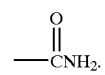

(x) A is phenyl; and (y) A is pyridyl wherein the nitrogen is at the 5-, 6-, 7- or 8-position.

Further typical examples of compounds of formula I which are useful in the present invention include:

5-hydroxy-7-(5-cyanopentyl)-9-methyl-1,2,3,4-tetrahydrocarbazole-4-carboxamide;

6-(2-carboxyethoxy)-8-methoxy-9-cyclopentylmethyl-1,2,3,4-tetrahydrocarbazole-4-carboxamide;

5-(3-phenylpropoxy)-7-ethoxy-9-butyl-1,2,3,4-tetrahydrocarbazole-4-carboxamide;

6-(2-phosphonoethoxy)-8-phenylhexyl-9-(cyclotetradecyl)methyl-1,2,3,4-tetrahydrocarbazole-4-carboxamide;

5-ethoxycarbonylmethoxy-8-(5-carbamoylpent-1-yl)-9-(3,5-dipropylphenyl)methyl-1,2,3,4-tetrahydrocarbazole-4-carboxamide;

6-(diethoxyphosphonyl)methoxy-9-(4-methoxyphenyl)methyl-1,2,3,4-tetrahydrocarbazole-4-carboxamide;

6-(3-(4-carboxyphenyl)prop-1-yl)oxy-8-heptyl-9-(3-phenylethyl)phenyl)methyl-1,2,3,4-tetrahydrocarbazole-4-carboxamide;

6-(2-propoxycarbonyl)ethoxy-8-(3-(N,N-dimethylamino)
prop-1-yl)-9-methyl-1,2,3,4-tetrahydrocarbazole-4-
caboxamide;

5-(di-t-butoxyphosphonyl)methoxy-7-nonyl-9-(3-
propylthiophenyl)methyl-1,2,3,4-tetrahydrocarbazole-4-
carboxamide;

5-(2-(3-methoxycarbonyl)phenyl)ethoxy-7-pentyl-9-
methyl-1,2,3,4-tetrahydrocarbazole-4-carboxamide;

6-hydroxy-8-(4-(N,N-diethylamino)but-1-yl)-9-(3-
fluorophenyl)methyl-1,2,3,4-tetrahydrocarbazole-4-
carboxamide;

6-(2-phenylethoxy)-9-(2-phenylphenyl)methyl-1,2,3,4-
tetrahydrocarbazole-4-carboxamide;

(S)-6-((3-carboxy)prop-1-yl)oxy-8-propoxy-9-(7-
cyanohept-1-yl)-1,2,3,4-tetrahydrocarbazole-4-
carboxamide;

5-(propoxycarbonyl)methoxy-9-cyclopentylmethyl-1,2,3,4-
tetrahydrocarbazole-4-carboxamide;

(S)-5-(2-ethoxyphosphonyl)ethoxy-(4-carbamoyl)but-1-yl-
9-(3-methylthiophenyl)methyl-1,2,3,4-
tetrahydrocarbazole-4-carboxamide;

5-(3-(ethoxycarbonyl)prop-1-yl)oxy-7-propoxy-9-
(cyclononyl)methyl-1,2,3,4-tetrahydrocarbazole-4-
carboxamide;

5-(3-phosphonoprop-1-yl)oxy-8-heptyl-9-(4-chlorophenyl)
methyl-1,2,3,4-tetrahydrocarbazole-4-carboxamide;

6-methoxycarbonylmethoxy-7-(5-cyanopent-1-yl)-9-
tridecylmethyl-1,2,3,4-tetrahydrocarbazole-4-
carboxamide;

(S)-6-propoxycarbonylmethoxy-9-((3-isopropyl-5-
methoxy)phenyl)methyl-1,2,3,4-tetrahydrocarbazole-4-
carboxamide;

(S)-6-dimethoxyphosphonoethoxy-8-(6-(N,N-
dimethylamino)hex-1-yl-9-(3,5-dimethoxyphenyl)
methyl-1,2,3,4-tetrahydrocarbazole-4-carboxamide;

5-hydroxy-7-(5-cyanopentyl)-9-methylcarbazole-4-
carboxamide;

6-(2-carboxyethoxy)-8-methoxy-9-
cyclopentylmethylcarbazole-4-carboxamide;

5-(3-phenylprop-1-yl)oxy-7-ethoxy-9-butylcarbazole-4-
carboxamide;

6-(2-phosphonoethoxy)-8-phenylhexyl-9-(cyclotetradecyl)
methylcarbazole-4-carboxamide;

5-ethoxycarbonylmethoxy-8-(5-carbamoylpent-1-yl)-9-(3,
5-dipropylphenyl)methylcarbazole-4-carboxamide;

6-(diethoxyphosphonyl)methoxy-9-(4-methoxyphenyl)
methylcarbazole-4-carboxamide;

6-(3-(4-carboxyphenyl)prop-1-yl)oxy-8-heptyl-9-(3-
phenylethyl)phenyl)methylcarbazole-4-carboxamide;

6-(2-propoxycarbonyl)ethoxy-8-(3-(N,N-dimethylamino)
prop-1-yl)-9-methylcarbazole-4-carboxamide;

5-((di-t-butoxyphosphonyl)methoxy-7-nonyl-9-(3-
propylthiopheny)methylcarbazole-4-carboxamide;

(S)-5-(2-(3-methoxycarbonyl)phenyl)ethoxy-7-pentyl-9-
methylcarbazole-4-carboxamide;

(S)-6-hydroxy-8-(4-(N,N-diethylamino)but-1-yl)-9-(3-
fluorophenyl)methylcarbazole-4-carboxamide;

(S)-6-(2-phenylethoxy)-9-((2-phenyl)phenyl)
methylcarbazole-4-carboxamide;

6-((3-carboxy)prop-1-yl)oxy-8-propoxy-9-(7-cyanohept-1-
yl)-carbazole-4-carboxamide;

5-(propoxycarbonyl)methoxy-9-
cyclopentylmethylcarbazole-4-carboxamide;

5-(2-ethoxyphosphonyl)ethoxy-(4-carbamoyl)but-1-yl-9-
(3-methylthiophenyl)methylcarbazole-4-carboxamide;

5-((3-ethoxycarbonyl)prop-1-yl)oxy-7-propoxy-9-
(cyclononyl)methylcarbazole-4-carboxamide;

(S)-5-(3-phosphonoprop-1-yl)oxy-8-heptyl-9-(4-
chlorophenyl)methylcarbazole-4-carboxamide;

(S)-6-methoxycarbonylmethoxy-7-(5-cyanopent-1-yl)-9-
tridecylmethylcarbazole-4-carboxamide;

6-(propoxycarbonyl)methoxy-9-(3-isopropyl-5-methoxy)
phenyl)methylcarbazole-4-carboxamide;

6-dimethoxyphosphonoethoxy-8-(6-(N,N-dimethylamino)
hex-1-yl-9-(3,5-dimethoxyphenyl)methyl-carbazole-4-
carboxamide;

5-hydroxy-7-(5-cyanopentyl)-9-methyl-1,2,3,4-
tetrahydrocarbazole-4-carboxylic acid hydrazide;

6-(2-carboxyethoxy-8-methoxy-9-cyclopentyl)methyl-1,2,
3,4-tetrahydrocarbazole-4-carboxylic acid hydrazide;

5-(3-phenylprop-1-yl)oxy-7-ethoxy-9-butyl-1,2,3,4-
tetrahydrocarbazole-4-carboxylic acid hydrazide;

6-(2-phosphonoethoxy)-8-phenylhexyl-9-(cyclotetradecyl)
methyl-1,2,3,4-tetrahydrocarbazole-4-carboxylic acid
hydrazide;

5-ethoxycarbonylmethoxy-8-(5-carbamoylpent-1-yl)-9-(3,
5-dipropylphenyl)methyl-1,2,3,4-tetrahydrocarbazole-4-
carboxylic acid hydrazide;

(S)-6-(diethoxyphosphonyl)methoxy-9-(4-methoxyphenyl)
methyl-1,2,3,4-tetrahydrocarbazole-4-carboxylic acid
hydrazide;

6-(3-(4-carboxyphenyl)prop-1-yl)oxy-8-heptyl-9-((3-
phenylethyl)phenyl)methyl-1,2,3,4-tetrahydrocarbazole-
4-carboxylic acid hydrazide;

(S)-6-(2-propoxycarbonyl)ethoxy-8-(3-(N,N-
dimethylamino)prop-1-yl)-9-methyl-1,2,3,4-
tetrahydrocarbazole-4-carboxylic acid hydrazide;

5-(di-t-butoxyphosphonyl)methoxy-7-nonyl-9-(3-
propylthipheny)methyl-1,2,3,4-tetrahydrocarbazole-4-
carboxylic acid hydrazide;

(S)-5-(2-(3-methoxycarbonyl)phenyl)ethoxy-7-pentyl-9-
methyl-1,2,3,4-tetrahydrocarbazole-4-carboxylic acid
hydrazide;

6-hydroxy-8-(4-(N,N-diethylamino)but-1-yl)-9-(3-
fluorophenyl)methyl-1,2,3,4-tetrahydrocarbazole-4-
carboxylic acid hydrazide;

(S)-6-(2-phenylethoxy)-9-(2-phenylphenyl)methyl-1,2,3,4-
tetrahydrocarbazole-4-carboxylic acid hydrazide;

6-((3-carboxy)prop-1-yl)oxy-8-propoxy-9-(7-cyanohept-1-
yl)methyl-1,2,3,4-tetrahydrocarbazole-4-carboxylic acid
hydrazide;

5-(propoxycarbonyl)methoxy-9-cyclopentylmethyl-1,2,3,4-
tetrahydrocarbazole-4-carboxylic acid hydrazide;

5-(2-ethoxyphosphonyl)ethoxy-(4-carbamoyl)but-1-yl-9-
(3-methylthiophenyl)methyl-1,2,3,4-
tetrahydrocarbazole-4-carboxylic acid hydrazide;

5-((3-(ethoxycarbonyl)prop-1-yl)oxy-7-propoxy-9-
(cyclononyl)methyl-1,2,3,4-tetrahydrocarbazole-4-
carboxylic acid hydrazide;

5-(3-phosphonoprop-1-yl)oxy-8-heptyl-9-(4-chlorophenyl)
methyl-1,2,3,4-tetrahydrocarbazole-4-carboxylic acid
hydrazide;

6-methoxycarbonylmethoxy-7-(5-cyanopent-1-yl)-9-
tridecyl-1,2,3,4-tetrahydrocarbazole-4-carboxylic acid
hydrazide;

6-propoxycarbonylmethoxy-9-(3-isopropyl-5-
methoxyphenyl)methyl-1,2,3,4-tetrahydrocarbazole-4-
carboxylic acid hydrazide;

6-dimethoxyphosphonoethoxy-8-(6-(N,N-dimethylamino)
hex-1-yl-9-(3,5-dimethoxyphenyl)methyl-1,2,3,4-
tetrahydrocarbazole-4-carboxylic acid hydrazide;

5-hydroxy-7-(5-cyanopentyl)-9-methylcarbazole-4-
carboxylic acid hydrazide;

6-(2-carboxyethyloxy)-8-methoxy-9-cyclopentylmethyl-
carbazole-4-carboxylic acid hydrazide;

5-(3-phenylprop-1-yl)oxy-7-ethoxy-9-butylcarbazole-4-carboxylic acid hydrazide;
6-(2-phosphonoethoxy-8-phenylhexyl-9-(cyclotetradecyl)methylcarbazole-4-carboxylic acid hydrazide;
5-ethoxycarbonylmethoxy-8-(5-carbamoylpent-1-yl)-9-(3,5-dipropylphenyl)methylcarbazole-4-carboxylic acid hydrazide;
6-(diethoxyphosphonyl)methoxy-9-(4-methoxyphenyl)methylcarbazole-4-carboxylic acid hydrazide;
6-(3-(4-carboxyphenyl)prop-1-yl)oxy-8-heptyl-9-((3-phenylethyl)phenyl)methylcarbazole-4-carboxylic acid hydrazide;
6-(2-propoxycarbonyl)ethoxy-8-(3-(N,N-dimethylamino)prop-1-yl)-9-methylcarbazole-4-carboxylic acid hydrazide;
5-(di-t-butoxyphosphonyl)methoxy-7-nonyl-9-(3-propylthiophenyl)methylcarbazole-4-carboxylic acid hydrazide;
5-(2-(3-methoxycarbonyl)phenyl)ethoxy-7-pentyl-9-methylcarbazole-4-carboxylic acid hydrazide;
6-hydroxy-8-(4-(N,N-diethylamino)but-1-yl)-9-(3-fluorophenyl)methylcarbazole-4-carbazole;
6-(2-phenylethoxy)-9-(2-phenylphenyl)methylcarbazole-4-carboxylic acid hydrazide;
6-((3-carboxy)prop-1-yl)oxy-8-propoxy-9-(7-cyanohept-1-yl)-carbazole-4-carboxylic acid hydrazide;
(S)-5-(propoxycarbonyl)methoxy-9-cyclopentylmethylcarbazole-4-carboxylic acid hydrazide;
5-(2-ethoxyphosphonyl)ethoxy-(4-carbamoyl)but-1-yl-9-(3-methylthiophenyl)methylcarbazole-4-carboxylic acid hydrazide;
(S)-5-(3-(ethoxycarbonyl)prop-1-yl)oxy-7-propoxy-9-(cyclononyl)methylcarbazole-4-carboxylic acid hydrazide;
5-(3-phosphonoprop-1-yl)oxy-8-heptyl-9-(4-chlorophenyl)methylcarbazole-4-carboxylic acid hydrazide;
6-methoxycarbonylmethoxy-7-(5-cyanopent-1-yl)-9-tridecylcarbazole-4-carboxylic acid hydrazide;
6-propoxycarbonylmethoxy-9-((3-isopropyl-5-methoxy)phenyl)methylcarbazole-4-carboxylic acid hydrazide;
(S)-6-dimethoxyphosphonoethoxy-8-(6-(N,N-dimethylamino)hex-1-yl-9-(3,5-dimethoxyphenyl)methylcarbazole-4-carboxylic acid hydrazide;
9-[(phenyl)methyl]-5-carbamoylcarbazol-4-yl}oxyacetic acid;
9-[(2-phenoxyphenyl)methyl]-5-carbamoylcarbazol-4-yl}oxyacetic acid;
9-[(3-phenoxyphenyl)methyl]-5-carbamoylcarbazol-4-yl}oxyacetic acid;
9-[(4-phenoxyphenyl)methyl]-5-carbamoylcarbazol-4-yl}oxyacetic acid;
9-[(2-fluorophenyl)methyl]-5-carbamoylcarbazol-4-yl}oxyacetic acid;
9-[(3-fluorophenyl)methyl]-5-carbamoylcarbazol-4-yl}oxyacetic acid;
9-[(4-fluorophenyl)methyl]-5-carbamoylcarbazol-4-yl}oxyacetic acid;
9-[(2-chlorophenyl)methyl]-5-carbamoylcarbazol-4-yl}oxyacetic acid;
9-[(3-chlorophenyl)methyl]-5-carbamoylcarbazol-4-yl}oxyacetic acid;
9-[(4-chlorophenyl)methyl]-5-carbamoylcarbazol-4-yl}oxyacetic acid;
9-[(2-bromophenyl)methyl]-5-carbamoylcarbazol-4-yl}oxyacetic acid;
9-[(3-bromophenyl)methyl]-5-carbamoylcarbazol-4-yl}oxyacetic acid;
9-[(4-bromophenyl)methyl]-5-carbamoylcarbazol-4-yl}oxyacetic acid;
9-[(2-iodophenyl)methyl]-5-carbamoylcarbazol-4-yl}oxyacetic acid;
9-[(3-iodophenyl)methyl]-5-carbamoylcarbazol-4-yl}oxyacetic acid;
9-[(4-iodophenyl)methyl]-5-carbamoylcarbazol-4-yl}oxyacetic acid;
9-[(2-acetamidophenyl)methyl]-5-carbamoylcarbazol-4-yl}oxyacetic acid;
9-[(3-acetamidophenyl)methyl]-5-carbamoylcarbazol-4-yl}oxyacetic acid;
9-[(4-acetamidophenyl)methyl]-5-carbamoylcarbazol-4-yl}oxyacetic acid;
9-[(2-carbamoylphenyl)methyl]-5-carbamoylcarbazol-4-yl}oxyacetic acid;
9-[(3-carbamoylphenyl)methyl]-5-carbamoylcarbazol-4-yl}oxyacetic acid;
9-[(4-carbamoylphenyl)methyl]-5-carbamoylcarbazol-4-yl}oxyacetic acid;
9-[(2-methylsulfonylphenyl)methyl]-5-carbamoylcarbazol-4-yl}oxyacetic acid;
9-[(3-methylsulfonylphenyl)methyl]-5-carbamoylcarbazol-4-yl}oxyacetic acid;
9-[(4-methylsulfonylphenyl)methyl]-5-carbamoylcarbazol-4-yl}oxyacetic acid;
9-[(2-methylphenyl)methyl]-5-carbamoylcarbazol-4-yl}oxyacetic acid;
9-[(3-methylphenyl)methyl]-5-carbamoylcarbazol-4-yl}oxyacetic acid;
9-[(4-methylphenyl)methyl]-5-carbamoylcarbazol-4-yl}oxyacetic acid;
9-[(2-ethylphenyl)methyl]-5-carbamoylcarbazol-4-yl}oxyacetic acid;
9-[(3-ethylphenyl)methyl]-5-carbamoylcarbazol-4-yl}oxyacetic acid;
9-[(4-ethylphenyl)methyl]-5-carbamoylcarbazol-4-yl}oxyacetic acid;
9-[(2-trifluoromethylphenyl)methyl]-5-carbamoylcarbazol-4-yl}oxyacetic acid;
9-[(3-trifluoromethylphenyl)methyl]-5-carbamoylcarbazol-4-yl}oxyacetic acid;
9-[(4-trifluoromethylphenyl)methyl]-5-carbamoylcarbazol-4-yl}oxyacetic acid;
9-[(cyclopropyl)methyl]-5-carbamoylcarbazol-4-yl}oxyacetic acid;
9-[(cyclobutyl)methyl]-5-carbamoylcarbazol-4-yl}oxyacetic acid;
9-[(cyclopentyl)methyl]-5-carbamoylcarbazol-4-yl}oxyacetic acid;
9-[(cyclohexyl)methyl]-5-carbamoylcarbazol-4-yl}oxyacetic acid;
9-[(2-methoxyphenyl)methyl]-5-carbamoylcarbazol-4-yl}oxyacetic acid;
9-[(3-methoxyphenyl)methyl]-5-carbamoylcarbazol-4-yl}oxyacetic acid;
9-[(4-methoxyphenyl)methyl]-5-carbamoylcarbazol-4-yl}oxyacetic acid;
9-[(2-ethoxyphenyl)methyl]-5-carbamoylcarbazol-4-yl}oxyacetic acid;
9-[(3-ethoxyphenyl)methyl]-5-carbamoylcarbazol-4-yl}oxyacetic acid;
9-[(4-ethoxyphenyl)methyl]-5-carbamoylcarbazol-4-yl}oxyacetic acid;
9-[(2-trifluoromethoxyphenyl)methyl]-5-carbamoylcarbazol-4-yl}oxyacetic acid;
9-[(3-trifluoromethoxyphenyl)methyl]-5-carbamoylcarbazol-4-yl}oxyacetic acid;

9-[(4-trifluoromethoxyphenyl)methyl]-5-carbamoylcarbazol-4-yl}oxyacetic acid;
9-[(2-difluoromethoxyphenyl)methyl]-5-carbamoylcarbazol-4-yl}oxyacetic acid;
9-[(3-difluoromethoxyphenyl)methyl]-5-carbamoylcarbazol-4-yl}oxyacetic acid;
9-[(4-difluoromethoxyphenyl)methyl]-5-carbamoylcarbazol-4-yl}oxyacetic acid;
9-[(2-cyanophenyl)methyl]-5-carbamoylcarbazol-4-yl}oxyacetic acid;
9-[(3-cyanophenyl)methyl]-5-carbamoylcarbazol-4-yl}oxyacetic acid;
9-[(4-cyanophenyl)methyl]-5-carbamoylcarbazol-4-yl}oxyacetic acid;
9-[(2-pyridyl)methyl]-5-carbamoylcarbazol-4-yl}oxyacetic acid;
9-[(3-pyridyl)methyl]-5-carbamoylcarbazol-4-yl}oxyacetic acid;
9-[(4-pyridyl)methyl]-5-carbamoylcarbazol-4-yl}oxyacetic acid;
9-[(2-furyl)methyl]-5-carbamoylcarbazol-4-yl}oxyacetic acid;
9-[(3-furyl)methyl]-5-carbamoylcarbazol-4-yl}oxyacetic acid;
9-[(2-thienyl)methyl]-5-carbamoylcarbazol-4-yl}oxyacetic acid;
9-[(3-thienyl)methyl]-5-carbamoylcarbazol-4-yl}oxyacetic acid;
9-[(2-benzylphenyl)methyl]-5-carbamoylcarbazol-4-yl}oxyacetic acid;
9-[(3-benzylphenyl)methyl]-5-carbamoylcarbazol-4-yl}oxyacetic acid;
9-[(4-benzylphenyl)methyl]-5-carbamoylcarbazol-4-yl}oxyacetic acid;
9-[(2-benzoylphenyl)methyl]-5-carbamoylcarbazol-4-yl}oxyacetic acid;
9-[(3-benzoylphenyl)methyl]-5-carbamoylcarbazol-4-yl}oxyacetic acid;
9-[(4-benzoylphenyl)methyl]-5-carbamoylcarbazol-4-yl}oxyacetic acid;
9-[(2-benzyloxyphenyl)methyl]-5-carbamoylcarbazol-4-yl}oxyacetic acid;
9-[(3-benzyloxyphenyl)methyl]-5-carbamoylcarbazol-4-yl}oxyacetic acid;
9-[(4-benzyloxyphenyl)methyl]-5-carbamoylcarbazol-4-yl}oxyacetic acid;
9-[(2-phenylphenyl)methyl]-5-carbamoylcarbazol-4-yl}oxyacetic acid;
9-[(3-phenylphenyl)methyl]-5-carbamoylcarbazol-4-yl}oxyacetic acid;
9-[(4-phenylphenyl)methyl]-5-carbamoylcarbazol-4-yl}oxyacetic acid;
9-[(1-naphthyl)methyl]-5-carbamoylcarbazol-4-yl}oxyacetic acid;
9-[(2-naphthyl)methyl]-5-carbamoylcarbazol-4-yl}oxyacetic acid;
9-[(2,3-difluorophenyl)methyl]-5-carbamoylcarbazol-4-yl}oxyacetic acid;
9-[(2,4-difluorophenyl)methyl]-5-carbamoylcarbazol-4-yl}oxyacetic acid;
9-[(2,5-difluorophenyl)methyl]-5-carbamoylcarbazol-4-yl}oxyacetic acid;
9-[(2,6-difluorophenyl)methyl]-5-carbamoylcarbazol-4-yl}oxyacetic acid;
9-[(3,4-difluorophenyl)methyl]-5-carbamoylcarbazol-4-yl}oxyacetic acid;
9-[(3,5-difluorophenyl)methyl]-5-carbamoylcarbazol-4-yl}oxyacetic acid;
9-[(2,3,4-trifluorophenyl)methyl]-5-carbamoylcarbazol-4-yl}oxyacetic acid;
9-[(2,3,5-trifluorophenyl)methyl]-5-carbamoylcarbazol-4-yl}oxyacetic acid;
9-[(2,3,6-trifluorophenyl)methyl]-5-carbamoylcarbazol-4-yl}oxyacetic acid;
9-[(2,4,5-trifluorophenyl)methyl]-5-carbamoylcarbazol-4-yl}oxyacetic acid;
9-[(2,4,6-trifluorophenyl)methyl]-5-carbamoylcarbazol-4-yl}oxyacetic acid;
9-[(3,4,5-trifluorophenyl)methyl]-5-carbamoylcarbazol-4-yl}oxyacetic acid;
9-[(pentafluorophenyl)methyl]-5-carbamoylcarbazol-4-yl}oxyacetic acid;
9-[(2,3-dichlorophenyl)methyl]-5-carbamoylcarbazol-4-yl}oxyacetic acid;
9-[(2,4-dichlorophenyl)methyl]-5-carbamoylcarbazol-4-yl}oxyacetic acid;
9-[(2,5-dichlorophenyl)methyl]-5-carbamoylcarbazol-4-yl}oxyacetic acid;
9-[(2,6-dichlorophenyl)methyl]-5-carbamoylcarbazol-4-yl}oxyacetic acid;
9-[(3,4-dichlorophenyl)methyl]-5-carbamoylcarbazol-4-yl}oxyacetic acid;
9-[(3,5-dichlorophenyl)methyl]-5-carbamoylcarbazol-4-yl}oxyacetic acid;
9-[(2,3-dimethylphenyl)methyl]-5-carbamoylcarbazol-4-yl}oxyacetic acid;
9-[(2,4-dimethylphenyl)methyl]-5-carbamoylcarbazol-4-yl}oxyacetic acid;
9-[(2,5dimethylphenyl)methyl]-5-carbamoylcarbazol-4-yl}oxyacetic acid;
9-[(2,6-dimethylphenyl)methyl]-5-carbamoylcarbazol-4-yl}oxyacetic acid;
9-[(3,4-dimethylphenyl)methyl]-5-carbamoylcarbazol-4-yl}oxyacetic acid;
9-[(3,5-dimethylphenyl)methyl]-5-carbamoylcarbazol-4-yl}oxyacetic acid;
9-[(2,4,6-trimethylphenyl)methyl]-5-carbamoylcarbazol-4-yl}oxyacetic acid;
9-[(3,5-bis(trifluoromethyl)phenyl)methyl]-5-carbamoylcarbazol-4-yl}oxyacetic acid;
9-[(2,4-bis(trifluoromethyl)phenyl)methyl]-5-carbamoylcarbazol-4-yl}oxyacetic acid;
9-[(2-fluoro-3-trifluoromethylphenyl)methyl]-5-carbamoylcarbazol-4-yl}oxyacetic acid;
9-[(2-fluoro-4-trifluoromethylphenyl)methyl]-5-carbamoylcarbazol-4-yl}oxyacetic acid;
9-[(2-fluoro-5-trifluoromethylphenyl)methyl]-5-carbamoylcarbazol-4-yl}oxyacetic acid;
9-[(2-fluoro-6-trifluoromethylphenyl)methyl]-5-carbamoylcarbazol-4-yl}oxyacetic acid;
9-[(3-fluoro-5-trifluoromethylphenyl)methyl]-5-carbamoylcarbazol-4-yl}oxyacetic acid;
9-[(4-fluoro-2-trifluoromethylphenyl)methyl]-5-carbamoylcarbazol-4-yl}oxyacetic acid;
9-[(4-fluoro-3-trifluoromethylphenyl)methyl]-5-carbamoylcarbazol-4-yl}oxyacetic acid;
9-[3-(2-fluorophenoxy)methyl]-5-carbamoylcarbazol-4-yl}oxyacetic acid;
9-[3-(4-fluorophenoxy)methyl]-5-carbamoylcarbazol-4-yl}oxyacetic acid;
9-[(2-fluoro-3-methylphenyl)methyl]-5-carbamoylcarbazol-4-yl}oxyacetic acid;
9-[(3-chloro-2-fluorophenyl)methyl]-5-carbamoylcarbazol-4-yl}oxyacetic acid;
9-[(2-chloro-6-fluorophenyl)methyl]-5-carbamoylcarbazol-4-yl}oxyacetic acid;

9-[(4-bromo-2-fluorophenyl)methyl]-5-carbamoylcarbazol-4-yl}oxyacetic acid;
9-[(2-bromo-5-fluorophenyl)methyl]-5-carbamoylcarbazol-4-yl}oxyacetic acid;
9-[(3-chloro-4-methylphenyl)methyl]-5-carbamoylcarbazol-4-yl}oxyacetic acid;
9-[(3-chloro-4-methoxyphenyl)methyl]-5-carbamoylcarbazol-4-yl}oxyacetic acid;
9-[(4-methoxy-3-methylphenyl)methyl]-5-carbamoylcarbazol-4-yl}oxyacetic acid;
9-[(4-trifluoromethylthiophenyl)methyl]-5-carbamoylcarbazol-4-yl}oxyacetic acid;
9-[(1-bromo-2-naphthylphenyl)methyl]-5-carbamoylcarbazol-4-yl}oxyacetic acid;
9-[(2-methyl-1-naphthylphenyl)methyl]-5-carbamoylcarbazol-4-yl}oxyacetic acid;
9-[(4-methyl-1-naphthylphenyl)methyl]-5-carbamoylcarbazol-4-yl}oxyacetic acid;
9-[(6-methyl-2-naphthylphenyl)methyl]-5-carbamoylcarbazol-4-yl}oxyacetic acid;
9-[(2-((phenylsulfonyl)methyl)phenyl)methyl]-5-carbamoylcarbazol-4-yl}oxyacetic acid;
9-[(1-fluorenylmethyl]-5-carbamoylcarbazol-4-yl}oxyacetic acid;
9-[(1-tetrazolylmethyl]-5-carbamoylcarbazol-4-yl}oxyacetic acid;
9-[(5-methyl-1-tetrazolylmethyl]-5-carbamoylcarbazol-4-yl}oxyacetic acid;
9-[(5-benzyl-1-tetrazolylmethyl]-5-carbamoylcarbazol-4-yl}oxyacetic acid;
9-[(phenyl)methyl]-2-methyl-5-carbamoylcarbazol-4-yl}oxyacetic acid;
9-[(2-phenoxyphenyl)methyl]-2-methyl-5-carbamoylcarbazol-4-yl}oxyacetic acid;
9-[(3-phenoxyphenyl)methyl]-2-methyl-5-carbamoylcarbazol-4-yl}oxyacetic acid;
9-[(4-phenoxyphenyl)methyl]-2-methyl-5-carbamoylcarbazol-4-yl}oxyacetic acid;
9-[(2-fluorophenyl)methyl]-2-methyl-5-carbamoylcarbazol-4-yl}oxyacetic acid;
9-[(3-fluorophenyl)methyl]-2-methyl-5-carbamoylcarbazol-4-yl}oxyacetic acid;
9-[(4-fluorophenyl)methyl]-2-methyl-5-carbamoylcarbazol-4-yl}oxyacetic acid;
9-[(2-chlorophenyl)methyl]-2-methyl-5-carbamoylcarbazol-4-yl}oxyacetic acid;
9-[(3-chlorophenyl)methyl]-2-methyl-5-carbamoylcarbazol-4-yl}oxyacetic acid;
9-[(4-chlorophenyl)methyl]-2-methyl-5-carbamoylcarbazol-4-yl}oxyacetic acid;
9-[(2-bromophenyl)methyl]-2-methyl-5-carbamoylcarbazol-4-yl}oxyacetic acid;
9-[(3-bromophenyl)methyl]-2-methyl-5-carbamoylcarbazol-4-yl}oxyacetic acid;
9-[(4-bromophenyl)methyl]-2-methyl-5-carbamoylcarbazol-4-yl}oxyacetic acid;
9-[(2-iodophenyl)methyl]-2-methyl-5-carbamoylcarbazol-4-yl}oxyacetic acid;
9-[(3-iodophenyl)methyl]-2-methyl-5-carbamoylcarbazol-4-yl}oxyacetic acid;
9-[(4-iodophenyl)methyl]-2-methyl-5-carbamoylcarbazol-4-yl}oxyacetic acid;
9-[(2-acetamidophenyl)methyl]-2-methyl-5-carbamoylcarbazol-4-yl}oxyacetic acid;
9-[(3-acetamidophenyl)methyl]-2-methyl-5-carbamoylcarbazol-4-yl}oxyacetic acid;
9-[(4-acetamidophenyl)methyl]-2-methyl-5-carbamoylcarbazol-4-yl}oxyacetic acid;
9-[(2-carbamoylphenyl)methyl]-2-methyl-5-carbamoylcarbazol-4-yl}oxyacetic acid;
9-[(3-carbamoylphenyl)methyl]-2-methyl-5-carbamoylcarbazol-4-yl}oxyacetic acid;
9-[(4-carbamoylphenyl)methyl]-2-methyl-5-carbamoylcarbazol-4-yl}oxyacetic acid;
9-[(2-methylsulfonylphenyl)methyl]-2-methyl-5-carbamoylcarbazol-4-yl}oxyacetic acid;
9-[(3-methylsulfonylphenyl)methyl]-2-methyl-5-carbamoylcarbazol-4-yl}oxyacetic acid;
9-[(4-methylsulfonylphenyl)methyl]-2-methyl-5-carbamoylcarbazol-4-yl}oxyacetic acid;
9-[(2-methylphenyl)methyl]-2-methyl-5-carbamoylcarbazol-4-yl}oxyacetic acid;
9-[(3-methylphenyl)methyl]-2-methyl-5-carbamoylcarbazol-4-yl}oxyacetic acid;
9-[(4-methylphenyl)methyl]-2-methyl-5-carbamoylcarbazol-4-yl}oxyacetic acid;
9-[(2-ethylphenyl)methyl]-2-methyl-5-carbamoylcarbazol-4-yl}oxyacetic acid;
9-[(3-ethylphenyl)methyl]-2-methyl-5-carbamoylcarbazol-4-yl}oxyacetic acid;
9-[(4-ethylphenyl)methyl]-2-methyl-5-carbamoylcarbazol-4-yl}oxyacetic acid;
9-[(2-trifluoromethylphenyl)methyl]-2-methyl-5-carbamoylcarbazol-4-yl}oxyacetic acid;
9-[(3-trifluoromethylphenyl)methyl]-2-methyl-5-carbamoylcarbazol-4-yl}oxyacetic acid;
9-[(4-trifluoromethylphenyl)methyl]-2-methyl-5-carbamoylcarbazol-4-yl}oxyacetic acid;
9-[(cyclopropyl)methyl]-2-methyl-5-carbamoylcarbazol-4-yl}oxyacetic acid;
9-[(cyclobutyl)methyl]-2-methyl-5-carbamoylcarbazol-4-yl}oxyacetic acid;
9-[(cyclopentyl)methyl]-2-methyl-5-carbamoylcarbazol-4-yl}oxyacetic acid;
9-[(cyclohexyl)methyl]-2-methyl-5-carbamoylcarbazol-4-yl}oxyacetic acid;
9-[(2-methoxyphenyl)methyl]-2-methyl-5-carbamoylcarbazol-4-yl}oxyacetic acid;
9-[(3-methoxyphenyl)methyl]-2-methyl-5-carbamoylcarbazol-4-yl}oxyacetic acid;
9-[(4-methoxyphenyl)methyl]-2-methyl-5-carbamoylcarbazol-4-yl}oxyacetic acid;
9-[(2-ethoxyphenyl)methyl]-2-methyl-5-carbamoylcarbazol-4-yl}oxyacetic acid;
9-[(3-ethoxyphenyl)methyl]-2-methyl-5-carbamoylcarbazol-4-yl}oxyacetic acid;
9-[(4-ethoxyphenyl)methyl]-2-methyl-5-carbamoylcarbazol-4-yl}oxyacetic acid;
9-[(2-trifluoromethoxyphenyl)methyl]-2-methyl-5-carbamoylcarbazol-4-yl}oxyacetic acid;
9-[(3-trifluoromethoxyphenyl)methyl]-2-methyl-5-carbamoylcarbazol-4-yl}oxyacetic acid;
9-[(4-trifluoromethoxyphenyl)methyl]-2-methyl-5-carbamoylcarbazol-4-yl}oxyacetic acid;
9-[(2-difluoromethoxyphenyl)methyl]-2-methyl-5-carbamoylcarbazol-4-yl}oxyacetic acid;
9-[(3-difluoromethoxyphenyl)methyl]-2-methyl-5-carbamoylcarbazol-4-yl}oxyacetic acid;
9-[(4-difluoromethoxyphenyl)methyl]-2-methyl-5-carbamoylcarbazol-4-yl}oxyacetic acid;
9-[(2-cyanophenyl)methyl]-2-methyl-5-carbamoylcarbazol-4-yl}oxyacetic acid;
9-[(3-cyanophenyl)methyl]-2-methyl-5-carbamoylcarbazol-4-yl}oxyacetic acid;
9-[(4-cyanophenyl)methyl]-2-methyl-5-carbamoylcarbazol-4-yl}oxyacetic acid;

9-[(2-pyridyl)methyl]-2-methyl-5-carbamoylcarbazol-4-yl}oxyacetic acid;
9-[(3-pyridyl)methyl]-2-methyl-5-carbamoylcarbazol-4-yl}oxyacetic acid;
9-[(4-pyridyl)methyl]-2-methyl-5-carbamoylcarbazol-4-yl}oxyacetic acid;
9-[(2-furyl)methyl]-2-methyl-5-carbamoylcarbazol-4-yl}oxyacetic acid;
9-[(3-furyl)methyl]-2-methyl-5-carbamoylcarbazol-4-yl}oxyacetic acid;
9-[(2-thienyl)methyl]-2-methyl-5-carbamoylcarbazol-4-yl}oxyacetic acid;
9-[(3-thienyl)methyl]-2-methyl-5-carbamoylcarbazol-4-yl}oxyacetic acid;
9-[(2-benzylphenyl)methyl]-2-methyl-5-carbamoylcarbazol-4-yl}oxyacetic acid;
9-[(3-benzylphenyl)methyl]-2-methyl-5-carbamoylcarbazol-4-yl}oxyacetic acid;
9-[(4-benzylphenyl)methyl]-2-methyl-5-carbamoylcarbazol-4-yl}oxyacetic acid;
9-[(2-benzoylphenyl)methyl]-2-methyl-5-carbamoylcarbazol-4-yl}oxyacetic acid;
9-[(3-benzoylphenyl)methyl]-2-methyl-5-carbamoylcarbazol-4-yl}oxyacetic acid;
9-[(4-benzoylphenyl)methyl]-2-methyl-5-carbamoylcarbazol-4-yl}oxyacetic acid;
9-[(2-benzyloxyphenyl)methyl]-2-methyl-5-carbamoylcarbazol-4-yl}oxyacetic acid;
9-[(3-benzyloxyphenyl)methyl]-2-methyl-5-carbamoylcarbazol-4-yl}oxyacetic acid;
9-[(4-benzyloxyphenyl)methyl]-2-methyl-5-carbamoylcarbazol-4-yl}oxyacetic acid;
9-[(2-phenylphenyl)methyl]-2-methyl-5-carbamoylcarbazol-4-yl}oxyacetic acid;
9-[(3-phenylphenyl)methyl]-2-methyl-5-carbamoylcarbazol-4-yl}oxyacetic acid;
9-[(4-phenylphenyl)methyl]-2-methyl-5-carbamoylcarbazol-4-yl}oxyacetic acid;
9-[(1-naphthyl)methyl]-2-methyl-5-carbamoylcarbazol-4-yl}oxyacetic acid;
9-[(2-naphthyl)methyl]-2-methyl-5-carbamoylcarbazol-4-yl}oxyacetic acid;
9-[(2,3-difluorophenyl)methyl]-2-methyl-5-carbamoylcarbazol-4-yl}oxyacetic acid;
9-[(2,4-difluorophenyl)methyl]-2-methyl-5-carbamoylcarbazol-4-yl}oxyacetic acid;
9-[(2,5-difluorophenyl)methyl]-2-methyl-5-carbamoylcarbazol-4-yl}oxyacetic acid;
9-[(2,6-difluorophenyl)methyl]-2-methyl-5-carbamoylcarbazol-4-yl}oxyacetic acid;
9-[(3,4-difluorophenyl)methyl]-2-methyl-5-carbamoylcarbazol-4-yl}oxyacetic acid;
9-[(3,5-difluorophenyl)methyl]-2-methyl-5-carbamoylcarbazol-4-yl}oxyacetic acid;
9-[(2,3,4-trifluorophenyl)methyl]-2-methyl-8-carbamoylcarbazol-4-yl}oxyacetic acid;
9-[(2,3,5-trifluorophenyl)methyl]-2-methyl-5-carbamoylcarbazol-4-yl}oxyacetic acid;
9-[(2,3,6-trifluorophenyl)methyl]-2-methyl-5-carbamoylcarbazol-4-yl}oxyacetic acid;
9-[(2,4,5-trifluorophenyl)methyl]-2-methyl-5-carbamoylcarbazol-4-yl}oxyacetic acid;
9-[(2,4,6-trifluorophenyl)methyl]-2-methyl-5-carbamoylcarbazol-4-yl}oxyacetic acid;
9-[(3,4,5-trifluorophenyl)methyl]-2-methyl-5-carbamoylcarbazol-4-yl}oxyacetic acid;
9-[(pentafluorophenyl)methyl]-2-methyl-5-carbamoylcarbazol-4-yl}oxyacetic acid;
9-[(2,3-dichlorophenyl)methyl]-2-methyl-5-carbamoylcarbazol-4-yl}oxyacetic acid;
9-[(2,4-dichlorophenyl)methyl]-2-methyl-5-carbamoylcarbazol-4-yl}oxyacetic acid;
9-[(2,5-dichlorophenyl)methyl]-2-methyl-5-carbamoylcarbazol-4-yl}oxyacetic acid;
9-[(2,6-dichlorophenyl)methyl]-2-methyl-5-carbamoylcarbazol-4-yl}oxyacetic acid;
9-[(3,4-dichlorophenyl)methyl]-2-methyl-5-carbamoylcarbazol-4-yl}oxyacetic acid;
9-[(3,5-dichlorophenyl)methyl]-2-methyl-5-carbamoylcarbazol-4-yl}oxyacetic acid;
9-[(2,3-dimethylphenyl)methyl]-2-methyl-5-carbamoylcarbazol-4-yl}oxyacetic acid;
9-[(2,4-dimethylphenyl)methyl]-2-methyl-5-carbamoylcarbazol-4-yl}oxyacetic acid;
9-[(2,5-dimethylphenyl)methyl]-2-methyl-5-carbamoylcarbazol-4-yl}oxyacetic acid;
9-[(2,6-dimethylphenyl)methyl]-2-methyl-5-carbamoylcarbazol-4-yl}oxyacetic acid;
9-[(3,4-dimethylphenyl)methyl]-2-methyl-5-carbamoylcarbazol-4-yl}oxyacetic acid;
9-[(3,5-dimethylphenyl)methyl]-2-methyl-5-carbamoylcarbazol-4-yl}oxyacetic acid;
9-[(2,4,6-trimethylphenyl)methyl]-2-methyl-5-carbamoylcarbazol-4-yl}oxyacetic acid;
9-[(3,5-bis(trifluoromethyl)phenyl)methyl]-2-methyl-5-carbamoylcarbazol-4-yl}oxyacetic acid;
9-[(2,4-bis(trifluoromethyl)phenyl)methyl]-2-methyl-5-carbamoylcarbazol-4-yl}oxyacetic acid;
9-[(2-fluoro-3-trifluoromethylphenyl)methyl]-2-methyl-5-carbamoylcarbazol-4-yl}oxyacetic acid;
9-[(2-fluoro-4-trifluoromethylphenyl)methyl]-2-methyl-5-carbamoylcarbazol-4-yl}oxyacetic acid;
9-[(2-fluoro-5-trifluoromethylphenyl)methyl]-2-methyl-5-carbamoylcarbazol-4-yl}oxyacetic acid;
9-[(2-fluoro-6-trifluoromethylphenyl)methyl]-2-methyl-5-carbamoylcarbazol-4-yl}oxyacetic acid;
9-[(3-fluoro-5-trifluoromethylphenyl)methyl]-2-methyl-5-carbamoylcarbazol-4-yl}oxyacetic acid;
9-[(4-fluoro-2-trifluoromethylphenyl)methyl]-2-methyl-5-carbamoylcarbazol-4-yl}oxyacetic acid;
9-[(4-fluoro-3-trifluoromethylphenyl)methyl]-2-methyl-5-carbamoylcarbazol-4-yl}oxyacetic acid;
9-[(3-(2-fluorophenoxy)methyl]-2-methyl-5-carbamoylcarbazol-4-yl}oxyacetic acid;
9-[3-(4-fluorophenoxy)methyl]-2-methyl-5-carbamoylcarbazol-4-yl}oxyacetic acid;
9-[(2-fluoro-3-methylphenyl)methyl]-2-methyl-5-carbamoylcarbazol-4-yl}oxyacetic acid;
9-[(3-chloro-2-fluorophenyl)methyl]-2-methyl-5-carbamoylcarbazol-4-yl}oxyacetic acid;
9-[(2-chloro-6-fluorophenyl)methyl]-2-methyl-5-carbamoylcarbazol-4-yl}oxyacetic acid;
9-[(4-bromo-2-fluorophenyl)methyl]-2-methyl-5-carbamoylcarbazol-4-yl}oxyacetic acid;
9-[(2-bromo-5-fluorophenyl)methyl]-2-methyl-5-carbamoylcarbazol-4-yl}oxyacetic acid;
9-[(3-chloro-4-methylphenyl)methyl]-2-methyl-5-carbamoylcarbazol-4-yl}oxyacetic acid;
9-[(3-chloro-4-methoxyphenyl)methyl]-2-methyl-5-carbamoylcarbazol-4-yl}oxyacetic acid;
9-[(4-methoxy-3-methylphenyl)methyl]-2-methyl-5-carbamoylcarbazol-4-yl}oxyacetic acid;
9-[(4-trifluoromethylthiophenyl)methyl]-2-methyl-5-carbamoylcarbazol-4-yl}oxyacetic acid;
9-[(1-bromo-2-naphthylphenyl)methyl]-2-methyl-5-carbamoylcarbazol-4-yl}oxyacetic acid;

9-[(2-methyl-1-naphthylphenyl)methyl]-2-methyl-5-carbamoylcarbazol-4-yl}oxyacetic acid;
9-[(4-methyl-1-naphthylphenyl)methyl]-2-methyl-5-carbamoylcarbazol-4-yl}oxyacetic acid;
9-[(6-methyl-2-naphthylphenyl)methyl]-2-methyl-5-carbamoylcarbazol-4-yl}oxyacetic acid;
9-[(2-((phenylsulfonyl)methyl)phenyl)methyl]-2-methyl-5-carbamoylcarbazol-4-yl}oxyacetic acid;
9-[(1-fluorenylmethyl]-2-methyl-5-carbamoylcarbazol-4-yl}oxyacetic acid;
9-[(1-tetrazolylmethyl]-2-methyl-5-carbamoylcarbazol-4-yl}oxyacetic acid;
9-[(5-methyl-1-tetrazolylmethyl]-2-methyl-5-carbamoylcarbazol-4-yl}oxyacetic acid;
9-[(5-benzyl-1-tetrazolylmethyl]-2-methyl-5-carbamoylcarbazol-4-yl}oxyacetic acid;
9-[(phenyl)methyl]-2-ethyl-5-carbamoylcarbazol-4-yl}oxyacetic acid;
9-[(2-phenoxyphenyl)methyl]-2-ethyl-5-carbamoylcarbazol-4-yl}oxyacetic acid;
9-[(3-phenoxyphenyl)methyl]-2-ethyl-5-carbamoylcarbazol-4-yl}oxyacetic acid;
9-[(4-phenoxyphenyl)methyl]-2-ethyl-5-carbamoylcarbazol-4-yl}oxyacetic acid;
9-[(2-fluorophenyl)methyl]-2-ethyl-5-carbamoylcarbazol-4-yl}oxyacetic acid;
9-[(3-fluorophenyl)methyl]-2-ethyl-5-carbamoylcarbazol-4-yl}oxyacetic acid;
9-[(4-fluorophenyl)methyl]-2-ethyl-5-carbamoylcarbazol-4-yl}oxyacetic acid;
9-[(2-fluorophenyl)methyl]-2-ethyl-5-carbamoylcarbazol-4-yl}oxyacetic acid;
9-[(3-chlorophenyl)methyl]-2-ethyl-5-carbamoylcarbazol-4-yl}oxyacetic acid;
9-[(4-chlorophenyl)methyl]-2-ethyl-5-carbamoylcarbazol-4-yl}oxyacetic acid;
9-[(2-bromophenyl)methyl]-2-ethyl-5-carbamoylcarbazol-4-yl}oxyacetic acid;
9-[(3-bromophenyl)methyl]-2-ethyl-5-carbamoylcarbazol-4-yl}oxyacetic acid;
9-[(4-bromophenyl)methyl]-2-ethyl-5-carbamoylcarbazol-4-yl}oxyacetic acid;
9-[(2-iodophenyl)methyl]-2-ethyl-5-carbamoylcarbazol-4-yl}oxyacetic acid;
9-[(3-iodophenyl)methyl]-2-ethyl-5-carbamoylcarbazol-4-yl}oxyacetic acid;
9-[(4-iodophenyl)methyl]-2-ethyl-5-carbamoylcarbazol-4-yl}oxyacetic acid;
9-[(2-acetamidophenyl)methyl]-2-ethyl-5-carbamoylcarbazol-4-yl}oxyacetic acid;
9-[(3-acetamidophenyl)methyl]-2-ethyl-5-carbamoylcarbazol-4-yl}oxyacetic acid;
9-[(4-acetamidophenyl)methyl]-2-ethyl-5-carbamoylcarbazol-4-yl}oxyacetic acid;
9-[(2-carbamoylphenyl)methyl]-2-ethyl-5-carbamoylcarbazol-4-yl}oxyacetic acid;
9-[(3-carbamoylphenyl)methyl]-2-ethyl-5-carbamoylcarbazol-4-yl}oxyacetic acid;
9-[(4-carbamoylphenyl)methyl]-2-ethyl-5-carbamoylcarbazol-4-yl}oxyacetic acid;
9-[(2-methylsulfonylphenyl)methyl]-2-ethyl-5-carbamoylcarbazol-4-yl}oxyacetic acid;
9-[(3-methylsulfonylphenyl)methyl]-2-ethyl-5-carbamoylcarbazol-4-yl}oxyacetic acid;
9-[(4-methylsulfonylphenyl)methyl]-2-ethyl-5-carbamoylcarbazol-4-yl}oxyacetic acid;
9-[(2-methylphenyl)methyl]-2-ethyl-5-carbamoylcarbazol-4-yl}oxyacetic acid;
9-[(3-methylphenyl)methyl]-2-ethyl-5-carbamoylcarbazol-4-yl}oxyacetic acid;
9-[(4-methylphenyl)methyl]-2-ethyl-5-carbamoylcarbazol-4-yl}oxyacetic acid;
9-[(2-ethylphenyl)methyl]-2-ethyl-5-carbamoylcarbazol-4-yl}oxyacetic acid;
9-[(3-ethylphenyl)methyl]-2-ethyl-5-carbamoylcarbazol-4-yl}oxyacetic acid;
9-[(4-ethylphenyl)methyl]-2-ethyl-5-carbamoylcarbazol-4-yl}oxyacetic acid;
9-[(2-trifluoromethylphenyl)methyl]-2-ethyl-5-carbamoylcarbazol-4-yl}oxyacetic acid;
9-[(3-trifluoromethylphenyl)methyl]-2-ethyl-5-carbamoylcarbazol-4-yl}oxyacetic acid,
9-[(4-trifluoromethylphenyl)methyl]-2-ethyl-5-carbamoylcarbazol-4-yl}oxyacetic acid;
9-[(cyclopropyl)methyl]-2-ethyl-5-carbamoylcarbazol-4-yl}oxyacetic acid;
9-[(cyclobutyl)methyl]-2-ethyl-5-carbamoylcarbazol-4-yl}oxyacetic acid;
9-[(cyclopentyl)methyl]-2-ethyl-5-carbamoylcarbazol-4-yl}oxyacetic acid;
9-[(cyclohexyl)methyl]-2-ethyl-5-carbamoylcarbazol-4-yl}oxyacetic acid;
9-[(2-methoxyphenyl)methyl]-2-ethyl-5-carbamoylcarbazol-4-yl}oxyacetic acid;
9-[(3-methoxyphenyl)methyl]-2-ethyl-5-carbamoylcarbazol-4-yl}oxyacetic acid;
9-[(4-methoxyphenyl)methyl]-2-ethyl-5-carbamoylcarbazol-4-yl}oxyacetic acid;
9-[(2-ethoxyphenyl)methyl]-2-ethyl-5-carbamoylcarbazol-4-yl}oxyacetic acid;
9-[(3-ethoxyphenyl)methyl]-2-ethyl-5-carbamoylcarbazol-4-yl}oxyacetic acid;
9-[(4-ethoxyphenyl)methyl]-2-ethyl-5-carbamoylcarbazol-4-yl}oxyacetic acid;
9-[(2-trifluoromethoxyphenyl)methyl]-2-ethyl-5-carbamoylcarbazol-4-yl}oxyacetic acid;
9-[(3-trifluoromethoxyphenyl)methyl]-2-ethyl-5-carbamoylcarbazol-4-yl}oxyacetic acid;
9-[(4-trifluoromethoxyphenyl)methyl]-2-ethyl-5-carbamoylcarbazol-4-yl}oxyacetic acid;
9-[(2-difluoromethoxyphenyl)methyl]-2-ethyl-5-carbamoylcarbazol-4-yl}oxyacetic acid;
9-[(3-difluoromethoxyphenyl)methyl]-2-ethyl-5-carbamoylcarbazol-4-yl}oxyacetic acid;
9-[(4-difluoromethoxyphenyl)methyl]-2-ethyl-5-carbamoylcarbazol-4-yl}oxyacetic acid;
9-[(2-cyanophenyl)methyl]-2-ethyl-5-carbamoylcarbazol-4-yl}oxyacetic acid;
9-[(3-cyanophenyl)methyl]-2-ethyl-5-carbamoylcarbazol-4-yl}oxyacetic acid;
9-[(4-cyanophenyl)methyl]-2-ethyl-5-carbamoylcarbazol-4-yl}oxyacetic acid;
9-[(2-pyridyl)methyl]-2-ethyl-5-carbamoylcarbazol-4-yl}oxyacetic acid;
9-[(3-pyridyl)methyl]-2-ethyl-5-carbamoylcarbazol-4-yl}oxyacetic acid;
9-[(4-pyridyl)methyl]-2-ethyl-5-carbamoylcarbazol-4-yl}oxyacetic acid;
9-[(2-furyl)methyl]-2-ethyl-5-carbamoylcarbazol-4-yl}oxyacetic acid;
9-[(3-furyl)methyl]-2-ethyl-5-carbamoylcarbazol-4-yl}oxyacetic acid;
9-[(2-thienyl)methyl]-2-ethyl-5-carbamoylcarbazol-4-yl}oxyacetic acid;
9-[(3-thienyl)methyl]-2-ethyl-5-carbamoylcarbazol-4-yl}oxyacetic acid;

9-[(2-benzylphenyl)methyl]-2-ethyl-5-carbamoylcarbazol-4-yl}oxyacetic acid;
9-[(3-benzylphenyl)methyl]-2-ethyl-5-carbamoylcarbazol-4-yl}oxyacetic acid;
9-[(4-benzylphenyl)methyl]-2-ethyl-5-carbamoylcarbazol-4-yl}oxyacetic acid;
9-[(2-benzoylphenyl)methyl]-2-ethyl-5-carbamoylcarbazol-4-yl}oxyacetic acid;
9-[(3-benzoylphenyl)methyl]-2-ethyl-5-carbamoylcarbazol-4-yl}oxyacetic acid;
9-[(4-benzoylphenyl)methyl]-2-ethyl-5-carbamoylcarbazol-4-yl}oxyacetic acid;
9-[(2-benzyloxyphenyl)methyl]-2-ethyl-5-carbamoylcarbazol-4-yl}oxyacetic acid;
9-[(3-benzyloxyphenyl)methyl]-2-ethyl-5-carbamoylcarbazol-4-yl}oxyacetic acid;
9-[(4-benzyloxyphenyl)methyl]-2-ethyl-5-carbamoylcarbazol-4-yl}oxyacetic acid;
9-[(2-phenylphenyl)methyl]-2-ethyl-5-carbamoylcarbazol-4-yl}oxyacetic acid;
9-[(3-phenylphenyl)methyl]-2-ethyl-5-carbamoylcarbazol-4-yl}oxyacetic acid;
9-[(4-phenylphenyl)methyl]-2-ethyl-5-carbamoylcarbazol-4-yl}oxyacetic acid;
9-[(1-naphthyl)methyl]-2-ethyl-5-carbamoylcarbazol-4-yl}oxyacetic acid;
9-[(2-naphthyl)methyl]-2-ethyl-5-carbamoylcarbazol-4-yl}oxyacetic acid;
9-[(2,3-difluorophenyl)methyl]-2-ethyl-5-carbamoylcarbazol-4-yl}oxyacetic acid;
9-[(2,4-difluorophenyl)methyl]-2-ethyl-5-carbamoylcarbazol-4-yl}oxyacetic acid;
9-[(2,5-difluorophenyl)methyl]-2-ethyl-5-carbamoylcarbazol-4-yl}oxyacetic acid;
9-[(2,6-difluorophenyl)methyl]-2-ethyl-5-carbamoylcarbazol-4-yl}oxyacetic acid;
9-[(3,4-difluorophenyl)methyl]-2-ethyl-5-carbamoylcarbazol-4-yl}oxyacetic acid;
9-[(3,5-difluorophenyl)methyl]-2-ethyl-5-carbamoylcarbazol-4-yl}oxyacetic acid;
9-[(2,3,4-trifluorophenyl)methyl]-2-ethyl-5-carbamoylcarbazol-4-yl}oxyacetic acid;
9-[(2,3,5-trifluorophenyl)methyl]-2-ethyl-5-carbamoylcarbazol-4-yl}oxyacetic acid;
9-[(2,3,6-trifluorophenyl)methyl]-2-ethyl-5-carbamoylcarbazol-4-yl}oxyacetic acid;
9-[(2,4,5-trifluorophenyl)methyl]-2-ethyl-5-carbamoylcarbazol-4-yl}oxyacetic acid;
9-[(2,4,6-trifluorophenyl)methyl]-2-ethyl-5-carbamoylcarbazol-4-yl}oxyacetic acid;
9-[(3,4,5-trifluorophenyl)methyl]-2-ethyl-5-carbamoylcarbazol-4-yl}oxyacetic acid;
9-[(pentafluorophenyl)methyl]-2-ethyl-5-carbamoylcarbazol-4-yl}oxyacetic acid;
9-[(2,3-dichlorophenyl)methyl]-2-ethyl-5-carbamoylcarbazol-4-yl}oxyacetic acid;
9-[(2,4-dichlorophenyl)methyl]-2-ethyl-5-carbamoylcarbazol-4-yl}oxyacetic acid;
9-[(2,5-dichlorophenyl)methyl]-2-ethyl-5-carbamoylcarbazol-4-yl}oxyacetic acid;
9-[(2,6-dichlorophenyl)methyl]-2-ethyl-5-carbamoylcarbazol-4-yl}oxyacetic acid;
9-[(3,4-dichlorophenyl)methyl]-2-ethyl-5-carbamoylcarbazol-4-yl}oxyacetic acid;
9-[(3,5-dichlorophenyl)methyl]-2-ethyl-5-carbamoylcarbazol-4-yl}oxyacetic acid;
9-[(2,3-dimethylphenyl)methyl]-2-ethyl-5-carbamoylcarbazol-4-yl}oxyacetic acid;
9-[(2,4-dimethylphenyl)methyl]-2-ethyl-5-carbamoylcarbazol-4-yl}oxyacetic acid;
9-[(2,5-dimethylphenyl)methyl]-2-ethyl-5-carbamoylcarbazol-4-yl}oxyacetic acid;
9-[(2,6-dimethylphenyl)methyl]-2-ethyl-5-carbamoylcarbazol-4-yl}oxyacetic acid;
9-[(3,4-dimethylphenyl)methyl]-2-ethyl-5-carbamoylcarbazol-4-yl}oxyacetic acid;
9-[(3,5-dimethylphenyl)methyl]-2-ethyl-5-carbamoylcarbazol-4-yl}oxyacetic acid;
9-[(2,4,6-trimethylphenyl)methyl]-2-ethyl-5-carbamoylcarbazol-4-yl}oxyacetic acid;
9-[(3,5-bis(trifluoromethyl)phenyl)methyl]-2-ethyl-5-carbamoylcarbazol-4-yl}oxyacetic acid;
9-[(2,4-bis(trifluoromethyl)phenyl)methyl]-2-ethyl-5-carbamoylcarbazol-4-yl}oxyacetic acid;
9-[(2-fluoro-3-trifluoromethylphenyl)methyl]-2-ethyl-5-carbamoylcarbazol-4-yl}oxyacetic acid;
9-[(2-fluoro-4-trifluoromethylphenyl)methyl]-2-ethyl-5-carbamoylcarbazol-4-yl}oxyacetic acid;
9-[(2-fluoro-5-trifluoromethylphenyl)methyl]-2-ethyl-5-carbamoylcarbazol-4-yl}oxyacetic acid;
9-[(2-fluoro-6-trifluoromethylphenyl)methyl]-2-ethyl-5-carbamoylcarbazol-4-yl}oxyacetic acid;
9-[(3-fluoro-5-trifluoromethylphenyl)methyl]-2-ethyl-5-carbamoylcarbazol-4-yl}oxyacetic acid;
9-[(4-fluoro-2-trifluoromethylphenyl)methyl]-2-ethyl-5-carbamoylcarbazol-4-yl}oxyacetic acid;
9-[(4-fluoro-3-trifluoromethylphenyl)methyl]-2-ethyl-5-carbamoylcarbazol-4-yl}oxyacetic acid;
9-[3-(2-fluorophenoxy)methyl]-2-ethyl-5-carbamoylcarbazol-4-yl}oxyacetic acid;
9-[3-(4-fluorophenoxy)methyl]-2-ethyl-5-carbamoylcarbazol-4-yl}oxyacetic acid;
9-[(2-fluoro-3-methylphenyl)methyl]-2-ethyl-5-carbamoylcarbazol-4-yl}oxyacetic acid;
9-[(3-chloro-2-fluorophenyl)methyl]-2-ethyl-5-carbamoylcarbazol-4-yl}oxyacetic acid;
9-[(2-chloro-6-fluorophenyl)methyl]-2-ethyl-5-carbamoylcarbazol-4-yl}oxyacetic acid;
9-[(4-bromo-2-fluorophenyl)methyl]-2-ethyl-5-carbamoylcarbazol-4-yl}oxyacetic acid;
9-[(2-bromo-5-fluorophenyl)methyl]-2-ethyl-5-carbamoylcarbazol-4-yl}oxyacetic acid;
9-[(3-chloro-4-methylphenyl)methyl]-2-ethyl-5-carbamoylcarbazol-4-yl}oxyacetic acid;
9-[(3-chloro-4-methoxyphenyl)methyl]-2-ethyl-5-carbamoylcarbazol-4-yl}oxyacetic acid;
9-[(4-methoxy-3-methylphenyl)methyl]-2-ethyl-5-carbamoylcarbazol-4-yl}oxyacetic acid;
9-[(4-trifluoromethylthiophenyl)methyl]-2-ethyl-5-carbamoylcarbazol-4-yl}oxyacetic acid;
9-[(1-bromo-2-naphthylphenyl)methyl]-2-ethyl-5-carbamoylcarbazol-4-yl}oxyacetic acid;
9-[(2-methyl-1-naphthylphenyl)methyl]-2-ethyl-5-carbamoylcarbazol-4-yl}oxyacetic acid;
9-[(4-methyl-1-naphthylphenyl)methyl]-2-ethyl-5-carbamoylcarbazol-4-yl}oxyacetic acid;
9-[(6-methyl-2-naphthylphenyl)methyl]-2-ethyl-5-carbamoylcarbazol-4-yl}oxyacetic acid;
9-[(2-((phenylsulfonyl)methyl)phenyl)methyl]-2-ethyl-5-carbamoylcarbazol-4-yl}oxyacetic acid;
9-[(1-fluorenylmethyl]-2-ethyl-5-carbamoylcarbazol-4-yl}oxyacetic acid;
9-[(1-tetrazolylmethyl]-2-ethyl-5-carbamoylcarbazol-4-yl}oxyacetic acid;
9-[(5-methyl-1-tetrazolylmethyl]-2-ethyl-5-carbamoylcarbazol-4-yl}oxyacetic acid;

9-[(5-benzyl-1-tetrazolylmethyl]-2-ethyl-5-carbamoylcarbazol-4-yl}oxyacetic acid;
9-[(phenyl)methyl]-2-propyl-5-carbamoylcarbazol-4-yl}oxyacetic acid;
9-[(2-phenoxyphenyl)methyl]-2-propyl-5-carbamoylcarbazol-4-yl}oxyacetic acid;
9-[(3-phenoxyphenyl)methyl]-2-propyl-5-carbamoylcarbazol-4-yl}oxyacetic acid;
9-[(4-phenoxyphenyl)methyl]-2-propyl-5-carbamoylcarbazol-4-yl}oxyacetic acid;
9-[(2-fluorophenyl)methyl]-2-propyl-5-carbamoylcarbazol-4-yl}oxyacetic acid;
9-[(3-fluorophenyl)methyl]-2-propyl-5-carbamoylcarbazol-4-yl}oxyacetic acid;
9-[(4-fluorophenyl)methyl]-2-propyl-5-carbamoylcarbazol-4-yl}oxyacetic acid;
9-[(2-chlorophenyl)methyl]-2-propyl-5-carbamoylcarbazol-4-yl}oxyacetic acid;
9-[(3-chlorophenyl)methyl]-2-propyl-5-carbamoylcarbazol-4-yl}oxyacetic acid;
9-[(4-chlorophenyl)methyl]-2-propyl-5-carbamoylcarbazol-4-yl}oxyacetic acid;
9-[(2-bromophenyl)methyl]-2-propyl-5-carbamoylcarbazol-4-yl}oxyacetic acid;
9-[(3-bromophenyl)methyl]-2-propyl-5-carbamoylcarbazol-4-yl}oxyacetic acid;
9-[(4-bromophenyl)methyl]-2-propyl-5-carbamoylcarbazol-4-yl}oxyacetic acid;
9-[(2-iodophenyl)methyl]-2-propyl-5-carbamoylcarbazol-4-yl}oxyacetic acid;
9-[(3-iodophenyl)methyl]-2-propyl-5-carbamoylcarbazol-4-yl}oxyacetic acid;
9-[(4-iodophenyl)methyl]-2-propyl-5-carbamoylcarbazol-4-yl}oxyacetic acid;
9-[(2-acetamidophenyl)methyl]-2-propyl-5-carbamoylcarbazol-4-yl}oxyacetic acid;
9-[(3-acetamidophenyl)methyl]-2-propyl-5-carbamoylcarbazol-4-yl}oxyacetic acid;
9-[(4-acetamidophenyl)methyl]-2-propyl-5-carbamoylcarbazol-4-yl}oxyacetic acid;
9-[(2-carbamoylphenyl)methyl]-2-propyl-5-carbamoylcarbazol-4-yl}oxyacetic acid;
9-[(3-carbamoylphenyl)methyl]-2-propyl-5-carbamoylcarbazol-4-yl}oxyacetic acid;
9-[(4-carbamoylphenyl)methyl]-2-propyl-5-carbamoylcarbazol-4-yl}oxyacetic acid;
9-[(2-methylsulfonylphenyl)methyl]-2-propyl-5-carbamoylcarbazol-4-yl}oxyacetic acid;
9-[(3-methylsulfonylphenyl)methyl]-2-propyl-5-carbamoylcarbazol-4-yl}oxyacetic acid;
9-[(4-methylsulfonylphenyl)methyl]-2-propyl-5-carbamoylcarbazol-4-yl}oxyacetic acid;
9-[(2-methylphenyl)methyl]-2-propyl-5-carbamoylcarbazol-4-yl}oxyacetic acid;
9-[(3-methylphenyl)methyl]-2-propyl-5-carbamoylcarbazol-4-yl}oxyacetic acid;
9-[(4-methylphenyl)methyl]-2-propyl-5-carbamoylcarbazol-4-yl}oxyacetic acid;
9-[(2-ethylphenyl)methyl]-2-propyl-5-carbamoylcarbazol-4-yl}oxyacetic acid;
9-[(3-ethylphenyl)methyl]-2-propyl-5-carbamoylcarbazol-4-yl}oxyacetic acid;
9-[(4-ethylphenyl)methyl]-2-propyl-5-carbamoylcarbazol-4-yl}oxyacetic acid;
9-[(2-trifluoromethylphenyl)methyl]-2-propyl-5-carbamoylcarbazol-4-yl}oxyacetic acid;
9-[(3-trifluoromethylphenyl)methyl]-2-propyl-5-carbamoylcarbazol-4-yl}oxyacetic acid;
9-[(4-trifluoromethylphenyl)methyl]-2-propyl-5-carbamoylcarbazol-4-yl}oxyacetic acid;
9-[(cyclopropyl)methyl]-2-propyl-5-carbamoylcarbazol-4-yl}oxyacetic acid;
9-[(cyclobutyl)methyl]-2-propyl-5-carbamoylcarbazol-4-yl}oxyacetic acid;
9-[(cyclopentyl)methyl]-2-propyl-5-carbamoylcarbazol-4-yl}oxyacetic acid;
9-[(cyclohexyl)methyl]-2-propyl-5-carbamoylcarbazol-4-yl}oxyacetic acid;
9-[(2-methoxyphenyl)methyl]-2-propyl-5-carbamoylcarbazol-4-yl}oxyacetic acid;
9-[(3-methoxyphenyl)methyl]-2-propyl-5-carbamoylcarbazol-4-yl}oxyacetic acid;
9-[(4-methoxyphenyl)methyl]-2-propyl-5-carbamoylcarbazol-4-yl}oxyacetic acid;
9-[(2-ethoxyphenyl)methyl]-2-propyl-5-carbamoylcarbazol-4-yl}oxyacetic acid;
9-[(3-ethoxyphenyl)methyl]-2-propyl-5-carbamoylcarbazol-4-yl}oxyacetic acid;
9-[(4-ethoxyphenyl)methyl]-2-propyl-5-carbamoylcarbazol-4-yl}oxyacetic acid;
9-[(2-trifluoromethoxyphenyl)methyl]-2-propyl-5-carbamoylcarbazol-4-yl}oxyacetic acid;
9-[(3-trifluoromethoxyphenyl)methyl]-2-propyl-5-carbamoylcarbazol-4-yl}oxyacetic acid;
9-[(4-trifluoromethoxyphenyl)methyl]-2-propyl-5-carbamoylcarbazol-4-yl}oxyacetic acid;
9-[(2-difluoromethoxyphenyl)methyl]-2-propyl-5-carbamoylcarbazol-4-yl}oxyacetic acid;
9-[(3-difluoromethoxyphenyl)methyl]-2-propyl-5-carbamoylcarbazol-4-yl}oxyacetic acid;
9-[(4-difluoromethoxyphenyl)methyl]-2-propyl-5-carbamoylcarbazol-4-yl}oxyacetic acid;
9-[(2-cyanophenyl)methyl]-2-propyl-5-carbamoylcarbazol-4-yl}oxyacetic acid;
9-[(3-cyanophenyl)methyl]-2-propyl-5-carbamoylcarbazol-4-yl}oxyacetic acid;
9-[(4-cyanophenyl)methyl]-2-propyl-5-carbamoylcarbazol-4-yl}oxyacetic acid;
9-[(2-pyridyl)methyl]-2-propyl-5-carbamoylcarbazol-4-yl}oxyacetic acid;
9-[(3-pyridyl)methyl]-2-propyl-5-carbamoylcarbazol-4-yl}oxyacetic acid;
9-[(4-pyridyl)methyl]-2-propyl-5-carbamoylcarbazol-4-yl}oxyacetic acid;
9-[(2-furyl)methyl]-2-propyl-5-carbamoylcarbazol-4-yl}oxyacetic acid;
9-[(3-furyl)methyl]-2-propyl-5-carbamoylcarbazol-4-yl}oxyacetic acid;
9-[(2-thienyl)methyl]-2-propyl-5-carbamoylcarbazol-4-yl}oxyacetic acid;
9-[(3-thienyl)methyl]-2-propyl-5-carbamoylcarbazol-4-yl}oxyacetic acid;
9-[(2-benzylphenyl)methyl]-2-propyl-5-carbamoylcarbazol-4-yl}oxyacetic acid;
9-[(3-benzylphenyl)methyl]-2-propyl-5-carbamoylcarbazol-4-yl}oxyacetic acid;
9-[(4-benzylphenyl)methyl]-2-propyl-5-carbamoylcarbazol-4-yl}oxyacetic acid;
9-[(2-benzoylphenyl)methyl]-2-propyl-5-carbamoylcarbazol-4-yl}oxyacetic acid;
9-[(3-benzoylphenyl)methyl]-2-propyl-5-carbamoylcarbazol-4-yl}oxyacetic acid;
9-[(4-benzoylphenyl)methyl]-2-propyl-5-carbamoylcarbazol-4-yl}oxyacetic acid;
9-[(2-benzyloxyphenyl)methyl]-2-propyl-5-carbamoylcarbazol-4-yl}oxyacetic acid;

9-[(3-benzyloxyphenyl)methyl]-2-propyl-5-carbamoylcarbazol-4-yl}oxyacetic acid;
9-[(4-benzyloxyphenyl)methyl]-2-propyl-5-carbamoylcarbazol-4-yl}oxyacetic acid;
9-[(2-phenylphenyl)methyl]-2-propyl-5-carbamoylcarbazol-4-yl}oxyacetic acid;
9-[(3-phenylphenyl)methyl]-2-propyl-5-carbamoylcarbazol-4-yl}oxyacetic acid;
9-[(4-phenylphenyl)methyl]-2-propyl-5-carbamoylcarbazol-4-yl}oxyacetic acid;
9-[(1-naphthyl)methyl]-2-propyl-5-carbamoylcarbazol-4-yl}oxyacetic acid;
9-[(2-naphthyl)methyl]-2-propyl-5-carbamoylcarbazol-4-yl}oxyacetic acid;
9-[(2,3-difluorophenyl)methyl]-2-propyl-5-carbamoylcarbazol-4-yl}oxyacetic acid;
9-[(2,4-difluorophenyl)methyl]-2-propyl-5-carbamoylcarbazol-4-yl}oxyacetic acid;
9-[(2,5-difluorophenyl)methyl]-2-propyl-5-carbamoylcarbazol-4-yl}oxyacetic acid;
9-[(2,6-difluorophenyl)methyl]-2-propyl-5-carbamoylcarbazol-4-yl}oxyacetic acid;
9-[(3,4-difluorophenyl)methyl]-2-propyl-5-carbamoylcarbazol-4-yl}oxyacetic acid;
9-[(3,5-difluorophenyl)methyl]-2-propyl-5-carbamoylcarbazol-4-yl}oxyacetic acid;
9-[(2,3,4-trifluorophenyl)methyl]-2-propyl-5-carbamoylcarbazol-4-yl}oxyacetic acid;
9-[(2,3,5-trifluorophenyl)methyl]-2-propyl-5-carbamoylcarbazol-4-yl}oxyacetic acid;
9-[(2,3,6-trifluorophenyl)methyl]-2-propyl-5-carbamoylcarbazol-4-yl}oxyacetic acid;
9-[(2,4,5-trifluorophenyl)methyl]-2-propyl-5-carbamoylcarbazol-4-yl}oxyacetic acid;
9-[(2,4,6-trifluorophenyl)methyl]-2-propyl-5-carbamoylcarbazol-4-yl}oxyacetic acid;
9-[(3,4,5-trifluorophenyl)methyl]-2-propyl-5-carbamoylcarbazol-4-yl}oxyacetic acid;
9-[(pentafluorophenyl)methyl]-2-propyl-5-carbamoylcarbazol-4-yl}oxyacetic acid;
9-[(2,3-dichlorophenyl)methyl]-2-propyl-5-carbamoylcarbazol-4-yl}oxyacetic acid;
9-[(2,4-dichlorophenyl)methyl]-2-propyl-5-carbamoylcarbazol-4-yl}oxyacetic acid;
9-[(2,5-dichlorophenyl)methyl]-2-propyl-5-carbamoylcarbazol-4-yl}oxyacetic acid;
9-[(2,6-dichlorophenyl)methyl]-2-propyl-5-carbamoylcarbazol-4-yl}oxyacetic acid;
9-[(3,4-dichlorophenyl)methyl]-2-propyl-5-carbamoylcarbazol-4-yl}oxyacetic acid;
9-[(3,5-dichlorophenyl)methyl]-2-propyl-5-carbamoylcarbazol-4-yl}oxyacetic acid;
9-[(2,3-dimethylphenyl)methyl]-2-propyl-5-carbamoylcarbazol-4-yl}oxyacetic acid;
9-[(2,4-dimethylphenyl)methyl]-2-propyl-5-carbamoylcarbazol-4-yl}oxyacetic acid;
9-[(2,5-dimethylphenyl)methyl]-2-propyl-5-carbamoylcarbazol-4-yl}oxyacetic acid;
9-[(2,6-dimethylphenyl)methyl]-2-propyl-5-carbamoylcarbazol-4-yl}oxyacetic acid;
9-[(3,4-dimethylphenyl)methyl]-2-propyl-5-carbamoylcarbazol-4-yl}oxyacetic acid;
9-[(3,5-dimethylphenyl)methyl]-2-propyl-5-carbamoylcarbazol-4-yl}oxyacetic acid;
9-[(2,4,6-trimethylphenyl)methyl]-2-propyl-5-carbamoylcarbazol-4-yl}oxyacetic acid;
9-[(3,5-bis(trifluoromethyl)phenyl)methyl]-2-propyl-5-carbamoylcarbazol-4-yl}oxyacetic acid;
9-[(2,4-bis(trifluoromethyl)phenyl)methyl]-2-propyl-5-carbamoylcarbazol-4-yl}oxyacetic acid;
9-[(2-fluoro-3-trifluoromethylphenyl)methyl]-2-propyl-5-carbamoylcarbazol-4-yl}oxyacetic acid;
9-[(2-fluoro-4-trifluoromethylphenyl)methyl]-2-propyl-5-carbamoylcarbazol-4-yl}oxyacetic acid;
9-[(2-fluoro-5-trifluoromethylphenyl)methyl]-2-propyl-5-carbamoylcarbazol-4-yl}oxyacetic acid;
9-[(2-fluoro-6-trifluoromethylphenyl)methyl]-2-propyl-5-carbamoylcarbazol-4-yl}oxyacetic acid;
9-[(3-fluoro-5-trifluoromethylphenyl)methyl]-2-propyl-5-carbamoylcarbazol-4-yl}oxyacetic acid;
9-[(4-fluoro-2-trifluoromethylphenyl)methyl]-2-propyl-5-carbamoylcarbazol-4-yl}oxyacetic acid;
9-[(4-fluoro-3-trifluoromethylphenyl)methyl]-2-propyl-5-carbamoylcarbazol-4-yl}oxyacetic acid;
9-[3-(2-fluorophenoxy)methyl]-2-propyl-5-carbamoylcarbazol-4-yl}oxyacetic acid;
9-[3-(4-fluorophenoxy)methyl]-2-propyl-5-carbamoylcarbazol-4-yl}oxyacetic acid;
9-[(2-fluoro-3-methylphenyl)methyl]-2-propyl-5-carbamoylcarbazol-4-yl}oxyacetic acid;
9-[(3-chloro-2-fluorophenyl)methyl]-2-propyl-5-carbamoylcarbazol-4-yl}oxyacetic acid;
9-[(2-chloro-6-fluorophenyl)methyl]-2-propyl-5-carbamoylcarbazol-4-yl}oxyacetic acid;
9-[(4-bromo-2-fluorophenyl)methyl]-2-propyl-5-carbamoylcarbazol-4-yl}oxyacetic acid;
9-[(2-bromo-5-fluorophenyl)methyl]-2-propyl-5-carbamoylcarbazol-4-yl)oxyacetic acid;
9-[(3-chloro-4-methylphenyl)methyl]-2-propyl-5-carbamoylcarbazol-4-yl}oxyacetic acid;
9-[(3-chloro-4-methoxyphenyl)methyl]-2-propyl-5-carbamoylcarbazol-4-yl}oxyacetic acid;
9-[(4-methoxy-3-methylphenyl)methyl]-2-propyl-5-carbamoylcarbazol-4-yl}oxyacetic acid;
9-[(4-trifluoromethylthiophenyl)methyl]-2-propyl-5-carbamoylcarbazol-4-yl}oxyacetic acid;
9-[(1-bromo-2-naphthylphenyl)methyl]-2-propyl-5-carbamoylcarbazol-4-yl}oxyacetic acid;
9-[(2-methyl-1-naphthylphenyl)methyl]-2-propyl-5-carbamoylcarbazol-4-yl}oxyacetic acid;
9-[(4-methyl-1-naphthylphenyl)methyl]-2-propyl-5-carbamoylcarbazol-4-yl}oxyacetic acid;
9-[(6-methyl-2-naphthylphenyl)methyl]-2-propyl-5-carbamoylcarbazol-4-yl}oxyacetic acid;
9-[(2-((phenylsulfonyl)methyl)phenyl)methyl]-2-propyl-5-carbamoylcarbazol-4-yl}oxyacetic acid;
9-[(1-fluorenylmethyl]-2-propyl-5-carbamoylcarbazol-4-yl}oxyacetic acid;
9-[(1-tetrazolylmethyl]-2-propyl-5-carbamoylcarbazol-4-yl}oxyacetic acid;
9-[(5-methyl-1-tetrazolylmethyl]-2-propyl-5-carbamoylcarbazol-4-yl}oxyacetic acid;
9-[(5-benzyl-1-tetrazolylmethyl]-2-propyl-5-carbamoylcarbazol-4-yl}oxyacetic acid;
9-[(phenyl)methyl]-2-isopropyl-5-carbamoylcarbazol-4-yl}oxyacetic acid;
9-[(2-phenoxyphenyl)methyl]-2-isopropyl-5-carbamoylcarbazol-4-yl}oxyacetic acid;
9-[(3-phenoxyphenyl)methyl]-2-isopropyl-5-carbamoylcarbazol-4-yl}oxyacetic acid;
9-[(4-phenoxyphenyl)methyl]-2-isopropyl-5-carbamoylcarbazol-4-yl}oxyacetic acid;
9-[(2-fluorophenyl)methyl]-2-isopropyl-5-carbamoylcarbazol-4-yl}oxyacetic acid;
9-[(3-fluorophenyl)methyl]-2-isopropyl-5-carbamoylcarbazol-4-yl}oxyacetic acid;

9-[(4-fluorophenyl)methyl]-2-isopropyl-5-carbamoylcarbazol-4-yl}oxyacetic acid;
9-[(2-chlorophenyl)methyl]-2-isopropyl-5-carbamoylcarbazol-4-yl}oxyacetic acid;
9-[(3-chlorophenyl)methyl]-2-isopropyl-5-carbamoylcarbazol-4-yl}oxyacetic acid;
9-[(4-chlorophenyl)methyl]-2-isopropyl-5-carbamoylcarbazol-4-yl}oxyacetic acid;
9-[(2-bromophenyl)methyl]-2-isopropyl-5-carbamoylcarbazol-4-yl}oxyacetic acid;
9-[(3-bromophenyl)methyl]-2-isopropyl-5-carbamoylcarbazol-4-yl}oxyacetic acid;
9-[(4-bromophenyl)methyl]-2-isopropyl-5-carbamoylcarbazol-4-yl}oxyacetic acid;
9-[(2-iodophenyl)methyl]-2-isopropyl-5-carbamoylcarbazol-4-yl}oxyacetic acid;
9-[(3-iodophenyl)methyl]-2-isopropyl-5-carbamoylcarbazol-4-yl}oxyacetic acid;
9-[(4-iodophenyl)methyl]-2-isopropyl-5-carbamoylcarbazol-4-yl}oxyacetic acid;
9-[(2-acetamidophenyl)methyl]-2-isopropyl-5-carbamoylcarbazol-4-yl}oxyacetic acid;
9-[(3-acetamidophenyl)methyl]-2-isopropyl-5-carbamoylcarbazol-4-yl}oxyacetic acid;
9-[(4-acetamidophenyl)methyl]-2-isopropyl-5-carbamoylcarbazol-4-yl}oxyacetic acid;
9-[(2-carbamoylphenyl)methyl]-2-isopropyl-5-carbamoylcarbazol-4-yl}oxyacetic acid;
9-[(3-carbamoylphenyl)methyl]-2-isopropyl-5-carbamoylcarbazol-4-yl}oxyacetic acid;
9-[(4-carbamoylphenyl)methyl]-2-isopropyl-5-carbamoylcarbazol-4-yl}oxyacetic acid;
9-[(2-methylsulfonylphenyl)methyl]-2-isopropyl-5-carbamoylcarbazol-4-yl}oxyacetic acid;
9-[(3-methylsulfonylphenyl)methyl]-2-isopropyl-5-carbamoylcarbazol-4-yl}oxyacetic acid;
9-[(4-methylsulfonylphenyl)methyl]-2-isopropyl-5-carbamoylcarbazol-4-yl}oxyacetic acid;
9-[(2-methylphenyl)methyl]-2-isopropyl-5-carbamoylcarbazol-4-yl}oxyacetic acid;
9-[(3-methylphenyl)methyl]-2-isopropyl-5-carbamoylcarbazol-4-yl}oxyacetic acid;
9-[(4-methylphenyl)methyl]-2-isopropyl-5-carbamoylcarbazol-4-yl}oxyacetic acid;
9-[(2-ethylphenyl)methyl]-2-isopropyl-5-carbamoylcarbazol-4-yl}oxyacetic acid;
9-[(3-ethylphenyl)methyl]-2-isopropyl-5-carbamoylcarbazol-4-yl}oxyacetic acid;
9-[(4-ethylphenyl)methyl]-2-isopropyl-5-carbamoylcarbazol-4-yl}oxyacetic acid;
9-[(2-trifluoromethylphenyl)methyl]-2-isopropyl-5-carbamoylcarbazol-4-yl}oxyacetic acid;
9-[(3-trifluoromethylphenyl)methyl]-2-isopropyl-5-carbamoylcarbazol-4-yl}oxyacetic acid;
9-[(4-trifluoromethylphenyl)methyl]-2-isopropyl-5-carbamoylcarbazol-4-yl}oxyacetic acid;
9-[(cyclopropyl)methyl]-2-isopropyl-5-carbamoylcarbazol-4-yl}oxyacetic acid;
9-[(cyclobutyl)methyl]-2-isopropyl-5-carbamoylcarbazol-4-yl}oxyacetic acid;
9-[(cyclopentyl)methyl]-2-isopropyl-5-carbamoylcarbazol-4-yl}oxyacetic acid;
9-[(cyclohexyl)methyl]-2-isopropyl-5-carbamoylcarbazol-4-yl}oxyacetic acid;
9-[(2-methoxyphenyl)methyl]-2-isopropyl-5-carbamoylcarbazol-4-yl}oxyacetic acid;
9-[(3-methoxyphenyl)methyl]-2-isopropyl-5-carbamoylcarbazol-4-yl}oxyacetic acid;
9-[(4-methoxyphenyl)methyl]-2-isopropyl-5-carbamoylcarbazol-4-yl}oxyacetic acid;
9-[(2-ethoxyphenyl)methyl]-2-isopropyl-5-carbamoylcarbazol-4-yl}oxyacetic acid;
9-[(3-ethoxyphenyl)methyl]-2-isopropyl-5-carbamoylcarbazol-4-yl}oxyacetic acid;
9-[(4-ethoxyphenyl)methyl]-2-isopropyl-5-carbamoylcarbazol-4-yl}oxyacetic acid;
9-[(2-trifluoromethoxyphenyl)methyl]-2-isopropyl-5-carbamoylcarbazol-4-yl}oxyacetic acid;
9-[(3-trifluoromethoxyphenyl)methyl]-2-isopropyl-5-carbamoylcarbazol-4-yl}oxyacetic acid;
9-[(4-trifluoromethoxyphenyl)methyl]-2-isopropyl-5-carbamoylcarbazol-4-yl}oxyacetic acid;
9-[(2-difluoromethoxyphenyl)methyl]-2-isopropyl-5-carbamoylcarbazol-4-yl}oxyacetic acid;
9-[(3-difluoromethoxyphenyl)methyl]-2-isopropyl-5-carbamoylcarbazol-4-yl}oxyacetic acid;
9-[(4-difluoromethoxyphenyl)methyl]-2-isopropyl-5-carbamoylcarbazol-4-yl}oxyacetic acid;
9-[(2-cyanophenyl)methyl]-2-isopropyl-5-carbamoylcarbazol-4-yl}oxyacetic acid;
9-[(3-cyanophenyl)methyl]-2-isopropyl-5-carbamoylcarbazol-4-yl}oxyacetic acid;
9-[(4-cyanophenyl)methyl]-2-isopropyl-5-carbamoylcarbazol-4-yl}oxyacetic acid;
9-[(2-pyridyl)methyl]-2-isopropyl-5-carbamoylcarbazol-4-yl}oxyacetic acid;
9-[(3-pyridyl)methyl]-2-isopropyl-5-carbamoylcarbazol-4-yl}oxyacetic acid;
9-[(4-pyridyl)methyl]-2-isopropyl-5-carbamoylcarbazol-4-yl}oxyacetic acid;
9-[(2-furyl)methyl]-2-isopropyl-5-carbamoylcarbazol-4-yl}oxyacetic acid;
9-[(3-furyl)methyl]-2-isopropyl-5-carbamoylcarbazol-4-yl}oxyacetic acid;
9-[(2-thienyl)methyl]-2-isopropyl-5-carbamoylcarbazol-4-yl}oxyacetic acid;
9-[(3-thienyl)methyl]-2-isopropyl-5-carbamoylcarbazol-4-yl}oxyacetic acid;
9-[(2-benzylphenyl)methyl]-2-isopropyl-5-carbamoylcarbazol-4-yl}oxyacetic acid;
9-[(3-benzylphenyl)methyl]-2-isopropyl-5-carbamoylcarbazol-4-yl}oxyacetic acid;
9-[(4-benzylphenyl)methyl]-2-isopropyl-5-carbamoylcarbazol-4-yl}oxyacetic acid;
9-[(2-benzoylphenyl)methyl]-2-isopropyl-5-carbamoylcarbazol-4-yl}oxyacetic acid;
9-[(3-benzoylphenyl)methyl]-2-isopropyl-5-carbamoylcarbazol-4-yl}oxyacetic acid;
9-[(4-benzoylphenyl)methyl]-2-isopropyl-5-carbamoylcarbazol-4-yl}oxyacetic acid;
9-[(2-benzyloxyphenyl)methyl]-2-isopropyl-5-carbamoylcarbazol-4-yl}oxyacetic acid;
9-[(3-benzyloxyphenyl)methyl]-2-isopropyl-5-carbamoylcarbazol-4-yl}oxyacetic acid;
9-[(4-benzyloxyphenyl)methyl]-2-isopropyl-5-carbamoylcarbazol-4-yl}oxyacetic acid;
9-[(2-phenylphenyl)methyl]-2-isopropyl-5-carbamoylcarbazol-4-yl}oxyacetic acid;
9-[(3-phenylphenyl)methyl]-2-isopropyl-5-carbamoylcarbazol-4-yl}oxyacetic acid;
9-[(4-phenylphenyl)methyl]-2-isopropyl-5-carbamoylcarbazol-4-yl}oxyacetic acid;
9-[(1-naphthyl)methyl]-2-isopropyl-5-carbamoylcarbazol-4-yl}oxyacetic acid;
9-[(2-naphthyl)methyl]-2-isopropyl-5-carbamoylcarbazol-4-yl}oxyacetic acid;

9-[(2,3-difluorophenyl)methyl]-2-isopropyl-5-carbamoylcarbazol-4-yl}oxyacetic acid;
9-[(2,4-difluorophenyl)methyl]-2-isopropyl-5-carbamoylcarbazol-4-yl}oxyacetic acid;
9-[(2,5-difluorophenyl)methyl]-2-isopropyl-5-carbamoylcarbazol-4-yl}oxyacetic acid;
9-[(2,6-difluorophenyl)methyl]-2-isopropyl-5-carbamoylcarbazol-4-yl}oxyacetic acid;
9-[(3,4-difluorophenyl)methyl]-2-isopropyl-5-carbamoylcarbazol-4-yl}oxyacetic acid;
9-[(3,5-difluorophenyl)methyl]-2-isopropyl-5-carbamoylcarbazol-4-yl}oxyacetic acid;
9-[(2,3,4-trifluorophenyl)methyl]-2-isopropyl-5-carbamoylcarbazol-4-yl}oxyacetic acid;
9-[(2,3,5-trifluorophenyl)methyl]-2-isopropyl-5-carbamoylcarbazol-4-yl}oxyacetic acid;
9-[(2,3,6-trifluorophenyl)methyl]-2-isopropyl-5-carbamoylcarbazol-4-yl}oxyacetic acid;
9-[(2,4,5-trifluorophenyl)methyl]-2-isopropyl-5-carbamoylcarbazol-4-yl}oxyacetic acid;
9-[(2,4,6-trifluorophenyl)methyl]-2-isopropyl-5-carbamoylcarbazol-4-yl}oxyacetic acid;
9-[(3,4,5-trifluorophenyl)methyl]-2-isopropyl-5-carbamoylcarbazol-4-yl}oxyacetic acid;
9-[(pentafluorophenyl)methyl]-2-isopropyl-5-carbamoylcarbazol-4-yl}oxyacetic acid;
9-[(2,3-dichlorophenyl)methyl]-2-isopropyl-5-carbamoylcarbazol-4-yl}oxyacetic acid;
9-[(2,4-dichlorophenyl)methyl]-2-isopropyl-5-carbamoylcarbazol-4-yl}oxyacetic acid;
9-[(2,5-dichlorophenyl)methyl]-2-isopropyl-5-carbamoylcarbazol-4-yl}oxyacetic acid;
9-[(2,6-dichlorophenyl)methyl]-2-isopropyl-5-carbamoylcarbazol-4-yl}oxyacetic acid;
9-[(3,4-dichlorophenyl)methyl]-2-isopropyl-5-carbamoylcarbazol-4-yl}oxyacetic acid;
9-[(3,5-dichlorophenyl)methyl]-2-isopropyl-5-carbamoylcarbazol-4-yl}oxyacetic acid;
9-[(2,3-dimethylphenyl)methyl]-2-isopropyl-5-carbamoylcarbazol-4-yl}oxyacetic acid;
9-[(2,4-dimethylphenyl)methyl]-2-isopropyl-5-carbamoylcarbazol-4-yl}oxyacetic acid;
9-[(2,5-dimethylphenyl)methyl]-2-isopropyl-5-carbamoylcarbazol-4-yl}oxyacetic acid;
9-[(2,6-dimethylphenyl)methyl]-2-isopropyl-5-carbamoylcarbazol-4-yl}oxyacetic acid;
9-[(3,4-dimethylphenyl)methyl]-2-isopropyl-5-carbamoylcarbazol-4-yl}oxyacetic acid;
9-[(3,5-dimethylphenyl)methyl]-2-isopropyl-5-carbamoylcarbazol-4-yl}oxyacetic acid;
9-[(2,4,6-trimethylphenyl)methyl]-2-isopropyl-5-carbamoylcarbazol-4-yl}oxyacetic acid;
9-[(3,5-bis(trifluoromethyl)phenyl)methyl]-2-isopropyl-5-carbamoylcarbazol-4-yl}oxyacetic acid;
9-[(2,4-bis(trifluoromethyl)phenyl)methyl]-2-isopropyl-5-carbamoylcarbazol-4-yl}oxyacetic acid;
9-[(2-fluoro-3-trifluoromethylphenyl)methyl]-2-isopropyl-5-carbamoylcarbazol-4-yl}oxyacetic acid;
9-[(2-fluoro-4-trifluoromethylphenyl)methyl]-2-isopropyl-5-carbamoylcarbazol-4-yl}oxyacetic acid;
9-[(2-fluoro-5-trifluoromethylphenyl)methyl]-2-isopropyl-5-carbamoylcarbazol-4-yl}oxyacetic acid;
9-[(2-fluoro-6-trifluoromethylphenyl)methyl]-2-isopropyl-5-carbamoylcarbazol-4-yl}oxyacetic acid;
9-[(3-fluoro-5-trifluoromethylphenyl)methyl]-2-isopropyl-5-carbamoylcarbazol-4-yl}oxyacetic acid;
9-[(4-fluoro-2-trifluoromethylphenyl)methyl]-2-isopropyl-5-carbamoylcarbazol-4-yl}oxyacetic acid;
9-[(4-fluoro-3-trifluoromethylphenyl)methyl]-2-isopropyl-5-carbamoylcarbazol-4-yl}oxyacetic acid;
9-[3-(2-fluorophenoxy)methyl]-2-isopropyl-5-carbamoylcarbazol-4-yl}oxyacetic acid;
9-[3-(4-fluorophenoxy)methyl]-2-isopropyl-5-carbamoylcarbazol-4-yl}oxyacetic acid;
9-[(2-fluoro-3-methylphenyl)methyl]-2-isopropyl-5-carbamoylcarbazol-4-yl}oxyacetic acid;
9-[(3-chloro-2-fluorophenyl)methyl]-2-isopropyl-5-carbamoylcarbazol-4-yl}oxyacetic acid;
9-[(2-chloro-6-fluorophenyl)methyl]-2-isopropyl-5-carbamoylcarbazol-4-yl}oxyacetic acid;
9-[(4-bromo-2-fluorophenyl)methyl]-2-isopropyl-5-carbamoylcarbazol-4-yl}oxyacetic acid;
9-[(2-bromo-5-fluorophenyl)methyl]-2-isopropyl-5-carbamoylcarbazol-4-yl}oxyacetic acid;
9-[(3-chloro-4-methylphenyl)methyl]-2-isopropyl-5-carbamoylcarbazol-4-yl}oxyacetic acid;
9-[(3-chloro-4-methoxyphenyl)methyl]-2-isopropyl-5-carbamoylcarbazol-4-yl}oxyacetic acid;
9-[(4-methoxy-3-methylphenyl)methyl]-2-isopropyl-5-carbamoylcarbazol-4-yl}oxyacetic acid;
9-[(4-trifluoromethylthiophenyl)methyl]-2-isopropyl-5-carbamoylcarbazol-4-yl}oxyacetic acid;
9-[(1-bromo-2-naphthylphenyl)methyl]-2-isopropyl-5-carbamoylcarbazol-4-yl}oxyacetic acid;
9-[(2-methyl-1-naphthylphenyl)methyl]-2-isopropyl-5-carbamoylcarbazol-4-yl}oxyacetic acid;
9-[(4-methyl-1-naphthylphenyl)methyl]-2-isopropyl-5-carbamoylcarbazol-4-yl}oxyacetic acid;
9-[(6-methyl-2-naphthylphenyl)methyl]-2-isopropyl-5-carbamoylcarbazol-4-yl}oxyacetic acid;
9-[(2-((phenylsulfonyl)methyl)phenyl)methyl]-2-isopropyl-5-carbamoylcarbazol-4-yl}oxyacetic acid;
9-[(1-fluorenylmethyl]-2-isopropyl-5-carbamoylcarbazol-4-yl}oxyacetic acid;
9-[(1-tetrazolylmethyl]-2-isopropyl-5-carbamoylcarbazol-4-yl}oxyacetic acid;
9-[(5-methyl-1-tetrazolylmethyl]-2-isopropyl-5-carbamoylcarbazol-4-yl}oxyacetic acid;
9-[(5-benzyl-1-tetrazolylmethyl]-2-isopropyl-5-carbamoylcarbazol-4-yl}oxyacetic acid;
9-[(phenyl)methyl]-2-n-butyl-5-carbamoylcarbazol-4-yl}oxyacetic acid;
9-[(2-phenoxyphenyl)methyl]-2-n-butyl-5-carbamoylcarbazol-4-yl}oxyacetic acid;
9-[(3-phenoxyphenyl)methyl]-2-n-butyl-5-carbamoylcarbazol-4-yl}oxyacetic acid;
9-[(4-phenoxyphenyl)methyl]-2-n-butyl-5-carbamoylcarbazol-4-yl}oxyacetic acid;
9-[(2-fluorophenyl)methyl]-2-n-butyl-5-carbamoylcarbazol-4-yl}oxyacetic acid;
9-[(3-fluorophenyl)methyl]-2-n-butyl-5-carbamoylcarbazol-4-yl}oxyacetic acid;
9-[(4-fluorophenyl)methyl]-2-n-butyl-5-carbamoylcarbazol-4-yl}oxyacetic acid;
9-[(2-chlorophenyl)methyl]-2-n-butyl-5-carbamoylcarbazol-4-yl}oxyacetic acid;
9-[(3-chlorophenyl)methyl]-2-n-butyl-5-carbamoylcarbazol-4-yl}oxyacetic acid;
9-[(4-chlorophenyl)methyl]-2-n-butyl-5-carbamoylcarbazol-4-yl}oxyacetic acid;
9-[(2-bromophenyl)methyl]-2-n-butyl-5-carbamoylcarbazol-4-yl}oxyacetic acid;
9-[(3-bromophenyl)methyl]-2-n-butyl-5-carbamoylcarbazol-4-yl}oxyacetic acid;
9-[(4-bromophenyl)methyl]-2-n-butyl-5-carbamoylcarbazol-4-yl}oxyacetic acid;

9-[(2-iodophenyl)methyl]-2-n-butyl-5-carbamoylcarbazol-4-yl}oxyacetic acid;
9-[(3-iodophenyl)methyl]-2-n-butyl-5-carbamoylcarbazol-4-yl}oxyacetic acid;
9-[(4-iodophenyl)methyl]-2-n-butyl-5-carbamoylcarbazol-4-yl}oxyacetic acid;
9-[(2-acetamidophenyl)methyl]-2-n-butyl-5-carbamoylcarbazol-4-yl}oxyacetic acid;
9-[(3-acetamidophenyl)methyl]-2-n-butyl-5-carbamoylcarbazol-4-yl}oxyacetic acid;
9-[(4-acetamidophenyl)methyl]-2-n-butyl-5-carbamoylcarbazol-4-yl}oxyacetic acid;
9-[(2-carbamoylphenyl)methyl]-2-n-butyl-5-carbamoylcarbazol-4-yl}oxyacetic acid;
9-[(3-carbamoylphenyl)methyl]-2-n-butyl-5-carbamoylcarbazol-4-yl}oxyacetic acid;
9-[(4-carbamoylphenyl)methyl]-2-n-butyl-5-carbamoylcarbazol-4-yl}oxyacetic acid;
9-[(2-methylsulfonylphenyl)methyl]-2-n-butyl-5-carbamoylcarbazol-4-yl}oxyacetic acid;
9-[(3-methylsulfonylphenyl)methyl]-2-n-butyl-5-carbamoylcarbazol-4-yl}oxyacetic acid;
9-[(4-methylsulfonylphenyl)methyl]-2-n-butyl-5-carbamoylcarbazol-4-yl}oxyacetic acid;
9-[(2-methylphenyl)methyl]-2-n-butyl-5-carbamoylcarbazol-4-yl}oxyacetic acid;
9-[(3-methylphenyl)methyl]-2-n-butyl-5-carbamoylcarbazol-4-yl}oxyacetic acid;
9-[(4-methylphenyl)methyl]-2-n-butyl-5-carbamoylcarbazol-4-yl}oxyacetic acid;
9-[(2-ethylphenyl)methyl]-2-n-butyl-5-carbamoylcarbazol-4-yl}oxyacetic acid;
9-[(3-ethylphenyl)methyl]-2-n-butyl-5-carbamoylcarbazol-4-yl}oxyacetic acid;
9-[(4-ethylphenyl)methyl]-2-n-butyl-5-carbamoylcarbazol-4-yl}oxyacetic acid;
9-[(2-trifluoromethylphenyl)methyl]-2-n-butyl-5-carbamoylcarbazol-4-yl}oxyacetic acid;
9-[(3-trifluoromethylphenyl)methyl]-2-n-butyl-5-carbamoylcarbazol-4-yl}oxyacetic acid;
9-[(4-trifluoromethylphenyl)methyl]-2-n-butyl-5-carbamoylcarbazol-4-yl}oxyacetic acid;
9-[(cyclopropyl)methyl]-2-n-butyl-5-carbamoylcarbazol-4-yl}oxyacetic acid;
9-[(cyclobutyl)methyl]-2-n-butyl-5-carbamoylcarbazol-4-yl}oxyacetic acid;
9-[(cyclopentyl)methyl]-2-n-butyl-5-carbamoylcarbazol-4-yl}oxyacetic acid;
9-[(cyclohexyl)methyl]-2-n-butyl-5-carbamoylcarbazol-4-yl}oxyacetic acid;
9-[(2-methoxyphenyl)methyl]-2-n-butyl-5-carbamoylcarbazol-4-yl}oxyacetic acid;
9-[(3-methoxyphenyl)methyl]-2-n-butyl-5-carbamoylcarbazol-4-yl}oxyacetic acid;
9-[(4-methoxyphenyl)methyl]-2-n-butyl-5-carbamoylcarbazol-4-yl}oxyacetic acid;
9-[(2-ethoxyphenyl)methyl]-2-n-butyl-5-carbamoylcarbazol-4-yl}oxyacetic acid;
9-[(3-ethoxyphenyl)methyl]-2-n-butyl-5-carbamoylcarbazol-4-yl}oxyacetic acid;
9-[(4-ethoxyphenyl)methyl]-2-n-butyl-5-carbamoylcarbazol-4-yl}oxyacetic acid;
9-[(2-trifluoromethoxyphenyl)methyl]-2-n-butyl-5-carbamoylcarbazol-4-yl}oxyacetic acid;
9-[(3-trifluoromethoxyphenyl)methyl]-2-n-butyl-5-carbamoylcarbazol-4-yl}oxyacetic acid;
9-[(4-trifluoromethoxyphenyl)methyl]-2-n-butyl-5-carbamoylcarbazol-4-yl}oxyacetic acid;
9-[(2-difluoromethoxyphenyl)methyl]-2-n-butyl-5-carbamoylcarbazol-4-yl}oxyacetic acid;
9-[(3-difluoromethoxyphenyl)methyl]-2-n-butyl-5-carbamoylcarbazol-4-yl}oxyacetic acid;
9-[(4-difluoromethoxyphenyl)methyl]-2-n-butyl-5-carbamoylcarbazol-4-yl}oxyacetic acid;
9-[(2-cyanophenyl)methyl]-2-n-butyl-5-carbamoylcarbazol-4-yl}oxyacetic acid;
9-[(3-cyanophenyl)methyl]-2-n-butyl-5-carbamoylcarbazol-4-yl}oxyacetic acid;
9-[(4-cyanophenyl)methyl]-2-n-butyl-5-carbamoylcarbazol-4-yl}oxyacetic acid;
9-[(2-pyridyl)methyl]-2-n-butyl-5-carbamoylcarbazol-4-yl}oxyacetic acid;
9-[(3-pyridyl)methyl]-2-n-butyl-5-carbamoylcarbazol-4-yl}oxyacetic acid;
9-[(4-pyridyl)methyl]-2-n-butyl-5-carbamoylcarbazol-4-yl}oxyacetic acid;
9-[(2-furyl)methyl]-2-n-butyl-5-carbamoylcarbazol-4-yl}oxyacetic acid;
9-[(3-furyl)methyl]-2-n-butyl-5-carbamoylcarbazol-4-yl}oxyacetic acid;
9-[(2-thienyl)methyl]-2-n-butyl-5-carbamoylcarbazol-4-yl}oxyacetic acid;
9-[(3-thienyl)methyl]-2-n-butyl-5-carbamoylcarbazol-4-yl}oxyacetic acid;
9-[(2-benzylphenyl)methyl]-2-n-butyl-5-carbamoylcarbazol-4-yl}oxyacetic acid;
9-[(3-benzylphenyl)methyl]-2-n-butyl-5-carbamoylcarbazol-4-yl}oxyacetic acid;
9-[(4-benzylphenyl)methyl]-2-n-butyl-5-carbamoylcarbazol-4-yl}oxyacetic acid;
9-[(2-benzoylphenyl)methyl]-2-n-butyl-5-carbamoylcarbazol-4-yl}oxyacetic acid;
9-[(3-benzoylphenyl)methyl]-2-n-butyl-5-carbamoylcarbazol-4-yl}oxyacetic acid;
9-[(4-benzoylphenyl)methyl]-2-n-butyl-5-carbamoylcarbazol-4-yl}oxyacetic acid;
9-[(2-benzyloxyphenyl)methyl]-2-n-butyl-5-carbamoylcarbazol-4-yl}oxyacetic acid;
9-[(3-benzyloxyphenyl)methyl]-2-n-butyl-5-carbamoylcarbazol-4-yl}oxyacetic acid;
9-[(4-benzyloxyphenyl)methyl]-2-n-butyl-5-carbamoylcarbazol-4-yl}oxyacetic acid;
9-[(2-phenylphenyl)methyl]-2-n-butyl-5-carbamoylcarbazol-4-yl}oxyacetic acid;
9-[(3-phenylphenyl)methyl]-2-n-butyl-5-carbamoylcarbazol-4-yl}oxyacetic acid;
9-[(4-phenylphenyl)methyl]-2-n-butyl-5-carbamoylcarbazol-4-yl}oxyacetic acid;
9-[(1-naphthyl)methyl]-2-n-butyl-5-carbamoylcarbazol-4-yl}oxyacetic acid;
9-[(2-naphthyl)methyl]-2-n-butyl-5-carbamoylcarbazol-4-yl}oxyacetic acid;
9-[(2,3-difluorophenyl)methyl]-2-n-butyl-5-carbamoylcarbazol-4-yl}oxyacetic acid;
9-[(2,4-difluorophenyl)methyl]-2-n-butyl-5-carbamoylcarbazol-4-yl}oxyacetic acid;
9-[(2,5-difluorophenyl)methyl]-2-n-butyl-5-carbamoylcarbazol-4-yl}oxyacetic acid;
9-[(2,6-difluorophenyl)methyl]-2-n-butyl-5-carbamoylcarbazol-4-yl}oxyacetic acid;
9-[(3,4-difluorophenyl)methyl]-2-n-butyl-5-carbamoylcarbazol-4-yl}oxyacetic acid;
9-[(3,5-difluorophenyl)methyl]-2-n-butyl-5-carbamoylcarbazol-4-yl}oxyacetic acid;
9-[(2,3,4-trifluorophenyl)methyl]-2-n-butyl-5-carbamoylcarbazol-4-yl}oxyacetic acid;

9-[(2,3,5-trifluorophenyl)methyl]-2-n-butyl-5-carbamoylcarbazol-4-yl}oxyacetic acid;
9-[(2,3,6-trifluorophenyl)methyl]-2-n-butyl-5-carbamoylcarbazol-4-yl}oxyacetic acid;
9-[(2,4,5-trifluorophenyl)methyl]-2-n-butyl-5-carbamoylcarbazol-4-yl}oxyacetic acid;
9-[(2,4,6-trifluorophenyl)methyl]-2-n-butyl-5-carbamoylcarbazol-4-yl}oxyacetic acid;
9-[(3,4,5-trifluorophenyl)methyl]-2-n-butyl-5-carbamoylcarbazol-4-yl}oxyacetic acid;
9-[(pentafluorophenyl)methyl]-2-n-butyl-5-carbamoylcarbazol-4-yl}oxyacetic acid;
9-[(2,3-dichlorophenyl)methyl]-2-n-butyl-5-carbamoylcarbazol-4-yl}oxyacetic acid;
9-[(2,4-dichlorophenyl)methyl]-2-n-butyl-5-carbamoylcarbazol-4-yl}oxyacetic acid;
9-[(2,5-dichlorophenyl)methyl]-2-n-butyl-5-carbamoylcarbazol-4-yl}oxyacetic acid;
9-[(2,6-dichlorophenyl)methyl]-2-n-butyl-5-carbamoylcarbazol-4-yl}oxyacetic acid;
9-[(3,4-dichlorophenyl)methyl]-2-n-butyl-5-carbamoylcarbazol-4-yl}oxyacetic acid;
9-[(3,5-dichlorophenyl)methyl]-2-n-butyl-5-carbamoylcarbazol-4-yl}oxyacetic acid;
9-[(2,3-dimethylphenyl)methyl]-2-n-butyl-5-carbamoylcarbazol-4-yl}oxyacetic acid;
9-[(2,4-dimethylphenyl)methyl]-2-n-butyl-5-carbamoylcarbazol-4-yl}oxyacetic acid;
9-[(2,5-dimethylphenyl)methyl]-2-n-butyl-5-carbamoylcarbazol-4-yl}oxyacetic acid;
9-[(2,6-dimethylphenyl)methyl]-2-n-butyl-5-carbamoylcarbazol-4-yl}oxyacetic acid;
9-[(3,4-dimethylphenyl)methyl]-2-n-butyl-5-carbamoylcarbazol-4-yl}oxyacetic acid;
9-[(3,5-dimethylphenyl)methyl]-2-n-butyl-5-carbamoylcarbazol-4-yl}oxyacetic acid;
9-[(2,4,6-trimethylphenyl)methyl]-2-n-butyl-5-carbamoylcarbazol-4-yl}oxyacetic acid;
9-[(3,5-bis(trifluoromethyl)phenyl)methyl]-2-n-butyl-5-carbamoylcarbazol-4-yl}oxyacetic acid;
9-[(2,4-bis(trifluoromethyl)phenyl)methyl]-2-n-butyl-5-carbamoylcarbazol-4-yl}oxyacetic acid;
9-[(2-fluoro-3-trifluoromethylphenyl)methyl]-2-n-butyl-5-carbamoylcarbazol-4-yl}oxyacetic acid;
9-[(2-fluoro-4-trifluoromethylphenyl)methyl]-2-n-butyl-5-carbamoylcarbazol-4-yl}oxyacetic acid;
9-[(2-fluoro-5-trifluoromethylphenyl)methyl]-2-n-butyl-5-carbamoylcarbazol-4-yl}oxyacetic acid;
9-[(2-fluoro-6-trifluoromethylphenyl)methyl]-2-n-butyl-5-carbamoylcarbazol-4-yl}oxyacetic acid;
9-[(3-fluoro-5-trifluoromethylphenyl)methyl]-2-n-butyl-5-carbamoylcarbazol-4-yl}oxyacetic acid;
9-[(4-fluoro-2-trifluoromethylphenyl)methyl]-2-n-butyl-5-carbamoylcarbazol-4-yl}oxyacetic acid;
9-[(4-fluoro-3-trifluoromethylphenyl)methyl]-2-n-butyl-5-carbamoylcarbazol-4-yl}oxyacetic acid;
9-[3-(2-fluorophenoxy)methyl]-2-n-butyl-5-carbamoylcarbazol-4-yl}oxyacetic acid;
9-[3-(4-fluorophenoxy)methyl]-2-n-butyl-5-carbamoylcarbazol-4-yl}oxyacetic acid;
9-[(2-fluoro-3-methylphenyl)methyl]-2-n-butyl-5-carbamoylcarbazol-4-yl}oxyacetic acid;
9-[(3-chloro-2-fluorophenyl)methyl]-2-n-butyl-5-carbamoylcarbazol-4-yl}oxyacetic acid;
9-[(2-chloro-6-fluorophenyl)methyl]-2-n-butyl-5-carbamoylcarbazol-4-yl}oxyacetic acid;
9-[(4-bromo-2-fluorophenyl)methyl]-2-n-butyl-5-carbamoylcarbazol-4-yl}oxyacetic acid;
9-[(2-bromo-5-fluorophenyl)methyl]-2-n-butyl-5-carbamoylcarbazol-4-yl}oxyacetic acid;
9-[(3-chloro-4-methylphenyl)methyl]-2-n-butyl-5-carbamoylcarbazol-4-yl}oxyacetic acid;
9-[(3-chloro-4-methoxyphenyl)methyl]-2-n-butyl-5-carbamoylcarbazol-4-yl}oxyacetic acid;
9-[(4-methoxy-3-methylphenyl)methyl]-2-n-butyl-5-carbamoylcarbazol-4-yl}oxyacetic acid;
9-[(4-trifluoromethylthiophenyl)methyl]-2-n-butyl-5-carbamoylcarbazol-4-yl}oxyacetic acid;
9-[(1-bromo-2-naphthylphenyl)methyl]-2-n-butyl-5-carbamoylcarbazol-4-yl}oxyacetic acid;
9-[(2-methyl-1-naphthylphenyl)methyl]-2-n-butyl-5-carbamoylcarbazol-4-yl}oxyacetic acid;
9-[(4-methyl-1-naphthylphenyl)methyl]-2-n-butyl-5-carbamoylcarbazol-4-yl}oxyacetic acid;
9-[(6-methyl-2-naphthylphenyl)methyl]-2-n-butyl-5-carbamoylcarbazol-4-yl}oxyacetic acid;
9-[(2-((phenylsulfonyl)methyl)phenyl)methyl]-2-n-butyl-5-carbamoylcarbazol-4-yl}oxyacetic acid;
9-[(1-fluorenylmethyl]-2-n-butyl-5-carbamoylcarbazol-4-yl}oxyacetic acid;
9-[(1-tetrazolylmethyl]-2-n-butyl-5-carbamoylcarbazol-4-yl}oxyacetic acid;
9-[(5-methyl-1-tetrazolylmethyl]-2-n-butyl-5-carbamoylcarbazol-4-yl}oxyacetic acid;
9-[(5-benzyl-1-tetrazolylmethyl]-2-n-butyl-5-carbamoylcarbazol-4-yl}oxyacetic acid;
9-[(2-phenoxyphenyl)methyl]-2-n-pentyl-5-carbamoylcarbazol-4-yl}oxyacetic acid;
9-[(3-phenoxyphenyl)methyl]-2-n-pentyl-5-carbamoylcarbazol-4-yl}oxyacetic acid;
9-[(4-phenoxyphenyl)methyl]-2-n-pentyl-5-carbamoylcarbazol-4-yl}oxyacetic acid;
9-[(2-fluorophenyl)methyl]-2-n-pentyl-5-carbamoylcarbazol-4-yl}oxyacetic acid;
9-[(3-fluorophenyl)methyl]-2-n-pentyl-5-carbamoylcarbazol-4-yl}oxyacetic acid;
9-[(4-fluorophenyl)methyl]-2-n-pentyl-5-carbamoylcarbazol-4-yl}oxyacetic acid;
9-[(2-chlorophenyl)methyl]-2-n-pentyl-5-carbamoylcarbazol-4-yl}oxyacetic acid;
9-[(3-chlorophenyl)methyl]-2-n-pentyl-5-carbamoylcarbazol-4-yl}oxyacetic acid;
9-[(4-chlorophenyl)methyl]-2-n-pentyl-5-carbamoylcarbazol-4-yl}oxyacetic acid;
9-[(2-bromophenyl)methyl]-2-n-pentyl-5-carbamoylcarbazol-4-yl}oxyacetic acid;
9-[(3-bromophenyl)methyl]-2-n-pentyl-5-carbamoylcarbazol-4-yl}oxyacetic acid;
9-[(4-bromophenyl)methyl]-2-n-pentyl-5-carbamoylcarbazol-4-yl}oxyacetic acid;
9-[(2-iodophenyl)methyl]-2-n-pentyl-5-carbamoylcarbazol-4-yl}oxyacetic acid;
9-[(3-iodophenyl)methyl]-2-n-pentyl-5-carbamoylcarbazol-4-yl}oxyacetic acid;
9-[(4-iodophenyl)methyl]-2-n-pentyl-5-carbamoylcarbazol-4-yl}oxyacetic acid;
9-[(2-acetamidophenyl)methyl]-2-n-pentyl-5-carbamoylcarbazol-4-yl}oxyacetic acid;
9-[(3-acetamidophenyl)methyl]-2-n-pentyl-5-carbamoylcarbazol-4-yl}oxyacetic acid;
9-[(4-acetamidophenyl)methyl]-2-n-pentyl-5-carbamoylcarbazol-4-yl}oxyacetic acid;
9-[(2-carbamoylphenyl)methyl]-2-n-pentyl-5-carbamoylcarbazol-4-yl}oxyacetic acid;
9-[(3-carbamoylphenyl)methyl]-2-n-pentyl-5-carbamoylcarbazol-4-yl}oxyacetic acid;

9-[(4-carbamoylphenyl)methyl]-2-n-pentyl-5-carbamoylcarbazol-4-yl}oxyacetic acid;
9-[(2-methylsulfonylphenyl)methyl]-2-n-pentyl-5-carbamoylcarbazol-4-yl}oxyacetic acid;
9-[(3-methylsulfonylphenyl)methyl]-2-n-pentyl-5-carbamoylcarbazol-4-yl}oxyacetic acid;
9-[(4-methylsulfonylphenyl)methyl]-2-n-pentyl-5-carbamoylcarbazol-4-yl}oxyacetic acid;
9-[(2-methylphenyl)methyl]-2-n-pentyl-5-carbamoylcarbazol-4-yl}oxyacetic acid;
9-[(3-methylphenyl)methyl]-2-n-pentyl-5-carbamoylcarbazol-4-yl}oxyacetic acid;
9-[(4-methylphenyl)methyl]-2-n-pentyl-5-carbamoylcarbazol-4-yl}oxyacetic acid;
9-[(2-ethylphenyl)methyl]-2-n-pentyl-5-carbamoylcarbazol-4-yl}oxyacetic acid;
9-[(3-ethylphenyl)methyl]-2-n-pentyl-5-carbamoylcarbazol-4-yl}oxyacetic acid;
9-[(4-ethylphenyl)methyl]-2-n-pentyl-5-carbamoylcarbazol-4-yl}oxyacetic acid;
9-[(2-trifluoromethylphenyl)methyl]-2-n-pentyl-5-carbamoylcarbazol-4-yl}oxyacetic acid;
9-[(3-trifluoromethylphenyl)methyl]-2-n-pentyl-5-carbamoylcarbazol-4-yl}oxyacetic acid;
9-[(4-trifluoromethylphenyl)methyl]-2-n-pentyl-5-carbamoylcarbazol-4-yl}oxyacetic acid;
9-[(cyclopropyl)methyl]-2-n-pentyl-5-carbamoylcarbazol-4-yl}oxyacetic acid;
9-[(cyclobutyl)methyl]-2-n-pentyl-5-carbamoylcarbazol-4-yl}oxyacetic acid;
9-[(cyclopentyl)methyl]-2-n-pentyl-5-carbamoylcarbazol-4-yl}oxyacetic acid;
9-[(cyclohexyl)methyl]-2-n-pentyl-5-carbamoylcarbazol-4-yl}oxyacetic acid;
9-[(2-methoxyphenyl)methyl]-2-n-pentyl-5-carbamoylcarbazol-4-yl}oxyacetic acid;
9-[(3-methoxyphenyl)methyl]-2-n-pentyl-5-carbamoylcarbazol-4-yl}oxyacetic acid;
9-[(4-methoxyphenyl)methyl]-2-n-pentyl-5-carbamoylcarbazol-4-yl}oxyacetic acid;
9-[(2-ethoxyphenyl)methyl]-2-n-pentyl-5-carbamoylcarbazol-4-yl}oxyacetic acid;
9-[(3-ethoxyphenyl)methyl]-2-n-pentyl-5-carbamoylcarbazol-4-yl}oxyacetic acid;
9-[(4-ethoxyphenyl)methyl]-2-n-pentyl-5-carbamoylcarbazol-4-yl}oxyacetic acid;
9-[(2-trifluoromethoxyphenyl)methyl]-2-n-pentyl-5-carbamoylcarbazol-4-yl}oxyacetic acid;
9-[(3-trifluoromethoxyphenyl)methyl]-2-n-pentyl-5-carbamoylcarbazol-4-yl}oxyacetic acid;
9-[(4-trifluoromethoxyphenyl)methyl]-2-n-pentyl-5-carbamoylcarbazol-4-yl}oxyacetic acid;
9-[(2-difluoromethoxyphenyl)methyl]-2-n-pentyl-5-carbamoylcarbazol-4-yl}oxyacetic acid;
9-[(3-difluoromethoxyphenyl)methyl]-2-n-pentyl-5-carbamoylcarbazol-4-yl}oxyacetic acid;
9-[(4-difluoromethoxyphenyl)methyl]-2-n-pentyl-5-carbamoylcarbazol-4-yl}oxyacetic acid;
9-[(2-cyanophenyl)methyl]-2-n-pentyl-5-carbamoylcarbazol-4-yl}oxyacetic acid;
9-[(3-cyanophenyl)methyl]-2-n-pentyl-5-carbamoylcarbazol-4-yl}oxyacetic acid;
9-[(4-cyanophenyl)methyl]-2-n-pentyl-5-carbamoylcarbazol-4-yl}oxyacetic acid;
9-[(2-pyridyl)methyl]-2-n-pentyl-5-carbamoylcarbazol-4-yl}oxyacetic acid;
9-[(3-pyridyl)methyl]-2-n-pentyl-5-carbamoylcarbazol-4-yl}oxyacetic acid;
9-[(4-pyridyl)methyl]-2-n-pentyl-5-carbamoylcarbazol-4-yl}oxyacetic acid;
9-[(2-furyl)methyl]-2-n-pentyl-5-carbamoylcarbazol-4-yl}oxyacetic acid;
9-[(3-furyl)methyl]-2-n-pentyl-5-carbamoylcarbazol-4-yl}oxyacetic acid;
9-[(2-thienyl)methyl]-2-n-pentyl-5-carbamoylcarbazol-4-yl}oxyacetic acid;
9-[(3-thienyl)methyl]-2-n-pentyl-5-carbamoylcarbazol-4-yl}oxyacetic acid;
9-[(2-benzylphenyl)methyl]-2-n-pentyl-5-carbamoylcarbazol-4-yl}oxyacetic acid;
9-[(3-benzylphenyl)methyl]-2-n-pentyl-5-carbamoylcarbazol-4-yl}oxyacetic acid;
9-[(4-benzylphenyl)methyl]-2-n-pentyl-5-carbamoylcarbazol-4-yl}oxyacetic acid;
9-[(2-benzoylphenyl)methyl]-2-n-pentyl-5-carbamoylcarbazol-4-yl}oxyacetic acid;
9-[(3-benzoylphenyl)methyl]-2-n-pentyl-5-carbamoylcarbazol-4-yl}oxyacetic acid;
9-[(4-benzoylphenyl)methyl]-2-n-pentyl-5-carbamoylcarbazol-4-yl}oxyacetic acid;
9-[(2-benzyloxyphenyl)methyl]-2-n-pentyl-5-carbamoylcarbazol-4-yl}oxyacetic acid;
9-[(3-benzyloxyphenyl)methyl]-2-n-pentyl-5-carbamoylcarbazol-4-yl}oxyacetic acid;
9-[(4-benzyloxyphenyl)methyl]-2-n-pentyl-5-carbamoylcarbazol-4-yl}oxyacetic acid;
9-[(2-phenylphenyl)methyl]-2-n-pentyl-5-carbamoylcarbazol-4-yl}oxyacetic acid;
9-[(3-phenylphenyl)methyl]-2-n-pentyl-5-carbamoylcarbazol-4-yl}oxyacetic acid;
9-[(4-phenylphenyl)methyl]-2-n-pentyl-5-carbamoylcarbazol-4-yl}oxyacetic acid;
9-[(1-naphthyl)methyl]-2-n-pentyl-5-carbamoylcarbazol-4-yl}oxyacetic acid;
9-[(2-naphthyl)methyl]-2-n-pentyl-5-carbamoylcarbazol-4-yl}oxyacetic acid;
9-[(2,3-difluorophenyl)methyl]-2-n-pentyl-5-carbamoylcarbazol-4-yl}oxyacetic acid;
9-[(2,4-difluorophenyl)methyl]-2-n-pentyl-5-carbamoylcarbazol-4-yl}oxyacetic acid; 9-[(2,5-difluorophenyl)methyl]-2-n-pentyl-5-carbamoylcarbazol-4-yl}oxyacetic acid;
9-[(2,6-difluorophenyl)methyl]-2-n-pentyl-5-carbamoylcarbazol-4-yl}oxyacetic acid;
9-[(3,4-difluorophenyl)methyl]-2-n-pentyl-5-carbamoylcarbazol-4-yl}oxyacetic acid;
9-[(3,5-difluorophenyl)methyl]-2-n-pentyl-5-carbamoylcarbazol-4-yl}oxyacetic acid;
9-[(2,3,4-trifluorophenyl)methyl]-2-n-pentyl-5-carbamoylcarbazol-4-yl}oxyacetic acid;
9-[(2,3,5-trifluorophenyl)methyl]-2-n-pentyl-5-carbamoylcarbazol-4-yl}oxyacetic acid;
9-[(2,3,6-trifluorophenyl)methyl]-2-n-pentyl-5-carbamoylcarbazol-4-yl}oxyacetic acid;
9-[(2,4,5-trifluorophenyl)methyl]-2-n-pentyl-5-carbamoylcarbazol-4-yl}oxyacetic acid;
9-[(2,4,6-trifluorophenyl)methyl]-2-n-pentyl-5-carbamoylcarbazol-4-yl}oxyacetic acid;
9-[(3,4,5-trifluorophenyl)methyl]-2-n-pentyl-5-carbamoylcarbazol-4-yl}oxyacetic acid;
9-[(pentafluorophenyl)methyl]-2-n-pentyl-5-carbamoylcarbazol-4-yl}oxyacetic acid;
9-[(2,3-dichlorophenyl)methyl]-2-n-pentyl-5-carbamoylcarbazol-4-yl}oxyacetic acid;
9-[(2,4-dichlorophenyl)methyl]-2-n-pentyl-5-carbamoylcarbazol-4-yl}oxyacetic acid;

9-[(2,5-dichlorophenyl)methyl]-2-n-pentyl-5-carbamoylcarbazol-4-yl}oxyacetic acid;
9-[(2,6-dichlorophenyl)methyl]-2-n-pentyl-5-carbamoylcarbazol-4-yl}oxyacetic acid;
9-[(3,4-dichlorophenyl)methyl]-2-n-pentyl-5-carbamoylcarbazol-4-yl}oxyacetic acid;
9-[(3,5-dichlorophenyl)methyl]-2-n-pentyl-5-carbamoylcarbazol-4-yl}oxyacetic acid;
9-[(2,3-dimethylphenyl)methyl]-2-n-pentyl-5-carbamoylcarbazol-4-yl}oxyacetic acid;
9-[(2,4-dimethylphenyl)methyl]-2-n-pentyl-5-carbamoylcarbazol-4-yl}oxyacetic acid;
9-[(2,5-dimethylphenyl)methyl]-2-n-pentyl-5-carbamoylcarbazol-4-yl}oxyacetic acid;
9-[(2,6-dimethylphenyl)methyl]-2-n-pentyl-5-carbamoylcarbazol-4-yl}oxyacetic acid;
9-[(3,4-dimethylphenyl)methyl]-2-n-pentyl-5-carbamoylcarbazol-4-yl}oxyacetic acid;
9-[(3,5-dimethylphenyl)methyl]-2-n-pentyl-5-carbamoylcarbazol-4-yl}oxyacetic acid;
9-[(2,4,6-trimethylphenyl)methyl]-2-n-pentyl-5-carbamoylcarbazol-4-yl}oxyacetic acid;
9-[(3,5-bis(trifluoromethyl)phenyl)methyl]-2-n-pentyl-5-carbamoylcarbazol-4-yl}oxyacetic acid;
9-[(2,4-bis(trifluoromethyl)phenyl)methyl]-2-n-pentyl-5-carbamoylcarbazol-4-yl}oxyacetic acid;
9-[(2-fluoro-3-trifluoromethylphenyl)methyl]-2-n-pentyl-5-carbamoylcarbazol-4-yl}oxyacetic acid;
9-[(2-fluoro-4-trifluoromethylphenyl)methyl]-2-n-pentyl-5-carbamoylcarbazol-4-yl}oxyacetic acid;
9-[(2-fluoro-5-trifluoromethylphenyl)methyl]-2-n-pentyl-5-carbamoylcarbazol-4-yl}oxyacetic acid;
9-[(2-fluoro-6-trifluoromethylphenyl)methyl]-2-n-pentyl-5-carbamoylcarbazol-4-yl}oxyacetic acid;
9-[(3-fluoro-5-trifluoromethylphenyl)methyl]-2-n-pentyl-5-carbamoylcarbazol-4-yl}oxyacetic acid;
9-[(4-fluoro-2-trifluoromethylphenyl)methyl]-2-n-pentyl-5-carbamoylcarbazol-4-yl}oxyacetic acid;
9-[(4-fluoro-3-trifluoromethylphenyl)methyl]-2-n-pentyl-5-carbamoylcarbazol-4-yl}oxyacetic acid;
9-[3-(2-fluorophenoxy)methyl]-2-n-pentyl-5-carbamoylcarbazol-4-yl}oxyacetic acid;
9-[3-(4-fluorophenoxy)methyl]-2-n-pentyl-5-carbamoylcarbazol-4-yl}oxyacetic acid;
9-[(2-fluoro-3-methylphenyl)methyl]-2-n-pentyl-5-carbamoylcarbazol-4-yl}oxyacetic acid;
9-[(3-chloro-2-fluorophenyl)methyl]-2-n-pentyl-5-carbamoylcarbazol-4-yl}oxyacetic acid;
9-[(2-chloro-6-fluorophenyl)methyl]-2-n-pentyl-5-carbamoylcarbazol-4-yl}oxyacetic acid;
9-[(4-bromo-2-fluorophenyl)methyl]-2-n-pentyl-5-carbamoylcarbazol-4-yl}oxyacetic acid;
9-[(2-bromo-5-fluorophenyl)methyl]-2-n-pentyl-5-carbamoylcarbazol-4-yl}oxyacetic acid;
9-[(3-chloro-4-methylphenyl)methyl]-2-n-pentyl-5-carbamoylcarbazol-4-yl}oxyacetic acid;
9-[(3-chloro-4-methoxyphenyl)methyl]-2-n-pentyl-5-carbamoylcarbazol-4-yl}oxyacetic acid;
9-[(4-methoxy-3-methylphenyl)methyl]-2-n-pentyl-5-carbamoylcarbazol-4-yl}oxyacetic acid;
9-[(4-trifluoromethylthiophenyl)methyl]-2-n-pentyl-5-carbamoylcarbazol-4-yl}oxyacetic acid;
9-[(1-bromo-2-naphthylphenyl)methyl]-2-n-pentyl-5-carbamoylcarbazol-4-yl}oxyacetic acid;
9-[(2-methyl-1-naphthylphenyl)methyl]-2-n-pentyl-5-carbamoylcarbazol-4-yl}oxyacetic acid;
9-[(4-methyl-1-naphthylphenyl)methyl]-2-n-pentyl-5-carbamoylcarbazol-4-yl}oxyacetic acid;
9-[(6-methyl-2-naphthylphenyl)methyl]-2-n-pentyl-5-carbamoylcarbazol-4-yl}oxyacetic acid;
9-[(2-((phenylsulfonyl)methyl)phenyl)methyl]-2-n-pentyl-5-carbamoylcarbazol-4-yl}oxyacetic acid;
9-[(1-fluorenylmethyl]-2-n-pentyl-5-carbamoylcarbazol-4-yl}oxyacetic acid;
9-[(1-tetrazolylmethyl]-2-n-pentyl-5-carbamoylcarbazol-4-yl}oxyacetic acid;
9-[(5-methyl-1-tetrazolylmethyl]-2-n-pentyl-5-carbamoylcarbazol-4-yl}oxyacetic acid;
9-[(5-benzyl-1-tetrazolylmethyl]-2-n-pentyl-5-carbamoylcarbazol-4-yl}oxyacetic acid;
9-[(phenyl)methyl]-2-trifluoromethyl-5-carbamoylcarbazol-4-yl}oxyacetic acid;
9-[(2-phenoxyphenyl)methyl]-2-trifluoromethyl-5-carbamoylcarbazol-4-yl}oxyacetic acid;
9-[(3-phenoxyphenyl)methyl]-2-trifluoromethyl-5-carbamoylcarbazol-4-yl}oxyacetic acid;
9-[(4-phenoxyphenyl)methyl]-2-trifluoromethyl-5-carbamoylcarbazol-4-yl}oxyacetic acid;
9-[(2-fluorophenyl)methyl]-2-trifluoromethyl-5-carbamoylcarbazol-4-yl}oxyacetic acid;
9-[(3-fluorophenyl)methyl]-2-trifluoromethyl-5-carbamoylcarbazol-4-yl}oxyacetic acid;
9-[(4-fluorophenyl)methyl]-2-trifluoromethyl-5-carbamoylcarbazol-4-yl}oxyacetic acid;
9-[(2-chlorophenyl)methyl]-2-trifluoromethyl-5-carbamoylcarbazol-4-yl}oxyacetic acid;
9-[(3-chlorophenyl)methyl]-2-trifluoromethyl-5-carbamoylcarbazol-4-yl}oxyacetic acid;
9-[(4-chlorophenyl)methyl]-2-trifluoromethyl-5-carbamoylcarbazol-4-yl}oxyacetic acid;
9-[(2-bromophenyl)methyl]-2-trifluoromethyl-5-carbamoylcarbazol-4-yl}oxyacetic acid;
9-[(3-bromophenyl)methyl]-2-trifluoromethyl-5-carbamoylcarbazol-4-yl}oxyacetic acid;
9-[(4-bromophenyl)methyl]-2-trifluoromethyl-5-carbamoylcarbazol-4-yl}oxyacetic acid;
9-[(2-iodophenyl)methyl]-2-trifluoromethyl-5-carbamoylcarbazol-4-yl}oxyacetic acid;
9-[(3-iodophenyl)methyl]-2-trifluoromethyl-5-carbamoylcarbazol-4-yl}oxyacetic acid;
9-[(4-iodophenyl)methyl]-2-trifluoromethyl-5-carbamoylcarbazol-4-yl}oxyacetic acid;
9-[(2-acetamidophenyl)methyl]-2-trifluoromethyl-5-carbamoylcarbazol-4-yl}oxyacetic acid;
9-[(3-acetamidophenyl)methyl]-2-trifluoromethyl-5-carbamoylcarbazol-4-yl}oxyacetic acid;
9-[(4-acetamidophenyl)methyl]-2-trifluoromethyl-5-carbamoylcarbazol-4-yl}oxyacetic acid;
9-[(2-carbamoylphenyl)methyl]-2-trifluoromethyl-5-carbamoylcarbazol-4-yl}oxyacetic acid;
9-[(3-carbamoylphenyl)methyl]-2-trifluoromethyl-5-carbamoylcarbazol-4-yl}oxyacetic acid;
9-[(4-carbamoylphenyl)methyl]-2-trifluoromethyl-5-carbamoylcarbazol-4-yl}oxyacetic acid;
9-[(2-methylsulfonylphenyl)methyl]-2-trifluoromethyl-5-carbamoylcarbazol-4-yl}oxyacetic acid;
9-[(3-methylsulfonylphenyl)methyl]-2-trifluoromethyl-5-carbamoylcarbazol-4-yl}oxyacetic acid;
9-[(4-methylsulfonylphenyl)methyl]-2-trifluoromethyl-5-carbamoylcarbazol-4-yl}oxyacetic acid;
9-[(2-methylphenyl)methyl]-2-trifluoromethyl-5-carbamoylcarbazol-4-yl}oxyacetic acid;
9-[(3-methylphenyl)methyl]-2-trifluoromethyl-5-carbamoylcarbazol-4-yl}oxyacetic acid;
9-[(4-methylphenyl)methyl]-2-trifluoromethyl-5-carbamoylcarbazol-4-yl}oxyacetic acid;

9-[(2-ethylphenyl)methyl]-2-trifluoromethyl-5-carbamoylcarbazol-4-yl}oxyacetic acid;
9-[(3-ethylphenyl)methyl]-2-trifluoromethyl-5-carbamoylcarbazol-4-yl}oxyacetic acid;
9-[(4-ethylphenyl)methyl]-2-trifluoromethyl-5-carbamoylcarbazol-4-yl}oxyacetic acid;
9-[(2-trifluoromethylphenyl)methyl]-2-trifluoromethyl-5-carbamoylcarbazol-4-yl}oxyacetic acid;
9-[(3-trifluoromethylphenyl)methyl]-2-trifluoromethyl-5-carbamoylcarbazol-4-yl}oxyacetic acid;
9-[(4-trifluoromethylphenyl)methyl]-2-trifluoromethyl-5-carbamoylcarbazol-4-yl}oxyacetic acid;
9-[(cyclopropyl)methyl]-2-trifluoromethyl-5-carbamoylcarbazol-4-yl}oxyacetic acid;
9-[(cyclobutyl)methyl]-2-trifluoromethyl-5-carbamoylcarbazol-4-yl}oxyacetic acid;
9-[(cyclopentyl)methyl]-2-trifluoromethyl-5-carbamoylcarbazol-4-yl}oxyacetic acid;
9-[(cyclohexyl)methyl]-2-trifluoromethyl-5-carbamoylcarbazol-4-yl}oxyacetic acid;
9-[(2-methoxyphenyl)methyl]-2-trifluoromethyl-5-carbamoylcarbazol-4-yl}oxyacetic acid;
9-[(3-methoxyphenyl)methyl]-2-trifluoromethyl-5-carbamoylcarbazol-4-yl}oxyacetic acid;
9-[(4-methoxyphenyl)methyl]-2-trifluoromethyl-5-carbamoylcarbazol-4-yl}oxyacetic acid;
9-[(2-ethoxyphenyl)methyl]-2-trifluoromethyl-5-carbamoylcarbazol-4-yl}oxyacetic acid;
9-[(3-ethoxyphenyl)methyl]-2-trifluoromethyl-5-carbamoylcarbazol-4-yl}oxyacetic acid;
9-[(4-ethoxyphenyl)methyl]-2-trifluoromethyl-5-carbamoylcarbazol-4-yl}oxyacetic acid;
9-[(2-trifluoromethoxyphenyl)methyl]-2-trifluoromethyl-5-carbamoylcarbazol-4-yl}oxyacetic acid;
9-[(3-trifluoromethoxyphenyl)methyl]-2-trifluoromethyl-5-carbamoylcarbazol-4-yl}oxyacetic acid;
9-[(4-trifluoromethoxyphenyl)methyl]-2-trifluoromethyl-5-carbamoylcarbazol-4-yl}oxyacetic acid;
9-[(2-difluoromethoxyphenyl)methyl]-2-trifluoromethyl-5-carbamoylcarbazol-4-yl}oxyacetic acid;
9-[(3-difluoromethoxyphenyl)methyl]-2-trifluoromethyl-5-carbamoylcarbazol-4-yl}oxyacetic acid;
9-[(4-difluoromethoxyphenyl)methyl]-2-trifluoromethyl-5-carbamoylcarbazol-4-yl}oxyacetic acid;
9-[(2-cyanophenyl)methyl]-2-trifluoromethyl-5-carbamoylcarbazol-4-yl}oxyacetic acid;
9-[(3-cyanophenyl)methyl]-2-trifluoromethyl-5-carbamoylcarbazol-4-yl}oxyacetic acid;
9-[(4-cyanophenyl)methyl]-2-trifluoromethyl-5-carbamoylcarbazol-4-yl}oxyacetic acid;
9-[(2-pyridyl)methyl]-2-trifluoromethyl-5-carbamoylcarbazol-4-yl}oxyacetic acid;
9-[(3-pyridyl)methyl]-2-trifluoromethyl-5-carbamoylcarbazol-4-yl}oxyacetic acid;
9-[(4-pyridyl)methyl]-2-trifluoromethyl-5-carbamoylcarbazol-4-yl}oxyacetic acid;
9-[(2-furyl)methyl]-2-trifluoromethyl-5-carbamoylcarbazol-4-yl}oxyacetic acid;
9-[(3-furyl)methyl]-2-trifluoromethyl-5-carbamoylcarbazol-4-yl}oxyacetic acid;
9-[(2-thienyl)methyl]-2-trifluoromethyl-5-carbamoylcarbazol-4-yl}oxyacetic acid;
9-[(3-thienyl)methyl]-2-trifluoromethyl-5-carbamoylcarbazol-4-yl}oxyacetic acid;
9-[(2-benzylphenyl)methyl]-2-trifluoromethyl-5-carbamoylcarbazol-4-yl}oxyacetic acid;
9-[(3-benzylphenyl)methyl]-2-trifluoromethyl-5-carbamoylcarbazol-4-yl}oxyacetic acid;
9-[(4-benzylphenyl)methyl]-2-trifluoromethyl-5-carbamoylcarbazol-4-yl}oxyacetic acid;
9-[(2-benzoylphenyl)methyl]-2-trifluoromethyl-5-carbamoylcarbazol-4-yl}oxyacetic acid;
9-[(3-benzoylphenyl)methyl]-2-trifluoromethyl-5-carbamoylcarbazol-4-yl}oxyacetic acid;
9-[(4-benzoylphenyl)methyl]-2-trifluoromethyl-5-carbamoylcarbazol-4-yl}oxyacetic acid;
9-[(2-benzyloxyphenyl)methyl]-2-trifluoromethyl-5-carbamoylcarbazol-4-yl}oxyacetic acid;
9-[(3-benzyloxyphenyl)methyl]-2-trifluoromethyl-5-carbamoylcarbazol-4-yl}oxyacetic acid;
9-[(4-benzyloxyphenyl)methyl]-2-trifluoromethyl-5-carbamoylcarbazol-4-yl}oxyacetic acid;
9-[(2-phenylphenyl)methyl]-2-trifluoromethyl-5-carbamoylcarbazol-4-yl}oxyacetic acid;
9-[(3-phenylphenyl)methyl]-2-trifluoromethyl-5-carbamoylcarbazol-4-yl}oxyacetic acid;
9-[(4-phenylphenyl)methyl]-2-trifluoromethyl-5-carbamoylcarbazol-4-yl}oxyacetic acid;,
9-[(1-naphthyl)methyl]-2-trifluoromethyl-5-carbamoylcarbazol-4-yl}oxyacetic acid;
9-[(2-naphthyl)methyl]-2-trifluoromethyl-5-carbamoylcarbazol-4-yl}oxyacetic acid;
9-[(2,3-difluorophenyl)methyl]-2-trifluoromethyl-5-carbamoylcarbazol-4-yl}oxyacetic acid;
9-[(2,4-difluorophenyl)methyl]-2-trifluoromethyl-5-carbamoylcarbazol-4-yl}oxyacetic acid;
9-[(2,5-difluorophenyl)methyl]-2-trifluoromethyl-5-carbamoylcarbazol-4-yl}oxyacetic acid;
9-[(2,6-difluorophenyl)methyl]-2-trifluoromethyl-5-carbamoylcarbazol-4-yl}oxyacetic acid;
9-[(3,4-difluorophenyl)methyl]-2-trifluoromethyl-5-carbamoylcarbazol-4-yl}oxyacetic acid;
9-[(3,5-difluorophenyl)methyl]-2-trifluoromethyl-5-carbamoylcarbazol-4-yl}oxyacetic acid;
9-[(2,3,4-trifluorophenyl)methyl]-2-trifluoromethyl-5-carbamoylcarbazol-4-yl}oxyacetic acid;
9-[(2,3,5-trifluorophenyl)methyl]-2-trifluoromethyl-5-carbamoylcarbazol-4-yl}oxyacetic acid;
9-[(2,3,6-trifluorophenyl)methyl]-2-trifluoromethyl-5-carbamoylcarbazol-4-yl}oxyacetic acid;
9-[(2,4,5-trifluorophenyl)methyl]-2-trifluoromethyl-5-carbamoylcarbazol-4-yl}oxyacetic acid;
9-[(2,4,6-trifluorophenyl)methyl]-2-trifluoromethyl-5-carbamoylcarbazol-4-yl}oxyacetic acid;
9-[(3,4,5-trifluorophenyl)methyl]-2-trifluoromethyl-5-carbamoylcarbazol-4-yl}oxyacetic acid;
9-[(pentafluorophenyl)methyl]-2-trifluoromethyl-5-carbamoylcarbazol-4-yl}oxyacetic acid;
9-[(2,3-dichlorophenyl)methyl]-2-trifluoromethyl-5-carbamoylcarbazol-4-yl}oxyacetic acid;
9-[(2,4-dichlorophenyl)methyl]-2-trifluoromethyl-5-carbamoylcarbazol-4-yl}oxyacetic acid;
9-[(2,5-dichlorophenyl)methyl]-2-trifluoromethyl-5-carbamoylcarbazol-4-yl}oxyacetic acid;
9-[(2,6-dichlorophenyl)methyl]-2-trifluoromethyl-5-carbamoylcarbazol-4-yl}oxyacetic acid;
9-[(3,4-dichlorophenyl)methyl]-2-trifluoromethyl-5-carbamoylcarbazol-4-yl}oxyacetic acid;
9-[(3,5-dichlorophenyl)methyl]-2-trifluoromethyl-5-carbamoylcarbazol-4-yl}oxyacetic acid;
9-[(2,3-dimethylphenyl)methyl]-2-trifluoromethyl-5-carbamoylcarbazol-4-yl}oxyacetic acid;
9-[(2,4-dimethylphenyl)methyl]-2-trifluoromethyl-5-carbamoylcarbazol-4-yl}oxyacetic acid;
9-[(2,5-dimethylphenyl)methyl]-2-trifluoromethyl-5-carbamoylcarbazol-4-yl}oxyacetic acid;

9-[(2,6-dimethylphenyl)methyl]-2-trifluoromethyl-5-carbamoylcarbazol-4-yl}oxyacetic acid;
9-[(3,4-dimethylphenyl)methyl]-2-trifluoromethyl-5-carbamoylcarbazol-4-yl}oxyacetic acid;
9-[(3,5-dimethylphenyl)methyl]-2-trifluoromethyl-5-carbamoylcarbazol-4-yl}oxyacetic acid;
9-[(2,4,6-trimethylphenyl)methyl]-2-trifluoromethyl-5-carbamoylcarbazol-4-yl}oxyacetic acid;
9-[(3,5-bis(trifluoromethyl)phenyl)methyl]-2-trifluoromethyl-5-carbamoylcarbazol-4-yl}oxyacetic acid;
9-[(2,4-bis(trifluoromethyl)phenyl)methyl]-2-trifluoromethyl-5-carbamoylcarbazol-4-yl}oxyacetic acid;
9-[(2-fluoro-3-trifluoromethylphenyl)methyl]-2-trifluoromethyl-5-carbamoylcarbazol-4-yl}oxyacetic acid;
9-[(2-fluoro-4-trifluoromethylphenyl)methyl]-2-trifluoromethyl-5-carbamoylcarbazol-4-yl}oxyacetic acid;
9-[(2-fluoro-5-trifluoromethylphenyl)methyl]-2-trifluoromethyl-5-carbamoylcarbazol-4-yl}oxyacetic acid;
9-[(2-fluoro-6-trifluoromethylphenyl)methyl]-2-trifluoromethyl-5-carbamoylcarbazol-4-yl}oxyacetic acid;
9-[(3-fluoro-5-trifluoromethylphenyl)methyl]-2-trifluoromethyl-5-carbamoylcarbazol-4-yl}oxyacetic acid;
9-[(4-fluoro-2-trifluoromethylphenyl)methyl]-2-trifluoromethyl-5-carbamoylcarbazol-4-yl}oxyacetic acid;
9-[(4-fluoro-3-trifluoromethylphenyl)methyl]-2-trifluoromethyl-5-carbamoylcarbazol-4-yl}oxyacetic acid;
9-[3-(2-fluorophenoxy)methyl]-2-trifluoromethyl-5-carbamoylcarbazol-4-yl}oxyacetic acid;
9-[3-(4-fluorophenoxy)methyl]-2-trifluoromethyl-5-carbamoylcarbazol-4-yl}oxyacetic acid;
9-[(2-fluoro-3-methylphenyl)methyl]-2-trifluoromethyl-5-carbamoylcarbazol-4-yl}oxyacetic acid;
9-[(3-chloro-2-fluorophenyl)methyl]-2-trifluoromethyl-5-carbamoylcarbazol-4-yl}oxyacetic acid;
9-[(2-chloro-6-fluorophenyl)methyl]-2-trifluoromethyl-5-carbamoylcarbazol-4-yl}oxyacetic acid;
9-[(4-bromo-2-fluorophenyl)methyl]-2-trifluoromethyl-5-carbamoylcarbazol-4-yl}oxyacetic acid;
9-[(2-bromo-5-fluorophenyl)methyl]-2-trifluoromethyl-5-carbamoylcarbazol-4-yl}oxyacetic acid;
9-[(3-chloro-4-methylphenyl)methyl]-2-trifluoromethyl-5-carbamoylcarbazol-4-yl}oxyacetic acid;
9-[(3-chloro-4-methoxyphenyl)methyl]-2-trifluoromethyl-5-carbamoylcarbazol-4-yl}oxyacetic acid;
9-[(4-methoxy-3-methylphenyl)methyl]-2-trifluoromethyl-5-carbamoylcarbazol-4-yl}oxyacetic acid;
9-[(4-trifluoromethylthiophenyl)methyl]-2-trifluoromethyl-5-carbamoylcarbazol-4-yl}oxyacetic acid;
9-[(1-bromo-2-naphthylphenyl)methyl]-2-trifluoromethyl-5-carbamoylcarbazol-4-yl}oxyacetic acid;
9-[(2-methyl-1-naphthylphenyl)methyl]-2-trifluoromethyl-5-carbamoylcarbazol-4-yl}oxyacetic acid;
9-[(4-methyl-1-naphthylphenyl)methyl]-2-trifluoromethyl-5-carbamoylcarbazol-4-yl}oxyacetic acid;
9-[(6-methyl-2-naphthylphenyl)methyl]-2-trifluoromethyl-5-carbamoylcarbazol-4-yl}oxyacetic acid;
9-[(2-((phenylsulfonyl)methyl)phenyl)methyl]-2-trifluoromethyl-5-carbamoylcarbazol-4-yl}oxyacetic acid;
9-[(1-fluorenylmethyl)-2-trifluoromethyl-5-carbamoylcarbazol-4-yl}oxyacetic acid;
9-[(1-tetrazolylmethyl)-2-trifluoromethyl-5-carbamoylcarbazol-4-yl}oxyacetic acid;
9-[(5-methyl-1-tetrazolylmethyl)-2-trifluoromethyl-5-carbamoylcarbazol-4-yl}oxyacetic acid;
9-[(5-benzyl-1-tetrazolylmethyl)-2-trifluoromethyl-5-carbamoylcarbazol-4-yl}oxyacetic acid;
9-[(phenyl)methyl]-2-phenyl-5-carbamoylcarbazol-4-yl}oxyacetic acid;
9-[(2-phenoxyphenyl)methyl]-2-phenyl-5-carbamoylcarbazol-4-yl}oxyacetic acid;
9-[(3-phenoxyphenyl)methyl]-2-phenyl-5-carbamoylcarbazol-4-yl}oxyacetic acid;
9-[(4-phenoxyphenyl)methyl]-2-phenyl-5-carbamoylcarbazol-4-yl}oxyacetic acid;
9-[(2-fluorophenyl)methyl]-2-phenyl-5-carbamoylcarbazol-4-yl}oxyacetic acid;
9-[(3-fluorophenyl)methyl]-2-phenyl-5-carbamoylcarbazol-4-yl}oxyacetic acid;
9-[(4-fluorophenyl)methyl]-2-phenyl-5-carbamoylcarbazol-4-yl}oxyacetic acid;
9-[(2-chlorophenyl)methyl]-2-phenyl-5-carbamoylcarbazol-4-yl}oxyacetic acid;
9-[(3-chlorophenyl)methyl]-2-phenyl-5-carbamoylcarbazol-4-yl}oxyacetic acid;
9-[(4-chlorophenyl)methyl]-2-phenyl-5-carbamoylcarbazol-4-yl}oxyacetic acid;
9-[(2-bromophenyl)methyl]-2-phenyl-5-carbamoylcarbazol-4-yl}oxyacetic acid;
9-[(3-bromophenyl)methyl]-2-phenyl-5-carbamoylcarbazol-4-yl}oxyacetic acid;
9-[(4-bromophenyl)methyl]-2-phenyl-5-carbamoylcarbazol-4-yl}oxyacetic acid;
9-[(2-iodophenyl)methyl]-2-phenyl-5-carbamoylcarbazol-4-yl}oxyacetic acid;
9-[(3-iodophenyl)methyl]-2-phenyl-5-carbamoylcarbazol-4-yl}oxyacetic acid;
9-[(4-iodophenyl)methyl]-2-phenyl-5-carbamoylcarbazol-4-yl}oxyacetic acid;
9-[(2-acetamidophenyl)methyl]-2-phenyl-5-carbamoylcarbazol-4-yl}oxyacetic acid;
9-[(3-acetamidophenyl)methyl]-2-phenyl-5-carbamoylcarbazol-4-yl}oxyacetic acid;
9-[(4-acetamidophenyl)methyl]-2-phenyl-5-carbamoylcarbazol-4-yl}oxyacetic acid;
9-[(2-carbamoylphenyl)methyl]-2-phenyl-5-carbamoylcarbazol-4-yl}oxyacetic acid;
9-[(3-carbamoylphenyl)methyl]-2-phenyl-5-carbamoylcarbazol-4-yl}oxyacetic acid;
9-[(4-carbamoylphenyl)methyl]-2-phenyl-5-carbamoylcarbazol-4-yl}oxyacetic acid;
9-[(2-methylsulfonylphenyl)methyl]-2-phenyl-5-carbamoylcarbazol-4-yl}oxyacetic acid;
9-[(3-methylsulfonylphenyl)methyl]-2-phenyl-5-carbamoylcarbazol-4-yl}oxyacetic acid;
9-[(4-methylsulfonylphenyl)methyl]-2-phenyl-5-carbamoylcarbazol-4-yl}oxyacetic acid;
9-[(2-methylphenyl)methyl]-2-phenyl-5-carbamoylcarbazol-4-yl}oxyacetic acid;
9-[(3-methylphenyl)methyl]-2-phenyl-5-carbamoylcarbazol-4-yl}oxyacetic acid;
9-[(4-methylphenyl)methyl]-2-phenyl-5-carbamoylcarbazol-4-yl}oxyacetic acid;
9-[(2-ethylphenyl)methyl]-2-phenyl-5-carbamoylcarbazol-4-yl}oxyacetic acid;
9-[(3-ethylphenyl)methyl]-2-phenyl-5-carbamoylcarbazol-4-yl}oxyacetic acid;

9-[(4-ethylphenyl)methyl]-2-phenyl-5-carbamoylcarbazol-4-yl}oxyacetic acid;
9-[(2-trifluoromethylphenyl)methyl]-2-phenyl-5-carbamoylcarbazol-4-yl}oxyacetic acid;
9-[(3-trifluoromethylphenyl)methyl]-2-phenyl-5-carbamoylcarbazol-4-yl}oxyacetic acid;
9-[(4-trifluoromethylphenyl)methyl]-2-phenyl-5-carbamoylcarbazol-4-yl}oxyacetic acid;
9-[(cyclopropyl)methyl]-2-phenyl-5-carbamoylcarbazol-4-yl}oxyacetic acid;
9-[(cyclobutyl)methyl]-2-phenyl-5-carbamoylcarbazol-4-yl}oxyacetic acid;
9-[(cyclopentyl)methyl]-2-phenyl-5-carbamoylcarbazol-4-yl}oxyacetic acid;
9-[(cyclohexyl)methyl]-2-phenyl-5-carbamoylcarbazol-4-yl}oxyacetic acid;
9-[(2-methoxyphenyl)methyl]-2-phenyl-5-carbamoylcarbazol-4-yl}oxyacetic acid;
9-[(3-methoxyphenyl)methyl]-2-phenyl-5-carbamoylcarbazol-4-yl}oxyacetic acid
9-[(4-methoxyphenyl)methyl]-2-phenyl-5-carbamoylcarbazol-4-yl}oxyacetic acid;
9-[(2-ethoxyphenyl)methyl]-2-phenyl-5-carbamoylcarbazol-4-yl}oxyacetic acid;
9-[(3-ethoxyphenyl)methyl]-2-phenyl-5-carbamoylcarbazol-4-yl}oxyacetic acid;
9-[(4-ethoxyphenyl)methyl]-2-phenyl-5-carbamoylcarbazol-4-yl}oxyacetic acid;
9-[(2-trifluoromethoxyphenyl)methyl]-2-phenyl-5-carbamoylcarbazol-4-yl}oxyacetic acid;
9-[(3-trifluoromethoxyphenyl)methyl]-2-phenyl-5-carbamoylcarbazol-4-yl}oxyacetic acid;
9-[(4-trifluoromethoxyphenyl)methyl]-2-phenyl-5-carbamoylcarbazol-4-yl}oxyacetic acid;
9-[(2-difluoromethoxyphenyl)methyl]-2-phenyl-5-carbamoylcarbazol-4-yl}oxyacetic acid;
9-[(3-difluoromethoxyphenyl)methyl]-2-phenyl-5-carbamoylcarbazol-4-yl}oxyacetic acid;
9-[(4-difluoromethoxyphenyl)methyl]-2-phenyl-5-carbamoylcarbazol-4-yl}oxyacetic acid;
9-[(2-cyanophenyl)methyl]-2-phenyl-5-carbamoylcarbazol-4-yl}oxyacetic acid;
9-[(3-cyanophenyl)methyl]-2-phenyl-5-carbamoylcarbazol-4-yl}oxyacetic acid;
9-[(4-cyanophenyl)methyl]-2-phenyl-5-carbamoylcarbazol-4-yl}oxyacetic acid;
9-[(2-pyridyl)methyl]-2-phenyl-5-carbamoylcarbazol-4-yl}oxyacetic acid;
9-[(3-pyridyl)methyl]-2-phenyl-5-carbamoylcarbazol-4-yl}oxyacetic acid;
9-[(4-pyridyl)methyl]-2-phenyl-5-carbamoylcarbazol-4-yl}oxyacetic acid;
9-[(2-furyl)methyl]-2-phenyl-5-carbamoylcarbazol-4-yl}oxyacetic acid;
9-[(3-furyl)methyl]-2-phenyl-5-carbamoylcarbazol-4-yl}oxyacetic acid;
9-[(2-thienyl)methyl]-2-phenyl-5-carbamoylcarbazol-4-yl}oxyacetic acid;
9-[(3-thienyl)methyl]-2-phenyl-5-carbamoylcarbazol-4-yl}oxyacetic acid;
9-[(2-benzylphenyl)methyl]-2-phenyl-5-carbamoylcarbazol-4-yl}oxyacetic acid;
9-[(3-benzylphenyl)methyl]-2-phenyl-5-carbamoylcarbazol-4-yl}oxyacetic acid;
9-[(4-benzylphenyl)methyl]-2-phenyl-5-carbamoylcarbazol-4-yl}oxyacetic acid;
9-[(2-benzoylphenyl)methyl]-2-phenyl-5-carbamoylcarbazol-4-yl}oxyacetic acid;
9-[(3-benzoylphenyl)methyl]-2-phenyl-5-carbamoylcarbazol-4-yl}oxyacetic acid;
9-[(4-benzoylphenyl)methyl]-2-phenyl-5-carbamoylcarbazol-4-yl}oxyacetic acid;
9-[(2-benzyloxyphenyl)methyl]-2-phenyl-5-carbamoylcarbazol-4-yl}oxyacetic acid;
9-[(3-benzyloxyphenyl)methyl]-2-phenyl-5-carbamoylcarbazol-4-yl}oxyacetic acid;
9-[(4-benzyloxyphenyl)methyl]-2-phenyl-5-carbamoylcarbazol-4-yl}oxyacetic acid;
9-[(2-phenylphenyl)methyl]-2-phenyl-5-carbamoylcarbazol-4-yl}oxyacetic acid;
9-[(3-phenylphenyl)methyl]-2-phenyl-5-carbamoylcarbazol-4-yl}oxyacetic acid;
9-[(4-phenylphenyl)methyl]-2-phenyl-5-carbamoylcarbazol-4-yl}oxyacetic acid;
9-[(1-naphthyl)methyl]-2-phenyl-5-carbamoylcarbazol-4-yl}oxyacetic acid;
9-[(2-naphthyl)methyl]-2-phenyl-5-carbamoylcarbazol-4-yl}oxyacetic acid;
9-[(2,3-difluorophenyl)methyl]-2-phenyl-5-carbamoylcarbazol-4-yl}oxyacetic acid;
9-[(2,4-difluorophenyl)methyl]-2-phenyl-5-carbamoylcarbazol-4-yl}oxyacetic acid;
9-[(2,5-difluorophenyl)methyl]-2-phenyl-5-carbamoylcarbazol-4-yl}oxyacetic acid;
9-[(2,6-difluorophenyl)methyl]-2-phenyl-5-carbamoylcarbazol-4-yl}oxyacetic acid;
9-[(3,4-difluorophenyl)methyl]-2-phenyl-5-carbamoylcarbazol-4-yl}oxyacetic acid;
9-[(3,5-difluorophenyl)methyl]-2-phenyl-5-carbamoylcarbazol-4-yl}oxyacetic acid;
9-[(2,3,4-trifluorophenyl)methyl]-2-phenyl-5-carbamoylcarbazol-4-yl}oxyacetic acid;
9-[(2,3,5-trifluorophenyl)methyl]-2-phenyl-5-carbamoylcarbazol-4-yl}oxyacetic acid;
9-[(2,3,6-trifluorophenyl)methyl]-2-phenyl-5-carbamoylcarbazol-4-yl}oxyacetic acid;
9-[(2,4,5-trifluorophenyl)methyl]-2-phenyl-5-carbamoylcarbazol-4-yl}oxyacetic acid;
9-[(2,4,6-trifluorophenyl)methyl]-2-phenyl-5-carbamoylcarbazol-4-yl}oxyacetic acid;
9-[(3,4,5-trifluorophenyl)methyl]-2-phenyl-5-carbamoylcarbazol-4-yl}oxyacetic acid;
9-[(pentafluorophenyl)methyl]-2-phenyl-5-carbamoylcarbazol-4-yl}oxyacetic acid;
9-[(2,3-dichlorophenyl)methyl]-2-phenyl-5-carbamoylcarbazol-4-yl}oxyacetic acid;
9-[(2,4-dichlorophenyl)methyl]-2-phenyl-5-carbamoylcarbazol-4-yl}oxyacetic acid;
9-[(2,5-dichlorophenyl)methyl]-2-phenyl-5-carbamoylcarbazol-4-yl}oxyacetic acid;
9-[(2,6-dichlorophenyl)methyl]-2-phenyl-5-carbamoylcarbazol-4-yl}oxyacetic acid;
9-[(3,4-dichlorophenyl)methyl]-2-phenyl-5-carbamoylcarbazol-4-yl}oxyacetic acid;
9-[(3,5-dichlorophenyl)methyl]-2-phenyl-5-carbamoylcarbazol-4-yl}oxyacetic acid;
9-[(2,3-dimethylphenyl)methyl]-2-phenyl-5-carbamoylcarbazol-4-yl}oxyacetic acid;
9-[(2,4-dimethylphenyl)methyl]-2-phenyl-5-carbamoylcarbazol-4-yl}oxyacetic acid;
9-[(2,5-dimethylphenyl)methyl]-2-phenyl-5-carbamoylcarbazol-4-yl}oxyacetic acid;
9-[(2,6-dimethylphenyl)methyl]-2-phenyl-5-carbamoylcarbazol-4-yl}oxyacetic acid;
9-[(3,4-dimethylphenyl)methyl]-2-phenyl-5-carbamoylcarbazol-4-yl}oxyacetic acid;

9-[(3,5-dimethylphenyl)methyl]-2-phenyl-5-carbamoylcarbazol-4-yl}oxyacetic acid;
9-[(2,4,6-trimethylphenyl)methyl]-2-phenyl-5-carbamoylcarbazol-4-yl}oxyacetic acid;
9-[(3,5-bis(trifluoromethyl)phenyl)methyl]-2-phenyl-5-carbamoylcarbazol-4-yl}oxyacetic acid;
9-[(2,4-bis(trifluoromethyl)phenyl)methyl]-2-phenyl-5-carbamoylcarbazol-4-yl}oxyacetic acid;
9-[(2-fluoro-3-trifluoromethylphenyl)methyl]-2-phenyl-5-carbamoylcarbazol-4-yl}oxyacetic acid;
9-[(2-fluoro-4-trifluoromethylphenyl)methyl]-2-phenyl-5-carbamoylcarbazol-4-yl}oxyacetic acid;
9-[(2-fluoro-5-trifluoromethylphenyl)methyl]-2-phenyl-5-carbamoylcarbazol-4-yl}oxyacetic acid;
9-[(2-fluoro-6-trifluoromethylphenyl)methyl]-2-phenyl-5-carbamoylcarbazol-4-yl}oxyacetic acid;
9-[(3-fluoro-5-trifluoromethylphenyl)methyl]-2-phenyl-5-carbamoylcarbazol-4-yl}oxyacetic acid;
9-[(4-fluoro-2-trifluoromethylphenyl)methyl]-2-phenyl-5-carbamoylcarbazol-4-yl}oxyacetic acid;
9-[(4-fluoro-3-trifluoromethylphenyl)methyl]-2-phenyl-5-carbamoylcarbazol-4-yl}oxyacetic acid;
9-[3-(2-fluorophenoxy)methyl]-2-phenyl-5-carbamoylcarbazol-4-yl}oxyacetic acid;
9-[3-(4-fluorophenoxy)methyl]-2-phenyl-5-carbamoylcarbazol-4-yl}oxyacetic acid;
9-[(2-fluoro-3-methylphenyl)methyl]-2-phenyl-5-carbamoylcarbazol-4-yl}oxyacetic acid;
9-[(3-chloro-2-fluorophenyl)methyl]-2-phenyl-5-carbamoylcarbazol-4-yl}oxyacetic acid;
9-[(2-chloro-6-fluorophenyl)methyl]-2-phenyl-5-carbamoylcarbazol-4-yl}oxyacetic acid;
9-[(4-bromo-2-fluorophenyl)methyl]-2-phenyl-5-carbamoylcarbazol-4-yl}oxyacetic acid;
9-[(2-bromo-5-fluorophenyl)methyl]-2-phenyl-5-carbamoylcarbazol-4-yl}oxyacetic acid;
9-[(3-chloro-4-methylphenyl)methyl]-2-phenyl-5-carbamoylcarbazol-4-yl}oxyacetic acid;
9-[(3-chloro-4-methoxyphenyl)methyl]-2-phenyl-5-carbamoylcarbazol-4-yl}oxyacetic acid;
9-[(4-methoxy-3-methylphenyl)methyl]-2-phenyl-5-carbamoylcarbazol-4-yl}oxyacetic acid;
9-[(4-trifluoromethylthiophenyl)methyl]-2-phenyl-5-carbamoylcarbazol-4-yl}oxyacetic acid;
9-[(1-bromo-2-naphthylphenyl)methyl]-2-phenyl-5-carbamoylcarbazol-4-yl}oxyacetic acid;
9-[(2-methyl-1-naphthylphenyl)methyl]-2-phenyl-5-carbamoylcarbazol-4-yl}oxyacetic acid;
9-[(4-methyl-1-naphthylphenyl)methyl]-2-phenyl-5-carbamoylcarbazol-4-yl}oxyacetic acid;
9-[(6-methyl-2-naphthylphenyl)methyl]-2-phenyl-5-carbamoylcarbazol-4-yl}oxyacetic acid;
9-[(2-((phenylsulfonyl)methyl)phenyl)methyl]-2-phenyl-5-carbamoylcarbazol-4-yl}oxyacetic acid;
9-[(1-fluorenylmethyl]-2-phenyl-5-carbamoylcarbazol-4-yl}oxyacetic acid;
9-[(1-tetrazolylmethyl]-2-phenyl-5-carbamoylcarbazol-4-yl}oxyacetic acid;
9-[(5-methyl-1-tetrazolylmethyl]-2-phenyl-5-carbamoylcarbazol-4-yl}oxyacetic acid;
9-[(5-benzyl-1-tetrazolylmethyl]-2-phenyl-5-carbamoylcarbazol-4-yl}oxyacetic acid;
9-[(phenyl)methyl]-2-(4-chlorophenyl)-5-carbamoylcarbazol-4-yl}oxyacetic acid;
9-[(2-phenoxyphenyl)methyl]-2-(4-chlorophenyl)-5-carbamoylcarbazol-4-yl}oxyacetic acid;
9-[(3-phenoxyphenyl)methyl]-2-(4-chlorophenyl)-5-carbamoylcarbazol-4-yl}oxyacetic acid;
9-[(4-phenoxyphenyl)methyl]-2-(4-chlorophenyl)-5-carbamoylcarbazol-4-yl}oxyacetic acid;
9-[(2-fluorophenyl)methyl]-2-(4-chlorophenyl)-5-carbamoylcarbazol-4-yl}oxyacetic acid;
9-[(3-fluorophenyl)methyl]-2-(4-chlorophenyl)-5-carbamoylcarbazol-4-yl}oxyacetic acid;
9-[(4-fluorophenyl)methyl]-2-(4-chlorophenyl)-5-carbamoylcarbazol-4-yl}oxyacetic acid;
9-[(2-chlorophenyl)methyl]-2-(4-chlorophenyl)-5-carbamoylcarbazol-4-yl}oxyacetic acid;
9-[(3-chlorophenyl)methyl]-2-(4-chlorophenyl)-5-carbamoylcarbazol-4-yl}oxyacetic acid;
9-[(4-chlorophenyl)methyl]-2-(4-chlorophenyl)-5-carbamoylcarbazol-4-yl}oxyacetic acid;
9-[(2-bromophenyl)methyl]-2-(4-chlorophenyl)-5-carbamoylcarbazol-4-yl}oxyacetic acid;
9-[(3-bromophenyl)methyl]-2-(4-chlorophenyl)-5-carbamoylcarbazol-4-yl}oxyacetic acid;
9-[(4-bromophenyl)methyl]-2-(4-chlorophenyl)-5-carbamoylcarbazol-4-yl}oxyacetic acid;
9-[(2-iodophenyl)methyl]-2-(4-chlorophenyl)-5-carbamoylcarbazol-4-yl}oxyacetic acid;
9-[(3-iodophenyl)methyl]-2-(4-chlorophenyl)-5-carbamoylcarbazol-4-yl}oxyacetic acid;
9-[(4-iodophenyl)methyl]-2-(4-chlorophenyl)-5-carbamoylcarbazol-4-yl}oxyacetic acid;
9-[(2-acetamidophenyl)methyl]-2-(4-chlorophenyl)-5-carbamoylcarbazol-4-yl}oxyacetic acid;
9-[(3-acetamidophenyl)methyl]-2-(4-chlorophenyl)-5-carbamoylcarbazol-4-yl}oxyacetic acid;
9-[(4-acetamidophenyl)methyl]-2-(4-chlorophenyl)-5-carbamoylcarbazol-4-yl}oxyacetic acid;
9-[(2-carbamoylphenyl)methyl]-2-(4-chlorophenyl)-5-carbamoylcarbazol-4-yl}oxyacetic acid;
9-[(3-carbamoylphenyl)methyl]-2-(4-chlorophenyl)-5-carbamoylcarbazol-4-yl}oxyacetic acid;
9-[(4-carbamoylphenyl)methyl]-2-(4-chlorophenyl)-5-carbamoylcarbazol-4-yl}oxyacetic acid;
9-[(2-methylsulfonylphenyl)methyl]-2-(4-chlorophenyl)-5-carbamoylcarbazol-4-yl}oxyacetic acid;
9-[(3-methylsulfonylphenyl)methyl]-2-(4-chlorophenyl)-5-carbamoylcarbazol-4-yl}oxyacetic acid;
9-[(4-methylsulfonylphenyl)methyl]-2-(4-chlorophenyl)-5-carbamoylcarbazol-4-yl}oxyacetic acid;
9-[(2-methylphenyl)methyl]-2-(4-chlorophenyl)-5-carbamoylcarbazol-4-yl}oxyacetic acid;
9-[(3-methylphenyl)methyl]-2-(4-chlorophenyl)-5-carbamoylcarbazol-4-yl}oxyacetic acid;
9-[(4-methylphenyl)methyl]-2-(4-chlorophenyl)-5-carbamoylcarbazol-4-yl}oxyacetic acid;
9-[(2-ethylphenyl)methyl]-2-(4-chlorophenyl)-5-carbamoylcarbazol-4-yl}oxyacetic acid;
9-[(3-ethylphenyl)methyl]-2-(4-chlorophenyl)-5-carbamoylcarbazol-4-yl}oxyacetic acid;
9-[(4-ethylphenyl)methyl]-2-(4-chlorophenyl)-5-carbamoylcarbazol-4-yl}oxyacetic acid;
9-[(2-trifluoromethylphenyl)methyl]-2-(4-chlorophenyl)-5-carbamoylcarbazol-4-yl}oxyacetic acid;
9-[(3-trifluoromethylphenyl)methyl]-2-(4-chlorophenyl)-5-carbamoylcarbazol-4-yl}oxyacetic acid;
9-[(4-trifluoromethylphenyl)methyl]-2-(4-chlorophenyl)-5-carbamoylcarbazol-4-yl}oxyacetic acid;
9-[(cyclopropyl)methyl]-2-(4-chlorophenyl)-5-carbamoylcarbazol-4-yl}oxyacetic acid;
9-[(cyclobutyl)methyl]-2-(4-chlorophenyl)-5-carbamoylcarbazol-4-yl}oxyacetic acid;
9-[(cyclopentyl)methyl]-2-(4-chlorophenyl)-5-carbamoylcarbazol-4-yl}oxyacetic acid;

9-[(cyclohexyl)methyl]-2-(4-chlorophenyl)-5-carbamoylcarbazol-4-yl}oxyacetic acid;
9-[(2-methoxyphenyl)methyl]-2-(4-chlorophenyl)-5-carbamoylcarbazol-4-yl}oxyacetic acid;
9-[(3-methoxyphenyl)methyl]-2-(4-chlorophenyl)-5-carbamoylcarbazol-4-yl}oxyacetic acid;
9-[(4-methoxyphenyl)methyl]-2-(4-chlorophenyl)-5-carbamoylcarbazol-4-yl}oxyacetic acid;
9-[(2-ethoxyphenyl)methyl]-2-(4-chlorophenyl)-5-carbamoylcarbazol-4-yl}oxyacetic acid;
9-[(3-ethoxyphenyl)methyl]-2-(4-chlorophenyl)-5-carbamoylcarbazol-4-yl}oxyacetic acid;
9-[(4-ethoxyphenyl)methyl]-2-(4-chlorophenyl)-5-carbamoylcarbazol-4-yl}oxyacetic acid;
9-[(2-trifluoromethoxyphenyl)methyl]-2-(4-chlorophenyl)-5-carbamoylcarbazol-4-yl}oxyacetic acid;
9-[(3-trifluoromethoxyphenyl)methyl]-2-(4-chlorophenyl)-5-carbamoylcarbazol-4-yl}oxyacetic acid;
9-[(4-trifluoromethoxyphenyl)methyl]-2-(4-chlorophenyl)-5-carbamoylcarbazol-4-yl}oxyacetic acid;
9-[(2-difluoromethoxyphenyl)methyl]-2-(4-chlorophenyl)-5-carbamoylcarbazol-4-yl}oxyacetic acid;
9-[(3-difluoromethoxyphenyl)methyl]-2-(4-chlorophenyl)-5-carbamoylcarbazol-4-yl}oxyacetic acid;
9-[(4-difluoromethoxyphenyl)methyl]-2-(4-chlorophenyl)-5-carbamoylcarbazol-4-yl}oxyacetic acid;
9-[(2-cyanophenyl)methyl]-2-(4-chlorophenyl)-5-carbamoylcarbazol-4-yl}oxyacetic acid;
9-[(3-cyanophenyl)methyl]-2-(4-chlorophenyl)-5-carbamoylcarbazol-4-yl}oxyacetic acid;
9-[(4-cyanophenyl)methyl]-2-(4-chlorophenyl)-5-carbamoylcarbazol-4-yl}oxyacetic acid;
9-[(2-pyridyl)methyl]-2-(4-chlorophenyl)-5-carbamoylcarbazol-4-yl}oxyacetic acid;
9-[(3-pyridyl)methyl]-2-(4-chlorophenyl)-5-carbamoylcarbazol-4-yl}oxyacetic acid;
9-[(4-pyridyl)methyl]-2-(4-chlorophenyl)-5-carbamoylcarbazol-4-yl}oxyacetic acid;
9-[(2-furyl)methyl]-2-(4-chlorophenyl)-5-carbamoylcarbazol-4-yl}oxyacetic acid;
9-[(3-furyl)methyl]-2-(4-chlorophenyl)-5-carbamoylcarbazol-4-yl}oxyacetic acid;
9-[(2-thienyl)methyl]-2-(4-chlorophenyl)-5-carbamoylcarbazol-4-yl}oxyacetic acid;
9-[(3-thienyl)methyl]-2-(4-chlorophenyl)-5-carbamoylcarbazol-4-yl}oxyacetic acid;
9-[(2-benzylphenyl)methyl]-2-(4-chlorophenyl)-5-carbamoylcarbazol-4-yl}oxyacetic acid;
9-[(3-benzylphenyl)methyl]-2-(4-chlorophenyl)-5-carbamoylcarbazol-4-yl}oxyacetic acid;
9-[(4-benzylphenyl)methyl]-2-(4-chlorophenyl)-5-carbamoylcarbazol-4-yl}oxyacetic acid;
9-[(2-benzoylphenyl)methyl]-2-(4-chlorophenyl)-5-carbamoylcarbazol-4-yl}oxyacetic acid;
9-[(3-benzoylphenyl)methyl]-2-(4-chlorophenyl)-5-carbamoylcarbazol-4-yl}oxyacetic acid;
9-[(4-benzoylphenyl)methyl]-2-(4-chlorophenyl)-5-carbamoylcarbazol-4-yl}oxyacetic acid;
9-[(2-benzyloxyphenyl)methyl]-2-(4-chlorophenyl)-5-carbamoylcarbazol-4-yl}oxyacetic acid;
9-[(3-benzyloxyphenyl)methyl]-2-(4-chlorophenyl)-5-carbamoylcarbazol-4-yl}oxyacetic acid;
9-[(4-benzyloxyphenyl)methyl]-2-(4-chlorophenyl)-5-carbamoylcarbazol-4-yl}oxyacetic acid;
9-[(2-phenylphenyl)methyl]-2-(4-chlorophenyl)-5-carbamoylcarbazol-4-yl}oxyacetic acid;
9-[(3-phenylphenyl)methyl]-2-(4-chlorophenyl)-5-carbamoylcarbazol-4-yl}oxyacetic acid;
9-[(4-phenylphenyl)methyl]-2-(4-chlorophenyl)-5-carbamoylcarbazol-4-yl}oxyacetic acid;
9-[(1-naphthyl)methyl]-2-(4-chlorophenyl)-5-carbamoylcarbazol-4-yl}oxyacetic acid;
9-[(2-naphthyl)methyl]-2-(4-chlorophenyl)-5-carbamoylcarbazol-4-yl}oxyacetic acid;
9-[(2,3-difluorophenyl)methyl]-2-(4-chlorophenyl)-5-carbamoylcarbazol-4-yl}oxyacetic acid;
9-[(2,4-difluorophenyl)methyl]-2-(4-chlorophenyl)-5-carbamoylcarbazol-4-yl}oxyacetic acid;
9-[(2,5-difluorophenyl)methyl]-2-(4-chlorophenyl)-5-carbamoylcarbazol-4-yl}oxyacetic acid;
9-[(2,6-difluorophenyl)methyl]-2-(4-chlorophenyl)-5-carbamoylcarbazol-4-yl}oxyacetic acid;
9-[(3,4-difluorophenyl)methyl]-2-(4-chlorophenyl)-5-carbamoylcarbazol-4-yl}oxyacetic acid;
9-[(3,5-difluorophenyl)methyl]-2-(4-chlorophenyl)-5-carbamoylcarbazol-4-yl}oxyacetic acid;
9-[(2,3,4-trifluorophenyl)methyl]-2-(4-chlorophenyl)-5-carbamoylcarbazol-4-yl}oxyacetic acid;
9-[(2,3,5-trifluorophenyl)methyl]-2-(4-chlorophenyl)-5-carbamoylcarbazol-4-yl}oxyacetic acid;
9-[(2,3,6-trifluorophenyl)methyl]-2-(4-chlorophenyl)-5-carbamoylcarbazol-4-yl}oxyacetic acid;
9-[(2,4,5-trifluorophenyl)methyl]-2-(4-chlorophenyl)-5-carbamoylcarbazol-4-yl}oxyacetic acid;
9-[(2,4,6-trifluorophenyl)methyl]-2-(4-chlorophenyl)-5-carbamoylcarbazol-4-yl}oxyacetic acid;
9-[(3,4,5-trifluorophenyl)methyl]-2-(4-chlorophenyl)-5-carbamoylcarbazol-4-yl}oxyacetic acid;
9-[(pentafluorophenyl)methyl]-2-(4-chlorophenyl)-5-carbamoylcarbazol-4-yl}oxyacetic acid;
9-[(2,3-dichlorophenyl)methyl]-2-(4-chlorophenyl)-5-carbamoylcarbazol-4-yl}oxyacetic acid;
9-[(2,4-dichlorophenyl)methyl]-2-(4-chlorophenyl)-5-carbamoylcarbazol-4-yl}oxyacetic acid;
9-[(2,5-dichlorophenyl)methyl]-2-(4-chlorophenyl)-5-carbamoylcarbazol-4-yl}oxyacetic acid;
9-[(2,6-dichlorophenyl)methyl]-2-(4-chlorophenyl)-5-carbamoylcarbazol-4-yl}oxyacetic acid;
9-[(3,4-dichlorophenyl)methyl]-2-(4-chlorophenyl)-5-carbamoylcarbazol-4-yl}oxyacetic acid;
9-[(3,5-dichlorophenyl)methyl]-2-(4-chlorophenyl)-5-carbamoylcarbazol-4-yl}oxyacetic acid;
9-[(2,3-dimethylphenyl)methyl]-2-(4-chlorophenyl)-5-carbamoylcarbazol-4-yl}oxyacetic acid;
9-[(2,4-dimethylphenyl)methyl]-2-(4-chlorophenyl)-5-carbamoylcarbazol-4-yl}oxyacetic acid;
9-[(2,5-dimethylphenyl)methyl]-2-(4-chlorophenyl)-5-carbamoylcarbazol-4-yl}oxyacetic acid;
9-[(2,6-dimethylphenyl)methyl]-2-(4-chlorophenyl)-5-carbamoylcarbazol-4-yl}oxyacetic acid;
9-[(3,4-dimethylphenyl)methyl]-2-(4-chlorophenyl)-5-carbamoylcarbazol-4-yl}oxyacetic acid;
9-[(3,5-dimethylphenyl)methyl]-2-(4-chlorophenyl)-5-carbamoylcarbazol-4-yl}oxyacetic acid;
9-[(2,4,6-trimethylphenyl)methyl]-2-(4-chlorophenyl)-5-carbamoylcarbazol-4-yl}oxyacetic acid;
9-[(3,5-bis(trifluoromethyl)phenyl)methyl]-2-(4-chlorophenyl)-5-carbamoylcarbazol-4-yl}oxyacetic acid;
9-[(2,4-bis(trifluoromethyl)phenyl)methyl]-2-(4-chlorophenyl)-5-carbamoylcarbazol-4-yl}oxyacetic acid;
9-[(2-fluoro-3-trifluoromethylphenyl)methyl]-2-(4-chlorophenyl)-5-carbamoylcarbazol-4-yl}oxyacetic acid;
9-[(2-fluoro-4-trifluoromethylphenyl)methyl]-2-(4-chlorophenyl)-5-carbamoylcarbazol-4-yl}oxyacetic acid;
9-[(2-fluoro-5-trifluoromethylphenyl)methyl]-2-(4-chlorophenyl)-5-carbamoylcarbazol-4-yl}oxyacetic acid;

9-[(2-fluoro-6-trifluoromethylphenyl)methyl]-2-(4-chlorophenyl)-5-carbamoylcarbazol-4-yl}oxyacetic acid;
9-[(3-fluoro-5-trifluoromethylphenyl)methyl]-2-(4-chlorophenyl)-5-carbamoylcarbazol-4-yl}oxyacetic acid;
9-[(4-fluoro-2-trifluoromethylphenyl)methyl]-2-(4-chlorophenyl)-5-carbamoylcarbazol-4-yl}oxyacetic acid;
9-[(4-fluoro-3-trifluoromethylphenyl)methyl]-2-(4-chlorophenyl)-5-carbamoylcarbazol-4-yl}oxyacetic acid;
9-[3-(2-fluorophenoxy)methyl]-2-(4-chlorophenyl)-5-carbamoylcarbazol-4-yl}oxyacetic acid;
9-[3-(4-fluorophenoxy)methyl]-2-(4-chlorophenyl)-5-carbamoylcarbazol-4-yl}oxyacetic acid;
9-[(2-fluoro-3-methylphenyl)methyl]-2-(4-chlorophenyl)-5-carbamoylcarbazol-4-yl}oxyacetic acid;
9-[(3-chloro-2-fluorophenyl)methyl]-2-(4-chlorophenyl)-5-carbamoylcarbazol-4-yl}oxyacetic acid;
9-[(2-chloro-6-fluorophenyl)methyl]-2-(4-chlorophenyl)-5-carbamoylcarbazol-4-yl}oxyacetic acid;
9-[(4-bromo-2-fluorophenyl)methyl]-2-(4-chlorophenyl)-5-carbamoylcarbazol-4-yl}oxyacetic acid;
9-[(2-bromo-5-fluorophenyl)methyl]-2-(4-chlorophenyl)-5-carbamoylcarbazol-4-yl}oxyacetic acid;
9-[(3-chloro-4-methylphenyl)methyl]-2-(4-chlorophenyl)-5-carbamoylcarbazol-4-yl}oxyacetic acid;
9-[(3-chloro-4-methoxyphenyl)methyl]-2-(4-chlorophenyl)-5-carbamoylcarbazol-4-yl}oxyacetic acid;
9-[(4-methoxy-3-methylphenyl)methyl]-2-(4-chlorophenyl)-5-carbamoylcarbazol-4-yl}oxyacetic acid;
9-[(4-trifluoromethylthiophenyl)methyl]-2-(4-chlorophenyl)-5-carbamoylcarbazol-4-yl}oxyacetic acid;
9-[(1-bromo-2-naphthylphenyl)methyl]-2-(4-chlorophenyl)-5-carbamoylcarbazol-4-yl}oxyacetic acid;
9-[(2-methyl-1-naphthylphenyl)methyl]-2-(4-chlorophenyl)-5-carbamoylcarbazol-4-yl}oxyacetic acid;
9-[(4-methyl-1-naphthylphenyl)methyl]-2-(4-chlorophenyl)-5-carbamoylcarbazol-4-yl}oxyacetic acid;
9-[(6-methyl-2-naphthylphenyl)methyl]-2-(4-chlorophenyl)-5-carbamoylcarbazol-4-yl}oxyacetic acid;
9-[(2-((phenylsulfonyl)methyl)phenyl)methyl]-2-(4-chlorophenyl)-5-carbamoylcarbazol-4-yl}oxyacetic acid;
9-[(1-fluorenylmethyl]-2-(4-chlorophenyl)-5-carbamoylcarbazol-4-yl}oxyacetic acid;
9-[(1-tetrazolylmethyl]-2-(4-chlorophenyl)-5-carbamoylcarbazol-4-yl}oxyacetic acid;
9-[(5-methyl-1-tetrazolylmethyl]-2-(4-chlorophenyl)-5-carbamoylcarbazol-4-yl}oxyacetic acid;
9-[(5-benzyl-1-tetrazolylmethyl]-2-(4-chlorophenyl)-5-carbamoylcarbazol-4-yl}oxyacetic acid;
9-[(phenyl)methyl]-2-(2,4-dichlorophenyl)-5-carbamoylcarbazol-4-yl}oxyacetic acid;
9-[(2-phenoxyphenyl)methyl]-2-(2,4-dichlorophenyl)-5-carbamoylcarbazol-4-yl}oxyacetic acid;
9-[(3-phenoxyphenyl)methyl]-2-(2,4-dichlorophenyl)-5-carbamoylcarbazol-4-yl}oxyacetic acid;
9-[(4-phenoxyphenyl)methyl]-2-(2,4-dichlorophenyl)-5-carbamoylcarbazol-4-yl}oxyacetic acid;
9-[(2-fluorophenyl)methyl]-2-(2,4-dichlorophenyl)-5-carbamoylcarbazol-4-yl}oxyacetic acid;
9-[(3-fluorophenyl)methyl]-2-(2,4-dichlorophenyl)-5-carbamoylcarbazol-4-yl}oxyacetic acid;
9-[(4-fluorophenyl)methyl]-2-(2,4-dichlorophenyl)-5-carbamoylcarbazol-4-yl}oxyacetic acid;
9-[(2-chlorophenyl)methyl]-2-(2,4-dichlorophenyl)-5-carbamoylcarbazol-4-yl}oxyacetic acid;
9-[(3-chlorophenyl)methyl]-2-(2,4-dichlorophenyl)-5-carbamoylcarbazol-4-yl}oxyacetic acid;
9-[(4-chlorophenyl)methyl]-2-(2,4-dichlorophenyl)-5-carbamoylcarbazol-4-yl}oxyacetic acid;
9-[(2-bromophenyl)methyl]-2-(2,4-dichlorophenyl)-5-carbamoylcarbazol-4-yl}oxyacetic acid;
9-[(3-bromophenyl)methyl]-2-(2,4-dichlorophenyl)-5-carbamoylcarbazol-4-yl}oxyacetic acid;
9-[(4-bromophenyl)methyl]-2-(2,4-dichlorophenyl)-5-carbamoylcarbazol-4-yl}oxyacetic acid;
9-[(2-iodophenyl)methyl]-2-(2,4-dichlorophenyl)-5-carbamoylcarbazol-4-yl}oxyacetic acid;
9-[(3-iodophenyl)methyl]-2-(2,4-dichlorophenyl)-5-carbamoylcarbazol-4-yl}oxyacetic acid;
9-[(4-iodophenyl)methyl]-2-(2,4-dichlorophenyl)-5-carbamoylcarbazol-4-yl}oxyacetic acid;
9-[(2-acetamidophenyl)methyl]-2-(2,4-dichlorophenyl)-5-carbamoylcarbazol-4-yl}oxyacetic acid;
9-[(3-acetamidophenyl)methyl]-2-(2,4-dichlorophenyl)-5-carbamoylcarbazol-4-yl}oxyacetic acid;
9-[(4-acetamidophenyl)methyl]-2-(2,4-dichlorophenyl)-5-carbamoylcarbazol-4-yl}oxyacetic acid;
9-[(2-carbamoylphenyl)methyl]-2-(2,4-dichlorophenyl)-5-carbamoylcarbazol-4-yl}oxyacetic acid;
9-[(3-carbamoylphenyl)methyl]-2-(2,4-dichlorophenyl)-5-carbamoylcarbazol-4-yl}oxyacetic acid;
9-[(4-carbamoylphenyl)methyl]-2-(2,4-dichlorophenyl)-5-carbamoylcarbazol-4-yl}oxyacetic acid;
9-[(2-methylsulfonylphenyl)methyl]-2-(2,4-dichlorophenyl)-5-carbamoylcarbazol-4-yl}oxyacetic acid;
9-[(3-methylsulfonylphenyl)methyl]-2-(2,4-dichlorophenyl)-5-carbamoylcarbazol-4-yl}oxyacetic acid;
9-[(4-methylsulfonylphenyl)methyl]-2-(2,4-dichlorophenyl)-5-carbamoylcarbazol-4-yl}oxyacetic acid;
9-[(2-methylphenyl)methyl]-2-(2,4-dichlorophenyl)-5-carbamoylcarbazol-4-yl}oxyacetic acid;
9-[(3-methylphenyl)methyl]-2-(2,4-dichlorophenyl)-5-carbamoylcarbazol-4-yl}oxyacetic acid;
9-[(4-methylphenyl)methyl]-2-(2,4-dichlorophenyl)-5-carbamoylcarbazol-4-yl}oxyacetic acid;
9-[(2-ethylphenyl)methyl]-2-(2,4-dichlorophenyl)-5-carbamoylcarbazol-4-yl}oxyacetic acid;
9-[(3-ethylphenyl)methyl]-2-(2,4-dichlorophenyl)-5-carbamoylcarbazol-4-yl}oxyacetic acid;
9-[(4-ethylphenyl)methyl]-2-(2,4-dichlorophenyl)-5-carbamoylcarbazol-4-yl}oxyacetic acid;
9-[(2-trifluoromethylphenyl)methyl]-2-(2,4-dichlorophenyl)-5-carbamoylcarbazol-4-yl}oxyacetic acid;
9-[(3-trifluoromethylphenyl)methyl]-2-(2,4-dichlorophenyl)-5-carbamoylcarbazol-4-yl}oxyacetic acid;
9-[(4-trifluoromethylphenyl)methyl]-2-(2,4-dichlorophenyl)-5-carbamoylcarbazol-4-yl}oxyacetic acid;
9-[(cyclopropyl)methyl]-2-(2,4-dichlorophenyl)-5-carbamoylcarbazol-4-yl}oxyacetic acid;
9-[(cyclobutyl)methyl]-2-(2,4-dichlorophenyl)-5-carbamoylcarbazol-4-yl}oxyacetic acid;
9-[(cyclopentyl)methyl]-2-(2,4-dichlorophenyl)-5-carbamoylcarbazol-4-yl}oxyacetic acid;
9-[(cyclohexyl)methyl]-2-(2,4-dichlorophenyl)-5-carbamoylcarbazol-4-yl}oxyacetic acid;
9-[(2-methoxyphenyl)methyl]-2-(2,4-dichlorophenyl)-5-carbamoylcarbazol-4-yl}oxyacetic acid;
9-[(3-methoxyphenyl)methyl]-2-(2,4-dichlorophenyl)-5-carbamoylcarbazol-4-yl}oxyacetic acid;
9-[(4-methoxyphenyl)methyl]-2-(2,4-dichlorophenyl)-5-carbamoylcarbazol-4-yl}oxyacetic acid;

9-[(2-ethoxyphenyl)methyl]-2-(2,4-dichlorophenyl)-5-carbamoylcarbazol-4-yl}oxyacetic acid;
9-[(3-ethoxyphenyl)methyl]-2-(2,4-dichlorophenyl)-5-carbamoylcarbazol-4-yl}oxyacetic acid;
9-[(4-ethoxyphenyl)methyl]-2-(2,4-dichlorophenyl)-5-carbamoylcarbazol-4-yl}oxyacetic acid;
9-[(2-trifluoromethoxyphenyl)methyl]-2-(2,4-dichlorophenyl)-5-carbamoylcarbazol-4-yl}oxyacetic acid;
9-[(3-trifluoromethoxyphenyl)methyl]-2-(2,4-dichlorophenyl)-5-carbamoylcarbazol-4-yl}oxyacetic acid;
9-[(4-trifluoromethoxyphenyl)methyl]-2-(2,4-dichlorophenyl)-5-carbamoylcarbazol-4-yl}oxyacetic acid;
9-[(2-difluoromethoxyphenyl)methyl]-2-(2,4-dichlorophenyl)-5-carbamoylcarbazol-4-yl}oxyacetic acid;
9-[(3-difluoromethoxyphenyl)methyl]-2-(2,4-dichlorophenyl)-5-carbamoylcarbazol-4-yl}oxyacetic acid;
9-[(4-difluoromethoxyphenyl)methyl]-2-(2,4-dichlorophenyl)-5-carbamoylcarbazol-4-yl}oxyacetic acid;
9-[(2-cyanophenyl)methyl]-2-(2,4-dichlorophenyl)-5-carbamoylcarbazol-4-yl}oxyacetic acid;
9-[(3-cyanophenyl)methyl]-2-(2,4-dichlorophenyl)-5-carbamoylcarbazol-4-yl}oxyacetic acid;
9-[(4-cyanophenyl)methyl]-2-(2,4-dichlorophenyl)-5-carbamoylcarbazol-4-yl}oxyacetic acid;
9-[(2-pyridyl)methyl]-2-(2,4-dichlorophenyl)-5-carbamoylcarbazol-4-yl}oxyacetic acid;
9-[(3pyridyl)methyl]-2-(2,4-dichlorophenyl)-5-carbamoylcarbazol-4-yl}oxyacetic acid;
9-[(4-pyridyl)methyl]-2-(2,4-dichlorophenyl)-5-carbamoylcarbazol-4-yl}oxyacetic acid;
9-[(2-furyl)methyl]-2-(2,4-dichlorophenyl)-5-carbamoylcarbazol-4-yl}oxyacetic acid;
9-[(3-furyl)methyl]-2-(2,4-dichlorophenyl)-5-carbamoylcarbazol-4-yl}oxyacetic acid;
9-[(2-thienyl)methyl]-2-(2,4-dichlorophenyl)-5-carbamoylcarbazol-4-yl}oxyacetic acid;
9-[(3-thienyl)methyl]-2-(2,4-dichlorophenyl)-5-carbamoylcarbazol-4-yl}oxyacetic acid;
9-[(2-benzylphenyl)methyl]-2-(2,4-dichlorophenyl)-5-carbamoylcarbazol-4-yl}oxyacetic acid;
9-[(3-benzylphenyl)methyl]-2-(2,4-dichlorophenyl)-5-carbamoylcarbazol-4-yl}oxyacetic acid;
9-[(4-benzylphenyl)methyl]-2-(2,4-dichlorophenyl)-5-carbamoylcarbazol-4-yl}oxyacetic acid;
9-[(2-benzoylphenyl)methyl]-2-(2,4-dichlorophenyl)-5-carbamoylcarbazol-4-yl}oxyacetic acid;
9-[(3-benzoylphenyl)methyl]-2-(2,4-dichlorophenyl)-5-carbamoylcarbazol-4-yl}oxyacetic acid;
9-[(4-benzoylphenyl)methyl]-2-(2,4-dichlorophenyl)-5-carbamoylcarbazol-4-yl}oxyacetic acid;
9-[(2-benzyloxyphenyl)methyl]-2-(2,4-dichlorophenyl)-5-carbamoylcarbazol-4-yl}oxyacetic acid;
9-[(3-benzyloxyphenyl)methyl]-2-(2,4-dichlorophenyl)-5-carbamoylcarbazol-4-yl}oxyacetic acid;
9-[(4-benzyloxyphenyl)methyl]-2-(2,4-dichlorophenyl)-5-carbamoylcarbazol-4-yl}oxyacetic acid;
9-[(2-phenylphenyl)methyl]-2-(2,4-dichlorophenyl)-5-carbamoylcarbazol-4-yl}oxyacetic acid;
9-[(3-phenylphenyl)methyl]-2-(2,4-dichlorophenyl)-5-carbamoylcarbazol-4-yl}oxyacetic acid;
9-[(4-phenylphenyl)methyl]-2-(2,4-dichlorophenyl)-5-carbamoylcarbazol-4-yl}oxyacetic acid;
9-[(1-naphthyl)methyl]-2-(2,4-dichlorophenyl)-5-carbamoylcarbazol-4-yl}oxyacetic acid;
9-[(2-naphthyl)methyl]-2-(2,4-dichlorophenyl)-5-carbamoylcarbazol-4-yl}oxyacetic acid;
9-[(2,3-difluorophenyl)methyl]-2-(2,4-dichlorophenyl)-5-carbamoylcarbazol-4-yl}oxyacetic acid;
9-[(2,4-difluorophenyl)methyl]-2-(2,4-dichlorophenyl)-5-carbamoylcarbazol-4-yl}oxyacetic acid;
9-[(2,5-difluorophenyl)methyl]-2-(2,4-dichlorophenyl)-5-carbamoylcarbazol-4-yl}oxyacetic acid;
9-[(2,6-difluorophenyl)methyl]-2-(2,4-dichlorophenyl)-5-carbamoylcarbazol-4-yl}oxyacetic acid;
9-[(3,4-difluorophenyl)methyl]-2-(2,4-dichlorophenyl)-5-carbamoylcarbazol-4-yl}oxyacetic acid;
9-[(3,5-difluorophenyl)methyl]-2-(2,4-dichlorophenyl)-5-carbamoylcarbazol-4-yl}oxyacetic acid;
9-[(2,3,4-trifluorophenyl)methyl]-2-(2,4-dichlorophenyl)-5-carbamoylcarbazol-4-yl}oxyacetic acid;
9-[(2,3,5-trifluorophenyl)methyl]-2-(2,4-dichlorophenyl)-5-carbamoylcarbazol-4-yl}oxyacetic acid;
9-[(2,3,6-trifluorophenyl)methyl]-2-(2,4-dichlorophenyl)-5-carbamoylcarbazol-4-yl}oxyacetic acid;
9-[(2,4,5-trifluorophenyl)methyl]-2-(2,4-dichlorophenyl)-5-carbamoylcarbazol-4-yl}oxyacetic acid;
9-[(2,4,6-trifluorophenyl)methyl]-2-(2,4-dichlorophenyl)-5-carbamoylcarbazol-4-yl}oxyacetic acid;
9-[(3,4,5-trifluorophenyl)methyl]-2-(2,4-dichlorophenyl)-5-carbamoylcarbazol-4-yl}oxyacetic acid;
9-[(pentafluorophenyl)methyl]-2-(2,4-dichlorophenyl)-5-carbamoylcarbazol-4-yl}oxyacetic acid;
9-[(2,3-dichlorophenyl)methyl]-2-(2,4-dichlorophenyl)-5-carbamoylcarbazol-4-yl}oxyacetic acid;
9-[(2,4-dichlorophenyl)methyl]-2-(2,4-dichlorophenyl)-5-carbamoylcarbazol-4-yl}oxyacetic acid;
9-[(2,5-dichlorophenyl)methyl]-2-(2,4-dichlorophenyl)-5-carbamoylcarbazol-4-yl}oxyacetic acid;
9-[(2,6-dichlorophenyl)methyl]-2-(2,4-dichlorophenyl)-5-carbamoylcarbazol-4-yl}oxyacetic acid;
9-[(3,4-dichlorophenyl)methyl]-2-(2,4-dichlorophenyl)-5-carbamoylcarbazol-4-yl}oxyacetic acid;
9-[(3,5-dichlorophenyl)methyl]-2-(2,4-dichlorophenyl)-5-carbamoylcarbazol-4-yl}oxyacetic acid;
9-[(2,3-dimethylphenyl)methyl]-2-(2,4-dichlorophenyl)-5-carbamoylcarbazol-4-yl}oxyacetic acid;
9-[(2,4-dimethylphenyl)methyl]-2-(2,4-dichlorophenyl)-5-carbamoylcarbazol-4-yl}oxyacetic acid;
9-[(2,5-dimethylphenyl)methyl]-2-(2,4-dichlorophenyl)-5-carbamoylcarbazol-4-yl}oxyacetic acid;
9-[(2,6-dimethylphenyl)methyl]-2-(2,4-dichlorophenyl)-5-carbamoylcarbazol-4-yl}oxyacetic acid;
9-[(3,4-dimethylphenyl)methyl]-2-(2,4-dichlorophenyl)-5-carbamoylcarbazol-4-yl}oxyacetic acid;
9-[(3,5-dimethylphenyl)methyl]-2-(2,4-dichlorophenyl)-5-carbamoylcarbazol-4-yl}oxyacetic acid;
9-(2,4,6-trimethylphenyl)methyl]-2-(2,4-dichlorophenyl)-5-carbamoylcarbazol-4-yl}oxyacetic acid;
9-[(3,5-bis(trifluoromethyl)phenyl)methyl]-2-(2,4-dichlorophenyl)-5-carbamoylcarbazol-4-yl}oxyacetic acid;
9-[(2,4-bis(trifluoromethyl)phenyl)methyl]-2-(2,4-dichlorophenyl)-5-carbamoylcarbazol-4-yl}oxyacetic acid;
9-[(2-fluoro-3-trifluoromethylphenyl)methyl]-2-(2,4-dichlorophenyl)-5-carbamoylcarbazol-4-yl}oxyacetic acid;
9-[(2-fluoro-4-trifluoromethylphenyl)methyl]-2-(2,4-dichlorophenyl)-5-carbamoylcarbazol-4-yl}oxyacetic acid;

9-[(2-fluoro-5-trifluoromethylphenyl)methyl]-2-(2,4-dichlorophenyl)-5-carbamoylcarbazol-4-yl}oxyacetic acid;
9-[(2-fluoro-6-trifluoromethylphenyl)methyl]-2-(2,4-dichlorophenyl)-5-carbamoylcarbazol-4-yl}oxyacetic acid;
9-[(3-fluoro-5-trifluoromethylphenyl)methyl]-2-(2,4-dichlorophenyl)-5-carbamoylcarbazol-4-yl}oxyacetic acid;
9-[(4-fluoro-2-trifluoromethylphenyl)methyl]-2-(2,4-dichlorophenyl)-5-carbamoylcarbazol-4-yl}oxyacetic acid;
9-[(4-fluoro-3-trifluoromethylphenyl)methyl]-2-(2,4-dichlorophenyl)-5-carbamoylcarbazol-4-yl}oxyacetic acid;
9-[3-(2-fluorophenoxy)methyl]-2-(2,4-dichlorophenyl)-5-carbamoylcarbazol-4-yl}oxyacetic acid;
9-[3-(4-fluorophenoxy)methyl]-2-(2,4-dichlorophenyl)-5-carbamoylcarbazol-4-yl}oxyacetic acid;
9-[(2-fluoro-3-methylphenyl)methyl]-2-(2,4-dichlorophenyl)-5-carbamoylcarbazol-4-yl}oxyacetic acid;
9-[(3-chloro-2-fluorophenyl)methyl]-2-(2,4-dichlorophenyl)-5-carbamoylcarbazol-4-yl}oxyacetic acid;
9-[(2-chloro-6-fluorophenyl)methyl]-2-(2,4-dichlorophenyl)-5-carbamoylcarbazol-4-yl}oxyacetic acid;
9-[(4-bromo-2-fluorophenyl)methyl]-2-(2,4-dichlorophenyl)-5-carbamoylcarbazol-4-yl}oxyacetic acid;
9-[(2-bromo-5-fluorophenyl)methyl]-2-(2,4-dichlorophenyl)-5-carbamoylcarbazol-4-yl}oxyacetic acid;
9-[(3-chloro-4-methylphenyl)methyl]-2-(2,4-dichlorophenyl)-5-carbamoylcarbazol-4-yl}oxyacetic acid;
9-[(3-chloro-4-methoxyphenyl)methyl]-2-(2,4-dichlorophenyl)-5-carbamoylcarbazol-4-yl}oxyacetic acid;
9-[(4-methoxy-3-methylphenyl)methyl]-2-(2,4-dichlorophenyl)-5-carbamoylcarbazol-4-yl}oxyacetic acid;
9-[(4-trifluoromethylthiophenyl)methyl]-2-(2,4-dichlorophenyl)-5-carbamoylcarbazol-4-yl}oxyacetic acid;
9-[(1-bromo-2-naphthylphenyl)methyl]-2-(2,4-dichlorophenyl)-5-carbamoylcarbazol-4-yl}oxyacetic acid;
9-[(2-methyl-1-naphthylphenyl)methyl]-2-(2,4-dichlorophenyl)-5-carbamoylcarbazol-4-yl}oxyacetic acid;
9-[(4-methyl-1-naphthylphenyl)methyl]-2-(2,4-dichlorophenyl)-5-carbamoylcarbazol-4-yl}oxyacetic acid;
9-[(6-methyl-2-naphthylphenyl)methyl]-2-(2,4-dichlorophenyl)-5-carbamoylcarbazol-4-yl}oxyacetic acid;
9-[(2-((phenylsulfonyl)methyl)phenyl)methyl]-2-(2,4-dichlorophenyl)-5-carbamoylcarbazol-4-yl}oxyacetic acid;
9-[(1-fluorenylmethyl]-2-(2,4-dichlorophenyl)-5-carbamoylcarbazol-4-yl}oxyacetic acid;
9-[(1-tetrazolylmethyl]-2-(2,4-dichlorophenyl)-5-carbamoylcarbazol-4-yl}oxyacetic acid;
9-[(5-methyl-1-tetrazolylmethyl]-2-(2,4-dichlorophenyl)-5-carbamoylcarbazol-4-yl}oxyacetic acid;
9-[(5-benzyl-1-tetrazolylmethyl]-2-(2,4-dichlorophenyl)-5-carbamoylcarbazol-4-yl}oxyacetic acid;
9-[(phenyl)methyl]-2-(2,6-dichlorophenyl)-5-carbamoylcarbazol-4-yl}oxyacetic acid;
9-[(2-phenoxyphenyl)methyl]-2-(2,6-dichlorophenyl)-5-carbamoylcarbazol-4-yl}oxyacetic acid;
9-[(3-phenoxyphenyl)methyl]-2-(2,6-dichlorophenyl)-5-carbamoylcarbazol-4-yl}oxyacetic acid;
9-[(4-phenoxyphenyl)methyl]-2-(2,6-dichlorophenyl)-5-carbamoylcarbazol-4-yl}oxyacetic acid;
9-[(2-fluorophenyl)methyl]-2-(2,6-dichlorophenyl)-5-carbamoylcarbazol-4-yl}oxyacetic acid;
9-[(3-fluorophenyl)methyl]-2-(2,6-dichlorophenyl)-5-carbamoylcarbazol-4-yl}oxyacetic acid;
9-[(4-fluorophenyl)methyl]-2-(2,6-dichlorophenyl)-5-carbamoylcarbazol-4-yl}oxyacetic acid;
9-[(2-chlorophenyl)methyl]-2-(2,6-dichlorophenyl)-5-carbamoylcarbazol-4-yl}oxyacetic acid;
9-[(3-chlorophenyl)methyl]-2-(2,6-dichlorophenyl)-5-carbamoylcarbazol-4-yl}oxyacetic acid;
9-[(4-chlorophenyl)methyl]-2-(2,6-dichlorophenyl)-5-carbamoylcarbazol-4-yl}oxyacetic acid;
9-[(2-bromophenyl)methyl]-2-(2,6-dichlorophenyl)-5-carbamoylcarbazol-4-yl}oxyacetic acid;
9-[(3-bromophenyl)methyl]-2-(2,6-dichlorophenyl)-5-carbamoylcarbazol-4-yl}oxyacetic acid;
9-[(4-bromophenyl)methyl]-2-(2,6-dichlorophenyl)-5-carbamoylcarbazol-4-yl}oxyacetic acid;
9-[(2-iodophenyl)methyl]-2-(2,6-dichlorophenyl)-5-carbamoylcarbazol-4-yl}oxyacetic acid;
9-[(3-iodophenyl)methyl]-2-(2,6-dichlorophenyl)-5-carbamoylcarbazol-4-yl}oxyacetic acid;
9-[(4-iodophenyl)methyl]-2-(2,6-dichlorophenyl)-5-carbamoylcarbazol-4-yl}oxyacetic acid;
9-[(2-acetamidophenyl)methyl]-2-(2,6-dichlorophenyl)-5-carbamoylcarbazol-4-yl}oxyacetic acid;
9-[(3-acetamidophenyl)methyl]-2-(2,6-dichlorophenyl)-5-carbamoylcarbazol-4-yl}oxyacetic acid;
9-[(4-acetamidophenyl)methyl]-2-(2,6-dichlorophenyl)-5-carbamoylcarbazol-4-yl}oxyacetic acid;
9-[(2-carbamoylphenyl)methyl]-2-(2,6-dichlorophenyl)-5-carbamoylcarbazol-4-yl}oxyacetic acid;
9-[(3-carbamoylphenyl)methyl]-2-(2,6-dichlorophenyl)-5-carbamoylcarbazol-4-yl}oxyacetic acid;
9-[(4-carbamoylphenyl)methyl]-2-(2,6-dichlorophenyl)-5-carbamoylcarbazol-4-yl}oxyacetic acid;
9-[(2-methylsulfonylphenyl)methyl]-2-(2,6-dichlorophenyl)-5-carbamoylcarbazol-4-yl}oxyacetic acid;
9-[(3-methylsulfonylphenyl)methyl]-2-(2,6-dichlorophenyl)-5-carbamoylcarbazol-4-yl}oxyacetic acid;
9-[(4-methylsulfonylphenyl)methyl]-2-(2,6-dichlorophenyl)-5-carbamoylcarbazol-4-yl}oxyacetic acid;
9-[(2-methylphenyl)methyl]-2-(2,6-dichlorophenyl)-5-carbamoylcarbazol-4-yl}oxyacetic acid;
9-[(3-methylphenyl)methyl]-2-(2,6-dichlorophenyl)-5-carbamoylcarbazol-4-yl}oxyacetic acid;
9-[(4-methylphenyl)methyl]-2-(2,6-dichlorophenyl)-5-carbamoylcarbazol-4-yl}oxyacetic acid;
9-[(2-ethylphenyl)methyl]-2-(2,6-dichlorophenyl)-5-carbamoylcarbazol-4-yl}oxyacetic acid;
9-[(3-ethylphenyl)methyl]-2-(2,6-dichlorophenyl)-5-carbamoylcarbazol-4-yl}oxyacetic acid;
9-[(4-ethylphenyl)methyl]-2-(2,6-dichlorophenyl)-5-carbamoylcarbazol-4-yl}oxyacetic acid;

9-[(2-trifluoromethylphenyl)methyl]-2-(2,6-dichlorophenyl)-5-carbamoylcarbazol-4-yl}oxyacetic acid;

9-[(3-trifluoromethylphenyl)methyl]-2-(2,6-dichlorophenyl)-5-carbamoylcarbazol-4-yl}oxyacetic acid;

9-[(4-trifluoromethylphenyl)methyl]-2-(2,6-dichlorophenyl)-5-carbamoylcarbazol-4-yl}oxyacetic acid;

9-[(cyclopropyl)methyl]-2-(2,6-dichlorophenyl)-5-carbamoylcarbazol-4-yl}oxyacetic acid;

9-[(cyclobutyl)methyl]-2-(2,6-dichlorophenyl)-5-carbamoylcarbazol-4-yl}oxyacetic acid;

9-[(cyclopentyl)methyl]-2-(2,6-dichlorophenyl)-5-carbamoylcarbazol-4-yl}oxyacetic acid;

9-[(cyclohexyl)methyl]-2-(2,6-dichlorophenyl)-5-carbamoylcarbazol-4-yl}oxyacetic acid;

9-[(2-methoxyphenyl)methyl]-2-(2,6-dichlorophenyl)-5-carbamoylcarbazol-4-yl}oxyacetic acid;

9-[(3-methoxyphenyl)methyl]-2-(2,6-dichlorophenyl)-5-carbamoylcarbazol-4-yl}oxyacetic acid;

9-[(4-methoxyphenyl)methyl]-2-(2,6-dichlorophenyl)-5-carbamoylcarbazol-4-yl}oxyacetic acid;

9-[(2-ethoxyphenyl)methyl]-2-(2,6-dichlorophenyl)-5-carbamoylcarbazol-4-yl}oxyacetic acid;

9-[(3-ethoxyphenyl)methyl]-2-(2,6-dichlorophenyl)-5-carbamoylcarbazol-4-yl}oxyacetic acid;

9-[(4-ethoxyphenyl)methyl]-2-(2,6-dichlorophenyl)-5-carbamoylcarbazol-4-yl}oxyacetic acid;

9-[(2-trifluoromethoxyphenyl)methyl]-2-(2,6-dichlorophenyl)-5-carbamoylcarbazol-4-yl}oxyacetic acid;

9-[(3-trifluoromethoxyphenyl)methyl]-2-(2,6-dichlorophenyl)-5-carbamoylcarbazol-4-yl}oxyacetic acid;

9-[(4-trifluoromethoxyphenyl)methyl]-2-(2,6-dichlorophenyl)-5-carbamoylcarbazol-4-yl}oxyacetic acid;

9-[(2-difluoromethoxyphenyl)methyl]-2-(2,6-dichlorophenyl)-5-carbamoylcarbazol-4-yl}oxyacetic acid;

9-[(3-difluoromethoxyphenyl)methyl]-2-(2,6-dichlorophenyl)-5-carbamoylcarbazol-4-yl}oxyacetic acid;

9-[(4-difluoromethoxyphenyl)methyl]-2-(2,6-dichlorophenyl)-5-carbamoylcarbazol-4-yl}oxyacetic acid;

9-[(2-cyanophenyl)methyl]-2-(2,6-dichlorophenyl)-5-carbamoylcarbazol-4-yl}oxyacetic acid;

9-[(3-cyanophenyl)methyl]-2-(2,6-dichlorophenyl)-5-carbamoylcarbazol-4-yl}oxyacetic acid;

9-[(4-cyanophenyl)methyl]-2-(2,6-dichlorophenyl)-5-carbamoylcarbazol-4-yl}oxyacetic acid;

9-[(2-pyridyl)methyl]-2-(2,6-dichlorophenyl)-5-carbamoylcarbazol-4-yl}oxyacetic acid;

9-[(3-pyridyl)methyl]-2-(2,6-dichlorophenyl)-5-carbamoylcarbazol-4-yl}oxyacetic acid;

9-[(4-pyridyl)methyl]-2-(2,6-dichlorophenyl)-5-carbamoylcarbazol-4-yl}oxyacetic acid;

9-[(2-furyl)methyl]-2-(2,6-dichlorophenyl)-5-carbamoylcarbazol-4-yl}oxyacetic acid;

9-[(3-furyl)methyl]-2-(2,6-dichlorophenyl)-5-carbamoylcarbazol-4-yl}oxyacetic acid;

9-[(2-thienyl)methyl]-2-(2,6-dichlorophenyl)-5-carbamoylcarbazol-4-yl}oxyacetic acid;

9-[(3-thienyl)methyl]-2-(2,6-dichlorophenyl)-5-carbamoylcarbazol-4-yl}oxyacetic acid;

9-[(2-benzylphenyl)methyl]-2-(2,6-dichlorophenyl)-5-carbamoylcarbazol-4-yl}oxyacetic acid;

9-[(3-benzylphenyl)methyl]-2-(2,6-dichlorophenyl)-5-carbamoylcarbazol-4-yl}oxyacetic acid;

9-[(4-benzylphenyl)methyl]-2-(2,6-dichlorophenyl)-5-carbamoylcarbazol-4-yl}oxyacetic acid;

9-[(2-benzoylphenyl)methyl]-2-(2,6-dichlorophenyl)-5-carbamoylcarbazol-4-yl}oxyacetic acid;

9-[(3-benzoylphenyl)methyl]-2-(2,6-dichlorophenyl)-5-carbamoylcarbazol-4-yl}oxyacetic acid;

9-[(4-benzoylphenyl)methyl]-2-(2,6-dichlorophenyl)-5-carbamoylcarbazol-4-yl}oxyacetic acid;

9-[(2-benzyloxyphenyl)methyl]-2-(2,6-dichlorophenyl)-5-carbamoylcarbazol-4-yl}oxyacetic acid;

9-[(3-benzyloxyphenyl)methyl]-2-(2,6-dichlorophenyl)-5-carbamoylcarbazol-4-yl}oxyacetic acid;

9-[(4-benzyloxyphenyl)methyl]-2-(2,6-dichlorophenyl)-5-carbamoylcarbazol-4-yl}oxyacetic acid;

9-[(2-phenylphenyl)methyl]-2-(2,6-dichlorophenyl)-5-carbamoylcarbazol-4-yl}oxyacetic acid;

9-[(3-phenylphenyl)methyl]-2-(2,6-dichlorophenyl)-5-carbamoylcarbazol-4-yl}oxyacetic acid;

9-[(4-phenylphenyl)methyl]-2-(2,6-dichlorophenyl)-5-carbamoylcarbazol-4-yl}oxyacetic acid;

9-[(1-naphthyl)methyl]-2-(2,6-dichlorophenyl)-5-carbamoylcarbazol-4-yl}oxyacetic acid;

9-[(2-naphthyl)methyl]-2-(2,6-dichlorophenyl)-5-carbamoylcarbazol-4-yl}oxyacetic acid;

9-[(2,3-difluorophenyl)methyl]-2-(2,6-dichlorophenyl)-5-carbamoylcarbazol-4-yl}oxyacetic acid;

9-[(2,4-difluorophenyl)methyl]-2-(2,6-dichlorophenyl)-5-carbamoylcarbazol-4-yl}oxyacetic acid;

9-[(2,5-difluorophenyl)methyl]-2-(2,6-dichlorophenyl)-5-carbamoylcarbazol-4-yl}oxyacetic acid;

9-[(2,6-difluorophenyl)methyl]-2-(2,6-dichlorophenyl)-5-carbamoylcarbazol-4-yl}oxyacetic acid;

9-[(3,4-difluorophenyl)methyl]-2-(2,6-dichlorophenyl)-5-carbamoylcarbazol-4-yl}oxyacetic acid;

9-[(3,5-difluorophenyl)methyl]-2-(2,6-dichlorophenyl)-5-carbamoylcarbazol-4-yl}oxyacetic acid;

9-[(2,3,4-trifluorophenyl)methyl]-2-(2,6-dichlorophenyl)-5-carbamoylcarbazol-4-yl}oxyacetic acid;

9-[(2,3,5-trifluorophenyl)methyl]-2-(2,6-dichlorophenyl)-5-carbamoylcarbazol-4-yl}oxyacetic acid;

9-[(2,3,6-trifluorophenyl)methyl]-2-(2,6-dichlorophenyl)-5-carbamoylcarbazol-4-yl}oxyacetic acid;

9-[(2,4,5-trifluorophenyl)methyl]-2-(2,6-dichlorophenyl)-5-carbamoylcarbazol-4-yl}oxyacetic acid;

9-[(2,4,6-trifluorophenyl)methyl]-2-(2,6-dichlorophenyl)-5-carbamoylcarbazol-4-yl}oxyacetic acid;

9-[(3,4,5-trifluorophenyl)methyl]-2-(2,6-dichlorophenyl)-5-carbamoylcarbazol-4-yl}oxyacetic acid;

9-[(pentafluorophenyl)methyl]-2-(2,6-dichlorophenyl)-5-carbamoylcarbazol-4-yl}oxyacetic acid;

9-[(2,3-dichlorophenyl)methyl]-2-(2,6-dichlorophenyl)-5-carbamoylcarbazol-4-yl}oxyacetic acid;

9-[(2,4-dichlorophenyl)methyl]-2-(2,6-dichlorophenyl)-5-carbamoylcarbazol-4-yl}oxyacetic acid;

9-[(2,5-dichlorophenyl)methyl]-2-(2,6-dichlorophenyl)-5-carbamoylcarbazol-4-yl}oxyacetic acid;

9-[(2,6-dichlorophenyl)methyl]-2-(2,6-dichlorophenyl)-5-carbamoylcarbazol-4-yl}oxyacetic acid;

9-[(3,4-dichlorophenyl)methyl]-2-(2,6-dichlorophenyl)-5-carbamoylcarbazol-4-yl}oxyacetic acid;

9-[(3,5-dichlorophenyl)methyl]-2-(2,6-dichlorophenyl)-5-carbamoylcarbazol-4-yl}oxyacetic acid;

9-[(2,3-dimethylphenyl)methyl]-2-(2,6-dichlorophenyl)-5-carbamoylcarbazol-4-yl}oxyacetic acid;

9-[(2,4-dimethylphenyl)methyl]-2-(2,6-dichlorophenyl)-5-carbamoylcarbazol-4-yl}oxyacetic acid;
9-[(2,5-dimethylphenyl)methyl]-2-(2,6-dichlorophenyl)-5-carbamoylcarbazol-4-yl}oxyacetic acid;
9-[(2,6-dimethylphenyl)methyl]-2-(2,6-dichlorophenyl)-5-carbamoylcarbazol-4-yl}oxyacetic acid;
9-[(3,4-dimethylphenyl)methyl]-2-(2,6-dichlorophenyl)-5-carbamoylcarbazol-4-yl}oxyacetic acid;
9-[(3,5-dimethylphenyl)methyl]-2-(2,6-dichlorophenyl)-5-carbamoylcarbazol-4-yl}oxyacetic acid;
9-[(2,4,6-trimethylphenyl)methyl]-2-(2,6-dichlorophenyl)-5-carbamoylcarbazol-4-yl}oxyacetic acid;
9-[(3,5-bis(trifluoromethyl)phenyl)methyl]-2-(2,6-dichlorophenyl)-5-carbamoylcarbazol-4-yl}oxyacetic acid;
9-[(2,4-bis(trifluoromethyl)phenyl)methyl]-2-(2,6-dichlorophenyl)-5-carbamoylcarbazol-4-yl}oxyacetic acid;
9-[(2-fluoro-3-trifluoromethylphenyl)methyl]-2-(2,6-dichlorophenyl)-5-carbamoylcarbazol-4-yl}oxyacetic acid;
9-[(2-fluoro-4-trifluoromethylphenyl)methyl]-2-(2,6-dichlorophenyl)-5-carbamoylcarbazol-4-yl}oxyacetic acid;
9-[(2-fluoro-5-trifluoromethylphenyl)methyl]-2-(2,6-dichlorophenyl)-5-carbamoylcarbazol-4-yl}oxyacetic acid;
9-[(2-fluoro-6-trifluoromethylphenyl)methyl]-2-(2,6-dichlorophenyl)-5-carbamoylcarbazol-4-yl}oxyacetic acid;
9-[(3-fluoro-5-trifluoromethylphenyl)methyl]-2-(2,6-dichlorophenyl)-5-carbamoylcarbazol-4-yl}oxyacetic acid;
9-[(4-fluoro-2-trifluoromethylphenyl)methyl]-2-(2,6-dichlorophenyl)-5-carbamoylcarbazol-4-yl}oxyacetic acid;
9-[(4-fluoro-3-trifluoromethylphenyl)methyl]-2-(2,6-dichlorophenyl)-5-carbamoylcarbazol-4-yl}oxyacetic acid;
9-[3-(2-fluorophenoxy)methyl]-2-(2,6-dichlorophenyl)-5-carbamoylcarbazol-4-yl}oxyacetic acid;
9-[3-(4-fluorophenoxy)methyl]-2-(2,6-dichlorophenyl)-5-carbamoylcarbazol-4-yl}oxyacetic acid;
9-[(2-fluoro-3-methylphenyl)methyl]-2-(2,6-dichlorophenyl)-5-carbamoylcarbazol-4-yl}oxyacetic acid;
9-[(3-chloro-2-fluorophenyl)methyl]-2-(2,6-dichlorophenyl)-5-carbamoylcarbazol-4-yl}oxyacetic acid;
9-[(2-chloro-6-fluorophenyl)methyl]-2-(2,6-dichlorophenyl)-5-carbamoylcarbazol-4-yl}oxyacetic acid;
9-[(4-bromo-2-fluorophenyl)methyl]-2-(2,6-dichlorophenyl)-5-carbamoylcarbazol-4-yl}oxyacetic acid;
9-[(2-bromo-5-fluorophenyl)methyl]-2-(2,6-dichlorophenyl)-5-carbamoylcarbazol-4-yl}oxyacetic acid;
9-[(3-chloro-4-methylphenyl)methyl]-2-(2,6-dichlorophenyl)-5-carbamoylcarbazol-4-yl}oxyacetic acid;
9-[(3-chloro-4-methoxyphenyl)methyl]-2-(2,6-dichlorophenyl)-5-carbamoylcarbazol-4-yl}oxyacetic acid;
9-[(4-methoxy-3-methylphenyl)methyl]-2-(2,6-dichlorophenyl)-5-carbamoylcarbazol-4-yl}oxyacetic acid;
9-[(4-trifluoromethylthiophenyl)methyl]-2-(2,6-dichlorophenyl)-5-carbamoylcarbazol-4-yl}oxyacetic acid;
9-[(1-bromo-2-naphthylphenyl)methyl]-2-(2,6-dichlorophenyl)-5-carbamoylcarbazol-4-yl}oxyacetic acid;
9-[(2-methyl-1-naphthylphenyl)methyl]-2-(2,6-dichlorophenyl)-5-carbamoylcarbazol-4-yl}oxyacetic acid;
9-[(4-methyl-1-naphthylphenyl)methyl]-2-(2,6-dichlorophenyl)-5-carbamoylcarbazol-4-yl}oxyacetic acid;
9-[(6-methyl-2-naphthylphenyl)methyl]-2-(2,6-dichlorophenyl)-5-carbamoylcarbazol-4-yl}oxyacetic acid;
9-[(2-((phenylsulfonyl)methyl)phenyl)methyl]-2-(2,6-dichlorophenyl)-5-carbamoylcarbazol-4-yl}oxyacetic acid;
9-[(1-fluorenylmethyl]-2-(2,6-dichlorophenyl)-5-carbamoylcarbazol-4-yl}oxyacetic acid;
9-[(1-tetrazolylmethyl]-2-(2,6-dichlorophenyl)-5-carbamoylcarbazol-4-yl}oxyacetic acid;
9-[(5-methyl-1-tetrazolylmethyl]-2-(2,6-dichlorophenyl)-5-carbamoylcarbazol-4-yl}oxyacetic acid;
9-[(5-benzyl-1-tetrazolylmethyl]-2-(2,6-dichlorophenyl)-5-carbamoylcarbazol-4-yl}oxyacetic acid;
9-[(phenyl)methyl]-2-(4-methoxyphenyl)-5-carbamoylcarbazol-4-yl}oxyacetic acid;
9-[(2-phenoxyphenyl)methyl]-2-(4-methoxyphenyl)-5-carbamoylcarbazol-4-yl}oxyacetic acid;
9-[(3-phenoxyphenyl)methyl]-2-(4-methoxyphenyl)-5-carbamoylcarbazol-4-yl}oxyacetic acid;
9-[(4-phenoxyphenyl)methyl]-2-(4-methoxyphenyl)-5-carbamoylcarbazol-4-yl}oxyacetic acid;
9-[(2-fluorophenyl)methyl]-2-(4-methoxyphenyl)-5-carbamoylcarbazol-4-yl}oxyacetic acid;
9-[(3-fluorophenyl)methyl]-2-(4-methoxyphenyl)-5-carbamoylcarbazol-4-yl}oxyacetic acid;
9-[(4-fluorophenyl)methyl]-2-(4-methoxyphenyl)-5-carbamoylcarbazol-4-yl}oxyacetic acid;
9-[(2-chlorophenyl)methyl]-2-(4-methoxyphenyl)-5-carbamoylcarbazol-4-yl}oxyacetic acid;
9-[(3-chlorophenyl)methyl]-2-(4-methoxyphenyl)-5-carbamoylcarbazol-4-yl}oxyacetic acid;
9-[(4-chlorophenyl)methyl]-2-(4-methoxyphenyl)-5-carbamoylcarbazol-4-yl}oxyacetic acid;
9-[(2-bromophenyl)methyl]-2-(4-methoxyphenyl)-5-carbamoylcarbazol-4-yl}oxyacetic acid;
9-[(3-bromophenyl)methyl]-2-(4-methoxyphenyl)-5-carbamoylcarbazol-4-yl}oxyacetic acid;
9-[(4-bromophenyl)methyl]-2-(4-methoxyphenyl)-5-carbamoylcarbazol-4-yl}oxyacetic acid;
9-[(2-iodophenyl)methyl]-2-(4-methoxyphenyl)-5-carbamoylcarbazol-4-yl}oxyacetic acid;
9-[(3-iodophenyl)methyl]-2-(4-methoxyphenyl)-5-carbamoylcarbazol-4-yl}oxyacetic acid;
9-[(4-iodophenyl)methyl]-2-(4-methoxyphenyl)-5-carbamoylcarbazol-4-yl}oxyacetic acid;
9-[(2-acetamidophenyl)methyl]-2-(4-methoxyphenyl)-5-carbamoylcarbazol-4-yl}oxyacetic acid;
9-[(3-acetamidophenyl)methyl]-2-(4-methoxyphenyl)-5-carbamoylcarbazol4-yl}oxyacetic acid;
9-[(4-acetamidophenyl)methyl]-2-(4-methoxyphenyl)-5-carbamoylcarbazol-4-yl}oxyacetic acid;
9-[(2-carbamoylphenyl)methyl]-2-(4-methoxyphenyl)-5-carbamoylcarbazol-4-yl}oxyacetic acid;
9-[(3-carbamoylphenyl)methyl]-2-(4-methoxyphenyl)-5-carbamoylcarbazol-4-yl}oxyacetic acid;

9-[(4-carbamoylphenyl)methyl]-2-(4-methoxyphenyl)-5-carbamoylcarbazol-4-yl}oxyacetic acid;
9-[(2-methylsulfonylphenyl)methyl]-2-(4-methoxyphenyl)-5-carbamoylcarbazol-4-yl}oxyacetic acid;
9-[(3-methylsulfonylphenyl)methyl]-2-(4-methoxyphenyl)-5-carbamoylcarbazol-4-yl}oxyacetic acid;
9-[(4-methylsulfonylphenyl)methyl]-2-(4-methoxyphenyl)-5-carbamoylcarbazol-4-yl}oxyacetic acid;
9-[(2-methylphenyl)methyl]-2-(4-methoxyphenyl)-5-carbamoylcarbazol-4-yl}oxyacetic acid;
9-[(3-methylphenyl)methyl]-2-(4-methoxyphenyl)-5-carbamoylcarbazol-4-yl}oxyacetic acid;
9-[(4-methylphenyl)methyl]-2-(4-methoxyphenyl)-5-carbamoylcarbazol-4-yl}oxyacetic acid;
9-[(2-ethylphenyl)methyl]-2-(4-methoxyphenyl)-5-carbamoylcarbazol-4-yl}oxyacetic acid;
9-[(3-ethylphenyl)methyl]-2-(4-methoxyphenyl)-5-carbamoylcarbazol-4-yl}oxyacetic acid;
9-[(4-ethylphenyl)methyl]-2-(4-methoxyphenyl)-5-carbamoylcarbazol-4-yl}oxyacetic acid;
9-[(2-trifluoromethylphenyl)methyl]-2-(4-methoxyphenyl)-5-carbamoylcarbazol-4-yl}oxyacetic acid;
9-[(3-trifluoromethylphenyl)methyl]-2-(4-methoxyphenyl)-5-carbamoylcarbazol-4-yl}oxyacetic acid;
9-[(4-trifluoromethylphenyl)methyl]-2-(4-methoxyphenyl)-5-carbamoylcarbazol-4-yl}oxyacetic acid;
9-[(cyclopropyl)methyl]-2-(4-methoxyphenyl)-5-carbamoylcarbazol-4-yl}oxyacetic acid;
9-[(cyclobutyl)methyl]-2-(4-methoxyphenyl)-5-carbamoylcarbazol-4-yl}oxyacetic acid;
9-[(cyclopentylmethyl]-2-(4-methoxyphenyl)-5-carbamoylcarbazol-4-yl}oxyacetic acid;
9-[(cyclohexyl)methyl]-2-(4-methoxyphenyl)-5-carbamoylcarbazol-4-yl}oxyacetic acid;
9-[(2-methoxyphenyl)methyl]-2-(4-methoxyphenyl)-5-carbamoylcarbazol-4-yl}oxyacetic acid;
9-[(3-methoxyphenyl)methyl]-2-(4-methoxyphenyl)-5-carbamoylcarbazol-4-yl}oxyacetic acid;
9-[(4-methoxyphenyl)methyl]-2-(4-methoxyphenyl)-5-carbamoylcarbazol-4-yl}oxyacetic acid;
9-[(2-ethoxyphenyl)methyl]-2-(4-methoxyphenyl)-5-carbamoylcarbazol-4-yl}oxyacetic acid;
9-[(3-ethoxyphenyl)methyl]-2-(4-methoxyphenyl)-5-carbamoylcarbazol-4-yl}oxyacetic acid;
9-[(4-ethoxyphenyl)methyl]-2-(4-methoxyphenyl)-5-carbamoylcarbazol-4-yl}oxyacetic acid;
9-[(2-trifluoromethoxyphenyl)methyl]-2-(4-methoxyphenyl)-5-carbamoylcarbazol-4-yl}oxyacetic acid;
9-[(3-trifluoromethoxyphenyl)methyl]-2-(4-methoxyphenyl)-5-carbamoylcarbazol-4-yl}oxyacetic acid;
9-[(4-trifluoromethoxyphenyl)methyl]-2-(4-methoxyphenyl)-5-carbamoylcarbazol-4-yl}oxyacetic acid;
9-[(2-difluoromethoxyphenyl)methyl]-2-(4-methoxyphenyl)-5-carbamoylcarbazol-4-yl}oxyacetic acid;
9-[(3-difluoromethoxyphenyl)methyl]-2-(4-methoxyphenyl)-5-carbamoylcarbazol-4-yl}oxyacetic acid;
9-[(4-difluoromethoxyphenyl)methyl]-2-(4-methoxyphenyl)-5-carbamoylcarbazol-4-yl}oxyacetic acid;
9-[(2-cyanophenyl)methyl]-2-(4-methoxyphenyl)-5-carbamoylcarbazol-4-yl}oxyacetic acid;
9-[(3-cyanophenyl)methyl]-2-(4-methoxyphenyl)-5-carbamoylcarbazol-4-yl}oxyacetic acid;
9-[(4-cyanophenyl)methyl]-2-(4-methoxyphenyl)-5-carbamoylcarbazol-4-yl}oxyacetic acid;
9-[(2-pyridyl)methyl]-2-(4-methoxyphenyl)-5-carbamoylcarbazol-4-yl}oxyacetic acid;
9-[(3-pyridyl)methyl]-2-(4-methoxyphenyl)-5-carbamoylcarbazol-4-yl}oxyacetic acid;
9-[(4-pyridyl)methyl]-2-(4-methoxyphenyl)-5-carbamoylcarbazol-4-yl}oxyacetic acid;
9-[(2-furyl)methyl]-2-(4-methoxyphenyl)-5-carbamoylcarbazol-4-yl}oxyacetic acid;
9-[(3-furyl)methyl]-2-(4-methoxyphenyl)-5-carbamoylcarbazol-4-yl}oxyacetic acid;
9-[(2-thienyl)methyl]-2-(4-methoxyphenyl)-5-carbamoylcarbazol-4-yl}oxyacetic acid;
9-[(3-thienyl)methyl]-2-(4-methoxyphenyl)-5-carbamoylcarbazol-4-yl}oxyacetic acid;
9-[(2-benzylphenyl)methyl]-2-(4-methoxyphenyl)-5-carbamoylcarbazol-4-yl}oxyacetic acid;
9-[(3-benzylphenyl)methyl]-2-(4-methoxyphenyl)-5-carbamoylcarbazol-4-yl}oxyacetic acid;
9-[(4-benzylphenyl)methyl]-2-(4-methoxyphenyl)-5-carbamoylcarbazol-4-yl}oxyacetic acid;
9-[(2-benzoylphenyl)methyl]-2-(4-methoxyphenyl)-5-carbamoylcarbazol-4-yl}oxyacetic acid;
9-[(3-benzoylphenyl)methyl]-2-(4-methoxyphenyl)-5-carbamoylcarbazol-4-yl}oxyacetic acid;
9-[(4-benzoylphenyl)methyl]-2-(4-methoxyphenyl)-5-carbamoylcarbazol-4-yl}oxyacetic acid;
9-[(2-benzyloxyphenyl)methyl]-2-(4-methoxyphenyl)-5-carbamoylcarbazol-4-yl}oxyacetic acid;
9-[(3-benzyloxyphenyl)methyl]-2-(4-methoxyphenyl)-5-carbamoylcarbazol-4-yl}oxyacetic acid;
9-[(4-benzyloxyphenyl)methyl]-2-(4-methoxyphenyl)-5-carbamoylcarbazol-4-yl}oxyacetic acid;
9-[(2-phenylphenyl)methyl]-2-(4-methoxyphenyl)-5-carbamoylcarbazol-4-yl}oxyacetic acid;
9-[(3-phenylphenyl)methyl]-2-(4-methoxyphenyl)-5-carbamoylcarbazol-4-yl}oxyacetic acid;
9-[(4-phenylphenyl)methyl]-2-(4-methoxyphenyl)-5-carbamoylcarbazol-4-yl}oxyacetic acid;
9-[(1-naphthyl)methyl]-2-(4-methoxyphenyl)-5-carbamoylcarbazol-4-yl}oxyacetic acid;
9-[(2-naphthyl)methyl]-2-(4-methoxyphenyl)-5-carbamoylcarbazol-4-yl}oxyacetic acid;
9-[(2,3-difluorophenyl)methyl]-2-(4-methoxyphenyl)-5-carbamoylcarbazol-4-yl}oxyacetic acid;
9-[(2,4-difluorophenyl)methyl]-2-(4-methoxyphenyl)-5-carbamoylcarbazol-4-yl}oxyacetic acid;
9-[(2,5-difluorophenyl)methyl]-2-(4-methoxyphenyl)-5-carbamoylcarbazol-4-yl}oxyacetic acid;
9-[(2,6-difluorophenyl)methyl]-2-(4-methoxyphenyl)-5-carbamoylcarbazol-4-yl}oxyacetic acid;
9-[(3,4-difluorophenyl)methyl]-2-(4-methoxyphenyl)-5-carbamoylcarbazol-4-yl}oxyacetic acid;
9-[(3,5-difluorophenyl)methyl]-2-(4-methoxyphenyl)-5-carbamoylcarbazol-4-yl}oxyacetic acid;
9-[(2,3,4-trifluorophenyl)methyl]-2-(4-methoxyphenyl)-5-carbamoylcarbazol-4-yl}oxyacetic acid;
9-[(2,3,5-trifluorophenyl)methyl]-2-(4-methoxyphenyl)-5-carbamoylcarbazol-4-yl}oxyacetic acid;
9-[(2,3,6-trifluorophenyl)methyl]-2-(4-methoxyphenyl)-5-carbamoylcarbazol-4-yl}oxyacetic acid;
9-[(2,4,5-trifluorophenyl)methyl]-2-(4-methoxyphenyl)-5-carbamoylcarbazol-4-yl}oxyacetic acid;
9-[(2,4,6-trifluorophenyl)methyl]-2-(4-methoxyphenyl)-5-carbamoylcarbazol-4-yl}oxyacetic acid;
9-[(3,4,5-trifluorophenyl)methyl]-2-(4-methoxyphenyl)-5-carbamoylcarbazol-4-yl}oxyacetic acid;

9-[(pentafluorophenyl)methyl]-2-(4-methoxyphenyl)-5-carbamoylcarbazol-4-yl}oxyacetic acid;
9-[(2,3-dichlorophenyl)methyl]-2-(4-methoxyphenyl)-5-carbamoylcarbazol-4-yl}oxyacetic acid;
9-[(2,4-dichlorophenyl)methyl]-2-(4-methoxyphenyl)-5-carbamoylcarbazol-4-yl}oxyacetic acid;
9-[(2,5-dichlorophenyl)methyl]-2-(4-methoxyphenyl)-5-carbamoylcarbazol-4-yl}oxyacetic acid;
9-[(2,6-dichlorophenyl)methyl]-2-(4-methoxyphenyl)-5-carbamoylcarbazol-4-yl}oxyacetic acid;
9-[(3,4-dichlorophenyl)methyl]-2-(4-methoxyphenyl)-5-carbamoylcarbazol-4-yl}oxyacetic acid;
9-[(3,5-dichlorophenyl)methyl]-2-(4-methoxyphenyl)-5-carbamoylcarbazol-4-yl}oxyacetic acid;
9-[(2,3-dimethylphenyl)methyl]-2-(4-methoxyphenyl)-5-carbamoylcarbazol-4-yl}oxyacetic acid;
9-[(2,4-dimethylphenyl)methyl]-2-(4-methoxyphenyl)-5-carbamoylcarbazol-4-yl}oxyacetic acid;
9-[(2,5-dimethylphenyl)methyl]-2-(4-methoxyphenyl)-5-carbamoylcarbazol-4-yl}oxyacetic acid;
9-[(2,6-dimethylphenyl)methyl]-2-(4-methoxyphenyl)-5-carbamoylcarbazol-4-yl}oxyacetic acid;
9-[(3,4-dimethylphenyl)methyl]-2-(4-methoxyphenyl)-5-carbamoylcarbazol-4-yl}oxyacetic acid;
9-[(3,5-dimethylphenyl)methyl]-2-(4-methoxyphenyl)-5-carbamoylcarbazol-4-yl}oxyacetic acid;
9-[(2,4,6-trimethylphenyl)methyl]-2-(4-methoxyphenyl)-5-carbamoylcarbazol-4-yl}oxyacetic acid;
9-[(3,5-bis(trifluoromethyl)phenyl)methyl]-2-(4-methoxyphenyl)-5-carbamoylcarbazol-4-yl}oxyacetic acid;
9-[(2,4-bis(trifluoromethyl)phenyl)methyl]-2-(4-methoxyphenyl)-5-carbamoylcarbazol-4-yl}oxyacetic acid;
9-[(2-fluoro-3-trifluoromethylphenyl)methyl]-2-(4-methoxyphenyl)-5-carbamoylcarbazol-4-yl}oxyacetic acid;
9-[(2-fluoro-4-trifluoromethylphenyl)methyl]-2-(4-methoxyphenyl)-5-carbamoylcarbazol-4-yl}oxyacetic acid;
9-[(2-fluoro-5-trifluoromethylphenyl)methyl]-2-(4-methoxyphenyl)-5-carbamoylcarbazol-4-yl}oxyacetic acid;
9-[(2-fluoro-6-trifluoromethylphenyl)methyl]-2-(4-methoxyphenyl)-5-carbamoylcarbazol-4-yl}oxyacetic acid;
9-[(3-fluoro-5-trifluoromethylphenyl)methyl]-2-(4-methoxyphenyl)-5-carbamoylcarbazol-4-yl}oxyacetic acid;
9-[(4-fluoro-2-trifluoromethylphenyl)methyl]-2-(4-methoxyphenyl)-5-carbamoylcarbazol-4-yl}oxyacetic acid;
9-[(4-fluoro-3-trifluoromethylphenyl)methyl]-2-(4-methoxyphenyl)-5-carbamoylcarbazol-4-yl}oxyacetic acid;
9-[3-(2-fluorophenoxy)methyl]-2-(4-methoxyphenyl)-5-carbamoylcarbazol-4-yl}oxyacetic acid;
9-[3-(4-fluorophenoxy)methyl]-2-(4-methoxyphenyl)-5-carbamoylcarbazol-4-yl}oxyacetic acid;
9-[(2-fluoro-3-methylphenyl)methyl]-2-(4-methoxyphenyl)-5-carbamoylcarbazol-4-yl}oxyacetic acid;
9-[(3-chloro-2-fluorophenyl)methyl]-2-(4-methoxyphenyl)-5-carbamoylcarbazol-4-yl}oxyacetic acid;
9-[(2-chloro-6-fluorophenyl)methyl]-2-(4-methoxyphenyl)-5-carbamoylcarbazol-4-yl}oxyacetic acid;
9-[(4-bromo-2-fluorophenyl)methyl]-2-(4-methoxyphenyl)-5-carbamoylcarbazol-4-yl}oxyacetic acid;
9-[(2-bromo-5-fluorophenyl)methyl]-2-(4-methoxyphenyl)-5-carbamoylcarbazol-4-yl}oxyacetic acid;
9-[(3-chloro-4-methylphenyl)methyl]-2-(4-methoxyphenyl)-5-carbamoylcarbazol-4-yl}oxyacetic acid;
9-[(3-chloro-4-methoxyphenyl)methyl]-2-(4-methoxyphenyl)-5-carbamoylcarbazol-4-yl}oxyacetic acid;
9-[(4-methoxy-3-methylphenyl)methyl]-2-(4-methoxyphenyl)-5-carbamoylcarbazol-4-yl}oxyacetic acid;
9-[(4-trifluoromethylthiophenyl)methyl]-2-(4-methoxyphenyl)-5-carbamoylcarbazol-4-yl}oxyacetic acid;
9-[(1-bromo-2-naphthylphenyl)methyl]-2-(4-methoxyphenyl)-5-carbamoylcarbazol-4-yl}oxyacetic acid;
9-[(2-methyl-1-naphthylphenyl)methyl]-2-(4-methoxyphenyl)-5-carbamoylcarbazol-4-yl}oxyacetic acid;
9-[(4-methyl-1-naphthylphenyl)methyl]-2-(4-methoxyphenyl)-5-carbamoylcarbazol-4-yl}oxyacetic acid;
9-[(6-methyl-2-naphthylphenyl)methyl]-2-(4-methoxyphenyl)-5-carbamoylcarbazol-4-yl}oxyacetic acid;
9-[(2-((phenylsulfonyl)methyl)phenyl)methyl]-2-(4-methoxyphenyl)-5-carbamoylcarbazol-4-yl}oxyacetic acid;
9-[(1-fluorenylmethyl]-2-(4-methoxyphenyl)-5-carbamoylcarbazol-4-yl}oxyacetic acid;
9-[(1-tetrazolylmethyl]-2-(4-methoxyphenyl)-5-carbamoylcarbazol-4-yl}oxyacetic acid;
9-[(5-methyl-1-tetrazolylmethyl]-2-(4-methoxyphenyl)-5-carbamoylcarbazol-4-yl}oxyacetic acid;
9-[(5-benzyl-1-tetrazolylmethyl]-2-(4-methoxyphenyl)-5-carbamoylcarbazol-4-yl}oxyacetic acid;
9-[(phenyl)methyl]-2-(hydroxymethyl)-5-carbamoylcarbazol-4-yl}oxyacetic acid;
9-[(2-phenoxyphenyl)methyl]-2-(hydroxymethyl)-5-carbamoylcarbazol-4-yl}oxyacetic acid;
9-[(3-phenoxyphenyl)methyl]-2-(hydroxymethyl)-5-carbamoylcarbazol-4-yl}oxyacetic acid;
9-[(4-phenoxyphenyl)methyl]-2-(hydroxymethyl)-5-carbamoylcarbazol-4-yl}oxyacetic acid;
9-[(2-fluorophenyl)methyl]-2-(hydroxymethyl)-5-carbamoylcarbazol-4-yl}oxyacetic acid;
9-[(3-fluorophenyl)methyl]-2-(hydroxymethyl)-5-carbamoylcarbazol-4-yl}oxyacetic acid;
9-[(4-fluorophenyl)methyl]-2-(hydroxymethyl)-5-carbamoylcarbazol-4-yl}oxyacetic acid;
9-[(2-chlorophenyl)methyl]-2-(hydroxymethyl)-5-carbamoylcarbazol-4-yl}oxyacetic acid;
9-[(3-chlorophenyl)methyl]-2-(hydroxymethyl)-5-carbamoylcarbazol-4-yl}oxyacetic acid;
9-[(4-chlorophenyl)methyl]-2-(hydroxymethyl)-5-carbamoylcarbazol-4-yl}oxyacetic acid;
9-[(2-bromophenyl)methyl]-2-(hydroxymethyl)-5-carbamoylcarbazol-4-yl}oxyacetic acid;
9-[(3-bromophenyl)methyl]-2-(hydroxymethyl)-5-carbamoylcarbazol-4-yl}oxyacetic acid;
9-[(4-bromophenyl)methyl]-2-(hydroxymethyl)-5-carbamoylcarbazol-4-yl}oxyacetic acid;
9-[(2-iodophenyl)methyl]-2-(hydroxymethyl)-5-carbamoylcarbazol-4-yl}oxyacetic acid;
9-[(3-iodophenyl)methyl]-2-(hydroxymethyl)-5-carbamoylcarbazol-4-yl}oxyacetic acid;

9-[(4-iodophenyl)methyl]-2-(hydroxymethyl)-5-carbamoylcarbazol-4-yl}oxyacetic acid;
9-[(2-acetamidophenyl)methyl]-2-(hydroxymethyl)-5-carbamoylcarbazol-4-yl}oxyacetic acid;
9-[(3-acetamidophenyl)methyl]-2-(hydroxymethyl)-5-carbamoylcarbazol-4-yl}oxyacetic acid;
9-[(4-acetamidophenyl)methyl]-2-(hydroxymethyl)-5-carbamoylcarbazol-4-yl}oxyacetic acid;
9-[(2-carbamoylphenyl)methyl]-2-(hydroxymethyl)-5-carbamoylcarbazol-4-yl}oxyacetic acid;
9-[(3-carbamoylphenyl)methyl]-2-(hydroxymethyl)-5-carbamoylcarbazol-4-yl}oxyacetic acid;
9-[(4-carbamoylphenyl)methyl]-2-(hydroxymethyl)-5-carbamoylcarbazol-4-yl}oxyacetic acid;
9-[(2-methylsulfonylphenyl)methyl]-2-(hydroxymethyl)-5-carbamoylcarbazol-4-yl}oxyacetic acid;
9-[(3-methylsulfonylphenyl)methyl]-2-(hydroxymethyl)-5-carbamoylcarbazol-4-yl}oxyacetic acid;
9-[(4-methylsulfonylphenyl)methyl]-2-(hydroxymethyl)-5-carbamoylcarbazol-4-yl}oxyacetic acid;
9-[(2-methylphenyl)methyl]-2-(hydroxymethyl)-5-carbamoylcarbazol-4-yl}oxyacetic acid;
9-[(3-methylphenyl)methyl]-2-(hydroxymethyl)-5-carbamoylcarbazol-4-yl}oxyacetic acid;
9-[(4-methylphenyl)methyl]-2-(hydroxymethyl)-5-carbamoylcarbazol-4-yl}oxyacetic acid;
9-[(2-ethylphenyl)methyl]-2-(hydroxymethyl)-5-carbamoylcarbazol-4-yl}oxyacetic acid;
9-[(3-ethylphenyl)methyl]-2-(hydroxymethyl)-5-carbamoylcarbazol-4-yl}oxyacetic acid;
9-[(4-ethylphenyl)methyl]-2-(hydroxymethyl)-5-carbamoylcarbazol-4-yl}oxyacetic acid;
9-[(2-trifluoromethylphenyl)methyl]-2-(hydroxymethyl)-5-carbamoylcarbazol-4-yl}oxyacetic acid;
9-[(3-trifluoromethylphenyl)methyl]-2-(hydroxymethyl)-5-carbamoylcarbazol-4-yl}oxyacetic acid;
9-[(4-trifluoromethylphenyl)methyl]-2-(hydroxymethyl)-5-carbamoylcarbazol-4-yl}oxyacetic acid;
9-[(cyclopropyl)methyl]-2-(hydroxymethyl)-5-carbamoylcarbazol-4-yl}oxyacetic acid;
9-[(cyclobutyl)methyl]-2-(hydroxymethyl)-5-carbamoylcarbazol-4-yl}oxyacetic acid;
9-[(cyclopentyl)methyl]-2-(hydroxymethyl)-5-carbamoylcarbazol-4-yl}oxyacetic acid;
9-[(cyclohexyl)methyl]-2-(hydroxymethyl)-5-carbamoylcarbazol-4-yl}oxyacetic acid;
9-[(2-methoxyphenyl)methyl]-2-(hydroxymethyl)-5-carbamoylcarbazol-4-yl}oxyacetic acid;
9-[(3-methoxyphenyl)methyl]-2-(hydroxymethyl)-5-carbamoylcarbazol-4-yl}oxyacetic acid;
9-[(4-methoxyphenyl)methyl]-2-(hydroxymethyl)-5-carbamoylcarbazol-4-yl}oxyacetic acid;
9-[(2-ethoxyphenyl)methyl]-2-(hydroxymethyl)-5-carbamoylcarbazol-4-yl}oxyacetic acid;
9-[(3-ethoxyphenyl)methyl]-2-(hydroxymethyl)-5-carbamoylcarbazol-4-yl}oxyacetic acid;
9-[(4-ethoxyphenyl)methyl]-2-(hydroxymethyl)-5-carbamoylcarbazol-4-yl}oxyacetic acid;
9-[(2-trifluoromethoxyphenyl)methyl]-2-(hydroxymethyl)-5-carbamoylcarbazol-4-yl}oxyacetic acid;
9-[(3-trifluoromethoxyphenyl)methyl]-2-(hydroxymethyl)-5-carbamoylcarbazol-4-yl}oxyacetic acid;
9-[(4-trifluoromethoxyphenyl)methyl]-2-(hydroxymethyl)-5-carbamoylcarbazol-4-yl}oxyacetic acid;
9-[(2-difluoromethoxyphenyl)methyl]-2-(hydroxymethyl)-5-carbamoylcarbazol-4-yl}oxyacetic acid;
9-[(3-difluoromethoxyphenyl)methyl]-2-(hydroxymethyl)-5-carbamoylcarbazol-4-yl}oxyacetic acid;
9-[(4-difluoromethoxyphenyl)methyl]-2-(hydroxymethyl)-5-carbamoylcarbazol-4-yl}oxyacetic acid;
9-[(2-cyanophenyl)methyl]-2-(hydroxymethyl)-5-carbamoylcarbazol-4-yl}oxyacetic acid;
9-[(3-cyanophenyl)methyl]-2-(hydroxymethyl)-5-carbamoylcarbazol-4-yl}oxyacetic acid;
9-[(4-cyanophenyl)methyl]-2-(hydroxymethyl)-5-carbamoylcarbazol-4-yl}oxyacetic acid;
9-[(2-pyridyl)methyl]-2-(hydroxymethyl)-5-carbamoylcarbazol-4-yl}oxyacetic acid;
9-[(3-pyridyl)methyl]-2-(hydroxymethyl)-5-carbamoylcarbazol-4-yl}oxyacetic acid;
9-[(4-pyridyl)methyl]-2-(hydroxymethyl)-5-carbamoylcarbazol-4-yl}oxyacetic acid;
9-[(2-furyl)methyl]-2-(hydroxymethyl)-5-carbamoylcarbazol-4-yl}oxyacetic acid;
9-[(3-furyl)methyl]-2-(hydroxymethyl)-5-carbamoylcarbazol-4-yl}oxyacetic acid;
9-[(2-thienyl)methyl]-2-(hydroxymethyl)-5-carbamoylcarbazol-4-yl}oxyacetic acid;
9-[(3-thienyl)methyl]-2-(hydroxymethyl)-5-carbamoylcarbazol-4-yl}oxyacetic acid;
9-[(2-benzylphenyl)methyl]-2-(hydroxymethyl)-5-carbamoylcarbazol-4-yl}oxyacetic acid;
9-[(3-benzylphenyl)methyl]-2-(hydroxymethyl)-5-carbamoylcarbazol-4-yl}oxyacetic acid;
9-[(4-benzylphenyl)methyl]-2-(hydroxymethyl)-5-carbamoylcarbazol-4-yl}oxyacetic acid;
9-[(2-benzoylphenyl)methyl]-2-(hydroxymethyl)-5-carbamoylcarbazol-4-yl}oxyacetic acid;
9-[(3-benzoylphenyl)methyl]-2-(hydroxymethyl)-5-carbamoylcarbazol-4-yl}oxyacetic acid;
9-[(4-benzoylphenyl)methyl]-2-(hydroxymethyl)-5-carbamoylcarbazol-4-yl}oxyacetic acid;
9-[(2-benzyloxyphenyl)methyl]-2-(hydroxymethyl)-5-carbamoylcarbazol-4-yl}oxyacetic acid;
9-[(3-benzyloxyphenyl)methyl]-2-(hydroxymethyl)-5-carbamoylcarbazol-4-yl}oxyacetic acid;
9-[(4-benzyloxyphenyl)methyl]-2-(hydroxymethyl)-5-carbamoylcarbazol-4-yl}oxyacetic acid;
9-[(2-phenylphenyl)methyl]-2-(hydroxymethyl)-5-carbamoylcarbazol-4-yl}oxyacetic acid;
9-[(3-phenylphenyl)methyl]-2-(hydroxymethyl)-5-carbamoylcarbazol-4-yl}oxyacetic acid;
9-[(4-phenylphenyl)methyl]-2-(hydroxymethyl)-5-carbamoylcarbazol-4-yl}oxyacetic acid;
9-[(1-naphthyl)methyl]-2-(hydroxymethyl)-5-carbamoylcarbazol-4-yl}oxyacetic acid;
9-[(2-naphthyl)methyl]-2-(hydroxymethyl)-5-carbamoylcarbazol-4-yl}oxyacetic acid;
9-[(2,3-difluorophenyl)methyl]-2-(hydroxymethyl)-5-carbamoylcarbazol-4-yl}oxyacetic acid;
9-[(2,4-difluorophenyl)methyl]-2-(hydroxymethyl)-5-carbamoylcarbazol-4-yl}oxyacetic acid;
9-[(2,5-difluorophenyl)methyl]-2-(hydroxymethyl)-5-carbamoylcarbazol-4-yl}oxyacetic acid;
9-[(2,6-difluorophenyl)methyl]-2-(hydroxymethyl)-5-carbamoylcarbazol-4-yl}oxyacetic acid;
9-[(3,4-difluorophenyl)methyl]-2-(hydroxymethyl)-5-carbamoylcarbazol-4-yl}oxyacetic acid;
9-[(3,5-difluorophenyl)methyl]-2-(hydroxymethyl)-5-carbamoylcarbazol-4-yl}oxyacetic acid;
9-[(2,3,4-trifluorophenyl)methyl]-2-(hydroxymethyl)-5-carbamoylcarbazol-4-yl}oxyacetic acid;
9-[(2,3,5-trifluorophenyl)methyl]-2-(hydroxymethyl)-5-carbamoylcarbazol-4-yl}oxyacetic acid;
9-[(2,3,6-trifluorophenyl)methyl]-2-(hydroxymethyl)-5-carbamoylcarbazol-4-yl}oxyacetic acid;

9-[(2,4,5-trifluorophenyl)methyl]-2-(hydroxymethyl)-5-carbamoylcarbazol-4-yl}oxyacetic acid;
9-[(2,4,6-trifluorophenyl)methyl]-2-(hydroxymethyl)-5-carbamoylcarbazol-4-yl}oxyacetic acid;
9-[(3,4,5-trifluorophenyl)methyl]-2-(hydroxymethyl)-5-carbamoylcarbazol-4-yl}oxyacetic acid;
9-[(pentafluorophenyl)methyl]-2-(hydroxymethyl)-5-carbamoylcarbazol-4-yl}oxyacetic acid;
9-[(2,3-dichlorophenyl)methyl]-2-(hydroxymethyl)-5-carbamoylcarbazol-4-yl}oxyacetic acid;
9-[(2,4-dichlorophenyl)methyl]-2-(hydroxymethyl)-5-carbamoylcarbazol-4-yl}oxyacetic acid;
9-[(2,5-dichlorophenyl)methyl]-2-(hydroxymethyl)-5-carbamoylcarbazol-4-yl}oxyacetic acid;
9-[(2,6-dichlorophenyl)methyl]-2-(hydroxymethyl)-5-carbamoylcarbazol-4-yl}oxyacetic acid;
9-[(3,4-dichlorophenyl)methyl]-2-(hydroxymethyl)-5-carbamoylcarbazol-4-yl}oxyacetic acid;
9-[(3,5-dichlorophenyl)methyl]-2-(hydroxymethyl)-5-carbamoylcarbazol-4-yl}oxyacetic acid;
9-[(2,3-dimethylphenyl)methyl]-2-(hydroxymethyl)-5-carbamoylcarbazol-4-yl}oxyacetic acid;
9-[(2,4-dimethylphenyl)methyl]-2-(hydroxymethyl)-5-carbamoylcarbazol-4-yl}oxyacetic acid;
9-[(2,5-dimethylphenyl)methyl]-2-(hydroxymethyl)-5-carbamoylcarbazol-4-yl}oxyacetic acid;
9-[(2,6-dimethylphenyl)methyl]-2-(hydroxymethyl)-5-carbamoylcarbazol-4-yl}oxyacetic acid;
9-[(3,4-dimethylphenyl)methyl]-2-(hydroxymethyl)-5-carbamoylcarbazol-4-yl}oxyacetic acid;
9-[(3,5-dimethylphenyl)methyl]-2-(hydroxymethyl)-5-carbamoylcarbazol-4-yl}oxyacetic acid;
9-[(2,4,6-trimethylphenyl)methyl]-2-(hydroxymethyl)-5-carbamoylcarbazol-4-yl}oxyacetic acid;
9-[(3,5-bis(trifluoromethyl)phenyl)methyl]-2-(hydroxymethyl)-5-carbamoylcarbazol-4-yl}oxyacetic acid;
9-[(2,4-bis(trifluoromethyl)phenyl)methyl]-2-(hydroxymethyl)-5-carbamoylcarbazol-4-yl}oxyacetic acid;
9-[(2-fluoro-3-trifluoromethylphenyl)methyl]-2-(hydroxymethyl)-5-carbamoylcarbazol-4-yl}oxyacetic acid;
9-[(2-fluoro-4-trifluoromethylphenyl)methyl]-2-(hydroxymethyl)-5-carbamoylcarbazol-4-yl}oxyacetic acid;
9-[(2-fluoro-5-trifluoromethylphenyl)methyl]-2-(hydroxymethyl)-5-carbamoylcarbazol-4-yl}oxyacetic acid;
9-[(2-fluoro-6-trifluoromethylphenyl)methyl]-2-(hydroxymethyl)-5-carbamoylcarbazol-4-yl}oxyacetic acid;
9-[(3-fluoro-5-trifluoromethylphenyl)methyl]-2-(hydroxymethyl)-5-carbamoylcarbazol-4-yl}oxyacetic acid;
9-[(4-fluoro-2-trifluoromethylphenyl)methyl]-2-(hydroxymethyl)-5-carbamoylcarbazol-4-yl}oxyacetic acid;
9-[(4-fluoro-3-trifluoromethylphenyl)methyl]-2-(hydroxymethyl)-5-carbamoylcarbazol-4-yl}oxyacetic acid;
9-[3-(2-fluorophenoxy)methyl]-2-(hydroxymethyl)-5-carbamoylcarbazol-4-yl}oxyacetic acid;
9-[3-(4-fluorophenoxy)methyl]-2-(hydroxymethyl)-5-carbamoylcarbazol-4-yl}oxyacetic acid;
9-[(2-fluoro-3-methylphenyl)methyl]-2-(hydroxymethyl)-5-carbamoylcarbazol-4-yl}oxyacetic acid;
9-[(3-chloro-2-fluorophenyl)methyl]-2-(hydroxymethyl)-5-carbamoylcarbazol-4-yl}oxyacetic acid;
9-[(2-chloro-6-fluorophenyl)methyl]-2-(hydroxymethyl)-5-carbamoylcarbazol-4-yl}oxyacetic acid;
9-[(4-bromo-2-fluorophenyl)methyl]-2-(hydroxymethyl)-5-carbamoylcarbazol-4-yl}oxyacetic acid;
9-[(2-bromo-5-fluorophenyl)methyl]-2-(hydroxymethyl)-5-carbamoylcarbazol-4-yl}oxyacetic acid;
9-[(3-chloro-4-methylphenyl)methyl]-2-(hydroxymethyl)-5-carbamoylcarbazol-4-yl}oxyacetic acid;
9-[(3-chloro-4-methoxyphenyl)methyl]-2-(hydroxymethyl)-5-carbamoylcarbazol-4-yl}oxyacetic acid;
9-[(4-methoxy-3-methylphenyl)methyl]-2-(hydroxymethyl)-5-carbamoylcarbazol-4-yl}oxyacetic acid;
9-[(4-trifluoromethylthiophenyl)methyl]-2-(hydroxymethyl)-5-carbamoylcarbazol-4-yl}oxyacetic acid;
9-[(1-bromo-2-naphthylphenyl)methyl]-2-(hydroxymethyl)-5-carbamoylcarbazol-4-yl}oxyacetic acid;
9-[(2-methyl-1-naphthylphenyl)methyl]-2-(hydroxymethyl)-5-carbamoylcarbazol-4-yl}oxyacetic acid;
9-[(4-methyl-1-naphthylphenyl)methyl]-2-(hydroxymethyl)-5-carbamoylcarbazol-4-yl}oxyacetic acid;
9-[(6-methyl-2-naphthylphenyl)methyl]-2-(hydroxymethyl)-5-carbamoylcarbazol-4-yl}oxyacetic acid;
9-[(2-((phenylsulfonyl)methyl)phenyl)methyl]-2-(hydroxymethyl)-5-carbamoylcarbazol-4-yl}oxyacetic acid;
9-[(1-fluorenylmethyl]-2-(hydroxymethyl)-5-carbamoylcarbazol-4-yl}oxyacetic acid;
9-[(1-tetrazolylmethyl]-2-(hydroxymethyl)-5-carbamoylcarbazol-4-yl}oxyacetic acid;
9-[(5-methyl-1-tetrazolylmethyl]-2-(hydroxymethyl)-5-carbamoylcarbazol-4-yl}oxyacetic acid;
9-[(5-benzyl-1-tetrazolylmethyl]-2-(hydroxymethyl)-5-carbamoylcarbazol-4-yl}oxyacetic acid;
9-[(phenyl)methyl]-2-(methoxymethyl)-5-carbamoylcarbazol-4-yl}oxyacetic acid;
9-[(2-phenoxyphenyl)methyl]-2-(methoxymethyl)-5-carbamoylcarbazol-4-yl}oxyacetic acid;
9-[(3-phenoxyphenyl)methyl]-2-(methoxymethyl)-5-carbamoylcarbazol-4-yl}oxyacetic acid;
9-[(4-phenoxyphenyl)methyl]-2-(methoxymethyl)-5-carbamoylcarbazol-4-yl}oxyacetic acid;
9-[(2-fluorophenyl)methyl]-2-(methoxymethyl)-5-carbamoylcarbazol-4-yl}oxyacetic acid;
9-[(3-fluorophenyl)methyl]-2-(methoxymethyl)-5-carbamoylcarbazol-4-yl}oxyacetic acid;
9-[(4-fluorophenyl)methyl]-2-(methoxymethyl)-5-carbamoylcarbazol-4-yl}oxyacetic acid;
9-[(2-chlorophenyl)methyl]-2-(methoxymethyl)-5-carbamoylcarbazol-4-yl}oxyacetic acid;
9-[(3-chlorophenyl)methyl]-2-(methoxymethyl)-5-carbamoylcarbazol-4-yl}oxyacetic acid;
9-[(4-chlorophenyl)methyl]-2-(methoxymethyl)-5-carbamoylcarbazol-4-yl}oxyacetic acid;
9-[(2-bromophenyl)methyl]-2-(methoxymethyl)-5-carbamoylcarbazol-4-yl}oxyacetic acid;
9-[(3-bromophenyl)methyl]-2-(methoxymethyl)-5-carbamoylcarbazol-4-yl}oxyacetic acid;
9-[(4-bromophenyl)methyl]-2-(methoxymethyl)-5-carbamoylcarbazol-4-yl}oxyacetic acid;

9-[(2-iodophenyl)methyl]-2-(methoxymethyl)-5-carbamoylcarbazol-4-yl}oxyacetic acid;
9-[(3-iodophenyl)methyl]-2-(methoxymethyl)-5-carbamoylcarbazol-4-yl}oxyacetic acid;
9-[(4-iodophenyl)methyl]-2-(methoxymethyl)-5-carbamoylcarbazol-4-yl}oxyacetic acid;
9-[(2-acetamidophenyl)methyl]-2-(methoxymethyl)-5-carbamoylcarbazol-4-yl}oxyacetic acid;
9-[(3-acetamidophenyl)methyl]-2-(methoxymethyl)-5-carbamoylcarbazol-4-yl}oxyacetic acid;
9-[(4-acetamidophenyl)methyl]-2-(methoxymethyl)-5-carbamoylcarbazol-4-yl}oxyacetic acid;
9-[(2-carbamoylphenyl)methyl]-2-(methoxymethyl)-5-carbamoylcarbazol-4-yl}oxyacetic acid;
9-[(3-carbamoylphenyl)methyl]-2-(methoxymethyl)-5-carbamoylcarbazol-4-yl}oxyacetic acid;
9-[(4-carbamoylphenyl)methyl]-2-(methoxymethyl)-5-carbamoylcarbazol-4-yl}oxyacetic acid;
9-[(2-methylsulfonylphenyl)methyl]-2-(methoxymethyl)-5-carbamoylcarbazol-4-yl}oxyacetic acid;
9-[(3-methylsulfonylphenyl)methyl]-2-(methoxymethyl)-5-carbamoylcarbazol-4-yl}oxyacetic acid;
9-[(4-methylsulfonylphenyl)methyl]-2-(methoxymethyl)-5-carbamoylcarbazol-4-yl}oxyacetic acid;
9-[(2-methylphenyl)methyl]-2-(methoxymethyl)-5-carbamoylcarbazol-4-yl}oxyacetic acid;
9-[(3-methylphenyl)methyl]-2-(methoxymethyl)-5-carbamoylcarbazol-4-yl}oxyacetic acid;
9-[(4-methylphenyl)methyl]-2-(methoxymethyl)-5-carbamoylcarbazol-4-yl}oxyacetic acid;
9-[(2-ethylphenyl)methyl]-2-(methoxymethyl)-5-carbamoylcarbazol-4-yl}oxyacetic acid;
9-[(3-ethylphenyl)methyl]-2-(methoxymethyl)-5-carbamoylcarbazol-4-yl}oxyacetic acid;
9-[(4-ethylphenyl)methyl]-2-(methoxymethyl)-5-carbamoylcarbazol-4-yl}oxyacetic acid;
9-[(2-trifluoromethylphenyl)methyl]-2-(methoxymethyl)-5-carbamoylcarbazol-4-yl}oxyacetic acid;
9-[(3-trifluoromethylphenyl)methyl]-2-(methoxymethyl)-5-carbamoylcarbazol-4-yl}oxyacetic acid;
9-[(4-trifluoromethylphenyl)methyl]-2-(methoxymethyl)-5-carbamoylcarbazol-4-yl}oxyacetic acid;
9-[(cyclopropyl)methyl]-2-(methoxymethyl)-5-carbamoylcarbazol-4-yl}oxyacetic acid;
9-[(cyclobutyl)methyl]-2-(methoxymethyl)-5-carbamoylcarbazol-4-yl}oxyacetic acid;
9-[(cyclopentyl)methyl]-2-(methoxymethyl)-5-carbamoylcarbazol-4-yl}oxyacetic acid;
9-[(cyclohexyl)methyl]-2-(methoxymethyl)-5-carbamoylcarbazol-4-yl}oxyacetic acid;
9-[(2-methoxyphenyl)methyl]-2-(methoxymethyl)-5-carbamoylcarbazol-4-yl}oxyacetic acid;
9-[(3-methoxyphenyl)methyl]-2-(methoxymethyl)-5-carbamoylcarbazol-4-yl}oxyacetic acid;
9-[(4-methoxyphenyl)methyl]-2-(methoxymethyl)-5-carbamoylcarbazol-4-yl}oxyacetic acid;
9-[(2-ethoxyphenyl)methyl]-2-(methoxymethyl)-5-carbamoylcarbazol-4-yl}oxyacetic acid;
9-[(3-ethoxyphenyl)methyl]-2-(methoxymethyl)-5-carbamoylcarbazol-4-yl}oxyacetic acid;
9-[(4-ethoxyphenyl)methyl]-2-(methoxymethyl)-5-carbamoylcarbazol-4-yl}oxyacetic acid;
9-[(2-trifluoromethoxyphenyl)methyl]-2-(methoxymethyl)-5-carbamoylcarbazol-4-yl}oxyacetic acid;
9-[(3-trifluoromethoxyphenyl)methyl]-2-(methoxymethyl)-5-carbamoylcarbazol-4-yl}oxyacetic acid;
9-[(4-trifluoromethoxyphenyl)methyl]-2-(methoxymethyl)-5-carbamoylcarbazol-4-yl}oxyacetic acid;
9-[(2-difluoromethoxyphenyl)methyl]-2-(methoxymethyl)-5-carbamoylcarbazol-4-yl}oxyacetic acid;
9-[(3-difluoromethoxyphenyl)methyl]-2-(methoxymethyl)-5-carbamoylcarbazol-4-yl}oxyacetic acid;
9-[(4-difluoromethoxyphenyl)methyl]-2-(methoxymethyl)-5-carbamoylcarbazol-4-yl}oxyacetic acid;
9-[(2-cyanophenyl)methyl]-2-(methoxymethyl)-5-carbamoylcarbazol-4-yl}oxyacetic acid;
9-[(3-cyanophenyl)methyl]-2-(methoxymethyl)-5-carbamoylcarbazol-4-yl}oxyacetic acid;
9-[(4-cyanophenyl)methyl]-2-(methoxymethyl)-5-carbamoylcarbazol-4-yl}oxyacetic acid;
9-[(2-pyridyl)methyl]-2-(methoxymethyl)-5-carbamoylcarbazol-4-yl}oxyacetic acid;
9-[(3-pyridyl)methyl]-2-(methoxymethyl)-5-carbamoylcarbazol-4-yl}oxyacetic acid;
9-[(4-pyridyl)methyl]-2-(methoxymethyl)-5-carbamoylcarbazol-4-yl}oxyacetic acid;
9-[(2-furyl)methyl]-2-(methoxymethyl)-5-carbamoylcarbazol-4-yl}oxyacetic acid;
9-[(3-furyl)methyl]-2-(methoxymethyl)-5-carbamoylcarbazol-4-yl}oxyacetic acid;
9-[(2-thienyl)methyl]-2-(methoxymethyl)-5-carbamoylcarbazol-4-yl}oxyacetic acid;
9-[(3-thienyl)methyl]-2-(methoxymethyl)-5-carbamoylcarbazol-4-yl}oxyacetic acid;
9-[(2-benzylphenyl)methyl]-2-(methoxymethyl)-5-carbamoylcarbazol-4-yl}oxyacetic acid;
9-[(3-benzylphenyl)methyl]-2-(methoxymethyl)-5-carbamoylcarbazol-4-yl}oxyacetic acid;
9-[(4-benzylphenyl)methyl]-2-(methoxymethyl)-5-carbamoylcarbazol-4-yl}oxyacetic acid;
9-[(2-benzoylphenyl)methyl]-2-(methoxymethyl)-5-carbamoylcarbazol-4-yl}oxyacetic acid;
9-[(3-benzoylphenyl)methyl]-2-(methoxymethyl)-5-carbamoylcarbazol-4-yl}oxyacetic acid;
9-[(4-benzoylphenyl)methyl]-2-(methoxymethyl)-5-carbamoylcarbazol-4-yl}oxyacetic acid;
9-[(2-benzyloxyphenyl)methyl]-2-(methoxymethyl)-5-carbamoylcarbazol-4-yl}oxyacetic acid;
9-[(3-benzyloxyphenyl)methyl]-2-(methoxymethyl)-5-carbamoylcarbazol-4-yl}oxyacetic acid;
9-[(4-benzyloxyphenyl)methyl]-2-(methoxymethyl)-5-carbamoylcarbazol-4-yl}oxyacetic acid;
9-[(2-phenylphenyl)methyl]-2-(methoxymethyl)-5-carbamoylcarbazol-4-yl}oxyacetic acid;
9-[(3-phenylphenyl)methyl]-2-(methoxymethyl)-5-carbamoylcarbazol-4-yl}oxyacetic acid;
9-[(4-phenylphenyl)methyl]-2-(methoxymethyl)-5-carbamoylcarbazol-4-yl}oxyacetic acid;
9-[(1-naphthyl)methyl]-2-(methoxymethyl)-5-carbamoylcarbazol-4-yl}oxyacetic acid;
9-[(2-naphthyl)methyl]-2-(methoxymethyl)-5-carbamoylcarbazol-4-yl}oxyacetic acid;
9-[(2,3-difluorophenyl)methyl]-2-(methoxymethyl)-5-carbamoylcarbazol-4-yl}oxyacetic acid;
9-[(2,4-difluorophenyl)methyl]-2-(methoxymethyl)-5-carbamoylcarbazol-4-yl}oxyacetic acid;
9-[(2,5-difluorophenyl)methyl]-2-(methoxymethyl)-5-carbamoylcarbazol-4-yl}oxyacetic acid;
9-[(2,6-difluorophenyl)methyl]-2-(methoxymethyl)-5-carbamoylcarbazol-4-yl}oxyacetic acid;
9-[(3,4-difluorophenyl)methyl]-2-(methoxymethyl)-5-carbamoylcarbazol-4-yl}oxyacetic acid;
9-[(3,5-difluorophenyl)methyl]-2-(methoxymethyl)-5-carbamoylcarbazol-4-yl}oxyacetic acid;
9-[(2,3,4-trifluorophenyl)methyl]-2-(methoxymethyl)-5-carbamoylcarbazol-4-yl}oxyacetic acid;

9-[(2,3,5-trifluorophenyl)methyl]-2-(methoxymethyl)-5-carbamoylcarbazol-4-yl}oxyacetic acid;
9-[(2,3,6-trifluorophenyl)methyl]-2-(methoxymethyl)-5-carbamoylcarbazol-4-yl}oxyacetic acid;
9-[(2,4,5-trifluorophenyl)methyl]-2-(methoxymethyl)-5-carbamoylcarbazol-4-yl}oxyacetic acid;
9-[(2,4,6-trifluorophenyl)methyl]-2-(methoxymethyl)-5-carbamoylcarbazol-4-yl}oxyacetic acid;
9-[(3,4,5-trifluorophenyl)methyl]-2-(methoxymethyl)-5-carbamoylcarbazol-4-yl-}oxyacetic acid;
9-[(pentafluorophenyl)methyl]-2-(methoxymethyl)-5-carbamoylcarbazol-4-yl}oxyacetic acid;
9-[(2,3-dichlorophenyl)methyl]-2-(methoxymethyl)-5-carbamoylcarbazol-4-yl}oxyacetic acid;
9-[(2,4-dichlorophenyl)methyl]-2-(methoxymethyl)-5-carbamoylcarbazol-4-yl}oxyacetic acid;
9-[(2,5-dichlorophenyl)methyl]-2-(methoxymethyl)-5-carbamoylcarbazol-4-yl}oxyacetic acid;
9-[(2,6-dichlorophenyl)methyl]-2-(methoxymethyl)-5-carbamoylcarbazol-4-yl}oxyacetic acid;
9-[(3,4-dichlorophenyl)methyl]-2-(methoxymethyl)-5-carbamoylcarbazol-4-yl}oxyacetic acid;
9-[(3,5-dichlorophenyl)methyl]-2-(methoxymethyl)-5-carbamoylcarbazol-4-yl}oxyacetic acid;
9-[(2,3-dimethylphenyl)methyl]-2-(methoxymethyl)-5-carbamoylcarbazol-4-yl}oxyacetic acid;
9-[(2,4-dimethylphenyl)methyl]-2-(methoxymethyl)-5-carbamoylcarbazol-4-yl}oxyacetic acid;
9-[(2,5-dimethylphenyl)methyl]-2-(methoxymethyl)-5-carbamoylcarbazol-4-yl}oxyacetic acid;
9-[(2,6-dimethylphenyl)methyl]-2-(methoxymethyl)-5-carbamoylcarbazol-4-yl}oxyacetic acid;
9-[(3,4-dimethylphenyl)methyl]-2-(methoxymethyl)-5-carbamoylcarbazol-4-yl}oxyacetic acid;
9-[(3,5-dimethylphenyl)methyl]-2-(methoxymethyl)-5-carbamoylcarbazol-4-yl}oxyacetic acid;
9-[(2,4,6-trimethylphenyl)methyl]-2-(methoxymethyl)-5-carbamoylcarbazol-4-yl}oxyacetic acid;
9-[(3,5-bis(trifluoromethyl)phenyl)methyl]-2-(methoxymethyl)-5-carbamoylcarbazol-4-yl}oxyacetic acid;
9-[(2,4-bis(trifluoromethyl)phenyl)methyl]-2-(methoxymethyl)-5-carbamoylcarbazol-4-yl}oxyacetic acid;
9-[(2-fluoro-3-trifluoromethylphenyl)methyl]-2-(methoxymethyl)-5-carbamoylcarbazol-4-yl}oxyacetic acid;
9-[(2-fluoro-4-trifluoromethylphenyl)methyl]-2-(methoxymethyl)-5-carbamoylcarbazol-4-yl}oxyacetic acid;
9-[(2-fluoro-5-trifluoromethylphenyl)methyl]-2-(methoxymethyl)-5-carbamoylcarbazol-4-yl}oxyacetic acid;
9-[(2-fluoro-6-trifluoromethylphenyl)methyl]-2-(methoxymethyl)-5-carbamoylcarbazol-4-yl}oxyacetic acid;
9-[(3-fluoro-5-trifluoromethylphenyl)methyl]-2-(methoxymethyl)-5-carbamoylcarbazol-4-yl}oxyacetic acid;
9-[(4-fluoro-2-trifluoromethylphenyl)methyl]-2-(methoxymethyl)-5-carbamoylcarbazol-4-yl}oxyacetic acid;
9-[(4-fluoro-3-trifluoromethylphenyl)methyl]-2-(methoxymethyl)-5-carbamoylcarbazol-4-yl}oxyacetic acid;
9-[3-(2-fluorophenoxy)methyl]-2-(methoxymethyl)-5-carbamoylcarbazol-4-yl}oxyacetic acid;
9-[3-(4-fluorophenoxy)methyl]-2-(methoxymethyl)-5-carbamoylcarbazol-4-yl}oxyacetic acid;
9-[(2-fluoro-3-methylphenyl)methyl]-2-(methoxymethyl)-5-carbamoylcarbazol-4-yl}oxyacetic acid;
9-[(3-chloro-2-fluorophenyl)methyl]-2-(methoxymethyl)-5-carbamoylcarbazol-4-yl}oxyacetic acid;
9-[(2-chloro-6-fluorophenyl)methyl]-2-(methoxymethyl)-5-carbamoylcarbazol-4-yl}oxyacetic acid;
9-[(4-bromo-2-fluorophenyl)methyl]-2-(methoxymethyl)-5-carbamoylcarbazol-4-yl}oxyacetic acid;
9-[(2-bromo-5-fluorophenyl)methyl]-2-(methoxymethyl)-5-carbamoylcarbazol-4-yl}oxyacetic acid;
9-[(3-chloro-4-methylphenyl)methyl]-2-(methoxymethyl)-5-carbamoylcarbazol-4-yl}oxyacetic acid;
9-[(3-chloro-4-methoxyphenyl)methyl]-2-(methoxymethyl)-5-carbamoylcarbazol-4-yl}oxyacetic acid;
9-[(4-methoxy-3-methylphenyl)methyl]-2-(methoxymethyl)-5-carbamoylcarbazol-4-yl}oxyacetic acid;
9-[(4-trifluoromethylthiophenyl)methyl]-2-(methoxymethyl)-5-carbamoylcarbazol-4-yl}oxyacetic acid;
9-[(1-bromo-2-naphthylphenyl)methyl]-2-(methoxymethyl)-5-carbamoylcarbazol-4-yl}oxyacetic acid;
9-[(2-methyl-1-naphthylphenyl)methyl]-2-(methoxymethyl)-5-carbamoylcarbazol-4-yl}oxyacetic acid;
9-[(4-methyl-1-naphthylphenyl)methyl]-2-(methoxymethyl)-5-carbamoylcarbazol-4-yl}oxyacetic acid;
9-[(6-methyl-2-naphthylphenyl)methyl]-2-(methoxymethyl)-5-carbamoylcarbazol-4-yl}oxyacetic acid;
9-[(2-((phenylsulfonyl)methyl)phenyl)methyl]-2-(methoxymethyl)-5-carbamoylcarbazol-4-yl}oxyacetic acid;
9-[(1-fluorenylmethyl]-2-(methoxymethyl)-5-carbamoylcarbazol-4-yl}oxyacetic acid;
9-[(1-tetrazolylmethyl]-2-(methoxymethyl)-5-carbamoylcarbazol-4-yl}oxyacetic acid;
9-[(5-methyl-1-tetrazolylmethyl)-2-(methoxymethyl)-5-carbamoylcarbazol-4-yl}oxyacetic acid;
9-[(5-benzyl-1-tetrazolylmethyl)-2-(methoxymethyl)-5-carbamoylcarbazol-4-yl}oxyacetic acid;
9-[(phenyl)methyl]-2-(2-furanyl)-5-carbamoylcarbazol-4-yl}oxyacetic acid;
9-[(2-phenoxyphenyl)methyl]-2-(2-furanyl)-5-carbamoylcarbazol-4-yl}oxyacetic acid;
9-[(3-phenoxyphenyl)methyl]-2-(2-furanyl)-5-carbamoylcarbazol-4-yl}oxyacetic acid;
9-[(4-phenoxyphenyl)methyl]-2-(2-furanyl)-5-carbamoylcarbazol-4-yl}oxyacetic acid;
9-[(2-fluorophenyl)methyl]-2-(2-furanyl)-5-carbamoylcarbazol-4-yl}oxyacetic acid;
9-[(3-fluorophenyl)methyl]-2-(2-furanyl)-5-carbamoylcarbazol-4-yl}oxyacetic acid;
9-[(4-fluorophenyl)methyl]-2-(2-furanyl)-5-carbamoylcarbazol-4-yl}oxyacetic acid;
9-[(2-chlorophenyl)methyl]-2-(2-furanyl)-5-carbamoylcarbazol-4-yl}oxyacetic acid;
9-[(3-chlorophenyl)methyl]-2-(2-furanyl)-5-carbamoylcarbazol-4-yl}oxyacetic acid;
9-[(4-chlorophenyl)methyl]-2-(2-furanyl)-5-carbamoylcarbazol-4-yl}oxyacetic acid;
9-[(2-bromophenyl)methyl]-2-(2-furanyl)-5-carbamoylcarbazol-4-yl}oxyacetic acid;

9-[(3-bromophenyl)methyl]-2-(2-furanyl)-5-carbamoylcarbazol-4-yl}oxyacetic acid;
9-[(4-bromophenyl)methyl]-2-(2-furanyl)-5-carbamoylcarbazol-4-yl}oxyacetic acid;
9-[(2-iodophenyl)methyl]-2-(2-furanyl)-5-carbamoylcarbazol-4-yl}oxyacetic acid;
9-[(3-iodophenyl)methyl]-2-(2-furanyl)-5-carbamoylcarbazol-4-yl}oxyacetic acid;
9-[(4-iodophenyl)methyl]-2-(2-furanyl)-5-carbamoylcarbazol-4-yl}oxyacetic acid;
9-[(2-acetamidophenyl)methyl]-2-(2-furanyl)-5-carbamoylcarbazol-4-yl}oxyacetic acid;
9-[(3-acetamidophenyl)methyl]-2-(2-furanyl)-5-carbamoylcarbazol-4-yl}oxyacetic acid;
9-[(4-acetamidophenyl)methyl]-2-(2-furanyl)-5-carbamoylcarbazol-4-yl}oxyacetic acid;
9-[(2-carbamoylphenyl)methyl]-2-(2-furanyl)-5-carbamoylcarbazol-4-yl}oxyacetic acid;
9-[(3-carbamoylphenyl)methyl]-2-(2-furanyl)-5-carbamoylcarbazol-4-yl}oxyacetic acid;
9-[(4-carbamoylphenyl)methyl]-2-(2-furanyl)-5-carbamoylcarbazol-4-yl}oxyacetic acid;
9-[(2-methylsulfonylphenyl)methyl]-2-(2-furanyl)-5-carbamoylcarbazol-4-yl}oxyacetic acid;
9-[(3-methylsulfonylphenyl)methyl]-2-(2-furanyl)-5-carbamoylcarbazol-4-yl}oxyacetic acid;
9-[(4-methylsulfonylphenyl)methyl]-2-(2-furanyl)-5-carbamoylcarbazol-4-yl}oxyacetic acid;
9-[(2-methylphenyl)methyl]-2-(2-furanyl)-5-carbamoylcarbazol-4-yl}oxyacetic acid;
9-[(3-methylphenyl)methyl]-2-(2-furanyl)-5-carbamoylcarbazol-4-yl}oxyacetic acid;
9-[(4-methylphenyl)methyl]-2-(2-furanyl)-5-carbamoylcarbazol-4-yl}oxyacetic acid;
9-[(2-ethylphenyl)methyl]-2-(2-furanyl)-5-carbamoylcarbazol-4-yl}oxyacetic acid;
9-[(3-ethylphenyl)methyl]-2-(2-furanyl)-5-carbamoylcarbazol-4-yl}oxyacetic acid;
9-[(4-ethylphenyl)methyl]-2-(2-furanyl)-5-carbamoylcarbazol-4-yl}oxyacetic acid;
9-[(2-trifluoromethylphenyl)methyl]-2-(2-furanyl)-5-carbamoylcarbazol-4-yl}oxyacetic acid;
9-[(3-trifluoromethylphenyl)methyl]-2-(2-furanyl)-5-carbamoylcarbazol-4-yl}oxyacetic acid;
9-[(4-trifluoromethylphenyl)methyl]-2-(2-furanyl)-5-carbamoylcarbazol-4-yl}oxyacetic acid;
9-[(cyclopropyl)methyl]-2-(2-furanyl)-5-carbamoylcarbazol-4-yl}oxyacetic acid;
9-[(cyclobutyl)methyl]-2-(2-furanyl)-5-carbamoylcarbazol-4-yl}oxyacetic acid;
9-[(cyclopentyl)methyl]-2-(2-furanyl)-5-carbamoylcarbazol-4-yl}oxyacetic acid;
9-[(cyclohexyl)methyl]-2-(2-furanyl)-5-carbamoylcarbazol-4-yl}oxyacetic acid;
9-[(2-methoxyphenyl)methyl]-2-(2-furanyl)-5-carbamoylcarbazol-4-yl}oxyacetic acid;
9-[(3-methoxyphenyl)methyl]-2-(2-furanyl)-5-carbamoylcarbazol-4-yl}oxyacetic acid;
9-[(4-methoxyphenyl)methyl]-2-(2-furanyl)-5-carbamoylcarbazol-4-yl}oxyacetic acid;
9-[(2-ethoxyphenyl)methyl]-2-(2-furanyl)-5-carbamoylcarbazol-4-yl}oxyacetic acid;
9-[(3-ethoxyphenyl)methyl]-2-(2-furanyl)-5-carbamoylcarbazol-4-yl}oxyacetic acid;
9-[(4-ethoxyphenyl)methyl]-2-(2-furanyl)-5-carbamoylcarbazol-4-yl}oxyacetic acid;
9-[(2-trifluoromethoxyphenyl)methyl]-2-(2-furanyl)-5-carbamoylcarbazol-4-yl}oxyacetic acid;
9-[(3-trifluoromethoxyphenyl)methyl]-2-(2-furanyl)-5-carbamoylcarbazol-4-yl}oxyacetic acid;
9-[(4-trifluoromethoxyphenyl)methyl]-2-(2-furanyl)-5-carbamoylcarbazol-4-yl}oxyacetic acid;
9-[(2-difluoromethoxyphenyl)methyl]-2-(2-furanyl)-5-carbamoylcarbazol-4-yl}oxyacetic acid;
9-[(3-difluoromethoxyphenyl)methyl]-2-(2-furanyl)-5-carbamoylcarbazol-4-yl}oxyacetic acid;
9-[(4-difluoromethoxyphenyl)methyl]-2-(2-furanyl)-5-carbamoylcarbazol-4-yl}oxyacetic acid;
9-[(2-cyanophenyl)methyl]-2-(2-furanyl)-5-carbamoylcarbazol-4-yl}oxyacetic acid;
9-[(3-cyanophenyl)methyl]-2-(2-furanyl)-5-carbamoylcarbazol-4-yl}oxyacetic acid;
9-[(4-cyanophenyl)methyl]-2-(2-furanyl)-5-carbamoylcarbazol-4-yl}oxyacetic acid;
9-[(2-pyridyl)methyl]-2-(2-furanyl)-5-carbamoylcarbazol-4-yl}oxyacetic acid;
9-[(3-pyridyl)methyl]-2-(2-furanyl)-5-carbamoylcarbazol-4-yl}oxyacetic acid;
9-[(4-pyridyl)methyl]-2-(2-furanyl)-5-carbamoylcarbazol-4-yl}oxyacetic acid;
9-[(2-furyl)methyl]-2-(2-furanyl)-5-carbamoylcarbazol-4-yl}oxyacetic acid;
9-[(3-furyl)methyl]-2-(2-furanyl)-5-carbamoylcarbazol-4-yl}oxyacetic acid;
9-[(2-thienyl)methyl]-2-(2-furanyl)-5-carbamoylcarbazol-4-yl}oxyacetic acid;
9-[(3-thienyl)methyl]-2-(2-furanyl)-5-carbamoylcarbazol-4-yl}oxyacetic acid;
9-[(2-benzylphenyl)methyl]-2-(2-furanyl)-5-carbamoylcarbazol-4-yl}oxyacetic acid;
9-[(3-benzylphenyl)methyl]-2-(2-furanyl)-5-carbamoylcarbazol-4-yl}oxyacetic acid;
9-[(4-benzylphenyl)methyl]-2-(2-furanyl)-5-carbamoylcarbazol-4-yl}oxyacetic acid;
9-[(2-benzoylphenyl)methyl]-2-(2-furanyl)-5-carbamoylcarbazol-4-yl}oxyacetic acid;
9-[(3-benzoylphenyl)methyl]-2-(2-furanyl)-5-carbamoylcarbazol-4-yl}oxyacetic acid;
9-[(4-benzoylphenyl)methyl]-2-(2-furanyl)-5-carbamoylcarbazol-4-yl}oxyacetic acid;
9-[(2-benzyloxyphenyl)methyl]-2-(2-furanyl)-5-carbamoylcarbazol-4-yl}oxyacetic acid;
9-[(3-benzyloxyphenyl)methyl]-2-(2-furanyl)-5-carbamoylcarbazol-4-yl}oxyacetic acid;
9-[(4-benzyloxyphenyl)methyl]-2-(2-furanyl)-5-carbamoylcarbazol-4-yl}oxyacetic acid;
9-[(2-phenylphenyl)methyl]-2-(2-furanyl)-5-carbamoylcarbazol-4-yl}oxyacetic acid;
9-[(3-phenylphenyl)methyl]-2-(2-furanyl)-5-carbamoylcarbazol-4-yl}oxyacetic acid;
9-[(4-phenylphenyl)methyl]-2-(2-furanyl)-5-carbamoylcarbazol-4-yl}oxyacetic acid;
9-[(1-naphthyl)methyl]-2-(2-furanyl)-5-carbamoylcarbazol-4-yl}oxyacetic acid;
9-[(2-naphthyl)methyl]-2-(2-furanyl)-5-carbamoylcarbazol-4-yl}oxyacetic acid;
9-[(2,3-difluorophenyl)methyl]-2-(2-furanyl)-5-carbamoylcarbazol-4-yl}oxyacetic acid;
9-[(2,4-difluorophenyl)methyl]-2-(2-furanyl)-5-carbamoylcarbazol-4-yl}oxyacetic acid;
9-[(2,5-difluorophenyl)methyl]-2-(2-furanyl)-5-carbamoylcarbazol-4-yl}oxyacetic acid;
9-[(2,6-difluorophenyl)methyl]-2-(2-furanyl)-5-carbamoylcarbazol-4-yl}oxyacetic acid;
9-[(3,4-difluorophenyl)methyl]-2-(2-furanyl)-5-carbamoylcarbazol-4-yl}oxyacetic acid;

9-[(3,5-difluorophenyl)methyl]-2-(2-furanyl)-5-carbamoylcarbazol-4-yl}oxyacetic acid;
9-[(2,3,4-trifluorophenyl)methyl]-2-(2-furanyl)-5-carbamoylcarbazol-4-yl}oxyacetic acid;
9-[(2,3,5-trifluorophenyl)methyl]-2-(2-furanyl)-5-carbamoylcarbazol-4-yl}oxyacetic acid;
9-[(2,3,6-trifluorophenyl)methyl]-2-(2-furanyl)-5-carbamoylcarbazol-4-yl}oxyacetic acid;
9-[(2,4,5-trifluorophenyl)methyl]-2-(2-furanyl)-5-carbamoylcarbazol-4-yl}oxyacetic acid;
9-[(2,4,6-trifluorophenyl)methyl]-2-(2-furanyl)-5-carbamoylcarbazol-4-yl}oxyacetic acid;
9-[(3,4,5-trifluorophenyl)methyl]-2-(2-furanyl)-5-carbamoylcarbazol-4-yl}oxyacetic acid;
9-[(pentafluorophenyl)methyl]-2-(2-furanyl)-5-carbamoylcarbazol-4-yl}oxyacetic acid;
9-[(2,3-dichlorophenyl)methyl]-2-(2-furanyl)-5-carbamoylcarbazol-4-yl}oxyacetic acid;
9-[(2,4-dichlorophenyl)methyl]-2-(2-furanyl)-5-carbamoylcarbazol-4-yl}oxyacetic acid;
9-[(2,5-dichlorophenyl)methyl]-2-(2-furanyl)-5-carbamoylcarbazol-4-yl}oxyacetic acid;
9-[(2,6-dichlorophenyl)methyl]-2-(2-furanyl)-5-carbamoylcarbazol-4-yl}oxyacetic acid;
9-[(3,4-dichlorophenyl)methyl]-2-(2-furanyl)-5-carbamoylcarbazol-4-yl}oxyacetic acid;
9-[(3,5-dichlorophenyl)methyl]-2-(2-furanyl)-5-carbamoylcarbazol-4-yl}oxyacetic acid;
9-[(2,3-dimethylphenyl)methyl]-2-(2-furanyl)-5-carbamoylcarbazol-4-yl}oxyacetic acid;
9-[(2,4-dimethylphenyl)methyl]-2-(2-furanyl)-5-carbamoylcarbazol-4-yl}oxyacetic acid;
9-[(2,5-dimethylphenyl)methyl]-2-(2-furanyl)-5-carbamoylcarbazol-4-yl}oxyacetic acid;
9-[(2,6-dimethylphenyl)methyl]-2-(2-furanyl)-5-carbamoylcarbazol-4-yl}oxyacetic acid;
9-[(3,4-dimethylphenyl)methyl]-2-(2-furanyl)-5-carbamoylcarbazol-4-yl}oxyacetic acid;
9-[(3,5-dimethylphenyl)methyl]-2-(2-furanyl)-5-carbamoylcarbazol-4-yl}oxyacetic acid;
9-[(2,4,6-trimethylphenyl)methyl]-2-(2-furanyl)-5-carbamoylcarbazol-4-yl}oxyacetic acid;
9-[(3,5-bis(trifluoromethyl)phenyl)methyl]-2-(2-furanyl)-5-carbamoylcarbazol-4-yl}oxyacetic acid;
9-[(2,4-bis(trifluoromethyl)phenyl)methyl]-2-(2-furanyl)-5-carbamoylcarbazol-4-yl}oxyacetic acid;
9-[(2-fluoro-3-trifluoromethylphenyl)methyl]-2-(2-furanyl)-5-carbamoylcarbazol-4-yl}oxyacetic acid;
9-[(2-fluoro-4-trifluoromethylphenyl)methyl]-2-(2-furanyl)-5-carbamoylcarbazol-4-yl}oxyacetic acid;
9-[(2-fluoro-5-trifluoromethylphenyl)methyl]-2-(2-furanyl)-5-carbamoylcarbazol-4-yl}oxyacetic acid;
9-[(2-fluoro-6-trifluoromethylphenyl)methyl]-2-(2-furanyl)-5-carbamoylcarbazol-4-yl}oxyacetic acid;
9-[(3-fluoro-5-trifluoromethylphenyl)methyl]-2-(2-furanyl)-5-carbamoylcarbazol-4-yl}oxyacetic acid;
9-[(4-fluoro-2-trifluoromethylphenyl)methyl]-2-(2-furanyl)-5-carbamoylcarbazol-4-yl}oxyacetic acid;
9-[(4-fluoro-3-trifluoromethylphenyl)methyl]-2-(2-furanyl)-5-carbamoylcarbazol-4-yl}oxyacetic acid;
9-[3-(2-fluorophenoxy)methyl]-2-(2-furanyl)-5-carbamoylcarbazol-4-yl}oxyacetic acid;
9-[3-(4-fluorophenoxy)methyl]-2-(2-furanyl)-5-carbamoylcarbazol-4-yl}oxyacetic acid;
9-[(2-fluoro-3-methylphenyl)methyl]-2-(2-furanyl)-5-carbamoylcarbazol-4-yl}oxyacetic acid;
9-[(3-chloro-2-fluorophenyl)methyl]-2-(2-furanyl)-5-carbamoylcarbazol-4-yl}oxyacetic acid;
9-[(2-chloro-6-fluorophenyl)methyl]-2-(2-furanyl)-5-carbamoylcarbazol-4-yl}oxyacetic acid;
9-[(4-bromo-2-fluorophenyl)methyl]-2-(2-furanyl)-5-carbamoylcarbazol-4-yl}oxyacetic acid;
9-[(2-bromo-5-fluorophenyl)methyl]-2-(2-furanyl)-5-carbamoylcarbazol-4-yl}oxyacetic acid;
9-[(3-chloro-4-methylphenyl)methyl]-2-(2-furanyl)-5-carbamoylcarbazol-4-yl}oxyacetic acid;
9-[(3-chloro-4-methoxyphenyl)methyl]-2-(2-furanyl)-5-carbamoylcarbazol-4-yl}oxyacetic acid;
9-[(4-methoxy-3-methylphenyl)methyl]-2-(2-furanyl)-5-carbamoylcarbazol-4-yl}oxyacetic acid;
9-[(4-trifluoromethylthiophenyl)methyl]-2-(2-furanyl)-5-carbamoylcarbazol-4-yl}oxyacetic acid;
9-[(1-bromo-2-naphthylphenyl)methyl]-2-(2-furanyl)-5-carbamoylcarbazol-4-yl}oxyacetic acid;
9-[(2-methyl-1-naphthylphenyl)methyl]-2-(2-furanyl)-5-carbamoylcarbazol-4-yl}oxyacetic acid;
9-[(4-methyl-1-naphthylphenyl)methyl]-2-(2-furanyl)-5-carbamoylcarbazol-4-yl}oxyacetic acid;
9-[(6-methyl-2-naphthylphenyl)methyl]-2-(2-furanyl)-5-carbamoylcarbazol-4-yl}oxyacetic acid;
9-[(2-((phenylsulfonyl)methyl)phenyl)methyl]-2-(2-furanyl)-5-carbamoylcarbazol-4-yl}oxyacetic acid;
9-[(1-fluorenylmethyl]-2-(2-furanyl)-5-carbamoylcarbazol-4-yl}oxyacetic acid;
9-[(1-tetrazolylmethyl]-2-(2-furanyl)-5-carbamoylcarbazol-4-yl}oxyacetic acid;
9-[(5-methyl-1-tetrazolylmethyl]-2-(2-furanyl)-5-carbamoylcarbazol-4-yl}oxyacetic acid;
9-[(5-benzyl-1-tetrazolylmethyl]-2-(2-furanyl)-5-carbamoylcarbazol-4-yl}oxyacetic acid;
9-[(phenyl)methyl]-(2-thienyl)-5-carbamoylcarbazol-4-yl}oxyacetic acid;
9-[(2-phenoxyphenyl)methyl]-2-(2-thienyl)-5-carbamoylcarbazol-4-yl}oxyacetic acid;
9-[(3-phenoxyphenyl)methyl]-2-(2-thienyl)-5-carbamoylcarbazol-4-yl}oxyacetic acid;
9-[(4-phenoxyphenyl)methyl]-2-(2-thienyl)-5-carbamoylcarbazol-4-yl}oxyacetic acid;
9-[(2-fluorophenyl)methyl]-2-(2-thienyl)-5-carbamoylcarbazol-4-yl}oxyacetic acid;
9-[(3-fluorophenyl)methyl]-2-(2-thienyl)-5-carbamoylcarbazol-4-yl}oxyacetic acid;
9-[(4-fluorophenyl)methyl]-2-(2-thienyl)-5-carbamoylcarbazol-4-yl}oxyacetic acid;
9-[(2-chlorophenyl)methyl]-2-(2-thienyl)-5-carbamoylcarbazol-4-yl}oxyacetic acid;
9-[(3-chlorophenyl)methyl]-2-(2-thienyl)-5-carbamoylcarbazol-4-yl}oxyacetic acid;
9-[(4-chlorophenyl)methyl]-2-(2-thienyl)-5-carbamoylcarbazol-4-yl}oxyacetic acid;
9-[(2-bromophenyl)methyl]-2-(2-thienyl)-5-carbamoylcarbazol-4-yl}oxyacetic acid;
9-[(3-bromophenyl)methyl]-2-(2-thienyl)-5-carbamoylcarbazol-4-yl}oxyacetic acid;
9-[(4-bromophenyl)methyl]-2-(2-thienyl)-5-carbamoylcarbazol-4-yl}oxyacetic acid;
9-[(2-iodophenyl)methyl]-2-(2-thienyl)-5-carbamoylcarbazol-4-yl}oxyacetic acid;
9-[(3-iodophenyl)methyl]-2-(2-thienyl)-5-carbamoylcarbazol-4-yl}oxyacetic acid;
9-[(4-iodophenyl)methyl]-2-(2-thienyl)-5-carbamoylcarbazol-4-yl}oxyacetic acid;
9-[(2-acetamidophenyl)methyl]-2-(2-thienyl)-5-carbamoylcarbazol-4-yl}oxyacetic acid;
9-[(3-acetamidophenyl)methyl]-2-(2-thienyl)-5-carbamoylcarbazol-4-yl}oxyacetic acid;

9-[(4-acetamidophenyl)methyl]-2-(2-thienyl)-5-carbamoylcarbazol-4-yl}oxyacetic acid;
9-[(2-carbamoylphenyl)methyl]-2-(2-thienyl)-5-carbamoylcarbazol-4-yl}oxyacetic acid;
9-[(3-carbamoylphenyl)methyl]-2-(2-thienyl)-5-carbamoylcarbazol-4-yl}oxyacetic acid;
9-[(4-carbamoylphenyl)methyl]-2-(2-thienyl)-5-carbamoylcarbazol-4-yl}oxyacetic acid;
9-[(2-methylsulfonylphenyl)methyl]-2-(2-thienyl)-5-carbamoylcarbazol-4-yl}oxyacetic acid;
9-[(3-methylsulfonylphenyl)methyl]-2-(2-thienyl)-5-carbamoylcarbazol-4-yl}oxyacetic acid;
9-[(4-methylsulfonylphenyl)methyl]-2-(2-thienyl)-5-carbamoylcarbazol-4-yl}oxyacetic acid;
9-[(2-methylphenyl)methyl]-2-(2-thienyl)-5-carbamoylcarbazol-4-yl}oxyacetic acid;
9-[(3-methylphenyl)methyl]-2-(2-thienyl)-5-carbamoylcarbazol-4-yl}oxyacetic acid;
9-[(4-methylphenyl)methyl]-2-(2-thienyl)-5-carbamoylcarbazol-4-yl}oxyacetic acid;
9-[(2-ethylphenyl)methyl]-2-(2-thienyl)-5-carbamoylcarbazol-4-yl}oxyacetic acid;
9-[(3-ethylphenyl)methyl]-2-(2-thienyl)-5-carbamoylcarbazol-4-yl}oxyacetic acid;
9-[(4-ethylphenyl)methyl]-2-(2-thienyl)-5-carbamoylcarbazol-4-yl}oxyacetic acid;
9-[(2-trifluoromethylphenyl)methyl]-2-(2-thienyl)-5-carbamoylcarbazol-4-yl}oxyacetic acid;
9-[(3-trifluoromethylphenyl)methyl]-2-(2-thienyl)-5-carbamoylcarbazol-4-yl}oxyacetic acid;
9-[(4-trifluoromethylphenyl)methyl]-2-(2-thienyl)-5-carbamoylcarbazol-4-yl}oxyacetic acid;
9-[(cyclopropyl)methyl]-2-(2-thienyl)-5-carbamoylcarbazol-4-yl}oxyacetic acid;
9-[(cyclobutyl)methyl]-2-(2-thienyl)-5-carbamoylcarbazol-4-yl}oxyacetic acid;
9-[(cyclopentyl)methyl]-2-(2-thienyl)-5-carbamoylcarbazol-4-yl}oxyacetic acid;
9-[(cyclohexyl)methyl]-2-(2-thienyl)-5-carbamoylcarbazol-4-yl}oxyacetic acid;
9-[(2-methoxyphenyl)methyl]-2-(2-thienyl)-5-carbamoylcarbazol-4-yl}oxyacetic acid;
9-[(3-methoxyphenyl)methyl]-2-(2-thienyl)-5-carbamoylcarbazol-4-yl}oxyacetic acid;
9-[(4-methoxyphenyl)methyl]-2-(2-thienyl)-5-carbamoylcarbazol-4-yl}oxyacetic acid;
9-[(2-ethoxyphenyl)methyl]-2-(2-thienyl)-5-carbamoylcarbazol-4-yl}oxyacetic acid;
9-[(3-ethoxyphenyl)methyl]-2-(2-thienyl)-5-carbamoylcarbazol-4-yl}oxyacetic acid;
9-[(4-ethoxyphenyl)methyl]-2-(2-thienyl)-5-carbamoylcarbazol-4-yl}oxyacetic acid;
9-[(2-trifluoromethoxyphenyl)methyl]-2-(2-thienyl)-5-carbamoylcarbazol-4-yl}oxyacetic acid;
9-[(3-trifluoromethoxyphenyl)methyl]-2-(2-thienyl)-5-carbamoylcarbazol-4-yl}oxyacetic acid;
9-[(4-trifluoromethoxyphenyl)methyl]-2-(2-thienyl)-5-carbamoylcarbazol-4-yl}oxyacetic acid;
9-[(2-difluoromethoxyphenyl)methyl]-2-(2-thienyl)-5-carbamoylcarbazol-4-yl}oxyacetic acid;
9-[(3-difluoromethoxyphenyl)methyl]-2-(2-thienyl)-5-carbamoylcarbazol-4-yl}oxyacetic acid;
9-[(4-difluoromethoxyphenyl)methyl]-2-(2-thienyl)-5-carbamoylcarbazol-4-yl}oxyacetic acid;
9-[(2-cyanophenyl)methyl]-2-(2-thienyl)-5-carbamoylcarbazol-4-yl}oxyacetic acid;
9-[(3-cyanophenyl)methyl]-2-(2-thienyl)-5-carbamoylcarbazol-4-yl}oxyacetic acid;
9-[(4-cyanophenyl)methyl]-2-(2-thienyl)-5-carbamoylcarbazol-4-yl}oxyacetic acid;
9-[(2-pyridyl)methyl]-2-(2-thienyl)-5-carbamoylcarbazol-4-yl}oxyacetic acid;
9-[(3-pyridyl)methyl]-2-(2-thienyl)-5-carbamoylcarbazol-4-yl}oxyacetic acid;
9-[(4-pyridyl)methyl]-2-(2-thienyl)-5-carbamoylcarbazol-4-yl}oxyacetic acid;
9-[(2-furyl)methyl]-2-(2-thienyl)-5-carbamoylcarbazol-4-yl}oxyacetic acid;
9-[(3-furyl)methyl]-2-(2-thienyl)-5-carbamoylcarbazol-4-yl}oxyacetic acid;
9-[(2-thienyl)methyl]-2-(2-thienyl)-5-carbamoylcarbazol-4-yl}oxyacetic acid;
9-[(3-thienyl)methyl]-2-(2-thienyl)-5-carbamoylcarbazol-4-yl}oxyacetic acid;
9-[(2-benzylphenyl)methyl]-2-(2-thienyl)-5-carbamoylcarbazol-4-yl}oxyacetic acid;
9-[(3-benzylphenyl)methyl]-2-(2-thienyl)-5-carbamoylcarbazol-4-yl}oxyacetic acid;
9-[(4-benzylphenyl)methyl]-2-(2-thienyl)-5-carbamoylcarbazol-4-yl}oxyacetic acid;
9-[(2-benzoylphenyl)methyl]-2-(2-thienyl)-5-carbamoylcarbazol-4-yl}oxyacetic acid;
9-[(3-benzoylphenyl)methyl]-2-(2-thienyl)-5-carbamoylcarbazol-4-yl}oxyacetic acid;
9-[(4-benzoylphenyl)methyl]-2-(2-thienyl)-5-carbamoylcarbazol-4-yl}oxyacetic acid;
9-[(2-benzyloxyphenyl)methyl]-2-(2-thienyl)-5-carbamoylcarbazol-4-yl}oxyacetic acid;
9-[(3-benzyloxyphenyl)methyl]-2-(2-thienyl)-5-carbamoylcarbazol-4-yl}oxyacetic acid;
9-[(4-benzyloxyphenyl)methyl]-2-(2-thienyl)-5-carbamoylcarbazol-4-yl}oxyacetic acid;
9-[(2-phenylphenyl)methyl]-2-(2-thienyl)-5-carbamoylcarbazol-4-yl}oxyacetic acid;
9-[(3-phenylphenyl)methyl]-2-(2-thienyl)-5-carbamoylcarbazol-4-yl}oxyacetic acid;
9-[(4-phenylphenyl)methyl]-2-(2-thienyl)-5-carbamoylcarbazol-4-yl}oxyacetic acid;
9-[(1-naphthyl)methyl]-2-(2-thienyl)-5-carbamoylcarbazol-4-yl}oxyacetic acid;
9-[(2-naphthyl)methyl]-2-(2-thienyl)-5-carbamoylcarbazol-4-yl}oxyacetic acid;
9-[(2,3-difluorophenyl)methyl]-2-(2-thienyl)-5-carbamoylcarbazol-4-yl}oxyacetic acid;
9-[(2,4-difluorophenyl)methyl]-2-(2-thienyl)-5-carbamoylcarbazol-4-yl}oxyacetic acid;
9-[(2,5-difluorophenyl)methyl]-2-(2-thienyl)-5-carbamoylcarbazol-4-yl}oxyacetic acid;
9-[(2,6-difluorophenyl)methyl]-2-(2-thienyl)-5-carbamoylcarbazol-4-yl}oxyacetic acid;
9-[(3,4-difluorophenyl)methyl]-2-(2-thienyl)-5-carbamoylcarbazol-4-yl}oxyacetic acid;
9-[(3,5-difluorophenyl)methyl]-2-(2-thienyl)-5-carbamoylcarbazol-4-yl}oxyacetic acid;
9-[(2,3,4-trifluorophenyl)methyl]-2-(2-thienyl)-5-carbamoylcarbazol-4-yl}oxyacetic acid;
9-[(2,3,5-trifluorophenyl)methyl]-2-(2-thienyl)-5-carbamoylcarbazol-4-yl}oxyacetic acid;
9-[(2,3,6-trifluorophenyl)methyl]-2-(2-thienyl)-5-carbamoylcarbazol-4-yl}oxyacetic acid;
9-[(2,4,5-trifluorophenyl)methyl]-2-(2-thienyl)-5-carbamoylcarbazol-4-yl}oxyacetic acid;
9-[(2,4,6-trifluorophenyl)methyl]-2-(2-thienyl)-5-carbamoylcarbazol-4-yl}oxyacetic acid;
9-[(3,4,5-trifluorophenyl)methyl]-2-(2-thienyl)-5-carbamoylcarbazol-4-yl}oxyacetic acid;

9-[(pentafluorophenyl)methyl]-2-(2-thienyl)-5-carbamoylcarbazol-4-yl}oxyacetic acid;
9-[(2,3-dichlorophenyl)methyl]-2-(2-thienyl)-5-carbamoylcarbazol-4-yl}oxyacetic acid;
9-[(2,4-dichlorophenyl)methyl]-2-(2-thienyl)-5-carbamoylcarbazol-4-yl}oxyacetic acid;
9-[(2,5-dichlorophenyl)methyl]-2-(2-thienyl)-5-carbamoylcarbazol-4-yl}oxyacetic acid;
9-[(2,6-dichlorophenyl)methyl]-2-(2-thienyl)-5-carbamoylcarbazol-4-yl}oxyacetic acid;
9-[(3,4-dichlorophenyl)methyl]-2-(2-thienyl)-5-carbamoylcarbazol-4-yl}oxyacetic acid;
9-[(3,5-dichlorophenyl)methyl]-2-(2-thienyl)-5-carbamoylcarbazol-4-yl}oxyacetic acid;
9-[(2,3-dimethylphenyl)methyl]-2-(2-thienyl)-5-carbamoylcarbazol-4-yl}oxyacetic acid;
9-[(2,4-dimethylphenyl)methyl]-2-(2-thienyl)-5-carbamoylcarbazol-4-yl}oxyacetic acid;
9-[(2,5-dimethylphenyl)methyl]-2-(2-thienyl)-5-carbamoylcarbazol-4-yl}oxyacetic acid;
9-[(2,6-dimethylphenyl)methyl]-2-(2-thienyl)-5-carbamoylcarbazol-4-yl}oxyacetic acid;
9-[(3,4-dimethylphenyl)methyl]-2-(2-thienyl)-5-carbamoylcarbazol-4-yl}oxyacetic acid;
9-[(3,5-dimethylphenyl)methyl]-2-(2-thienyl)-5-carbamoylcarbazol-4-yl}oxyacetic acid;
9-[(2,4,6-trimethylphenyl)methyl]-2-(2-thienyl)-5-carbamoylcarbazol-4-yl}oxyacetic acid;
9-[(3,5-bis(trifluoromethyl)phenyl)methyl]-2-(2-thienyl)-5-carbamoylcarbazol-4-yl}oxyacetic acid;
9-[(2,4-bis(trifluoromethyl)phenyl)methyl]-2-(2-thienyl)-5-carbamoylcarbazol-4-yl}oxyacetic acid;
9-[(2-fluoro-3-trifluoromethylphenyl)methyl]-2-(2-thienyl)-5-carbamoylcarbazol-4-yl}oxyacetic acid;
9-[(2-fluoro-4-trifluoromethylphenyl)methyl]-2-(2-thienyl)-5-carbamoylcarbazol-4-yl}oxyacetic acid;
9-[(2-fluoro-5-trifluoromethylphenyl)methyl]-2-(2-thienyl)-5-carbamoylcarbazol-4-yl}oxyacetic acid;
9-[(2-fluoro-6-trifluoromethylphenyl)methyl]-2-(2-thienyl)-5-carbamoylcarbazol-4-yl}oxyacetic acid;
9-[(3-fluoro-5-trifluoromethylphenyl)methyl]-2-(2-thienyl)-5-carbamoylcarbazol-4-yl}oxyacetic acid;
9-[(4-fluoro-2-trifluoromethylphenyl)methyl]-2-(2-thienyl)-5-carbamoylcarbazol-4-yl}oxyacetic acid;
9-[(4-fluoro-3-trifluoromethylphenyl)methyl]-2-(2-thienyl)-5-carbamoylcarbazol-4-yl}oxyacetic acid;
9-[3-(2-fluorophenoxy)methyl]-2-(2-thienyl)-5-carbamoylcarbazol-4-yl}oxyacetic acid;
9-[3-(4-fluorophenoxy)methyl]-2-(2-thienyl)-5-carbamoylcarbazol-4-yl}oxyacetic acid;
9-[(2-fluoro-3-methylphenyl)methyl]-2-(2-thienyl)-5-carbamoylcarbazol-4-yl}oxyacetic acid;
9-[(3-chloro-2-fluorophenyl)methyl]-2-(2-thienyl)-5-carbamoylcarbazol-4-yl}oxyacetic acid;
9-[(2-chloro-6-fluorophenyl)methyl]-2-(2-thienyl)-5-carbamoylcarbazol-4-yl}oxyacetic acid;
9-[(4-bromo-2-fluorophenyl)methyl]-2-(2-thienyl)-5-carbamoylcarbazol-4-yl}oxyacetic acid;
9-[(2-bromo-5-fluorophenyl)methyl]-2-(2-thienyl)-5-carbamoylcarbazol-4-yl}oxyacetic acid;
9-[(3-chloro-4-methylphenyl)methyl]-2-(2-thienyl)-5-carbamoylcarbazol-4-yl}oxyacetic acid;
9-[(3-chloro-4-methoxyphenyl)methyl]-2-(2-thienyl)-5-carbamoylcarbazol-4-yl}oxyacetic acid;
9-[(4-methoxy-3-methylphenyl)methyl]-2-(2-thienyl)-5-carbamoylcarbazol-4-yl}oxyacetic acid;
9-[(4-trifluoromethylthiophenyl)methyl]-2-(2-thienyl)-5-carbamoylcarbazol-4-yl}oxyacetic acid;
9-[(1-bromo-2-naphthylphenyl)methyl]-2-(2-thienyl)-5-carbamoylcarbazol-4-yl}oxyacetic acid;
9-[(2-methyl-1-naphthylphenyl)methyl]-2-(2-thienyl)-5-carbamoylcarbazol-4-yl}oxyacetic acid;
9-[(4-methyl-1-naphthylphenyl)methyl]-2-(2-thienyl)-5-carbamoylcarbazol-4-yl}oxyacetic acid;
9-[(6-methyl-2-naphthylphenyl)methyl]-2-(2-thienyl)-5-carbamoylcarbazol-4-yl}oxyacetic acid;
9-[(2-((phenylsulfonyl)methyl)phenyl)methyl]-2-(2-thienyl)-5-carbamoylcarbazol-4-yl}oxyacetic acid;
9-[(1-fluorenylmethyl]-2-(2-thienyl)-5-carbamoylcarbazol-4-yl}oxyacetic acid;
9-[(1-tetrazolylmethyl]-2-(2-thienyl)-5-carbamoylcarbazol-4-yl}oxyacetic acid;
9-[(5-methyl-1-tetrazolylmethyl]-2-(2-thienyl)-5-carbamoylcarbazol-4-yl}oxyacetic acid;
9-[(5-benzyl-1-tetrazolylmethyl]-2-(2-thienyl)-5-carbamoylcarbazol-4-yl}oxyacetic acid;
9-[(2-phenoxyphenyl)methyl]-5-carbamoyl-2-fluorocarbazol-4-yl}oxyacetic acid;
9-[(3-phenoxyphenyl)methyl]-5-carbamoyl-2-fluorocarbazol-4-yl}oxyacetic acid;
9-[(2-fluorophenyl)methyl]-5-carbamoyl-2-fluorocarbazol-4-yl}oxyacetic acid;
9-[(3-fluorophenyl)methyl]-5-carbamoyl-2-fluorocarbazol-4-yl}oxyacetic acid;
9-[(4-fluorophenyl)methyl]-5-carbamoyl-2-fluorocarbazol-4-yl}oxyacetic acid;
9-[(2-chlorophenyl)methyl]-5-carbamoyl-2-fluorocarbazol-4-yl}oxyacetic acid;
9-[(3-chlorophenyl)methyl]-5-carbamoyl-2-fluorocarbazol-4-yl}oxyacetic acid;
9-[(2-bromophenyl)methyl]-5-carbamoyl-2-fluorocarbazol-4-yl}oxyacetic acid;
9-[(3-bromophenyl)methyl]-5-carbamoyl-2-fluorocarbazol-4-yl}oxyacetic acid;
9-[(2-iodophenyl)methyl]-5-carbamoyl-2-fluorocarbazol-4-yl}oxyacetic acid;
9-[(3-iodophenyl)methyl]-5-carbamoyl-2-fluorocarbazol-4-yl}oxyacetic acid;
9-[(2-acetamidophenyl)methyl]-5-carbamoyl-2-fluorocarbazol-4-yl}oxyacetic acid;
9-[(3-acetamidophenyl)methyl]-5-carbamoyl-2-fluorocarbazol-4-yl}oxyacetic acid;
9-[(2-carbamoylphenyl)methyl]-5-carbamoyl-2-fluorocarbazol-4-yl}oxyacetic acid;
9-[(3-carbamoylphenyl)methyl]-5-carbamoyl-2-fluorocarbazol-4-yl}oxyacetic acid;
9-[(2-methylsulfonylphenyl)methyl]-5-carbamoyl-2-fluorocarbazol-4-yl}oxyacetic acid;
9-[(3-methylsulfonylphenyl)methyl]-5-carbamoyl-2-fluorocarbazol-4-yl}oxyacetic acid;
9-[(2-methylphenyl)methyl]-5-carbamoyl-2-fluorocarbazol-4-yl}oxyacetic acid;
9-[(3-methylphenyl)methyl]-5-carbamoyl-2-fluorocarbazol-4-yl}oxyacetic acid;
9-[(2-ethylphenyl)methyl]-5-carbamoyl-2-fluorocarbazol-4-yl}oxyacetic acid;
9-[(3-ethylphenyl)methyl]-5-carbamoyl-2-fluorocarbazol-4-yl}oxyacetic acid;
9-[(2-trifluoromethylphenyl)methyl]-5-carbamoyl-2-fluorocarbazol-4-yl}oxyacetic acid;
9-[(3-trifluoromethylphenyl)methyl]-5-carbamoyl-2-fluorocarbazol-4-yl}oxyacetic acid;
9-[(2-methoxyphenyl)methyl]-5-carbamoyl-2-fluorocarbazol-4-yl}oxyacetic acid;
9-[(cyclopropyl)methyl]-5-carbamoyl-2-fluorocarbazol-4-yl}oxyacetic acid;

9-[(cyclobutyl)methyl]-5-carbamoyl-2-fluorocarbazol-4-yl}oxyacetic acid;
9-[(cyclopentyl)methyl]-5-carbamoyl-2-fluorocarbazol-4-yl}oxyacetic acid;
9-[(cyclohexyl)methyl]-5-carbamoyl-2-fluorocarbazol-4-yl}oxyacetic acid;
9-[(3-methoxyphenyl)methyl]-5-carbamoyl-2-fluorocarbazol-4-yl}oxyacetic acid;
9-[(2-ethoxyphenyl)methyl]-5-carbamoyl-2-fluorocarbazol-4-yl}oxyacetic acid;
9-[(3-ethoxyphenyl)methyl]-5-carbamoyl-2-fluorocarbazol-4-yl}oxyacetic acid;
9-[(2-trifluoromethoxyphenyl)methyl]-5-carbamoyl-2-fluorocarbazol-4-yl}oxyacetic acid;
9-[(3-trifluoromethoxyphenyl)methyl]-5-carbamoyl-2-fluorocarbazol-4-yl}oxyacetic acid;
9-[(2-difluoromethoxyphenyl)methyl]-5-carbamoyl-2-fluorocarbazol-4-yl}oxyacetic acid;
9-[(3-difluoromethoxyphenyl)methyl]-5-carbamoyl-2-fluorocarbazol-4-yl}oxyacetic acid;
9-[(2-cyanophenyl)methyl]-5-carbamoyl-2-fluorocarbazol-4-yl}oxyacetic acid;
9-[(3-cyanophenyl)methyl]-5-carbamoyl-2-fluorocarbazol-4-yl}oxyacetic acid;
9-[(4-cyanophenyl)methyl]-5-carbamoyl-2-fluorocarbazol-4-yl}oxyacetic acid;
9-[(2-pyridyl)methyl]-5-carbamoyl-2-fluorocarbazol-4-yl}oxyacetic acid;
9-[(3-pyridyl)methyl]-5-carbamoyl-2-fluorocarbazol-4-yl}oxyacetic acid;
9-[(2-furyl)methyl]-5-carbamoyl-2-fluorocarbazol-4-yl}oxyacetic acid;
9-[(3-furyl)methyl]-5-carbamoyl-2-fluorocarbazol-4-yl}oxyacetic acid;
9-[(2-thienyl)methyl]-5-carbamoyl-2-fluorocarbazol-4-yl}oxyacetic acid;
9-[(3-thienyl)methyl]-5-carbamoyl-2-fluorocarbazol-4-yl}oxyacetic acid;
9-[(2-benzylphenyl)methyl]-5-carbamoyl-2-fluorocarbazol-4-yl}oxyacetic acid;
9-[(3-benzylphenyl)methyl]-5-carbamoyl-2-fluorocarbazol-4-yl}oxyacetic acid;
9-[(2-benzoylphenyl)methyl]-5-carbamoyl-2-fluorocarbazol-4-yl}oxyacetic acid;
9-[(3-benzoylphenyl)methyl]-5-carbamoyl-2-fluorocarbazol-4-yl}oxyacetic acid;
9-[(2-benzyloxyphenyl)methyl]-5-carbamoyl-2-fluorocarbazol-4-yl}oxyacetic acid;
9-[(3-benzyloxyphenyl)methyl]-5-carbamoyl-2-fluorocarbazol-4-yl}oxyacetic acid;
9-[(4-benzyloxyphenyl)methyl]-5-carbamoyl-2-fluorocarbazol-4-yl}oxyacetic acid;
9-[(2-phenylphenyl)methyl]-5-carbamoyl-2-fluorocarbazol-4-yl}oxyacetic acid;
9-[(3-phenylphenyl)methyl]-5-carbamoyl-2-fluorocarbazol-4-yl}oxyacetic acid;
9-[(1-naphthyl)methyl]-5-carbamoyl-2-fluorocarbazol-4-yl}oxyacetic acid;
9-[(2-naphthyl)methyl]-5-carbamoyl-2-fluorocarbazol-4-yl}oxyacetic acid;
9-[(2,3-difluorophenyl)methyl]-5-carbamoyl-2-fluorocarbazol-4-yl}oxyacetic acid;
9-[(2,4-difluorophenyl)methyl]-5-carbamoyl-2-fluorocarbazol-4-yl}oxyacetic acid;
9-[(2,5-difluorophenyl)methyl]-5-carbamoyl-2-fluorocarbazol-4-yl}oxyacetic acid;
9-[(2,6-difluorophenyl)methyl]-5-carbamoyl-2-fluorocarbazol-4-yl}oxyacetic acid;
9-[(3,4-difluorophenyl)methyl]-5-carbamoyl-2-fluorocarbazol-4-yl}oxyacetic acid;
9-[(3,5-difluorophenyl)methyl]-5-carbamoyl-2-fluorocarbazol-4-yl}oxyacetic acid;
9-[(2,3,4-trifluorophenyl)methyl]-5-carbamoyl-2-fluorocarbazol-4-yl}oxyacetic acid;
9-[(2,3,5-trifluorophenyl)methyl]-5-carbamoyl-2-fluorocarbazol-4-yl}oxyacetic acid;
9-[(2,3,6-trifluorophenyl)methyl]-5-carbamoyl-2-fluorocarbazol-4-yl}oxyacetic acid;
9-[(2,4,5-trifluorophenyl)methyl]-5-carbamoyl-2-fluorocarbazol-4-yl}oxyacetic acid;
9-[(2,4,6-trifluorophenyl)methyl]-5-carbamoyl-2-fluorocarbazol-4-yl}oxyacetic acid;
9-[(3,4,5-trifluorophenyl)methyl]-5-carbamoyl-2-fluorocarbazol-4-yl}oxyacetic acid;
9-[(pentafluorophenyl)methyl]-5-carbamoyl-2-fluorocarbazol-4-yl}oxyacetic acid;
9-[(2,3-dichlorophenyl)methyl]-5-carbamoyl-2-fluorocarbazol-4-yl}oxyacetic acid;
9-[(2,4-dichlorophenyl)methyl]-5-carbamoyl-2-fluorocarbazol-4-yl}oxyacetic acid;
9-[(2,5-dichlorophenyl)methyl]-5-carbamoyl-2-fluorocarbazol-4-yl}oxyacetic acid;
9-[(2,6-dichlorophenyl)methyl]-5-carbamoyl-2-fluorocarbazol-4-yl}oxyacetic acid;
9-[(2-phenoxyphenyl)methyl]-5-carbamoyl-2-chlorocarbazol-4-yl}oxyacetic acid;
9-[(3-phenoxyphenyl)methyl]-5-carbamoyl-2-chlorocarbazol-4-yl}oxyacetic acid;
9-[(2-fluorophenyl)methyl]-5-carbamoyl-2-chlorocarbazol-4-yl}oxyacetic acid;
9-[(3-fluorophenyl)methyl]-5-carbamoyl-2-chlorocarbazol-4-yl}oxyacetic acid;
9-[(4-fluorophenyl)methyl]-5-carbamoyl-2-chlorocarbazol-4-yl}oxyacetic acid;
9-[(2-chlorophenyl)methyl]-5-carbamoyl-2-chlorocarbazol-4-yl}oxyacetic acid;
9-[(3-chlorophenyl)methyl]-5-carbamoyl-2-chlorocarbazol-4-yl}oxyacetic acid;
9-[(2-bromophenyl)methyl]-5-carbamoyl-2-chlorocarbazol-4-yl}oxyacetic acid;
9-[(3-bromophenyl)methyl]-5-carbamoyl-2-chlorocarbazol-4-yl}oxyacetic acid;
9-[(2-iodophenyl)methyl]-5-carbamoyl-2-chlorocarbazol-4-yl}oxyacetic acid;
9-[(3-iodophenyl)methyl]-5-carbamoyl-2-chlorocarbazol-4-yl}oxyacetic acid;
9-[(2-acetamidophenyl)methyl]-5-carbamoyl-2-chlorocarbazol-4-yl}oxyacetic acid;
9-[(3-acetamidophenyl)methyl]-5-carbamoyl-2-chlorocarbazol-4-yl}oxyacetic acid;
9-[(2-carbamoylphenyl)methyl]-5-carbamoyl-2-chlorocarbazol-4-yl}oxyacetic acid;
9-[(3-carbamoylphenyl)methyl]-5-carbamoyl-2-chlorocarbazol-4-yl}oxyacetic acid;
9-[(2-methylsulfonylphenyl)methyl]-5-carbamoyl-2-chlorocarbazol-4-yl}oxyacetic acid;
9-[(3-methylsulfonylphenyl)methyl]-5-carbamoyl-2-chlorocarbazol-4-yl}oxyacetic acid;
9-[(2-methylphenyl)methyl]-5-carbamoyl-2-chlorocarbazol-4-yl}oxyacetic acid;
9-[(3-methylphenyl)methyl]-5-carbamoyl-2-chlorocarbazol-4-yl}oxyacetic acid;
9-[(2-ethylphenyl)methyl]-5-carbamoyl-2-chlorocarbazol-4-yl}oxyacetic acid;
9-[(3-ethylphenyl)methyl]-5-carbamoyl-2-chlorocarbazol-4-yl}oxyacetic acid;

9-[(2-trifluoromethylphenyl)methyl]-5-carbamoyl-2-chlorocarbazol-4-yl}oxyacetic acid;
9-[(3-trifluoromethylphenyl)methyl]-5-carbamoyl-2-chlorocarbazol-4-yl}oxyacetic acid;
9-[(2-methoxyphenyl)methyl]-5-carbamoyl-2-chlorocarbazol-4-yl}oxyacetic acid;
9-[(cyclopropyl)methyl]-5-carbamoyl-2-chlorocarbazol-4-yl}oxyacetic acid;
9-[(cyclobutyl)methyl]-5-carbamoyl-2-chlorocarbazol-4-yl}oxyacetic acid;
9-[(cyclopentyl)methyl]-5-carbamoyl-2-chlorocarbazol-4-yl}oxyacetic acid;
9-[(cyclohexyl)methyl]-5-carbamoyl-2-chlorocarbazol-4-yl}oxyacetic acid;
9-[(3-methoxyphenyl)methyl]-5-carbamoyl-2-chlorocarbazol-4-yl}oxyacetic acid;
9-[(2-ethoxyphenyl)methyl]-5-carbamoyl-2-chlorocarbazol-4-yl}oxyacetic acid;
9-[(3-ethoxyphenyl)methyl]-5-carbamoyl-2-chlorocarbazol-4-yl}oxyacetic acid;
9-[(2-trifluoromethoxyphenyl)methyl]-5-carbamoyl-2-chlorocarbazol-4-yl}oxyacetic acid;
9-[(3-trifluoromethoxyphenyl)methyl]-5-carbamoyl-2-chlorocarbazol-4-yl}oxyacetic acid;
9-[(2-difluoromethoxyphenyl)methyl]-5-carbamoyl-2-chlorocarbazol-4-yl}oxyacetic acid;
9-[(3-difluoromethoxyphenyl)methyl]-5-carbamoyl-2-chlorocarbazol-4-yl}oxyacetic acid;
9-[(2-cyanophenyl)methyl]-5-carbamoyl-2-chlorocarbazol-4-yl}oxyacetic acid;
9-[(3-cyanophenyl)methyl]-5-carbamoyl-2-chlorocarbazol-4-yl}oxyacetic acid;
9-[(4-cyanophenyl)methyl]-5-carbamoyl-2-chlorocarbazol-4-yl}oxyacetic acid;
9-[(2-pyridyl)methyl]-5-carbamoyl-2-chlorocarbazol-4-yl}oxyacetic acid;
9-[(3-pyridyl)methyl]-5-carbamoyl-2-chlorocarbazol-4-yl}oxyacetic acid;
9-[(2-furyl)methyl]-5-carbamoyl-2-chlorocarbazol-4-yl}oxyacetic acid;
9-[(3-furyl)methyl]-5-carbamoyl-2-chlorocarbazol-4-yl}oxyacetic acid;
9-[(2-thienyl)methyl]-5-carbamoyl-2-chlorocarbazol-4-yl}oxyacetic acid;
9-[(3-thienyl)methyl]-5-carbamoyl-2-chlorocarbazol-4-yl}oxyacetic acid;
9-[(2-benzylphenyl)methyl]-5-carbamoyl-2-chlorocarbazol-4-yl}oxyacetic acid;
9-[(3-benzylphenyl)methyl]-5-carbamoyl-2-chlorocarbazol-4-yl}oxyacetic acid;
9-[(2-benzoylphenyl)methyl]-5-carbamoyl-2-chlorocarbazol-4-yl}oxyacetic acid;
9-[(3-benzoylphenyl)methyl]-5-carbamoyl-2-chlorocarbazol-4-yl}oxyacetic acid;
9-[(2-benzyloxyphenyl)methyl]-5-carbamoyl-2-chlorocarbazol-4-yl}oxyacetic acid;
9-[(3-benzyloxyphenyl)methyl]-5-carbamoyl-2-chlorocarbazol-4-yl}oxyacetic acid;
9-[(4-benzyloxyphenyl)methyl]-5-carbamoyl-2-chlorocarbazol-4-yl}oxyacetic acid;
9-[(2-phenylphenyl)methyl]-5-carbamoyl-2-chlorocarbazol-4-yl}oxyacetic acid;
9-[(3-phenylphenyl)methyl]-5-carbamoyl-2-chlorocarbazol-4-yl}oxyacetic acid;
9-[(1-naphthyl)methyl]-5-carbamoyl-2-chlorocarbazol-4-yl}oxyacetic acid;
9-[(2-naphthyl)methyl]-5-carbamoyl-2-chlorocarbazol-4-yl}oxyacetic acid;
9-[(2,3-difluorophenyl)methyl]-5-carbamoyl-2-chlorocarbazol-4-yl}oxyacetic acid;
9-[(2,4-difluorophenyl)methyl]-5-carbamoyl-2-chlorocarbazol-4-yl}oxyacetic acid;
9-[(2,5-difluorophenyl)methyl]-5-carbamoyl-2-chlorocarbazol-4-yl}oxyacetic acid;
9-[(2,6-difluorophenyl)methyl]-5-carbamoyl-2-chlorocarbazol-4-yl}oxyacetic acid;
9-[(3,4-difluorophenyl)methyl]-5-carbamoyl-2-chlorocarbazol-4-yl}oxyacetic acid;
9-[(3,5-difluorophenyl)methyl]-5-carbamoyl-2-chlorocarbazol-4-yl}oxyacetic acid;
9-[(2,3,4-trifluorophenyl)methyl]-5-carbamoyl-2-chlorocarbazol-4-yl}oxyacetic acid;
9-[(2,3,5-trifluorophenyl)methyl]-5-carbamoyl-2-chlorocarbazol-4-yl}oxyacetic acid;
9-[(2,3,6-trifluorophenyl)methyl]-5-carbamoyl-2-chlorocarbazol-4-yl}oxyacetic acid;
9-[(2,4,5-trifluorophenyl)methyl]-5-carbamoyl-2-chlorocarbazol-4-yl}oxyacetic acid;
9-[(2,4,6-trifluorophenyl)methyl]-5-carbamoyl-2-chlorocarbazol-4-yl}oxyacetic acid;
9-[(3,4,5-trifluorophenyl)methyl]-5-carbamoyl-2-chlorocarbazol-4-yl}oxyacetic acid;
9-[(pentafluorophenyl)methyl]-5-carbamoyl-2-chlorocarbazol-4-yl}oxyacetic acid;
9-[(2,3-dichlorophenyl)methyl]-5-carbamoyl-2-chlorocarbazol-4-yl}oxyacetic acid;
9-[(2,4-dichlorophenyl)methyl]-5-carbamoyl-2-chlorocarbazol-4-yl}oxyacetic acid;
9-[(2,5-dichlorophenyl)methyl]-5-carbamoyl-2-chlorocarbazol-4-yl}oxyacetic acid;
9-[(2,6-dichlorophenyl)methyl]-5-carbamoyl-2-chlorocarbazol-4-yl}oxyacetic acid;
9-[(2-fluoro-3-trifluoromethylphenyl)methyl]-5-carbamoyl-2-fluorocarbazol-4-yl}oxyacetic acid;
9-[(2-fluoro-5-trifluoromethylphenyl)methyl]-5-carbamoyl-2-fluorocarbazol-4-yl}oxyacetic acid;
9-[(2-fluoro-6-trifluoromethylphenyl)methyl]-5-carbamoyl-2-fluorocarbazol-4-yl}oxyacetic acid;
9-[(3-fluoro-5-trifluoromethylphenyl)methyl]-5-carbamoyl-2-fluorocarbazol-4-yl}oxyacetic acid;
9-[(4-fluoro-2-trifluoromethylphenyl)methyl]-5-carbamoyl-2-fluorocarbazol-4-yl}oxyacetic acid;
9-[(4-fluoro-3-trifluoromethylphenyl)methyl]-5-carbamoyl-2-fluorocarbazol-4-yl}oxyacetic acid;
9-[3-(2-fluorophenoxy)methyl]-5-carbamoyl-2-fluorocarbazol-4-yl}oxyacetic acid;
9-[3-(4-fluorophenoxy)methyl]-5-carbamoyl-2-fluorocarbazol-4-yl}oxyacetic acid;
9-[(2-fluoro-3-methylphenyl)methyl]-5-carbamoyl-2-fluorocarbazol-4-yl}oxyacetic acid;
9-[(3-chloro-2-fluorophenyl)methyl]-5-carbamoyl-2-fluorocarbazol-4-yl}oxyacetic acid;
9-[(2-chloro-6-fluorophenyl)methyl]-5-carbamoyl-2-fluorocarbazol-4-yl}oxyacetic acid;
9-[(2-bromo-5-fluorophenyl)methyl]-5-carbamoyl-2-fluorocarbazol-4-yl}oxyacetic acid;
9-[(1-bromo-2-naphthylphenyl)methyl]-5-carbamoyl-2-fluorocarbazol-4-yl}oxyacetic acid;
9-[(2-methyl-1-naphthylphenyl)methyl]-5-carbamoyl-2-fluorocarbazol-4-yl}oxyacetic acid;
9-[(6-methyl-2-naphthylphenyl)methyl]-5-carbamoyl-2-fluorocarbazol-4-yl}oxyacetic acid;
9-[(2-((phenylsulfonyl)methyl)phenyl)methyl]-5-carbamoyl-2-fluorocarbazol-4-yl}oxyacetic acid;
9-[(1-fluorenylmethyl]-5-carbamoyl-2-fluorocarbazol-4-yl}oxyacetic acid;

9-[(2-fluoro-3-trifluoromethylphenyl)methyl]-5-carbamoyl-2-chlorocarbazol-4-yl}oxyacetic acid;
9-[(2-fluoro-5-trifluoromethylphenyl)methyl]-5-carbamoyl-2-chlorocarbazol-4-yl}oxyacetic acid;
9-[(2-fluoro-6-trifluoromethylphenyl)methyl]-5-carbamoyl-2-chlorocarbazol-4-yl}oxyacetic acid;
9-[(3-fluoro-5-trifluoromethylphenyl)methyl]-5-carbamoyl-2-chlorocarbazol-4-yl}oxyacetic acid;
9-[(4-fluoro-2-trifluoromethylphenyl)methyl]-5-carbamoyl-2-chlorocarbazol-4-yl}oxyacetic acid;
9-[(4-fluoro-3-trifluoromethylphenyl)methyl]-5-carbamoyl-2-chlorocarbazol-4-yl}oxyacetic acid;
9-[3-(2-fluorophenoxy)methyl]-5-carbamoyl-2-chlorocarbazol-4-yl}oxyacetic acid;
9-[3-(4-fluorophenoxy)methyl]-5-carbamoyl-2-chlorocarbazol-4-yl}oxyacetic acid;
9-[(2-fluoro-3-methylphenyl)methyl]-5-carbamoyl-2-chlorocarbazol-4-yl}oxyacetic acid;
9-[(3-chloro-2-fluorophenyl)methyl]-5-carbamoyl-2-chlorocarbazol-4-yl}oxyacetic acid;
9-[(2-chloro-6-fluorophenyl)methyl]-5-carbamoyl-2-chlorocarbazol-4-yl}oxyacetic acid;
9-[(2-bromo-5-fluorophenyl)methyl]-5-carbamoyl-2-chlorocarbazol-4-yl}oxyacetic acid;
9-[(1-bromo-2-naphthylphenyl)methyl]-5-carbamoyl-2-chlorocarbazol-4-yl}oxyacetic acid;
9-[(2-methyl-1-naphthylphenyl)methyl]-5-carbamoyl-2-chlorocarbazol-4-yl}oxyacetic acid;
9-[(6-methyl-2-naphthylphenyl)methyl]-5-carbamoyl-2-chlorocarbazol-4-yl}oxyacetic acid;
9-[(2-((phenylsulfonyl)methyl)phenyl)methyl]-5-carbamoyl-2-chlorocarbazol-4-yl}oxyacetic acid;
9-[(1-fluorenylmethyl]-5-carbamoyl-2-chlorocarbazol-4-yl}oxyacetic acid;
9-[(2-phenoxyphenyl)methyl]-5-carbamoyl-1-fluorocarbazol-4-yl}oxyacetic acid;
9-[(3-phenoxyphenyl)methyl]-5-carbamoyl-1-fluorocarbazol-4-yl}oxyacetic acid;
9-[(2-fluorophenyl)methyl]-5-carbamoyl-1-fluorocarbazol-4-yl}oxyacetic acid;
9-[(3-fluorophenyl)methyl]-5-carbamoyl-1-fluorocarbazol-4-yl}oxyacetic acid;
9-[(4-fluorophenyl)methyl]-5-carbamoyl-1-fluorocarbazol-4-yl}oxyacetic acid;
9-[(2-chlorophenyl)methyl]-5-carbamoyl-1-fluorocarbazol-4-yl}oxyacetic acid;
9-[(3-chlorophenyl)methyl]-5-carbamoyl-1-fluorocarbazol-4-yl}oxyacetic acid;
9-[(2-bromophenyl)methyl]-5-carbamoyl-1-fluorocarbazol-4-yl}oxyacetic acid;
9-[(3-bromophenyl)methyl]-5-carbamoyl-1-fluorocarbazol-4-yl}oxyacetic acid;
9-[(2-iodophenyl)methyl]-5-carbamoyl-1-fluorocarbazol-4-yl}oxyacetic acid;
9-[(3-iodophenyl)methyl]-5-carbamoyl-1-fluorocarbazol-4-yl}oxyacetic acid;
9-[(2-acetamidophenyl)methyl]-5-carbamoyl-1-fluorocarbazol-4-yl}oxyacetic acid;
9-[(3-acetamidophenyl)methyl]-5-carbamoyl-1-fluorocarbazol-4-yl}oxyacetic acid;
9-[(2-carbamoylphenyl)methyl]-5-carbamoyl-1-fluorocarbazol-4-yl}oxyacetic acid;
9-[(3-carbamoylphenyl)methyl]-5-carbamoyl-1-fluorocarbazol-4-yl}oxyacetic acid;
9-[(2-methylsulfonylphenyl)methyl]-5-carbamoyl-1-fluorocarbazol-4-yl}oxyacetic acid;
9-[(3-methylsulfonylphenyl)methyl]-5-carbamoyl-1-fluorocarbazol-4-yl}oxyacetic acid;
9-[(2-methylphenyl)methyl]-5-carbamoyl-1-fluorocarbazol-4-yl}oxyacetic acid;
9-[(3-methylphenyl)methyl]-5-carbamoyl-1-fluorocarbazol-4-yl}oxyacetic acid;
9-[(2-ethylphenyl)methyl]-5-carbamoyl-1-fluorocarbazol-4-yl}oxyacetic acid;
9-[(3-ethylphenyl)methyl]-5-carbamoyl-1-fluorocarbazol-4-yl}oxyacetic acid;
9-[(2-trifluoromethylphenyl)methyl]-5-carbamoyl-1-fluorocarbazol-4-yl}oxyacetic acid;
9-[(3-trifluoromethylphenyl)methyl]-5-carbamoyl-1-fluorocarbazol-4-yl}oxyacetic acid;
9-[(2-methoxyphenyl)methyl]-5-carbamoyl-1-fluorocarbazol-4-yl}oxyacetic acid;
9-[(cyclopropyl)methyl]-5-carbamoyl-1-fluorocarbazol-4-yl}oxyacetic acid;
9-[(cyclobutyl)methyl]-5-carbamoyl-1-fluorocarbazol-4-yl}oxyacetic acid;
9-[(cyclopentyl)methyl]-5-carbamoyl-1-fluorocarbazol-4-yl}oxyacetic acid;
9-[(cyclohexyl)methyl]-5-carbamoyl-1-fluorocarbazol-4-yl}oxyacetic acid;
9-[(3-methoxyphenyl)methyl]-5-carbamoyl-1-fluorocarbazol-4-yl}oxyacetic acid;
9-[(2-ethoxyphenyl)methyl]-5-carbamoyl-1-fluorocarbazol-4-yl}oxyacetic acid;
9-[(3-ethoxyphenyl)methyl]-5-carbamoyl-1-fluorocarbazol-4-yl}oxyacetic acid;
9-[(2-trifluoromethoxyphenyl)methyl]-5-carbamoyl-1-fluorocarbazol-4-yl}oxyacetic acid;
9-[(3-trifluoromethoxyphenyl)methyl]-5-carbamoyl-1-fluorocarbazol-4-yl}oxyacetic acid;
9-[(2-difluoromethoxyphenyl)methyl]-5-carbamoyl-1-fluorocarbazol-4-yl}oxyacetic acid;
9-[(3-difluoromethoxyphenyl)methyl]-5-carbamoyl-1-fluorocarbazol-4-yl}oxyacetic acid;
9-[(2-cyanophenyl)methyl]-5-carbamoyl-1-fluorocarbazol-4-yl}oxyacetic acid;
9-[(3-cyanophenyl)methyl]-5-carbamoyl-1-fluorocarbazol-4-yl}oxyacetic acid;
9-[(4-cyanophenyl)methyl]-5-carbamoyl-1-fluorocarbazol-4-yl}oxyacetic acid;
9-[(2-pyridyl)methyl]-5-carbamoyl-1-fluorocarbazol-4-yl}oxyacetic acid;
9-[(3-pyridyl)methyl]-5-carbamoyl-1-fluorocarbazol-4-yl}oxyacetic acid;
9-[(2-furyl)methyl]-5-carbamoyl-1-fluorocarbazol-4-yl}oxyacetic acid;
9-[(3-furyl)methyl]-5-carbamoyl-1-fluorocarbazol-4-yl}oxyacetic acid;
9-[(2-thienyl)methyl]-5-carbamoyl-1-fluorocarbazol-4-yl}oxyacetic acid;
9-[(3-thienyl)methyl]-5-carbamoyl-1-fluorocarbazol-4-yl}oxyacetic acid;
9-[(2-benzylphenyl)methyl]-5-carbamoyl-1-fluorocarbazol-4-yl}oxyacetic acid;
9-[(3-benzylphenyl)methyl]-5-carbamoyl-1-fluorocarbazol-4-yl}oxyacetic acid;
9-[(2-benzoylphenyl)methyl]-5-carbamoyl-1-fluorocarbazol-4-yl}oxyacetic acid;
9-[(3-benzoylphenyl)methyl]-5-carbamoyl-1-fluorocarbazol-4-yl}oxyacetic acid;
9-[(2-benzyloxyphenyl)methyl]-5-carbamoyl-1-fluorocarbazol-4-yl}oxyacetic acid;
9-[(3-benzyloxyphenyl)methyl]-5-carbamoyl-1-fluorocarbazol-4-yl}oxyacetic acid;
9-[(4-benzyloxyphenyl)methyl]-5-carbamoyl-1-fluorocarbazol-4-yl}oxyacetic acid;

9-[(2-phenylphenyl)methyl]-5-carbamoyl-1-fluorocarbazol-4-yl}oxyacetic acid;
9-[(3-phenylphenyl)methyl]-5-carbamoyl-1-fluorocarbazol-4-yl}oxyacetic acid;
9-[(1-naphthyl)methyl]-5-carbamoyl-1-fluorocarbazol-4-yl}oxyacetic acid;
9-[(2-naphthyl)methyl]-5-carbamoyl-1-fluorocarbazol-4-yl}oxyacetic acid;
9-[(2,3-difluorophenyl)methyl]-5-carbamoyl-1-fluorocarbazol-4-yl}oxyacetic acid;
9-[(2,4-difluorophenyl)methyl]-5-carbamoyl-1-fluorocarbazol-4-yl}oxyacetic acid;
9-[(2,5-difluorophenyl)methyl]-5-carbamoyl-1-fluorocarbazol-4-yl}oxyacetic acid;
9-[(2,6-difluorophenyl)methyl]-5-carbamoyl-1-fluorocarbazol-4-yl}oxyacetic acid;
9-[(3,4-difluorophenyl)methyl]-5-carbamoyl-1-fluorocarbazol-4-yl}oxyacetic acid;
9-[(3,5-difluorophenyl)methyl]-5-carbamoyl-1-fluorocarbazol-4-yl}oxyacetic acid;
9-[(2,3,4-trifluorophenyl)methyl]-5-carbamoyl-1-fluorocarbazol-4-yl}oxyacetic acid;
9-[(2,3,5-trifluorophenyl)methyl]-5-carbamoyl-1-fluorocarbazol-4-yl}oxyacetic acid;
9-[(2,3,6-trifluorophenyl)methyl]-5-carbamoyl-1-fluorocarbazol-4-yl}oxyacetic acid;
9-[(2,4,5-trifluorophenyl)methyl]-5-carbamoyl-1-fluorocarbazol-4-yl}oxyacetic acid;
9-[(2,4,6-trifluorophenyl)methyl]-5-carbamoyl-1-fluorocarbazol-4-yl}oxyacetic acid;
9-[(3,4,5-trifluorophenyl)methyl]-5-carbamoyl-1-fluorocarbazol-4-yl}oxyacetic acid;
9-[(pentafluorophenyl)methyl]-5-carbamoyl-1-fluorocarbazol-4-yl}oxyacetic acid;
9-[(2,3-dichlorophenyl)methyl]-5-carbamoyl-1-fluorocarbazol-4-yl}oxyacetic acid;
9-[(2,4-dichlorophenyl)methyl]-5-carbamoyl-1-fluorocarbazol-4-yl}oxyacetic acid;
9-[(2,5-dichlorophenyl)methyl]-5-carbamoyl-1-fluorocarbazol-4-yl}oxyacetic acid;
9-[(2,6-dichlorophenyl)methyl]-5-carbamoyl-1-fluorocarbazol-4-yl}oxyacetic acid;
9-[(2-phenoxyphenyl)methyl]-5-carbamoyl-1-chlorocarbazol-4-yl}oxyacetic acid;
9-[(3-phenoxyphenyl)methyl]-5-carbamoyl-1-chlorocarbazol-4-yl}oxyacetic acid;
9-[(2-fluorophenyl)methyl]-5-carbamoyl-1-chlorocarbazol-4-yl}oxyacetic acid;
9-[(3-fluorophenyl)methyl]-5-carbamoyl-1-chlorocarbazol-4-yl}oxyacetic acid;
9-[(4-fluorophenyl)methyl]-5-carbamoyl-1-chlorocarbazol-4-yl}oxyacetic acid;
9-[(2-chlorophenyl)methyl]-5-carbamoyl-1-chlorocarbazol-4-yl}oxyacetic acid;
9-[(3-chlorophenyl)methyl]-5-carbamoyl-1-chlorocarbazol-4-yl}oxyacetic acid;
9-[(2-bromophenyl)methyl]-5-carbamoyl-1-chlorocarbazol-4-yl}oxyacetic acid;
9-[(3-bromophenyl)methyl]-5-carbamoyl-1-chlorocarbazol-4-yl}oxyacetic acid;
9-[(2-iodophenyl)methyl]-5-carbamoyl-1-chlorocarbazol-4-yl}oxyacetic acid;
9-[(3-iodophenyl)methyl]-5-carbamoyl-1-chlorocarbazol-4-yl}oxyacetic acid;
9-[(2-acetamidophenyl)methyl]-5-carbamoyl-1-chlorocarbazol-4-yl}oxyacetic acid;
9-[(3-acetamidophenyl)methyl]-5-carbamoyl-1-chlorocarbazol-4-yl}oxyacetic acid;
9-[(2-carbamoylphenyl)methyl]-5-carbamoyl-1-chlorocarbazol-4-yl}oxyacetic acid;
9-[(3-carbamoylphenyl)methyl]-5-carbamoyl-1-chlorocarbazol-4-yl}oxyacetic acid;
9-[(2-methylsulfonylphenyl)methyl]-5-carbamoyl-1-chlorocarbazol-4-yl}oxyacetic acid;
9-[(3-methylsulfonylphenyl)methyl]-5-carbamoyl-1-chlorocarbazol-4-yl}oxyacetic acid;
9-[(2-methylphenyl)methyl]-5-carbamoyl-1-chlorocarbazol-4-yl}oxyacetic acid;
9-[(3-methylphenyl)methyl]-5-carbamoyl-1-chlorocarbazol-4-yl}oxyacetic acid;
9-[(2-ethylphenyl)methyl]-5-carbamoyl-1-chlorocarbazol-4-yl}oxyacetic acid;
9-[(3-ethylphenyl)methyl]-5-carbamoyl-1-chlorocarbazol-4-yl}oxyacetic acid;
9-[(2-trifluoromethylphenyl)methyl]-5-carbamoyl-1-chlorocarbazol-4-yl}oxyacetic acid;
9-[(3-trifluoromethylphenyl)methyl]-5-carbamoyl-1-chlorocarbazol-4-yl}oxyacetic acid;
9-[(2-methoxyphenyl)methyl]-5-carbamoyl-1-chlorocarbazol-4-yl}oxyacetic acid;
9-[(cyclopropyl)methyl]-5-carbamoyl-1-chlorocarbazol-4-yl}oxyacetic acid;
9-[(cyclobutyl)methyl]-5-carbamoyl-1-chlorocarbazol-4-yl}oxyacetic acid;
9-[(cyclopentyl)methyl]-5-carbamoyl-1-chlorocarbazol-4-yl}oxyacetic acid;
9-[(cyclohexyl)methyl]-5-carbamoyl-1-chlorocarbazol-4-yl}oxyacetic acid;
9-[(3-methoxyphenyl)methyl]-5-carbamoyl-1-chlorocarbazol-4-yl}oxyacetic acid;
9-[(2-ethoxyphenyl)methyl]-5-carbamoyl-1-chlorocarbazol-4-yl}oxyacetic acid;
9-[(3-ethoxyphenyl)methyl]-5-carbamoyl-1-chlorocarbazol-4-yl}oxyacetic acid;
9-[(2-trifluoromethoxyphenyl)methyl]-5-carbamoyl-1-chlorocarbazol-4-yl}oxyacetic acid;
9-[(3-trifluoromethoxyphenyl)methyl]-5-carbamoyl-1-chlorocarbazol-4-yl}oxyacetic acid;
9-[(2-difluoromethoxyphenyl)methyl]-5-carbamoyl-1-chlorocarbazol-4-yl}oxyacetic acid;
9-[(3-difluoromethoxyphenyl)methyl]-5-carbamoyl-1-chlorocarbazol-4-yl}oxyacetic acid;
9-[(2-cyanophenyl)methyl]-5-carbamoyl-1-chlorocarbazol-4-yl}oxyacetic acid;
9-[(3-cyanophenyl)methyl]-5-carbamoyl-1-chlorocarbazol-4-yl}oxyacetic acid;
9-[(4-cyanophenyl)methyl]-5-carbamoyl-1-chlorocarbazol-4-yl}oxyacetic acid;
9-[(2-pyridyl)methyl]-5-carbamoyl-1-chlorocarbazol-4-yl}oxyacetic acid;
9-[(3-pyridyl)methyl]-5-carbamoyl-1-chlorocarbazol-4-yl}oxyacetic acid;
9-[(2-furyl)methyl]-5-carbamoyl-1-chlorocarbazol-4-yl}oxyacetic acid;
9-[(3-furyl)methyl]-5-carbamoyl-1-chlorocarbazol-4-yl}oxyacetic acid;
9-[(2-thienyl)methyl]-5-carbamoyl-1-chlorocarbazol-4-yl}oxyacetic acid;
9-[(3-thienyl)methyl]-5-carbamoyl-1-chlorocarbazol-4-yl}oxyacetic acid;
9-[(2-benzylphenyl)methyl]-5-carbamoyl-1-chlorocarbazol-4-yl}oxyacetic acid;
9-[(3-benzylphenyl)methyl]-5-carbamoyl-1-chlorocarbazol-4-yl}oxyacetic acid;
9-[(2-benzoylphenyl)methyl]-5-carbamoyl-1-chlorocarbazol-4-yl}oxyacetic acid;

9-[(3-benzoylphenyl)methyl]-5-carbamoyl-1-chlorocarbazol-4-yl}oxyacetic acid;
9-[(2-benzyloxyphenyl)methyl]-5-carbamoyl-1-chlorocarbazol-4-yl}oxyacetic acid;
9-[(3-benzyloxyphenyl)methyl]-5-carbamoyl-1-chlorocarbazol-4-yl}oxyacetic acid;
9-[(4-benzyloxyphenyl)methyl]-5-carbamoyl-1-chlorocarbazol-4-yl}oxyacetic acid;
9-[(2-phenylphenyl)methyl]-5-carbamoyl-1-chlorocarbazol-4-yl}oxyacetic acid;
9-[(3-phenylphenyl)methyl]-5-carbamoyl-1-chlorocarbazol-4-yl}oxyacetic acid;
9-[(1-naphthyl)methyl]-5-carbamoyl-1-chlorocarbazol-4-yl}oxyacetic acid;
9-[(2-naphthyl)methyl]-5-carbamoyl-1-chlorocarbazol-4-yl}oxyacetic acid;
9-[(2,3-difluorophenyl)methyl]-5-carbamoyl-1-chlorocarbazol-4-yl}oxyacetic acid;
9-[(2,4-difluorophenyl)methyl]-5-carbamoyl-1-chlorocarbazol-4-yl}oxyacetic acid;
9-[(2,5-difluorophenyl)methyl]-5-carbamoyl-1-chlorocarbazol-4-yl}oxyacetic acid;
9-[(2,6-difluorophenyl)methyl]-5-carbamoyl-1-chlorocarbazol-4-yl}oxyacetic acid;
9-[(3,4-difluorophenyl)methyl]-5-carbamoyl-1-chlorocarbazol-4-yl}oxyacetic acid;
9-[(3,5-difluorophenyl)methyl]-5-carbamoyl-1-chlorocarbazol-4-yl}oxyacetic acid;
9-[(2,3,4-trifluorophenyl)methyl]-5-carbamoyl-1-chlorocarbazol-4-yl}oxyacetic acid;
9-[(2,3,5-trifluorophenyl)methyl]-5-carbamoyl-1-chlorocarbazol-4-yl}oxyacetic acid;
9-[(2,3,6-trifluorophenyl)methyl]-5-carbamoyl-1-chlorocarbazol-4-yl}oxyacetic acid;
9-[(2,4,5-trifluorophenyl)methyl]-5-carbamoyl-1-chlorocarbazol-4-yl}oxyacetic acid;
9-[(2,4,6-trifluorophenyl)methyl]-5-carbamoyl-1-chlorocarbazol-4-yl}oxyacetic acid;
9-[(3,4,5-trifluorophenyl)methyl]-5-carbamoyl-1-chlorocarbazol-4-yl}oxyacetic acid;
9-[(pentafluorophenyl)methyl]-5-carbamoyl-1-chlorocarbazol-4-yl}oxyacetic acid;
9-[(2,3-dichlorophenyl)methyl]-5-carbamoyl-1-chlorocarbazol-4-yl}oxyacetic acid;
9-[(2,4-dichlorophenyl)methyl]-5-carbamoyl-1-chlorocarbazol-4-yl}oxyacetic acid;
9-[(2,5-dichlorophenyl)methyl]-5-carbamoyl-1-chlorocarbazol-4-yl}oxyacetic acid;
9-[(2,6-dichlorophenyl)methyl]-5-carbamoyl-1-chlorocarbazol-4-yl}oxyacetic acid;
9-[(2-phenoxyphenyl)methyl]-5-carbamoyl-3-fluorocarbazol-4-yl}oxyacetic acid;
9-[(3-phenoxyphenyl)methyl]-5-carbamoyl-3-fluorocarbazol-4-yl}oxyacetic acid;
9-[(2-fluorophenyl)methyl]-5-carbamoyl-3-fluorocarbazol-4-yl}oxyacetic acid;
9-[(3-fluorophenyl)methyl]-5-carbamoyl-3-fluorocarbazol-4-yl}oxyacetic acid;
9-[(4-fluorophenyl)methyl]-5-carbamoyl-3-fluorocarbazol-4-yl}oxyacetic acid;
9-[(2-chlorophenyl)methyl]-5-carbamoyl-3-fluorocarbazol-4-yl}oxyacetic acid;
9-[(3-chlorophenyl)methyl]-5-carbamoyl-3-fluorocarbazol-4-yl}oxyacetic acid;
9-[(2-bromophenyl)methyl]-5-carbamoyl-3-fluorocarbazol-4-yl}oxyacetic acid;
9-[(3-bromophenyl)methyl]-5-carbamoyl-3-fluorocarbazol-4-yl}oxyacetic acid;
9-[(2-iodophenyl)methyl]-5-carbamoyl-3-fluorocarbazol-4-yl}oxyacetic acid;
9-[(3-iodophenyl)methyl]-5-carbamoyl-3-fluorocarbazol-4-yl}oxyacetic acid;
9-[(2-acetamidophenyl)methyl]-5-carbamoyl-3-fluorocarbazol-4-yl}oxyacetic acid;
9-[(3-acetamidophenyl)methyl]-5-carbamoyl-3-fluorocarbazol-4-yl}oxyacetic acid;
9-[(2-carbamoylphenyl)methyl]-5-carbamoyl-3-fluorocarbazol-4-yl}oxyacetic acid;
9-[(3-carbamoylphenyl)methyl]-5-carbamoyl-3-fluorocarbazol-4-yl}oxyacetic acid;
9-[(2-methylsulfonylphenyl)methyl]-5-carbamoyl-3-fluorocarbazol-4-yl}oxyacetic acid;
9-[(3-methylsulfonylphenyl)methyl]-5-carbamoyl-3-fluorocarbazol-4-yl}oxyacetic acid;
9-[(2-methylphenyl)methyl]-5-carbamoyl-3-fluorocarbazol-4-yl}oxyacetic acid;
9-[(3-methylphenyl)methyl]-5-carbamoyl-3-fluorocarbazol-4-yl}oxyacetic acid;
9-[(2-ethylphenyl)methyl]-5-carbamoyl-3-fluorocarbazol-4-yl}oxyacetic acid;
9-[(3-ethylphenyl)methyl]-5-carbamoyl-3-fluorocarbazol-4-yl}oxyacetic acid;
9-[(2-trifluoromethylphenyl)methyl]-5-carbamoyl-3-fluorocarbazol-4-yl}oxyacetic acid;
9-[(3-trifluoromethylphenyl)methyl]-5-carbamoyl-3-fluorocarbazol-4-yl}oxyacetic acid;
9-[(2-methoxyphenyl)methyl]-5-carbamoyl-3-fluorocarbazol-4-yl}oxyacetic acid;
9-[(cyclopropyl)methyl]-5-carbamoyl-3-fluorocarbazol-4-yl}oxyacetic acid;
9-[(cyclobutyl)methyl]-5-carbamoyl-3-fluorocarbazol-4-yl}oxyacetic acid;
9-[(cyclopentyl)methyl]-5-carbamoyl-3-fluorocarbazol-4-yl}oxyacetic acid;
9-8 (cyclohexyl)methyl]-5-carbamoyl-3-fluorocarbazol-4-yl}oxyacetic acid;
9-[(3-methoxyphenyl)methyl]-5-carbamoyl-3-fluorocarbazol-4-yl}oxyacetic acid;
9-[(2-ethoxyphenyl)methyl]-5-carbamoyl-3-fluorocarbazol-4-yl}oxyacetic acid;
9-[(3-ethoxyphenyl)methyl]-5-carbamoyl-3-fluorocarbazol-4-yl}oxyacetic acid;
9-[(2-trifluoromethoxyphenyl)methyl]-5-carbamoyl-3-fluorocarbazol-4-yl}oxyacetic acid;
9-[(3-trifluoromethoxyphenyl)methyl]-5-carbamoyl-3-fluorocarbazol-4-yl}oxyacetic acid;
9-[(2-difluoromethoxyphenyl)methyl]-5-carbamoyl-3-fluorocarbazol-4-yl}oxyacetic acid;
9-[(3-difluoromethoxyphenyl)methyl]-5-carbamoyl-3-fluorocarbazol-4-yl}oxyacetic acid;
9-[(2-cyanophenyl)methyl]-5-carbamoyl-3-fluorocarbazol-4-yl}oxyacetic acid;
9-[(3-cyanophenyl)methyl]-5-carbamoyl-3-fluorocarbazol-4-yl}oxyacetic acid;
9-[(4-cyanophenyl)methyl]-5-carbamoyl-3-fluorocarbazol-4-yl}oxyacetic acid;
9-[(2-pyridyl)methyl]-5-carbamoyl-3-fluorocarbazol-4-yl}oxyacetic acid;
9-[(3-pyridyl)methyl]-5-carbamoyl-3-fluorocarbazol-4-yl}oxyacetic acid;
9-[(2-furyl)methyl]-5-carbamoyl-3-fluorocarbazol-4-yl}oxyacetic acid;
9-[(3-furyl)methyl]-5-carbamoyl-3-fluorocarbazol-4-yl}oxyacetic acid;
9-[(2-thienyl)methyl]-5-carbamoyl-3-fluorocarbazol-4-yl}oxyacetic acid;

9-[(3-thienyl)methyl]-5-carbamoyl-3-fluorocarbazol-4-yl}oxyacetic acid;
9-[(2-benzylphenyl)methyl]-5-carbamoyl-3-fluorocarbazol-4-yl}oxyacetic acid;
9-[(3-benzylphenyl)methyl]-5-carbamoyl-3-fluorocarbazol-4-yl}oxyacetic acid;
9-[(2-benzoylphenyl)methyl]-5-carbamoyl-3-fluorocarbazol-4-yl}oxyacetic acid;
9-[(3-benzoylphenyl)methyl]-5-carbamoyl-3-fluorocarbazol-4-yl}oxyacetic acid;
9-[(2-benzyloxyphenyl)methyl]-5-carbamoyl-3-fluorocarbazol-4-yl}oxyacetic acid;
9-[(3-benzyloxyphenyl)methyl]-5-carbamoyl-3-fluorocarbazol-4-yl}oxyacetic acid;
9-[(4-benzyloxyphenyl)methyl]-5-carbamoyl-3-fluorocarbazol-4-yl}oxyacetic acid;
9-[(2-phenylphenyl)methyl]-5-carbamoyl-3-fluorocarbazol-4-yl}oxyacetic acid;
9-[(3-phenylphenyl)methyl]-5-carbamoyl-3-fluorocarbazol-4-yl}oxyacetic acid;
9-[(1-naphthyl)methyl]-5-carbamoyl-3-fluorocarbazol-4-yl}oxyacetic acid;
9-[(2-naphthyl)methyl]-5-carbamoyl-3-fluorocarbazol-4-yl}oxyacetic acid;
9-[(2,3-difluorophenyl)methyl]-5-carbamoyl-3-fluorocarbazol-4-yl}oxyacetic acid;
9-[(2,4-difluorophenyl)methyl]-5-carbamoyl-3-fluorocarbazol-4-yl}oxyacetic acid;
9-[(2,5-difluorophenyl)methyl]-5-carbamoyl-3-fluorocarbazol-4-yl}oxyacetic acid;
9-[(2,6-difluorophenyl)methyl]-5-carbamoyl-3-fluorocarbazol-4-yl}oxyacetic acid;
9-[(3,4-difluorophenyl)methyl]-5-carbamoyl-3-fluorocarbazol-4-yl}oxyacetic acid;
9-[(3,5-difluorophenyl)methyl]-5-carbamoyl-3-fluorocarbazol-4-yl}oxyacetic acid;
9-[(2,3,4-trifluorophenyl)methyl]-5-carbamoyl-3-fluorocarbazol-4-yl}oxyacetic acid;
9-[(2,3,5-trifluorophenyl)methyl]-5-carbamoyl-3-fluorocarbazol-4-yl}oxyacetic acid;
9-[(2,3,6-trifluorophenyl)methyl]-5-carbamoyl-3-fluorocarbazol-4-yl}oxyacetic acid;
9-[(2,4,5-trifluorophenyl)methyl]-5-carbamoyl-3-fluorocarbazol-4-yl}oxyacetic acid;
9-[(2,4,6-trifluorophenyl)methyl]-5-carbamoyl-3-fluorocarbazol-4-yl}oxyacetic acid;
9-[(3,4,5-trifluorophenyl)methyl]-5-carbamoyl-3-fluorocarbazol-4-yl}oxyacetic acid;
9-[(pentafluorophenyl)methyl]-5-carbamoyl-3-fluorocarbazol-4-yl}oxyacetic acid;
9-[(2,3-dichlorophenyl)methyl]-5-carbamoyl-3-fluorocarbazol-4-yl}oxyacetic acid;
9-[(2,4-dichlorophenyl)methyl]-5-carbamoyl-3-fluorocarbazol-4-yl}oxyacetic acid;
9-[(2,5-dichlorophenyl)methyl]-5-carbamoyl-3-fluorocarbazol-4-yl}oxyacetic acid;
9-[(2,6-dichlorophenyl)methyl]-5-carbamoyl-3-fluorocarbazol-4-yl}oxyacetic acid;
9-[(2-fluoro-3-trifluoromethylphenyl)methyl]-5-carbamoyl-1-fluorocarbazol-4-yl}oxyacetic acid;
9-[(2-fluoro-5-trifluoromethylphenyl)methyl]-5-carbamoyl-1-fluorocarbazol-4-yl}oxyacetic acid;
9-[(2-fluoro-6-trifluoromethylphenyl)methyl]-5-carbamoyl-1-fluorocarbazol-4-yl}oxyacetic acid;
9-[(3-fluoro-5-trifluoromethylphenyl)methyl]-5-carbamoyl-1-fluorocarbazol-4-yl}oxyacetic acid;
9-[(4-fluoro-2-trifluoromethylphenyl)methyl]-5-carbamoyl-1-fluorocarbazol-4-yl}oxyacetic acid;
9-[(4-fluoro-3-trifluoromethylphenyl)methyl]-5-carbamoyl-1-fluorocarbazol-4-yl}oxyacetic acid;
9-[3-(2-fluorophenoxy)methyl]-5-carbamoyl-1-fluorocarbazol-4-yl}oxyacetic acid;
9-[3-(4-fluorophenoxy)methyl]-5-carbamoyl-1-fluorocarbazol-4-yl}oxyacetic acid;
9-[(2-fluoro-3-methylphenyl)methyl]-5-carbamoyl-1-fluorocarbazol-4-yl}oxyacetic acid;
9-[(3-chloro-2-fluorophenyl)methyl]-5-carbamoyl-1-fluorocarbazol-4-yl}oxyacetic acid;
9-[(2-chloro-6-fluorophenyl)methyl]-5-carbamoyl-1-fluorocarbazol-4-yl}oxyacetic acid;
9-[(2-bromo-5-fluorophenyl)methyl]-5-carbamoyl-1-fluorocarbazol-4-yl}oxyacetic acid;
9-[(1-bromo-2-naphthylphenyl)methyl]-5-carbamoyl-1-fluorocarbazol-4-yl}oxyacetic acid;
9-[(2-methyl-1-naphthylphenyl)methyl]-5-carbamoyl-1-fluorocarbazol-4-yl}oxyacetic acid;
9-[(6-methyl-2-naphthylphenyl)methyl]-5-carbamoyl-1-fluorocarbazol-4-yl}oxyacetic acid;
9-[(2-((phenylsulfonyl)methyl)phenyl)methyl]-5-carbamoyl-1-fluorocarbazol-4-yl}oxyacetic acid;
9-[(1-fluorenylmethyl]-5-carbamoyl-1-fluorocarbazol-4-yl}oxyacetic acid;
9-[(2-fluoro-3-trifluoromethylphenyl)methyl]]-carbamoyl-1-chlorocarbazol-4-yl}oxyacetic acid;
9-[(2-fluoro-5-trifluoromethylphenyl)methyl]-5-carbamoyl-1-chlorocarbazol-4-yl}oxyacetic acid;
9-[(2-fluoro-6-trifluoromethylphenyl)methyl]-5-carbamoyl-1-chlorocarbazol-4-yl}oxyacetic acid;
9-[(3-fluoro-5-trifluoromethylphenyl)methyl]-5-carbamoyl-1-chlorocarbazol-4-yl}oxyacetic acid;
9-[(4-fluoro-2-trifluoromethylphenyl)methyl]-5-carbamoyl-1-chlorocarbazol-4-yl}oxyacetic acid;
9-[(4-fluoro-3-trifluoromethylphenyl)methyl]-5-carbamoyl-1-chlorocarbazol-4-yl}oxyacetic acid;
9-[3-(2-fluorophenoxy)methyl]-5-carbamoyl-1-chlorocarbazol-4-yl}oxyacetic acid;
9-[3-(4-fluorophenoxy)methyl]-5-carbamoyl-1-chlorocarbazol-4-yl}oxyacetic acid;
9-[(2-fluoro-3-methylphenyl)methyl]-5-carbamoyl-1-chlorocarbazol-4-yl}oxyacetic acid;
9-[(3-chloro-2-fluorophenyl)methyl]-5-carbamoyl-1-chlorocarbazol-4-yl}oxyacetic acid;
9-[(2-chloro-6-fluorophenyl)methyl]-5-carbamoyl-1-chlorocarbazol-4-yl}oxyacetic acid;
9-[(2-bromo-5-fluorophenyl)methyl]-5-carbamoyl-1-chlorocarbazol-4-yl}oxyacetic acid;
9-[(1-bromo-2-naphthylphenyl)methyl]-5-carbamoyl-1-chlorocarbazol-4-yl}oxyacetic acid;
9-[(2-methyl-1-naphthylphenyl)methyl]-5-carbamoyl-1-chlorocarbazol-4-yl}oxyacetic acid;
9-[(6-methyl-2-naphthylphenyl)methyl]-5-carbamoyl-1-chlorocarbazol-4-yl}oxyacetic acid;
9-[(2-((phenylsulfonyl)methyl)phenyl)methyl]-5-carbamoyl-1-chlorocarbazol-4-yl}oxyacetic acid;
9-[(1-fluorenylmethyl]-5-carbamoyl-1-chlorocarbazol-4-yl}oxyacetic acid;
9-[(2-fluoro-3-trifluoromethylphenyl)methyl]-5-carbamoyl-3-fluorocarbazol-4-yl}oxyacetic acid;
9-[(2-fluoro-5-trifluoromethylphenyl)methyl]-5-carbamoyl-3-fluorocarbazol-4-yl}oxyacetic acid;
9-[(2-fluoro-6-trifluoromethylphenyl)methyl]-5-carbamoyl-3-fluorocarbazol-4-yl}oxyacetic acid;
9-[(3-fluoro-5-trifluoromethylphenyl)methyl]-5-carbamoyl-3-fluorocarbazol-4-yl}oxyacetic acid;
9-[(4-fluoro-2-trifluoromethylphenyl)methyl]-5-carbamoyl-3-fluorocarbazol-4-yl}oxyacetic acid;

9-[(4-fluoro-3-trifluoromethylphenyl)methyl]-5-carbamoyl-3-fluorocarbazol-4-yl}oxyacetic acid;
9-[3-(2-fluorophenoxy)methyl]-5-carbamoyl-3-fluorocarbazol-4-yl}oxyacetic acid;
9-[3-(4-fluorophenoxy)methyl]-5-carbamoyl-3-fluorocarbazol-4-yl}oxyacetic acid;
9-[(2-fluoro-3-methylphenyl)methyl]-5-carbamoyl-3-fluorocarbazol-4-yl}oxyacetic acid;
9-[(3-chloro-2-fluorophenyl)methyl]-5-carbamoyl-3-fluorocarbazol-4-yl}oxyacetic acid;
9-[(2-chloro-6-fluorophenyl)methyl]-5-carbamoyl-3-fluorocarbazol-4-yl}oxyacetic acid;
9-[(2-bromo-5-fluorophenyl)methyl]-5-carbamoyl-3-fluorocarbazol-4-yl}oxyacetic acid;
9-[(1-bromo-2-naphthylphenyl)methyl]-5-carbamoyl-3-fluorocarbazol-4-yl}oxyacetic acid;
9-[(2-methyl-1-naphthylphenyl)methyl]-5-carbamoyl-3-fluorocarbazol-4-yl}oxyacetic acid;
9-[(6-methyl-2-naphthylphenyl)methyl]-5-carbamoyl-3-fluorocarbazol-4-yl}oxyacetic acid;
9-[(2-((phenylsulfonyl)methyl)phenyl)methyl]-5-carbamoyl-3-fluorocarbazol-4-yl}oxyacetic acid;
9-[(1-fluorenylmethyl]-5-carbamoyl-3-fluorocarbazol-4-yl}oxyacetic acid;
9-[(2-thiophenoxymethylphenyl)-5-carbamoylcarbazol-4-yl]oxyacetic acid;
9-[(3-thiophenoxymethylphenyl)-5-carbamoylcarbazol-4-yl]oxyacetic acid;
9-[(4-thiophenoxymethylphenyl)-5-carbamoylcarbazol-4-yl]oxyacetic acid;
9-[(2-methyl-9-oxo-9H-xanthenyl)-5-carbamoylcarbazol-4-yl]oxyacetic acid;
9-[(2-methyl-9-oxo-9H-thioxanthenyl)-5-carbamoylcarbazol-4-yl]oxyacetic acid;
9-[(2-phenoxyphenyl)methyl]-5-carbamoyl-1-fluorocarbazol-4-yl}oxyacetic acid methyl ester;
9-[(3-phenoxyphenyl)methyl]-5-carbamoyl-1-fluorocarbazol-4-yl}oxyacetic acid methyl ester;
9-[(2-fluorophenyl)methyl]-5-carbamoyl-1-fluorocarbazol-4-yl}oxyacetic acid methyl ester;
9-[(3-fluorophenyl)methyl]-5-carbamoyl-1-fluorocarbazol-4-yl}oxyacetic acid methyl ester;
9-[(4-fluorophenyl)methyl]-5-carbamoyl-1-fluorocarbazol-4-yl}oxyacetic acid methyl ester;
9-[(2-chlorophenyl)methyl]-5-carbamoyl-1-fluorocarbazol-4-yl}oxyacetic acid methyl ester;
9-[(3-chlorophenyl)methyl]-5-carbamoyl-1-fluorocarbazol-4-yl}oxyacetic acid methyl ester;
9-[(2-bromophenyl)methyl]-5-carbamoyl-1-fluorocarbazol-4-yl}oxyacetic acid methyl ester;
9-[(3-bromophenyl)methyl]-5-carbamoyl-1-fluorocarbazol-4-yl}oxyacetic acid methyl ester;
9-[(2-iodophenyl)methyl]-5-carbamoyl-1-fluorocarbazol-4-yl}oxyacetic acid methyl ester;
9-[(3-iodophenyl)methyl]-5-carbamoyl-1-fluorocarbazol-4-yl}oxyacetic acid methyl ester;
9-[(2-acetamidophenyl)methyl]-5-carbamoyl-1-fluorocarbazol-4-yl}oxyacetic acid methyl ester;
9-[(3-acetamidophenyl)methyl]-5-carbamoyl-1-fluorocarbazol-4-yl}oxyacetic acid methyl ester;
9-[(2-carbamoylphenyl)methyl]-5-carbamoyl-1-fluorocarbazol-4-yl}oxyacetic acid methyl ester;
9-[(3-carbamoylphenyl)methyl]-5-carbamoyl-1-fluorocarbazol-4-yl}oxyacetic acid methyl ester;
9-[(2-methylsulfonylphenyl)methyl]-5-carbamoyl-1-fluorocarbazol-4-yl}oxyacetic acid methyl ester;
9-[(3-methylsulfonylphenyl)methyl]-5-carbamoyl-1-fluorocarbazol-4-yl}oxyacetic acid methyl ester;
9-[(2-methylphenyl)methyl]-5-carbamoyl-1-fluorocarbazol-4-yl}oxyacetic acid methyl ester;
9-[(3-methylphenyl)methyl]-5-carbamoyl-1-fluorocarbazol-4-yl}oxyacetic acid methyl ester;
9-[(2-ethylphenyl)methyl]-5-carbamoyl-1-fluorocarbazol-4-yl}oxyacetic acid methyl ester;
9-[(3-ethylphenyl)methyl]-5-carbamoyl-1-fluorocarbazol-4-yl}oxyacetic acid methyl ester;
9-[(2-trifluoromethylphenyl)methyl]-5-carbamoyl-1-fluorocarbazol-4-yl}oxyacetic acid methyl ester;
9-[(3-trifluoromethylphenyl)methyl]-5-carbamoyl-1-fluorocarbazol-4-yl}oxyacetic acid methyl ester;
9-[(2-methoxyphenyl)methyl]-5-carbamoyl-1-fluorocarbazol-4-yl}oxyacetic acid methyl ester;
9-[(cyclopropyl)methyl]-5-carbamoyl-1-fluorocarbazol-4-yl}oxyacetic acid methyl ester;
9-[(cyclobutyl)methyl]-5-carbamoyl-1-fluorocarbazol-4-yl}oxyacetic acid methyl ester;
9-[(cyclopentyl)methyl]-5-carbamoyl-1-fluorocarbazol-4-yl}oxyacetic acid methyl ester;
9-[(cyclohexyl)methyl]-5-carbamoyl-1-fluorocarbazol-4-yl}oxyacetic acid methyl ester;
9-[(3-methoxyphenyl)methyl]-5-carbamoyl-1-fluorocarbazol-4-yl}oxyacetic acid methyl ester;
9-[(2-ethoxyphenyl)methyl]-5-carbamoyl-1-fluorocarbazol-4-yl}oxyacetic acid methyl ester;
9-[(3-ethoxyphenyl)methyl]-5-carbamoyl-1-fluorocarbazol-4-yl}oxyacetic acid methyl ester;
9-[(2-trifluoromethoxyphenyl)methyl]-5-carbamoyl-1-fluorocarbazol-4-yl}oxyacetic acid methyl ester;
9-[(3-trifluoromethoxyphenyl)methyl]-5-carbamoyl-1-fluorocarbazol-4-yl}oxyacetic acid methyl ester;
9-[(2-difluoromethoxyphenyl)methyl]-5-carbamoyl-1-fluorocarbazol-4-yl}oxyacetic acid methyl ester;
9-[(3-difluoromethoxyphenyl)methyl]-5-carbamoyl-1-fluorocarbazol-4-yl}oxyacetic acid methyl ester;
9-[(2-cyanophenyl)methyl]-5-carbamoyl-1-fluorocarbazol-4-yl}oxyacetic acid methyl ester;
9-[(3-cyanophenyl)methyl]-5-carbamoyl-1-fluorocarbazol-4-yl}oxyacetic acid methyl ester;
9-[(4-cyanophenyl)methyl]-5-carbamoyl-1-fluorocarbazol-4-yl}oxyacetic acid methyl ester;
9-[(2-pyridyl)methyl]-5-carbamoyl-1-fluorocarbazol-4-yl}oxyacetic acid methyl ester;
9-[(3-pyridyl)methyl]-5-carbamoyl-1-fluorocarbazol-4-yl}oxyacetic acid methyl ester;
9-[(2-furyl)methyl]-5-carbamoyl-1-fluorocarbazol-4-yl}oxyacetic acid methyl ester;
9-[(3-furyl)methyl]-5-carbamoyl-1-fluorocarbazol-4-yl}oxyacetic acid methyl ester;
9-[(2-thienyl)methyl]-5-carbamoyl-1-fluorocarbazol-4-yl}oxyacetic acid methyl ester;
9-[(3-thienyl)methyl]-5-carbamoyl-1-fluorocarbazol-4-yl}oxyacetic acid methyl ester;
9-[(2-benzylphenyl)methyl]-5-carbamoyl-1-fluorocarbazol-4-yl}oxyacetic acid methyl ester;
9-[(3-benzylphenyl)methyl]-5-carbamoyl-1-fluorocarbazol-4-yl}oxyacetic acid methyl ester;
9-[(2-benzoylphenyl)methyl]-5-carbamoyl-1-fluorocarbazol-4-yl}oxyacetic acid methyl ester;
9-[(3-benzoylphenyl)methyl]-5-carbamoyl-1-fluorocarbazol-4-yl}oxyacetic acid methyl ester;
9-[(2-benzyloxyphenyl)methyl]-5-carbamoyl-1-fluorocarbazol-4-yl}oxyacetic acid methyl ester;
9-[(3-benzyloxyphenyl)methyl]-5-carbamoyl-1-fluorocarbazol-4-yl}oxyacetic acid methyl ester;
9-[(4-benzyloxyphenyl)methyl]-5-carbamoyl-1-fluorocarbazol-4-yl}oxyacetic acid methyl ester;

9-[(2-phenylphenyl)methyl]-5-carbamoyl-1-fluorocarbazol-4-yl}oxyacetic acid methyl ester;
9-[(3-phenylphenyl)methyl]-5-carbamoyl-1-fluorocarbazol-4-yl}oxyacetic acid methyl ester;
9-[(1-naphthyl)methyl]-5-carbamoyl-1-fluorocarbazol-4-yl}oxyacetic acid methyl ester;
9-[(2-naphthyl)methyl]-5-carbamoyl-1-fluorocarbazol-4-yl}oxyacetic acid methyl ester;
9-[(2,3-difluorophenyl)methyl]-5-carbamoyl-1-fluorocarbazol-4-yl}oxyacetic acid methyl ester;
9-[(2,4-difluorophenyl)methyl]-5-carbamoyl-1-fluorocarbazol-4-yl}oxyacetic acid methyl ester;
9-[(2,5-difluorophenyl)methyl]-5-carbamoyl-1-fluorocarbazol-4-yl}oxyacetic acid methyl ester;
9-[(2,6-difluorophenyl)methyl]-5-carbamoyl-1-fluorocarbazol-4-yl}oxyacetic acid methyl ester;
9-[(3,4-difluorophenyl)methyl]-5-carbamoyl-1-fluorocarbazol-4-yl}oxyacetic acid methyl ester;
9-[(3,5-difluorophenyl)methyl]-5-carbamoyl-1-fluorocarbazol-4-yl}oxyacetic acid methyl ester;
9-[(2,3,4-trifluorophenyl)methyl]-5-carbamoyl-1-fluorocarbazol-4-yl}oxyacetic acid methyl ester;
9-[(2,3,5-trifluorophenyl)methyl]-5-carbamoyl-1-fluorocarbazol-4-yl}oxyacetic acid methyl ester;
9-[(2,3,6-trifluorophenyl)methyl]-5-carbamoyl-1-fluorocarbazol-4-yl}oxyacetic acid methyl ester;
9-[(2,4,5-trifluorophenyl)methyl]-5-carbamoyl-1-fluorocarbazol-4-yl}oxyacetic acid methyl ester;
9-[(2,4,6-trifluorophenyl)methyl]-5-carbamoyl-1-fluorocarbazol-4-yl}oxyacetic acid methyl ester;
9-[(3,4,5-trifluorophenyl)methyl]-5-carbamoyl-1-fluorocarbazol-4-yl}oxyacetic acid methyl ester;
9-[(pentafluorophenyl)methyl]-5-carbamoyl-1-fluorocarbazol-4-yl}oxyacetic acid methyl ester;
9-[(2,3-dichlorophenyl)methyl]-5-carbamoyl-1-fluorocarbazol-4-yl}oxyacetic acid methyl ester;
9-[(2,4-dichlorophenyl)methyl]-5-carbamoyl-1-fluorocarbazol-4-yl}oxyacetic acid methyl ester;
9-[(2,5-dichlorophenyl)methyl]-5-carbamoyl-1-fluorocarbazol-4-yl}oxyacetic acid methyl ester;
9-[(2,6-dichlorophenyl)methyl]-5-carbamoyl-1-fluorocarbazol-4-yl}oxyacetic acid methyl ester;
9-[(2-phenoxyphenyl)methyl]-5-carbamoyl-1-chlorocarbazol-4-yl}oxyacetic acid methyl ester;
9-[(3-phenoxyphenyl)methyl]-5-carbamoyl-1-chlorocarbazol-4-yl}oxyacetic acid methyl ester;
9-[(2-fluorophenyl)methyl]-5-carbamoyl-1-chlorocarbazol-4-yl}oxyacetic acid methyl ester;
9-[(3-fluorophenyl)methyl]-5-carbamoyl-1-chlorocarbazol-4-yl,}oxyacetic acid methyl ester;
9-[(4-fluorophenyl)methyl]-5-carbamoyl-1-chlorocarbazol-4-yl}oxyacetic acid methyl ester;
9-[(2-chlorophenyl)methyl]-5-carbamoyl-1-chlorocarbazol-4-yl}oxyacetic acid methyl ester;
9-[(3-chlorophenyl)methyl]-5-carbamoyl-1-chlorocarbazol-4-yl}oxyacetic acid methyl ester;
9-[(2-bromophenyl)methyl]-5-carbamoyl-1-chlorocarbazol-4-yl}oxyacetic acid methyl ester;
9-[(3-bromophenyl)methyl]-5-carbamoyl-1-chlorocarbazol-4-yl}oxyacetic acid methyl ester;
9-[(2-iodophenyl)methyl]-5-carbamoyl-1-chlorocarbazol-4-yl}oxyacetic acid methyl ester;
9-[(3-iodophenyl)methyl]-5-carbamoyl-1-chlorocarbazol-4-yl}oxyacetic acid methyl ester;
9-[(2-acetamidophenyl)methyl]-5-carbamoyl-1-chlorocarbazol-4-yl}oxyacetic acid methyl ester;
9-[(3-acetamidophenyl)methyl]-5-carbamoyl-1-chlorocarbazol-4-yl}oxyacetic acid methyl ester;
9-[(2-carbamoylphenyl)methyl]-5-carbamoyl-1-chlorocarbazol-4-yl}oxyacetic acid methyl ester;
9-[(3-carbamoylphenyl)methyl]-5-carbamoyl-1-chlorocarbazol-4-yl}oxyacetic acid methyl ester;
9-[(2-methylsulfonylphenyl)methyl]-5-carbamoyl-1-chlorocarbazol-4-yl}oxyacetic acid methyl ester;
9-[(3-methylsulfonylphenyl)methyl]-5-carbamoyl-1-chlorocarbazol-4-yl}oxyacetic acid methyl ester;
9-[(2-methylphenyl)methyl]-5-carbamoyl-1-chlorocarbazol-4-yl}oxyacetic acid methyl ester;
9-[(3-methylphenyl)methyl]-5-carbamoyl-1-chlorocarbazol-4-yl}oxyacetic acid methyl ester;
9-[(2-ethylphenyl)methyl]-5-carbamoyl-1-chlorocarbazol-4-yl}oxyacetic acid methyl ester;
9-[(3-ethylphenyl)methyl]-5-carbamoyl-1-chlorocarbazol-4yl}oxyacetic acid methyl ester;
9-[(2-trifluoromethylphenyl)methyl]-5-carbamoyl-1-chlorocarbazol-4-yl}oxyacetic acid methyl ester;
9-[(3-trifluoromethylphenyl)methyl]-5-carbamoyl-1-chlorocarbazol-4-yl}oxyacetic acid methyl ester;
9-[(2-methoxyphenyl)methyl]-5-carbamoyl-1-chlorocarbazol-4-yl}oxyacetic acid methyl ester;
9-[(cyclopropyl)methyl]-5-carbamoyl-1-chlorocarbazol-4-yl}oxyacetic acid methyl ester;
9-[(cyclobutyl)methyl]-5-carbamoyl-1-chlorocarbazol-4-yl}oxyacetic acid methyl ester;
9-[(cyclopentyl)methyl]-5-carbamoyl-1-chlorocarbazol-4-yl}oxyacetic acid methyl ester;
9-[(cyclohexyl)methyl]-5-carbamoyl-1-chlorocarbazol-4-yl}oxyacetic acid methyl ester;
9-[(3-methoxyphenyl)methyl]-5-carbamoyl-1-chlorocarbazol-4-yl}oxyacetic acid methyl ester;
9-[(2-ethoxyphenyl)methyl]-5-carbamoyl-1-chlorocarbazol-4-yl}oxyacetic acid methyl ester;
9-[(3-ethoxyphenyl)methyl]-5-carbamoyl-1-chlorocarbazol-4-yl}oxyacetic acid methyl ester;
9-[(2-trifluoromethoxyphenyl)methyl]-5-carbamoyl-1-chlorocarbazol-4-yl}oxyacetic acid methyl ester;
9-[(3-trifluoromethoxyphenyl)methyl]-5-carbamoyl-1-chlorocarbazol-4-yl}oxyacetic acid methyl ester;
9-[(2-difluoromethoxyphenyl)methyl]-5-carbamoyl-1-chlorocarbazol-4-yl}oxyacetic acid methyl ester;
9-[(3-difluoromethoxyphenyl)methyl]-5-carbamoyl-1-chlorocarbazol-4-yl}oxyacetic acid methyl ester;
9-[(2-cyanophenyl)methyl]-5-carbamoyl-1-chlorocarbazol-4-yl}oxyacetic acid methyl ester;
9-[(3-cyanophenyl)methyl]-5-carbamoyl-1-chlorocarbazol-4-yl}oxyacetic acid methyl ester;
9-[(4-cyanophenyl)methyl]-5-carbamoyl-1-chlorocarbazol-4-yl}oxyacetic acid methyl ester;
9-[(2-pyridyl)methyl]-5-carbamoyl-1-chlorocarbazol-4-yl}oxyacetic acid methyl ester;
9-[(3-pyridyl)methyl]-5-carbamoyl-1-chlorocarbazol-4-yl}oxyacetic acid methyl ester;
9-[(2-furyl)methyl]-5-carbamoyl-1-chlorocarbazol-4-yl}oxyacetic acid methyl ester;
9-[(3-furyl)methyl]-5-carbamoyl-1-chlorocarbazol-4-yl}oxyacetic acid methyl ester;
9-[(2-thienyl)methyl]-5-carbamoyl-1-chlorocarbazol-4-yl}oxyacetic acid methyl ester;
9-[(3-thienyl)methyl]-5-carbamoyl-1-chlorocarbazol-4-yl}oxyacetic acid methyl ester;
9-[(2-benzylphenyl)methyl]-5-carbamoyl-1-chlorocarbazol-4-yl}oxyacetic acid methyl ester;
9-[(3-benzylphenyl)methyl]-5-carbamoyl-1-chlorocarbazol-4-yl}oxyacetic acid methyl ester;
9-[(2-benzoylphenyl)methyl]-5-carbamoyl-1-chlorocarbazol-4-yl}oxyacetic acid methyl ester;

9-[(3-benzoylphenyl)methyl]-5-carbamoyl-1-chlorocarbazol-4-yl}oxyacetic acid methyl ester;
9-[(2-benzyloxyphenyl)methyl]-5-carbamoyl-1-chlorocarbazol-4-yl}oxyacetic acid methyl ester;
9-[(3-benzyloxyphenyl)methyl]-5-carbamoyl-1-chlorocarbazol-4-yl}oxyacetic acid methyl ester;
9-[(4-benzyloxyphenyl)methyl]-5-carbamoyl-1-chlorocarbazol-4-yl}oxyacetic acid methyl ester;
9-[(2-phenylphenyl)methyl]-5-carbamoyl-1-chlorocarbazol-4-yl}oxyacetic acid methyl ester;
9-[(3-phenylphenyl)methyl]-5-carbamoyl-1-chlorocarbazol-4-yl}oxyacetic acid methyl ester;
9-[(1-naphthyl)methyl]-5-carbamoyl-1-chlorocarbazol-4-yl}oxyacetic acid methyl ester;
9-[(2-naphthyl)methyl]-5-carbamoyl-1-chlorocarbazol-4-yl}oxyacetic acid methyl ester;
9-[(2,3-difluorophenyl)methyl]-5-carbamoyl-1-chlorocarbazol-4-yl}oxyacetic acid methyl ester;
9-[(2,4-difluorophenyl)methyl]-5-carbamoyl-1-chlorocarbazol-4-yl}oxyacetic acid methyl ester;
9-[(2,5-difluorophenyl)methyl]-5-carbamoyl-1-chlorocarbazol-4-yl}oxyacetic acid methyl ester;
9-[(2,6-difluorophenyl)methyl]-5-carbamoyl-1-chlorocarbazol-4-yl}oxyacetic acid methyl ester;
9-[(3,4-difluorophenyl)methyl]-5-carbamoyl-1-chlorocarbazol-4-yl}oxyacetic acid methyl ester;
9-[(3,5-difluorophenyl)methyl]-5-carbamoyl-1-chlorocarbazol-4-yl}oxyacetic acid methyl ester;
9-[(2,3,4-trifluorophenyl)methyl]-5-carbamoyl-1-chlorocarbazol-4-yl}oxyacetic acid methyl ester;
9-[(2,3,5-trifluorophenyl)methyl]-5-carbamoyl-1-chlorocarbazol-4-yl}oxyacetic acid methyl ester;
9-[(2,3,6-trifluorophenyl)methyl]-5-carbamoyl-1-chlorocarbazol-4-yl}oxyacetic acid methyl ester;
9-[(2,4,5-trifluorophenyl)methyl]-5-carbamoyl-1-chlorocarbazol-4-yl}oxyacetic acid methyl ester;
9-[(2,4,6-trifluorophenyl)methyl]-5-carbamoyl-1-chlorocarbazol-4-yl}oxyacetic acid methyl ester;
9-[(3,4,5-trifluorophenyl)methyl]-5-carbamoyl-1-chlorocarbazol-4-yl}oxyacetic acid methyl ester;
9-[(pentafluorophenyl)methyl]-5-carbamoyl-1-chlorocarbazol-4-yl}oxyacetic acid methyl ester;
9-[(2,3-dichlorophenyl)methyl]-5-carbamoyl-1-chlorocarbazol-4-yl}oxyacetic acid methyl ester;
9-[(2,4-dichlorophenyl)methyl]-5-carbamoyl-1-chlorocarbazol-4-yl}oxyacetic acid methyl ester;
9-[(2,5-dichlorophenyl)methyl]-5-carbamoyl-1-chlorocarbazol-4-yl}oxyacetic acid methyl ester;
9-[(2,6-dichlorophenyl)methyl]-5-carbamoyl-1-chlorocarbazol-4-yl}oxyacetic acid methyl ester;
9-[(2-phenoxyphenyl)methyl]-5-carbamoyl-3-fluorocarbazol-4-yl}oxyacetic acid methyl ester;
9-[(3-phenoxyphenyl)methyl]-5-carbamoyl-3-fluorocarbazol-4-yl}oxyacetic acid methyl ester;
9-[(2-fluorophenyl)methyl]-5-carbamoyl-3-fluorocarbazol-4-yl}oxyacetic acid methyl ester;
9-[(3-fluorophenyl)methyl]-5-carbamoyl-3-fluorocarbazol-4-yl}oxyacetic acid methyl ester;
9-[(4-fluorophenyl)methyl]-5-carbamoyl-3-fluorocarbazol-4-yl}oxyacetic acid methyl ester;
9-[(2-chlorophenyl)methyl]-5-carbamoyl-3-fluorocarbazol-4-yl}oxyacetic acid methyl ester;
9-[(3-chlorophenyl)methyl]-5-carbamoyl-3-fluorocarbazol-4-yl}oxyacetic acid methyl ester;
9-[(2-bromophenyl)methyl]-5-carbamoyl-3-fluorocarbazol-4-yl}oxyacetic acid methyl ester;
9-[(3-bromophenyl)methyl]-5-carbamoyl-3-fluorocarbazol-4-yl}oxyacetic acid methyl ester;
9-[(2-iodophenyl)methyl]-5-carbamoyl-3-fluorocarbazol-4-yl}oxyacetic acid methyl ester;
9-[(3-iodophenyl)methyl]-5-carbamoyl-3-fluorocarbazol-4-yl}oxyacetic acid methyl ester;
9-[(2-acetamidophenyl)methyl]-5-carbamoyl-3-fluorocarbazol-4-yl}oxyacetic acid methyl ester;
9-[(3-acetamidophenyl)methyl]-5-carbamoyl-3-fluorocarbazol-4-yl}oxyacetic acid methyl ester;
9-[(2-carbamoylphenyl)methyl]-5-carbamoyl-3-fluorocarbazol-4-yl}oxyacetic acid methyl ester;
9-[(3-carbamoylphenyl)methyl]-5-carbamoyl-3-fluorocarbazol-4-yl}oxyacetic acid methyl ester;
9-[(2-methylsulfonylphenyl)methyl]-5-carbamoyl-3-fluorocarbazol-4-yl}oxyacetic acid methyl ester;
9-[(3-methylsulfonylphenyl)methyl]-5-carbamoyl-3-fluorocarbazol-4-yl}oxyacetic acid methyl ester;
9-[(2-methylphenyl)methyl]-5-carbamoyl-3-fluorocarbazol-4-yl}oxyacetic acid methyl ester;
9-[(3-methylphenyl)methyl]-5-carbamoyl-3-fluorocarbazol-4-yl}oxyacetic acid methyl ester;
9-[(2-ethylphenyl)methyl]-5-carbamoyl-3-fluorocarbazol-4-yl}oxyacetic acid methyl ester;
9-[(3-ethylphenyl)methyl]-5-carbamoyl-3-fluorocarbazol-4-yl}oxyacetic acid methyl ester;
9-[(2-trifluoromethylphenyl)methyl]-5-carbamoyl-3-fluorocarbazol-4-yl}oxyacetic acid methyl ester;
9-[(3-trifluoromethylphenyl)methyl]-5-carbamoyl-3-fluorocarbazol-4-yl}oxyacetic acid methyl ester;
9-[(2-methoxyphenyl)methyl]-5-carbamoyl-3-fluorocarbazol-4-yl}oxyacetic acid methyl ester;
9-[(cyclopropyl)methyl]-5-carbamoyl-3-fluorocarbazol-4-yl}oxyacetic acid methyl ester;
9-[(cyclobutyl)methyl]-5-carbamoyl-3-fluorocarbazol-4-yl}oxyacetic acid methyl ester;
9-[(cyclopentyl)methyl]-5-carbamoyl-3-fluorocarbazol-4-yl}oxyacetic acid methyl ester;
9-[(cyclohexyl)methyl]-5-carbamoyl-3-fluorocarbazol-4-yl}oxyacetic acid methyl ester;
9-[(3-methoxyphenyl)methyl]-5-carbamoyl-3-fluorocarbazol-4-yl}oxyacetic acid methyl ester;
9-[(2-ethoxyphenyl)methyl]-5-carbamoyl-3-fluorocarbazol-4-yl}oxyacetic acid methyl ester;
9-[(3-ethoxyphenyl)methyl]-5-carbamoyl-3-fluorocarbazol-4-yl}oxyacetic acid methyl ester;
9-[(2-trifluoromethoxyphenyl)methyl]-5-carbamoyl-3-fluorocarbazol-4-yl}oxyacetic acid methyl ester;
9-[(3-trifluoromethoxyphenyl)methyl]-5-carbamoyl-3-fluorocarbazol-4-yl}oxyacetic acid methyl ester;
9-[(2-difluoromethoxyphenyl)methyl]-5-carbamoyl-3-fluorocarbazol-4-yl}oxyacetic acid methyl ester;
9-[(3-difluoromethoxyphenyl)methyl]-5-carbamoyl-3-fluorocarbazol-4-yl}oxyacetic acid methyl ester;
9-[(2-cyanophenyl)methyl]-5-carbamoyl-3-fluorocarbazol-4-yl}oxyacetic acid methyl ester;
9-[(3-cyanophenyl)methyl]-5-carbamoyl-3-fluorocarbazol-4-yl}oxyacetic acid methyl ester;
9-[(4-cyanophenyl)methyl]-5-carbamoyl-3-fluorocarbazol-4-yl}oxyacetic acid methyl ester;
9-[(2-pyridyl)methyl]-5-carbamoyl-3-fluorocarbazol-4-yl}oxyacetic acid methyl ester;
9-[(3-pyridyl)methyl]-5-carbamoyl-3-fluorocarbazol-4-yl}oxyacetic acid methyl ester;
9-[(2-furyl)methyl]-5-carbamoyl-3-fluorocarbazol-4-yl}oxyacetic acid methyl ester;
9-[(3-furyl)methyl]-5-carbamoyl-3-fluorocarbazol-4-yl}oxyacetic acid methyl ester;
9-[(2-thienyl)methyl]-5-carbamoyl-3-fluorocarbazol-4-yl}oxyacetic acid methyl ester;

9-[(3-thienyl)methyl]-5-carbamoyl-3-fluorocarbazol-4-yl}oxyacetic acid methyl ester;
9-[(2-benzylphenyl)methyl]-5-carbamoyl-3-fluorocarbazol-4-yl}oxyacetic acid methyl ester;
9-[(3-benzylphenyl)methyl]-5-carbamoyl-3-fluorocarbazol-4-yl}oxyacetic acid methyl ester;
9-[(2-benzoylphenyl)methyl]-5-carbamoyl-3-fluorocarbazol-4-yl}oxyacetic acid methyl ester;
9-[(3-benzoylphenyl)methyl]-5-carbamoyl-3-fluorocarbazol-4-yl}oxyacetic acid methyl ester;
9-[(2-benzyloxyphenyl)methyl]-5-carbamoyl-3-fluorocarbazol-4-yl}oxyacetic acid methyl ester;
9-[(3-benzyloxyphenyl)methyl]-5-carbamoyl-3-fluorocarbazol-4-yl}oxyacetic acid methyl ester;
9-[(4-benzyloxyphenyl)methyl]-5-carbamoyl-3-fluorocarbazol-4-yl}oxyacetic acid methyl ester;
9-[(2-phenylphenyl)methyl]-5-carbamoyl-3-fluorocarbazol-4-yl}oxyacetic acid methyl ester;
9-[(3-phenylphenyl)methyl]-5-carbamoyl-3-fluorocarbazol-4-yl}oxyacetic acid methyl ester;
9-[(1-naphthyl)methyl]-5-carbamoyl-3-fluorocarbazol-4-yl}oxyacetic acid methyl ester;
9-[(2-naphthyl)methyl]-5-carbamoyl-3-fluorocarbazol-4-yl}oxyacetic acid methyl ester;
9-[(2,3-difluorophenyl)methyl]-5-carbamoyl-3-fluorocarbazol-4-yl}oxyacetic acid methyl ester;
9-[(2,4-difluorophenyl)methyl]-5-carbamoyl-3-fluorocarbazol-4-yl}oxyacetic acid methyl ester;
9-[(2,5-difluorophenyl)methyl]-5-carbamoyl-3-fluorocarbazol-4-yl}oxyacetic acid methyl ester;
9-[(2,6-difluorophenyl)methyl]-5-carbamoyl-3-fluorocarbazol-4-yl}oxyacetic acid methyl ester;
9-[(3,4-difluorophenyl)methyl]-5-carbamoyl-3-fluorocarbazol-4-yl}oxyacetic acid methyl ester;
9-[(3,5-difluorophenyl)methyl]-5-carbamoyl-3-fluorocarbazol-4-yl}oxyacetic acid methyl ester;
9-[(2,3,4-trifluorophenyl)methyl]-5-carbamoyl-3-fluorocarbazol-4-yl}oxyacetic acid methyl ester;
9-[(2,3,5-trifluorophenyl)methyl]-5-carbamoyl-3-fluorocarbazol-4-yl}oxyacetic acid methyl ester;
9-[(2,3,6-trifluorophenyl)methyl]-5-carbamoyl-3-fluorocarbazol-4-yl}oxyacetic acid methyl ester;
9-[(2,4,5-trifluorophenyl)methyl]-5-carbamoyl-3-fluorocarbazol-4-yl}oxyacetic acid methyl ester;
9-[(2,4,6-trifluorophenyl)methyl]-5-carbamoyl-3-fluorocarbazol-4-yl}oxyacetic acid methyl ester;
9-[(3,4,5-trifluorophenyl)methyl]-5-carbamoyl-3-fluorocarbazol-4-yl}oxyacetic acid methyl ester;
9-[(pentafluorophenyl)methyl]-5-carbamoyl-3-fluorocarbazol-4-yl}oxyacetic acid methyl ester;
9-[(2,3-dichlorophenyl)methyl]-5-carbamoyl-3-fluorocarbazol-4-yl}oxyacetic acid methyl ester;
9-[(2,4-dichlorophenyl)methyl]-5-carbamoyl-3-fluorocarbazol-4-yl}oxyacetic acid methyl ester;
9-[(2,5-dichlorophenyl)methyl]-5-carbamoyl-3-fluorocarbazol-4-yl}oxyacetic acid methyl ester;
9-[(2,6-dichlorophenyl)methyl]-5-carbamoyl-3-fluorocarbazol-4-yl}oxyacetic acid methyl ester;
9-[(2-fluoro-3-trifluoromethylphenyl)methyl]-5-carbamoyl-1-fluorocarbazol-4-yl}oxyacetic acid methyl ester;
9-[(2-fluoro-5-trifluoromethylphenyl)methyl]-5-carbamoyl-1-fluorocarbazol-4-yl}oxyacetic acid methyl ester;
9-[(2-fluoro-6-trifluoromethylphenyl)methyl]-5-carbamoyl-1-fluorocarbazol-4-yl}oxyacetic acid methyl ester;
9-[(3-fluoro-5-trifluoromethylphenyl)methyl]-5-carbamoyl-1-fluorocarbazol-4-yl}oxyacetic acid methyl ester;
9-[(4-fluoro-2-trifluorbmethylphenyl)methyl]-5-carbamoyl-1-fluorocarbazol-4-yl}oxyacetic acid methyl ester;
9-[(4-fluoro-3-trifluoromethylphenyl)methyl]-5-carbamoyl-1-fluorocarbazol-4-yl}oxyacetic acid methyl ester;
9-[3-(2-fluorophenoxy)methyl]-5-carbamoyl-1-fluorocarbazol-4-yl}oxyacetic acid methyl ester;
9-[3-(4-fluorophenoxy)methyl]-5-carbamoyl-1-fluorocarbazol-4-yl}oxyacetic acid methyl ester;
9-[(2-fluoro-3-methylphenyl)methyl]-5-carbamoyl-1-fluorocarbazol-4-yl}oxyacetic acid methyl ester;
9-[(3-chloro-2-fluorophenyl)methyl]-5-carbamoyl-1-fluorocarbazol-4-yl}oxyacetic acid methyl ester;
9-[(2-chloro-6-fluorophenyl)methyl]-5-carbamoyl-1-fluorocarbazol-4-yl}oxyacetic acid methyl ester;
9-[(2-bromo-5-fluorophenyl)methyl]-5-carbamoyl-1-fluorocarbazol-4-yl}oxyacetic acid methyl ester;
9-[(1-bromo-2-naphthylphenyl)methyl]-5-carbamoyl-1-fluorocarbazol-4-yl}oxyacetic acid methyl ester;
9-[(2-methyl-1-naphthylphenyl)methyl]-5-carbamoyl-1-fluorocarbazol-4-yl}oxyacetic acid methyl ester;
9-[(6-methyl-2-naphthylphenyl)methyl]-5-carbamoyl-1-fluorocarbazol-4-yl}oxyacetic acid methyl ester;
9-[(2-((phenylsulfonyl)methyl)phenyl)methyl]-5-carbamoyl-1-fluorocarbazol-4-yl}oxyacetic acid methyl ester;
9-[(1-fluorenylmethyl]-5-carbamoyl-1-fluorocarbazol-4-yl}oxyacetic acid methyl ester;
9-[(2-fluoro-3-trifluoromethylphenyl)methyl]-5-carbamoyl-1-chlorocarbazol-4-yl}oxyacetic acid methyl ester;
9-[(2-fluoro-5-trifluoromethylphenyl)methyl]-5-carbamoyl-1-chlorocarbazol-4-yl}oxyacetic acid methyl ester;
9-[(2-fluoro-6-trifluoromethylphenyl)methyl]-5-carbamoyl-1-chlorocarbazol-4-yl}oxyacetic acid methyl ester;
9-[(3-fluoro-5-trifluoromethylphenyl)methyl]-5-carbamoyl-1-chlorocarbazol-4-yl}oxyacetic acid methyl ester;
9-[(4-fluoro-2-trifluoromethylphenyl)methyl]-5-carbamoyl-1-chlorocarbazol-4-yl}oxyacetic acid methyl ester;
9-[(4-fluoro-3-trifluoromethylphenyl)methyl]-5-carbamoyl-1-chlorocarbazol-4-yl}oxyacetic acid methyl ester;
9-[3-(2-fluorophenoxy)methyl]-5-carbamoyl-1-chlorocarbazol-4-yl}oxyacetic acid methyl ester;
9-[3-(4-fluorophenoxy)methyl]-5-carbamoyl-1-chlorocarbazol-4-yl}oxyacetic acid methyl ester;
9-[(2-fluoro-3-methylphenyl)methyl]-5-carbamoyl-1-chlorocarbazol-4-yl}oxyacetic acid methyl ester;
9-[(3-chloro-2-fluorophenyl)methyl]-5-carbamoyl-1-chlorocarbazol-4-yl}oxyacetic acid methyl ester;
9-[(2-chloro-6-fluorophenyl)methyl]-5-carbamoyl-1-chlorocarbazol-4-yl}oxyacetic acid methyl ester;
9-[(2-bromo-5-fluorophenyl)methyl]-5-carbamoyl-1-chlorocarbazol-4-yl}oxyacetic acid methyl ester;
9-[(1-bromo-2-naphthylphenyl)methyl]-5-carbamoyl-1-chlorocarbazol-4-yl}oxyacetic acid methyl ester;
9-[(2-methyl-1-naphthylphenyl)methyl]-5-carbamoyl-1-chlorocarbazol-4-yl}oxyacetic acid methyl ester;
9-[(6-methyl-2-naphthylphenyl)methyl]-5-carbamoyl-1-chlorocarbazol-4-yl}oxyacetic acid methyl ester;
9-[(2-((phenylsulfonyl)methyl)phenyl)methyl]-5-carbamoyl-1-chlorocarbazol-4-yl}oxyacetic acid methyl ester;
9-[(1-fluorenylmethyl]-5-carbamoyl-1-chlorocarbazol-4-yl}oxyacetic acid methyl ester;
9-[(2-fluoro-3-trifluoromethylphenyl)methyl]-5-carbamoyl-3-fluorocarbazol-4-yl}oxyacetic acid methyl ester;
9-[(2-fluoro-5-trifluoromethylphenyl)methyl]-5-carbamoyl-3-fluorocarbazol-4-yl}oxyacetic acid methyl ester;
9-[(2-fluoro-6-trifluoromethylphenyl)methyl]-5-carbamoyl-3-fluorocarbazol-4-yl}oxyacetic acid methyl ester;
9-[(3-fluoro-5-trifluoromethylphenyl)methyl]-5-carbamoyl-3-fluorocarbazol-4-yl}oxyacetic acid methyl ester;

9-[(4-fluoro-2-trifluoromethylphenyl)methyl]-5-carbamoyl-3-fluorocarbazol-4-yl}oxyacetic acid methyl ester;
9-[(4-fluoro-3-trifluoromethylphenyl)methyl]-5-carbamoyl-3-fluorocarbazol-4-yl}oxyacetic acid methyl ester;
9-[3-(2-fluorophenoxy)methyl]-5-carbamoyl-3-fluorocarbazol-4-yl}oxyacetic acid methyl ester;
9-[3-(4-fluorophenoxy)methyl]-5-carbamoyl-3-fluorocarbazol-4-yl}oxyacetic acid methyl ester;
9-[(2-fluoro-3-methylphenyl)methyl]-5-carbamoyl-3-fluorocarbazol-4-yl}oxyacetic acid methyl ester;
9-[(3-chloro-2-fluorophenyl)methyl]-5-carbamoyl-3-fluorocarbazol-4-yl}oxyacetic acid methyl ester;
9-[(2-chloro-6-fluorophenyl)methyl]-5-carbamoyl-3-fluorocarbazol-4-yl}oxyacetic acid methyl ester;
9-[(2-bromo-5-fluorophenyl)methyl]-5-carbamoyl-3-fluorocarbazol-4-yl}oxyacetic acid methyl ester;
9-[(1-bromo-2-naphthylphenyl)methyl]-5-carbamoyl-3-fluorocarbazol-4-yl}oxyacetic acid methyl ester;
9-[(2-methyl-1-naphthylphenyl)methyl]-5-carbamoyl-3-fluorocarbazol-4-yl}oxyacetic acid methyl ester;
9-[(6-methyl-2-naphthylphenyl)methyl]-5-carbamoyl-3-fluorocarbazol-4-yl}oxyacetic acid methyl ester;
9-[(2-((phenylsulfonyl)methyl)phenyl)methyl]-5-carbamoyl-3-fluorocarbazol-4-yl}oxyacetic acid methyl ester;
9-[(1-fluorenylmethyl]-5-carbamoyl-3-fluorocarbazol-4-yl}oxyacetic acid methyl ester;
9-[(2-phenoxyphenyl)methyl]-5-carbamoyl-2-fluorocarbazol-4-yl}oxyacetic acid methyl ester;
9-[(3-phenoxyphenyl)methyl]-5-carbamoyl-2-fluorocarbazol-4-yl}oxyacetic acid methyl ester;
9-[(2-fluorophenyl)methyl]-5-carbamoyl-2-fluorocarbazol-4-yl}oxyacetic acid methyl ester;
9-[(3-fluorophenyl)methyl]-5-carbamoyl-2-fluorocarbazol-4-yl}oxyacetic acid methyl ester;
9-[(4-fluorophenyl)methyl]-5-carbamoyl-2-fluorocarbazol-4-yl}oxyacetic acid methyl ester;
9-[(2-chlorophenyl)methyl]-5-carbamoyl-2-fluorocarbazol-4-yl}oxyacetic acid methyl ester;
9-[(3-chlorophenyl)methyl]-5-carbamoyl-2-fluorocarbazol-4-yl}oxyacetic acid methyl ester;
9-[(2-bromophenyl)methyl]-5-carbamoyl-2-fluorocarbazol-4-yl}oxyacetic acid methyl ester;
9-[(3-bromophenyl)methyl]-5-carbamoyl-2-fluorocarbazol-4-yl}oxyacetic acid methyl ester;
9-[(2-iodophenyl)methyl]-5-carbamoyl-2-fluorocarbazol-4-yl}oxyacetic acid methyl ester;
9-[(3-iodophenyl)methyl]-5-carbamoyl-2-fluorocarbazol-4-yl}oxyacetic acid methyl ester;
9-[(2-acetamidophenyl)methyl]-5-carbamoyl-2-fluorocarbazol-4-yl}oxyacetic acid methyl ester;
9-[(3-acetamidophenyl)methyl]-5-carbamoyl-2-fluorocarbazol-4-yl}oxyacetic acid methyl ester;
9-[(2-carbamoylphenyl)methyl]-5-carbamoyl-2-fluorocarbazol-4-yl}oxyacetic acid methyl ester;
9-[(3-carbamoylphenyl)methyl]-5-carbamoyl-2-fluorocarbazol-4-yl}oxyacetic acid methyl ester;
9-[(2-methylsulfonylphenyl)methyl]-5-carbamoyl-2-fluorocarbazol-4-yl}oxyacetic acid methyl ester;
9-[(3-methylsulfonylphenyl)methyl]-5-carbamoyl-2-fluorocarbazol-4-yl}oxyacetic acid methyl ester;
9-[(2-methylphenyl)methyl]-5-carbamoyl-2-fluorocarbazol-4-yl}oxyacetic acid methyl ester;
9-[(3-methylphenyl)methyl]-5-carbamoyl-2-fluorocarbazol-4-yl}oxyacetic acid methyl ester;
9-[(2-ethylphenyl)methyl]-5-carbamoyl-2-fluorocarbazol-4-yl}oxyacetic acid methyl ester;
9-[(3-ethylphenyl)methyl]-5-carbamoyl-2-fluorocarbazol-4-yl}oxyacetic acid methyl ester;
9-[(2-trifluoromethylphenyl)methyl]-5-carbamoyl-2-fluorocarbazol-4-yl}oxyacetic acid methyl ester;
9-[(3-trifluoromethylphenyl)methyl]-5-carbamoyl-2-fluorocarbazol-4-yl}oxyacetic acid methyl ester;
9-[(2-methoxyphenyl)methyl]-5-carbamoyl-2-fluorocarbazol-4-yl}oxyacetic acid methyl ester;
9-[(cyclopropyl)methyl]-5-carbamoyl-2-fluorocarbazol-4-yl}oxyacetic acid methyl ester;
9-[(cyclobutyl)methyl]-5-carbamoyl-2-fluorocarbazol-4-yl}oxyacetic acid methyl ester;
9-[(cyclopentyl)methyl]-5-carbamoyl-2-fluorocarbazol-4-yl}oxyacetic acid methyl ester;
9-[(cyclohexyl)methyl]-5-carbamoyl-2-fluorocarbazol-4-yl}oxyacetic acid methyl ester;
9-[(3-methoxyphenyl)methyl]-5-carbamoyl-2-fluorocarbazol-4-yl}oxyacetic acid methyl ester;
9-[(2-ethoxyphenyl)methyl]-5-carbamoyl-2-fluorocarbazol-4-yl}oxyacetic acid methyl ester;
9-[(3-ethoxyphenyl)methyl]-5-carbamoyl-2-fluorocarbazol-4-yl}oxyacetic acid methyl ester;
9-[(2-trifluoromethoxyphenyl)methyl]-5-carbamoyl-2-fluorocarbazol-4-yl}oxyacetic acid methyl ester;
9-[(3-trifluoromethoxyphenyl)methyl]-5-carbamoyl-2-fluorocarbazol-4-yl}oxyacetic acid methyl ester;
9-[(2-difluoromethoxyphenyl)methyl]-5-carbamoyl-2-fluorocarbazol-4-yl}oxyacetic acid methyl ester;
9-[(3-difluoromethoxyphenyl)methyl]-5-carbamoyl-2-fluorocarbazol-4-yl}oxyacetic acid methyl ester;
9-[(2-cyanophenyl)methyl]-5-carbamoyl-2-fluorocarbazol-4-yl}oxyacetic acid methyl ester;
9-[(3-cyanophenyl)methyl]-5-carbamoyl-2-fluorocarbazol-4-yl}oxyacetic acid methyl ester;
9-[(4-cyanophenyl)methyl]-5-carbamoyl-2-fluorocarbazol-4-yl}oxyacetic acid methyl ester;
9-[(2-pyridyl)methyl]-5-carbamoyl-2-fluorocarbazol-4-yl}oxyacetic acid methyl ester;
9-[(3-pyridyl)methyl]-5-carbamoyl-2-fluorocarbazol-4-yl}oxyacetic acid methyl ester;
9-[(2-furyl)methyl]-5-carbamoyl-2-fluorocarbazol-4-yl}oxyacetic acid methyl ester;
9-[(3-furyl)methyl]-5-carbamoyl-2-fluorocarbazol-4-yl}oxyacetic acid methyl ester;
9-[(2-thienyl)methyl]-5-carbamoyl-2-fluorocarbazol-4-yl}oxyacetic acid methyl ester;
9-[(3-thienyl)methyl]-5-carbamoyl-2-fluorocarbazol-4-yl}oxyacetic acid methyl ester;
9-[(2-benzylphenyl)methyl]-5-carbamoyl-2-fluorocarbazol-4-yl}oxyacetic acid methyl ester;
9-[(3-benzylphenyl)methyl]-5-carbamoyl-2-fluorocarbazol-4-yl}oxyacetic acid methyl ester;
9-[(2-benzoylphenyl)methyl]-5-carbamoyl-2-fluorocarbazol-4-yl}oxyacetic acid methyl ester;
9-[(3-benzoylphenyl)methyl]-5-carbamoyl-2-fluorocarbazol-4-yl}oxyacetic acid methyl ester;
9-[(2-benzyloxyphenyl)methyl]-5-carbamoyl-2-fluorocarbazol-4-yl}oxyacetic acid methyl ester;
9-[(3-benzyloxyphenyl)methyl]-5-carbamoyl-2-fluorocarbazol-4-yl}oxyacetic acid methyl ester;
9-[(4-benzyloxyphenyl)methyl]-5-carbamoyl-2-fluorocarbazol-4-yl}oxyacetic acid methyl ester;
9-[(2-phenylphenyl)methyl]-5-carbamoyl-2-fluorocarbazol-4-yl}oxyacetic acid methyl ester;
9-[(3-phenylphenyl)methyl]-5-carbamoyl-2-fluorocarbazol-4-yl}oxyacetic acid methyl ester;
9-[(1-naphthyl)methyl]-5-carbamoyl-2-fluorocarbazol-4-yl}oxyacetic acid methyl ester;

9-[(2-naphthyl)methyl]-5-carbamoyl-2-fluorocarbazol-4-yl}oxyacetic acid methyl ester;
9-[(2,3-difluorophenyl)methyl]-5-carbamoyl-2-fluorocarbazol-4-yl}oxyacetic acid methyl ester;
9-[(2,4-difluorophenyl)methyl]-5-carbamoyl-2-fluorocarbazol-4-yl}oxyacetic acid methyl ester;
9-[(2,5-difluorophenyl)methyl]-5-carbamoyl-2-fluorocarbazol-4-yl}oxyacetic acid methyl ester;
9-[(2,6-difluorophenyl)methyl]-5-carbamoyl-2-fluorocarbazol-4-yl}oxyacetic acid methyl ester;
9-[(3,4-difluorophenyl)methyl]-5-carbamoyl-2-fluorocarbazol-4-yl}oxyacetic acid methyl ester;
9-[(3,5-difluorophenyl)methyl]-5-carbamoyl-2-fluorocarbazol-4-yl}oxyacetic acid methyl ester;
9-[(2,3,4-trifluorophenyl)methyl]-5-carbamoyl-2-fluorocarbazol-4-yl}oxyacetic acid methyl ester;
9-[(2,3,5-trifluorophenyl)methyl]-5-carbamoyl-2-fluorocarbazol-4-yl}oxyacetic acid methyl ester;
9-[(2,3,6-trifluorophenyl)methyl]-5-carbamoyl-2-fluorocarbazol-4-yl}oxyacetic acid methyl ester;
9-[(2,4,5-trifluorophenyl)methyl]-5-carbamoyl-2-fluorocarbazol-4-yl}oxyacetic acid methyl ester;
9-[(2,4,6-trifluorophenyl)methyl]-5-carbamoyl-2-fluorocarbazol-4-yl}oxyacetic acid methyl ester;
9-[(3,4,5-trifluorophenyl)methyl]-5-carbamoyl-2-fluorocarbazol-4-yl}oxyacetic acid methyl ester;
9-[(pentafluorophenyl)methyl]-5-carbamoyl-2-fluorocarbazol-4-yl}oxyacetic acid methyl ester;
9-[(2,3-dichlorophenyl)methyl]-5-carbamoyl-2-fluorocarbazol-4-yl}oxyacetic acid methyl ester;
9-[(2,4-dichlorophenyl)methyl]-5-carbamoyl-2-fluorocarbazol-4-yl}oxyacetic acid methyl ester;
9-[(2,5-dichlorophenyl)methyl]-5-carbamoyl-2-fluorocarbazol-4-yl}oxyacetic acid methyl ester;
9-[(2,6-dichlorophenyl)methyl]-5-carbamoyl-2-fluorocarbazol-4-yl}oxyacetic acid methyl ester;
9-[(2-phenoxyphenyl)methyl]-5-carbamoyl-2-chlorocarbazol-4-yl}oxyacetic acid methyl ester;
9-[(3-phenoxyphenyl)methyl]-5-carbamoyl-2-chlorocarbazol-4-yl}oxyacetic acid methyl ester;
9-[(2-fluorophenyl)methyl]-5-carbamoyl-2-chlorocarbazol-4-yl}oxyacetic acid methyl ester;
9-[(3-fluorophenyl)methyl]-5-carbamoyl-2-chlorocarbazol-4-yl}oxyacetic acid methyl ester;
9-[(4-fluorophenyl)methyl]-5-carbamoyl-2-chlorocarbazol-4-yl}oxyacetic acid methyl ester;
9-[(2-chlorophenyl)methyl]-5-carbamoyl-2-chlorocarbazol-4-yl}oxyacetic acid methyl ester;
9-[(3-chlorophenyl)methyl]-5-carbamoyl-2-chlorocarbazol-4-yl}oxyacetic acid methyl ester;
9-[(2-bromophenyl)methyl]-5-carbamoyl-2-chlorocarbazol-4-yl}oxyacetic acid methyl ester;
9-[(3-bromophenyl)methyl]-5-carbamoyl-2-chlorocarbazol-4-yl}oxyacetic acid methyl ester;
9-[(2-iodophenyl)methyl]-5-carbamoyl-2-chlorocarbazol-4-yl}oxyacetic acid methyl ester;
9-[(3-iodophenyl)methyl]-5-carbamoyl-2-chlorocarbazol-4-yl}oxyacetic acid methyl ester;
9-[(2-acetamidophenyl)methyl]-5-carbamoyl-2-chlorocarbazol-4-yl}oxyacetic acid methyl ester;
9-[(3-acetamidophenyl)methyl]-5-carbamoyl-2-chlorocarbazol-4-yl}oxyacetic acid methyl ester;
9-[(2-carbamoylphenyl)methyl]-5-carbamoyl-2-chlorocarbazol-4-yl}oxyacetic acid methyl ester;
9-[(3-carbamoylphenyl)methyl]-5-carbamoyl-2-chlorocarbazol-4-yl}oxyacetic acid methyl ester;
9-[(2-methylsulfonylphenyl)methyl]-5-carbamoyl-2-chlorocarbazol-4-yl}oxyacetic acid methyl ester;
9-[(3-methylsulfonylphenyl)methyl]-5-carbamoyl-2-chlorocarbazol-4-yl}oxyacetic acid methyl ester;
9-[(2-methylphenyl)methyl]-5-carbamoyl-2-chlorocarbazol-4-yl}oxyacetic acid methyl ester;
9-[(3-methylphenyl)methyl]-5-carbamoyl-2-chlorocarbazol-4-yl}oxyacetic acid methyl ester;
9-[(2-ethylphenyl)methyl]-5-carbamoyl-2-chlorocarbazol-4-yl}oxyacetic acid methyl ester;
9-[(3-ethylphenyl)methyl]-5-carbamoyl-2-chlorocarbazol-4-yl}oxyacetic acid methyl ester;
9-[(2-trifluoromethylphenyl)methyl]-5-carbamoyl-2-chlorocarbazol-4-yl}oxyacetic acid methyl ester;
9-[(3-trifluoromethylphenyl)methyl]-5-carbamoyl-2-chlorocarbazol-4-yl}oxyacetic acid methyl ester;
9-[(2-methoxyphenyl)methyl]-5-carbamoyl-2-chlorocarbazol-4-yl}oxyacetic acid methyl ester;
9-[(cyclopropyl)methyl]-5-carbamoyl-2-chlorocarbazol-4-yl}oxyacetic acid methyl ester;
9-[(cyclobutyl)methyl]-5-carbamoyl-2-chlorocarbazol-4-yl}oxyacetic acid methyl ester;
9-[(cyclopentyl)methyl]-5-carbamoyl-2-chlorocarbazol-4-yl}oxyacetic acid methyl ester;
9-[(cyclohexyl)methyl]-5-carbamoyl-2-chlorocarbazol-4-yl}oxyacetic acid methyl ester;
9-[(3-methoxyphenyl)methyl]-5-carbamoyl-2-chlorocarbazol-4-yl}oxyacetic acid methyl ester;
9-[(2-ethoxyphenyl)methyl]-5-carbamoyl-2-chlorocarbazol-4-yl}oxyacetic acid methyl ester;
9-[(3-ethoxyphenyl)methyl]-5-carbamoyl-2-chlorocarbazol-4-yl}oxyacetic acid methyl ester;
9-[(2-trifluoromethoxyphenyl)methyl]-5-carbamoyl-2-chlorocarbazol-4-yl}oxyacetic acid methyl ester;
9-[(3-trifluoromethoxyphenyl)methyl]-5-carbamoyl-2-chlorocarbazol-4-yl}oxyacetic acid methyl ester;
9-[(2-difluoromethoxyphenyl)methyl]-5-carbamoyl-2-chlorocarbazol-4-yl}oxyacetic acid methyl ester;
9-[(3-difluoromethoxyphenyl)methyl]-5-carbamoyl-2-chlorocarbazol-4-yl}oxyacetic acid methyl ester;
9-[(2-cyanophenyl)methyl]-5-carbamoyl-2-chlorocarbazol-4-yl}oxyacetic acid methyl ester;
9-[(3-cyanophenyl)methyl]-5-carbamoyl-2-chlorocarbazol-4-yl}oxyacetic acid methyl ester;
9-[(4-cyanophenyl)methyl]-5-carbamoyl-2-chlorocarbazol-4-yl}oxyacetic acid methyl ester;
9-[(2-pyridyl)methyl]-5-carbamoyl-2-chlorocarbazol-4-yl}oxyacetic acid methyl ester;
9-[(3-pyridyl)methyl]-5-carbamoyl-2-chlorocarbazol-4-yl}oxyacetic acid methyl ester;
9-[(2-furyl)methyl]-5-carbamoyl-2-chlorocarbazol-4-yl}oxyacetic acid methyl ester;
9-[(3-furyl)methyl]-5-carbamoyl-2-chlorocarbazol-4-yl}oxyacetic acid methyl ester;
9-[(2-thienyl)methyl]-5-carbamoyl-2-chlorocarbazol-4-yl}oxyacetic acid methyl ester;
9-[(3-thienyl)methyl]-5-carbamoyl-2-chlorocarbazol-4-yl}oxyacetic acid methyl ester;
9-[(2-benzylphenyl)methyl]-5-carbamoyl-2-chlorocarbazol-4-yl}oxyacetic acid methyl ester;
9-[(3-benzylphenyl)methyl]-5-carbamoyl-2-chlorocarbazol-4-yl}oxyacetic acid methyl ester;
9-[(2-benzoylphenyl)methyl]-5-carbamoyl-2-chlorocarbazol-4-yl}oxyacetic acid methyl ester;
9-[(3-benzoylphenyl)methyl]-5-carbamoyl-2-chlorocarbazol-4-yl}oxyacetic acid methyl ester;
9-[(2-benzyloxyphenyl)methyl]-5-carbamoyl-2-chlorocarbazol-4-yl}oxyacetic acid methyl ester;
9-[(3-benzyloxyphenyl)methyl]-5-carbamoyl-2-chlorocarbazol-4-yl}oxyacetic acid methyl ester;

9-[(4-benzyloxyphenyl)methyl]-5-carbamoyl-2-chlorocarbazol-4-yl}oxyacetic acid methyl ester;
9-[(2-phenylphenyl)methyl]-5-carbamoyl-2-chlorocarbazol-4-yl}oxyacetic acid methyl ester;
9-[(3-phenylphenyl)methyl]-5-carbamoyl-2-chlorocarbazol-4-yl}oxyacetic acid methyl ester;
9-[(1-naphthyl)methyl]-5-carbamoyl-2-chlorocarbazol-4-yl}oxyacetic acid methyl ester;
9-[(2-naphthyl)methyl]-5-carbamoyl-2-chlorocarbazol-4-yl}oxyacetic acid methyl ester;
9-[(2,3-difluorophenyl)methyl]-5-carbamoyl-2-chlorocarbazol-4-yl}oxyacetic acid methyl ester;
9-[(2,4-difluorophenyl)methyl]-5-carbamoyl-2-chlorocarbazol-4-yl}oxyacetic acid methyl ester;
9-[(2,5-difluorophenyl)methyl]-5-carbamoyl-2-chlorocarbazol-4-yl}oxyacetic acid methyl ester;
9-[(2,6-difluorophenyl)methyl]-5-carbamoyl-2-chlorocarbazol-4-yl}oxyacetic acid methyl ester;
9-[(3,4-difluorophenyl)methyl]-5-carbamoyl-2-chlorocarbazol-4-yl}oxyacetic acid methyl ester;
9-[(3,5-difluorophenyl)methyl]-5-carbamoyl-2-chlorocarbazol-4-yl}oxyacetic acid methyl ester;
9-[(2,3,4-trifluorophenyl)methyl]-5-carbamoyl-2-chlorocarbazol-4-yl}oxyacetic acid methyl ester;
9-[(2,3,5-trifluorophenyl)methyl]-5-carbamoyl-2-chlorocarbazol-4-yl}oxyacetic acid methyl ester;
9-[(2,3,6-trifluorophenyl)methyl]-5-carbamoyl-2-chlorocarbazol-4-yl}oxyacetic acid methyl ester;
9-[(2,4,5-trifluorophenyl)methyl]-5-carbamoyl-2-chlorocarbazol-4-yl}oxyacetic acid methyl ester;
9-[(2,4,6-trifluorophenyl)methyl]-5-carbamoyl-2-chlorocarbazol-4-yl}oxyacetic acid methyl ester;
9-[(3,4,5-trifluorophenyl)methyl]-5-carbamoyl-2-chlorocarbazol-4-yl}oxyacetic acid methyl ester;
9-[(pentafluorophenyl)methyl]-5-carbamoyl-2-chlorocarbazol-4-yl}oxyacetic acid methyl ester;
9-[(2,3-dichlorophenyl)methyl]-5-carbamoyl-2-chlorocarbazol-4-yl}oxyacetic acid methyl ester;
9-[(2,4-dichlorophenyl)methyl]-5-carbamoyl-2-chlorocarbazol-4-yl}oxyacetic acid methyl ester;
9-[(2,5-dichlorophenyl)methyl]-5-carbamoyl-2-chlorocarbazol-4-yl}oxyacetic acid methyl ester;
9-[(2,6-dichlorophenyl)methyl]-5-carbamoyl-2-chlorocarbazol-4-yl}oxyacetic acid methyl ester;
9-[(2-fluoro-3-trifluoromethylphenyl)methyl]-5-carbamoyl-2-fluorocarbazol-4-yl}oxyacetic acid methyl ester;
9-[(2-fluoro-5-trifluoromethylphenyl)methyl]-5-carbamoyl-2-fluorocarbazol-4-yl}oxyacetic acid methyl ester;
9-[(2-fluoro-6-trifluoromethylphenyl)methyl]-5-carbamoyl-2-fluorocarbazol-4-yl}oxyacetic acid methyl ester;
9-[(3-fluoro-5-trifluoromethylphenyl)methyl]-5-carbamoyl-2-fluorocarbazol-4-yl}oxyacetic acid methyl ester;
9-[(4-fluoro-2-trifluoromethylphenyl)methyl]-5-carbamoyl-2-fluorocarbazol-4-yl}oxyacetic acid methyl ester;
9-[(4-fluoro-3-trifluoromethylphenyl)methyl]-5-carbamoyl-2-fluorocarbazol-4-yl}oxyacetic acid methyl ester;
9-[3-(2-fluorophenoxy)methyl]-5-carbamoyl-2-fluorocarbazol-4-yl}oxyacetic acid methyl ester;
9-[3-(4-fluorophenoxy)methyl]-5-carbamoyl-2-fluorocarbazol-4-yl}oxyacetic acid methyl ester;
9-[(2-fluoro-3-methylphenyl)methyl]-5-carbamoyl-2-fluorocarbazol-4-yl}oxyacetic acid methyl ester;
9-[(3-chloro-2-fluorophenyl)methyl]-5-carbamoyl-2-fluorocarbazol-4-yl}oxyacetic acid methyl ester;
9-[(2-chloro-6-fluorophenyl)methyl]-5-carbamoyl-2-fluorocarbazol-4-yl}oxyacetic acid methyl ester;
9-[(2-bromo-5-fluorophenyl)methyl]-5-carbamoyl-2-fluorocarbazol-4-yl}oxyacetic acid methyl ester;
9-[(1-bromo-2-naphthylphenyl)methyl]-5-carbamoyl-2-fluorocarbazol-4-yl}oxyacetic acid methyl ester;
9-[(2-methyl-1-naphthylphenyl)methyl]-5-carbamoyl-2-fluorocarbazol-4-yl}oxyacetic acid methyl ester;
9-[(6-methyl-2-naphthylphenyl)methyl]-5-carbamoyl-2-fluorocarbazol-4-yl}oxyacetic acid methyl ester;
9-[(2-((phenylsulfonyl)methyl)phenyl)methyl]-5-carbamoyl-2-fluorocarbazol-4-yl}oxyacetic acid methyl ester;
9-[(1-fluorenylmethyl]-5-carbamoyl-2-fluorocarbazol-4-yl}oxyacetic acid methyl ester;
9-[(2-fluoro-3-trifluoromethylphenyl)methyl]-5-carbamoyl-2-chlorocarbazol-4-yl}oxyacetic acid methyl ester;
9-[(2-fluoro-5-trifluoromethylphenyl)methyl]-5-carbamoyl-2-chlorocarbazol-4-yl}oxyacetic acid methyl ester;
9-[(2-fluoro-6-trifluoromethylphenyl)methyl]-5-carbamoyl-2-chlorocarbazol-4-yl}oxyacetic acid methyl ester;
9-[(3-fluoro-5-trifluoromethylphenyl)methyl]-5-carbamoyl-2-chlorocarbazol-4-yl}oxyacetic acid methyl ester;
9-[(4-fluoro-2-trifluoromethylphenyl)methyl]-5-carbamoyl-2-chlorocarbazol-4-yl}oxyacetic acid methyl ester;
9-[(4-fluoro-3-trifluoromethylphenyl)methyl]-5-carbamoyl-2-chlorocarbazol-4-yl}oxyacetic acid methyl ester;
9-[3-(2-fluorophenoxy)methyl]-5-carbamoyl-2-chlorocarbazol-4-yl}oxyacetic acid methyl ester;
9-[3-(4-fluorophenoxy)methyl]-5-carbamoyl-2-chlorocarbazol-4-yl}oxyacetic acid methyl ester;
9-[(2-fluoro-3-methylphenyl)methyl]-5-carbamoyl-2-chlorocarbazol-4-yl}oxyacetic acid methyl ester;
9-[(3-chloro-2-fluorophenyl)methyl]-5-carbamoyl-2-chlorocarbazol-4-yl}oxyacetic acid methyl ester;
9-[(2-chloro-6-fluorophenyl)methyl]-5-carbamoyl-2-chlorocarbazol-4-yl}oxyacetic acid methyl ester;
9-[(2-bromo-5-fluorophenyl)methyl]-5-carbamoyl-2-chlorocarbazol-4-yl}oxyacetic acid methyl ester;
9-[(1-bromo-2-naphthylphenyl)methyl]-5-carbamoyl-2-chlorocarbazol-4-yl}oxyacetic acid methyl ester;
9-[(2-methyl-1-naphthylphenyl)methyl]-5-carbamoyl-2-chlorocarbazol-4-yl}oxyacetic acid methyl ester;
9-[(6-methyl-2-naphthylphenyl)methyl]-5-carbamoyl-2-chlorocarbazol-4-yl}oxyacetic acid methyl ester;
9-[(2-((phenylsulfonyl)methyl)phenyl)methyl]-5-carbamoyl-2-chlorocarbazol-4-yl}oxyacetic acid methyl ester;
9-[(1-fluorenylmethyl]-5-carbamoyl-2-chlorocarbazol-4-yl}oxyacetic acid methyl ester;
9-benzyl-4-phenylsulfonamidoylmethyloxy-carbazole-5-carboxamide;
9-benzyl-4-phenylmethylsulfonamidoylmethyloxy-carbazole-5-carboxamide;
9-benzyl-4-(2-methylphenylsulfonamidoylmethyloxy)-carbazole-5-carboxamide;
9-benzyl-4-(naphth-2-ylsulfonamidoylmethyloxy)-carbazole-5-carboxamide;
9-benzyl-4-trifluoromethylsulfonamidoylmethyloxy-carbazole-5-carboxamide;

Further typical examples of intermediates of formula I which are useful in the present invention include:

3-(3-Carbomethoxy-2-chloroanilino)cyclohex-2-en-1-one;
3-(3-Carbomethoxy-2-bromoanilino)cyclohex-2-en-1-one;
3-(3-Carbomethoxy-2-iodoanilino)cyclohex-2-en-1-one;
3-(3-Carbomethoxy-2-chloroanilino)-4-methyl-cyclohex-2-en-1-one;
3-(3-Carbomethoxy-2-bromoanilino)-4-methyl-cyclohex-2-en-1-one;

3-(3-Carbomethoxy-2-iodoanilino)-4-methyl-cyclohex-2-en-1-one;
3-(3-Carbomethoxy-2-chloroanilino)-4-phenyl-cyclohex-2-en-1-one;
3-(3-Carbomethoxy-2-bromoanilino)-4-phenyl-cyclohex-2-en-1-one;
3-(3-Carbomethoxy-2-iodoanilino)-4-phenyl-cyclohex-2-en-1-one;
3-(3-Carbomethoxy-2-chloroanilino)-4-ethyl-cyclohex-2-en-1-one;
3-(3-Carbomethoxy-2-bromoanilino)-4-ethyl-cyclohex-2-en-1-one;
3-(3-Carbomethoxy-2-iodoanilino)-4-ethyl-cyclohex-2-en-1-one;
3-(3-Carbomethoxy-2-chloroanilino)-4-isopropyl-cyclohex-2-en-1-one;
3-(3-Carbomethoxy-2-bromoanilino)-4-isopropyl-cyclohex-2-en-1-one;
3-(3-Carbomethoxy-2-iodoanilino)-4-isopropyl-cyclohex-2-en-1-one;
3-(3-Carbomethoxy-2-chloroanilino)-4-pentyl-cyclohex-2-en-1-one;
3-(3-Carbomethoxy-2-bromoanilino)-4-pentyl-cyclohex-2-en-1-one;
3-(3-Carbomethoxy-2-iodoanilino)-4-pentyl-cyclohex-2-en-1-one;
3-(3-Carbomethoxy-2-chloroanilino)-4-(4'-chlorophenyl)cyclohex-2-en-1-one;
3-(3-Carbomethoxy-2-bromoanilino)-4-(4'-chlorophenyl)cyclohex-2-en-1-one;
3-(3-Carbomethoxy-2-iodoanilino)-4-(4'-chlorophenyl)cyclohex-2-en-1-one;
5-carbomethoxy-1,2-dihydro-9H-carbazol-4(3H)-one;
5-carbomethoxy-2-methyl-1,2-dihydro-9H-carbazol-4(3H)-one;
5-carbomethoxy-2-ethyl-1,2-dihydro-9H-carbazol-4(3H)-one;
5-carbomethoxy-2-pentyl-1,2-dihydro-9H-carbazol-4(3H)-one;
5-carbomethoxy-2-isopropyl-1,2-dihydro-9H-carbazol-4(3H)-one;
5-carbomethoxy-2-phenyl-1,2-dihydro-9H-carbazol-4(3H)-one;
5-carbomethoxy-2-(4'-chlorophenyl)-1,2-dihydro-9H-carbazol-4(3H)-one;
9-[(phenyl)methyl]-5-carbomethoxy-1,2-dihydrocarbazol-4(3H)-one;
9-[(2-phenoxyphenyl)methyl]-5-carbomethoxy-1,2-dihydrocarbazol-4(3H)-one;
9-[(3-phenoxyphenyl)methyl]-5-carbomethoxy-1,2-dihydrocarbazol-4(3H)-one;
9-[(2-fluorophenyl)methyl]-5-carbomethoxy-1,2-dihydrocarbazol-4(3H)-one;
9-[(3-fluorophenyl)methyl]-5-carbomethoxy-1,2-dihydrocarbazol-4(3H)-one;
9-[(2-chlorophenyl)methyl]-5-carbomethoxy-1,2-dihydrocarbazol-4(3H)-one;
9-[(3-chlorophenyl)methyl]-5-carbomethoxy-1,2-dihydrocarbazol-4(3H)-one;
9-[(2-bromophenyl)methyl]-5-carbomethoxy-1,2-dihydrocarbazol-4(3H)-one;
9-[(3-bromophenyl)methyl]-5-carbomethoxy-1,2-dihydrocarbazol-4(3H)-one;
9-[(2-methylphenyl)methyl]-5-carbomethoxy-1,2-dihydrocarbazol-4(3H)-one;
9-[(3-methylphenyl)methyl]-5-carbomethoxy-1,2-dihydrocarbazol-4(3H)-one;
9-[(2-cyanophenyl)methyl]-5-carbomethoxy-1,2-dihydrocarbazol-4(3H)-one;
9-[(3-cyanophenyl)methyl]-5-carbomethoxy-1,2-dihydrocarbazol-4(3H)-one;
9-[(2-trifluoromethylphenyl)methyl]-5-carbomethoxy-1,2-dihydrocarbazol-4(3H)-one;
9-[(3-trifluoromethylphenyl)methyl]-5-carbomethoxy-1,2-dihydrocarbazol-4(3H)-one;
9-[(2-benzylphenyl)methyl]-5-carbomethoxy-1,2-dihydrocarbazol-4(3H)-one;
9-[(3-benzylphenyl)methyl]-5-carbomethoxy-1,2-dihydrocarbazol-4(3H)-one;
9-[(2-phenylphenyl)methyl]-5-carbomethoxy-1,2-dihydrocarbazol-4(3H)-one;
9-[(3-phenylphenyl)methyl]-5-carbomethoxy-1,2-dihydrocarbazol-4(3H)-one;
9-[(2-naphthyl)methyl]-5-carbomethoxy-1,2-dihydrocarbazol-4(3H)-one;
9-[(1-naphthyl)methyl]-5-carbomethoxy-1,2-dihydrocarbazol-4(3H)-one;
9-[(phenyl)methyl]-2-methyl-5-carbomethoxy-1,2-dihydrocarbazol-4(3H)-one;
9-[(2-phenoxyphenyl)methyl]-2-methyl-5-carbomethoxy-1,2-dihydrocarbazol-4(3H)-one;
9-[(3-phenoxyphenyl)methyl]-2-methyl-5-carbomethoxy-1,2-dihydrocarbazol-4(3H)-one;
9-[(2-fluorophenyl)methyl]-2-methyl-5-carbomethoxy-1,2-dihydrocarbazol-4(3H)-one;
9-[(3-fluorophenyl)methyl]-2-methyl-5-carbomethoxy-1,2-dihydrocarbazol-4(3H)-one;
9-[(2-chlorophenyl)methyl]-2-methyl-5-carbomethoxy-1,2-dihydrocarbazol-4(3H)-one;
9-[(3-chlorophenyl)methyl]-2-methyl-5-carbomethoxy-1,2-dihydrocarbazol-4(3H)-one;
9-[(2-bromophenyl)methyl]-2-methyl-5-carbomethoxy-1,2-dihydrocarbazol-4(3H)-one;
9-[(3-bromophenyl)methyl]-2-methyl-5-carbomethoxy-1,2-dihydrocarbazol-4(3H)-one;
9-[(2-methylphenyl)methyl]-2-methyl-5-carbomethoxy-1,2-dihydrocarbazol-4(3H)-one;
9-[(3-methylphenyl)methyl]-2-methyl-5-carbomethoxy-1,2-dihydrocarbazol-4(3H)-one;
9-[(2-cyanophenyl)methyl]-2-methyl-5-carbomethoxy-1,2-dihydrocarbazol-4(3H)-one;
9-[(3-cyanophenyl)methyl]-2-methyl-5-carbomethoxy-1,2-dihydrocarbazol-4(3H)-one;
9-[(2-trifluoromethylphenyl)methyl]-2-methyl-5-carbomethoxy-1,2-dihydrocarbazol-4(3H)-one;
9-[(3-trifluoromethylphenyl)methyl]-2-methyl-5-carbomethoxy-1,2-dihydrocarbazol-4(3H)-one;
9-[(2-benzylphenyl)methyl]-2-methyl-5-carbomethoxy-1,2-dihydrocarbazol-4(3H)-one;
9-[(3-benzylphenyl)methyl]-2-methyl-5-carbomethoxy-1,2-dihydrocarbazol-4(3H)-one;
9-[(2-phenylphenyl)methyl]-2-methyl-5-carbomethoxy-1,2-dihydrocarbazol-4(3H)-one;
9-[(3-phenylphenyl)methyl]-2-methyl-5-carbomethoxy-1,2-dihydrocarbazol-4(3H)-one;
9-[(2-naphthyl)methyl]-2-methyl-5-carbomethoxy-1,2-dihydrocarbazol-4(3H)-one;
9-[(1-naphthyl)methyl]-2-methyl-5-carbomethoxy-1,2-dihydrocarbazol-4(3H)-one;
9-[(phenyl)methyl]-2-ethyl-5-carbomethoxy-1,2-dihydrocarbazol-4(3H)-one;
9-[(2-phenoxyphenyl)methyl]-2-ethyl-5-carbomethoxy-1,2-dihydrocarbazol-4(3H)-one;
9-[(3-phenoxyphenyl)methyl]-2-ethyl-5-carbomethoxy-1,2-dihydrocarbazol-4(3H)-one;

9-[(2-fluorophenyl)methyl]-2-ethyl-5-carbomethoxy-1,2-dihydrocarbazol-4(3H)-one;
9-[(3-fluorophenyl)methyl]-2-ethyl-5-carbomethoxy-1,2-dihydrocarbazol-4(3H)-one;
9-[(2-chlorophenyl)methyl]-2-ethyl-5-carbomethoxy-1,2-dihydrocarbazol-4(3H)-one;
9-[(3-chlorophenyl)methyl]-2-ethyl-5-carbomethoxy-1,2-dihydrocarbazol-4(3H)-one;
9-[(2-bromophenyl)methyl]-2-ethyl-5-carbomethoxy-1,2-dihydrocarbazol-4(3H)-one;
9-[(3-bromophenyl)methyl]-2-ethyl-5-carbomethoxy-1,2-dihydrocarbazol-4(3H)-one;
9-[(2-methylphenyl)methyl]-2-ethyl-5-carbomethoxy-1,2-dihydrocarbazol-4(3H)-one;
9-[(3-methylphenyl)methyl]-2-ethyl-5-carbomethoxy-1,2-dihydrocarbazol-4(3H)-one;
9-[(2-cyanophenyl)methyl]-2-ethyl-5-carbomethoxy-1,2-dihydrocarbazol-4(3H)-one;
9-[(3-cyanophenyl)methyl]-2-ethyl-5-carbomethoxy-1,2-dihydrocarbazol-4(3H)-one;
9-[(2-trifluoromethylphenyl)methyl]-2-ethyl-5-carbomethoxy-1,2-dihydrocarbazol-4(3H)-one;
9-[(3-trifluoromethylphenyl)methyl]-2-ethyl-5-carbomethoxy-1,2-dihydrocarbazol-4(3H)-one;
9-[(2-benzylphenyl)methyl]-2-ethyl-5-carbomethoxy-1,2-dihydrocarbazol-4(3H)-one;
9-[(3-benzylphenyl)methyl]-2-ethyl-5-carbomethoxy-1,2-dihydrocarbazol-4(3H)-one;
9-[(2-phenylphenyl)methyl]-2-ethyl-5-carbomethoxy-1,2-dihydrocarbazol-4(3H)-one;
9-[(3-phenylphenyl)methyl]-2-ethyl-5-carbomethoxy-1,2-dihydrocarbazol-4(3H)-one;
9-[(2-naphthyl)methyl]-2-ethyl-5-carbomethoxy-1,2-dihydrocarbazol-4(3H)-one;
9-[(1-naphthyl)methyl]-2-ethyl-5-carbomethoxy-1,2-dihydrocarbazol-4(3H)-one;
9-[(phenyl)methyl]-2-isopropyl-5-carbomethoxy-1,2-dihydrocarbazol-4(3H)-one;
9-[(2-phenoxyphenyl)methyl]-2-isopropyl-5-carbomethoxy-1,2-dihydrocarbazol-4(3H)-one;
9-[(3-phenoxyphenyl)methyl]-2-isopropyl-5-carbomethoxy-1,2-dihydrocarbazol-4(3H)-one;
9-[(2-fluorophenyl)methyl]-2-isopropyl-5-carbomethoxy-1,2-dihydrocarbazol-4(3H)-one;
9-[(3-fluorophenyl)methyl]-2-isopropyl-5-carbomethoxy-1,2-dihydrocarbazol-4(3H)-one;
9-[(2-chlorophenyl)methyl]-2-isopropyl-5-carbomethoxy-1,2-dihydrocarbazol-4(3H)-one;
9-[(3-chlorophenyl)methyl]-2-isopropyl-5-carbomethoxy-1,2-dihydrocarbazol-4(3H)-one;
9-[(2-bromophenyl)methyl]-2-isopropyl-5-carbomethoxy-1,2-dihydrocarbazol-4(3H)-one;
9-[(3-bromophenyl)methyl]-2-isopropyl-5-carbomethoxy-1,2-dihydrocarbazol-4(3H)-one;
9-[(2-methylphenyl)methyl]-2-isopropyl-5-carbomethoxy-1,2-dihydrocarbazol-4(3H)-one;
9-[(3-methylphenyl)methyl]-2-isopropyl-5-carbomethoxy-1,2-dihydrocarbazol-4(3H)-one;
9-[(2-cyanophenyl)methyl]-2-isopropyl-5-carbomethoxy-1,2-dihydrocarbazol-4(3H)-one;
9-[(3-cyanophenyl)methyl]-2-isopropyl-5-carbomethoxy-1,2-dihydrocarbazol-4(3H)-one;
9-[(2-trifluoromethylphenyl)methyl]-2-isopropyl-5-carbomethoxy-1,2-dihydrocarbazol-4(3H)-one;
9-[(3-trifluoromethylphenyl)methyl]-2-isopropyl-5-carbomethoxy-1,2-dihydrocarbazol-4(3H)-one;
9-[(2-benzylphenyl)methyl]-2-isopropyl-5-carbomethoxy-1,2-dihydrocarbazol-4(3H)-one;
9-[(3-benzylphenyl)methyl]-2-isopropyl-5-carbomethoxy-1,2-dihydrocarbazol-4(3H)-one;
9-[(2-phenylphenyl)methyl]-2-isopropyl-5-carbomethoxy-1,2-dihydrocarbazol-4(3H)-one;
9-[(3-phenylphenyl)methyl]-2-isopropyl-5-carbomethoxy-1,2-dihydrocarbazol-4(3H)-one;
9-[(2-naphthyl)methyl]-2-isopropyl-5-carbomethoxy-1,2-dihydrocarbazol-4(3H)-one;
9-[(1-naphthyl)methyl]-2-isopropyl-5-carbomethoxy-1,2-dihydrocarbazol-4(3H)-one;
9-[(phenyl)methyl]-2-pentyl-5-carbomethoxy-1,2-dihydrocarbazol-4(3H)-one;
9-[(2-phenoxyphenyl)methyl]-2-pentyl-5-carbomethoxy-1,2-dihydrocarbazol-4(3H)-one;
9-[(3-phenoxyphenyl)methyl]-2-pentyl-5-carbomethoxy-1,2-dihydrocarbazol-4(3H)-one;
9-[(2-fluorophenyl)methyl]-2-pentyl-5-carbomethoxy-1,2-dihydrocarbazol-4(3H)-one;
9-[(3-fluorophenyl)methyl]-2-pentyl-5-carbomethoxy-1,2-dihydrocarbazol-4(3H)-one;
9-[(2-chlorophenyl)methyl]-2-pentyl-5-carbomethoxy-1,2-dihydrocarbazol-4(3H)-one;
9-[(3-chlorophenyl)methyl]-2-pentyl-5-carbomethoxy-1,2-dihydrocarbazol-4(3H)-one;
9-[(2-bromophenyl)methyl]-2-pentyl-5-carbomethoxy-1,2-dihydrocarbazol-4(3H)-one;
9-[(3-bromophenyl)methyl]-2-pentyl-5-carbomethoxy-1,2-dihydrocarbazol-4(3H)-one;
9-[(2-methylphenyl)methyl]-2-pentyl-5-carbomethoxy-1,2-dihydrocarbazol-4(3H)-one;
9-[(3-methylphenyl)methyl]-2-pentyl-5-carbomethoxy-1,2-dihydrocarbazol-4(3H)-one;
9-[(2-cyanophenyl)methyl]-2-pentyl-5-carbomethoxy-1,2-dihydrocarbazol-4(3H)-one;
9-[(3-cyanophenyl)methyl]-2-pentyl-5-carbomethoxy-1,2-dihydrocarbazol-4(3H)-one;
9-[(2-trifluoromethylphenyl)methyl]-2-pentyl-5-carbomethoxy-1,2-dihydrocarbazol-4(3H)-one;
9-[(3-trifluoromethylphenyl)methyl]-2-pentyl-5-carbomethoxy-1,2-dihydrocarbazol-4(3H)-one;
9-[(2-benzylphenyl)methyl]-2-pentyl-5-carbomethoxy-1,2-dihydrocarbazol-4(3H)-one;
9-[(3-benzylphenyl)methyl]-2-pentyl-5-carbomethoxy-1,2-dihydrocarbazol-4(3H)-one;
9-[(2-phenylphenyl)methyl]-2-pentyl-5-carbomethoxy-1,2-dihydrocarbazol-4(3H)-one;
9-[(3-phenylphenyl)methyl]-2-pentyl-5-carbomethoxy-1,2-dihydrocarbazol-4(3H)-one;
9-[(2-naphthyl)methyl]-2-pentyl-5-carbomethoxy-1,2-dihydrocarbazol-4(3H)-one;
9-[(1-naphthyl)methyl]-2-pentyl-5-carbomethoxy-1,2-dihydrocarbazol-4(3H)-one;
9-[(phenyl)methyl]-2-phenyl-5-carbomethoxy-1,2-dihydrocarbazol-4(3H)-one;
9-[(2-phenoxyphenyl)methyl]-2-phenyl-5-carbomethoxy-1,2-dihydrocarbazol-4(3H)-one;
9-[(3-phenoxyphenyl)methyl]-2-phenyl-5-carbomethoxy-1,2-dihydrocarbazol-4(3H)-one;
9-[(2-fluorophenyl)methyl]-2-phenyl-5-carbomethoxy-1,2-dihydrocarbazol-4(3H)-one;
9-[(3-fluorophenyl)methyl]-2-phenyl-5-carbomethoxy-1,2-dihydrocarbazol-4(3H)-one;
9-[(2-chlorophenyl)methyl]-2-phenyl-5-carbomethoxy-1,2-dihydrocarbazol-4(3H)-one;
9-[(3-chlorophenyl)methyl]-2-phenyl-5-carbomethoxy-1,2-dihydrocarbazol-4(3H)-one;
9-[(2-bromophenyl)methyl]-2-phenyl-5-carbomethoxy-1,2-dihydrocarbazol-4(3H)-one;

9-[(3-bromophenyl)methyl]-2-phenyl-5-carbomethoxy-1,2-dihydrocarbazol-4(3H)-one;
9-[(2-methylphenyl)methyl]-2-phenyl-5-carbomethoxy-1,2-dihydrocarbazol-4(3H)-one;
9-[(3-methylphenyl)methyl]-2-phenyl-5-carbomethoxy-1,2-dihydrocarbazol-4(3H)-one;
9-[(2-cyanophenyl)methyl]-2-phenyl-5-carbomethoxy-1,2-dihydrocarbazol-4(3H)-one;
9-[(3-cyanophenyl)methyl]-2-phenyl-5-carbomethoxy-1,2-dihydrocarbazol-4(3H)-one;
9-[(2-trifluoromethylphenyl)methyl]-2-phenyl-5-carbomethoxy-1,2-dihydrocarbazol-4(3H)-one;
9-[(3-trifluoromethylphenyl)methyl]-2-phenyl-5-carbomethoxy-1,2-dihydrocarbazol-4(3H)-one;
9-[(2-benzylphenyl)methyl]-2-phenyl-5-carbomethoxy-1,2-dihydrocarbazol-4(3H)-one;
9-[(3-benzylphenyl)methyl]-2-phenyl-5-carbomethoxy-1,2-dihydrocarbazol-4(3H)-one;
9-[(2-phenylphenyl)methyl]-2-phenyl-5-carbomethoxy-1,2-dihydrocarbazol-4(3H)-one;
9-[(3-phenylphenyl)methyl]-2-phenyl-5-carbomethoxy-1,2-dihydrocarbazol-4(3H)-one;
9-[(2-naphthyl)methyl]-2-phenyl-5-carbomethoxy-1,2-dihydrocarbazol-4(3H)-one;
9-[(1-naphthyl)methyl]-2-phenyl-5-carbomethoxy-1,2-dihydrocarbazol-4(3H)-one;
9-[(phenyl)methyl]-2-(4'-chlorophenyl)-5-carbomethoxy-1,2-dihydrocarbazol-4(3H)-one;
9-[(2-phenoxyphenyl)methyl]-2-(4'-chlorophenyl)-5-carbomethoxy-1,2-dihydrocarbazol-4(3H)-one;
9-[(3-phenoxyphenyl)methyl]-2-(4'-chlorophenyl)-5-carbomethoxy-1,2-dihydrocarbazol-4(3H)-one;
9-[(2-fluorophenyl)methyl]-2-(4'-chlorophenyl)-5-carbomethoxy-1,2-dihydrocarbazol-4(3H)-one;
9-[(3-fluorophenyl)methyl]-2-(4'-chlorophenyl)-5-carbomethoxy-1,2-dihydrocarbazol-4(3H)-one;
9-[(2-chlorophenyl)methyl]-2-(4'-chlorophenyl)-5-carbomethoxy-1,2-dihydrocarbazol-4(3H)-one;
9-[(3-chlorophenyl)methyl]-2-(4'-chlorophenyl)-5-carbomethoxy-1,2-dihydrocarbazol-4(3H)-one;
9-[(2-bromophenyl)methyl]-2-(4'-chlorophenyl)-5-carbomethoxy-1,2-dihydrocarbazol-4(3H)-one;
9-[(3-bromophenyl)methyl]-2-(4'-chlorophenyl)-5-carbomethoxy-1,2-dihydrocarbazol-4(3H)-one;
9-[(2-methylphenyl)methyl]-2-(4'-chlorophenyl)-5-carbomethoxy-1,2-dihydrocarbazol-4(3H)-one;
9-[(3-methylphenyl)methyl]-2-(4'-chlorophenyl)-5-carbomethoxy-1,2-dihydrocarbazol-4(3H)-one;
9-[(2-cyanophenyl)methyl]-2-(4'-chlorophenyl)-5-carbomethoxy-1,2-dihydrocarbazol-4(3H)-one;
9-[(3-cyanophenyl)methyl]-2-(4'-chlorophenyl)-5-carbomethoxy-1,2-dihydrocarbazol-4(3H)-one;
9-[(2-trifluoromethylphenyl)methyl]-2-(4'-chlorophenyl)-5-carbomethoxy-1,2-dihydrocarbazol-4(3H)-one;
9-[(3-trifluoromethylphenyl)methyl]-2-(4'-chlorophenyl)-5-carbomethoxy-1,2-dihydrocarbazol-4(3H)-one;
9-[(2-benzylphenyl)methyl]-2-(4'-chlorophenyl)-5-carbomethoxy-1,2-dihydrocarbazol-4(3H)-one;
9-[(3-benzylphenyl)methyl]-2-(4'-chlorophenyl)-5-carbomethoxy-1,2-dihydrocarbazol-4(3H)-one;
9-[(2-phenylphenyl)methyl]-2-(4'-chlorophenyl)-5-carbomethoxy-1,2-dihydrocarbazol-4(3H)-one;
9-[(3-phenylphenyl)methyl]-2-(4'-chlorophenyl)-5-carbomethoxy-1,2-dihydrocarbazol-4(3H)-one;
9-[(2-naphthyl)methyl]-2-(4'-chlorophenyl)-5-carbomethoxy-1,2-dihydrocarbazol-4(3H)-one;
9-[(1-naphthyl)methyl]-2-(4'-chlorophenyl)-5-carbomethoxy-1,2-dihydrocarbazol-4(3H)-one;
9-[(phenyl)methyl]-4-hydroxy-5-carbomethyoxy carbazole;
9-[(2-phenoxyphenyl)methyl]-4-hydroxy-5-carbomethyoxy carbazole;
9-[(3-phenoxyphenyl)methyl]-4-hydroxy-5-carbomethyoxy carbazole;
9-[(2-fluorophenyl)methyl]-4-hydroxy-5-carbomethyoxy carbazole;
9-[(3-fluorophenyl)methyl]-4-hydroxy-5-carbomethyoxy carbazole;
9-[(2-chlorophenyl)methyl]-4-hydroxy-5-carbomethyoxy carbazole;
9-[(3-chlorophenyl)methyl]-4-hydroxy-5-carbomethyoxy carbazole;
9-[(2-bromophenyl)methyl]-4-hydroxy-5-carbomethyoxy carbazole;
9-[(3-bromophenyl)methyl]-4-hydroxy-5-carbomethyoxy carbazole;
9-[(2-methylphenyl)methyl]-4-hydroxy-5-carbomethyoxy carbazole;
9-[(3-methylphenyl)methyl]-4-hydroxy-5-carbomethyoxy carbazole;
9-[(2-cyanophenyl)methyl]-4-hydroxy-5-carbomethyoxy carbazole;
9-[(3-cyanophenyl)methyl]-4-hydroxy-5-carbomethyoxy carbazole;
9-[(2-trifluoromethylphenyl)methyl]-4-hydroxy-5-carbomethyoxy carbazole;
9-[(3-trifluoromethylphenyl)methyl]-4-hydroxy-5-carbomethyoxy carbazole;
9-[(2-benzylphenyl)methyl]-4-hydroxy-5-carbomethyoxy carbazole;
9-[(3-benzylphenyl)methyl]-4-hydroxy-5-carbomethyoxy carbazole;
9-[(2-phenylphenyl)methyl]-4-hydroxy-5-carbomethyoxy carbazole;
9-[(3-phenylphenyl)methyl]-4-hydroxy-5-carbomethyoxy carbazole;
9-[(2-naphthyl)methyl]-4-hydroxy-5-carbomethyoxy carbazole;
9-[(1-naphthyl)methyl]-4-hydroxy-5-carbomethyoxy carbazole;
9-[(phenyl)methyl]-2-methyl-4-hydroxy-5-carbomethyoxy carbazole;
9-[(2-phenoxyphenyl)methyl]-2-methyl-4-hydroxy-5-carbomethyoxy carbazole;
9-[(3-phenoxyphenyl)methyl]-2-methyl-4-hydroxy-5-carbomethyoxy carbazole;
9-[(2-fluorophenyl)methyl]-2-methyl-4-hydroxy-5-carbomethyoxy carbazole;
9-[(3-fluorophenyl)methyl]-2-methyl-4-hydroxy-5-carbomethyoxy carbazole;
9-[(2-chlorophenyl)methyl]-2-methyl-4-hydroxy-5-carbomethyoxy carbazole;
9-[(3-chlorophenyl)methyl]-2-methyl-4-hydroxy-5-carbomethyoxy carbazole;
9-[(2-bromophenyl)methyl]-2-methyl-4-hydroxy-5-carbomethyoxy carbazole;
9-[(3-bromophenyl)methyl]-2-methyl-4-hydroxy-5-carbomethyoxy carbazole;
9-[(2-methylphenyl)methyl]-2-methyl-4-hydroxy-5-carbomethyoxy carbazole;
9-[(3-methylphenyl)methyl]-2-methyl-4-hydroxy-5-carbomethyoxy carbazole;
9-[(2-cyanophenyl)methyl]-2-methyl-4-hydroxy-5-carbomethyoxy carbazole;
9-[(3-cyanophenyl)methyl]-2-methyl-4-hydroxy-5-carbomethyoxy carbazole;

9-[(2-trifluoromethylphenyl)methyl]-2-methyl-4-hydroxy-5-carbomethyoxy carbazole;
9-[(3-trifluoromethylphenyl)methyl]-2-methyl-4-hydroxy-5-carbomethyoxy carbazole;
9-[(2-benzylphenyl)methyl]-2-methyl-4-hydroxy-5-carbomethyoxy carbazole;
9-[(3-benzylphenyl)methyl]-2-methyl-4-hydroxy-5-carbomethyoxy carbazole;
9-[(2-phenylphenyl)methyl]-2-methyl-4-hydroxy-5-carbomethyoxy carbazole;
9-[(3-phenylphenyl)methyl]-2-methyl-4-hydroxy-5-carbomethyoxy carbazole;
9-[(2-naphthyl)methyl]-2-methyl-4-hydroxy-5-carbomethyoxy carbazole;
9-[(1-naphthyl)methyl]-2-methyl-4-hydroxy-5-carbomethyoxy carbazole;
9-[(phenyl)methyl]-2-ethyl-4-hydroxy-5-carbomethyoxy carbazole;
9-[(2-phenoxyphenyl)methyl]-2-ethyl-4-hydroxy-5-carbomethyoxy carbazole;
9-[(3-phenoxyphenyl)methyl]-2-ethyl-4-hydroxy-5-carbomethyoxy carbazole;
9-[(2-fluorophenyl)methyl]-2-ethyl-4-hydroxy-5-carbomethyoxy carbazole;
9-[(3-fluorophenyl)methyl]-2-ethyl-4-hydroxy-5-carbomethyoxy carbazole;
9-[(2-chlorophenyl)methyl]-2-ethyl-4-hydroxy-5-carbomethyoxy carbazole;
9-[(3-chlorophenyl)methyl]-2-ethyl-4-hydroxy-5-carbomethyoxy carbazole;
9-[(2-bromophenyl)methyl]-2-ethyl-4-hydroxy-5-carbomethyoxy carbazole;
9-[(3-bromophenyl)methyl]-2-ethyl-4-hydroxy-5-carbomethyoxy carbazole;
9-[(2-methylphenyl)methyl]-2-ethyl-4-hydroxy-5-carbomethyoxy carbazole;
9-[(3-methylphenyl)methyl]-2-ethyl-4-hydroxy-5-carbomethyoxy carbazole;
9-[(2-cyanophenyl)methyl]-2-ethyl-4-hydroxy-5-carbomethyoxy carbazole;
9-[(3-cyanophenyl)methyl]-2-ethyl-4-hydroxy-5-carbomethyoxy carbazole;
9-[(2-trifluoromethylphenyl)methyl]-2-ethyl-4-hydroxy-5-carbomethyoxy carbazole;
9-[(3-trifluoromethylphenyl)methyl]-2-ethyl-4-hydroxy-5-carbomethyoxy carbazole;
9-[(2-benzylphenyl)methyl]-2-ethyl-4-hydroxy-5-carbomethyoxy carbazole;
9-[(3-benzylphenyl)methyl]-2-ethyl-4-hydroxy-5-carbomethyoxy carbazole;
9-[(2-phenylphenyl)methyl]-2-ethyl-4-hydroxy-5-carbomethyoxy carbazole;
9-[(3-phenylphenyl)methyl]-2-ethyl-4-hydroxy-5-carbomethyoxy carbazole;
9-[(2-naphthyl)methyl]-2-ethyl-4-hydroxy-5-carbomethyoxy carbazole;
9-[(1-naphthyl)methyl]-2-ethyl-4-hydroxy-5-carbomethyoxy carbazole;
9-[(phenyl)methyl]-2-isopropyl-4-hydroxy-5-carbomethyoxy carbazole;
9-[(2-phenoxyphenyl)methyl]-2-isopropyl-4-hydroxy-5-carbomethyoxy carbazole;
9-[(3-phenoxyphenyl)methyl]-2-isopropyl-4-hydroxy-5-carbomethyoxy carbazole;
9-[(2-fluorophenyl)methyl]-2-isopropyl-4-hydroxy-5-carbomethyoxy carbazole;
9-[(3-fluorophenyl)methyl]-2-isopropyl-4-hydroxy-5-carbomethyoxy carbazole;
9-[(2-chlorophenyl)methyl]-2-isopropyl-4-hydroxy-5-carbomethyoxy carbazole;
9-[(3-chlorophenyl)methyl]-2-isopropyl-4-hydroxy-5-carbomethyoxy carbazole;
9-[(2-bromophenyl)methyl]-2-isopropyl-4-hydroxy-5-carbomethyoxy carbazole;
9-[(3-bromophenyl)methyl]-2-isopropyl-4-hydroxy-5-carbomethyoxy carbazole;
9-[(2-methylphenyl)methyl]-2-isopropyl-4-hydroxy-5-carbomethyoxy carbazole;
9-[(3-methylphenyl)methyl]-2-isopropyl-4-hydroxy-5-carbomethyoxy carbazole;
9-[(2-cyanophenyl)methyl]-2-isopropyl-4-hydroxy-5-carbomethyoxy carbazole;
9-[(3-cyanophenyl)methyl]-2-isopropyl-4-hydroxy-5-carbomethyoxy carbazole;
9-[(2-trifluoromethylphenyl)methyl]-2-isopropyl-4-hydroxy-5-carbomethyoxy carbazole;
9-[(3-trifluoromethylphenyl)methyl]-2-isopropyl-4-hydroxy-5-carbomethyoxy carbazole;
9-[(2-benzylphenyl)methyl]-2-isopropyl-4-hydroxy-5-carbomethyoxy carbazole;
9-[(3-benzylphenyl)methyl]-2-isopropyl-4-hydroxy-5-carbomethyoxy carbazole;
9-[(2-phenylphenyl)methyl]-2-isopropyl-4-hydroxy-5-carbomethyoxy carbazole;
9-[(3-phenylphenyl)methyl]-2-isopropyl-4-hydroxy-5-carbomethyoxy carbazole;
9-[(2-naphthyl)methyl]-2-isopropyl-4-hydroxy-5-carbomethyoxy carbazole;
9-[(1-naphthyl)methyl]-2-isopropyl-4-hydroxy-5-carbomethyoxy carbazole;
9-[(phenyl)methyl]-2-pentyl-4-hydroxy-5-carbomethyoxy carbazole;
9-[(2-phenoxyphenyl)methyl]-2-pentyl-4-hydroxy-5-carbomethyoxy carbazole;
9-[(3-phenoxyphenyl)methyl]-2-pentyl-4-hydroxy-5-carbomethyoxy carbazole;
9-[(2-fluorophenyl)methyl]-2-pentyl-4-hydroxy-5-carbomethyoxy carbazole;
9-[(3-fluorophenyl)methyl]-2-pentyl-4-hydroxy-5-carbomethyoxy carbazole;
9-[(2-chlorophenyl)methyl]-2-pentyl-4-hydroxy-5-carbomethyoxy carbazole;
9-[(3-chlorophenyl)methyl]-2-pentyl-4-hydroxy-5-carbomethyoxy carbazole;
9-[(2-bromophenyl)methyl]-2-pentyl-4-hydroxy-5-carbomethyoxy carbazole;
9-[(3-bromophenyl)methyl]-2-pentyl-4-hydroxy-5-carbomethyoxy carbazole;
9-[(2-methylphenyl)methyl]-2-pentyl-4-hydroxy-5-carbomethyoxy carbazole;
9-[(3-methylphenyl)methyl]-2-pentyl-4-hydroxy-5-carbomethyoxy carbazole;
9-[(2-cyanophenyl)methyl]-2-pentyl-4-hydroxy-5-carbomethyoxy carbazole;
9-[(3-cyanophenyl)methyl]-2-pentyl-4-hydroxy-5-carbomethyoxy carbazole;
9-[(2-trifluoromethylphenyl)methyl]-2-pentyl-4-hydroxy-5-carbomethyoxy carbazole;
9-[(3-trifluoromethylphenyl)methyl]-2-pentyl-4-hydroxy-5-carbomethyoxy carbazole;
9-[(2-benzylphenyl)methyl]-2-pentyl-4-hydroxy-5-carbomethyoxy carbazole;
9-[(3-benzylphenyl)methyl]-2-pentyl-4-hydroxy-5-carbomethyoxy carbazole;
9-[(2-phenylphenyl)methyl]-2-pentyl-4-hydroxy-5-carbomethyoxy carbazole;

9-[(3-phenylphenyl)methyl]-2-pentyl-4-hydroxy-5-carbomethyoxy carbazole;
9-[(2-naphthyl)methyl]-2-pentyl-4-hydroxy-5-carbomethyoxy carbazole;
9-[(1-naphthyl)methyl]-2-pentyl-4-hydroxy-5-carbomethyoxy carbazole;
9-[(phenyl)methyl]-2-phenyl-4-hydroxy-5-carbomethyoxy carbazole;
9-[(2-phenoxyphenyl)methyl]-2-phenyl-4-hydroxy-5-carbomethyoxy carbazole;
9-[(3-phenoxyphenyl)methyl]-2-phenyl-4-hydroxy-5-carbomethyoxy carbazole;
9-[(2-fluorophenyl)methyl]-2-phenyl-4-hydroxy-5-carbomethyoxy carbazole;
9-[(3-fluorophenyl)methyl]-2-phenyl-4-hydroxy-5-carbomethyoxy carbazole;
9-[(2-chlorophenyl)methyl]-2-phenyl-4-hydroxy-5-carbomethyoxy carbazole;
9-[(3-chlorophenyl)methyl]-2-phenyl-4-hydroxy-5-carbomethyoxy carbazole;
9-[(2-bromophenyl)methyl]-2-phenyl-4-hydroxy-5-carbomethyoxy carbazole;
9-[(3-bromophenyl)methyl]-2-phenyl-4-hydroxy-5-carbomethyoxy carbazole;
9-[(2-methylphenyl)methyl]-2-phenyl-4-hydroxy-5-carbomethyoxy carbazole;
9-[(3-methylphenyl)methyl]-2-phenyl-4-hydroxy-5-carbomethyoxy carbazole;
9-[(2-cyanophenyl)methyl]-2-phenyl-4-hydroxy-5-carbomethyoxy carbazole;
9-[(3-cyanophenyl)methyl]-2-phenyl-4-hydroxy-5-carbomethyoxy carbazole;
9-[(2-trifluoromethylphenyl)methyl]-4-hydroxy-5-carbomethyoxy carbazole;
9-[(3-trifluoromethylphenyl)methyl]-2-phenyl-4-hydroxy-5-carbomethyoxy carbazole;
9-[(2-benzylphenyl)methyl]-2-phenyl-4-hydroxy-5-carbomethyoxy carbazole;
9-[(3-benzylphenyl)methyl]-2-phenyl-4-hydroxy-5-carbomethyoxy carbazole;
9-[(2-phenylphenyl)methyl]-2-phenyl-4-hydroxy-5-carbomethyoxy carbazole;
9-[(3-phenylphenyl)methyl]-2-phenyl-4-hydroxy-5-carbomethyoxy carbazole;
9-[(2-naphthyl)methyl]-2-phenyl-4-hydroxy-5-carbomethyoxy carbazole;
9-[(1-naphthyl)methyl]-2-phenyl-4-hydroxy-5-carbomethyoxy carbazole;
9-[(phenyl)methyl]-2-(4'-chlorophenyl)-4-hydroxy-5-carbomethyoxy carbazole;
9-[(2-phenoxyphenyl)methyl]-2-(4'-chlorophenyl)-4-hydroxy-5-carbomethyoxy carbazole;
9-[(3-phenoxyphenyl)methyl]-2-(4'-chlorophenyl)-4-hydroxy-5-carbomethyoxy carbazole;
9-[(2-fluorophenyl)methyl]-2-(4'-chlorophenyl)-4-hydroxy-5-carbomethyoxy carbazole;
9-[(3-fluorophenyl)methyl]-2-(4'-chlorophenyl)-4-hydroxy-5-carbomethyoxy carbazole;
9-[(2-chlorophenyl)methyl]-2-(4'-chlorophenyl)-4-hydroxy-5-carbomethyoxy carbazole;
9-[(3-chlorophenyl)methyl]-2-(4'-chlorophenyl)-4-hydroxy-5-carbomethyoxy carbazole;
9-[(2-bromophenyl)methyl]-2-(4'-chlorophenyl)-4-hydroxy-5-carbomethyoxy carbazole;
9-[(3-bromophenyl)methyl]-2-(4'-chlorophenyl)-4-hydroxy-5-carbomethyoxy carbazole;
9-[(2-methylphenyl)methyl]-2-(4'-chlorophenyl)-4-hydroxy-5-carbomethyoxy carbazole;
9-[(3-methylphenyl)methyl]-2-(4'-chlorophenyl)-4-hydroxy-5-carbomethyoxy carbazole;
9-[(2-cyanophenyl)methyl]-2-(4'-chlorophenyl)-4-hydroxy-5-carbomethyoxy carbazole;
9-[(3-cyanophenyl)methyl]-2-(4'-chlorophenyl)-4-hydroxy-5-carbomethyoxy carbazole;
9-[(2trifluoromethylphenyl)methyl]-2-(4'-chlorophenyl)-4-hydroxy-5-carbomethyoxy carbazole;
9-[(3-trifluoromethylphenyl)methyl]-2-(4'-chlorophenyl)-4-hydroxy-5-carbomethyoxy carbazole;
9-[(2-benzylphenyl)methyl]-2-(4'-chlorophenyl)-4-hydroxy-5-carbomethyoxy carbazole;
9-[(3-benzylphenyl)methyl]-2-(4'-chlorophenyl)-4-hydroxy-5-carbomethyoxy carbazole;
9-[(2-phenylphenyl)methyl]-2-(4'-chlorophenyl)-4-hydroxy-5-carbomethyoxy carbazole;
9-[(3-phenylphenyl)methyl]-2-(4'-chlorophenyl)-4-hydroxy-5-carbomethyoxy carbazole;
9-[(2-naphthyl)methyl]-2-(4'-chlorophenyl)-4-hydroxy-5-carbomethyoxy carbazole;
9-[(1-naphthyl)methyl]-2-(4'-chlorophenyl)-4-hydroxy-5-carbomethyoxy carbazole;
9-[(phenyl)methyl]-4-hydroxy-5-carbamoyl carbazole;
9-[(2-phenoxyphenyl)methyl]-4-hydroxy-5-carbamoyl carbazole;
9-[(3-phenoxyphenyl)methyl]-4-hydroxy-5-carbamoyl carbazole;
9-[(2-fluorophenyl)methyl]-4-hydroxy-5-carbamoyl carbazole;
9-[(3-fluorophenyl)methyl]-4-hydroxy-5-carbamoyl carbazole;
9-[(2-chlorophenyl)methyl]-4-hydroxy-5-carbamoyl carbazole;
9-[(3-chlorophenyl)methyl]-4-hydroxy-5-carbamoyl carbazole;
9-[(2-bromophenyl)methyl]-4-hydroxy-5-carbamoyl carbazole;
9-[(3-bromophenyl)methyl]-4-hydroxy-5-carbamoyl carbazole;
9-[(2-methylphenyl)methyl]-4-hydroxy-5-carbamoyl carbazole;
9-[(3-methylphenyl)methyl]-4-hydroxy-5-carbamoyl carbazole;
9-[(2-cyanophenyl)methyl]-4-hydroxy-5-carbamoyl carbazole;
9-[(3-cyanophenyl)methyl]-4-hydroxy-5-carbamoyl carbazole;
9-[(2-trifluoromethylphenyl)methyl]-4-hydroxy-5-carbamoyl carbazole;
9-[(3-trifluoromethylphenyl)methyl]-4-hydroxy-5-carbamoyl carbazole;
9-[(2-benzylphenyl)methyl]-4-hydroxy-5-carbamoyl carbazole;
9-[(3-benzylphenyl)methyl]-4-hydroxy-5-carbamoyl carbazole;
9-[(2-phenylphenyl)methyl]-4-hydroxy-5-carbamoyl carbazole;
9-[(3-phenylphenyl)methyl]-4-hydroxy-5-carbamoyl carbazole;
9-[(2-naphthyl)methyl]-4-hydroxy-5-carbamoyl carbazole;
9-[(1-naphthyl)methyl]-4-hydroxy-5-carbamoyl carbazole;
9-[(phenyl)methyl]-2-methyl-4-hydroxy-5-carbamoyl carbazole;
9-[(2-phenoxyphenyl)methyl]-2-methyl-4-hydroxy-5-carbamoyl carbazole;
9-[(3-phenoxyphenyl)methyl]-2-methyl-4-hydroxy-5-carbamoyl carbazole;

9-[(2-fluorophenyl)methyl]-2-methyl-4-hydroxy-5-carbamoyl carbazole;
9-[(3-fluorophenyl)methyl]-2-methyl-4-hydroxy-5-carbamoyl carbazole;
9-[(2-chlorophenyl)methyl]-2-methyl-4-hydroxy-5-carbamoyl carbazole;
9-[(3-chlorophenyl)methyl]-2-methyl-4-hydroxy-5-carbamoyl carbazole;
9-[(2-bromophenyl)methyl]-2-methyl-4-hydroxy-5-carbamoyl carbazole;
9-[(3-bromophenyl)methyl]-2-methyl-4-hydroxy-5-carbamoyl carbazole;
9-[(2-methylphenyl)methyl]-2-methyl-4-hydroxy-5-carbamoyl carbazole;
9-[(3-methylphenyl)methyl]-2-methyl-4-hydroxy-5-carbamoyl carbazole;
9-[(2-cyanophenyl)methyl]-2-methyl-4-hydroxy-5-carbamoyl carbazole;
9-[(3-cyanophenyl)methyl]-2-methyl-4-hydroxy-5-carbamoyl carbazole;
9-[(2-trifluoromethylphenyl)methyl]-2-methyl-4-hydroxy-5-carbamoyl carbazole;
9-[(3-trifluoromethylphenyl)methyl]-2-methyl-4-hydroxy-5-carbamoyl carbazole;
9-[(2-benzylphenyl)methyl]-2-methyl-4-hydroxy-5-carbamoyl carbazole;
9-[(3-benzylphenyl)methyl]-2-methyl-4-hydroxy-5-carbamoyl carbazole;
9-[(2-phenylphenyl)methyl]-2-methyl-4-hydroxy-5-carbamoyl carbazole;
9-[(3-phenylphenyl)methyl]-2-methyl-4-hydroxy-5-carbamoyl carbazole;
9-[(2-naphthyl)methyl]-2-methyl-4-hydroxy-5-carbamoyl carbazole;
9-[(1-naphthyl)methyl]-2-methyl-4-hydroxy-5-carbamoyl carbazole;
9-[(phenyl)methyl]-2-ethyl-4-hydroxy-5-carbamoyl carbazole;
9-[(2-phenoxyphenyl)methyl]-2-ethyl-4-hydroxy-5-carbamoyl carbazole;
9-[(3-phenoxyphenyl)methyl]-2-ethyl-4-hydroxy-5-carbamoyl carbazole;
9-[(2-fluorophenyl)methyl]-2-ethyl-4-hydroxy-5-carbamoyl carbazole;
9-[(3-fluorophenyl)methyl]-2-ethyl-4-hydroxy-5-carbamoyl carbazole;
9-[(2-chlorophenyl)methyl]-2-ethyl-4-hydroxy-5-carbamoyl carbazole;
9-[(3-chlorophenyl)methyl]-2-ethyl-4-hydroxy-5-carbamoyl carbazole;
9-[(2-bromophenyl)methyl]-2-ethyl-4-hydroxy-5-carbamoyl carbazole;
9-[(3-bromophenyl)methyl]-2-ethyl-4-hydroxy-5-carbamoyl carbazole;
9-[(2-methylphenyl)methyl]-2-ethyl-4-hydroxy-5-carbamoyl carbazole;
9-[(3-methylphenyl)methyl]-2-ethyl-4-hydroxy-5-carbamoyl carbazole;
9-[(2-cyanophenyl)methyl]-2-ethyl-4-hydroxy-5-carbamoyl carbazole;
9-[(3-cyanophenyl)methyl]-2-ethyl-4-hydroxy-5-carbamoyl carbazole;
9-[(2-trifluoromethylphenyl)methyl]-2-ethyl-4-hydroxy-5-carbamoyl carbazole;
9-[(3-trifluoromethylphenyl)methyl]-2-ethyl-4-hydroxy-5-carbamoyl carbazole;
9-[(2-benzylphenyl)methyl]-2-ethyl-4-hydroxy-5-carbamoyl carbazole;
9-[(3-cyanophenyl)methyl]-2-isopropyl-4-hydroxy-5-carbamoyl carbazole;
9-[(2-trifluoromethylphenyl)methyl]-2-isopropyl-4-hydroxy-5-carbamoyl carbazole;
9-[(3-trifluoromethylphenyl)methyl]-2-isopropyl-4-hydroxy-5-carbamoyl carbazole;
9-[(2-benzylphenyl)methyl]-2-isopropyl-4-hydroxy-5-carbamoyl carbazole;
9-[(3-benzylphenyl)methyl]-2-isopropyl-4-hydroxy-5-carbamoyl carbazole;
9-[(2-phenylphenyl)methyl]-2-isopropyl-4-hydroxy-5-carbamoyl carbazole;
9-[(3-phenylphenyl)methyl]-2-isopropyl-4-hydroxy-5-carbamoyl carbazole;
9-[(2-naphthyl)methyl]-2-isopropyl-4-hydroxy-5-carbamoyl carbazole;
9-[(1-naphthyl)methyl]-2-isopropyl-4-hydroxy-5-carbamoyl carbazole;
9-[(phenyl)methyl]-2-pentyl-4-hydroxy-5-carbamoyl carbazole;
9-[(2-phenoxyphenyl)methyl]-2-pentyl-4-hydroxy-5-carbamoyl carbazole;
9-[(3-phenoxyphenyl)methyl]-2-pentyl-4-hydroxy-5-carbamoyl carbazole;
9-[(2-fluorophenyl)methyl]-2-pentyl-4-hydroxy-5-carbamoyl carbazole;
9-[(3-fluorophenyl)methyl]-2-pentyl-4-hydroxy-5-carbamoyl carbazole;
9-[(2-chlorophenyl)methyl]-2-pentyl-4-hydroxy-5-carbamoyl carbazole;
9-[(3-chlorophenyl)methyl]-2-pentyl-4-hydroxy-5-carbamoyl carbazole;
9-[(2-bromophenyl)methyl]-2-pentyl-4-hydroxy-5-carbamoyl carbazole;
9-[(3-benzylphenyl)methyl]-2-ethyl-4-hydroxy-5-carbamoyl carbazole;
9-[(2-phenylphenyl)methyl]-2-ethyl-4-hydroxy-5-carbamoyl carbazole;
9-[(3-phenylphenyl)methyl]-2-ethyl-4-hydroxy-5-carbamoyl carbazole;
9-[(2-naphthyl)methyl]-2-ethyl-4-hydroxy-5-carbamoyl carbazole;
9-[(1-naphthyl)methyl]-2-ethyl-4-hydroxy-5-carbamoyl carbazole;
9-[(phenyl)methyl]-2-isopropyl-4-hydroxy-5-carbamoyl carbazole;
9-[(2-phenoxyphenyl)methyl]-2-isopropyl-4-hydroxy-5-carbamoyl carbazole;
9-[(3-phenoxyphenyl)methyl]-2-isopropyl-4-hydroxy-5-carbamoyl carbazole;
9-[(2-fluorophenyl)methyl]-2-isopropyl-4-hydroxy-5-carbamoyl carbazole;
9-[(3-fluorophenyl)methyl]-2-isopropyl-4-hydroxy-5-carbamoyl carbazole;
9-[(2-chlorophenyl)methyl]-2-isopropyl-4-hydroxy-5-carbamoyl carbazole;
9-[(3-chlorophenyl)methyl]-2-isopropyl-4-hydroxy-5-carbamoyl carbazole;
9-[(2-bromophenyl)methyl]-2-isopropyl-4-hydroxy-5-carbamoyl carbazole;
9-[(3-bromophenyl)methyl]-2-isopropyl-4-hydroxy-5-carbamoyl carbazole;
9-[(2-methylphenyl)methyl]-2-isopropyl-4-hydroxy-5-carbamoyl carbazole;
9-[(3-methylphenyl)methyl]-2-isopropyl-4-hydroxy-5-carbamoyl carbazole;
9-[(2-cyanophenyl)methyl]-2-isopropyl-4-hydroxy-5-carbamoyl carbazole;

9-[(3-bromophenyl)methyl]-2-pentyl-4-hydroxy-5-carbamoyl carbazole;
9-[(2-methylphenyl)methyl]-2-pentyl-4-hydroxy-5-carbamoyl carbazole;
9-[(3-methylphenyl)methyl]-2-pentyl-4-hydroxy-5-carbamoyl carbazole;
9-[(2-cyanophenyl)methyl]-2-pentyl-4-hydroxy-5-carbamoyl carbazole;
9-[(3-cyanophenyl)methyl]-2-pentyl-4-hydroxy-5-carbamoyl carbazole;
9-[(2-trifluoromethylphenyl)methyl]-2-pentyl-4-hydroxy-5-carbamoyl carbazole;
9-[(3-trifluoromethylphenyl)methyl]-2-pentyl-4-hydroxy-5-carbamoyl carbazole;
9-[(2-benzylphenyl)methyl]-2-pentyl-4-hydroxy-5-carbamoyl carbazole;
9-[(3-benzylphenyl)methyl]-2-pentyl-4-hydroxy-5-carbamoyl carbazole;
9-[(2-phenylphenyl)methyl]-2-pentyl-4-hydroxy-5-carbamoyl carbazole;
9-[(3-phenylphenyl)methyl]-2-pentyl-4-hydroxy-5-carbamoyl carbazole;
9-[(2-naphthyl)methyl]-2-pentyl-4-hydroxy-5-carbamoyl carbazole;
9-[(1-naphthyl)methyl]-2-pentyl-4-hydroxy-5-carbamoyl carbazole;
9-[(phenyl)methyl]-2-phenyl-4-hydroxy-5-carbamoyl carbazole;
9-[(2-phenoxyphenyl)methyl]-2-phenyl-4-hydroxy-5-carbamoyl carbazole;
9-[(3-phenoxyphenyl)methyl]-2-phenyl-4-hydroxy-5-carbamoyl carbazole;
9-[(2-fluorophenyl)methyl]-2-phenyl-4-hydroxy-5-carbamoyl carbazole;
9-[(3-fluorophenyl)methyl]-2-phenyl-4-hydroxy-5-carbamoyl carbazole;
9-[(2-chlorophenyl)methyl]-2-phenyl-4-hydroxy-5-carbamoyl carbazole;
9-[(3-chlorophenyl)methyl]-2-phenyl-4-hydroxy-5-carbamoyl carbazole;
9-[(2-bromophenyl)methyl]-2-phenyl-4-hydroxy-5-carbamoyl carbazole;
9-[(3-bromophenyl)methyl]-2-phenyl-4-hydroxy-5-carbamoyl carbazole;
9-[(2-methylphenyl)methyl]-2-phenyl-4-hydroxy-5-carbamoyl carbazole;
9-[(3-methylphenyl)methyl]-2-phenyl-4-hydroxy-5-carbamoyl carbazole;
9-[(2-cyanophenyl)methyl]-2-phenyl-4-hydroxy-5-carbamoyl carbazole;
9-[(3-cyanophenyl)methyl]-2-phenyl-4-hydroxy-5-carbamoyl carbazole;
9-[(2-trifluoromethylphenyl)methyl]-2-phenyl-4-hydroxy-5-carbamoyl carbazole;
9-[(3-trifluoromethylphenyl)methyl]-2-phenyl-4-hydroxy-5-carbamoyl carbazole;
9-[(2-benzylphenyl)methyl]-2-phenyl-4-hydroxy-5-carbamoyl carbazole;
9-[(3-benzylphenyl)methyl]-2-phenyl-4-hydroxy-5-carbamoyl carbazole;
9-[(2-phenylphenyl)methyl]-2-phenyl-4-hydroxy-5-carbamoyl carbazole;
9-[(3-phenylphenyl)methyl]-2-phenyl-4-hydroxy-5-carbamoyl carbazole;
9-[(2-naphthyl)methyl]-2-phenyl-4-hydroxy-5-carbamoyl carbazole;
9-[(1-naphthyl)methyl]-2-phenyl-4-hydroxy-5-carbamoyl carbazole;
9-[(phenyl)methyl]-2-(4'-chlorophenyl)-4-hydroxy-5-carbamoyl carbazole;
9-[(2-phenoxyphenyl)methyl]-2-(4'-chlorophenyl)-4-hydroxy-5-carbamoyl carbazole;
9-[(3-phenoxyphenyl)methyl]-2-(4'-chlorophenyl)-4-hydroxy-5-carbamoyl carbazole;
9-[(2-fluorophenyl)methyl]-2-(4'-chlorophenyl)-4-hydroxy-5-carbamoyl carbazole;
9-[(3-fluorophenyl)methyl]-2-(4'-chlorophenyl)-4-hydroxy-5-carbamoyl carbazole;
9-[(2-chlorophenyl)methyl]-2-(4'-chlorophenyl)-4-hydroxy-5-carbamoyl carbazole;
9-[(3-chlorophenyl)methyl]-2-(4'-chlorophenyl)-4-hydroxy-5-carbamoyl carbazole;
9-[(2-bromophenyl)methyl]-2-(4'-chlorophenyl)-4-hydroxy-5-carbamoyl carbazole;
9-[(3-bromophenyl)methyl]-2-(4'-chlorophenyl)-4-hydroxy-5carbamoyl carbazole;
9-[(2-methylphenyl)methyl]-2-(4'-chlorophenyl)-4-hydroxy-5-carbamoyl carbazole;
9-[(3-methylphenyl)methyl]-2-(4'-chlorophenyl)-4-hydroxy-5-carbamoyl carbazole;
9-[(2-cyanophenyl)methyl]-2-(4'-chlorophenyl)-4-hydroxy-5-carbamoyl carbazole;
9-[(3-cyanophenyl)methyl]-2-(4'-chlorophenyl)-4-hydroxy-5-carbamoyl carbazole;
9-[(2-trifluoromethylphenyl)methyl]-2-(4'-chlorophenyl)-4-hydroxy-5-carbamoyl carbazole;
9-[(3-trifluoromethylphenyl)methyl]-2-(4'-chlorophenyl)-4-hydroxy-5-carbamoyl carbazole;
9-[(2-benzylphenyl)methyl]-2-(4'-chlorophenyl)-4-hydroxy-5-carbamoyl carbazole;
9-[(3-benzylphenyl)methyl]-2-(4'-chlorophenyl)-4-hydroxy-5-carbamoyl carbazole;
9-[(2-phenylphenyl)methyl]-2-(4'-chlorophenyl)-4-hydroxy-5-carbamoyl carbazole;
9-[(3-phenylphenyl)methyl]-2-(4'-chlorophenyl)-4-hydroxy-5-carbamoyl carbazole;
9-[(2-naphthyl)methyl]-2-(4'-chlorophenyl)-4-hydroxy-5-carbamoyl carbazole;
9-[(1-naphthyl)methyl]-2-(4'-chlorophenyl)-4-hydroxy-5-carbamoyl carbazole;
ethyl 5-methoxy-8-methyl-1,2,3,4-tetrahydrocarbazole-4-carboxylate;
ethyl 9-benzyl-5-methoxy-8-methyl-1,2,3,4-tetrahydrocarbazole-4-carboxylate;
9-benzyl-5-methoxy-8-methyl-1,2,3,4-tetrahydrocarbazole-4-carboxamide;
5-carbamoyl-4-methoxy-1-methylcarbazole;
9-benzyl-5-carbamoyl-4-methoxy-1-methylcarbazole;
Ethyl 9-benzyl-5-methoxy-8-fluoro-1,2,3,4-tetrahydrocarbazole-4-carboxylate;
9-Benzyl-5-methoxy-8-fluoro-1,2,3,4-tetrahydrocarbazole-4-carboxamide;
9-benzyl-5-carbamoyl-4-methoxy-1-fluorocarbazole;
Ethyl 9-benzyl-5-methoxy-8-chloro-1,2,3,4-tetrahydrocarbazole-4-carboxylate;
9-Benzyl-5-methoxy-8-chloro-1,2,3,4-tetrahydrocarbazole-4-carboxamide;
9-benzyl-5-carbamoyl-4-methoxy-1-chlorocarbazole;
5-carbamoyl-4-hydroxy-1-chlorocarbazole;
[5-carbamoyl-1-chlorocarbazol-4-yl]oxyacetic acid methyl ester;
{9-[(2-fluorophenyl)methyl]-5-carbamoylcarbazol-4-yl}oxyacetic acid; methyl ester;
9-[(phenyl)methyl]-5-carbamoylcarbazol-4-yl}oxyacetic acid; methyl ester;

9-[(2-phenoxyphenyl)methyl]-5-carbamoylcarbazol-4-yl}oxyacetic acid; methyl ester;
9-[(3-phenoxyphenyl)methyl]-5-carbamoylcarbazol-4-yl}oxyacetic acid; methyl ester;
9-[(2-fluorophenyl)methyl]-5-carbamoylcarbazol-4-yl}oxyacetic acid; methyl ester;
9-[(3-fluorophenyl)methyl]-5-carbamoylcarbazol-4-yl}oxyacetic acid; methyl ester;
9-[(2-chlorophenyl)methyl]-5-carbamoylcarbazol-4-yl}oxyacetic acid; methyl ester;
9-[(3-chlorophenyl)methyl]-5-carbamoylcarbazol-4-yl}oxyacetic acid; methyl ester;
9-[(2-bromophenyl)methyl]-5-carbamoylcarbazol-4-yl}oxyacetic acid; methyl ester;
9-[(3-bromophenyl)methyl]-5-carbamoylcarbazol-4-yl}oxyacetic acid; methyl ester;
9-[(2-methylphenyl)methyl]-5-carbamoylcarbazol-4-yl}oxyacetic acid; methyl ester;
9-[(3-methylphenyl)methyl]-5-carbamoylcarbazol-4-yl}oxyacetic acid; methyl ester;
9-[(2-cyanophenyl)methyl]-5-carbamoylcarbazol-4-yl}oxyacetic acid; methyl ester;
9-[(3-cyanophenyl)methyl]-5-carbamoylcarbazol-4-yl}oxyacetic acid; methyl ester;
9-[(2-trifluoromethylphenyl)methyl]-5-carbamoylcarbazol-4-yl}oxyacetic acid; methyl ester;
9-[(3-trifluoromethylphenyl)methyl]-5-carbamoylcarbazol-4-yl}oxyacetic acid; methyl ester;
9-[(2-benzylphenyl)methyl]-5-carbamoylcarbazol-4-yl}oxyacetic acid; methyl ester;
9-[(3-benzylphenyl)methyl]-5-carbamoylcarbazol-4-yl}oxyacetic acid; methyl ester;
9-[(2-phenylphenyl)methyl]-5-carbamoylcarbazol-4-yl}oxyacetic acid; methyl ester;
9-[(3-phenylphenyl)methyl]-5-carbamoylcarbazol-4-yl}oxyacetic acid; methyl ester;
9-[(2-naphthyl)methyl]-5-carbamoylcarbazol-4-yl}oxyacetic acid; methyl ester;
9-[(1-naphthyl)methyl]-5-carbamoylcarbazol-4-yl}oxyacetic acid; methyl ester;
9-[(phenyl)methyl]-2-methyl-5-carbamoylcarbazol-4-yl}oxyacetic acid; methyl ester;
9-[(2-phenoxyphenyl)methyl]-2-methyl-5-carbamoylcarbazol-4-yl}oxyacetic acid; methyl ester;
9-[(3-phenoxyphenyl)methyl]-2-methyl-5-carbamoylcarbazol-4-yl}oxyacetic acid; methyl ester;
9-[(2-fluorophenyl)methyl]-2-methyl-5-carbamoylcarbazol-4-yl}oxyacetic acid; methyl ester;
9-[(3-fluorophenyl)methyl]-2-methyl-5-carbamoylcarbazol-4-yl}oxyacetic acid; methyl ester;
9-[(2-chlorophenyl)methyl]-2-methyl-5-carbamoylcarbazol-4-yl}oxyacetic acid; methyl ester;
9-[(3-chlorophenyl)methyl]-2-methyl-5-carbamoylcarbazol-4-yl}oxyacetic acid; methyl ester;
9-[(2-bromophenyl)methyl]-2-methyl-5-carbamoylcarbazol-4-yl}oxyacetic acid; methyl ester;
9-[(3-bromophenyl)methyl]-2-methyl-5-carbamoylcarbazol-4-yl}oxyacetic acid; methyl ester;
9-[(2-methylphenyl)methyl]-2-methyl-5-carbamoylcarbazol-4-yl}oxyacetic acid; methyl ester;
9-[(3-methylphenyl)methyl]-2-methyl-5-carbamoylcarbazol-4-yl}oxyacetic acid; methyl ester;
9-[(2-cyanophenyl)methyl]-2-methyl-5-carbamoylcarbazol-4-yl}oxyacetic acid; methyl ester;
9-[(3-cyanophenyl)methyl]-2-methyl-5-carbamoylcarbazol-4-yl}oxyacetic acid; methyl ester;
9-[(2-trifluoromethylphenyl)methyl]-2-methyl-5-carbamoylcarbazol-4-yl}oxyacetic acid; methyl ester;
9-[(3-trifluoromethylphenyl)methyl]-2-methyl-5-carbamoylcarbazol-4-yl}oxyacetic acid; methyl ester;
9-[(2-benzylphenyl)methyl]-2-methyl-5-carbamoylcarbazol-4-yl}oxyacetic acid; methyl ester;
9-[(3-benzylphenyl)methyl]-2-methyl-5-carbamoylcarbazol-4-yl}oxyacetic acid; methyl ester;
9-[(2-phenylphenyl)methyl]-2-methyl-5-carbamoylcarbazol-4-yl}oxyacetic acid; methyl ester;
9-[(3-phenylphenyl)methyl]-2-methyl-5-carbamoylcarbazol-4-yl}oxyacetic acid; methyl ester;
9-[(2-naphthyl)methyl]-2-methyl-5-carbamoylcarbazol-4-yl}oxyacetic acid; methyl ester;
9-[(1-naphthyl)methyl]-2-methyl-5-carbamoylcarbazol-4-yl}oxyacetic acid; methyl ester;
9-[(phenyl)methyl]-2-ethyl-5-carbamoylcarbazol-4-yl)oxyacetic acid; methyl ester;
9-[(2-phenoxyphenyl)methyl]-2-ethyl-5-carbamoylcarbazol-4-yl}oxyacetic acid; methyl ester;
9-[(3-phenoxyphenyl)methyl]-2-ethyl-5-carbamoylcarbazol-4-yl}oxyacetic acid; methyl ester;
9-[(2-fluorophenyl)methyl]-2-ethyl-5-carbamoylcarbazol-4-yl}oxyacetic acid; methyl ester;
9-[(3-fluorophenyl)methyl]-2-ethyl-5-carbamoylcarbazol-4-yl}oxyacetic acid; methyl ester;
9-[(2-chlorophenyl)methyl]-2-ethyl-5-carbamoylcarbazol-4-yl}oxyacetic acid; methyl ester;
9-[(3-chlorophenyl)methyl]-2-ethyl-5-carbamoylcarbazol-4-yl}oxyacetic acid; methyl ester;
9-[(2-bromophenyl)methyl]-2-ethyl-5-carbamoylcarbazol-4-yl}oxyacetic acid; methyl ester;
9-[(3-bromophenyl)methyl]-2-ethyl-5-carbamoylcarbazol-4-yl}oxyacetic acid; methyl ester;
9-[(2-methylphenyl)methyl]-2-ethyl-5-carbamoylcarbazol-4-yl}oxyacetic acid; methyl ester;
9-[(3-methylphenyl)methyl]-2-ethyl-5-carbamoylcarbazol-4-yl}oxyacetic acid; methyl ester;
9-[(2-cyanophenyl)methyl]-2-ethyl-5-carbamoylcarbazol-4-yl}oxyacetic acid; methyl ester;
9-[(3-cyanophenyl)methyl]-2-ethyl-5-carbamoylcarbazol-4-yl}oxyacetic acid; methyl ester;
9-[(2-trifluoromethylphenyl)methyl]-2-ethyl-5-carbamoylcarbazol-4-yl}oxyacetic acid; methyl ester;
9-[(3-trifluoromethylphenyl)methyl]-2-ethyl-5-carbamoylcarbazol-4-yl}oxyacetic acid; methyl ester;
9-[(2-benzylphenyl)methyl]-2-ethyl-5-carbamoylcarbazol-4-yl}oxyacetic acid; methyl ester;
9-[(3-benzylphenyl)methyl]-2-ethyl-5-carbamoylcarbazol-4-yl}oxyacetic acid; methyl ester;
9-[(2-phenylphenyl)methyl]-2-ethyl-5-carbamoylcarbazol-4-yl}oxyacetic acid; methyl ester;
9-[(3-phenylphenyl)methyl]-2-ethyl-5-carbamoylcarbazol-4-yl}oxyacetic acid; methyl ester;
9-[(2-naphthyl)methyl]-2-ethyl-5-carbamoylcarbazol-4-yl}oxyacetic acid; methyl ester;
9-[(1-naphthyl)methyl]-2-ethyl-5-carbamoylcarbazol-4-yl}oxyacetic acid; methyl ester;
9-[(phenyl)methyl]-2-isopropyl-5-carbamoylcarbazol-4-yl}oxyacetic acid; methyl ester;
9-[(2-phenoxyphenyl)methyl]-2-isopropyl-5-carbamoylcarbazol-4-yl}oxyacetic acid; methyl ester;
9-[(3-phenoxyphenyl)methyl]-2-isopropyl-5-carbamoylcarbazol-4-yl}oxyacetic acid; methyl ester;
9-[(2-fluorophenyl)methyl]-2-isopropyl-5-carbamoylcarbazol-4-yl}oxyacetic acid; methyl ester;
9-[(3-fluorophenyl)methyl]-2-isopropyl-5-carbamoylcarbazol-4-yl}oxyacetic acid; methyl ester;
9-[(2-chlorophenyl)methyl]-2-isopropyl-5-carbamoylcarbazol-4-yl}oxyacetic acid; methyl ester;

9-[(3-chlorophenyl)methyl]-2-isopropyl-5-carbamoylcarbazol-4-yl}oxyacetic acid; methyl ester;
9-[(2-bromophenyl)methyl]-2-isopropyl-5-carbamoylcarbazol-4-yl}oxyacetic acid; methyl ester;
9-[(3-bromophenyl)methyl]-2-isopropyl-5-carbamoylcarbazol-4-yl}oxyacetic acid; methyl ester;
9-[(2-methylphenyl)methyl]-2-isopropyl-5-carbamoylcarbazol-4-yl}oxyacetic acid; methyl ester;
9-[(3-methylphenyl)methyl]-2-isopropyl-5-carbamoylcarbazol-4-yl}oxyacetic acid; methyl ester;
9-[(2-cyanophenyl)methyl]-2-isopropyl-5-carbamoylcarbazol-4-yl}oxyacetic acid; methyl ester;
9-[(3-cyanophenyl)methyl]-2-isopropyl-5-carbamoylcarbazol-4-yl}oxyacetic acid; methyl ester;
9-[(2-trifluoromethylphenyl)methyl]-2-isopropyl-5-carbamoylcarbazol-4-yl}oxyacetic acid; methyl ester;
9-[(3-trifluoromethylphenyl)methyl]-2-isopropyl-5-carbamoylcarbazol-4-yl}oxyacetic acid; methyl ester;
9-[(2-benzylphenyl)methyl]-2-isopropyl-5-carbamoylcarbazol-4-yl}oxyacetic acid; methyl ester;
9-[(3-benzylphenyl)methyl]-2-isopropyl-5-carbamoylcarbazol-4-yl}oxyacetic acid; methyl ester;
9-[(2-phenylphenyl)methyl]-2-isopropyl-5-carbamoylcarbazol-4-yl}oxyacetic acid; methyl ester;
9-[(3-phenylphenyl)methyl]-2-isopropyl-5-carbamoylcarbazol-4-yl}oxyacetic acid; methyl ester;
9-[(2-naphthyl)methyl]-2-isopropyl-5-carbamoylcarbazol-4-yl}oxyacetic acid; methyl ester;
9-[(1-naphthyl)methyl]-2-isopropyl-5-carbamoylcarbazol-4-yl}oxyacetic acid; methyl ester;
9-[(phenyl)methyl]-2-pentyl-5-carbamoylcarbazol-4-yl}oxyacetic acid; methyl ester;
9-[(2-phenoxyphenyl)methyl]-2-pentyl-5-carbamoylcarbazol-4-yl}oxyacetic acid; methyl ester;
9-[(3-phenoxyphenyl)methyl]-2-pentyl-5-carbamoylcarbazol-4-yl}oxyacetic acid; methyl ester;
9-[(2-fluorophenyl)methyl]-2-pentyl-5-carbamoylcarbazol-4-yl}oxyacetic acid; methyl ester;
9-[(3-fluorophenyl)methyl]-2-pentyl-5-carbamoylcarbazol-4-yl}oxyacetic acid; methyl ester;
9-[(2-chlorophenyl)methyl]-2-pentyl-5-carbamoylcarbazol-4-yl}oxyacetic acid; methyl ester;
9-[(3-chlorophenyl)methyl]-2-pentyl-5-carbamoylcarbazol-4-yl}oxyacetic acid; methyl ester;
9-[(2-bromophenyl)methyl]-2-pentyl-5-carbamoylcarbazol-4-yl}oxyacetic acid; methyl ester;
9-[(3-bromophenyl)methyl]-2-pentyl-5-carbamoylcarbazol-4-yl}oxyacetic acid; methyl ester;
9-[(2-methylphenyl)methyl]-2-pentyl-5-carbamoylcarbazol-4-yl}oxyacetic acid; methyl ester;
9-[(3-methylphenyl)methyl]-2-pentyl-5-carbamoylcarbazol-4-yl}oxyacetic acid; methyl ester;
9-[(2-cyanophenyl)methyl]-2-pentyl-5-carbamoylcarbazol-4-yl}oxyacetic acid; methyl ester;
9-[(3-cyanophenyl)methyl]-2-pentyl-5-carbamoylcarbazol-4-yl}oxyacetic acid; methyl ester;
9-[(2-trifluoromethylphenyl)methyl]-2-pentyl-5-carbamoylcarbazol-4-yl}oxyacetic acid; methyl ester;
9-[(3-trifluoromethylphenyl)methyl]-2-pentyl-5-carbamoylcarbazol-4-yl}oxyacetic acid; methyl ester;
9-[(2-benzylphenyl)methyl]-2-pentyl-5-carbamoylcarbazol-4-yl}oxyacetic acid; methyl ester;
9-[(3-benzylphenyl)methyl]-2-pentyl-5-carbamoylcarbazol-4-yl}oxyacetic acid; methyl ester;
9-[(2-phenylphenyl)methyl]-2-pentyl-5-carbamoylcarbazol-4-yl}oxyacetic acid; methyl ester;
9-[(3-phenylphenyl)methyl]-2-pentyl-5-carbamoylcarbazol-4-yl}oxyacetic acid; methyl ester;
9-[(2-naphthyl)methyl]-2-pentyl-5-carbamoylcarbazol-4-yl}oxyacetic acid; methyl ester;
9-[(1-naphthyl)methyl]-2-pentyl-5-carbamoylcarbazol-4-yl}oxyacetic acid; methyl ester;
9-[(phenyl)methyl]-2-phenyl-5-carbamoylcarbazol-4-yl}oxyacetic acid; methyl ester;
9-[(2-phenoxyphenyl)methyl]-2-phenyl-5-carbamoylcarbazol-4-yl}oxyacetic acid; methyl ester;
9-[(3-phenoxyphenyl)methyl]-2-phenyl-5-carbamoylcarbazol-4-yl}oxyacetic acid; methyl ester;
9-[(2-fluorophenyl)methyl]-2-phenyl-5-carbamoylcarbazol-4-yl}oxyacetic acid; methyl ester;
9-[(3-fluorophenyl)methyl]-2-phenyl-5-carbamoylcarbazol-4-yl}oxyacetic acid; methyl ester;
9-[(2-chlorophenyl)methyl]-2-phenyl-5-carbamoylcarbazol-4-yl}oxyacetic acid; methyl ester;
9-[(3-chlorophenyl)methyl]-2-phenyl-5-carbamoylcarbazol-4-yl}oxyacetic acid; methyl ester;
9-[(2-bromophenyl)methyl]-2-phenyl-5-carbamoylcarbazol-4-yl}oxyacetic acid; methyl ester;
9-[(3-bromophenyl)methyl]-2-phenyl-5-carbamoylcarbazol-4-yl}oxyacetic acid; methyl ester;
9-[(2-methylphenyl)methyl]-2-phenyl-5-carbamoylcarbazol-4-yl}oxyacetic acid; methyl ester;
9-[(3-methylphenyl)methyl]-2-phenyl-5-carbamoylcarbazol-4-yl}oxyacetic acid; methyl ester;
9-[(2-cyanophenyl)methyl]-2-phenyl-5-carbamoylcarbazol-4-yl}oxyacetic acid; methyl ester;
9-[(3-cyanophenyl)methyl]-2-phenyl-5-carbamoylcarbazol-4-yl}oxyacetic acid; methyl ester;
9-[(2-trifluoromethylphenyl)methyl]-2-phenyl-5-carbamoylcarbazol-4-yl}oxyacetic acid; methyl ester;
9-[(3-trifluoromethylphenyl)methyl]-2-phenyl-5-carbamoylcarbazol-4-yl}oxyacetic acid; methyl ester;
9-[(2-benzylphenyl)methyl]-2-phenyl-5-carbamoylcarbazol-4-yl}oxyacetic acid; methyl ester;
9-[(3-benzylphenyl)methyl]-2-phenyl-5-carbamoylcarbazol-4-yl}oxyacetic acid; methyl ester;
9-[(2-phenylphenyl)methyl]-2-phenyl-5-carbamoylcarbazol-4-yl}oxyacetic acid; methyl ester;
9-[(3-phenylphenyl)methyl]-2-phenyl-5-carbamoylcarbazol-4-yl}oxyacetic acid; methyl ester;
9-[(2-naphthyl)methyl]-2-phenyl-5-carbamoylcarbazol-4-yl}oxyacetic acid; methyl ester;
9-[(1-naphthyl)methyl]-2-phenyl-5-carbamoylcarbazol-4-yl}oxyacetic acid; methyl ester;
9-[(phenyl)methyl]-2-(4'-chlorophenyl)-5-carbamoylcarbazol-4-yl}oxyacetic acid; methyl ester;
9-[(2-phenoxyphenyl)methyl]-2-(4'-chlorophenyl)-5-carbamoylcarbazol-4-yl}oxyacetic acid; methyl ester;
9-[(3-phenoxyphenyl)methyl]-2-(4'-chlorophenyl)-5-carbamoylcarbazol-4-yl}oxyacetic acid; methyl ester;
9-[(2-fluorophenyl)methyl]-2-(4'-chlorophenyl)-5-carbamoylcarbazol-4-yl}oxyacetic acid; methyl ester;
9-[(3-fluorophenyl)methyl]-2-(4'-chlorophenyl)-5-carbamoylcarbazol-4-yl}oxyacetic acid; methyl ester;
9-[(2-chlorophenyl)methyl]-2-(4'-chlorophenyl)-5-carbamoylcarbazol-4-yl}oxyacetic acid; methyl ester;
9-[(3-chlorophenyl)methyl]-2-(4'-chlorophenyl)-5-carbamoylcarbazol-4-yl}oxyacetic acid; methyl ester;
9-[(2-bromophenyl)methyl]-2-(4'-chlorophenyl)-5-carbamoylcarbazol-4-yl}oxyacetic acid; methyl ester;
9-[(3-bromophenyl)methyl]-2-(4'-chlorophenyl)-5-carbamoylcarbazol-4-yl}oxyacetic acid; methyl ester;
9-[(2-methylphenyl)methyl]-2-(4'-chlorophenyl)-5-carbamoylcarbazol-4-yl}oxyacetic acid; methyl ester;
9-[(3-methylphenyl)methyl]-2-(4'-chlorophenyl)-5-carbamoylcarbazol-4-yl}oxyacetic acid; methyl ester;

9-[(2-cyanophenyl)methyl]-2-(4'-chlorophenyl)-5-carbamoylcarbazol-4-yl}oxyacetic acid; methyl ester;
9-[(3-cyanophenyl)methyl]-2-(4'-chlorophenyl)-5-carbamoylcarbazol-4-yl}oxyacetic acid; methyl ester;
9-[(2-trifluoromethylphenyl)methyl]-2-(4'-chlorophenyl)-5-carbamoylcarbazol-4-yl}oxyacetic acid; methyl ester;
9-[(3-trifluoromethylphenyl)methyl]-2-(4'-chlorophenyl)-5-carbamoylcarbazol-4-yl}oxyacetic acid; methyl ester;
9-[(2-benzylphenyl)methyl]-2-(4'-chlorophenyl)-5-carbamoylcarbazol-4-yl}oxyacetic acid; methyl ester;
9-[(3-benzylphenyl)methyl]-2-(4'-chlorophenyl)-5-carbamoylcarbazol-4-yl}oxyacetic acid; methyl ester
9-[(2-phenylphenyl)methyl]-2-(4'-chlorophenyl)-5-carbamoylcarbazol-4-yl}oxyacetic acid; methyl ester;
9-[(3-phenylphenyl)methyl]-2-(4'-chlorophenyl)-5-carbamoylcarbazol-4-yl}oxyacetic acid; methyl ester;
9-[(2-naphthyl)methyl]-2-(4'-chlorophenyl)-5-carbamoylcarbazol-4-yl}oxyacetic acid; methyl ester;
9-[(1-naphthyl)methyl]-2-(4'-chlorophenyl)-5-carbamoylcarbazol-4-yl}oxyacetic acid; methyl ester;
9-[(phenyl)methyl]-5-carbamoylcarbazol-4-yl}oxyacetic acid; t-butyl ester;
9-[(2-phenoxyphenyl)methyl]-5-carbamoylcarbazol-4-yl}oxyacetic acid; t-butyl ester;
9-[(3-phenoxyphenyl)methyl]-5-carbamoylcarbazol-4-yl}oxyacetic acid; t-butyl ester;
9-[(2-fluorophenyl)methyl]-5-carbamoylcarbazol-4-yl}oxyacetic acid; t-butyl ester;
9-[(3-fluorophenyl)methyl]-5-carbamoylcarbazol-4-yl}oxyacetic acid; t-butyl ester;
9-[(2-chlorophenyl)methyl]-5-carbamoylcarbazol-4-yl}oxyacetic acid; t-butyl ester;
9-[(3-chlorophenyl)methyl]-5-carbamoylcarbazol-4-yl}oxyacetic acid; t-butyl ester;
9-[(2-bromophenyl)methyl]-5-carbamoylcarbazol-4-yl}oxyacetic acid; t-butyl ester;
9-[(3-bromophenyl)methyl]-5-carbamoylcarbazol-4-yl}oxyacetic acid; t-butyl ester;
9-[(2-methylphenyl)methyl]-5-carbamoylcarbazol-4-yl}oxyacetic acid; t-butyl ester;
9-[(3-methylphenyl)methyl]-5-carbamoylcarbazol-4-yl}oxyacetic acid; t-butyl ester;
9-[(2-cyanophenyl)methyl]-5-carbamoylcarbazol-4-yl}oxyacetic acid; t-butyl ester;
9-[(3-cyanophenyl)methyl]-5-carbamoylcarbazol-4-yl}oxyacetic acid; t-butyl ester;
9-[(2-trifluoromethylphenyl)methyl]-5-carbamoylcarbazol-4-yl}oxyacetic acid; t-butyl ester;
9-[(3-trifluoromethylphenyl)methyl]-5-carbamoylcarbazol-4-yl}oxyacetic acid; t-butyl ester;
9-[(2-benzylphenyl)methyl]-5-carbamoylcarbazol-4-yl}oxyacetic acid; t-butyl ester;
9-[(3-benzylphenyl)methyl]-5-carbamoylcarbazol-4-yl}oxyacetic acid; t-butyl ester;
9-[(2-phenylphenyl)methyl]-5-carbamoylcarbazol-4-yl}oxyacetic acid; t-butyl ester;
9-[(3-phenylphenyl)methyl]-5-carbamoylcarbazol-4-yl}oxyacetic acid; t-butyl ester;
9-[(2-naphthyl)methyl]-5-carbamoylcarbazol-4-yl}oxyacetic acid; t-butyl ester;
9-[(1-naphthyl)methyl]-5-carbamoylcarbazol-4-yl}oxyacetic acid; t-butyl ester;
9-[(phenyl)methyl]-2-methyl-5-carbamoylcarbazol-4-yl}oxyacetic acid; t-butyl ester;
9-[(2-phenoxyphenyl)methyl]-2-methyl-5-carbamoylcarbazol-4-yl}oxyacetic acid; t-butyl ester;
9-[(3-phenoxyphenyl)methyl]-2-methyl-5-carbamoylcarbazol-4-yl}oxyacetic acid; t-butyl ester;
9-[(2-fluorophenyl)methyl]-2-methyl-5-carbamoylcarbazol-4-yl}oxyacetic acid; t-butyl ester;
9-[(3-fluorophenyl)methyl]-2-methyl-5-carbamoylcarbazol-4-yl}oxyacetic acid; t-butyl ester;
9-[(2-chlorophenyl)methyl]-2-methyl-5-carbamoylcarbazol-4-yl}oxyacetic acid; t-butyl ester;
9-[(3-chlorophenyl)methyl]-2-methyl-5-carbamoylcarbazol-4-yl}oxyacetic acid; t-butyl ester;
9-[(2-bromophenyl)methyl]-2-methyl-5-carbamoylcarbazol-4-yl}oxyacetic acid; t-butyl ester;
9-[(3-bromophenyl)methyl]-2-methyl-5-carbamoylcarbazol-4-yl}oxyacetic acid; t-butyl ester;
9-[(2-methylphenyl)methyl]-2-methyl-5-carbamoylcarbazol-4-yl}oxyacetic acid; t-butyl ester;
9-[(3-methylphenyl)methyl]-2-methyl-5-carbamoylcarbazol-4-yl}oxyacetic acid; t-butyl ester;
9-[(2-cyanophenyl)methyl]-2-methyl-5-carbamoylcarbazol-4-yl}oxyacetic acid; t-butyl ester;
9-[(3-cyanophenyl)methyl]-2-methyl-5-carbamoylcarbazol-4-yl}oxyacetic acid; t-butyl ester;
9-[(2-trifluoromethylphenyl)methyl]-2-methyl-5-carbamoylcarbazol-4-yl}oxyacetic acid; t-butyl ester;
9-[(3-trifluoromethylphenyl)methyl]-2-methyl-5-carbamoylcarbazol-4-yl}oxyacetic acid; t-butyl ester;
9-[(2-benzylphenyl)methyl]-2-methyl-5-carbamoylcarbazol-4-yl}oxyacetic acid; t-butyl ester;
9-[(3-benzylphenyl)methyl]-2-methyl-5-carbamoylcarbazol-4-yl}oxyacetic acid; t-butyl ester;
9-[(2-phenylphenyl)methyl]-2-methyl-5-carbamoylcarbazol-4-yl}oxyacetic acid; t-butyl ester;
9-[(3-phenylphenyl)methyl]-2-methyl-5-carbamoylcarbazol-4-yl}oxyacetic acid; t-butyl ester;
9-[(2-naphthyl)methyl]-2-methyl-5-carbamoylcarbazol-4-yl}oxyacetic acid; t-butyl ester;
9-[(1-naphthyl)methyl]-2-methyl-5-carbamoylcarbazol-4-yl}oxyacetic acid; t-butyl ester;
9-[(phenyl)methyl]-2-ethyl-5-carbamoylcarbazol-4-yl}oxyacetic acid; t-butyl ester;
9-[(2-phenoxyphenyl)methyl]-2-ethyl-5-carbamoylcarbazol-4-yl}oxyacetic acid; t-butyl ester;
9-[(3-phenoxyphenyl)methyl]-2-ethyl-5-carbamoylcarbazol-4-yl}oxyacetic acid; t-butyl ester;
9-[(2-fluorophenyl)methyl]-2-ethyl-5-carbamoylcarbazol-4-yl}oxyacetic acid; t-butyl ester;
9-[(3-fluorophenyl)methyl]-2-ethyl-5-carbamoylcarbazol-4-yl}oxyacetic acid; t-butyl ester;
9-[(2-chlorophenyl)methyl]-2-ethyl-5-carbamoylcarbazol-4-yl}oxyacetic acid; t-butyl ester;
9-[(3-chlorophenyl)methyl]-2-ethyl-5-carbamoylcarbazol-4-yl}oxyacetic acid; t-butyl ester;
9-[(2-bromophenyl)methyl]-2-ethyl-5-carbamoylcarbazol-4-yl}oxyacetic acid; t-butyl ester;
9-[(3-bromophenyl)methyl]-2-ethyl-5-carbamoylcarbazol-4-yl}oxyacetic acid; t-butyl ester;
9-[(2-methylphenyl)methyl]-2-ethyl-5-carbamoylcarbazol-4-yl}oxyacetic acid; t-butyl ester;
9-[(3-methylphenyl)methyl]-2-ethyl-5-carbamoylcarbazol-4-yl}oxyacetic acid; t-butyl ester;
9-[(2-cyanophenyl)methyl]-2-ethyl-5-carbamoylcarbazol-4-yl}oxyacetic acid; t-butyl ester;
9-[(3-cyanophenyl)methyl]-2-ethyl-5-carbamoylcarbazol-4-yl}oxyacetic acid; t-butyl ester;
9-[(2-trifluoromethylphenyl)methyl]-2-ethyl-5-carbamoylcarbazol-4-yl}oxyacetic acid; t-butyl ester;
9-[(3-trifluoromethylphenyl)methyl]-2-ethyl-5-carbamoylcarbazol-4-yl}oxyacetic acid; t-butyl ester;
9-[(2-benzylphenyl)methyl]-2-ethyl-5-carbamoylcarbazol-4-yl}oxyacetic acid; t-butyl ester;

9-[(3-benzylphenyl)methyl]-2-ethyl-5-carbamoylcarbazol-4-yl}oxyacetic acid; t-butyl ester;
9-[(2-phenylphenyl)methyl]-2-ethyl-5-carbamoylcarbazol-4-yl}oxyacetic acid; t-butyl ester;
9-[(3-phenylphenyl)methyl]-2-ethyl-5-carbamoylcarbazol-4-yl}oxyacetic acid; t-butyl ester;
9-[(2-naphthyl)methyl]-2-ethyl-5-carbamoylcarbazol-4-yl}oxyacetic acid; t-butyl ester;
9-[(1-naphthyl)methyl]-2-ethyl-5-carbamoylcarbazol-4-yl}oxyacetic acid; t-butyl ester;
9-[(phenyl)methyl]-2-isopropyl-5-carbamoylcarbazol-4-yl}oxyacetic acid; t-butyl ester;
9-[(2-phenoxyphenyl)methyl]-2-isopropyl-5-carbamoylcarbazol-4-yl}oxyacetic acid; t-butyl ester;
9-[(3-phenoxyphenyl)methyl]-2-isopropyl-5-carbamoylcarbazol-4-yl}oxyacetic acid; t-butyl ester;
9-[(2-fluorophenyl)methyl]-2-isopropyl-5-carbamoylcarbazol-4-yl}oxyacetic acid; t-butyl ester;
9-[(3-fluorophenyl)methyl]-2-isopropyl-5-carbamoylcarbazol-4-yl}oxyacetic acid; t-butyl ester;
9-[(2-chlorophenyl)methyl]-2-isopropyl-5-carbamoylcarbazol-4-yl}oxyacetic acid; t-butyl ester;
9-[(3-chlorophenyl)methyl]-2-isopropyl-5-carbamoylcarbazol-4-yl}oxyacetic acid; t-butyl ester;
9-[(2-bromophenyl)methyl]-2-isopropyl-5-carbamoylcarbazol-4-yl}oxyacetic acid; t-butyl ester;
9-[(3-bromophenyl)methyl]-2-isopropyl-5-carbamoylcarbazol-4-yl}oxyacetic acid; t-butyl ester;
9-[(2-methylphenyl)methyl]-2-isopropyl-5-carbamoylcarbazol-4-yl}oxyacetic acid; t-butyl ester;
9-[(3-methylphenyl)methyl]-2-isopropyl-5-carbamoylcarbazol-4-yl}oxyacetic acid; t-butyl ester;
9-[(2-cyanophenyl)methyl]-2-isopropyl-5-carbamoylcarbazol-4-yl}oxyacetic acid; t-butyl ester;
9-[(3-cyanophenyl)methyl]-2-isopropyl-5-carbamoylcarbazol-4-yl}oxyacetic acid; t-butyl ester;
9-[(2-trifluoromethylphenyl)methyl]-2-isopropyl-5-carbamoylcarbazol-4-yl}oxyacetic acid; t-butyl ester;
9-[(3-trifluoromethylphenyl)methyl]-2-isopropyl-5-carbamoylcarbazol-4-yl}oxyacetic acid; t-butyl ester;
9-[(2-benzylphenyl)methyl]-2-isopropyl-5-carbamoylcarbazol-4-yl}oxyacetic acid; t-butyl ester;
9-[(3-benzylphenyl)methyl]-2-isopropyl-5-carbamoylcarbazol-4-yl}oxyacetic acid; t-butyl ester;
9-[(2-phenylphenyl)methyl]-2-isopropyl-5-carbamoylcarbazol-4-yl}oxyacetic acid; t-butyl ester;
9-[(3-phenylphenyl)methyl]-2-isopropyl-5-carbamoylcarbazol-4-yl}oxyacetic acid; t-butyl ester;
9-[(2-naphthyl)methyl]-2-isopropyl-5-carbamoylcarbazol-4-yl}oxyacetic acid; t-butyl ester;
9-[(1-naphthyl)methyl]-2-isopropyl-5-carbamoylcarbazol-4-yl}oxyacetic acid; t-butyl ester;
9-[(phenyl)methyl]-2-pentyl-5-carbamoylcarbazol-4-yl}oxyacetic acid; t-butyl ester;
9-[(2-phenoxyphenyl)methyl]-2-pentyl-5-carbamoylcarbazol-4-yl}oxyacetic acid; t-butyl ester;
9-[(3-phenoxyphenyl)methyl]-2-pentyl-5-carbamoylcarbazol-4-yl}oxyacetic acid; t-butyl ester;
9-[(2-fluorophenyl)methyl]-2-pentyl-5-carbamoylcarbazol-4-yl}oxyacetic acid; t-butyl ester;
9-[(3-fluorophenyl)methyl]-2-pentyl-5-carbamoylcarbazol-4-yl}oxyacetic acid; t-butyl ester;
9-[(2-chlorophenyl)methyl]-2-pentyl-5-carbamoylcarbazol-4-yl}oxyacetic acid; t-butyl ester;
9-[(3-chlorophenyl)methyl]-2-pentyl-5-carbamoylcarbazol-4-yl}oxyacetic acid; t-butyl ester;
9-[(2-bromophenyl)methyl]-2-pentyl-5-carbamoylcarbazol-4-yl}oxyacetic acid; t-butyl ester;
9-[(3-bromophenyl)methyl]-2-pentyl-5-carbamoylcarbazol-4-yl}oxyacetic acid; t-butyl ester;
9-[(2-methylphenyl)methyl]-2-pentyl-5-carbamoylcarbazol-4-yl}oxyacetic acid; t-butyl ester;
9-[(3-methylphenyl)methyl]-2-pentyl-5-carbamoylcarbazol-4-yl}oxyacetic acid; t-butyl ester;
9-[(2-cyanophenyl)methyl]-2-pentyl-5-carbamoylcarbazol-4-yl}oxyacetic acid; t-butyl ester;
9-[(3-cyanophenyl)methyl]-2-pentyl-5-carbamoylcarbazol-4-yl}oxyacetic acid; t-butyl ester;
9-[(2-trifluoromethylphenyl)methyl]-2-pentyl-5-carbamoylcarbazol-4-yl}oxyacetic acid; t-butyl ester;
9-[(3-trifluoromethylphenyl)methyl]-2-pentyl-5-carbamoylcarbazol-4-yl}oxyacetic acid; t-butyl ester;
9-[(2-benzylphenyl)methyl]-2-pentyl-5-carbamoylcarbazol-4-yl}oxyacetic acid; t-butyl ester;
9-[(3-benzylphenyl)methyl]-2-pentyl-5-carbamoylcarbazol-4-yl}oxyacetic acid; t-butyl ester;
9-[(2-phenylphenyl)methyl]-2-pentyl-5-carbamoylcarbazol-4-yl}oxyacetic acid; t-butyl ester;
9-[(3-phenylphenyl)methyl]-2-pentyl-5-carbamoylcarbazol-4-yl}oxyacetic acid; t-butyl ester;
9-[(2-naphthyl)methyl]-2-pentyl-5-carbamoylcarbazol-4-yl}oxyacetic acid; t-butyl ester;
9-[(1-naphthyl)methyl]-2-pentyl-5-carbamoylcarbazol-4-yl}oxyacetic acid; t-butyl ester;
9-[(phenyl)methyl]-2-phenyl-5-carbamoylcarbazol-4-yl}oxyacetic acid; t-butyl ester;
9-[(2-phenoxyphenyl)methyl]-2-phenyl-5-carbamoylcarbazol-4-yl}oxyacetic acid; t-butyl ester;
9-[(3-phenoxyphenyl)methyl]-2-phenyl-5-carbamoylcarbazol-4-yl}oxyacetic acid; t-butyl ester;
9-[(2-fluorophenyl)methyl]-2-phenyl-5-carbamoylcarbazol-4-yl}oxyacetic acid; t-butyl ester;
9-[(3-fluorophenyl)methyl]-2-phenyl-5-carbamoylcarbazol-4-yl}oxyacetic acid; t-butyl ester;
9-[(2-chlorophenyl)methyl]-2-phenyl-5-carbamoylcarbazol-4-yl}oxyacetic acid; t-butyl ester;
9-[(3-chlorophenyl)methyl]-2-phenyl-5-carbamoylcarbazol-4-yl}oxyacetic acid; t-butyl ester;
9-[(2-bromophenyl)methyl]-2-phenyl-5-carbamoylcarbazol-4-yl}oxyacetic acid; t-butyl ester;
9-[(3-bromophenyl)methyl]-2-phenyl-5-carbamoylcarbazol-4-yl}oxyacetic acid; t-butyl ester;
9-[(2-methylphenyl)methyl]-2-phenyl-5-carbamoylcarbazol-4-yl}oxyacetic acid; t-butyl ester;
9-[(3-methylphenyl)methyl]-2-phenyl-5-carbamoylcarbazol-4-yl}oxyacetic acid; t-butyl ester;
9-[(2-cyanophenyl)methyl]-2-phenyl-5-carbamoylcarbazol-4-yl}oxyacetic acid; t-butyl ester;
9-[(3-cyanophenyl)methyl]-2-phenyl-5-carbamoylcarbazol-4-yl}oxyacetic acid; t-butyl ester;
9-[(2-trifluoromethylphenyl)methyl]-2-phenyl-5-carbamoylcarbazol-4-yl}oxyacetic acid; t-butyl ester;
9-[(3-trifluoromethylphenyl)methyl]-2-phenyl-5-carbamoylcarbazol-4-yl}oxyacetic acid; t-butyl ester;
9-[(2-benzylphenyl)methyl]-2-phenyl-5-carbamoylcarbazol-4-yl}oxyacetic acid; t-butyl ester;
9-[(3-benzylphenyl)methyl]-2-phenyl-5-carbamoylcarbazol-4-yl}oxyacetic acid; t-butyl ester;
9-[(2-phenylphenyl)methyl]-2-phenyl-5-carbamoylcarbazol-4-yl}oxyacetic acid; t-butyl ester;
9-[(3-phenylphenyl)methyl]-2-phenyl-5-carbamoylcarbazol-4-yl}oxyacetic acid; t-butyl ester;
9-[(2-naphthyl)methyl]-2-phenyl-5-carbamoylcarbazol-4-yl}oxyacetic acid; t-butyl ester;
9-[(1-naphthyl)methyl]-2-phenyl-5-carbamoylcarbazol-4-yl}oxyacetic acid; t-butyl ester;

9-[(phenyl)methyl]-2-(4'-chlorophenyl)-5-carbamoylcarbazol-4-yl}oxyacetic acid; t-butyl ester;
9-[(2-phenoxyphenyl)methyl]-2-(4'-chlorophenyl)-5-carbamoylcarbazol-4-yl}oxyacetic acid; t-butyl ester;
9-[(3-phenoxyphenyl)methyl]-2-(4'-chlorophenyl)-5-carbamoylcarbazol-4-yl}oxyacetic acid; t-butyl ester;
9-[(2-fluorophenyl)methyl]-2-(4'-chlorophenyl)-5-carbamoylcarbazol-4-yl}oxyacetic acid; t-butyl ester;
9-[(3-fluorophenyl)methyl]-2-(4'-chlorophenyl)-5-carbamoylcarbazol-4-yl}oxyacetic acid; t-butyl ester;
9-[(2-chlorophenyl)methyl]-2-(4'-chlorophenyl)-5-carbamoylcarbazol-4-yl}oxyacetic acid; t-butyl ester;
9-[(3-chlorophenyl)methyl]-2-(4'-chlorophenyl)-5-carbamoylcarbazol-4-yl}oxyacetic acid; t-butyl ester;
9-[(2-bromophenyl)methyl]-2-(4'-chlorophenyl)-5-carbamoylcarbazol-4-yl}oxyacetic acid; t-butyl ester;
9-[(3-bromophenyl)methyl]-2-(4'-chlorophenyl)-5-carbamoylcarbazol-4-yl}oxyacetic acid; t-butyl ester;
9-[(2-methylphenyl)methyl]-2-(4'-chlorophenyl)-5-carbamoylcarbazol-4-yl}oxyacetic acid; t-butyl ester;
9-[(3-methylphenyl)methyl]-2-(4'-chlorophenyl)-5-carbamoylcarbazol-4-yl}oxyacetic acid; t-butyl ester;
9-[(2-cyanophenyl)methyl]-2-(4'-chlorophenyl)-5-carbamoylcarbazol-4-yl}oxyacetic acid; t-butyl ester;
9-[(3-cyanophenyl)methyl]-2-(4'-chlorophenyl)-5-carbamoylcarbazol-4-yl}oxyacetic acid; t-butyl ester;
9-[(2-trifluoromethylphenyl)methyl]-2-(4'-chlorophenyl)-5-carbamoylcarbazol-4-yl}oxyacetic acid; t-butyl ester;
9-[(3-trifluoromethylphenyl)methyl]-2-(4'-chlorophenyl)-5-carbamoylcarbazol-4-yl}oxyacetic acid; t-butyl ester;
9-[(2-benzylphenyl)methyl]-2-(4'-chlorophenyl)-5-carbamoylcarbazol-4-yl}oxyacetic acid; t-butyl ester;
9-[(3-benzylphenyl)methyl]-2-(4'-chlorophenyl)-5-carbamoylcarbazol-4-yl}oxyacetic acid; t-butyl ester;
9-[(2-phenylphenyl)methyl]-2-(4'-chlorophenyl)-5-carbamoylcarbazol-4-yl}oxyacetic acid; t-butyl ester;
9-[(3-phenylphenyl)methyl]-2-(4'-chlorophenyl)-5-carbamoylcarbazol-4-yl}oxyacetic acid; t-butyl ester;
9-[(2-naphthyl)methyl]-2-(4'-chlorophenyl)-5-carbamoylcarbazol-4-yl}oxyacetic acid; t-butyl ester;
9-[(1-naphthyl)methyl]-2-(4'-chlorophenyl)-5-carbamoylcarbazol-4-yl}oxyacetic acid; t-butyl ester;
{9-[(2-(1-pyrrolidinyl)ethyl)]-5-carbamoylcarbazol-4-yl}oxyacetic acid;
{9-[(2-(1-piperidinyl)ethyl)]-5-carbamoylcarbazol-4-yl}oxyacetic acid;
{9-[(2-(1-morpholino)ethyl)]-5-carbamoylcarbazol-4-yl}oxyacetic acid;
{9-(1-methyl-2-pyrrolidinylmethyl)-5-carbamoylcarbazol-4-yl}oxyacetic acid;
{9-(1-methyl-2-piperidinylmethyl)-5-carbamoylcarbazol-4-yl}oxyacetic acid;
{9-(1-ethyl-2-piperidinyl)-5-carbamoylcarbazol-4-yl}oxyacetic acid;
{9-(1-methyl-2-piperidinyl)-5-carbamoylcarbazol-4-yl}oxyacetic acid;
{9-[1-ethyl-3-pyrrolidinyl]-5-carbamoylcarbazol-4-yl}oxyacetic acid;
{9-[1-methyl-3-pyrrolidinyl]-5-carbamoylcarbazol-4-yl}oxyacetic acid;
{9-[3-quinuclidine]-5-carbamoylcarbazol-4-yl}oxyacetic acid;
{9-[cinnamyl]-5-carbamoylcarbazol-4-yl}oxyacetic acid;
{9-[phenethyl]-5-carbamoylcarbazol-4-yl}oxyacetic acid;
{9-[3-phenyl-n-propyl]-5-carbamoylcarbazol-4-yl}oxyacetic acid;
{9-[3-(4-fluorophenoxy)-phenylmethyl]-5-carbamoylcarbazol-4-yl}oxyacetic acid;

2-[4-oxo-5-carboxamido-9-(2-methylbenzyl)-9H-pyrido[3,4-b]indolyl]acetic acid;
2-[4-oxo-5-carboxamido-9-(3-methylbenzyl)-9H-pyrido[3,4-b]indolyl]acetic acid;
2-[4-oxo-5-carboxamido-9-(4-methylbenzyl)-9H-pyrido[3,4-b]indolyl]acetic acid;
2-[4-oxo-5-carboxamido-9-(4-tert-butylbenzyl)-9H-pyrido[3,4-b]indolyl]acetic acid;
2-[4-oxo-5-carboxamido-9-pentafluorobenzyl-9H-pyrido[3,4-b]indolyl]acetic acid;
2-[4-oxo-5-carboxamido-9-(2-fluorobenzyl)-9H-pyrido[3,4-b]indolyl]acetic acid;
2-[4-oxo-5-carboxamido-9-(3-fluorobenzyl)-9H-pyrido[3,4-b]indolyl]acetic acid;
2-[4-oxo-5-carboxamido-9-(4-fluorobenzyl)-9H-pyrido[3,4-b]indolyl]acetic acid;
2-[4-oxo-5-carboxamido-9-(2,6-difluorobenzyl)-9H-pyrido[3,4-b]indolyl]acetic acid;
2-[4-oxo-5-carboxamido-9-(3,4-difluorobenzyl)-9H-pyrido[3,4-b]indolyl]acetic acid;
2-[4-oxo-5-carboxamido-9-(2,5-difluorobenzyl)-9H-pyrido[3,4-b]indolyl]acetic acid;
2-[4-oxo-5-carboxamido-9-(3,5-difluorobenzyl)-9H-pyrido[3,4-b]indolyl]acetic acid;
2-[4-oxo-5-carboxamido-9-(2,4-difluorobenzyl)-9H-pyrido[3,4-b]indolyl]acetic acid;
2-[4-oxo-5-carboxamido-9-(2,3-difluorobenzyl)-9H-pyrido[3,4-b]indolyl]acetic acid;
2-[4-oxo-5-carboxamido-9-[2-(trifluoromethyl)benzyl]-9H-pyrido[3,4-b]indolyl]acetic acid;
2-[4-oxo-5-carboxamido-9-[3-(trifluoromethyl)benzyl]-9H-pyrido[3,4-b]indolyl]acetic acid;
2-[4-oxo-5-carboxamido-9-[4-(trifluoromethyl)benzyl]-9H-pyrido[3,4-b]indolyl]acetic acid;
2-[4-oxo-5-carboxamido-9-[3,5-bis(trifluoromethyl)benzyl]-9H-pyrido[3,4-b]indolyl]acetic acid;
2-[4-oxo-5-carboxamido-9-[2,4-bis(trifluoromethyl)benzyl]-9H-pyrido[3,4-b]indolyl]acetic acid;
2-[4-oxo-5-carboxamido-9-(a-methylnaphthyl)-9H-pyrido[3,4-b]indolyl]acetic acid;
2-[4-oxo-5-carboxamido-9-(b-methylnaphthyl)-9H-pyrido[3,4-b]indolyl]acetic acid;
2-[4-oxo-5-carboxamido-9-(3,5-dimethylbenzyl)-9H-pyrido[3,4-b]indolyl]acetic acid;
2-[4-oxo-5-carboxamido-9-(2,4-dimethylbenzyl)-9H-pyrido[3,4-b]indolyl]acetic acid;
2-[4-oxo-5-carboxamido-9-(2-phenylbenzyl)-9H-pyrido[3,4-b]indolyl]acetic acid;
2-[4-oxo-5-carboxamido-9-(3-phenylbenzyl)-9H-pyrido[3,4-b]indolyl]acetic acid;
2-[4-oxo-5-carboxamido-9-(4-phenylbenzyl)-9H-pyrido[3,4-b]indolyl]acetic acid;
2-[4-oxo-5-carboxamido-9-(1-fluorenylmethyl)-9H-pyrido[3,4-b]indolyl]acetic acid;
2-[4-oxo-5-carboxamido-9-(2-fluoro-3-methylbenzyl)-9H-pyrido[3,4-b]indolyl]acetic acid;
2-[4-oxo-5-carboxamido-9-(3-benzoylbenzyl)-9H-pyrido[3,4-b]indolyl]acetic acid;
2-[4-oxo-5-carboxamido-9-(2-phenoxybenzyl)-9H-pyrido[3,4-b]indolyl]acetic acid;
2-[4-oxo-5-carboxamido-9-(3-phenoxybenzyl)-9H-pyrido[3,4-b]indolyl]acetic acid;
2-[4-oxo-5-carboxamido-9-(4-phenoxybenzyl)-9H-pyrido[3,4-b]indolyl]acetic acid;
2-[4-oxo-5-carboxamido-9-[3-[2-(fluorophenoxy)benzyl]]-9H-pyrido[3,4-b]indolyl]acetic acid;
2-[4-oxo-5-carboxamido-9-[3-[4-(fluorophenoxy)benzyl]]-9H-pyrido[3,4-b]indolyl]acetic acid;

2-[4-oxo-5-carboxamido-9-[2-fluoro-3-(trifluoromethyl)benzyl]-9H-pyrido[3,4-b]indolyl]acetic acid;
2-[4-oxo-5-carboxamido-9-[2-fluoro-4-(trifluoromethyl)benzyl]-9H-pyrido[3,4-b]indolyl]acetic acid;
2-[4-oxo-5-carboxamido-9-[2-fluoro-5-(trifluoromethyl)benzyl]-9H-pyrido[3,4-b]indolyl]acetic acid;
2-[4-oxo-5-carboxamido-9-[3-fluoro-5-(trifluoromethyl)benzyl]-9H-pyrido[3,4-b]indolyl]acetic acid;
2-[4-oxo-5-carboxamido-9-[4-fluoro-2-(trifluoromethyl)benzyl]-9H-pyrido[3,4-b]indolyl]acetic acid;
2-[4-oxo-5-carboxamido-9-[4-fluoro-3-(trifluoromethyl)benzyl]-9H-pyrido[3,4-b]indolyl]acetic acid;
2-[4-oxo-5-carboxamido-9-[2-fluoro-6-(trifluoromethyl)benzyl]-9H-pyrido[3,4-b]indolyl]acetic acid;
2-[4-oxo-5-carboxamido-9-(2,3,6-trifluorobenzyl)-9H-pyrido[3,4-b]indolyl]acetic acid;
2-[4-oxo-5-carboxamido-9-(2,3,5-trifluorobenzyl)-9H-pyrido[3,4-b]indolyl]acetic acid;
2-[4-oxo-5-carboxamido-9-(2,4,5-trifluorobenzyl)-9H-pyrido[3,4-b]indolyl]acetic acid;
2-[4-oxo-5-carboxamido-9-(2,4,6-trifluorobenzyl)-9H-pyrido[3,4-b]indolyl]acetic acid;
2-[4-oxo-5-carboxamido-9-(2,3,4-trifluorobenzyl)-9H-pyrido[3,4-b]indolyl]acetic acid;
2-[4-oxo-5-carboxamido-9-(3,4,5-trifluorobenzyl)-9H-pyrido[3,4-b]indolyl]acetic acid;
2-[4-oxo-5-carboxamido-9-[3-(trifluoromethoxyl)benzyl]-9H-pyrido[3,4-b]indolyl]acetic acid;
2-[4-oxo-5-carboxamido-9-[4-(trifluoromethoxyl)benzyl]-9H-pyrido[3,4-b]indolyl]acetic acid;
2-[4-oxo-5-carboxamido-9-[4-methoxy(tetrafluoro)benzyl]-9H-pyrido[3,4-b]indolyl]acetic acid;
2-[4-oxo-5-carboxamido-9-(2-methoxybenzyl)-9H-pyrido[3,4-b]indolyl]acetic acid;
2-[4-oxo-5-carboxamido-9-(3-methoxybenzyl)-9H-pyrido[3,4-b]indolyl]acetic acid;
2-[4-oxo-5-carboxamido-9-(4-methoxybenzyl)-9H-pyrido[3,4-b]indolyl]acetic acid;
2-[4-oxo-5-carboxamido-9-(4-ethylbenzyl)-9H-pyrido[3,4-b]indolyl]acetic acid;
2-[4-oxo-5-carboxamido-9-(4-isopropylbenzyl)-9H-pyrido[3,4-b]indolyl]acetic acid;
2-[4-oxo-5-carboxamido-9-(3,4,5-trimethoxybenzyl)-9H-pyrido[3,4-b]indolyl]acetic acid;
2-[4-oxo-5-carboxamido-9-(3,4-methylenedioxybenzyl)-9H-pyrido[3,4-b]indolyl]acetic acid;
2-[4-oxo-5-carboxamido-9-(4-methoxy-3-methylbenzyl)-9H-pyrido[3,4-b]indolyl]acetic acid;
2-[4-oxo-5-carboxamido-9-(3,5-dimethoxybenzyl)-9H-pyrido[3,4-b]indolyl]acetic acid;
2-[4-oxo-5-carboxamido-9-(2,5-dimethoxybenzyl)-9H-pyrido[3,4-b]indolyl]acetic acid;
2-[4-oxo-5-carboxamido-9-(4-ethoxybenzyl)-9H-pyrido[3,4-b]indolyl]acetic acid;
2-[4-oxo-5-carboxamido-9-(cyclohexylmethyl)-9H-pyrido[3,4-b]indolyl]acetic acid;
2-[4-oxo-5-carboxamido-9-(cyclopentylmethyl)-9H-pyrido[3,4-b]indolyl]acetic acid;
2-[4-oxo-5-carboxamido-9-ethyl-9H-pyrido[3,4-b]indolyl]acetic acid;
2-[4-oxo-5-carboxamido-9-(1-propyl)-9H-pyrido[3,4-b]indolyl]acetic acid;
2-[4-oxo-5-carboxamido-9-(2-propyl)-9H-pyrido[3,4-b]indolyl]acetic acid;
2-[4-oxo-5-carboxamido-9-(1-butyl)-9H-pyrido[3,4-b]indolyl]acetic acid;
2-[4-oxo-5-carboxamido-9-(2-butyl)-9H-pyrido[3,4-b]indolyl]acetic acid;
2-[4-oxo-5-carboxamido-9-isobutyl-9H-pyrido[3,4-b]indolyl]acetic acid;
2-[4-oxo-5-carboxamido-9-[2-(1-phenylethyl)]-9H-pyrido[3,4-b]indolyl]acetic acid;
2-[4-oxo-5-carboxamido-9-[3-(1-phenylpropyl)]-9H-pyrido[3,4-b]indolyl]acetic acid;
2-[4-oxo-5-carboxamido-9-[4-(1-phenylbutyl)]-9H-pyrido[3,4-b]indolyl]acetic acid;
2-[4-oxo-5-carboxamido-9-(1-pentyl)-9H-pyrido[3,4-b]indolyl]acetic acid; and
2-[4-oxo-5-carboxamido-9-(1-hexyl)-9H-pyrido[3,4-b]indolyl]acetic acid;

or a pharmaceutically acceptable racemate, solvate, tautomer, optical isomer, prodrug derivative or salt thereof.

Synthesis Methods

The compounds of formula I where Z is cyclohexene are prepared according to the following reaction Schemes I(a) and (c).

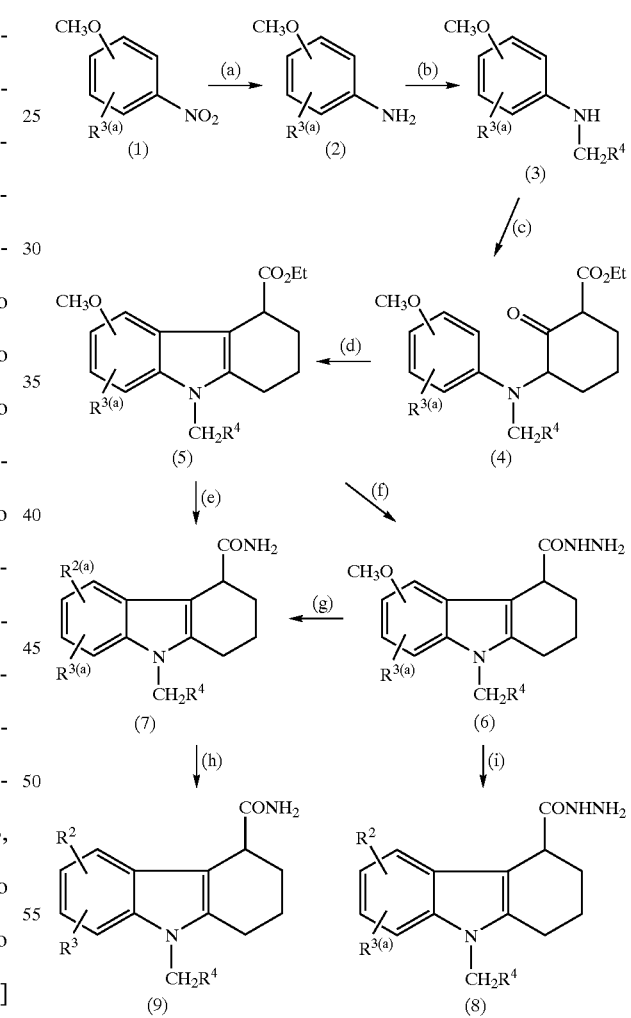

Wherein;
$R^1$ is —$NH_2$, $R^3(a)$ is H, —$O(C_1$–$C_4)$alkyl, halo, —$(C_1$–$C_6)$alkyl, phenyl, —$(C_1$–$C_4)$alkylphenyl; phenyl substituted with —$(C_1$–$C_6)$alkyl, halo, or —$CF_3$; —$CH_2OSi(C_1$–$C_6)$alkyl, furyl, thiophenyl, —$(C_1$–$C_6)$hydroxyalkyl, —$(C_1$–$C_6)$alkoxy$(C_1$–$C_6)$alkyl, —$(C_1$–$C_6)$alkoxy$(C_1$–$C_6)$alkenyl; or —$(CH_2)_nR^8$ where $R^8$ is H, —$CONH_2$, —$NR^9R^{10}$, —CN or phenyl where $R^9$ and $R^{10}$ are independently hydrogen, —$CF_3$, phenyl, —($C_1$-$C_4$)alkyl, —($C_1$-$C_4$)alkylphenyl or -phenyl($C_1$-$C_4$)alkyl and n is 1 to 8;

when $R^1$ is —$NHNH_2$, $R^3(a)$ is H, —O($C_1$-$C_4$)alkyl, halo, —($C_1$-$C_6$)alkyl, phenyl, —($C_1$-$C_4$)alkylphenyl; phenyl substituted with —($C_1$-$C_6$)alkyl, halo or —$CF_3$; —$CH_2OSi(C_1$-$C_6)$alkyl, furyl, thiophenyl, —($C_1$-$C_6$) hydroxyalkyl, —($C_1$-$C_6$)alkoxy ($C_1$-$C_6$)alkyl, —($C_1$-$C_6$)alkoxy ($C_1$-$C_6$)alkenyl; or —$(CH_2)_nR^8$ where $R^8$ is H, —$NR^9R^{10}$, —CN or phenyl where $R^9$ and $R^{10}$ are independently hydrogen, —$CF_3$, phenyl, —($C_1$-$C_4$)alkyl, —($C_1$-$C_4$)alkylphenyl or -phenyl ($C_1$-$C_4$)alkyl and n is 1 to 8;

$R^{2(a)}$ is —$OCH_3$ or —OH.

An appropriately substituted nitrobenzene (1) can be reduced to the aniline (2) by treatment with a reducing agent, such as hydrogen in the presence of Pd/C, preferably at room temperature.

Compound (2) is N-alkylated at temperatures of from about 0 to 20° C. using an alkylating agent such as an appropriately substituted aldehyde and sodium cyanoborohydride to form (3). Alternately, an appropriately substituted benzyl halide may be used for the first alkylation step. The resulting intermediate is further N-alkylated by treatment with 2-carbethoxy-6-bromocyclohexanone, preferably at temperatures of about 80° C. to yield (4) or by treatment with potassium hexamethyldisilazide and the bromoketoester.

The product (4) is cyclized to the tetrahydrocarbazole (5) by refluxing with $ZnCl_2$ in benzene for from about 1 to 2 days, preferably at 80° C. (Ref 1). Compound (5) is converted to the hydrazide (6) by treatment with hydrazine at temperatures of about 100° C., or to the amide (7) by reacting with methylchloroaluminum amide in benzene. (Ref 2) Alternatively, (7) may be produced by treatment of (6) with Raney nickel active catalyst.

It will be readily appreciated that when $R^{3(a)}$ is:

conversion to the amide will also be achieved in this procedure.

Compounds (6) and (7) may be dealkylated, preferably at 0° C. to room temperature, with a dealkylating agent, such as boron tribromide or sodium thioethoxide, to give compound (7) where $R^{2(a)}$ is —OH, which may then be further converted to compound (9), by realkylating with a base, such as sodium hydride, and an alkylating agent, such as $Br(CH_2)_mR^5$, where $R^5$ is the carboxylate or phosphonic diester or nitrile as defined above. Conversion of $R^2$ to the carboxylic acid may be accomplished by treatment with an aqueous base. When $R^2$ is nitrile, conversion to the tetrazole may be achieved by reacting with tri-butyl tin azide or conversion to the carboxamide may be achieved by reacting with basic hydrogen peroxide. When $R^2$ is the phosphonic diester, conversion to the acid may be achieved by reacting with a dealkylating agent such as trimethylsilyl bromide. The monoester may be accomplished by reacting the diester with an aqueous base.

When $R^2$ and $R^3$ are both methoxy, selective demethylation can be achieved by treating with sodium ethanethiolate in dimethylformamide at 100° C.

Ref 1 Julia, M.; Lenzi, J. Preparation d'acides tetrahydro-1,2,3,4-carbazole-1 ou -4. Bull.Soc.Chim.France, 1962, 2262–2263.

Ref 2 Levin, J. I.; Turos, E.; Weinreb, S. M. An alternative procedure for the aluminum-mediated conversion of esters to amides. Syn.Comm., 1982, 12, 989–993.

An alternative synthesis of intermediate (5) is shown in Scheme I(b), as follows.

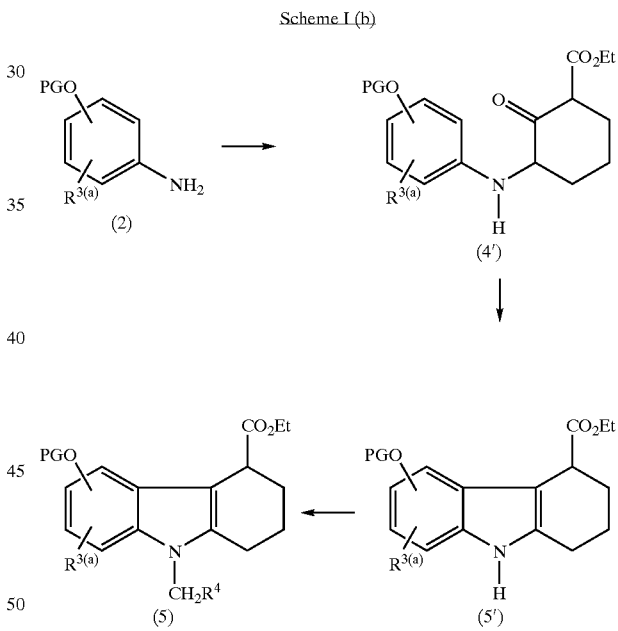

where PG is a protecting group;

$R^{3a}$ is as defined in Scheme 1, above.

The aniline (2) is N-alkylated with 2-carbethoxy-6-bromocyclohexanone in dimethyl formamide in the presence of sodium bicarbonate for 8–24 hours at 50° C. Preferred protecting groups include methyl, carbonate, and silyl groups, such as t-butyldimethylsilyl. The reaction product (4') is cyclized to (5') using the $ZnCl_2$ in benzene conditions described in Scheme I(a), above. N-alkylation of (5') to yield (5) is accomplished by treatment with sodium hydride and the appropriate alkyl halide in dimethylformamide at room temperature for 4–8 hours.

Scheme II

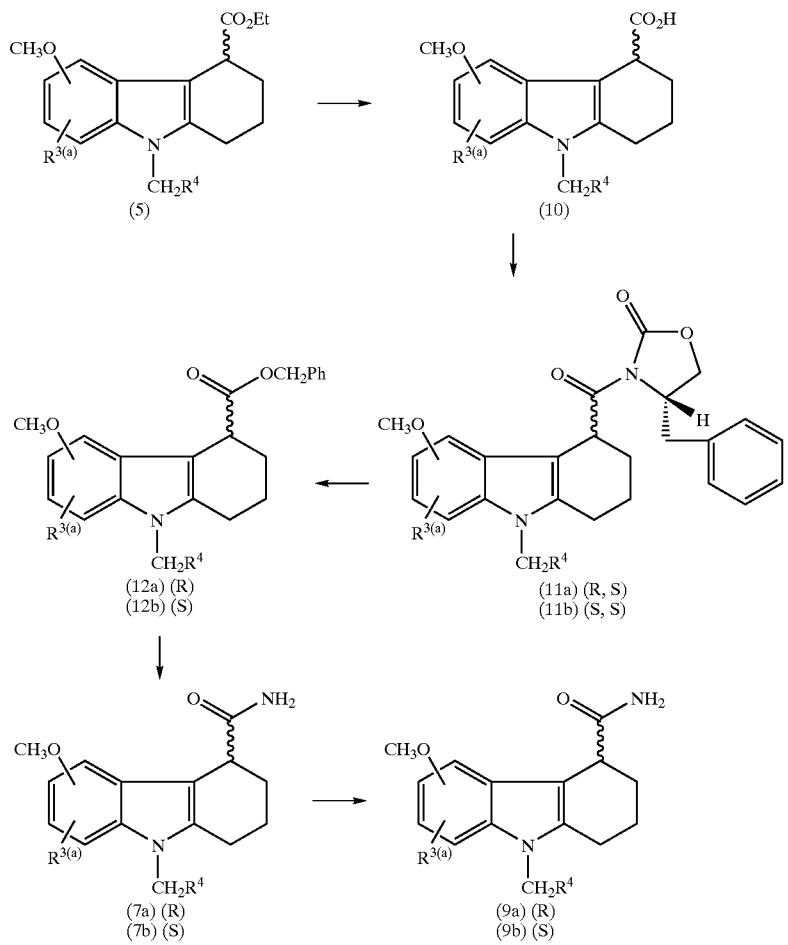

$R^{3(a)}$ is as defined in Scheme I.

As discussed in Scheme I above, carbazole (5) is hydrolyzed to the carboxylic acid (10) by treatment with an aqueous base, preferably at room temperature to about 100° C. The intermediate is then converted to an acid chloride utilizing, for example, oxalyl chloride and dimethylformamide, and then further reacted with a lithium salt of (S) or (R)-4-alkyl-2-oxazolidine at a temperature of about −75° C., to give (11a) and (11b), which are separable by chromatography.

The diastereomers are converted to the corresponding enantiomeric benzyl esters (12) by brief treatment at temperatures of about 0° C. to room temperature with lithium benzyl oxide. (Ref 3) The esters (12) are then converted to (7) preferably by treatment with methylchloroaluminum amide (Ref 2, above) or, alternately, by hydrogenation using, for example, hydrogen and palladium on carbon, as described above, to make the acid and then reacting with an acyl azide, such as diphenylphosphoryl azide followed by treatment with ammonia. Using the procedure described above in Scheme I, compound (9a) or (9b) may be accomplished.

Ref 3 Evans, D. A.; Ennis, M. D.; Mathre, D. J. Asymmetric alkylation reactions of chiral imide enolates. A practical approach to the enantioselective synthesis of alpha-substituted carboxylic acid derivatives. *J.Am.Chem.Soc.*, 1982, 104, 1737–1738.

Compounds of formula I where Z is phenyl can be prepared as follows in Schemes III(a)–(f), below.

Scheme III (a)

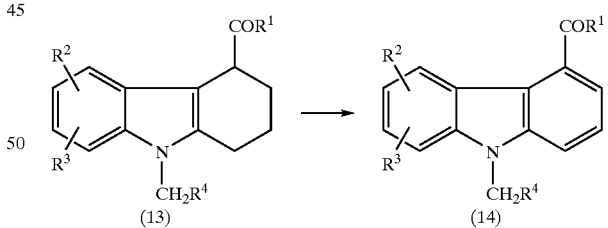

A 1,2,3,4-tetrahydrocarbazole-4-carboxamide or 4-carboxhydrazide (13) is dehydrogenated by refluxing in a solvent such as carbitol in the presence of Pd/C to produce the carbazole-4-carboxamide. Alternately, treatment of (13) with DDQ in an appropriate solvent such as dioxane yields carbozole (14).

Depending on the substituent pattern oxidation as described above may result in de-alkylation of the nitrogen. For example when $R^3$ is substituted at the 8-position with methyl, oxidation results in dealkylation of the nitrogen which may be realkylated by treatment with sodium hydride and the appropriate alkyl halide as described in Scheme I(a) above to prepare the deired product (14).

The intermediates and final products may be isolated and purified by conventional techniques, for example by concentration of the solvents, followed by washing of the residue with water, then purification by conventional techniques, such as chromatography or recrystallization.

It will be readily appreciated by the skilled artisan that the starting materials are either commercially available or can be readily prepared by known techniques from commercially available starting materials. All other reactants used to prepare the compounds in the instant invention are commercially available.

Scheme III (b)

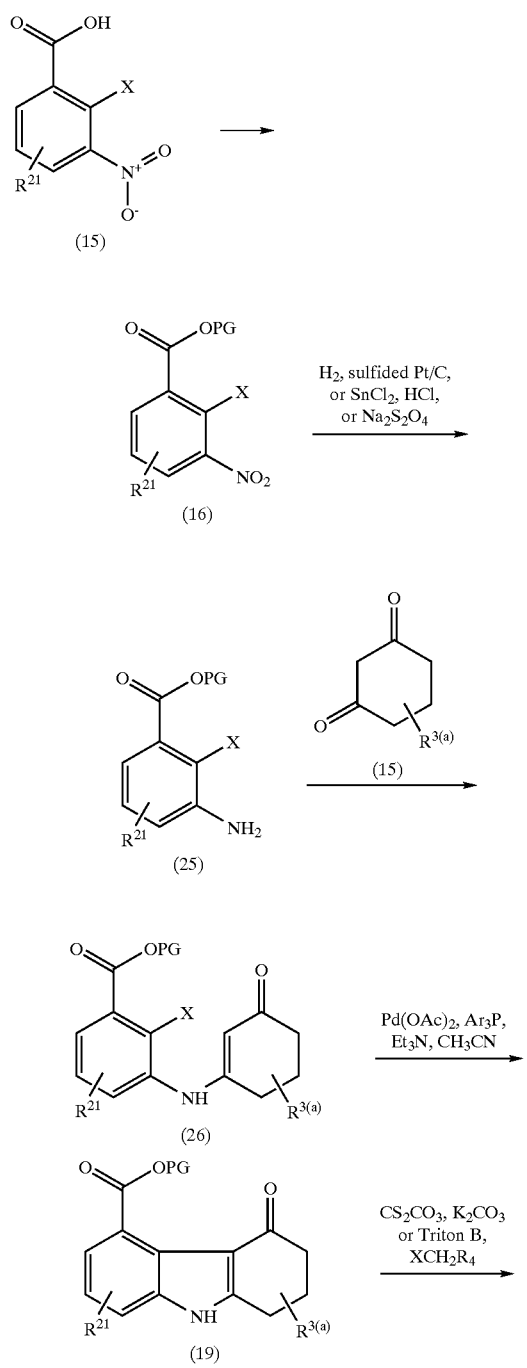

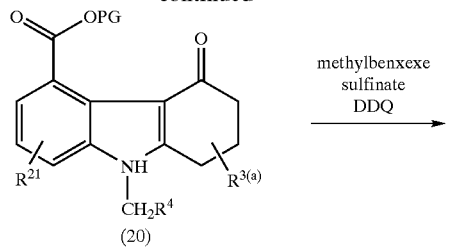

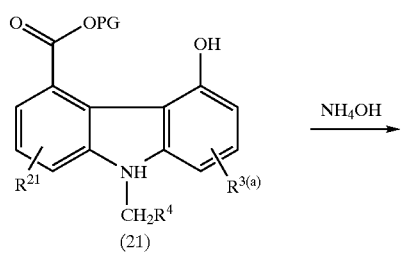

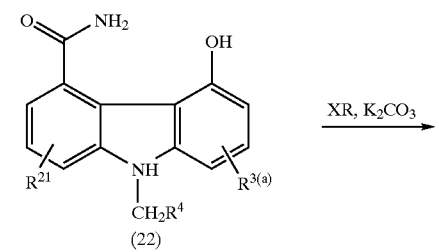

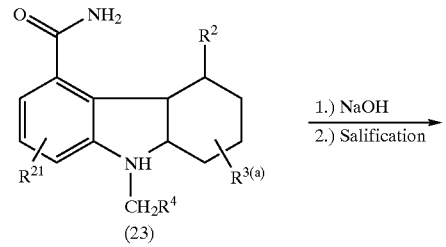

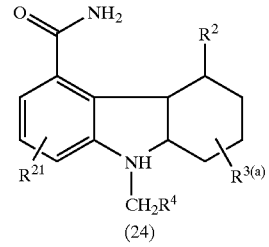

$R^{3(a)}$ is as defined in Scheme I (a) above
PG is an acid protecting group X is halo Benzoic acid derivative (16) where X is preferably chlorine, bromine or iodine and the protecting group is preferably —CH$_3$, are reduced to the corresponding aniline (25) with a reducing agent, such as stannous chloride in the presence of acid under the general conditions of Sakamoto et al, *Chem Pharm. Bull.* 35 (5), 1823–1828 (1987).

Alternatively, reduction with sodium dithionite in the presence of a base, such as sodium carbonate in a noninterfering solvent, such as water, ethanol, and/or tetrahydrofuran affords starting material (16).

Alternatively, reduction by hydrogenation over a sulfided platinum catalyst supported on carbon with hydrogen at 1 to 60 atmospheres in a noninterfering solvent, preferably ethyl acetate, to form a starting material (16).

The reactions are conducted at temperatures from about 0 to 100° C. preferably at ambient temperature, and are substantially complete in about 1 to 48 hours depending on conditions.

The aniline (25) and dione (15) are condensed under dehydrating conditions, for example, using the general procedure of Iida, et al., (Ref 5), with or without a noninterfering solvent, such as toluene, benzene, or methylene chloride, under dehydrating conditions at a temperature about 10 to 150° C. The water formed in the process can be removed by distillation, azetropic removal via a Dean-Stark apparatus, or the addition of a drying agent, such as molecular sieves, magnesium sulfate, calcium carbonate, sodium sulfate, and the like.

The process can be performed with or without a catalytic amount of an acid, such a p-toluenesulfonic acid or methanesulfonic acid. Other examples of suitable catalysts include hydrochloric acid, phenylsulfonic acid, calcium chloride, and acetic acid.

Examples of other suitable solvents include tetrahydrofuran, ethyl acetate, methanol, ethanol, 1,1,2,2-tetrachloroethane, chlorobenzene, bromobenzene, xylenes, and carbotetrachloride.

The condensation of the instant process is preferably carried out neat, at a temperature about 100 to 150° C. with the resultant water removed by distillation via a stream of inert gas, such as, nitrogen or argon.

The reaction is substantially complete in about 30 minutes to 24 hours.

Intermediate (26) may then be readily cyclized in the presence of a palladium catalyst, such as Pd(OAc)$_2$ or Pd(PPh$_3$)$_4$ and the like, a phosphine, preferably a trialkyl- or triarylphosphine, such as triphenylphosphine, tri-o-tolylphosphine, or tricyclohexylphosphine, and the like, a base, such as, sodium bicarbonate, triethylamine, or diisopropylethylamine, in a noninterfering solvent, such as, acetonitrile, triethylamine, or toluene at a temperature about 25 to 200° C. to form (19).

Examples of other suitable solvents include tetrahydrofuran, benzene, dimethylsulfoxide, or dimethylformamide.

Examples of other suitable palladium catalysts include Pd(PPh$_3$)Cl$_2$, Pd(OCOCF$_3$)$_2$, [(CH$_3$C$_6$H$_4$)$_3$P]$_2$PdCl$_2$, [(CH$_3$CH$_2$)$_3$P]$_2$PdCl$_2$, [(C$_6$H$_{11}$)$_3$P]$_2$PdCl$_2$, and [(C$_6$H$_5$)$_3$P]$_2$PdBr$_2$.

Examples of other suitable phosphines include triisopropylphosphine, triethylphosphine, tricyclopentylphosphine, 1,2-bis (diphenylphosphino) ethane, 1,3-bis(diphenylphosphino)propane, and 1,4-bis (diphenylphosphino)butane.

Examples of other suitable bases include tripropyl amine, 2,2,6,6-tetramethylpiperidine, 1,5-diazabicyclo[2.2.2] octane (DABCO), 1,8-diazabicyclo[5.4.0]undec-7-ene (DBU), 1,5-diazabicyclo[4.3.0]non-5-ene, (DBN) sodium carbonate, potassium carbonate, and potassium bicarbonate.

The cyclization of the instant process is preferably carried out with palladium(II)acetate as catalyst in the presence of either triphenylphosphine, tri-o-tolylphosphine, 1,3-bis (diphenylphosphino)propane, or tricyclohexylphosphine in acetonitrile as solvent and triethylamine as base at a temperature about 50 to 150° C. The reaction is substantially complete in about 1 hour to 14 days.

Alternatively, a preferred process for cyclization consists of the reaction of intermediate (26) with a palladacycle catalyst such as trans-di($\mu$-acetato)-bis[o-(di-o-tolylphosphino)benzyl]dipalladium (II) in a solvent such as dimethylacetamide (DMAC) at 120–140° C. in the presence of a base such as sodium acetate.

Intermediate (19) may be alkylated with an alkylating agent XCH$_2$R$_4$, where X is halo in the presence of a base to form (20). Suitable bases include potassium carbonate, sodium carbonate, lithium carbonate, cesium carbonate, sodium bicarbonate, potassium bicarbonate, potassium hydroxide, sodium hydroxide, sodium hydride, potassium hydride, lithium hydride, and Triton B (N-benzyltrimethylammonium hydroxide).

The reaction may or may not be carried out in the presence of a crown ether. Potassium carbonate and Triton B are preferred. The amount of alkylating agent is not critical, however, the reaction is best accomplished using an excess of alkyl halide relative to the starting material.

A catalytic amount of an iodide, such as sodium iodide or lithium iodide may or may not be added to the reaction mixture. The reaction is preferably carried out in an organic solvent, such as, acetone, dimethylformamide, dimethylsulfoxide, or acetonitrile. Other suitable solvents include tetrahydrofuran, methyl ethyl ketone, and t-butyl methyl ether.

The reaction is conducted at temperatures from about −10 to 100° C. preferably at ambient temperature, and is substantially complete in about 1 to 48 hours depending on conditions. Optionally, a phase transfer reagent such as tetrabutylammonium bromide or tetrabutylammonium chloride may be employed.

Intermediate (20) May by dehydrogenated by oxidation with 2,3-dichloro-5,6-dicyano-1,4-benzoquinone in a noninterfering solvent to form (21).

Suitable solvents include methylene chloride, chloroform, carbon tetrachloride, diethyl ether, methyl ethyl ketone, and t-butyl methyl ether. Toluene, benzene, dioxane, and tetrahydrofuran are preferred solvents. The reaction is carried out at a temperature about 0 to 120° C. Temperatures from 50 to 120° C. are preferred. The reaction is substantially complete in about 1 to 48 hours depending on conditions.

Intermediate (21) may be aminated with ammonia in the presence of a noninterfering solvent to form a(22). Ammonia may be in the form of ammonia gas or an ammonium salt, such as ammonium hydroxide, ammonium acetate, ammonium trifluoroacetate, ammonium chloride, and the like. Suitable solvents include ethanol, methanol, propanol, butanol, tetrahydrofuran, dioxane, and water. A mixture of concentrated aqueous ammonium hydroxide and tetrahydrofuran or methanol is preferred for the instant process. The reaction is carried out at a temperature about 20 to 100° C. Temperatures from 50 to 60° C. are preferred. The reaction is substantially complete in about 1 to 48 hours depending on conditions.

Alkylation of (22) is achieved by treatment with an alkylating agent of the formula XCH$_2$R$^9$ where X is halo and R$^{70}$ is —CO$_2$R$^{71}$, —SO$_3$R$^{71}$, —P(O)(OR$^{71}$)$_2$, or —P(O) (OR$^{71}$)H, where R$^{71}$ is an acid protecting group or a prodrug function, in the presence of a base in a noninterfering solvent to form (23). Methyl bromoacetate and t-butyl bromoacetate are the preferred alkylating agents.

Suitable bases include potassium carbonate, sodium carbonate, lithium carbonate, cesium carbonate, sodium bicarbonate, potassium bicarbonate, potassium hydroxide, sodium hydroxide, sodium hydride, potassium hydride, lithium hydride, and Triton B (N-benzyltrimethylammonium hydroxide). The reaction may or may not be carried out in the presence of a crown ether. Cesium carbonate and Triton B are preferred.

The amount of alkylating agent is not critical, however, the reaction is best accomplished using an excess of alkyl halide relative to the starting material. The reaction is preferably carried out in an organic solvent, such as, acetone, dimethylformamide, dimethylsulfoxide, or acetonitrile. Other suitable solvents include tetrahydrofuran, methyl ethyl ketone, and t-butyl methyl ether.

The reaction is conducted at temperatures from about −10 to 100° C. preferably at ambient temperature, and is substantially complete in about 1 to 48 hours depending on conditions. Optionally, a phase transfer reagent such as tetrabutylammonium bromide or tetrabutylammonium chloride may be employed.

Intermediate (23) may be optionally hydrolyzed with a base or acid to form desired product (24) and optionally salified.

Hydrolysis of (23) is achieved using a base such as sodium hydroxide, potassium hydroxide, lithium hydroxide, aqueous potassium carbonate, aqueous sodium carbonate, aqueous lithium carbonate, aqueous potassium bicarbonate, aqueous sodium bicarbonate, aqueous lithium bicarbonate, preferably sodium hydroxide and a lower alcohol solvent, such as, methanol, ethanol, isopropanol, and the like. Other suitable solvents include acetone, tetrahydrofuran, and dioxane.

Alternatively, the acid protecting group may be removed by organic and inorganic acids, such as trifluoroacetic acid and hydrochloric acid with or without a noninterferring solvent. Suitable solvents include methylene chloride, tetrahydrofuran, dioxane, and acetone. The t-butyl esters are preferably removed by neat trifluoroacetic acid.

The reaction is conducted at temperatures from about −10 to 100° C. preferably at ambient temperature, and is substantially complete in about 1 to 48 hours depending on conditions.

The starting material (16) is prepared by esterifying compound (15) with a alkyl halide=XPG; where X is halo and PG is an acid protecting group, in the presence of a base, preferably potassium carbonate or sodium cabonate, in a noninterferring solvent, preferably dimethylformamide or dimethylsulfoxide. The preferred alkyl halide is methyl iodide. The reaction is conducted at temperatures from about 0 to 100° C. preferably at ambient temperature, and is substantially complete in about 1 to 48 hours depending on conditions.

Alternatively the starting material (16) may be prepared by condensation with an alcohol HOPG, where PG is an acid protecting group, in the presence of a dehydrating catalyst such as, dicyclohexylcarbodiimide (DCC) or carbonyl diimidazole.

In addition, U.S. Pat. No. 4,885,338 and Jpn. Kokai Tokkyo Koho 05286912, November 1993 Hesei teach a method for preparing 2-fluoro-5-methoxyaniline derivatives.

Scheme III (c)

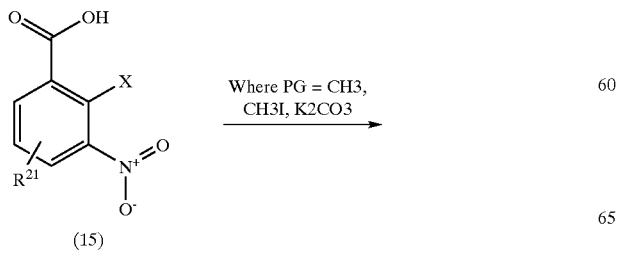

(15)

Where PG = CH3, CH3I, K2CO3

-continued

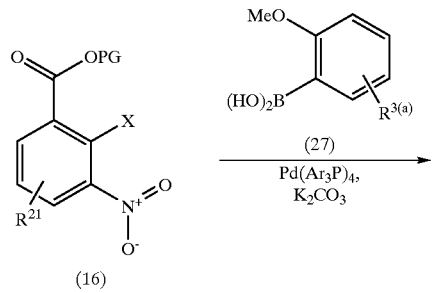

(16)

(27)
Pd(Ar3P)4, K2CO3

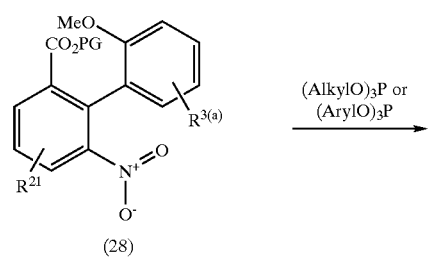

(28)

(AlkylO)3P or (ArylO)3P

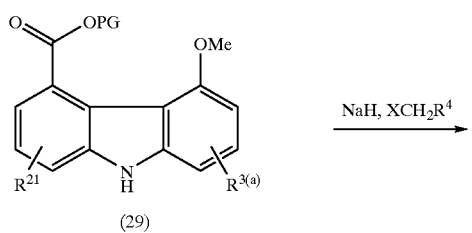

(29)

NaH, XCH2R4

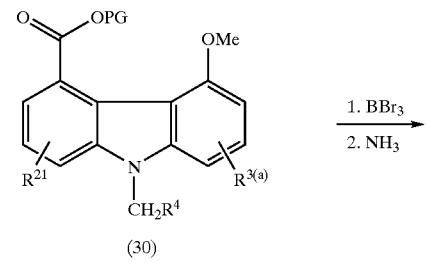

(30)

1. BBr3
2. NH3

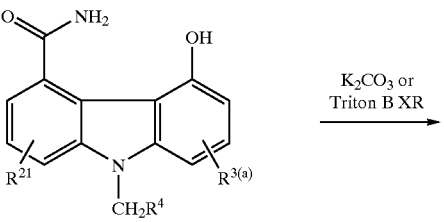

(22)

K2CO3 or Triton B XR

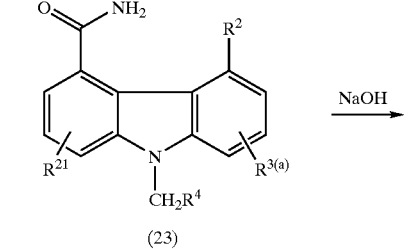

(23)

NaOH

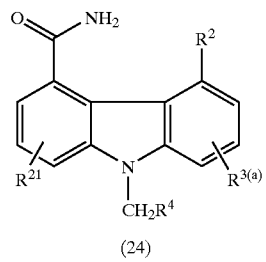

(24)

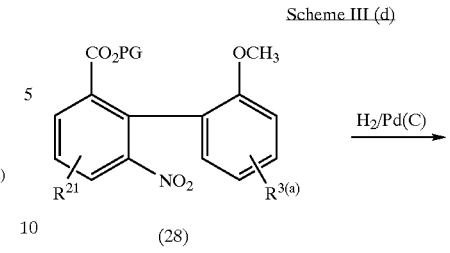

Scheme III (d)

R is as defined in Scheme III(b), $R^{3(a)}$ is as defined in Scheme I(a), above; and X is halo.

Benzoic acid derivatives (16) (X=Cl, Br, or I) and boronic acid derivative (27) (either commercially available or readily prepared by known techniques from commercially available starting materials) are condensed under the general procedure of Miyaura, et al., (Ref 8a) or Trecourt, et al., (Ref 8b) in the presence of a palladium catalyst, such as $Pd(Ph_3P)_4$, a base, such as sodium bicarbonate, in an inert solvent, such as THF, toluene or ethanol, to afford compound (28).

Compound (28) is converted to the carbazole product (29) by treatment with a trialkyl or triaryl phosphite or phosphine, such as, triethylphosphite or triphenyl phosphine, according to the general procedure of Cadogan, et al. (Ref 6).

Compound (29) is N-alkylated with an appropriately substituted alkyl or aryl halide $XCH_2R^4$ in the presence of a base, such as sodium hydride or potassium carbonate, in a noninterfering solvent, such as toluene, dimethylformamide, or dimethylsulfoxide to afford carbazole (30).

Compound (30) is converted to the corresponding amide (22) by treatment with boron tribromide or sodium thioethoxide, followed by ammonia or an ammonium salt, such as ammonium acetate, in an inert solvent, such as water or alcohol, or with methylchloroaluminum amide in an inert solvent, such as toluene, at a temperature between 0 to 110° C.

When $R^{3(a)}$ is substituted at the 8-position with chloro, de-alkylation of (30) with boron tribromide results in de-benzylation of the nitrogen as described above. Alkylation may be readily accomplished in a two step process. First, an O-alkylation by treatment with a haloalkyl acetate such as methyl bromo acetate using sodium hydride in tetrahydrofuran, followed by N-alkylation using for example a base such as sodium hydride and an appropriately substituted alkyl or aryl halide in dimethoxy formamide. Compound (22) can be converted to product carbazole product (24) as described previously in Scheme III(b) above.

Conversion to the desired prodrug may be accomplished by techniques known to the skilled artisan, such as for example, by treatment with a primary or secondary halide to make an ester prodrug.

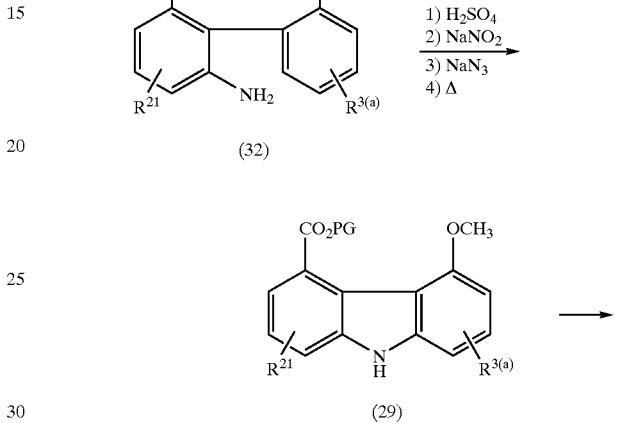

Alternatively, reduction of the nitro group of compound (28) with a reducing agent, such as hydrogen in the presence of palladium on carbon, in a noninterfering solvent, such as ethanol, at 1 to 60 atmospheres, at a temperature of 0 to 60° C. affords the corresponding aniline (32). Compound (32) is converted to the carbazole (29) according to the general procedure described by Trecourt, et al. (Ref 8b). The aniline is treated with sulfuric acid and sodium nitrite, followed by sodium azide to form an intermediate azide which is cyclized to carbazole (29) by heating in an inert sovent, such as toluene. Compound (29) is converted to carbazole product (24) as described previously in Schemes III(b) and III(c).

References 8) a. N. Miyaura, et al., Synth. Commun. 11, 513 (1981)
b. F. Trecourt, et al., Tetrahedron, 51, 11743 6)
6) J. Cadogan et al., J. Chem. Soc., 4831 (1965)

Scheme III (e)

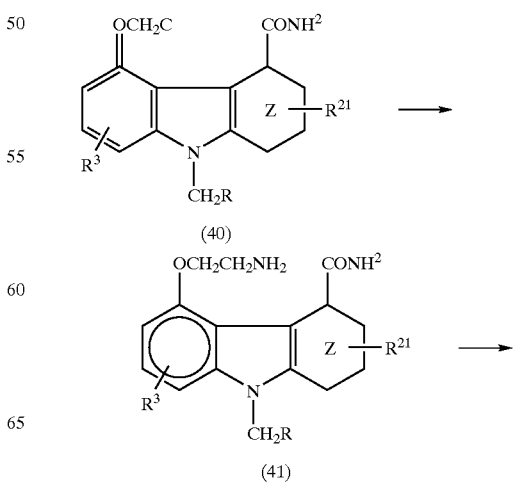

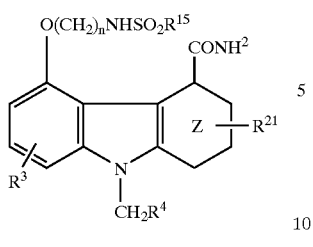

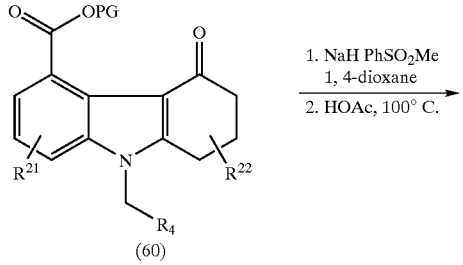

In an aprotic solvent, preferably tetrahydrofuran, reduction of (40) is achieved using a reducing agent such as aluminum trihydride. Preferably, the reaction is conducted under inert atmosphere such as nitrogen, at room temperature.

Sulfonylation may be achieved with an appropriate acylating agent in the presence of an acid scavenger such as triethyl amine.

Scheme III (f)

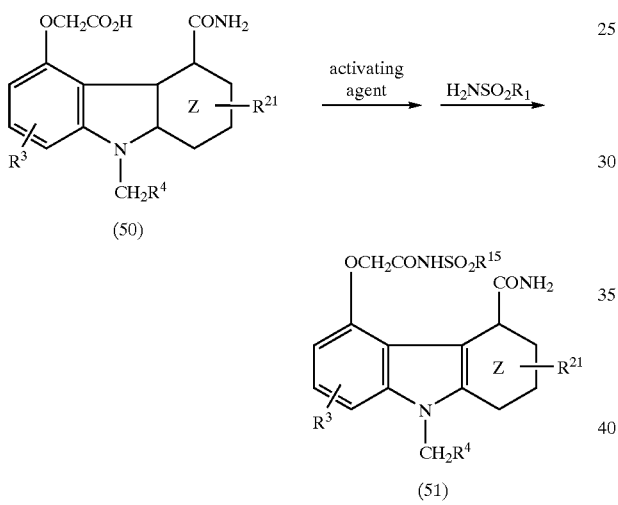

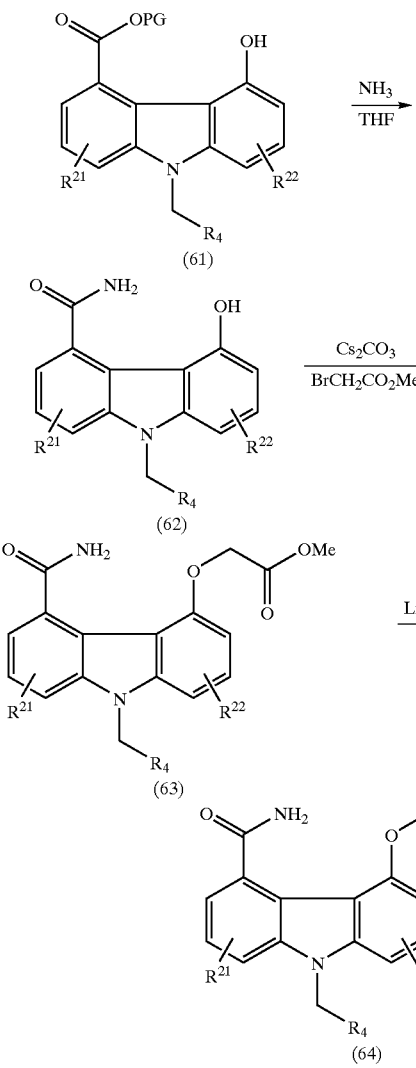

In a two-step, one-pot process, intermediate (50), prepared as described in Scheme I(a) above, is first activated with an activating agent such as carbonyl diimidazole. The reaction is preferably run in an aprotic polar or non-polar solvent such as tetrahydrofuran. Acylation with the activated intermediate is accomplished by reacting with $H_2NSOR^{15}$ in the presence of a base, preferably diazabicycloundecene.

Scheme III (g)

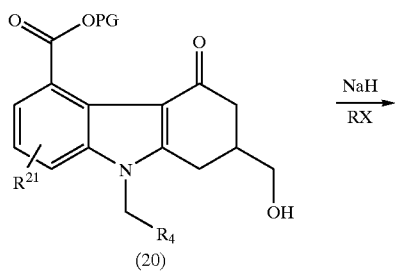

PG is an acid protecting group;
$R^{22}$ is $(C_1-C_6)$alkoxy $(C_1-C_6)$alkyl is $(C1-C_6)$alkoxy $(C_1-C_6)$alkenyl Starting material (20) is O-alkylated with an alkyl halide or alkenyl halide, using a base such as NaH, in an aprotic polar solvent preferably anhydrous DMF, at ambient temperature under a nitrogen atmosphere. The process of aromatization from a cyclohexenone functionality to a phenol functionality can be performed by treating the tetrahydrocabazole intermediate (60) with a base such as NaH in the presence of methyl benzenesulfinate in an anhydrous solvent, such as 1,4-dioxane or DMF, to form the ketosulfoxide derivative. Upon heating at about 100° C. for 1–2 hours, the ketosulfoxide derivative (60) is converted to the phenol derivative (61). Conversion of the ester (61) to the amide (62) can be achieved by treating a solution of (61) in an aprotic polar solvent such as tetrahydrofuran with ammonia gas. Phenolic O-alkylation of (62) with, for example, methyl bromoacetate can be carried out in anhydrous DMF at ambient temperature using $Cs_2CO_3$ or $K_2CO_3$ as a base to form (63). Desired product (64) can be derived from the basic hydrolysis of ester (63) using LiOH or NaOH as a base in an $H_2O/CH_3OH/THF$ solution at 50° C. for 1–2 hours.

When $R^{22}$ is —$(C_1–C_6)$alkoxy$(C_1–C_6)$alkenyl, hydrogenation of the double bond can be performed by treating (63) in THF using $PtO_2$ as a catalysis under a hydrogen atmosphere. Desired product can then be derived as described above in Scheme III(g) from the basic hydrolysis of ester (63) using LiOH or NaOH as a base in an $H_2O/CH_3OH/THF$ solution at 50° C. for 1–2 hours.

Compounds of formula I where the A ring is phenyl and the heteroatom in Z is sulfur, oxygen or nitrogen can be prepared as described in Schemes IV(a)–(f), below.

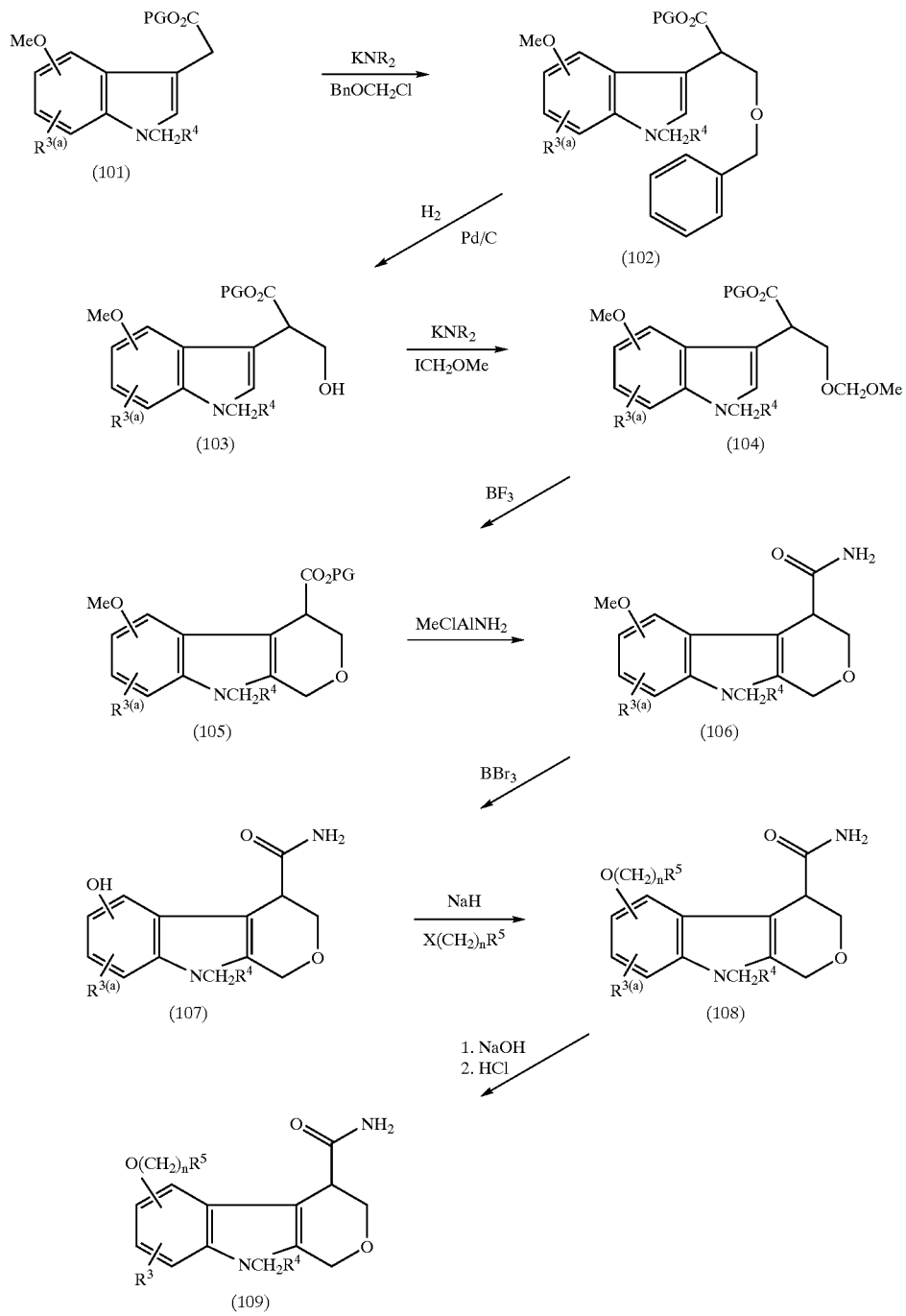

Scheme IV (a)

PG is an acid protecting group.
X is halo.
$R^3(a)$ is H, —$O(C_1$–$C_4)$alkyl, halo, —$(C_1$–$C_6)$alkyl, phenyl, —$(C_1$–$C_4)$alkylphenyl; phenyl substituted with minum amide, and then to the phenol (107) with boron tribromide. The phenol is O-alkylated to give (108) which is hydrolyzed to the acid (109).
10) Dillard, R. et al., J, Med Chem. Vol 39, No. 26, 5119–5136.

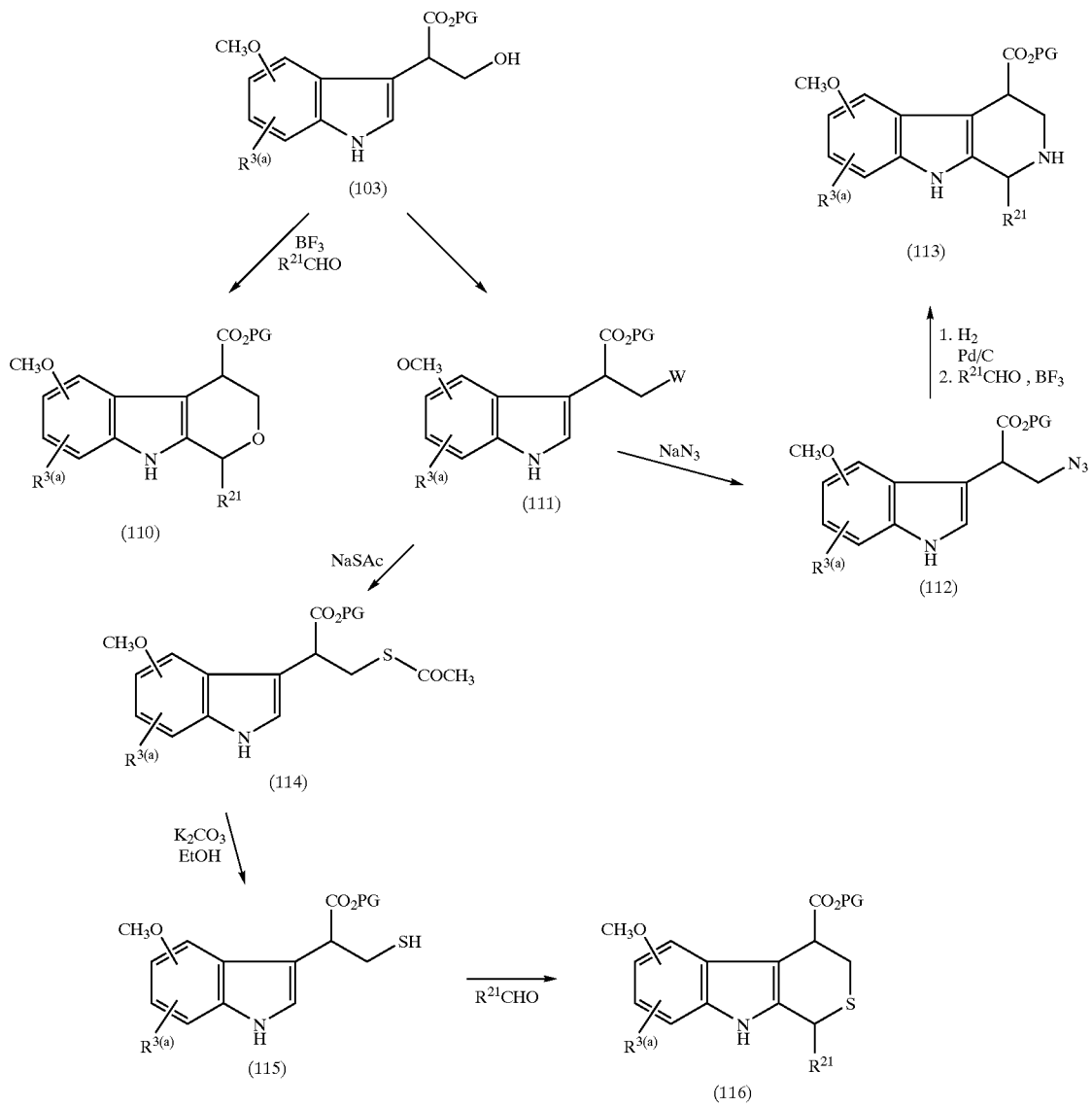

—$(C_1$–$C_6)$alkyl, halo or —$CF^3$; —$CH_2OSi(C_1$–$C_6)$ alkyl, furyl, thiophenyl, —$(C_1$–$C_6)$hydroxyalkyl; or —$(CH_2)_nR^8$ where $R^8$ is H, —$NR^9R^{10}$, —CN or phenyl where $R^9$ and $R^{10}$ are independently —$(C_1$–$C_4)$ alkyl or -phenyl$(C_1$–$C_4)$alkyl and n is 1 to 8;

An indole-3-acetic ester (101), Ref 10, is alkylated by treatment with alkalai metal amide and benzyloxymethyl chloride to give (102) which is converted to the alcohol (103) by catalytic hydrogenation. The alcohol is alkylated to provide the formaldehyde acetal (104) which is cyclized by Lewis acid to produce the pyrano[3,4-b]indole (105). The ester is converted to the amide (106) by methylchloroalu- PG is an acid protecting group
W is halo, alkyl or aryl sulfonyl
$R^3(a)$ is H, —$O(C_1$–$C_4)$alkyl, halo, —$(C_1$–$C_6)$alkyl, phenyl, —$(C_1$–$C_4)$alkylphenyl; phenyl substituted with —$(C_1$–$C_6)$alkyl, halo or —$CF^3$; —$CH_2OSi(C_1$–$C_6)$ alkyl, furyl, thiophenyl, —$(C_1$–$C_6)$hydroxyalkyl; or —$(CH_2)_nR^8$ where $R^8$ is H, —$NR^9R^{10}$, —CN or phenyl where $R^9$ and $R^{10}$ are independently —$(C_1$–$C_4)$ alkyl or -phenyl$(C_1$–$C_4)$alkyl and n is 1 to 8;

Reaction of this alcohol (103) with aldehyde and acid produces the pyranoindole (110).

Conversion of the hydroxyl function of (103) to a halide or sulfate functionality is achieved by treatment with triph enylphosphine and CH₃X (where X is a halogen) to make compounds of formula (111) where X is a halide; or by treatment with triethylamine and methanesulfonyl chloride to make the sulfonate. Displacement with the sodium salt of thiol acetic acid gives (114) which in turn is hydrolyzed by base to the thiol (115) which is reacted with an appropriately substituted aldehyde and acid to produce the thiopyranoindoles (116).

Intermediate (111) may also be reacted with sodium azide to give the azido derivative (112) which is reduced by hydrogen catalytically to give the amine which is converted to the carboline (113) with aldehyde and acid.

Intermediates (113), (110) and (116) may be N-alkylated, using sodium hydride and an appropriately substituted alkylhalide XCH₂R⁴.

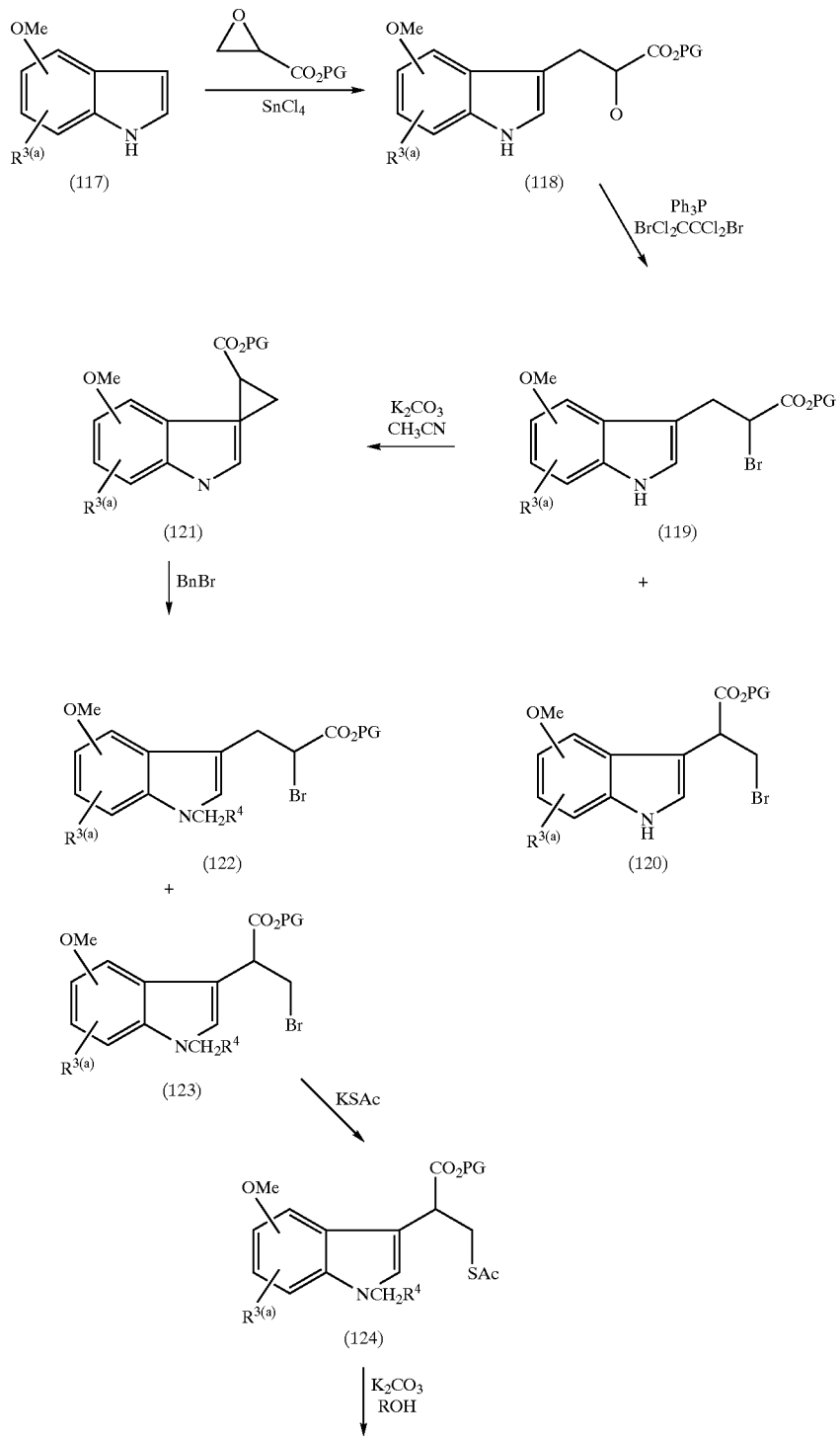

-continued
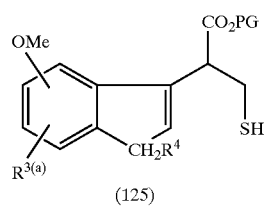
(125)
↓ KNR₂
  ICH₂OMe
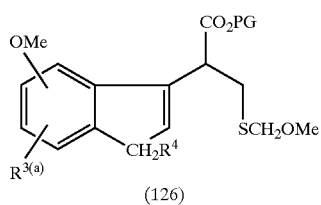
(126)
↓ ZnX₂
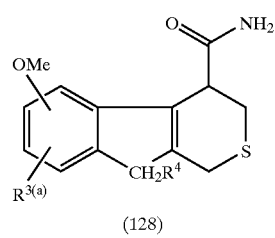 ← MeClAlNH₂ — 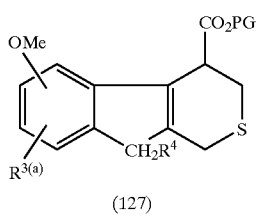
(128)                                    (127)
↓ BBr₃
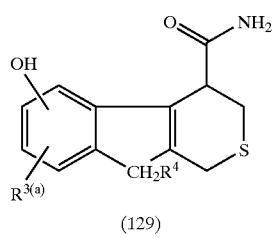 —NaH, Br(CH2)ₙCO₂Et→ 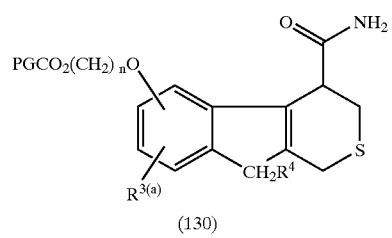
(129)                                     (130)
↓ 1. NaOH
  2. HCl
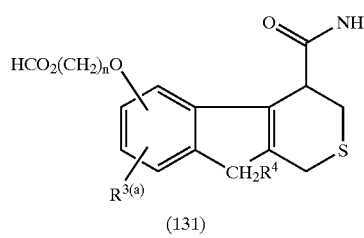
(131)
PG is an acid protecting group
R³⁽ᵃ⁾ is as defined above 4-Methoxyindole (117) is converted to the indole acetic acid derivative (118) by alkylation with an epoxy propionate. Treatment of (118) with a brominating reagent affords the mixture of bromo isomers (119) and (120) which give the spiro compound (121) upon basic treatment. Heating (121) with benzyl bromide provides a mixture of the isomeric bromo compounds (122) and (123) which react with potassium thioacetate to give a mixture of isomers from which (124) may be separated. Solvolysis of the thioester produces the thiol (125) which is alkylated to give (126). Lewis acids convert (126) to the thiopyrano[3,4-b]indole (127). The ester function is converted to amide using methylchloroaluminum amide, the methyl ether cleaved by boron tribromide, and the product phenol O-alkylated with bromoacetic ester to give (130) which is hydrolyzed to (131).

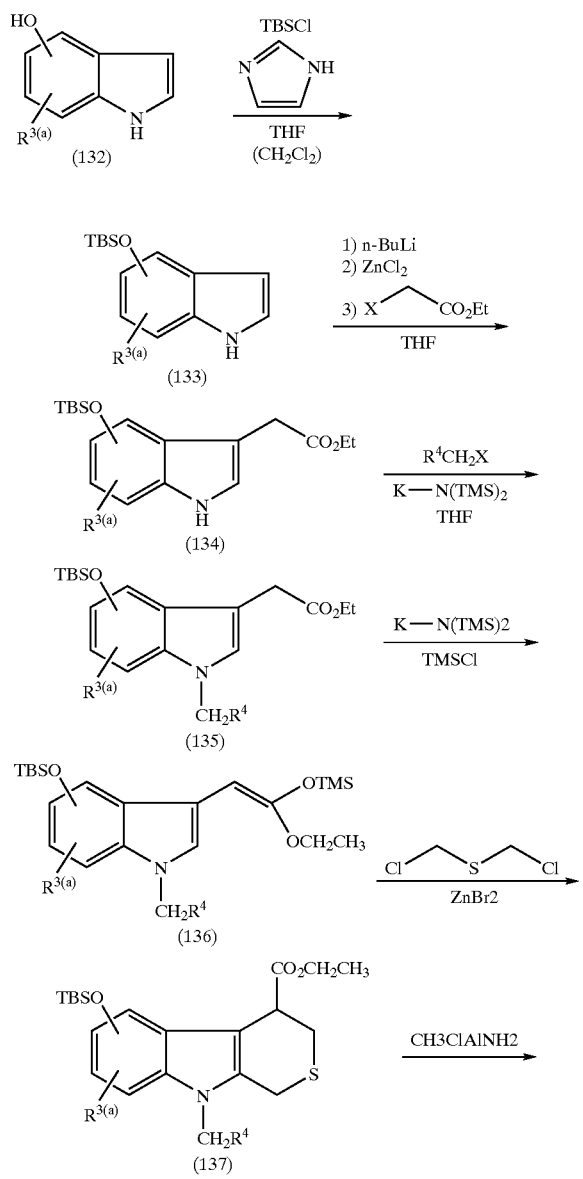

Scheme IV (d)

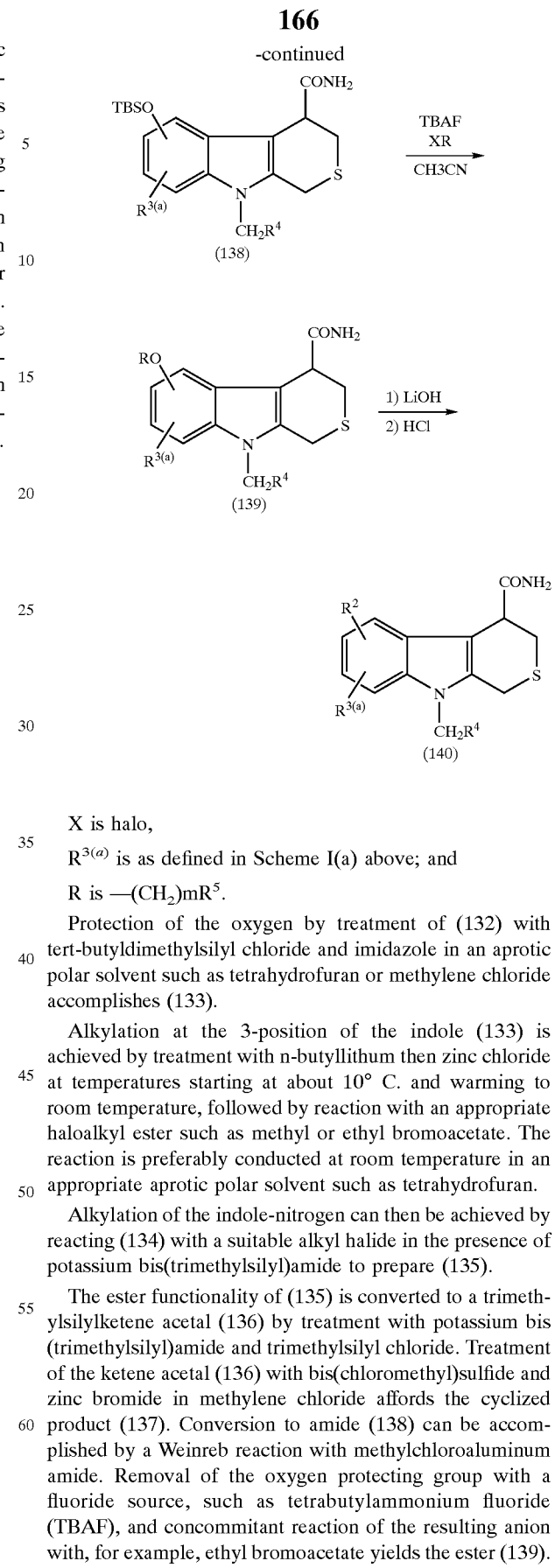

X is halo, $R^{3(a)}$ is as defined in Scheme I(a) above; and

R is —$(CH_2)mR^5$.

Protection of the oxygen by treatment of (132) with tert-butyldimethylsilyl chloride and imidazole in an aprotic polar solvent such as tetrahydrofuran or methylene chloride accomplishes (133).

Alkylation at the 3-position of the indole (133) is achieved by treatment with n-butyllithium then zinc chloride at temperatures starting at about 10° C. and warming to room temperature, followed by reaction with an appropriate haloalkyl ester such as methyl or ethyl bromoacetate. The reaction is preferably conducted at room temperature in an appropriate aprotic polar solvent such as tetrahydrofuran.

Alkylation of the indole-nitrogen can then be achieved by reacting (134) with a suitable alkyl halide in the presence of potassium bis(trimethylsilyl)amide to prepare (135).

The ester functionality of (135) is converted to a trimethylsilylketene acetal (136) by treatment with potassium bis(trimethylsilyl)amide and trimethylsilyl chloride. Treatment of the ketene acetal (136) with bis(chloromethyl)sulfide and zinc bromide in methylene chloride affords the cyclized product (137). Conversion to amide (138) can be accomplished by a Weinreb reaction with methylchloroaluminum amide. Removal of the oxygen protecting group with a fluoride source, such as tetrabutylammonium fluoride (TBAF), and concomitant reaction of the resulting anion with, for example, ethyl bromoacetate yields the ester (139).

Deprotection of the ester yields the desired acid (140).

Scheme IV (e)

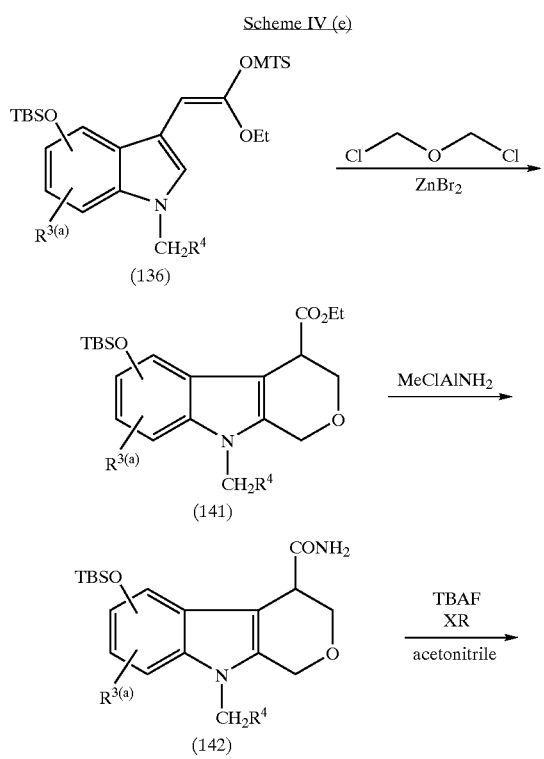

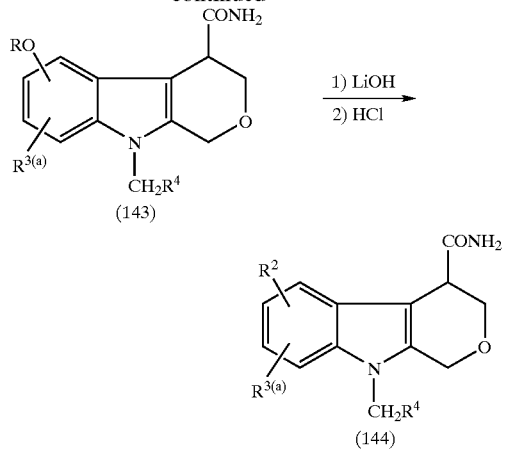

$R^{3(a)}$ is as described in Scheme I(a) and

R is as described in Scheme IV(d).

Treatment of the ketene acetal (136) with bis(chloromethyl)ether and zinc bromide in methylene chloride affords the cyclized product (141). Conversion to amide (142) can be accomplished by a Weinreb reaction with methylchloroaluminum amide. Removal of the oxygen protecting group with a fluoride source, such as tetrabutylammonium fluoride, and concommitant reaction of the resulting anion with ethyl bromoacetate yields the ester (143). Deprotection of the ester yields the desired acid (144).

Scheme IV (f)

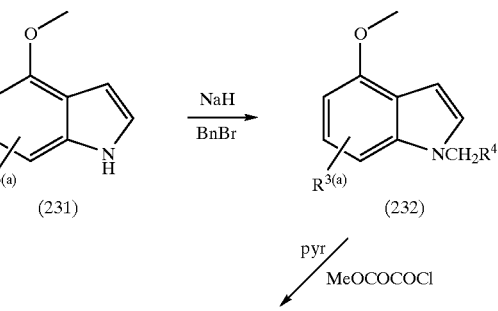

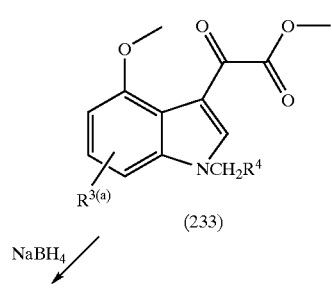

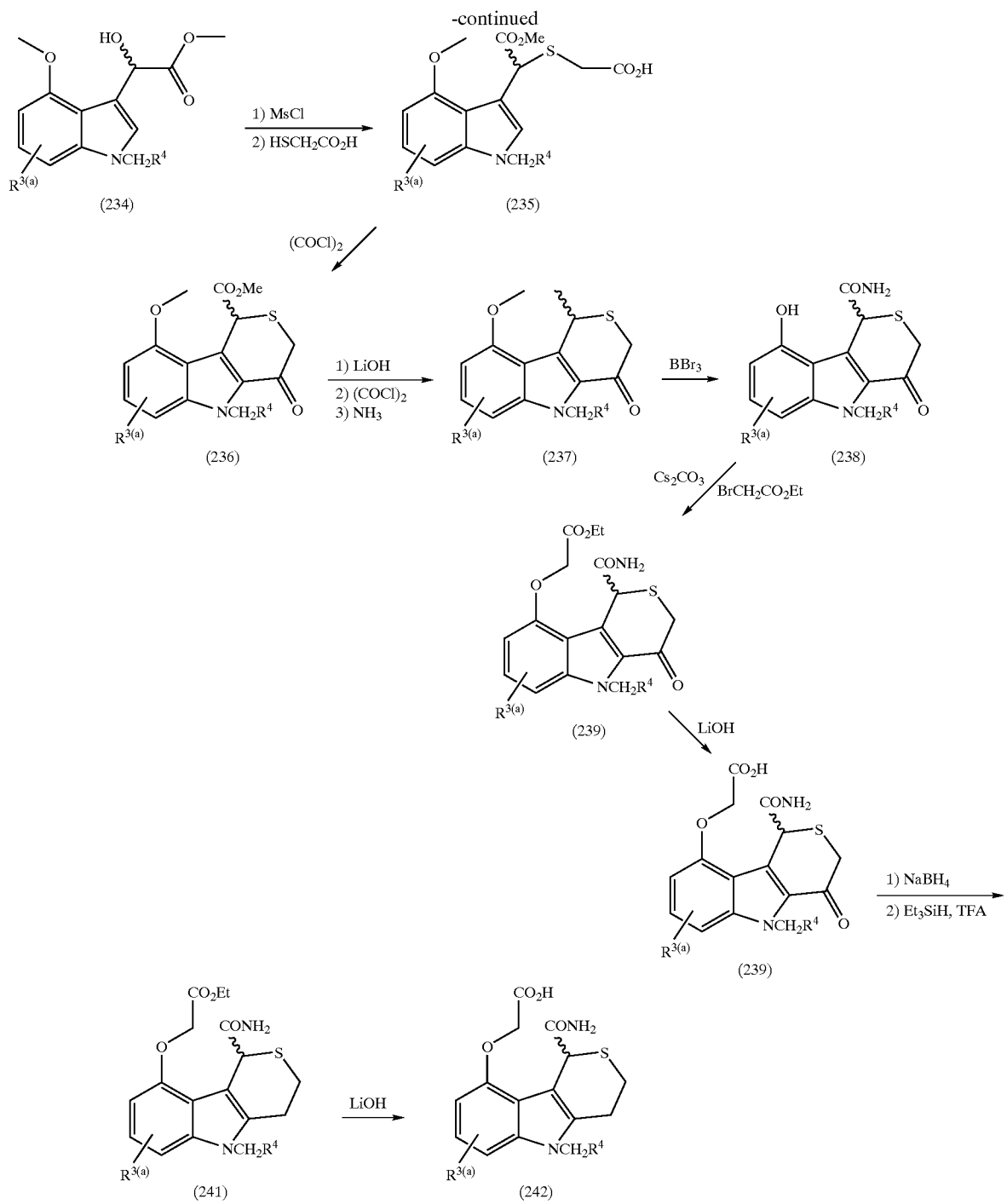

N-alkylation of commercially available 4-methoxy indole (231) under basic conditions using an alkyl halide affords the N-alkyl indole (232). Acylation with a suitable acid chloride provides the glyoxalate ester product (233) which can be reduced with a variety of hydride reducing agents to give intermediate alcohols (234). Conversion of the alcohol to a suitable leaving group and displacement with sulfur nucleophiles affords the thioether product (235). Conversion to the acid chloride and spontaneous cyclization affords the thioketone product (236). Cleavage of the ester can be effected under basic conditions to give the correponding acid which upon formation of the acid chloride and reaction with an appropriate amine gives the amide product (237). Cleavage of the methyl ether gives the phenol (238) which can be alkylated under basic conditions using alkyl halides to give the O-alkylated product (239). Cleavage of the ester under basic conditions gives the desired product (240). Alternatively, reduction of the benzylic ketone with a hydride reducing agent and subsequent deoxygenation of the resulting alcohol gives the deoxygenated product (244). Cleavage of the oxyacetic ester proceeds under basic conditions to give the desired oxyacetic acid (242).

Compounds where Z is an aromatic or heterocyclic ring containing nitrogen can be prepared as described in Schemes V(a)–(e), below.

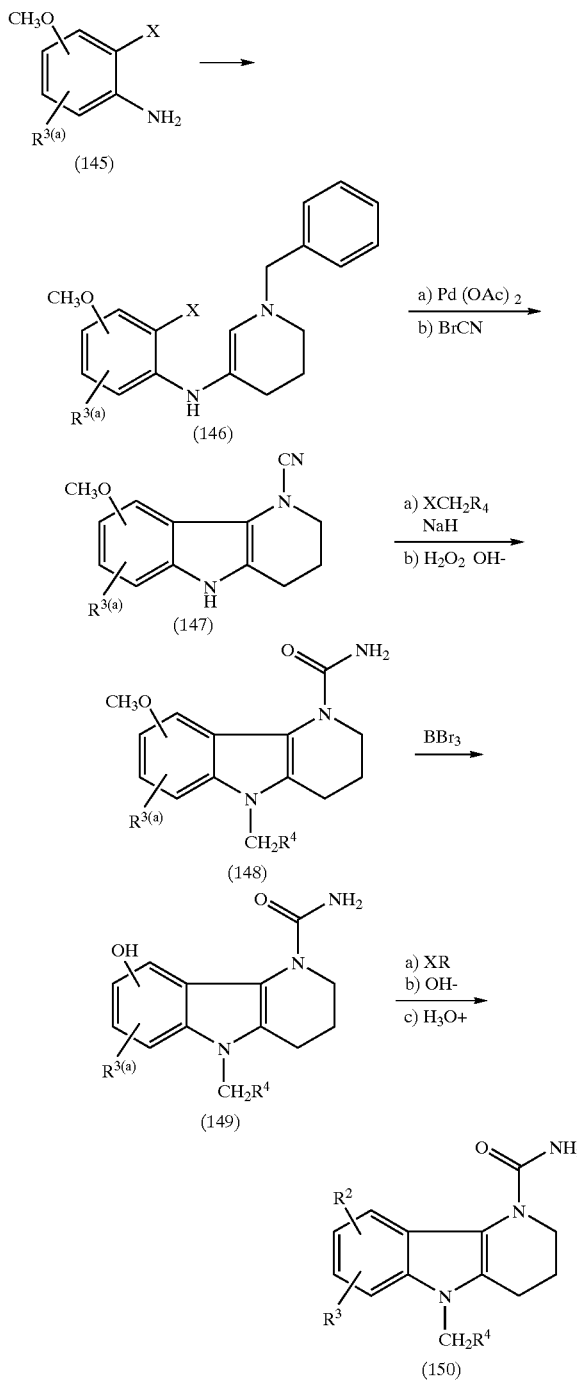

by treatment with boron tribromide in methylene chloride. The resulting phenol (149) is converted by the standard sequence of O-alkylation with methyl bromoacetate in the presence of a base, hydrolysis with hydroxide to provide the intermediate salt which is then protonated in aqueous acid to provide desired δ-carboline (150).

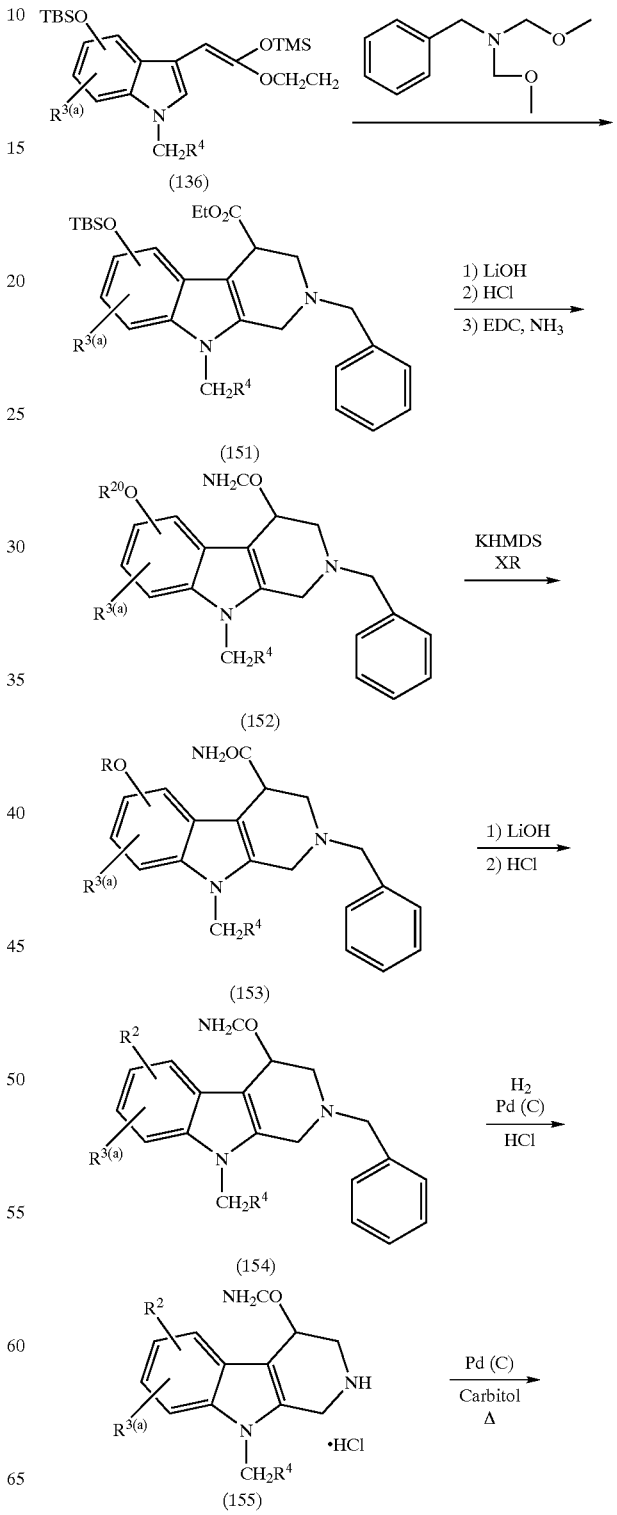

Substituted haloaniline (145) is condensed with N-benzyl-3-piperidone to provide enamine (146). Ring closure is effected by treatment of (146) with palladium (II) acetate and the resultant product is converted to (147) by treatment with cyanogen bromide. Alkylation of (147) is accomplished by treatment with the appropriate alkyl bromide using sodium hydride as base. Hydrolysis of this N-alkylated product with basic hydrogen peroxide under standard conditions provides (148). Demethylation of (148) is carried out

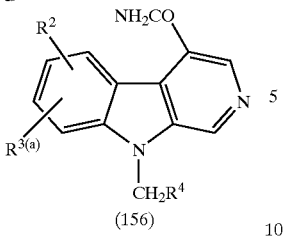

X is halo,
R is as defined in Scheme IV (d), and
R[3(a)] is as defined in Scheme I (a).

Ketene acetal (136), prepared as described in Scheme IV(d), is reacted with benzyl bis(methoxymethyl)amine in the presence of zinc chloride to give the tetrahydro-beta-carboline (151).

Treatment of (151) with lithium hydroxide, neutralization with hydrochloric acid and subsequent treatment with 1-(3-dimethylaminopropyl)-3-ethylcarbodiimide hydrochloride and ammonia provides the desilyated amide (152) where $R^{20}$ is hydrogen, which can be alkylated with, for example, ethylbromoacetate to give ester (153).

Alternatively, treatment of (115) with the appropriate Weinreb reagent provides amide (152) ($R^{20}$ is t-butyldimethylsilyl) which is desilylated with tetra-n-butylammonium fluoride and alkylated with, for example, ethyl bromoacetate to give ester (153). Lithium hydroxide-mediated hydrolysis gives acid (154), which may be hydrogenated over an appropriate catalyst in the presence of hydrochloride acid to give the tetrahydro-beta-carboline as the hydrochloride salt(155). Compound (155) may in turn be aromatized by refluxing in carbitol with palladium on carbon to provide beta-carboline (156).

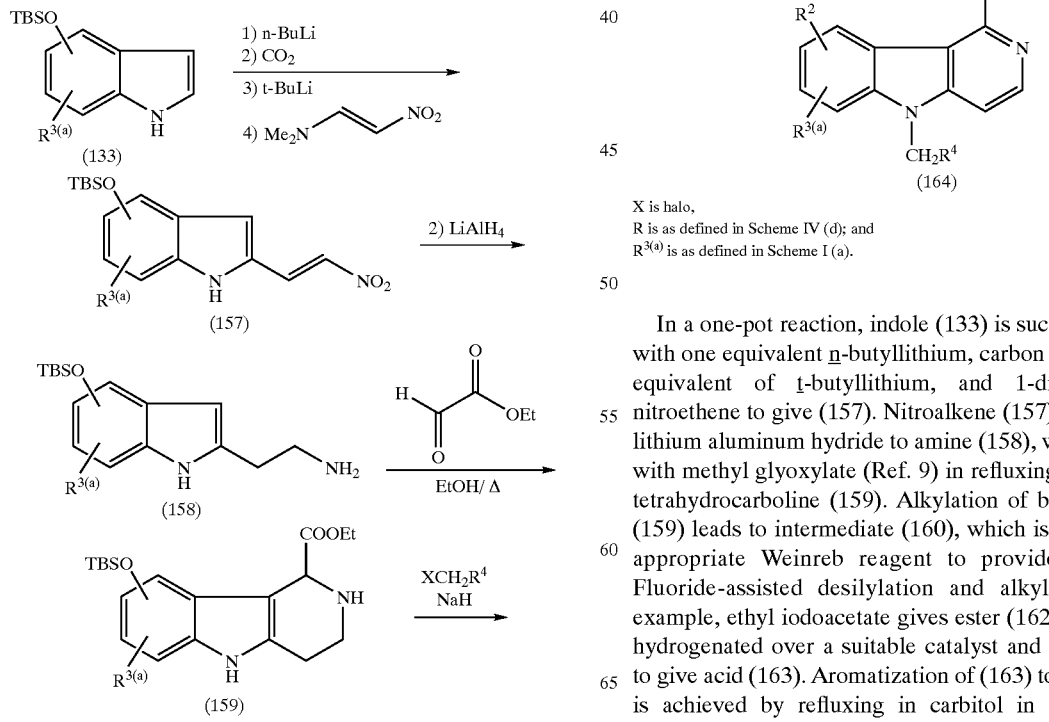

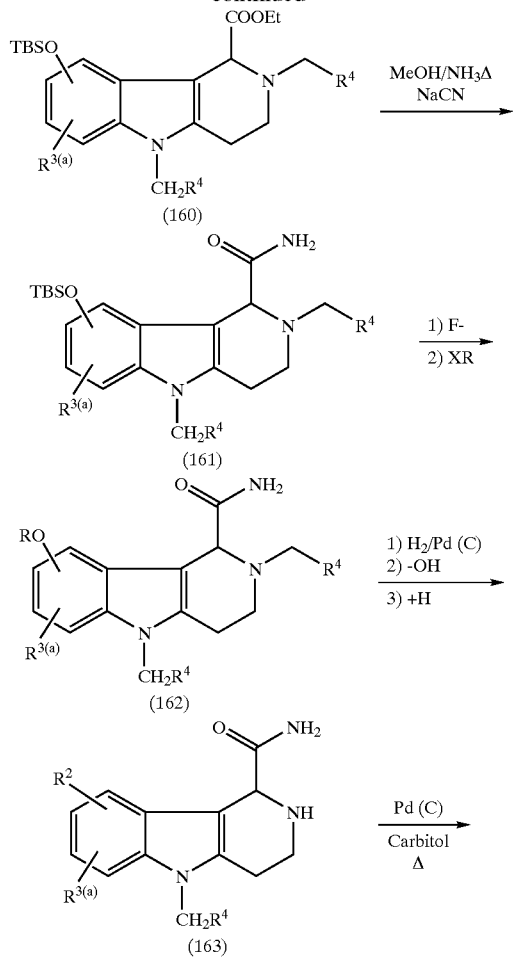

X is halo,
R is as defined in Scheme IV (d); and
R[3(a)] is as defined in Scheme I (a).

In a one-pot reaction, indole (133) is successively treated with one equivalent n-butyllithium, carbon dioxide gas, one equivalent of t-butyllithium, and 1-dimethylamino-2-nitroethene to give (157). Nitroalkene (157) is reduced with lithium aluminum hydride to amine (158), which is cyclized with methyl glyoxylate (Ref. 9) in refluxing ethanol to give tetrahydrocarboline (159). Alkylation of both nitrogens of (159) leads to intermediate (160), which is treated with the appropriate Weinreb reagent to provide amide (161). Fluoride-assisted desilylation and alkylation with, for example, ethyl iodoacetate gives ester (162), which may be hydrogenated over a suitable catalyst and base-hydrolyzed to give acid (163). Aromatization of (163) to carboline (164) is achieved by refluxing in carbitol in the presence of palladium-on-carbon.

Reference 9
Kelley, T. R.; Schmidt, T. E.; Haggerty, J. G. A convenient preparation of methyl and ethyl glyoxylate, *Synthesis*, 1972, 544–5.
Scheme V (d)
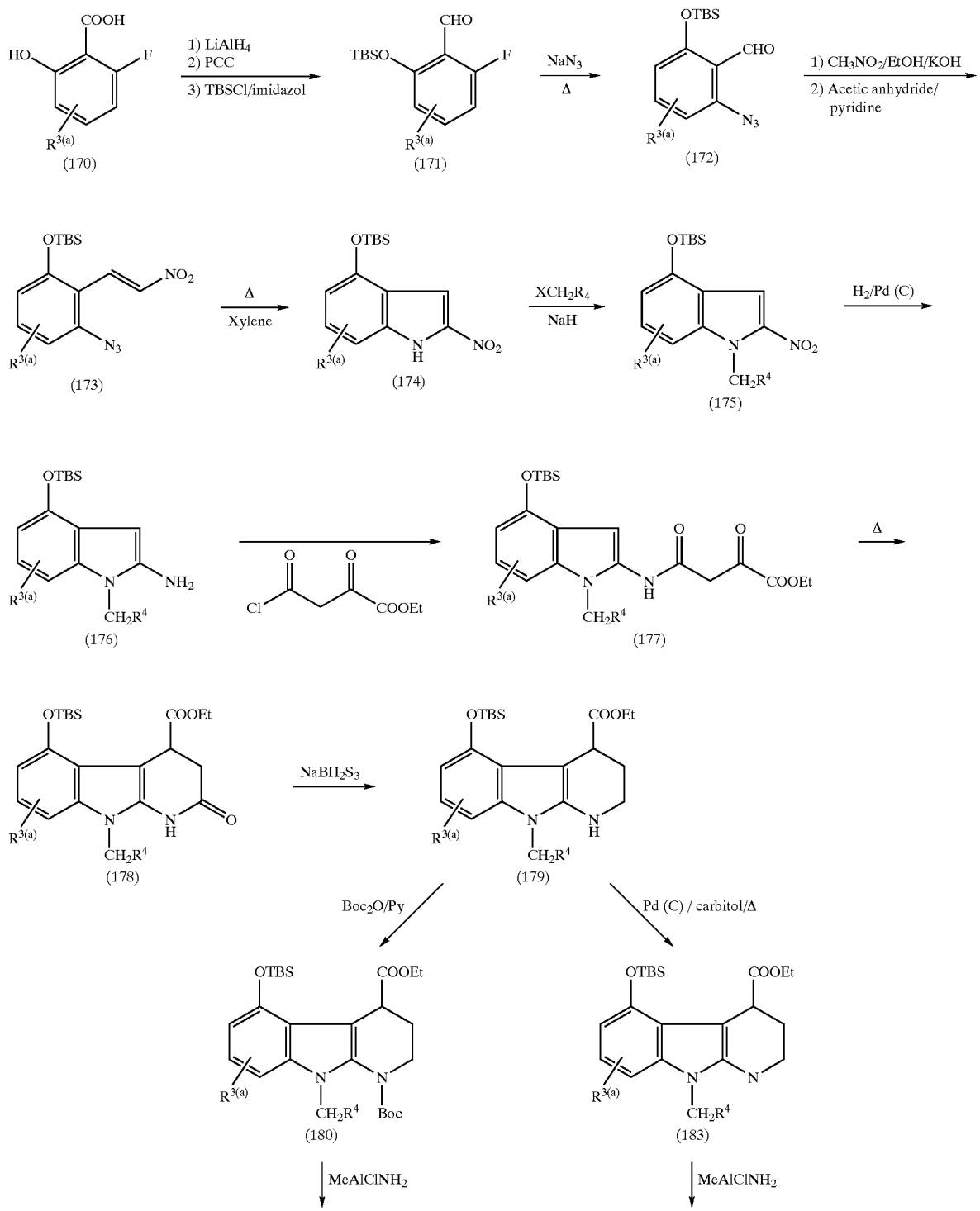

-continued

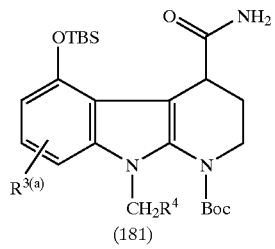
(181)

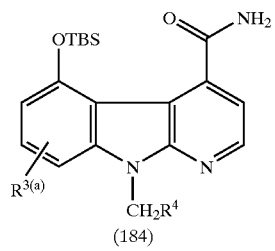
(184)

1) F-
2) RX/K₂CO₃
3) -OH
4) H⁺

1) F-
2) RX/K₂CO₃
3) NaOH

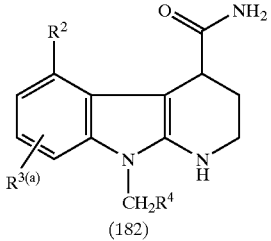
(182)

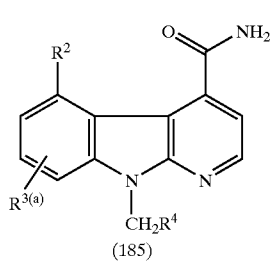
(185)

The commercially available acid (170) is reduced with lithium aluminum hydride, oxidized with pyridinium chlorochromate, and silylated with t-butyldimethylsilyl chloride to give (171). Treatment with sodium azide provides azide (172), which is reacted with nitromethane and potassium hydroxide in ethanol, followed by treatment with acetic anhydride and pyridine to give nitroolefin (173). Heating in xylene induces cyclization to produce indole (174). Alkylation with, for example, benzyl iodide and sodium hydride gives (175), which is hydrogenated in the presence of palladium-on-carbon to give amine (176). Acylation with the acid chloride of commercially available oxalacetic acid monoethyl ester gives (177), which is thermally cyclized to lactam (178). Selective reduction of the lactam carbonyl may be accomplished by treatment with NaBH₂S₃ to provide amine (179).

Protection of amine (179) with di-t-butyl dicarbonate and pyridine produces (180), which is converted via the appropriate Weinreb reagent to amide (181). Fluoride-assisted desilylation, alkylation with, for example, ethyl iodoacetate and potassium carbonate, base hydrolysis, and acid hydrolysis produce the tetrahydro-alpha-carboline (182).

Alternatively, amine (179) may be aromatized by refluxing in carbitol or some other suitable high boiling solvent to give alpha-carboline (183), which is converted via the appropriate Weinreb reagent to amide (184). Fluoride-assisted desilylation, alkylation with ethyl iodoacetate and potassium carbonate, and base hydrolysis as described above provides alpha-carboline (185).

Scheme V (e)

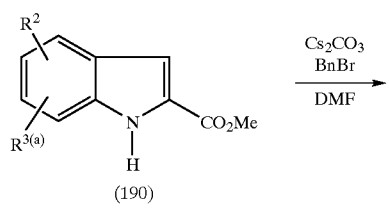
(190)

Cs₂CO₃
BnBr
─────→
DMF

-continued

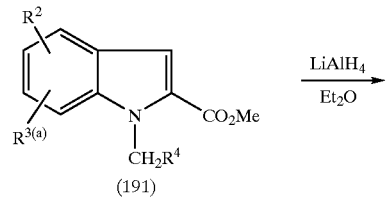
(191)

LiAlH₄
─────→
Et₂O

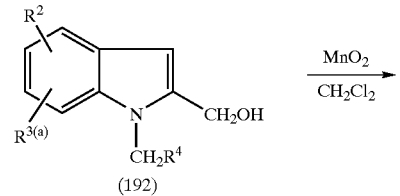
(192)

MnO₂
─────→
CH₂Cl₂

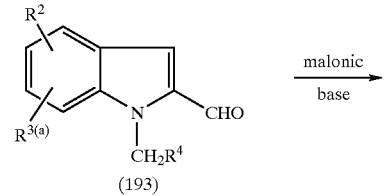
(193)

malonic
─────→
base

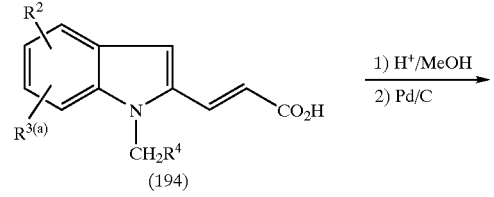
(194)

1) H⁺/MeOH
2) Pd/C

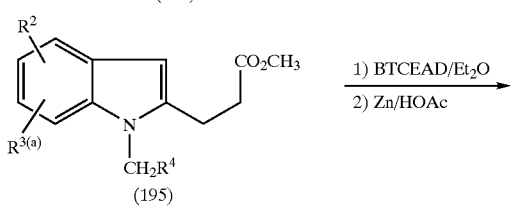
(195)

1) BTCEAD/Et₂O
2) Zn/HOAc

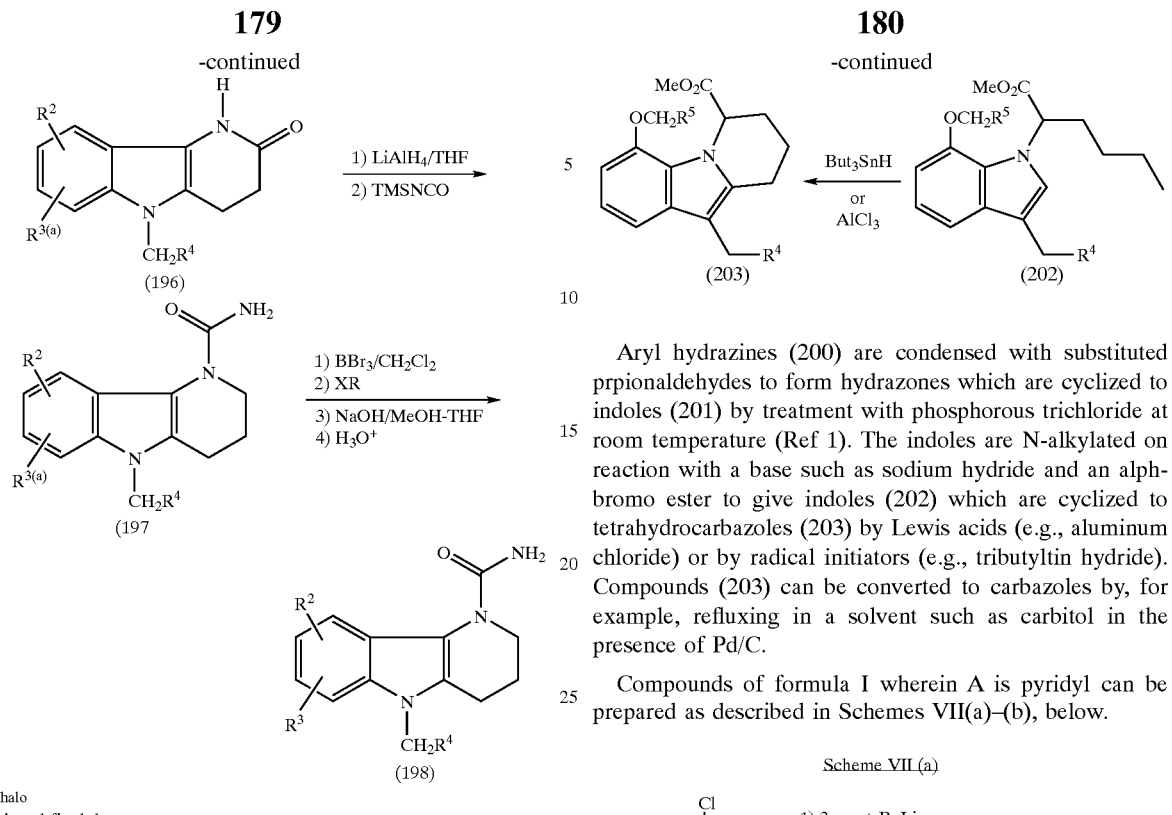

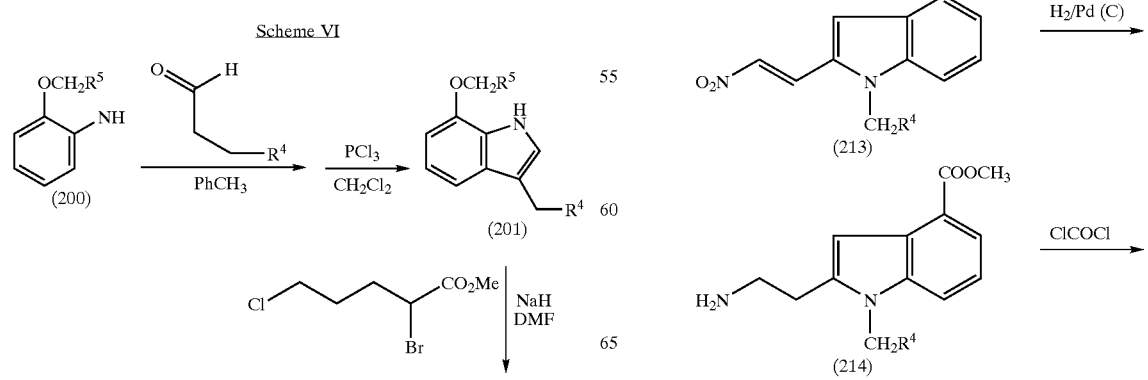

Scheme V(e) provides δ-carboline (198) by the indicated sequence of reactions. N-alkylation of 2-carboethoxyindole (190) followed by a standard two carbon homologation sequence provides 2-(3-propenoic acid)indoles (194). In this sequence, the condensation of aldehyde (193) with malonic acid utilized a mixture of pyridine and piperidine as the base. After methyl ester formation and hydrogenation (195), ring closure (196) was effected by treatment with bis(2,2,2-trichloroethyl)azodicarboxylate (BTCEAD) followed by zinc in acetic acid. Reduction of the cyclic amide with lithium aluminum hydride followed by treatment with tri-methylsilylisocyanate provided the urea (197). Conversion to the desired d-carboline (198) was accomplished under the usual conditions of demethylation and subsequent alkylation and ester hydrolysis steps.

Reverse indoles, i.e., compounds where B is carbon and D is nitrogen can be prepared as described in Scheme VI, below.

Aryl hydrazines (200) are condensed with substituted prpionaldehydes to form hydrazones which are cyclized to indoles (201) by treatment with phosphorous trichloride at room temperature (Ref 1). The indoles are N-alkylated on reaction with a base such as sodium hydride and an alph-bromo ester to give indoles (202) which are cyclized to tetrahydrocarbazoles (203) by Lewis acids (e.g., aluminum chloride) or by radical initiators (e.g., tributyltin hydride). Compounds (203) can be converted to carbazoles by, for example, refluxing in a solvent such as carbitol in the presence of Pd/C.

Compounds of formula I wherein A is pyridyl can be prepared as described in Schemes VII(a)–(b), below.

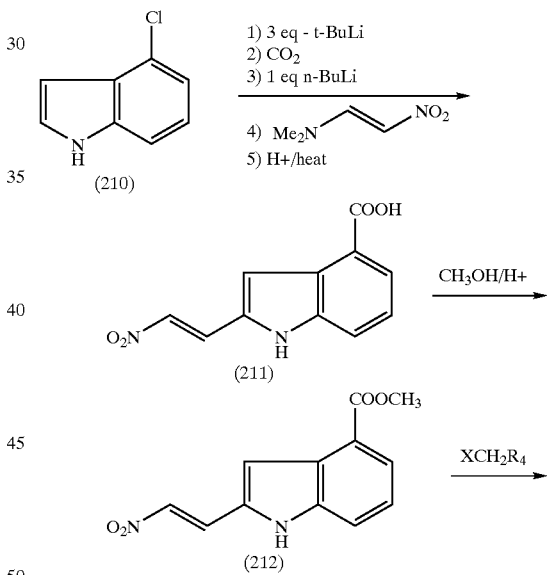

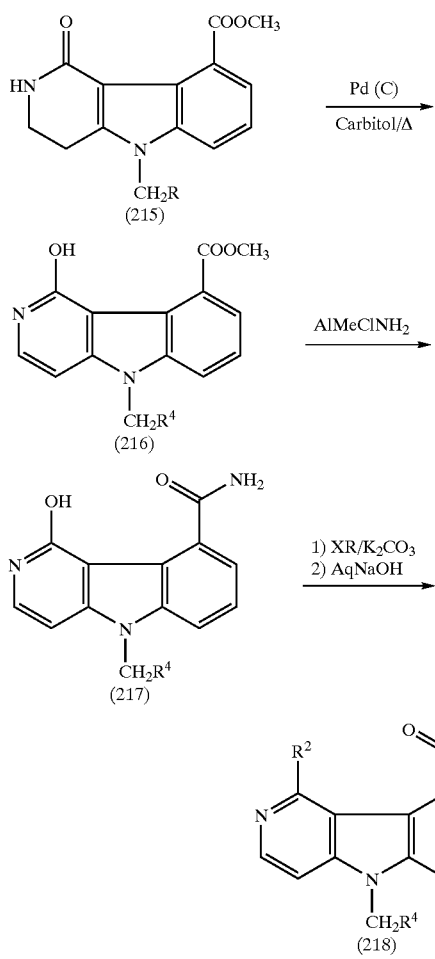
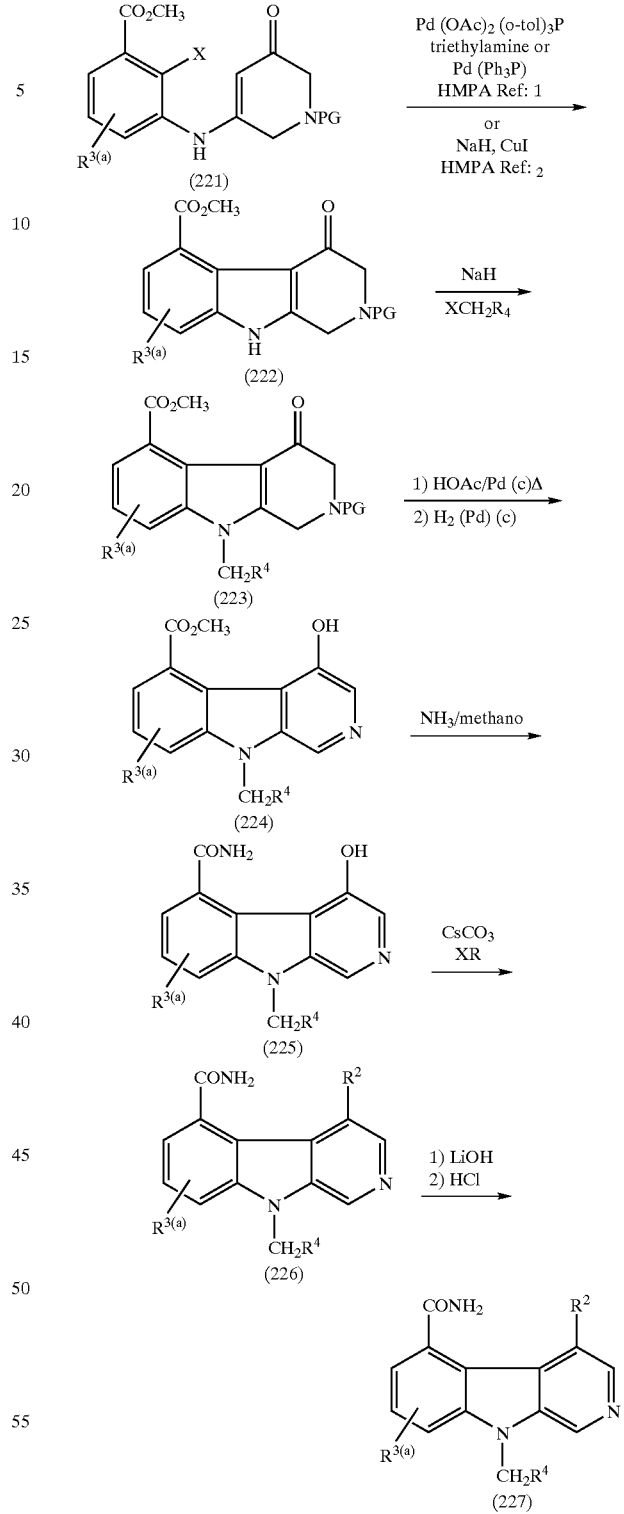

X is halo and
R is $(CH_2)_mR^5$.

Commercially available 4-chloroindole (210) is treated with 3 equivalents of t-butyllithium followed by carbon dioxide, 1 equivalent of n-butyllithium, 1-dimethylamino-2-nitroethene, and acid to provide carboxylic acid (211), which may be esterified to give (212). Alkylation at the 1-position followed by hydrogenation provides aminoethyl indole (214). Cyclization with phosgene to (215) followed by aromatization gives carboline (216). Treatment of (216) with the appropriate Weinreb reagent provides amide (217), which may be alkylated with, for example, ethyl bromoacetate and saponified with sodium hydroxide to give the carboline (218).

Scheme VII (b)

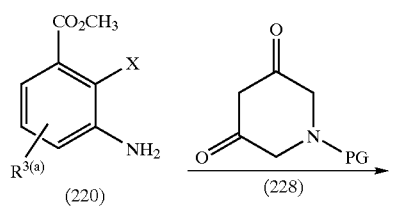

R3(a) is as defined in Scheme I(a),
X is halo, and
R is $(CH_2)_mR^5$.

The 1,3-dione structures (228) are either commercially available or readily prepared by known techniques from commercially available starting materials. Preparation of the aniline derivatives (220) (X=Cl, Br, or I) are accomplished by reducing an appropriately substituted benzoic acid derivative to the corresponding aniline by treatment with a reducing agent such as $SnCl_2$ in hydrochloric acid in an inert solvent such as ethanol or by hydrogenation using hydrogen gas and sulfided platinum or carbon or palladium on carbon. The amino group of (228) is protected with an appropriate protecting group, such as the, carboethoxyl, benzyl, CBZ (benzyloxycarbonyl) or BOC (tert-butoxycarbonyl) protecting group, and the like.

The dione (228) and aniline derivative (220) are condensed according to the general procedure of Chen, et al., (Ref 10) or Yang, et al., (Ref 11), with or without a noninterfering solvent, such as methanol, toluene, or methylene chloride, with or without an acid, such as p-toluenesulfonic acid or trifluoroacetic acid, with or without N-chlorosuccinimide and dimethyl sulfide, to afford the coupled product (221).

Compound (221) is cyclized under basic conditions with a copper (I) salt in an inert solvent according to the general procedure of Yang, et al., (Ref 8). The derivative (221) is treated with a base, such as sodium hydride, in an inert solvent, such as HMPA, at a temperature between 0 and 25° C. A copper (I) salt, such as copper (I) iodide, is added and the resultant mixture stirred at a temperature between 25 and 150° C. for 1 to 48 hours to afford compound (222).

Compound (221) may also be cyclized according to the general procedure of Chen, et al., (Ref 10). The derivative (221) is treated with a base, such as sodium bicarbonate, and a palladium catalyst, such as $Pd(PPh_3)_4$, in an inert solvent, such as HMPA, at a temperature between 25 and 150° C. to afford compound (222).

In a preferred method, intermediate (171) is treated with a transition metal catalyst, such as $Pd(OAc)_2(O\text{-tol})_3P$ in the presence of a base such as triethylamine using a cosolvent of DMF/acetonitrile to prepare (222).

Compound (222) is N-alkylated with an appropriately substituted benzyl halide in the presence of a base, such as sodium hydride or potassium carbonate, in a noninterfering solvent, such as dimethylformamide or dimethylsulfoxide to afford ketone (223). In a two step, one pot process (222) is aromatized by treatment with acetic acid and palladium on carbon in a noninterfering solvent, such as carbitol or cymene, followed by treatment with hydrogen gas and palladium on carbon to cleave the nitrogen protecting group and produce the phenolic derivative (224).

The ester (224) is converted to the corresponding amide (225) under standard conditions with ammonia (preferably) or an ammonium salt, such as ammonium acetate, in an inert solvent, such as water or alcohol, preferably methanol, or with $MeClAlNH_2$ in an inert solvent, such as toluene, at a temperature between 0 to 110° C. Alkylation of the phenolic oxygen of compound 38 with an appropriate haloester, such as methyl bromoacetate, in the presence of a base, such as cesium carbonate, potassium or sodium carbonate, in an inert solvent, such as dimethylformamide or dimethylsulfoxide affords the ester-amide (226). Other haloesters, such as ethyl bromoacetate, propyl bromoacetate, butyl bromoacetate, and the like can also be used to prepare the corresponding esters.

Saponification of compound (226), with lithium hydroxide in an inert solvent, such as methanol-water, affords (227). The intermediate and final products may isolated and purified by conventional techniques such as chromatography or recrystallization. Regioisomeric products and intermediates can be separated by standard methods, such as, recrystallization or chromatography.

References

10) L.-C. Chen et al., Synthesis 385 (1995)
11) S.-C. Yang et al., Heterocycles, 32, 2399 (1991)

The following list of abreviations are used in the Examples and Preparations.

| | |
|---|---|
| HCl = | hydrochloric acid |
| EtOAc = | ethyl acetate |
| DMF = | dimethyl formamide |
| THF = | tetrahydrofuran |
| $Et_2O$ = | diethyl ether |
| $H_2O$ = | water |
| NaOH = | sodium hydroxide |
| EtOH = | ethanol |
| $Na_2SO_4$ = | sodium sulfate |
| $NaHCO_3$ = | sodium bicarbonate |
| celite = | diatomaceous earth |
| $CH_2Cl_2$ = | methylene chloride |
| $H_2SO_4$ = | sulfuric acid |
| MeoH = | methanol |
| $Rh/Al_2O_3$ = | rhodium on alumina |
| DDQ = | 2,3-dichloro-5,6-dicyano-1,4-benzoquinone |
| TLC = | thin layer chromotography |
| NaH = | sodium hydride |
| $NH_4OH$ = | ammonium hydroxide |
| LiOH = | lithium hydroxide |
| $NH_3$ = | ammonia |
| $Cs_2CO_3$ = | cesium carbonate |
| $NH_4oAc$ = | ammonium acetate |

The following preparations of intermediates and examples of final products futher illustrate the preparation of the compounds of this invention. The examples are illustrative only and are not intended to limit the scope of the invention in any way.

EXAMPLE 1

Preparation of 9-benzyl-5,7-dimethoxy-1,2,3,4-tetrahydrocarbazole-4-carboxylic acid hydrazide A. Preparation of N-benzyl-3,5-dimethoxyaniline A solution of 25 gm. (0.163 mol) of 3,5-dimethoxyaniline and 18.3 ml. (0.18 mol) of benzaldehyde in 300 ml. of methanol was cooled in ice-water and treated with 10.3 gm. (0.18 mol) of sodium cyanoborohydride in portions. The solution was stirred and cooled for 3 hours, treated with 1–2 gm. of sodium borohydride for 30 minutes, diluted with water and extracted with ethyl acetate. The organic phase was washed with brine, dried over sodium sulfate, and evaporated in vacuo. The residue was chromatographed on silica gel eluting with a gradient hexane/15–70% ether to give 9-benzyl-3,5-dimethoxyaniline, 28.0 gm., 71%, as an oil.

Elemental Analyses for $C_{15}H_{17}NO_2$: Calculated: C, 74.05; H, 7.04; N, 5.76. Found: C, 74.30; H, 7.12; N, 5.70.

B. Preparation of 9-benzyl-5,7-dimethoxy-1,2,3,4-tetrahydrocarbazole-4-carboxylic acid hydrazide A solution of 9.72 gm of the compound of part A and 4.98 gm of 2-carbethoxy-6-bromocyclohexanone (J. Sheehan and C. E. Mumaw, *J.Am.Chem.Soc.*, 72, 2127–2129, (1950).) in 125 ml of benzene was refluxed for 72 hours, cooled, filtered, and evaporated in vacuo. The residue (12 gm) and 10 gm of zinc chloride were refluxed in 250 ml of benzene for 6 hours, cooled and evaporated in vacuo. The residue was taken up in ethyl acetate, washed with 1N hydrochloric acid, washed with water, dried over sodium sulfate, and evaporated in vacuo. The residue was chromatographed on silica gel eluting with a gradient toluene/0–5% ethyl acetate to give compound (5) ($R^2$=5-MeO $R^3$=7-MeO $R^4$=phenyl), 1.88 gm which was dissolved in 100 ml of ethanol containing 10 ml of hydrazine hydrate and refluxed for 5 days, cooled, the solution decanted, diluted with ethyl acetate, washed with brine, dried over sodium sulfate, and evaporated in vacuo to give title compound, 1.1 gm, 60%, mp 189–190° C./CH$_2$Cl$_2$-EtOH.

Elemental Analyses for C$_{22}$H$_{25}$N$_3$O$_3$: Calculated: C, 69.64; H, 6.64; N, 11.07. Found: C, 69.59; H, 6.74; N, 10.84.

EXAMPLE 2

Preparation of 9-benzyl-5,7-dimethoxy-1,2,3,4-tetrahydrocarbazole-4-carboxamide

A mixture of 980 mg of the compound of example 1, 2 gm of Raney nickel catalyst, 1–2 ml of hydrazine hydrate, and 125 ml of ethanol was refluxed 1 hour, the solution decanted, diluted with ethyl acetate, washed with water, washed with brine, dried over sodium sulfate, and evaporated in vacuo. The residue was chromatographed on silica gel eluting with a gradient methylene chloride/1–3% methanol to give title compound, 820 mg, 84%, mp 190–192° C./EtOH.

Elemental Analyses for C$_{22}$H$_{24}$N$_2$O$_3$: Calculated: C, 72.51; H, 6.64; N, 7.69. Found: C, 71.88; H, 6.89; N, 7.81.

EXAMPLE 3

Preparation of [9-benzyl-4-carbamoyl-7-methoxy-1,2,3,4-tetrahydrocarbazol-5-yl]oxyacetic acid sodium salt A. Preparation of 9-benzyl-5-hydroxy-7-methoxy-1,2,3,4-tetrahydrocarbazole-4-carboxamide A solution of 1.75 gm. (4.8 mmol) of the compound of example 6 in 50 ml. of dimethylformamide was mixed with a solution of sodium thioethoxide (13.5 mmol) in 75 ml. of dimethylformamide and then heated at 100° C. for 21 hours. The mixture was cooled, diluted with water, acidified with hydrochloric acid, and extracted with ethyl acetate. The organic phase was washed with brine, dried over sodium sulfate, and evaporated in vacuo. The residue was chromatographed on silica gel eluting with a gradient methylene chloride/0–4% methanol to give the sub-titled product, 825 mg., 50%, mp 225–7° C./ethanol.

Elemental Analyses for C$_{21}$H$_{22}$N$_2$O$_3$: Calculated: C, 71.98; H, 6.33; N, 7.99. Found: C, 71.71; H, 6.37; N, 7.72.

B. Preparation of [9-benzyl-4-carbamoyl-7-methoxy-1,2,3,4-tetrahydrocarbazol-5-yl]oxyacetic acid ethyl ester A solution of 700 mg. (2.0 mmol) of the product from Part A in 70 ml. of dimethylformamide and 15 ml. of tetrahydrofuran was treated with 100 mg. of sodium hydride (60% in mineral oil; 2.5 mmol) for 10 minutes and then with 0.3 ml. (2.7 mmol) of ethyl bromoacetate for 3 hours. The mixture was diluted with ethyl acetate, washed with water, washed with brine, dried over sodium sulfate, and evaporated in vacuo. The residue was chromatographed on silica gel eluting with a gradient methylene chloride/1–2% methanol to give sub-titled product, 670 mg., 77%, mp 167–169° C./ether.

Elemental Analyses for C$_{25}$H$_{28}$N$_2$O$_5$: Calculated: C, 68.79; H, 6.47; N, 6.42. Found: C, 69.57; H, 6.39; N, 5.77.

C. Preparation of [9-benzyl-4-carbamoyl-7-methoxy-1,2,3,4-tetrahydrocarbazol-5-yl]oxyacetic acid A suspension of 650 mg. of the product from Part B in 20 ml. of tetrahydrofuran and 70 ml. of ethanol was treated with 5 ml. of 2N sodium hydroxide and the resulting solution was stirred for 15.5 hours. The solution was diluted with ethyl acetate and water and acidified with hydrochloric acid. The organic phase was washed with brine, dried over sodium sulfate, concentrated in vacuo, and filtered to give title product, 540 mg., 87%, mp 251–254° C.

Elemental Analyses for C$_{23}$H$_{24}$N$_2$O$_5$: Calculated: C, 67.63; H, 5.92; N, 6.86. Found: C, 67.73; H, 5.74; N, 6.82.

D. Preparation of [9-benzyl-4-carbamoyl-7-methoxy-1,2,3,4-tetrahydrocarbazol-5-yl]oxyacetic acid sodium salt A suspension of 120 mg. of the product from Part C in 20 mL of ethanol was treated with 0.15 mL of 2.0 N sodium hydroxide and warmed until dissolved. The resulting solution was concentrated in vacuo, diluted with ethyl acetate and again concentrated in vacuo and left to stand overnight. The precipitate was filtered and air dried to give the title product as an amorphous solid, 80 mg, 63%.

Elemental Analyses for C$_{23}$H$_{23}$NaN$_2$O$_5$.0.4H$_2$O: Calculated: C, 63.18; H, 5.39; N, 6.40. Found: C, 63.31; H, 5.48; N, 6.25.

EXAMPLE 4

Preparation of [9-benzyl-4-carbamoyl-7-methoxycarbazol-5-yl]oxyacetic acid

A mixture of 430 mg. of the product from Example 3 Part D, 2.0 gm. of 5% Pd/C, and 20 mL of carbitol was heated to reflux and refluxed for 21 hours, cooled, and filtered. The filtrate was diluted with water, acidified with hydrochloric acid, and extracted well with ethyl acetate. The organic phase was washed with brine, dried over sodium sulfate and evaporated in vacuo. The residue was triturated with dichloromethane and filtered to remove solid tetrahydrocarbazole. The filtrate was evaporated in vacuo to give the title product, 125 mg, 31%.

Elemental Analyses for C$_{23}$H$_{20}$N$_2$O$_5$.0.4H$_2$O: Calculated: C, 67.11; H, 5.09; N, 6.81. Found: C, 67.25; H, 5.19; N, 6.75.

EXAMPLE 5

Preparation of methyl [9-benzyl-4-carbamoyl-7-methoxycarbazol-5-yl]oxyacetic acid A. Preparation of 9-benzyl-4-carbamoyl-5,7-dimethoxycarbazole A mixture of 2.0 gm. of the product from Example 2, 2 gm. of 5% Pd/C, and 100 mL of carbitol was refluxed for 17 hours, filtered while still hot, and the solid washed well with ethyl acetate. The combined filtrates were washed with water, washed with brine, dried over sodium sulfate, and evaporated in vacuo to give subtitled product, 1.4 gm., 70%, mp 240–243° C.

Elemental Analyses for C$_{22}$H$_{20}$N$_2$O$_3$: Calculated: C, 73.32; H, 5.59; N, 7.77. Found: C, 74.26; H, 5.73; N, 8.04.

B. Preparation of 9-benzyl-4-carbamoyl-5-hydroxy-7-methoxycarbazole

A solution of 1.2 gm. (3.3 mmol) of the product from Part A and 10 mmol of sodium ethanethiolate in 100 mL of dimethylformamide was heated at 100° C. for 42 hours, cooled, diluted with water, and the pH adjusted to 5–6 with hydrochloric acid. The mixture was extracted with ethyl acetate, the organic phase was washed with water, washed with brine, dried over sodium sulfate, and evaporated in vacuo. The residue was chromatographed on silica gel eluting with ethyl acetate to give product, 550 mg., 48%, mp 234–236° C. dec.

Elemental Analyses for C$_{21}$H$_{18}$N$_2$O$_3$: Calculated: C, 72.82; H, 5.24; N, 8.09. Found: C, 72.54; H, 5.19; N, 8.04.

C. Preparation of methyl [9-benzyl-4-carbamoyl-7-methoxycarbazol-5-yl]oxyacetic acid A solution of 430 mg. (1.2 mmol) of the product from Part B in 40 mL of dimethylformamide and a few mLs of tetrahydrofuran was treated with 60 mg. of sodium hydride (60% in mineral oil; 1.5 mmol) for 15 minutes and then with 0.13 mL (1.4 mmol) of methylbromoacetate for 16 hours, diluted with ethyl acetate, washed with water, washed with brine, dried over sodium sulfate, and evaporated in vacuo. The residue was chromatographed on silica gel eluting with a gradient dichloromethane/1–3% methanol to give title compound, 320 mg., 62%, mp 170–172° C.

Elemental Analyses for $C_{24}H_{22}N_2O_5$: Calculated: C, 68.89; H, 5.30; N, 6.69. Found: C, 68.64; H, 5.41; N, 6.57.

D. Preparation of [9-benzyl-4-carbamoyl-7-methoxycarbazol-5-yl]oxyacetic acid sodium salt To a suspension of 60 mg (0.15mmol) of the product from Part C in 30 mL of ethanol was added 0.075 mL of 2.0 N sodium hydroxide. The mixture was heated until solution, cooled, concentrated in vacuo, diluted with ethyl acetate, concentrated in vacuo, cooled, and filtered to give product, amorphous solid, 50 mg., 80%. MS (FAB+) 427.2: MS (ion spray) +Q1 405.5, –Q1 403.5

EXAMPLE 6

Preparation of 9-benzyl-7-methoxy-5-cyanomethyloxy-1,2,3,4-tetrahydrocarbazole-4-carboxamide A solution of 1.47 gram (4.19 mmol) of the product from Example 3, Part A in 146 ml. of dimethylformamide and 31 ml. tetrahydrofuran was treated with 210 mg. of sodium hydride (60% in mineral oil; 5.24 mmol) for 10 minutes and then with 0.39 ml. (0.66 mmol) of bromoacetonitrile for 3.5 hours. The mixture was diluted with ethyl acetate, washed with water, washed with brine, dried over sodium sulfate, and evaporated in vacuo. The residue was chromatographed on silica gel eluting with a gradient of 0 to 4% methanol in methylene chloride to give the titled product, 1.34 gram, 82%.

Elemental analysis for $C_{23}H_{23}N_3O_3$: Calculated: C, 70.93; H, 5.95; N, 10.79. Theory: C, 70.67; H, 6.06; N, 10.83.

EXAMPLE 7

Preparation of 9-benzyl-7-methoxy-5-(1H-tetrazol-5-yl-methyl)oxy)-1,2,3,4-tetrahydrocarbazole-4-carboxamide A portion of the compound of Example 6, 0.45 gram (1.16 mmol) was heated with 5 ml. tri-n-butyl in hydride at 95° C. for 1 hour. The reaction was then added to a mixture of 125 ml. acetonitrile, 25 ml. tetrahydrofuran, and 50 ml. acetic acid and stirred for 2 hours. The mixture was extracted 4 times with hexane and the residue evaporated in vacuo. Crystallization from acetone and hexane afforded the titled compound, 0.30 gram, 60%.

Elemental analysis for $C_{23}H_{24}N_6O_3$: Calculated: C, 63.88; H, 5.59; N, 19.43. Theory: C, 64.06; H, 5.64; N, 19.28.

Preparation 1

Preparation of 5-Carbomethoxy-1,2-dihydro-2-methyl-9H-carbazol-4(3H)-one from 2-bromo-3-nitrobenzoic acid

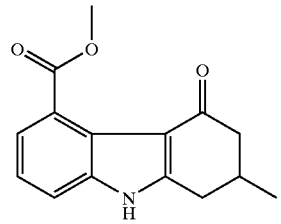

a) Methyl 2-bromo-3-nitrobenzoate

A solution of 2-bromo-3-nitrobenzoic acid (28.4 g, 115.0 mM), iodomethane (18.0 g, 127 mM), and potassium carbonate (19.0 g, 137.4 mM) in 100 mL dimethylformamide was stirred at room temperature for 72 hours. The mixture was poured into 1.5 liters of water. The resultant precipitate was collected by filtration and dried in vacuo to afford 28.79 g (96%) of methyl 2-bromo-3-nitrobenzoate as a white solid. $^1$H NMR (DMSO-d6) δ8.3 (dd, 1H, J=1 and 8 Hz), 7.9 (dd, 1H, J=1 and 8 Hz), 7.7 (t, 1H, J=8 Hz), and 3.9 (s, 3H). IR (KBr, cm$^{-1}$) 2950, 1738, 1541, 1435, 1364, 1298, and 1142. MS (FD) m/e 259, 261.

Elemental Analyses for $C_8H_6NO_4Br$: Calculated: C, 36.95; H, 2.33; N, 5.39. Found: C, 37.14; H, 2.37; N, 5.45.

b) Methyl 2-bromo-3-aminobenzoate

Hydrogen gas was passed through a solution of methyl 2-bromo-3-nitrobenzoate (0.20 g, 0.77 mM) and 0.1 g of 3% sulfided platinum on carbon in 25 mL ethyl acetate for 24 hours at room temperature. The catalyst was removed by filtration through celite. Concentration of the filtrate afforded 0.175 g (99%) of methyl 2-bromo-3-aminobenzoate as a yellow oil. $^1$H NMR (CDCl$_3$) δ7.15 (t, 1H, J=8 Hz), 7.1 (dd, 1H, J=1 and 8 Hz), 6.8 (dd, 1H, J=1 and 8 Hz), and 3.95 (s, 3H). IR (CHCl$_3$, cm$^{-1}$) 3550, 3380, 2980, 2900, 1729, 1613, 1465, 1451, 1434, 1324, 1266, and 1025. MS (FD) m/e 230, 232.

Elemental Analyses for $C_8H_8NO_2Br$: Calculated: C, 41.77; H, 3.51; N, 6.09. Found: C, 42.01; H, 3.29; N, 6.00.

c) 3-(3-Carbomethoxy-2-bromoanilino)-5-methyl-cyclohex-2-en-1-one

A mixture of methyl 2-bromo-3-aminobenzoate (10.2 g, 44.3 mM) and 5-methyl-1,3-cyclohexanedione (6.15 g, 48.7 mM) was heated at 125° C. under a stream of nitrogen for 1.5 hours. The resultant solid was triturated with ethyl acetate to afford 9.98 g (67%) of 3-(3-carbomethoxy-2-bromoanilino)-5-methyl-cyclohex-2-en-1-one. $^1$H NMR (CDCl$_3$) δ7.55 (m, 2H), 7.35 (dd, J=8 and 8 Hz, 1H), 6.4 (bs, 1H), 5.55 (s, 1H), 3.95 (s, 3H), 2.6–2.0 (m, 5H), 1.15 (d, J=7 Hz, 3H). MS (ES) m/e 338, 340.

d) 5-Carbomethoxy-1,2-dihydro-2-methyl-9H-carbazol-4(3H)-one

A suspension of 3-(3-carbomethoxy-2-bromoanilino)-5-methyl-cyclohex-2-en-1-one (9.98 g, 29.5 mM), palladium acetate (0.66 g, 2.95 mM), tri-o-tolylphosphine (1.8 g, 5.9 mM), and triethylamine (5.10 ml, 36.6 mM) in 75 mL acetonitrile was heated at reflux for 3 hours. The solvent was removed in vacuo. The residue was dissolved in methylene chloride, washed with 1 N HCl, then with saturated brine, dried over anhydrous sodium sulfate, filtered, and concentrated to afford 11 g of crude product. Purification by HPLC on silica gel (elution with gradient methylene chloride/ethyl acetate) afforded 5.7 g (75%) of 5-carbomethoxy-1,2- dihydro-2-methyl-9H-carbazol-4(3H)-one. ¹H NMR (CDCl₃) δ9.5 (bs, 1H), 7.4 (d, J=8 Hz, 1H), 7.35 (d, J=8 Hz, 1H), 7.2 (dd, J=8 and 8 Hz, 1H), 4.0 (s, 3H), 2.9 (dd, J=13 and 4 Hz, 1H), 2.55 (m, 2H), 2.4 (m, 1H), 2.25 (dd, J=15 and 9 Hz, 1H), 1.05 (d, J=7 Hz, 3H). MS (ES) m/e 226, 258.

EXAMPLE 8

Preparation of {9-[(phenyl)methyl]-5-carbamoyl-2-methyl-carbazol-4-yl}oxyacetic acid

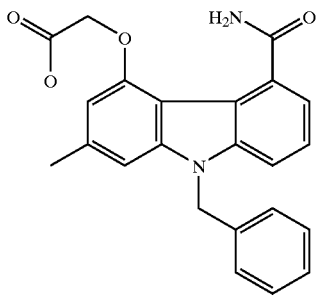

A. 9-[(Phenyl)methyl]-5-carbomethoxy-2-methyl-1,2-dihydrocarbazol-4(3H)-one

A suspension of 5-carbomethoxy-1,2-dihydro-2-methyl-9H-carbazol-4(3H)-one (2.0 g, 7.77 mM), benzyl bromide (0.94 ml, 7.93 mM), and potassium carbonate (2.15 g, 15.5 mM) in 39 mL DMF was stirred at room temperature for 22 hours. The mixture was diluted with ethyl acetate and 1N HCl. The layers were separated and the aqueous layer extracted with ethyl acetate. The combined ethyl acetate layers were extracted with 1N HCl twice, once with water and once with brine. After drying (NaSO₄), evaporation in vacuo afforded 2.61 g (97%) of 9-[(phenyl)methyl]-5-carbomethoxy-2-methyl-1,2-dihydrocarbazol-4(3H)-one. ¹H NMR (CDCl₃) δ7.6–7.4 (m, 6H), 7.0 (m, 2H), 5.4 (s, 2H), 4.05 (s, 3H), 3.0 (m, 1H), 2.65–2.45 (m, 3H), 2.3 (dd, J=15 and 9 Hz, 1H), 1.1 (d, J=7 Hz, 3H). MS (ES) m/e 316, 348.

B. 9-[(Phenyl)methyl]-2-methyl-4-hydroxy-5-carbomethoxy carbazole

A solution of the 9-[(phenyl)methyl]-5-carbomethoxy-2-methyl-1,2-dihydrocarbazol-4(3H)-one (1.30 g, 3.74 mM) and 2,3-dichloro-5,6-dicyano-1,4-benzoquinone (0.93 g, 4.12 mM) in 37 mL of toluene was stirred between 80–90° C. for 5 hours. The mixture was purified by column chromatography on silica gel (elution with methylene chloride) to afford 270 mg (21%) of the 9-[(phenyl)methyl]-2-methyl-4-hydroxy-5-carbomethoxy carbazole. ¹H NMR (CDCl₃) δ10.45 (s, 1H), 8.0 (d, J=8 Hz, 1H), 7.55 (d, J=8 Hz, 1H), 7.4 (dd, J=8 and 8 Hz, 1H), 7.3 (m, 3H), 7.05 (m, 2H), 6.65 (s, 1H), 6.6 (s, 1H), 5.5 (s, 2H), 4.1 (s, 3H), 2.45 (s, 3H). MS (ES) m/e 314, 346.

C. 9-[(Phenyl)methyl]-2-methyl-4-hydroxy-5-carbamoyl carbazole

A solution of the 9-[(phenyl)methyl]-2-methyl-4-hydroxy-5-carbomethoxy carbazole (470 mg, 1.36 mM) in 20 ml THF and 80 mL concentrated aqueous ammonium hydroxide was sonicated for 6 hours at 30–40° C. The precipitated solid was filtered and triturated with Et₂O to afford 200 mg (44%) of 9-[(phenyl)methyl]-2-methyl-4-hydroxy-5-carbamoyl carbazole. ¹H NMR (DMSO-d6) δ10.5 (s, 1H), 8.8 (bs, 1H), 8.4 (bs, 1H), 7.75 (m, 1H), 7.4 (m, 2H), 7.25 (m, 3H), 7.1 (m, 2H), 6.95 (s, 1H), 6.45 (s, 1H), 5.65 (s, 2H), 2.4 (s, 3H). MS (ES) m/e 314, 331.

D. {9-[(Phenyl)methyl]-2-methyl-5-carbamoylcarbazol-4-yl}oxyacetic acid, methyl ester 60% Sodium hydride in mineral oil (30.4 mg, 0.76 mM) was added to a solution of 9-[(phenyl)methyl]-2-methyl-4-hydroxy-5-carbamoyl carbazole (202 mg, 0.61 mM) in 21 mL DMF and 4.6 ml THF. After 10 minutes, methyl bromoacetate (77 μl, 0.482 mM) was added and the resultant mixture stirred at room temperature for 1.25 hours. The mixture was diluted with ethyl acetate and washed with H₂O. The aqueous layer was extracted with ethyl acetate. The combined organic layers were extracted with saturated brine, dried over sodium sulfate, filtered, and concentrated. The residue was purified by column chromatography on silica gel (elution with ethyl acetate) to afford 184 mg (75%) of {9-[(phenyl)methyl]-2-methyl-5-carbamoylcarbazol-4-yl}oxyacetic acid, methyl ester. ¹H NMR (DMSO-d6) δ7.55 (d, 1H, J=8 Hz), 7.5 (bs, 1H), 7.4–7.15 (m, 9H), 6.45 (s, 1H), 5.7 (s, 2H), 4.9 (s, 2H), 3.75 (s, 3H), 2.4 (s, 3H). MS (FD) m/e 386, 403.

Elemental Analyses for C₂₄H₂₂N₂O₄: Calculated: C, 71.63; H, 5.51; N, 6.96. Found: C, 71.74; H, 5.81; N, 6.69.

E. {9-[(Phenyl)methyl]-2-methyl-5-carbamoylcarbazol-4-yl}oxyacetic acid

A solution of the {9-[(phenyl)methyl]-2-methyl-5-carbamoylcarbazol-4-yl}oxyacetic acid, methyl ester (83.5 mg, 0.207 mM) and 1.0 mL (2.0 mM) of 2 N NaOH in 10 mL of ethanol was stirred for 45 minutes at 25° C. The resultant white precipitate was collected by filtration, washed with a small amount of EtOH, then dried in vacuo to afford 48 mg (56%) of the {9-[(phenyl)methyl]-2-methyl-5-carbamoylcarbazol-4-yl}oxyacetic acid sodium salt as a white powder. MS (ES) m/e 314, 372, 389, 411. The filtrate was acidified with 1N HCl to pH=1. After cooling to 5° C., the resultant white precipitate was collected by filtration, washed with water, then dried in vacuo to afford 24 mg (29%) {9-[(phenyl)methyl]-2-methyl-5-carbamoylcarbazol-4-yl}oxyacetic acid. ¹H NMR (DMSO-d6) δ11.2 (bs, 1H), 7.8 (bs, 1H), 7.6 (d, J=8 Hz, 1H), 7.45 (bs, 1H), 7.4–7.05 (m, 8H), 6.45 (s, 1H), 5.65 (s, 2H), 4.9 (s, 2H), 2.4 (s, 3H). MS (ES) m/e 314, 372, 389.

Elemental Analyses for C₂₃H₂₀N₂O₄: Calculated: C, 71.12; H, 5.19; N, 7.21. Found: C, 71.33; H, 5.47; N, 7.19.

EXAMPLE 9

Preparation of {9-[(3-fluorophenyl)methyl]-5-carbamoyl-2-methyl-carbazol-4-yl}oxyacetic acid

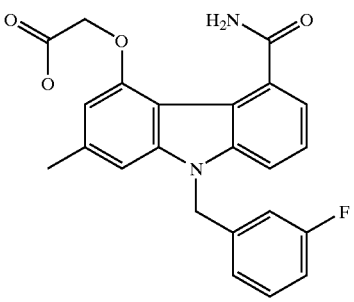

A. 9-[(3-Fluorophenyl)methyl]-5-carbomethoxy-2-methyl-1,2-dihydrocarbazol-4(3H)-one A suspension of 5-carbomethoxy-1,2-dihydro-2-methyl-9H-carbazol-4(3H)-one (1.0 g, 3.89 mM), 3-fluorobenzyl bromide (0.48 ml, 3.97 mM), and potassium carbonate (1.07 g, 7.78 mM) in 20 mL DMF was stirred at room temperature for 22 hours. The mixture was diluted with EtOAc and 1N HCl. The layers were separated and the aqueous extracted with EtOAc. The combined EtOAc layers were extracted with 1N HCl, water, then brine. After drying (Na$_2$SO$_4$), evaporation in vacuo afforded 1.38 g (97%) of the 9-[(3-fluorophenyl)methyl]-5-carbomethoxy-2-methyl-1,2-dihydrocarbazol-4(3H)-one. $^1$H NMR (CDCl$_3$) δ7.4–7.2 (m, 5H), 7.0 (m, 1H), 6.75 (m, 2H), 5.4 (s, 2H), 4.05 (s, 3H), 3.0 (m, 1H), 2.65–2.45 (m, 3H), 2.3 (dd, J=15 and 9 Hz, 1H), 1.1 (d, J=7 Hz, 3H). MS (ES) m/e 334, 366.

B. 9-[(3-Fluorophenyl)methyl]-2-methyl-4-hydroxy-5-carbomethoxy carbazole

A solution of the 9-[(3-fluorophenyl)methyl]-5-carbomethoxy-2-methyl-1,2-dihydrocarbazol-4(3H)-one (1.37 g; 3.75 mM) and 2,3-dichloro-5,6-dicyano-1,4-benzoquinone (0.94 g, 4.13 mM) in 38 mL of toluene was stirred between 80–90° C. for 3 hours. The mixture was purified by column chromatography on silica gel (elution with methylene chloride) to afford 0.33 g (24%) of 9-[(3-fluorophenyl)methyl]-2-methyl-4-hydroxy-5-carbomethoxy carbazole. $^1$H NMR (CDCl$_3$) δ10.45 (s, 1H), 8.0 (d, J=8 Hz, 1H), 7.55 (d, J=8 Hz, 1H), 7.4 (dd, J=8 and 8 Hz, 1H), 7.3 (m, 2H), 6.95 (m, 1H), 6.85 (d, J=8 Hz, 1H), 6.75 (m, 1H), 6.65 (s, 1H), 5.5 (s, 2H), 4.1 (s, 3H), 2.45 (s, 3H). MS (ES) m/e 332, 364.

C. 9-[(3-Fluorophenyl)methyl]-2-methyl-4-hydroxy-5-carbamoyl carbazole

A solution of the 9-[(3-fluorophenyl)methyl]-2-methyl-4-hydroxy-5-carbomethoxy carbazole (0.33 g, 0.91 mM) in 14 ml THF and 54 mL concentrated aqueous ammonium hydroxide was sonicated for 6.5 h at 30–40° C. The precipitated solid was filtered, washed with water, and triturated with 35 ml Et$_2$O to afford 182 mg (57%) of 9-[(3-fluorophenyl)methyl]-2-methyl-4-hydroxy-5-carbamoyl carbazole. $^1$H NMR (DMSO-d6) δ10.5 (s, 1H), 8.8 (bs, 1H), 8.4 (bs, 1H), 7.75 (m, 1H), 7.4 (m, 2H), 7.25 (m, 1H), 7.05 (m, 1H), 6.9 (m, 2H), 6.85 (d, J=8 Hz, 1H), 6.45 (s, 1H), 5.65 (s, 2H), 2.4 (s, 3H). MS (ES) m/e 332, 349.

D. {9-[(3-Fluorophenyl)methyl]-2-methyl-5-carbamoylcarbazol-4-yl}oxyacetic acid, methyl ester 60% Sodium hydride in mineral oil (25.9 mg, 0.65 mM) was added to a solution of 9-[(3-fluorophenyl)methyl]-2-methyl-4-hydroxy-5-carbamoyl carbazole (181 mg, 0.52 mM) in 18 mL DMF and 3.9 ml THF. After 10 minutes, methyl bromoacetate (66 μl, 0.70 mM) was added and the resultant mixture stirred at room temperature for 1.25 hours. The mixture was diluted with ethyl acetate and washed with H$_2$O. The aqueous layer was extracted with ethyl acetate. The combined organic layers were extracted with saturated brine, dried over sodium sulfate, filtered, and concentrated. The residue was purified by column chromatography on silica gel (elution with methylene chloride/acetone gradient) to afford 170 mg (78%) of the {9-[(3-fluorophenyl)methyl]-2-methyl-5-carbamoylcarbazol-4-yl}oxyacetic acid, methyl ester. $^1$H NMR (DMSO-d6) δ7.55 (d, 1H, J=8 Hz), 7.5 (bs, 1H), 7.4–7.25 (m, 2H), 7.2 (bs, 1H), 7.05 (m, 3H), 6.95 (d, J=8 Hz, 1H), 6.9 (d, J=8 Hz), 6.45 (s, 1H), 5.65 (s, 2H), 4.9 (s, 2H), 3.75 (s, 3H), 2.4 (s, 3H). MS (FD) m/e 404, 421.

Elemental Analyses for C$_{24}$H$_{21}$FN$_2$O$_4$: Calculated: C, 68.56; H, 5.03; N, 6.66. Found: C, 67.75; H, 4.95; N, 6.33.

E. {9-[(3-Fluorophenyl)methyl]-2-methyl-5-carbamoylcarbazol-4-yl}oxyacetic acid

A solution of {9-[(3-fluorophenyl)methyl]-2-methyl-5-carbamoylcarbazol-4-yl}oxyacetic acid, methyl ester (68.3 mg, 0.162 mM) and 0.81 mL (1.6 mM) of 2 N NaOH in 8.1 mL of ethanol was stirred for 30 minutes at 25° C. The resultant white precipitate was collected by filtration, washed with a small amount of EtOH, then dried in vacuo to afford 11 mg (16%) of {9-[(3-fluorophenyl)methyl]-2-methyl-5-carbamoylcarbazol-4-yl}oxyacetic acid, sodium salt as a white powder. The filtrate was acidified with 1N HCl to pH=2. After cooling to 5° C., the resultant white precipitate was collected by filtration, washed with water, then dried in vacuo to afford 31 mg (47%) {9-[(3-fluorophenyl)methyl]-2-methyl-5-carbamoylcarbazol-4-yl}oxyacetic acid. $^1$H NMR (DMSO-d6) δ7.75 (bs, 1H), .7.6 (d, 1H, J=8 Hz), 7.45 (bs, 1H), 7.4–7.25 (m, 2H), 7.05 (m, 3H), 6.95 (d, J=8 Hz, 1H), 6.9 (d, J=8 Hz, 1H), 6.45 (s, 1H), 5.65 (s, 2H), 4.8 (s, 2H), 2.4 (s, 3H). MS (ES) m/e 390, 407. Recrystallization from acetone/hexane provided an analytical sample:

Elemental Analyses for C$_{23}$H$_{19}$FN$_2$O$_4$: Calculated: C, 67.97; H, 4.71; N, 6.89. Found: C, 68.21; H, 4.93; N, 7.16.

EXAMPLE 10

Preparation of {9-[(3-methylphenyl)methyl]-5-carbamoyl-2-methyl-carbazol-4-yl}oxyacetic acid

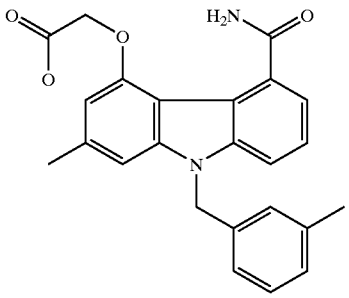

A. 9-[(3-Methylphenyl)methyl]-5-carbomethoxy-2-methyl-1,2-dihydrocarbazol-4(3H)-one A suspension of 5-carbomethoxy-1,2-dihydro-2-methyl-9H-carbazol-4(3H)-one (1.0 g, 3.89 mM), 3-methylbenzyl bromide (0.54 ml, 3.97 mM), and potassium carbonate (1.07 g, 7.78 mM) in 20 mL DMF was stirred at room temperature for 19 hours. The mixture was diluted with EtOAc and 1N HCl. The layers were separated and the aqueous layer extracted with EtOAc. The combined EtOAc layers were extracted with 1N HCl, water, then brine. After drying (NaSO$_4$), evaporation in vacuo afforded 1.41 g (100%) of 9-[(3-methylphenyl)methyl]-5-carbomethoxy-2-methyl-1,2-dihydrocarbazol-4(3H)-one. $^1$H NMR (CDCl$_3$) δ7.4–7.05 (m, 6H), 6.8 (m, 1H), 5.3 (s, 2H), 4.05 (s, 3H), 3.0 (m, 1H), 2.7–2.3 (m, 4H), 2.3 (s, 1H), 1.2 (d, J=7 Hz, 3H). MS (ES) m/e 362.

B. 9-[(3-Methylphenyl)methyl]-2-methyl-4-hydroxy-5-carbomethoxy carbazole

To a solution of 9-[(3-methylphenyl)methyl]-5-carbomethoxy-2-methyl-1,2-dihydrocarbazol-4(3H)-one (1.41 g, 3.89 mM) in 13 ml dioxane was added 60% sodium hydride in mineral oil (0.36 g, 8.95 mM). The reaction was stirred 6 minutes, then methyl benzenesulfinate (0.81 ml, 6.22 mM) was added. The reaction was stirred an additional 6 hours, then diluted with 20 ml dioxane and 0.51 ml acetic acid. The mixture was refluxed 30 minutes, diluted with ethyl acetate, and extracted with saturated NaHCO$_3$, brine, then water. After drying (NaSO$_4$), evaporation in vacuo afforded 2.30 g. The mixture was purified by column chromatography on silica gel (elution with toluene/methylene chloride) to afford 0.92 g (66%) of 9-[(3-methylphenyl) methyl]-2-methyl-4-hydroxy-5-carbomethoxy carbazole. $^1$H NMR (CDCl$_3$) δ10.45 (s, 1H), 8.0 (d, J=8 Hz, 1H), 7.55 (d, J=8 Hz, 1H), 7.4 (dd, J=8 and 8 Hz, 1H), 7.4 (dd, J=8 and 8 Hz, 1H), 7.05 (d, J=8 HZ, 1H), 6.9 (s, 1H), 6.85 (d, J=8 Hz, 1H), 6.75 (s, 1H), 6.7 (s, 1H), 5.45 (s, 2H), 4.1 (s, 3H), 2.4 (s, 3H), 2.25 (s, 3H). MS (ES) m/e 328, 360.

C. 9-[(3-Methylphenyl)methyl]-2-methyl-4-hydroxy-5-carbamoyl carbazole

A solution of 9-[(3-methylphenyl)methyl]-2-methyl-4-hydroxy-5-carbomethoxy carbazole (0.92 g, 2.56 mM) in 38 ml THF and 154 mL concentrated aqueous ammonium hydroxide was sonicated for 6 h at 30–40° C. The precipitated solid was filtered, washed with water to afford 0.55 g (63%) of 9-[(3-methylphenyl)methyl]-2-methyl-4-hydroxy-5-carbamoyl carbazole. $^1$H NMR (DMSO-d6) δ10.5 (s, 1H), 8.8 (bs, 1H), 8.4 (bs, 1H), 7.75 (m, 1H), 7.4 (m, 2H), 7.15 (dd, J=8 and 8 Hz, 1H), 7.05 (m, 1H), 7.0 (s, 1H), 6.9 (s, 1H), 6.8 (d, J=8 Hz, 1H), 6.45 (s, 1H), 5.65 (s, 2H), 2.4 (s, 3H)., 2.2 (s, 3H). MS (ES) m/e 328, 345.

D. {9-[(3-Methylphenyl)methyl]-2-methyl-5-carbamoylcarbazol-4-yl}oxyacetic acid, methyl ester 60% Sodium hydride in mineral oil (79.8 mg, 2.0 mM) was added to a solution of 9-[(3-methylphenyl)methyl]-2-methyl-4-hydroxy-5-carbamoyl carbazole (0.55 g, 1.60 mM) in 56 mL DMF and 12 ml THF. After 10 minutes, methyl bromoacetate (0.20 ml, 2.16 mM) was added and the resultant mixture stirred at room temperature for 1 hour. The mixture was diluted with ethyl acetate and washed with H$_2$O. The aqueous layer was extracted with ethyl acetate. The combined organic layers were extracted with saturated brine, dried over sodium sulfate, filtered, and concentrated. The residue was purified by column chromatography on silica gel (elution with methylene chloride/acetone gradient) to afford 0.51 g (76%) of {9-[(3-methylphenyl)methyl]-2-methyl-5-carbamoylcarbazol-4-yl}oxyacetic acid, methyl ester. $^1$H NMR (DMSO-d6) δ7.5 (m, 2H), 7.35 (dd, J=8 and 8 Hz, 1H), 7.2–7.1 (m, 2H), 7.05–6.95 (m, 4H), 6.85 (d, J=8 Hz, 1H), 6.45 (s, 1H), 5.6 (s, 2H), 4.9 (s, 2H), 3.75 (s, 3H), 2.4 (s, 3H), 2.2 (s, 3H). MS (FD) m/e 400, 417.

Elemental Analyses for C$_{25}$H$_{24}$N$_2$O$_4$: Calculated: C, 72.10; H, 5.81; N, 6.73. Found: C, 71.94; H, 5.71; N, 6.96.

E. {9-[(3-Methylphenyl)methyl]-2-methyl-5-carbamoylcarbazol-4-yl}oxyacetic acid A solution of {9-[(3-methylphenyl)methyl)-2-methyl-5-carbamoylcarbazol-4-yl}oxyacetic acid, methyl ester (0.12 g, 0.288 mM) and 1.4 mL (2.8 mM) of 2 N NaOH in 14 mL of ethanol was stirred for 30 minutes at 25° C. The reaction was acidified with 1N HCl to pH=2. After stirring 1 hour, the resultant white precipitate was collected by filtration, washed with water, then dried in vacuo to afford 114 mg (95%) {9-[(3-methylphenyl)methyl]-2-methyl-5-carbamoylcarbazol-4-yl}oxyacetic acid. $^1$H NMR (DMSO-d6) δ11.1 (bs, 1H), 7.75 (bs, 1H), 7.6 (d, J=8 Hz, 1H), 7.45 (bs, 1H), 7.35 (dd, J=8 and 8 Hz, 1H), 7.2–7.0 (m, 5H), 6.85 (d, J=8 Hz, 1H), 6.45 (s, 1H), 5.6 (s, 2H), 4.8 (s, 2H), 2.4 (s, 3H), 2.2 (s, 3H). MS (ES) m/e 386, 403. Recrystallization from acetone/hexane provided an analytical sample:

Elemental Analyses for C$_{24}$H$_{22}$N$_2$O$_4$: Calculated: C, 71.63; H, 5.51; N, 6.96. Found: C, 71.88; H, 5.65; N, 7.20.

Preparation 2

Preparation of 5-Carbomethoxy-1,2-dihydro-2-(4-trifluoromethylphenyl)-9H-carbazol-4(3H)-one from 2-bromo-3-nitrobenzoic acid

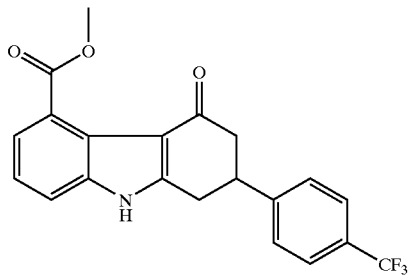

a) Methyl 2-bromo-3-nitrobenzoate

A solution of 2-bromo-3-nitrobenzoic acid (28.4 g, 115.0 mM), iodomethane (18.0 g, 127 mM), and potassium carbonate (19.0 g, 137.4 mM) in 100 mL DMF was stirred at room temperature for 72 hours. The mixture was poured into 1.5 liters of H$_2$O. The resultant precipitate was collected by filtration and dried in vacuo to afford 28.79 g (96%) of methyl 2-bromo-3-nitrobenzoate as a white solid. $^1$H NMR (DMSO-d6) δ8.3 (dd, 1H, J=1 and 8 Hz), 7.9 (dd, 1H, J=1 and 8 Hz), 7.7 (t, 1H, J=8 Hz), and 3.9 (s, 3H). IR (KBr, cm$^{-1}$) 2950, 1738, 1541, 1435, 1364, 1298, and 1142. MS (FD) m/e 259, 261.

Elemental Analyses for C$_8$H$_6$NO$_4$Br: Calculated: C, 36.95; H, 2.33; N, 5.39. Found: C, 37.14; H, 2.37; N, 5.45.

b) Methyl 2-bromo-3-aminobenzoate

Hydrogen gas was passed through a solution of methyl 2-bromo-3-nitrobenzoate (0.20 g, 0.77 mM) and 0.1 g of 3% sulfided platinum on carbon in 25 mL ethyl acetate for 24 hours at room temperature. The catalyst was removed by filtration through celite. Concentration of the filtrate afforded 0.175 g (99%) of methyl 2-bromo-3-aminobenzoate as a yellow oil. $^1$H NMR (CDCl$_3$) δ7.15 (t, 1H, J=8 Hz), 7.1 (dd, 1H, J=1 and 8 Hz), 6.8 (dd, 1H, J=1 and 8 Hz), and 3.95 (s, 3H). IR (CHCl$_3$, cm$^{-1}$) 3550, 3380, 2980, 2900, 1729, 1613, 1465, 1451, 1434, 1324, 1266, and 1025. MS (FD) m/e 230, 232.

Elemental Analyses for C$_8$H$_8$NO$_2$Br: Calculated: C, 41.77; H, 3.51; N, 6.09. Found: C, 42.01; H, 3.29; N, 6.00.

c) 3-(3-Carbomethoxy-2-bromoanilino)-5-(4-trifluoromethylphenyl-cyclohex-2-en-1-one A mixture of methyl 2-bromo-3-aminobenzoate (10.2 g, 44.3 mM) and 5-(4-trifluoromethylphenyl)-1,3-cyclohexanedione (1.77 g, 6.93 mM) was heated at 150° C. under a stream of nitrogen for 20 minutes. The resultant solid was triturated with 4:1 EtOAc/Et$_2$O to afford 2.18 g (74%) of 3-(3-carbomethoxy-2-bromoanilino)-5-(4-trifluoromethylphenyl)-cyclohex-2-en-1-one. $^1$H NMR (DMSO-d6) δ8.9 (s, 1H), 7.75–7.5 (m, 7H), 3.9 (s, 3H), 3.5 (m, 1H), 2.9 (dd, J=14 and 9 Hz, 1H), 2.7 (dd, J14 and 4 Hz, 1H), 2.55 (dd, J=14 and 9 Hz, 1H), 2.35 (dd, J=14 and 4 Hz, 1H). MS (ES) m/e 368, 370.

d) 5-Carbomethoxy-1,2-dihydro-2-(4-trifluoromethylphenyl)-9H-carbazol-4(3H)-one

A suspension of 3-(3-carbomethoxy-2-bromoanilino)-5 (4-trifluoromethylphenyl)-cyclohex-2-en-1-one (2.18 g, 4.66 mM), palladium acetate (0.10 g, 0.47 mM), tri-o-tolylphosphine (0.28 g, 0.93 mM), and triethylamine (0.8 ml, 5.78 mM) in 12 mL acetonitrile was heated at reflux for 3 hours. The solvent was removed in vacuo. The residue was dissolved in methylene chloride, washed with 1 N HCl, then with saturated brine, dried over anhydrous sodium sulfate, filtered, and concentrated to afford 2.21 g. Purification by HPLC on silica gel (elution with gradient methylene chloride/ethyl acetate) afforded 1.57 g (87%) of the 5-carbomethoxy-1,2-dihydro-2-(4-trifluoromethylphenyl)-9H-carbazol-4(3H)-one. $^1$H NMR (CDCl$_3$) δ9.2 (bs, 1H), 7.6 (d, J=8 Hz, 2H), 7.45–7.35 (m, 5H), 7.25 (d, J=8 Hz, 2H), 3.55 (m, 1H), 3.2–3.0 (m, 2H), 2.7 (m, 2H). MS (ES) m/e 356,388.

EXAMPLE 11

Preparation of {9-[(phenyl)methyl]-5-carbamoyl-2-(4-trifluoromethylphenyl)-carbazol-4-yl}oxyacetic acid

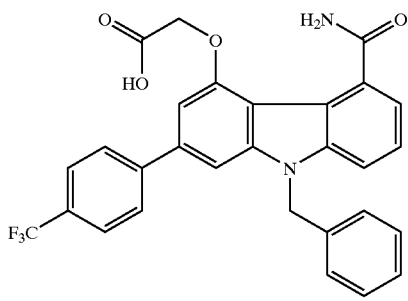

a) 9-[(Phenyl)methyl]-5-carbomethoxy-2-(4-trifluoromethylphenyl)-1,2-dihydrocarbazol-4(3H)-one A suspension of 5-carbomethoxy-1,2-dihydro-2-(4-trifluoromethylphenyl)-9H-carbazol-4(3H)-one (1.57 g, 4.05 mM), benzyl bromide (0.49 ml, 4.13 mM), and potassium carbonate (1.12 g, 8.10 mM) in 20 mL DMF was stirred at room temperature for 22 hours. The mixture was diluted with EtOAc and 1N HCl. The layers were separated and the aqueous extracted with EtOAc. The combined EtOAc layers were extracted with 1N HCl, water, then brine. After drying (NaSO$_4$), evaporation in vacuo afforded 1.87 g (96%) of the 9-[(phenyl)methyl]-5-carbomethoxy-2-(4-trifluoromethylphenyl)-1,2-dihydrocarbazol-4(3H)-one. $^1$H NMR (CDCl$_3$) δ7.6 (d, J=8 Hz, 2H), 7.45–7.25 (m, 8H), 6.95 (m, 2H), 5.35 (s, 2H), 4.05 (s, 3H), 3.65 (m, 1H), 3.2 (dd, J=16 and 5 Hz, 1H), 3.0 (dd, J=16 and 10 Hz, 1H), 2.8 (m, 2H). MS (ES) m/e 478.

b) 9-[(Phenyl)methyl]-2-(4-trifluoromethylphenyl)-4-hydroxy-5-carbomethoxy carbazole A solution of the 9-[(phenyl)methyl]-5-carbomethoxy-2-(4-trifluoromethylphenyl-1,2-dihydrocarbazol-4(3H)-one (1.87 g, 3.92 mM) and 2,3-dichloro-5,6-dicyano-1,4-benzoquinone (0.89 g, 3.92 mM) in 39 mL of toluene was refluxed for 25 minutes. The mixture was purified by column chromatography on silica gel (elution with toluene) to afford 1.10 g (59%) of the 9-[(phenyl)methyl]-2-(4-trifluoromethylphenyl)-4-hydroxy-5-carbomethoxy carbazole. $^1$H NMR (CDCl$_3$) δ10.65 (s, 1H), 8.05 (d, J=8 Hz, 1H), 7.8 (m, 3H), 7.65 (m, 3H), 7.6 (d, J=8 Hz, 1H), 7.45 (dd, J=8 and 8 Hz, 1H), 7.3–7.1 (m, 2H), 5.6 (s, 2H), 4.1 (s, 3H). MS (ES) m/e 444. 476.

c) 9-[(Phenyl)methyl]-2-(4-trifluoromethylphenyl)-4-hydroxy-5-carbamoyl carbazole A solution of the 9-[(phenyl)methyl]-2-(4-trifluoromethylphenyl)-4-hydroxy-5-carbomethoxy carbazole (1.10 g, 2.31 mM) in 35 ml THF and 140 mL concentrated aqueous ammonium hydroxide was sonicated for 6 hours at 30–40° C. The precipitated solid was filtered and washed with water. Trituration with Et$_2$O, then with 2:1 Et$_2$O/CH$_2$Cl$_2$ afforded 0.20 g (19%) of the 9-[(phenyl)methyl]-2-(4-trifluoromethylphenyl)-4-hydroxy-5-carbamoyl carbazole. $^1$H NMR (DMSO-d6) δ10.8 (s, 1H), 8.9 (bs, 1H), 8.45 (bs, 1H), 8.0 (d, J=8 Hz, 2H), 7.8 (d, J=8 Hz, 2H), 7.6 (s, 1H), 7.5 (m, 2H), 7.3–7.1 (m, 6H), 7.0 (s, 1H), 5.8 (s, 2H). MS (ES) m/e 444, 461.

d) {9-[(Phenyl)methyl]-2-(4-trifluoromethylphenyl)-5-carbamoylcarbazol-4-yl}oxyacetic acid, methyl ester 60% Sodium hydride in mineral oil (22 mg, 0.54 mM) was added to a solution of the 9-[(phenyl)methyl]-2-(4-trifluoromethylphenyl)-4-hydroxy-5-carbamoyl carbazole (0.20 g, 0.43 mM) in 15 mL DMF and 3 ml THF. After 7 minutes, methyl bromoacetate (56 μl, 0.59 mM) was added and the resultant mixture stirred at room temperature for 1 hour. The mixture was diluted with ethyl acetate and washed with H$_2$O. The aqueous layer was extracted with ethyl acetate. The combined organic layers were extracted with saturated brine, dried over sodium sulfate, filtered, and concentrated. The residue was purified by column chromatography on silica gel (elution with ethyl acetate) to afford 0.19 g (84%) of the {9-[(phenyl)methyl]-2-(4-trifluoromethylphenyl)-5-carbamoylcarbazol-4-yl}oxyacetic acid, methyl ester. $^1$H NMR (DMSO-d6) δ8.0 (d, J=8 Hz, 2H), 7.85 (d, J=8 Hz, 2H), 7.7 (s, 1H), 7.6 (d, J=8 Hz, 1H), 7.6 (bs, 1H), 7.4 (dd, J=8 and 8 Hz, 1H), 7.3–7.1 (m, 6H), 7.1 (d, J=8 Hz, 1H), 7.0 (s, 1H), 5.8 (s, 2H), 5.1 (s, 2H), 3.7 (s, 3H). MS (FD) m/e 516,533.

Elemental Analyses for C$_{30}$H$_{23}$F$_3$N$_2$O$_4$: Calculated: C, 67.66; H, 4.36; N, 5.26. Found: C, 68.38; H, 4.29; N, 5.67.

e) {9-[(Phenyl)methyl]-2-(4-trifluoromethylphenyl)-5-carbamoylcarbazol-4-yl}oxyacetic acid A solution of the {9-[(phenyl)methyl]-2-(4-trifluoromethylphenyl)-5-carbamoylcarbazol-4-yl}oxyacetic acid, methyl ester (101 mg, 0.19 mM) and 0.95 mL (1.9 mM) of 2 N NaOH in 9.5 mL of ethanol was stirred for 30 minutes at 25° C. The reaction was acidified with 1N HCl to pH=2. After stirring 30 minutes, the resultant white precipitate was collected by filtration, washed with water, then dried in vacuo to afford 73 mg (75%) {9-[(phenyl)methyl]-2-(4-trifluoromethylphenyl)-5-carbamoylcarbazol-4-yl}oxyacetic acid. $^1$H NMR (DMSO-d6) δ11.0 (bs, 1H), 8.0 (d, J=8 Hz, 2H), 7.85 (d, J=8 Hz, 2H), 7.8 (bs, 1H), 7.7 (s, 1H), 7.65 (d, J=8 Hz, 1H), 7.4 (m, 2H), 7.3–7.1 (m, 6H), 7.0 (s, 1H), 5.8 (s, 2H), 5.0 (s, 2H). MS (ES) m/e 502,519.

Elemental Analyses for C$_{29}$H$_{21}$F$_3$N$_2$O$_4$: Calculated: C, 67.17; H, 4.09; N, 5.40. Found: C, 67.05; H, 4.11; N, 5.31.

EXAMPLE 12

Preparation of 9-benzyl-5-(2-methanesulfonamido)ethyloxy-7-methoxy-1,2,3,4-tetrahydrocarbazole-4-carboxamide A. Preparation of 5-(2-amino)ethyloxy-9-benzyl-7-methoxy-1,2,3,4-tetrahydrocarbazole-4-carboxamide To 1.93 ml (1.93 mmol) 1M lithium aluminum hydride/THF in 13 ml THF at 0° C. was added H$_2$SO$_4$(53 μl, 0.97 mmol) dropwise over 5 min. The mixture was allowed to stir at room temperature 1 hour, then a solution of 9-benzyl-7-methoxy-5-cyanomethyloxy-1,2,3,4-tetrahydrocarbazole-4-carboxamide (0.50 g, 1.29 mmol) in 13 ml THF was added dropwise at a rate which kept the temperature below 26° C. After an additional 45 minutes, the reaction was quenched with 0.5 ml 1:1 THF/H$_2$O, 0.75 ml 13% NaOH, and finally 80 μl H$_2$O. The reaction was diluted with EtOAc and saturated NaHCO$_3$, and the layers separated. The organic layer was extracted with brine, dried over sodium sulfate, and evaporated in vacuo. The residue was chromatographed on silica gel eluting with 9:1:0.1 CH$_2$Cl$_2$/MeOH/NH$_4$OH to give the subtitled product (0.28 g, 55%). MS (ES+) 394

B. Preparation of 9-benzyl-5-(2-methanesulfonamido) ethyloxy-7-methoxy-1,2,3,4-tetrahydrocarbazole-4-carboxamide To 0.20 g (0.51 mmol) of the product from Part A in 10 ml THF at 0° C. was added triethylamine (71 µl, 0.51 mmol) and methanesulfonylchloride (39 µl, 0.51 mmol). After 40 minutes at 0° C., the reaction was diluted with EtOAc and saturated NaHCO$_3$, and the layers separated. The organic layer was extracted with brine, dried over sodium sulfate, and evaporated in vacuo. The residue was chromatographed on silica gel eluting with 20:1 CH$_2$Cl$_2$/MeOH and crystallized from EtOAc/hexane to give the titled product (0.13 g, 54%). MS (ES+) 472

Elemental Analyses for $C_{24}H_{29}N_3O_5S$: Calculated: C, 61.13; H, 6.20; N, 8.91. Found: C, 61.04; H, 6.16; N, 9.21.

EXAMPLE 13

Preparation of 9-benzyl-4-(2-methanesulfonamido) ethyloxy-2-methoxycarbazole-5-carboxamide A. Preparation of 4-(2-amino)ethyloxy-9-benzyl-2-methoxycarbazole-5-carboxamide To 1.25 ml (1.25 mmol) 1M lithium aluminum hydride/ THF in 8.3 ml THF at 0° C. was added H$_2$SO$_4$(34.5 µl, 0.63 mmol) dropwise over 5 min. The mixture was allowed to stir at room temperature 1 hour, then a suspension of 9-benzyl-4-cyanomethyloxy-2-methoxycarbazole-5-carboxamide (0.32 g, 0.83 mmol) in 8.3 ml THF was added dropwise at a rate which kept the temperature below 26° C. After an additional 45 minutes, the reaction was quenched with 0.32 ml 1:1 THF/H$_2$O, 0.48 ml 13% NaOH, and finally 51 µl H$_2$O. The reaction was diluted with EtOAc and saturated NaHCO$_3$, and the layers separated. The organic layer was extracted with brine, dried over sodium sulfate, and evaporated in vacuo. The residue was chromatographed on silica gel eluting with 9:1:0.1 CH$_2$Cl$_2$/MeOH/NH$_4$OH to give the subtitled product (148 mg, 46%). MS (ES+) 390

B. Preparation of 9-benzyl-4-(2-methanesulfonamido) ethyloxy-2-methoxycarbazole-5-carboxamide To 107 mg (0.27 mmol) of the product from Part A in 11 ml THF at 0° C. was added triethylamine (38 µl, 0.27 mmol) and methanesulfonylchloride (21 µl, 0.27 mmol). After 40 minutes at 0° C., the reaction was diluted with EtOAc and saturated NaHCO$_3$, and the layers separated. The organic layer was extracted with brine, dried over sodium sulfate, and evaporated in vacuo. The residue was chromatographed on silica gel eluting with 10:1 CH$_2$Cl$_2$/acetone and crystallized from EtOAc/hexane to give the titled product (28.6 mg, 22%). MS (ES+) 468

Elemental Analyses for $C_{24}H_{25}N_3O_5S$: Calculated: C, 61.66; H, 5.39; N, 8.99. Found: C, 61.52; H, 5.31; N, 8.81.

EXAMPLE 14

Preparation of 9-benzyl-4-(2-trifluoromethanesulfonamido)ethyloxy-2-methoxycarbazole-5-carboxamide To 31.2 mg (0.08 mmol) of the product from Example 13, Part A in 3.2 ml THF at 0° C. was added triethylamine (11.1 µl, 0.08 mmol) and trifluoromethanesulfonylchloride (8.5 µl, 0.08 mmol). After 40 min at 0° C., the reaction was diluted EtOAc and saturated NaHCO$_3$, and the layers separated. The organic layer was extracted with brine, dried over sodium sulfate, and evaporated in vacuo. The residue was chromatographed on silica gel eluting with a CH$_2$Cl$_2$/EtOAc gradient and triturated with ether to give the titled product (19.3 mg, 46%). MS (ES+) 522

Elemental Analyses for $C_{24}H_{22}F_3N_3O_5S$: Calculated: C, 55.27; H, 4.25; N, 8.06. Found: C, 55.11; H, 4.40; N, 7.99.

EXAMPLE 15

Preparation of 9-benzyl-5-methanesulfonamidoylmethyloxy-7-methoxy-1,2,3, 4-tetrahydrocarbazole-4-carboxamide To 51 mg (0.125 mmol) of (9-benzyl-4-carbamoyl-7-methoxy-1,2,3,4-tetrahydrocarbazol-5-yl)oxyacetic acid in 25 ml THF was added carbonyldiimidazole (20.2 mg, 0.125 mmol). The reaction was refluxed for 21 hours, then allowed to cool to room temperature. To this was added a mixture of methanesulfonamide (11.9 mg, 0.125 mmol) and diazabicycloundecene (18.7 µl, 0.125 mmol) in 2.5 ml THF. After 3.5 hours, the reaction was diluted with EtOAc and extracted with 10% NaHSO$_3$, saturated NaHCO$_3$, 10% NaHSO$_3$, and brine, respectively. The organic layer was dried with sodium sulfate and evaporated in vacuo. The residue was chromatographed on silica gel eluting with a CH$_2$Cl$_2$/EtOH gradient to give the titled product (8 mg, 10%).

High Resolution MS for $C_{24}H_{27}N_3O_6S$: Calculated: 485.1621. Found: 485.1625.

EXAMPLE 16

Preparation of 9-benzyl-4-methanesulfonamidoylmethyloxy-carbazole-5-carboxamide

To 48 mg (0.13 mmol) of (9-benzyl-5-carbamoyl-carbazol-4-yl)oxyacetic acid in 26 ml THF was added carbonyldiimidazole (21 mg, 0.13 mmol). The reaction was refluxed for 25 hours, then allowed to cool to room temperature. To this was added a mixture of methanesulfonamide (12 mg, 0.13 mmol) and diazabicycloundecene (19 µl, 0.13 mmol) in 2.6 ml THF. After 3 hours, the reaction was diluted with EtOAc and extracted with 10% NaHSO$_3$, then brine. The organic layer was dried with sodium sulfate and evaporated in vacuo. The residue was chromatographed on silica gel eluting with a CH$_2$Cl$_2$/EtOH gradient to give impure product. Extraction from EtOAc into saturated NaHCO$_3$ and reacidification gave the titled product (3.9 mg, 6.7%).

High Resolution MS for $C_{23}H_{21}N_3O_5S$: Calculated: 452.1280. Found: 452.1284.

EXAMPLE 17

[5-carbamoyl-2-pentyl-9-(phenylmethyl)carbazol-4-yl]oxyacetic acid

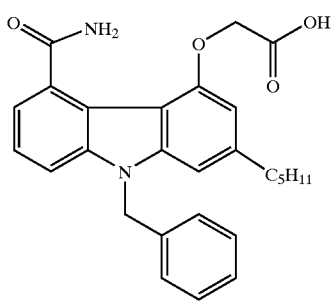

A. Preparation of a mixture of 5-pentylcyclohexa-1,3-dione and its enol isomer

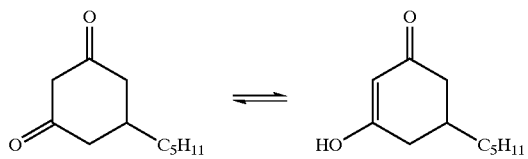

Sodium hydroxide (1.98 g, 49.5 mmol) was added to a stirred suspension of olivetol (7.20 g, 39.9 mmol) in THF (20 mL)/H$_2$O (20 mL) at ambient temperature under nitrogen atmosphere. The solution was stirred until it became a clear solution. Stir bar was removed before 5% Rh/Al$_2$O$_3$ (500 mg) was added to the solution. The mixture was then subject to hydrogenation condition under a 60 pounds per square inch hydrogen atmosphere in a Parr shaker for 17 hours. After filtration through celite, the filtrate was cooled to 0° C., then treated with 5 N HCl (10.9 mL). The mixture was evaporated in vacuo at 40° C. and the residue was chromatographed on silica (gradient 40–100% ethyl acetate in hexane, then 0–15% methanol in ethyl acetate) to give sub-titled compound (4.80 g, 66%) as a white solid mixture of keto/enol isomers in a 3:2 ratio. mp 68.5–69.5° C.; IR (KBr) 3200–2400 (br), 1610, 1542 cm$^{-1}$; 1H NMR (CDCl$_3$) δ0.88 (br t, J=6.6 Hz, 3H, —CH$_3$), 3.38 (s, 2H, —CH$_2$— of keto isomer), 4.13 (s, 1H, =CH— of enol isomer), 8.90 (br s, 1H, —OH); ESIMS m/e 183 (M$^+$+1);

Elemental Analyses for C$_{11}$H$_{18}$O$_2$: Calculated: C, 72.49; H, 9.95. Found: C, 72.72; H, 9.95.

B. Preparation of a mixture of 5-(hydroxymethyl)clohexa-1,3-dione and its enol isomer

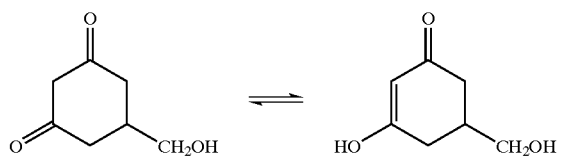

Following the experimental procedure as described in part A, above synthesis of subtitled compound was obtained in a 75% yield. IR (KBr) 3547, 3453 (br), 1633, 1580 cm$^{-1}$; $^1$H NMR (DMSO-d$_6$) δ1.90–2.30 (m, 5H), 3.30 (br s, 2H, —CH$_2$O—), 4.61 (br s, 1H, —OH), 5.13 (s, 1H), 10.94 (s, 1H, —OH); ESIMS m/e 143 (M$^+$+1);

Elemental Analyses for C$_7$H$_{10}$O$_3$: Calculated: C, 59.14; H, 7.09. Found: C, 59.44; H, 7.08.

C. Preparation of 3-(2-bromo-3-carbomethoxyanilino)-5-pentylcyclohex-2-en-1-one

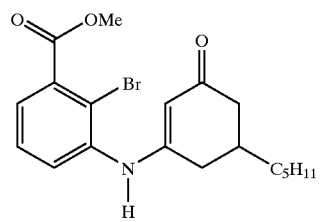

A stirred mixture of methyl-3-amino-2-bromobenzoate prepared as described in Preparation 4 (5.12 g, 22.3 mmol) and the compound of Part A (4.06 g, 22.3 mmol) was heated in an oil bath at 150° C. for 1.4 hours under a positive nitrogen pressure to continuously remove the water vapor.

At ambient temperature, the mixture was chromatographed on silica (gradient 30–100% ethyl acetate in hexane) to provide subtitled compound (6.06 g, 69%) as a white solid. mp 132.0–134.0° C.; IR (KBr) 3220 (br), 1726, 1580 cm$^{-1}$; $^1$H NMR (CDCl$_3$) δ0.90 (br t, J=6.6 Hz, 3H, —CH$_3$), 1.25–1.45 (m, 8H), 2.05–2.27 (m, 2H), 2.35–2.57 (m, 3H), 3.94 (s, 3H, —OCH$_3$), 5.57 (s, 1H, =CH—), 6.44 (br s, 1H, —NH), 7.35 (t, J=6.8 Hz, 1H), 7.53 (d, J=6.8 Hz, 2H); ESIMS m/e 394 (M$^+$+1, $^{79}$Br), 396(M$^+$+1, $^{81}$Br).

D. Preparation of 5-carbomethoxy-1,2-dihydro-2-pentyl-9H-carbazol-4(3H)-one

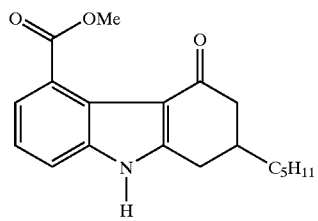

Triethylamine (2.09 mL, 15.0 mmol) was added to a stirred suspension of the compound of part C, above (3.94 g, 10.0 mmol), Pd(OAc)$_2$ (338 mg, 1.50 mmol), and tri-o-tolylphosphine (914 mg, 3.00 mmol) in acetonitrile (40 mL) at ambient temperature under nitrogen atmosphere. The resultant mixture was then heated in an oil bath at 85° C. for 1 h. The mixture was evaporated in vacuo at 35° C. and the residue was chromatographed on silica (gradient 20–100% ethyl acetate in hexane) to give subtitled compound (2.45 g, 78%) as a white solid. mp 116.0–117.5° C.; IR (KBr) 3379 (br), 3180 (Br), 1725, 1627 cm$^{-1}$; $^1$H NMR (CDCl$_3$) δ0.89 (br t, J=6.6 Hz, 3H, —CH$_3$), 1.20–1.47 (m, 8H), 2.20–2.32 (m, 2H), 2.50–2.67 (m, 2H), 2.92–3.05 (m, 1H), 4.02 (s, 3H, —OCH$_3$), 7.18–7.26 (m, 1H), 7.35–7.43 (m, 2H), 9.20–9.42 (br s, 1H, —NH); ESIMS m/e 314 (M$^+$+1);

Elemental Analyses for C$_{19}$H$_{23}$NO$_3$: Calculated: C, 72.82; H, 7.40; N, 4.47. Found: C, 72.59; H, 7.43; N, 4.51.

E. Preparation of 5-carbomethoxy-1,2-dihydro-2-pentyl-9-(phenylmethyl)carbazol-4(3H)-one

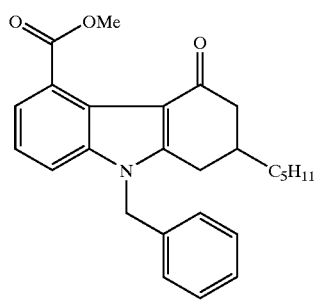

Benzylbromide (1.25 mL, 10.5 mmol) was added to a stirred suspension of the compound of example 17D (3.00 g, 9.57 mmol) and potassium carbonate (1.98 g, 14.4 mmol) in anhydrous DMF (30 mL) under nitrogen atmosphere. The resultant mixture was stirred for 5 hours. The mixture was evaporated in vacuo at 40° C. and the residue was chromatographed on silica (gradient 10–60% ethyl acetate in hexane) to give subtitled compound (3.28 g, 85%) as a white solid. mp 119.0–120.5° C.; IR (KBr) 1723, 1650 cm$^{-1}$; $^1$H NMR (CDCl$_3$) δ0.87 (br t, J=6.6 Hz, 3H, —CH$_3$), 1.23–1.52 (m, 8H), 2.25–2.40 (m, 2H), 2.47–2.57 (m, 1H), 2.69 (d, J=12.8 Hz, 1H), 2.99 (dd, J=16.6, 3.6 Hz, 1H), 4.05 (s, 3H, —OCH$_3$), 5.36 (s, 2H), 6.98–7.02 (m, 2H), 7.20–7.40 (m, 6H); ESIMS m/e 404 (M$^+$+1).

F. Preparation of 5-carbomethoxy-4-hydroxy-2-pentyl-9-(phenylmethyl)carbazole

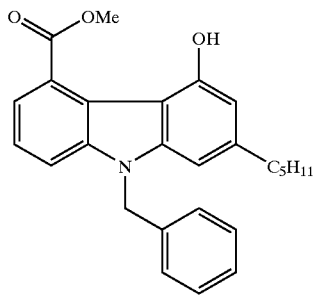

(a) from DDQ oxidation: DDQ (563 mg, 2.48 mmol) was added to a stirred suspension of the compound of part E, above (1.00 g, 2.48 mmol) in anhydrous toluene (30 mL) under nitrogen atmosphere. The resultant mixture was heated to reflux for 25 min. At ambient temperature, the mixture was subject to chromatographic purification on silica (gradient 0–30% ethyl acetate in toluene) to give subtitled compound (290 mg, 29%) as a yellow solid (310 mg, 31%). (b) from benzenesulfinate elimination: Sodium hydride (60% in oil, 192 mg, 4.80 mmol) was added to a stirred solution of the compound of part E, above (807 mg, 2.00 mmol) and methyl benzenesulfinate (375 mg, 2.40 mmol) in anhydrous 1,4-dioxane (10 mL) under nitrogen atmosphere. The mixture was heated in an oil bath at 50° C. for 2 h 15 min. After dilution with additional 15 mL 1,4-dioxane, the mixture was treated with acetic acid (0.343 mL, 6.00 mmol) and the resultant suspension was heated to reflux for 40 min. The mixture was evaporated in vacuo and the residue was chromatographed on silica (gradient 0–5% ethyl acetate in toluene) to afford subtitled compund (690 mg, 86%) as a yellow solid. mp 130.0–132.0° C.; IR (KBr) 3200 (br), 1686 cm$^{-1}$; $^1$H NMR (CDCl$_3$) δ0.87 (br t, J=6.6 Hz, 3H, —CH$_3$), 1.25–1.38 (m, 4H), 1.60–1.75 (m, 2H), 2.69 (t, J=7.7 Hz, 2H), 4.10 (s, 3H, —OCH$_3$), 5.52 (s, 2H), 6.71 (s, 1H), 6.76 (s, 1H), 7.09–7.11 (m, 2H), 7.20–7.30 (m, 3H), 7.37 (t, J=8.0 Hz, 1H), 7.55 (d, J=8.0 Hz, 1H), 7.97 (d, J=8.0 Hz, 1H), 10.43 (s, 1H, —OH); ESIMS m/e 402 (M$^+$+1);

Elemental Analyses for C$_{26}$H$_{27}$NO$_3$.0.2(C$_7$H$_8$): Calculated: C, 78.37; H, 6.86; N, 3.34. Found: C, 78.48; H, 6.68; N, 3.53.

G. Preparation of 5-carbamoyl-4-hydroxy-2-pentyl-9-(phenylmethyl)carbazole

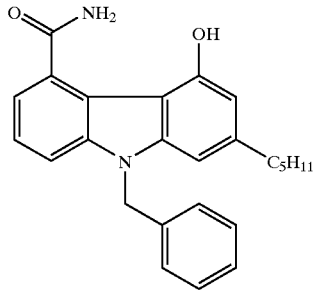

Ammonia was bubbled through a stirred suspension of the compund of part F, above (590 mg, 1.47 mmol) in ammonia water (50 mL)/THF (10 mL) at −25° C. for 5 minutes in a pressure bottle. The bottle was screw-capped before the mixture was allowed to stir at ambient temperature for 3 days. After cooling to −25° C., the screw cap was removed and the mixture was allowed to stir at ambient temperature for 10 minutes. After concentration, the residue was subject to chromatographic purification on silica (gradient 0–40% tetrahydrofuran in toluene) to recover the compound of part F (160 mg, 27%) and obtain the desired subtitled product (397 mg, 70%) as a yellowish solid. IR (KBr) 3437, 3200 (br), 1633, 1601 cm$^{-1}$; $^1$H NMR (CDCl$_3$) δ0.86 (br t, J=6.6 Hz, 3H, —CH$_3$), 1.22–1.38 (m, 4H), 1.60–1.75 (m, 2H), 2.69 (t, J=7.7 Hz, 2H), 5.52 (s, 2H), 6.16 (s, 1H, —NH), 6.53 (s, 1H, —NH), 6.72 (s, 1H), 6.76 (s, 1H), 7.07–7.11 (m, 2H), 7.23–7.30 (m, 3H), 7.35 (t, J=7.7 Hz, 1H), 7.43 (d, J=7.7 Hz, 1H), 7.48 (d, J=7.7 Hz, 1H), 9.80 (s, 1H, —OH); ESIMS m/e 387 (M$^+$+1);

Elemental Analyses for C$_{25}$H$_{26}$N$_2$O$_2$: Calculated: C, 77.69; H, 6.78; N, 7.25. Found: C, 77.69; H, 6.63; N, 7.15.

H. Preparation of [5-carbamoyl-2-pentyl-9-(phenylmethyl)carbazol-4-yl]oxyacetic acid, methyl ester

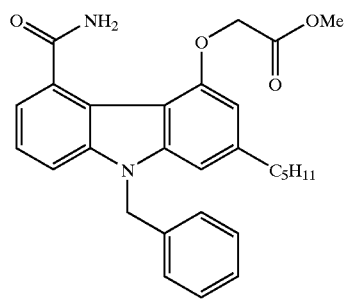

Methyl bromoacetate (48.0 mg, 0.314 mmol) was added to a stirred suspension of the compound of example 17G, above (110 mg, 0.285 mmol) and cesium carbonate (186 mg, 0.570 mmol) in anhydrous DMF (2 mL) at ambient temperature under nitrogen atmosphere. The resultant mixture was stirred for 1 hour. After concentration in vacuo at 40° C., the residue was chromatographed on silica (gradient 10–60% tetrahydrofuran in toluene) to give subtitled product (115 mg, 88%) as a white solid. mp 195.0–196.0° C.; IR (KBr) 3365 (br), 3157 (br), 1758, 1640 cm$^{-1}$; $^1$H NMR (CDCl$_3$) δ0.87 (br t, J=6.6 Hz, 3H, —CH$_3$), 1.22–1.35 (m, 4H), 1.58–1.70 (m, 2H), 2.69 (t, J=7.6 Hz, 2H), 3.84 (s, 3H, —OCH$_3$), 4.89 (s, 2H, —OCH$_2$—), 5.50 (s, 2H, —NCH$_2$—), 5.95 (br s, 1H, —NH), 6.08 (br s, 1H, —NH), 6.41 (s, 1H), 6.85 (s, 1H), 7.07–7.11 (m, 2H), 7.23–7.40 (m, 6H); ESIMS m/e 459 (M$^+$+1);

Elemental Analyses for C$_{28}$H$_{30}$N$_2$O$_4$: Calculated: C, 73.34; H, 6.59; N, 6.11. Found: C, 73.56; H, 6.43; N, 6.25.

I. Preparation of [5-carbamoyl-2-pentyl-9-(phenylmethyl)carbazol-4-yl]oxyacetic acid

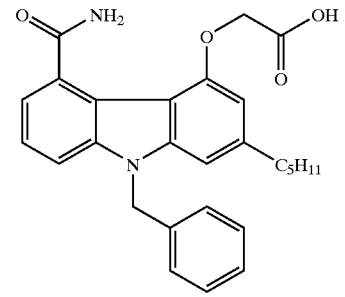

Lithium hydroxide (4.17 N, 86.3 mL, 0.360 mmol) was added to a stirred suspension of the compound of Example 17H, above (110 mg, 0.240 mmol) in THF (2 mL)/CH$_3$OH (0.3 mL)/H$_2$O (0.3 mL). The resultant mixture was stirred in an oil bath at 55° C. for 30 minutes to form a white suspension. Five milliliter of THF was added to the suspension before it was treated with 5 N HCl (96.0 mL, 0.480 mmol) to become a clear solution. After concentration, the white solid was resuspended in THF (0.5 mL)/H$_2$O (5 mL), sonicated, filtered, and dried to give the subtitled compound (106 mg, 99%) as a white solid. IR (KBr) 3458 (br), 3500–3100 (br), 1656, 1620 cm$^{-1}$; $^1$H NMR (DMSO-d$_6$) δ0.80 (br t, J=6.6 Hz, 3H, —CH$_3$), 1.18–1.30 (m, 4H), 1.50–1.62 (m, 2H), 2.61 (br t, J=7.3 Hz, 2H), 4.55 (s, 2H, —OCH$_2$—), 5.60 (s, 2H, —NCH$_2$—), 6.40 (s, 1H), 6.95–7.32 (m, 9H), 7.51 (d, J=8.0 Hz, 1H), 7.70 (br s, 1H, —NH); ESIMS m/e 445 (M$^+$+1).

EXAMPLE 18

(5-carbamoyl-2-(1-methylethyl)-9-(phenylmethyl) carbazol-4-yl]oxyacetic acid

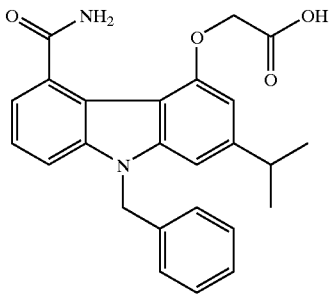

A. Preparation of 3-(2-bromo-3-carbomethoxyanilino)-5-[(1-methyl)ethyl]cyclohex-2-en-1-one

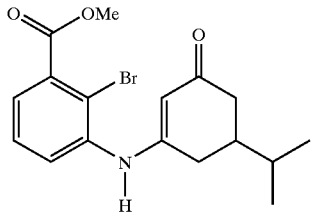

Prepared in 70% yield by the method of Example 17 part C. mp 129.0–130.0° C.; $^1$H NMR (CDCl$_3$) δ0.98 (t, J=5.5 Hz, 6H), 1.66 (m, 1H), 2.00 (m, 1H), 2.14 (t, J=14.8 Hz, 1H), 2.46 (m, 3H), 4.00 (s, 3H), 5.57 (s, 1H), 6.40 (br s, 1H), 7.35 (t, J=7.9 Hz, 1H), 7.35 (d, J=7.8 Hz, 2H); ESIMS m/e 366 (M$^+$+1, $^{79}$Br), 368 (M$^+$+1, $^{81}$Br)

B Preparation of 5-carbomethoxy-1,2-dihydro-2-(1-methylethyl)-9H-carbazol-4(3H)-one

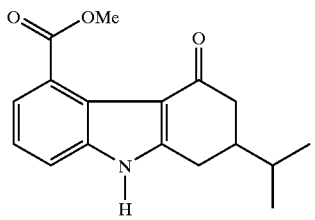

Prepared in 65% yield by the procedure of Example 17D. mp 175.0–177.0° C.; $^1$H NMR (CDCl$_3$) δ0.95 (t, J=6.7 Hz, 6H), 1.62 (m, 1H), 2.05 (m, 1H), 2.27 (dd, J=16.1, 12.6 Hz, 1H), 2.60 (m, 2H), 2.89 (dd, J=16.4, 4.3 Hz, 1H), 4.02 (s, 3H), 7.23 (m, 1H), 7.36 (m, 2H), 9.28 (br s, 1H); ESIMS m/e 286 (M$^+$+1);

Elemental Analyses for C$_{17}$H$_{19}$NO$_3$: Calculated: C, 71.56; H, 6.71; N, 4.91. Found: C, 71.43; H, 6.62; N, 4.74.

C. Preparation of 5-carbomethoxy-1,2-dihydro-2-(1-methylethyl)-9-(phenylmethyl)carbazol-4(3H)-one

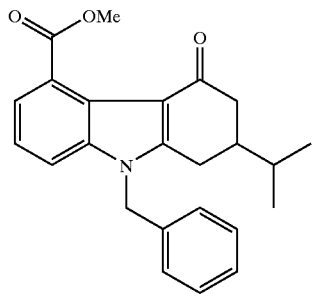

Prepared in 37% yield by the method of Example 17E. mp: 155.0–156.0° C.; $^1$H NMR (CDCl$_3$) δ1.28 (d, J=8.0 Hz, 6H), 3.00 (m, 1H), 4.10 (s, 3H), 5.23 (s, 2H), 6.78 (d, J=9.5 Hz, 2H), 7.11 (m, 2H), 7.28 (m, 3H), 7.37 (t, J=7.9 Hz, 1H), 7.54 (d, J=7.9 Hz, 1H), 7.98 (d, J=7.9 Hz, 1H), 10.46 (s, 1H); ESIMS m/e 374 (M$^+$+1);

Elemental Analyses for C$_{24}$H$_{23}$NO$_3$: Calculated: C, 77.19; H, 6.21; N, 3.75. Found: C, 76.96; H, 6.33; N, 3.77.

D. Preparation of 5-carbomethoxy-4-hydroxy-2-(1-methylethyl)-9-(phenylmethyl)carbazole

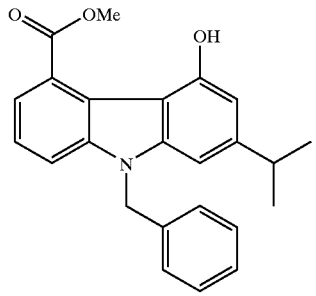

DDQ (1.15 g, 5.07 mmol) was added to a stirred suspension of the compound of Example 18C (1.90 g, 5.07 mmol) in anhydrous toluene (30 mL) under argon atmosphere. The resultant mixture was heated under reflux for 25 min. After cooling to room temperature, the mixture was subjected to chromatography on silica gel eluting with a gradient of hexanes/toluene(1:1) to toluene/EtOAc (97:3). The desired product was obtained a mixture with the corresponding isopropylidene compound. The mixture was dissolved in EtOAc (30 mL) under nitrogen atmosphere, and 0.1 g of PtO$_2$ was added. The mixture was stirred at room temperature under hydrogen at balloon pressure for 25 min. Filtration through celite, followed by recrystallization from Et$_2$O/hexanes gave the subtitled compound as a pale yellow crystalline solid (0.705 g; 37% yield). mp: 155.0–156.0° C.; $^1$H NMR (CDCl$_3$) δ1.28 (d, J=8.0 Hz, 6H), 3.00 (m, 1H), 4.10 (s, 3H), 5.23 (s, 2H), 6.78 (d, J=9.5 Hz, 2H), 7.11 (m, 2H), 7.28 (m, 3H), 7.37 (t, J=7.9 Hz, 1H), 7.54 (d, J=8.0 Hz, 1H), 7.98 (d, J=7.9 Hz, 1H), 10.46 (s, 1H); ESIMS m/e 374 (M$^+$+1);

Elemental Analyses for C$_{24}$H$_{23}$NO$_3$: Calculated: C, 77.19; H, 6.21; N, 3.75. Found: C, 76.96; H, 6.33; N, 3.77.

E. Preparation of 5-carbamoyl-4-hydroxy-2-(1-methylethyl)-9-(phenylmethyl)carbazole

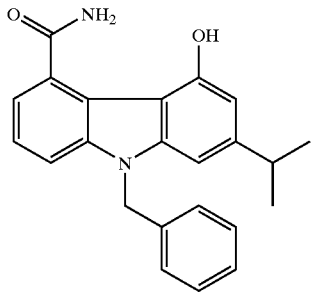

Prepared in 50% yield by the procedure of example 17G. mp 216.0–218.0° C.; $^1$H NMR (CDCl$_3$) δ1.29 (d, J=6.9, 6H), 3.00 (m, 1H), 5.53(s, 2H), 6.16 (br s, 1H), 6.52 (br s, 1H), 6.78 (d, J=8.6 Hz, 2H), 7.11 (m, 2H), 7.28 (m, 3H), 7.32 (m, 1H), 7.4 (m, 2H), 9.8 (br s, 1H); ESIMS m/e 359.3 (M$^+$+1);

Elemental Analyses for C$_{23}$H$_{22}$N$_2$O$_2$: Calculated: C, 77.07, H, 6.19; N, 7.82. Found: C, 77.10; H, 6.35; N, 7.74.

F. Preparation of [5-carbamoyl-2-(1-methylethyl)-9-(phenylmethyl)carbazol-4-yl]oxyacetic acid, methyl ester

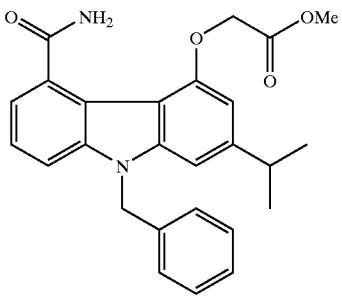

Prepared by the procedure of example 17H in 54% yield. mp 189.0–191.0° C.; $^1$H NMR (CDCl$_3$) δ1.27 (d, J=6.9 Hz, 6H), 2.98 (m, 1H), 3.84 (s, 3H), 4.90 (s, 2H), 5.51(s, 2H), 5.8–6.2 (m, 1H), 6.47 (s, 1H), 6.90 (s, 1H), 7.11 (m, 2H), 7.2–7.4 (m, 6H); ESIMS m/e 431 (M$^+$+1);

Elemental Analyses for C$_{26}$H$_{26}$N$_2$O$_4$: Calculated: C, 72.54; H, 6.09; N, 6.51. Found: C, 72.58; H, 6.24; N, 6.43.

G. Preparation of [5-carbamoyl-2-(1-methylethyl)-9-(phenylmethyl)carbazol-4-yl]oxyacetic acid

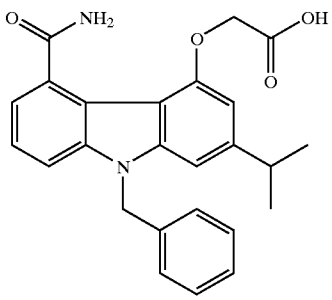

Prepared by the procedure of example Example 17I in 82% yield. $^1$H NMR (CDCl$_3$) δ1.20 (d, J=6.7, 6H), 2.94 (m, 1H), 4.79 (s, 2H), 5.63 (s, 2H), 6.49(s, 1H), 7.00–7.40 (m, 9H), 7.51 (m, 1H), 7.70 (br s, 1H), 12.94 (br s, 1H); ESIMS m/e 417 (M$^+$+1);

Elemental Analyses for C$_{25}$H$_{24}$N$_2$O$_4$: Calculated: C, 72.10; H, 5.81; N, 6.73. Found: C, 72.11; H, 5.62; N, 6.49.

EXAMPLE 19

[5-carbamoyl-9-(phenylmethyl)-2-[(tri(-1-methylethyl)silyl)oxymethyl]carbazol-4-yl]oxyacetic acid

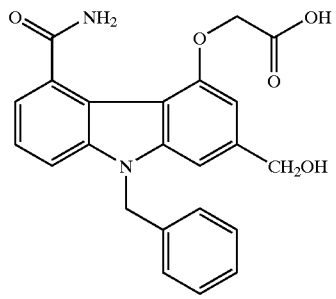

A. Preparation of 3-(2-bromo-3-carbomethoxyanilino)-5-(hydroxymethyl)cyclohex-2-en-1-one

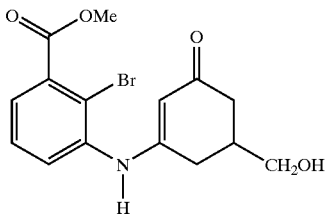

Following the experimental procedure as described in the synthesis of Example 17 part C, subtitled compound was obtained as a white solid in a 68% yield. IR (KBr) 3407 (br), 3364 (br), 3222 (br), 1738, 1600, 1566 cm$^{-1}$; $^1$H NMR (DMSO-d$_6$) δ1.94 (dd, J=16.5, 12.5 Hz, 1H), 2.02–2.15 (m, 2H), 2.32 (dd, J=16.5, 9.9 Hz, 1H), 2.50–2.58 (m, 1H), 3.27–3.42 (m, 2H), 3.83 (s, 3H, —OCH$_3$), 4.55 (s, 1H, =CH—), 4.64 (t, J=5.1 Hz, 1H, —OH), 7.42–7.58 (m, 3H), 8.76 (s, 1H, —NH); ESIMS m/e 354 (M$^+$+1, $^{79}$Br), 356 (M$^+$+1, $^{81}$Br);

Elemental Analyses for C$_{15}$H$_{16}$BrNO$_4$: Calculated: C, 50.87; H, 4.55; N, 3.95. Found: C, 51.07; H, 4.60; N, 3.93.

B. Preparation of 5-carbomethoxy-1,2-dihydro-2-(hydroxymethyl)-9H-carbazol-4(3H)-one

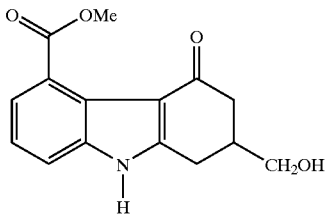

Following the experimental procedure as described in the synthesis of Example 17D, subtitled compound was obtained as a white solid in a 66% yield. IR (KBr) 3350 (br), 1720, 1624 cm$^{-1}$; $^1$H NMR (CDCl$_3$) δ1.92–2.20 (m, 2H), 2.33 (dd, J=16.0, 3.0 Hz, 1H), 2.44 (dd, J=16.8, 9.9 Hz, 1H), 2.67 (dd, J=16.8, 4.0 Hz, 1H), 3.33–3.48 (m, 2H), 4.05 (s, 3H, —OCH$_3$), 7.20–7.26 (m, 1H), 7.33 (d, J=7.3 Hz, 1H), 7.43 (d, J=7.9 Hz, 1H), 10.25 (s, 1H, —NH); ESIMS m/e 274 (M$^+$+1);

Elemental Analyses for C$_{15}$H$_{15}$NO$_4$: Calculated: C, 65.93; H, 5.53; N, 5.13. Found: C, 65.68; H, 5.78; N, 5.08.

C. Preparation of 5-carbomethoxy-1,2-dihydro-2-(hydroxymethyl)-9-(phenylmethyl)carbazol-4(3H)-one

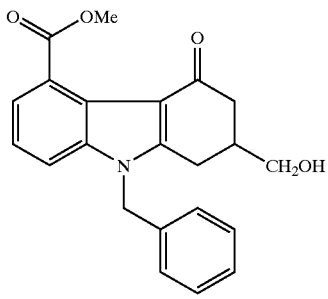

Following the experimental procedure as described in the synthesis of Example 17E, the subtitled compound was obtained as a white solid in a 88% yield. IR (KBr) 3366 (br), 1728, 1632 cm$^{-1}$; $^1$H NMR (CDCl$_3$) δ1.98 (s, 1H, —OH), 2.30–2.62 (m, 3H), 2.72 (dd, J=16.8, 9.7 Hz, 1H), 3.06 (dd, J=17.0, 3.6 Hz, 1H), 3.58–3.75 (m, 2H), 4.04 (s, 3H, —OCH$_3$), 5.25–5.40 (m, 2H, —NCH$_2$—), 6.98–7.05 (m, 2H), 7.20–7.40 (m, 6H); ESIMS m/e 364 (M$^+$+1).

D. Preparation of [5-carbamoyl-9-(phenylmethyl)-2-[(tri(-1-methylethyl)silyl)oxymethyl]carbazol-4-yl]oxyacetic acid, methyl ester

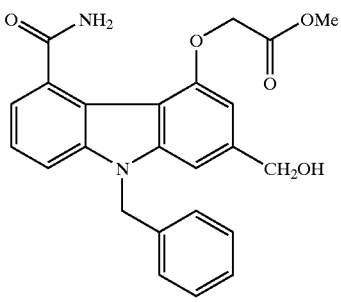

etrabutylammonium fluoride (1 N in THF, 0.626 mL) was added to a stirred solution of the compound of Example 23D (300 mg, 0.522 mmol) in THF (5 mL). The mixture was stirred at ambient temperature for 1 hour. After conentration in vacuo at 35° C., the residue was subject to chromatographic purification (gradient 50–100% tetrahydrofuran in toluene, then 5% methanol in tetrahydrofuran) to give subtitled compound (122 mg, 56%) as a white solid. IR (KBr) 3380 (br), 3205 (br), 1733, 1641, 1628 cm$^1$; $^1$H NMR (DMSO-d$_6$) δ3.69 (s, 3H, —OCH$_3$), 4.55 (s, 2H, —OCH$_2$—), 4.86 (s, 2H, —OCH$_2$—), 5.22 (br s, 1H, —OH), 5.62 (s, 2H, —NCH$_2$—), 6.53 (s, 1H), 7.00–7.25 (m, 8H), 7.32 (br t, J=7.7 Hz, 1H), 7.50 (br d, J=7.7 Hz, 1H), 7.53 (br d, J=7.7 Hz, 1H); ESIMS m/e 419 (M$^+$+1);

Elemental Analyses for C$_{24}$H$_{22}$N$_2$O$_5$: Calculated: C, 68.89; H, 5.30; N, 6.69. Found: C, 68.80; H, 5.17; N, 6.72.

E. Preparation of [5-carbamoyl-9-(phenylmethyl)-2-[(tri(-1-methylethyl)silyl)oxymethyl]carbazol-4-yl]oxyacetic acid

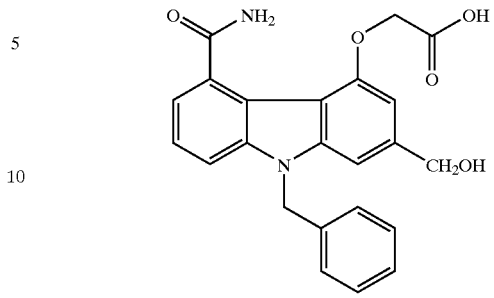

Following the experimental procedure as described in the synthesis of Example 17I, subtitled compound was obtained as a white solid in a 99% yield. IR (KBr) 3427, 3331 (br), 1732, 1682, 1636 cm$^{-1}$; $^1$H NMR (DMSO-d$_6$) δ4.55 (d, J=4.6 Hz, 2H, —OCH$_2$OH), 4.78 (s, 2H, —OCH$_2$—), 5.25 (br t, J=4.6 Hz, 1H, —OH), 5.62 (s, 2H, —NCH$_2$—), 6.57 (s, 1H), 7.00–7.25 (m, 7H), 7.33 (br t, J=7.8 Hz, 1H), 7.39 (s, 1H, —NH), 7.55 (d, J=7.8 Hz, 1H), 7.72 (s, 1H, —NH), 12.93 (s, 1H, —CO$_2$H); ESIMS m/e 405 (M$^+$+1);

Elemental Analyses for C$_{23}$H$_{20}$N$_2$O$_5$·0.3H$_2$O: Calculated: C, 67.41; H, 5.07; N, 6.84. Found: C, 67.34; H, 5.13; N, 6.98.

EXAMPLE 20

Preparation of [5-carbamoyl-2-phenyl-9-(phenylmethyl)carbazol-4-yl]oxyacetic acid

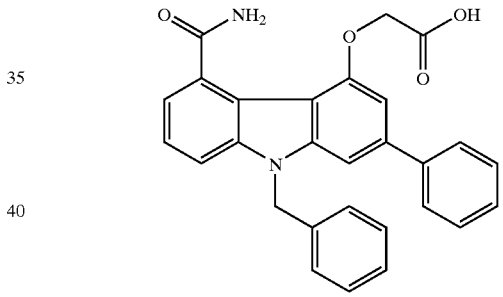

A. Preparation of 3-(2-bromo-3-carbomethoxyanilino)-5-phenylcyclohex-2-en-1-one

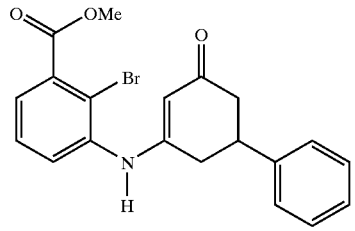

Prepared in 61% yield by the method of Example 17, part A. IR (KBr) 3180 (br), 1734, 1592 cm$^{-1}$; $^1$H NMR (CDCl$_3$) δ2.64–2.71 (m, 2H), 2.84 (dd, J=11.7, 16.2 Hz, 1H), 3.45–3.49 (m, 1H), 3.95 (s, 3H) 5.67 (s, 1H), 6.29 (br s, 1H), 7.29–7.40 (m, 6H), 7.54–7.59 (m, 2H); ESIMS m/e 400 (M$^+$+1, $^{79}$Br), 402 (M$^+$+1, $^{81}$Br);

Elemental Analyses for C$_{20}$H$_{18}$BrNO$_3$: Calculated: C, 60.01; H, 4.53; N, 3.50. Found: C, 60.23; H, 4.80; N, 3.47.

B. Preparation of 5-carbomethoxy-1,2-dihydro-2-phenyl-9H-carbazol-4(3H)-one

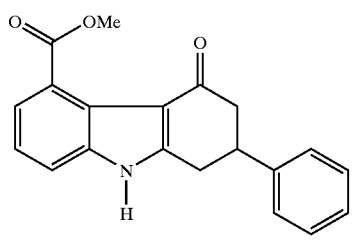

Prepared by the method of Example 17D in 70% yield. IR (KBr) 3180, 1736, 1628 cm$^{-1}$; $^1$H NMR (CDCl$_3$) δ2.70 (d, J=4 Hz, 1H), 2.72 (s, 1H), 2.97–3.03 (m, 2H), 4.03 (s, 3H), 7.18–7.39 (m, 8H), 9.52 (br s, 1H); ESIMS m/e 320 (M$^+$+1).

C. Preparation of 5-carbomethoxy-1,2-dihydro-2-phenyl-9-(phenylmethyl)carbazol-4(3H)-one

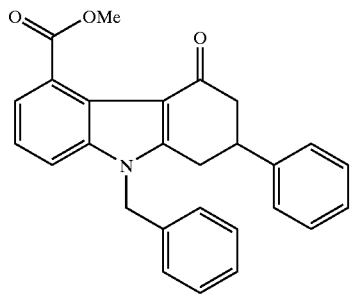

Prepared in 85% yield by the method of Example 17E. IR (KBr) 1723, 1652 cm$^{-1}$; ESIMS m/e 410 (M$^+$+1).

D. Preparation of 5-carbomethoxy-4-hydroxy-2-phenyl-9-(phenylmethyl)carbazole

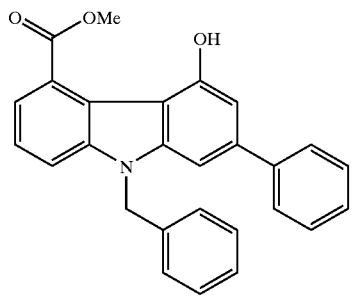

Prepared in 50% yield by the method (a) of Example 17F. IR (KBr) 3326, 1711 cm$^{-1}$; $^1$H NMR (CDCl$_3$) δ4.10 (s, 3H), 5.52 (s, 2H), 7.08–7.10 (m, 4H), 7.24–7.56 (m, 7H), 7.38 (d, J=8.1 Hz, 1H), 7.55 (d, J=8.0 Hz, 2H), 7.97 (d, J=8.1 Hz, 1H) 10.43 (br s, 1H); ESIMS m/e 408 (M$^+$+1);

Elemental Analyses for C$_{27}$H$_{21}$NO$_3$·0.1 C$_7$H$_8$: Calculated: C, 79.85; H, 5.27; N, 3.36. Found: C, 80.19; H, 5.32; N, 3.49.

E. Preparation of 5-carbamoyl-4-hydroxy-2-phenyl-9-(phenylmethyl)carbazole

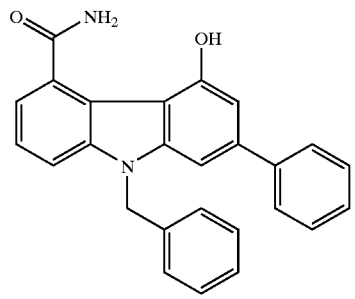

Prepared in 40% yield by the method of Example 17G. $^1$H NMR (CDCl$_3$) δ5.58 (s, 2H), 6.25 (s, 1H), 6.59 (s, 1H), 7.11–7.16 (m, 4H), 7.26–7.48 (m, 8H), 7.52 (d, J=8.1 Hz, 1H), 7.68 (d, J=7.2 Hz, 2H), 9.99 (br s, 1H); ESIMS m/e 393 (M$^+$+1).

F. Preparation of [5-carbamoyl-2-phenyl-9-(phenylmethyl)carbazol-4-yl]oxyacetic acid, methyl ester

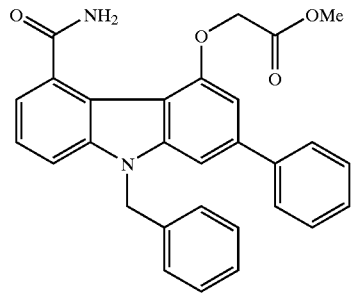

Prepared in 58% yield by the method of Example 17H. IR (KBr) 3359, 1755, 1634 cm$^{-1}$; $^1$H NMR (CDCl$_3$) δ3.85 (s, 3H), 4.96 (s, 2H), 5.58 (s, 2H), 5.92 (br s, 2H), 7.11 (s, 1H), 7.13–7.24 (m, 2H), 7.26–7.30 (m, 3H), 7.34–7.47 (m, 7H), 7.59 (d, J=7.3 Hz, 2H); ESIMS m/e 465 (M$^+$+1);

Elemental Analyses for C$_{29}$H$_{24}$N$_2$O$_4$: Calculated: C, 74.98; H, 5.21; N, 6.03. Found: C, 74.97; H, 5.22; N, 5.80.

G. Preparation of [5-carbamoyl-2-phenyl-9-(phenylmethyl)carbazol-4-yl]oxyacetic acid

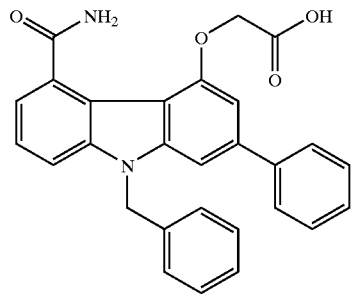

Prepared in 86% yield by the method of Example 17I. IR (KBr) 3426, 3332, 2625–2100 (br),1734, 1636 cm$^{-1}$; $^1$H NMR (DMSO-d$_6$) δ4.94 (s, 2H), 5.57 (s, 2H),6.96 (s, 1H), 7.06–7.31 (m, 6H), 7.33–7.47 (m, 5H), 7.55–7.60 (m, 2H), 7.71–7.73 (m, 3H), 12.94 (br s, 1H); ESIMS m/e 451 (M$^+$+1);

Elemental Analyses for C$_{28}$H$_{22}$N$_2$O$_4$: Calculated: C, 74.65; H, 4.92; N, 6.22. Found: C, 74.87; H, 5.15; N, 6.11.

EXAMPLE 21

[5-carbamoyl-2-(4-chlorophenyl)-9-(phenylmethyl)carbazol-4-yl]oxyacetic acid

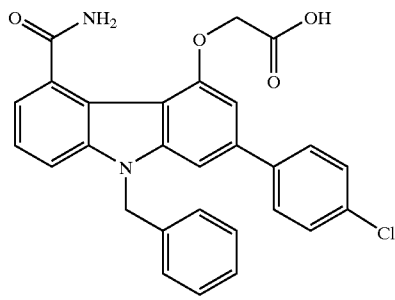

A. Preparation of 3-(2-bromo-3-carbomethoxyanilino)-5-(4-chlorophenyl)cyclohex-2-en-1-one

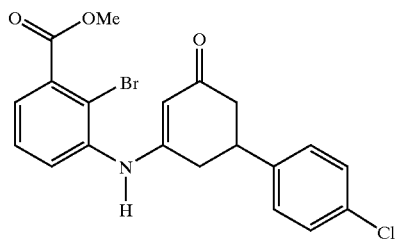

Prepared by the method of Example 17, part C in 80% yield. $^1$H NMR (CDCl$_3$) δ2.66 (m, 3H), 2.86 (m, 1H), 3.44 (m, 1H), 3.95 (s, 3H), 5.75 (s, 1H), 7.24 (m, 3H), 7.32 (m, 3H), 7.57 (t, J=7.1 Hz, 2H); ESIMS m/e 434 (M$^+$+1, $^{79}$Br$^{35}$Cl), 436 (M$^+$+1, $^{81}$Br$^{35}$Cl, $^{79}$Br$^{37}$Cl), 438 (M$^+$+1, $^{81}$Br$^{37}$Cl);

Elemental Analyses for C$_{20}$H$_{17}$BrClNO$_3$: Calculated: C, 55.26; H, 3.94; N, 3.22. Found: C, 55.55; H, 3.91; N, 3.21.

B. Preparation of 5-carbomethoxy-1,2-dihydro-2-(4-chlorophenyl)-9H-carbazol-4(3H)-one

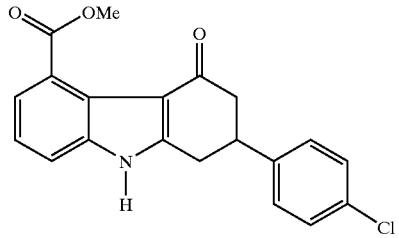

Prepared by the method of Example 17D in 64% yield. $^1$H NMR (CDCl$_3$) δ2.72 (m, 2H), 2.99 (dd, J=16.7, 16.5 Hz, 1H), 3.12 (dd, J=16.7, 4.7 Hz, 1H), 3.45 (m, 1H), 4.04 (s, 3H), 7.17 (d, J=8.5 Hz, 2H), 7.23 (d, J=7.9 Hz, 1H), 7.30 (d, J=8.4 Hz, 2H), 7.43 (t, J=7.9 Hz, 2H), 9.61 (br s, 1H); ESIMS m/e 354 (M$^+$+1, $^{35}$Cl), 356 (M$^+$+1, $^{37}$Cl);

Elemental Analyses for C$_{20}$H$_{16}$ClNO$_3$: Calculated: C, 67.90; H, 4.56; N, 3.96. Found: C, 68.14; H, 4.51; N, 3.90.

C. Preparation of 5-carbomethoxy-1,2-dihydro-2-(4-chlorophenyl)-9-(phenylmethyl)carbazol-4(3H)-one

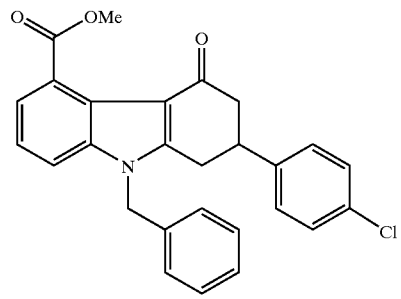

Prepared by the procedure of Example 17E in 90% yield. $^1$H NMR (CDCl$_3$) δ2.79 (d, J=3.7 Hz, 1H), 2.82 (s, 1H), 2.97 (dd, J=16.7, 11.5 Hz, 1H), 3.19 (dd, J=16.7, 4.7 Hz, 1H), 3.59 (m, 1H), 4.06 (s, 3H), 5.35 (s, 2H), 6.96 (t, J=3.6 Hz, 2H), 7.21 (m, 2H), 7.30 (m, 6H), 7.36 (t, J=7.5 Hz, 2H); ESIMS m/e 444 (M$^+$+1, $^{35}$Cl), 446 (M$^+$+1, $^{37}$Cl);

Elemental Analyses for C$_{27}$H$_{22}$ClNO$_3$: Calculated: C, 73.05; H, 5.00; N, 3.16. Found: C, 73.23; H, 5.15; N, 3.36.

D. Preparation of 5-carbomethoxy-2-(4-chlorophenyl)-4-hydroxy-9-(phenylmethyl)carbazole

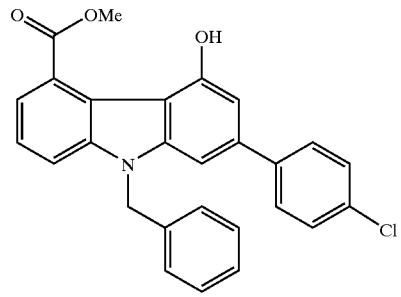

Prepared by method of example 17(b) in 66% yield. $^1$H NMR (CDCl$_3$) δ4.12 (s, 3H), 5.60 (s, 2H), 7.10 (t, J=4.5 Hz, 4H), 7.32 (m, 3H), 7.41 (m, 3H), 7.60 (d, J=8.5 Hz, 3H), 8.04 (d, J=7.2 Hz, 1H).

E. Preparation of 5-carbamoyl-2-(4-chlorophenyl)-4-hydroxy-9-(phenylmethyl)carbazole

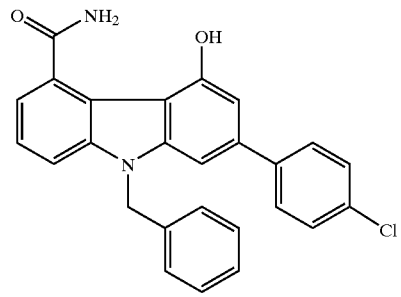

Prepared by the procedure of example Example 17G in 43% yield. $^1$H NMR (CDCl$_3$) δ5.77 (s, 2H), 6.89 (s, 1H), 7.07 (d, J=7.0 Hz, 2H), 7.23 (m, 3H), 7.45 (m, 5H), 7.76 (d, J=8.4 Hz, 3H), 8.40 (s, 1H), 8.85 (s, 1H); ESIMS m/e 427 (M$^+$+1, $^{35}$Cl), 429 (M$^+$+1, $^{37}$Cl);

Elemental Analyses for C$_{26}$H$_{19}$ClN$_2$O$_2$: calculated: C, 73.15; H, 4.49; N, 6.56. Found: C, 72.92; H, 4.57; N, 6.46.

F. Preparation of [5-carbamoyl-2-(4-chlorophenyl)-9-(phenylmethyl)carbazol-4-yl]oxyacetic acid, methyl ester

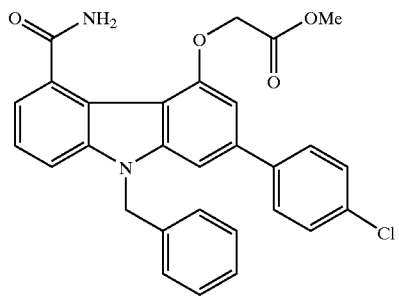

Prepared by the procedure of example Example 17H in 79% yield. $^1$H NMR (CDCl$_3$) δ3.84 (s, 3H), 4.97 (s, 2H), 5.57 (s, 2H), 6.08 (br s, 1H), 6.14 (br s, 1H), 6.74 (s, 1H), 7.12 (m, 2H), 7.18 (s, 1H), 7.22 (m, 2H), 7.41 (m, 6H), 7.51 (d, J=8.5 Hz, 2H); ESIMS m/e 499 (M$^+$+1, $^{35}$Cl), 501 (M$^+$+1, $^{37}$Cl).

G. Preparation of [5-carbamoyl-2-(4-chlorophenyl)-9-(phenylmethyl)carbazol-4-yl]oxyacetic acid

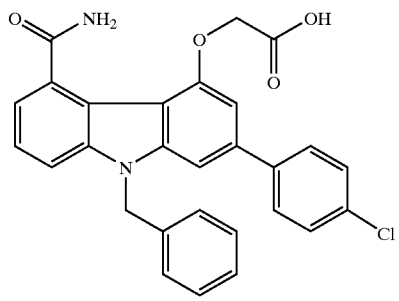

Prepared by the procedure of example Example 17I in 100% yield. $^1$H NMR (CDCl$_3$) δ4.95 (s, 2H), 5.75 (s, 2H), 6.88 (s, 1H), 7.20 (m, 4H), 7.52 (m, 6H), 7.76 (m, 3H), 12.92 (s, 1H); ESIMS m/e 485 (M$^+$+1, $^{35}$Cl), 487 (M$^+$+1, $^{37}$Cl).

EXAMPLE 22

[5-carbamoyl-2-(2-furyl)-9-(phenylmethyl)carbazol-4-yl]oxyacetic acid

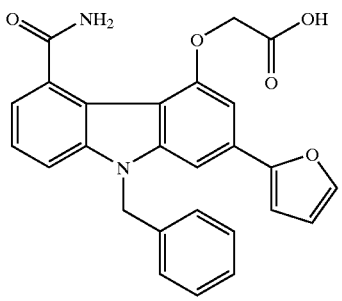

A. Preparation of 3-(2-bromo-3-carbomethoxyanilino)-5-(2-furyl)cyclohex-2-en-1-one

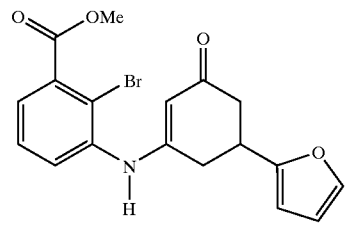

Prepared in 55% yield by the method of Example 17, part C. IR (KBr) 3201, 1735, 1593, 1575 cm$^{-1}$; $^1$H NMR (CDCl$_3$) δ2.56–2.94 (m, 4H), 3.53–3.60 (m, 1H), 3.94 (s, 1H), 5.60 (s, 1H), 6.11 (d, J=2.8 Hz, 1H), 6.22 (br s, 1H), 6.32–6.34 (m, 1H), 7.34–7.39 (m, 1H), 7.37 (br s, 1H), 7.55 (d, J=7.9 Hz, 2H); m/e 390 (M$^+$+1, $^{79}$Br), 392 (M$^+$+1, $^{81}$Br);

Elemental Analyses for C$_{18}$H$_{16}$BrNO$_4$: Calculated: C, 55.40; H, 4.13; N, 3.59. Found: C, 55.62; H, 4.27; N, 3.71.

B. Preparation of 5-carbomethoxy-1,2-dihydro-2-(2-furyl)-9H-carbazol-4(3H)-one

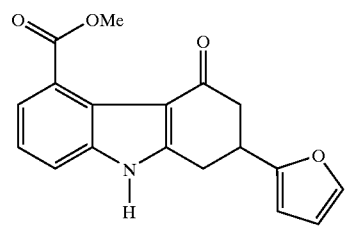

Prepared by the method of Example 17D in 47% yield. IR (KBr) 1736, 1633 cm$^{-1}$; $^1$H NMR (THF-d$_8$): δ2.59–2.77 (m, 2H) 3.14 (dd, J=16.5, 10.5 Hz, 1H), 3.30 (dd, J=16.5, 10.3 Hz, 1H), 3.56–3.69 (m, 1H), 3.81 (s, 3H), 6.13–6.14 (m, 1H), 6.27–6.29 (d, J=2.5 Hz, 1H), 7.11–7.21 (m, 2H), 7.37–7.39 (m, 1H), 7.39 (s, 1H), 11.03 (br s, 1H); ESIMS m/e 310 (M$^+$+1);

Elemental Analyses for C$_{18}$H$_{15}$NO$_4$.0.1C$_7$H$_8$: Calculated: C, 70.51; H, 4.50; N, 4.40. Found: C, 70.75; H, 4.85; N, 4.61.

C. Preparation of 5-carbomethoxy-1,2-dihydro-2-(2-furyl)-9-(phenylmethyl)carbazol-4(3H)-one

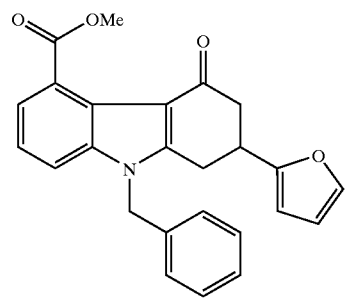

Prepared in 91% yield by the method of Example 17E. IR (KBr) 3500 (br), 1722, 1650 cm$^{-1}$; $^1$H NMR (CDCl$_3$) δ2.79 (dd, J=16.6, 10.8 Hz, 1H), 2.94 (dd, J=16.6, 4.2 Hz, 1H), 3.06 (dd, J=16.8, 9.8 Hz, 1H), 3.31 (dd, J=18.8, 4.7 Hz, 1H), 3.68–3.74 (m, 1H), 4.06 (s, 3H), 5.37 (s, 2H), 6.08 (d, J=2.7 Hz, 1H), 6.28 (m, 1H), 6.96 (m, 2H), 7.22–7.40 (m, 7H); ESIMS m/e 400 (M$^+$+1);

D. Preparation of 5-carbomethoxy-2-(2-furyl)-4-hydroxy-9-(phenylmethyl)carbazole

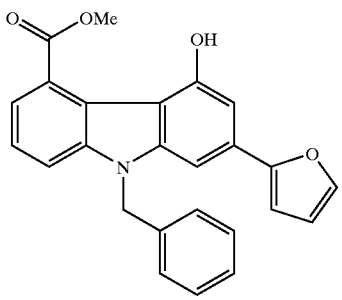

Prepared in 72% yield by the method (b) of Example 17F. IR (KBr) 3500 (br), 1674 cm$^{-1}$; $^1$H NMR (CDCl$_3$) δ4.11 (s, 3H), 5.58 (s, 2H), 6.48–6.50 (m, 1H), 6.75 (d, J=3.2 Hz, 1H), 7.09–7.12 (m, 2H), 7.16 (s, 1H), 7.26–7.30 (m, 4H), 7.36–7.44 (t, J=8.0 Hz, 1H), 7.48 (s, 1H), 7.56 (d, J=8.1 Hz, 1H), 8.01 (d, J=7.5 Hz, 1H), 10.50 (br s, 1H); ESIMS m/e 398 (M$^+$+1).

E. Preparation of 5-carbamoyl-2-(2-furyl)-4-hydroxy-9-(phenylmethyl)carbazole

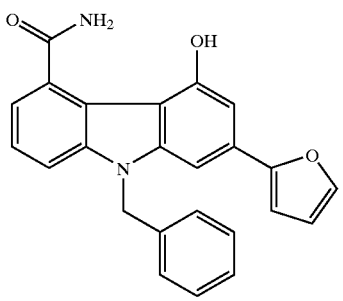

Prepared in 60% yield by the method of Example 17G. IR (KBr) 3425 (br), 3325 (br), 1642, 1628 cm$^{-1}$; $^1$H NMR (DMSO-d$_6$) δ5.72 (s, 2H), 6.56–6.57 (m, 1H), 6.95 (s, 1H), 6.98 (d, J=3.0 Hz, 1H), 7.07 (d, J=7.2 Hz, 2H), 7.17–7.26 (m, 3H), 7.42–7.43 (m, 3H), 7.71–7.76 (m, 2H), 8.38 (s, 1H), 8.83 (s, 1H), 10.70 (s, 1H); ESIMS m/e 381 (M$^-$−1); Elemental Analyses for C$_{24}$H$_{18}$N$_2$O$_3$: Calculated: C, 75.38; H, 4.74; N, 7.33. Found: C, 75.35; H, 4.95; N, 7.29.

F. Preparation of [5-carbamoyl-2-(2-furyl)-9-(phenylmethyl)carbazol-4-yl]oxyacetic acid, methyl ester

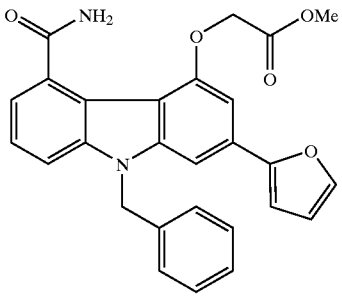

Prepared in 80% yield by the method of Example 17H. IR (KBr) 3358, 1756, 1643 cm$^{-1}$; $^1$H NMR (DMSO-d$_6$) δ3.70 (s, 3H), 4.98 (s, 2H), 5.70 (s, 2H), 6.58 (d, J=1.5 Hz, 1H), 6.93 (s, 1H), 7.01–7.30 (m, 8H), 7.35 (t, J=7.7 Hz, 1H), 7.51–7.57 (m, 3H), 7.72 (s, 1H); ESIMS m/e 455 (M$^+$+1); Elemental Analysis for C$_{25}$H$_{21}$NO$_4$: Calculated: C, 75.17; H, 5.30; N, 3.51. Found: C, 75.46; H, 5.32; N, 3.67.

Elemental Analyses for C$_{27}$H$_{22}$N$_2$O$_5$: Calculated: C, 71.36; H, 4.88; N, 6.16. Found: C, 71.46; H, 4.91; N, 6.24.

G. Preparation of [5-carbamoyl-2-(2-furyl)-9-(phenylmethyl)carbazol-4-yl]oxyacetic acid

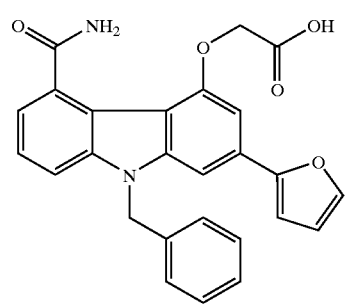

Prepared in 88% yield by the method of Example 17I. $^1$H NMR (DMSO-d$_6$) δ4.89 (s, 2H) 5.71 (s, 2H), 6.58 (s, 1H), 6.94 (s, 1H), 7.00–7.38 (m, 9H), 7.59 (d, J=9.2 Hz, 1H), 7.58 (s, 1H), 7.72 (br s, 2H), 12.98 (br s, 1H); ESIMS m/e 441 (M$^+$+1);

Elemental Analyses for C$_{26}$H$_{20}$N$_2$O$_5$: Calculated: C, 70.90; H, 4.58; N, 6.36. Found: C, 71.20; H, 4.67; N, 6.28.

EXAMPLE 23

[5-carbamoyl-9-(phenylmethyl)-2-[(tri(-1-methylethyl)silyl)oxymethyl]carbazol-4-yl]oxyacetic acid, lithium salt

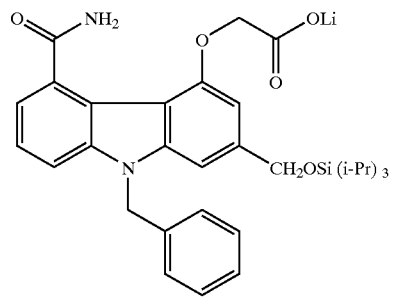

A. Preparation of 5-carbomethoxy-1,2-dihydro-9-(phenylmethyl)-2-[(tri(-1-methylethyl)silyl)oxymethyl]carbazol-4(3H)-one

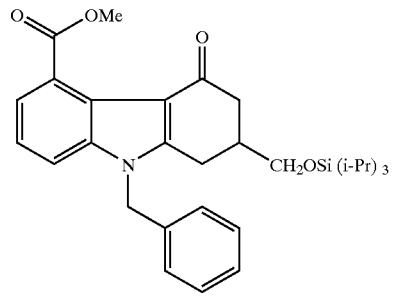

Triisopropylsilyl trifluoromethanesulfonate (2.46 mL, 9.15 mmol) was added to a stirred suspension of the compound of Example 19C (2.89 g, 7.95 mmol) and anhydrous pyridine (0.964 mL, 11.9 mmol) in anhydrous methylene chloride (29 mL) at 0° C. under a nitrogen atmosphere. The mixture was stirred at 0° C. for 1 hour. Methanol (0.5 mL) was added to the mixture and stirring was continued for 1 minute. After dilution with toluene (10 mL), the mixture was concentrated and the residue was subject to chromatographic purification on silica (gradient 10–50% ethyl acetate in hexane) to give subtitled compound (4.06 g, 98%) as a white solid. IR (KBr) 1725, 1645 cm$^{-1}$; $^1$H NMR (CDCl$_3$) δ0.90–1.15 (m, 21H, —CH(CH$_3$)$_2$), 2.50–2.63 (m, 3H), 2.74–2.86 (m, 1H), 3.02 (br d, J=7.7 Hz, 1H), 3.67–3.81 (m, 2H, —CH$_2$O—), 4.05 (s, 3H, —OCH$_3$), 5.37 (s, 2H, —NCH$_2$—), 7.00–7.04 (m, 2H), 7.22–7.44 (m, 6H); ESIMS m/e 520 (M$^+$+1);

Elemental Analyses for C$_{31}$H$_{41}$NO$_4$Si: Calculated: C, 71.64; H, 7.95; N, 2.69. Found: C, 71.75; H, 7.91; N, 2.82.

B. Preparation of 5-carbomethoxy-4-hydroxy-9-(phenylmethyl)-2-[(tri(-1-methylethyl)silyl)oxymethyl]carbazole

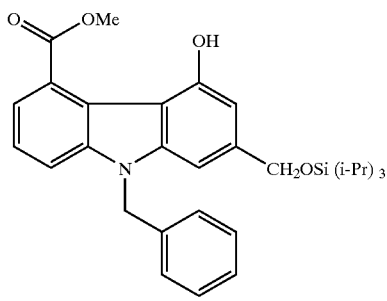

Following the experimental procedure (b) as described in the synthesis of Example 17F, subtitled compound was obtained as a yellowish solid in a 93% yield. IR (KBr) 3165 (br), 1671, 1629 cm$^{-1}$; $^1$H NMR (CDCl$_3$) δ1.00–1.22 (m, 21H, —CH(CH$_3$)$_2$), 4.10 (s, 3H, —CH$_3$), 4.97 (s, 2H, —OCH$_2$—), 5.51 (s, 2H, —NCH$_2$—), 6.79 (s, 1H), 7.05–7.14 (m, 3H), 7.20–7.30 (m, 3H), 7.39 (t, J=8.0 Hz, 1H), 7.59 (d, J=8.0 Hz, 1H), 7.98 (d, J=8.0 Hz, 1H), 10.50 (s, 1H, —OH); ESIMS m/e 518 (M$^+$+1);

Elemental Analyses for C$_{31}$H$_{39}$NO$_4$Si: Calculated: C, 71.92; H, 7.59; N, 2.71. Found: C, 72.19; H, 7.21; N, 2.76.

C. Preparation of 5-carbamoyl-4-hydroxy-9-(phenylmethyl)-2-[(tri(-1-methylethyl)silyl)oxymethyl]carbazole

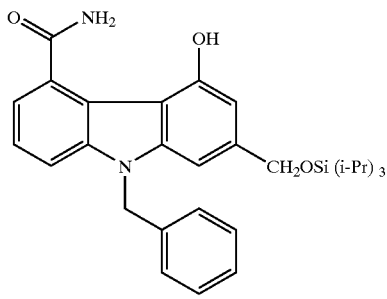

Following the experimental procedure as described in the synthesis of Example 17F(b), subtitled compound was obtained as a yellowish solid in a 80% yield. IR (KBr) 3348 (br), 3200, 1660, 1628 cm$^{-1}$; $^1$H NMR (CDCl$_3$) δ1.00–1.20 (m, 21H, —CH(CH$_3$)$_2$), 4.94 (s, 2H, —OCH$_2$—), 5.52 (s, 2H, —NCH$_2$—), 6.22 (s, 1H, —NH), 6.56 (s, 1H, —NH), 6.75 (s, 1H), 7.05–7.10 (m, 3H), 7.20–7.28 (m, 3H), 7.36 (t, J=7.6 Hz, 1H), 7.43 (d, J=7.6 Hz, 1H), 7.53 (d, J=7.6 Hz, 1H), 9.75 (br s, 1H, —OH); ESIMS m/e 503 (M$^+$+1).

D. Preparation of [5-carbamoyl-9-(phenylmethyl)-2-[(tri(-1-methylethyl)silyl)oxymethyl]carbazol-4-yl]oxyacetic acid, methyl ester

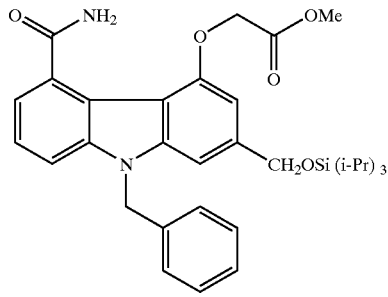

Following the experimental procedure as described in the synthesis of Example 17H, subtitled produce was obtained as a white solid in a 94% yield. IR (KBr) 3484, 3180 (br), 1764, 1675 cm$^{-1}$; $^1$H NMR (CDCl$_3$) δ1.00–1.20 (m, 21H, —CH(CH$_3$)$_2$), 3.82 (s, 3H, —OCH$_3$), 4.89 (s, 2H, —OCH$_2$—), 4.93 (s, 2H, —OCH$_2$—), 5.50 (s, 2H, —NCH$_2$—), 6.00 (br s, 2H, —NH$_2$), 6.60 (s, 1H), 7.05–7.12 (m, 3H), 7.22–7.28 (m, 3H), 7.32–7.38 (m, 1H), 7.39–7.41 (m, 2H); ESIMS m/e 575 (M$^+$+1);

Elemental Analyses for C$_{33}$H$_{42}$N$_2$O$_5$Si: Calculated: C, 68.96; H, 7.37; N, 4.87. Found: C, 69.14; H, 7.20; N, 4.95.

E. Preparation of [5-carbamoyl-9-(phenylmethyl)-2-[(tri(-1-methylethyl)silyl)oxymethyl]carbazol-4-yl]oxyacetic acid, lithium salt

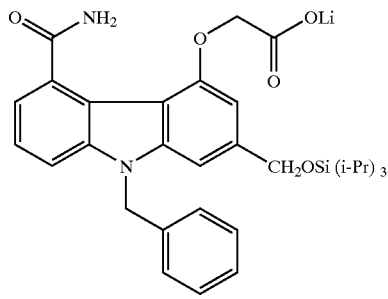

Lithium hydroxide (4.17 N, 42.5 mL, 0.177 mmol) was added to a stirred suspension of part D above (50.9 mg, 0.0886 mmol) in THF (1 mL)/CH$_3$OH (0.3 mL)/H$_2$O (0.3 mL). The resultant mixture was stirred in an oil bath at 55° C. for 1 hour to form a white suspension. At ambient temperature, the white suspension was diluted with water (5 mL) and THF was evaporated in vacuo. After filtration and washing with water, the white solid was dried under vacuum to give 11 (40.0 mg, 80%) of the title product. IR (KBr) 3470, 3315, 1652, 1621 cm$^{-1}$; $^1$H NMR (DMSO-d$_6$) δ0.90–1.15 (m, 21H, —CH(CH$_3$)$_2$), 4.29 (s, 2H, —OCH$_2$—), 4.84 (s, 2H, —OCH$_2$—), 5.57 (s, 2H, —NCH$_2$—), 6.49 (s, 1H), 7.00–7.25 (m, 7H), 7.31 (br t, J=7.9 Hz, 1H), 7.43 (br s, 1H, —NH), 7.59 (br d, J=7.9 Hz, 1H), 7.72 (br s, 1H, —NH); ESIMS m/e 567 (M$^+$+1).

Preparation 3

Preparation of 5-Carbomethoxy-1,2-dihydro-9H-carbazol-4(3H)-one from 2-chloro-3-nitrobenzoic acid

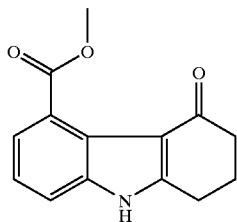

a) Methyl 2-chloro-3-nitrobenzoate

A solution of 2-chloro-3-nitrobenzoic acid (20.16 g, 100.0 mM), iodomethane (15.6 g, 110 mM), and potassium carbonate (15.0 g, 108.5 mM) in 100 mL DMF was stirred at room temperature for 48 hours. The mixture was poured into 1.5 liters of $H_2O$. The resultant precipitate was collected by 20.0 g (93%) of methyl 2-chloro-3-nitrobenzoate as a white solid. $^1$H NMR (CDCl$_3$) δ8.42 (dd, 1H, J=1 and 8 Hz), 8.18 (dd, 1H, J=1 and 8 Hz), 7.43 (t, 1H, J=8 Hz), and 3.9 (s, 3H). IR (KBr, cm$^{-1}$) 1743, 1719, 1595, 1540, 1532, 1433, 1357, 1300, and 730. MS (FD) m/e 215, 216.

Elemental Analyses for $C_8H_6NO_4Cl$: Calculated: C, 44.57; H, 3.81; N, 6.50. Found: C, 44.19; H, 3.45; N, 6.19.

b) Methyl 2-chloro-3-aminobenzoate

Hydrogen gas was passed through a solution of methyl 2-chloro-3-nitrobenzoate (10.0 g, 46.4 mM) and 1.0 g of 3% sulfided platinum on carbon in 150 mL ethyl acetate for 48 hours at room temperature. The catalyst was removed by filtration through celite. Concentration of the filtrate afforded 8.6 g (100%) of methyl 2-chloro-3-aminobenzoate as a yellow oil. $^1$H NMR (CDCl$_3$) δ7.25 (dd, 1H, J=1 and 8 Hz), 7.2 (t, 1H, J=8 Hz), 6.95 (dd, 1H, J=1 and 8 Hz), and 3.9 (s, 3H). IR (CHCl$_3$, cm$^{-1}$) 3450, 3380, 2980, 2900, 1729, 1615, 1456, 1434, 1322, 1290, and 1268. MS (ES) m/e 186, 188.

Elemental Analyses for $C_8H_8NO_2Cl$: Calculated: C, 51.77; H, 4.34; N, 7.55. Found: C, 51.52; H, 4.17; N, 7.54.

b) Methyl 2-chloro-3-aminobenzoate

A solution of stannous chloride (27.0 g, 137.0 mM) in 55 mL of concentrated hydrochloric acid was slowly added to a solution of methyl 2-chloro-3-nitrobenzoate (6.0 g, 27.9 mM) in 75 mL ethanol at 15–20° C. over 1 hour. The mixture was then heated at 50–60° C. for 15 minutes. The mixture was cooled to room temperature and made alkaline by slow addition of solid sodium hydroxide maintaining a temperature of 30–35° C. The resultant mixture was extracted three times with chloroform. The extracts were washed with brine, dried over sodium sulfate, filtered and concentrated to afford 2.6 g (50%) of methyl 2-chloro-3-aminobenzoate as a yellow oil, identical in all respects to the material derived via catalytic hydrogenation described above.

b) Methyl 2-chloro-3-aminobenzoate

A solution of sodium dithionite (14.0 g, 20.0 mM) and sodium carbonate (6.7 g) in 200 mL of water was slowly added to a solution of methyl 2-chloro-3-nitrobenzoate (6.0 g, 27.9 mM) in 40 mL methanol and 40 mL of tetrahydrofuran at 25° C. over 30 minutes. The mixture was stirred at room temperature for an additional 30 minutes, then extracted with ethyl acetate. The extracts were washed with brine, dried over sodium sulfate, filtered and concentrated to afford 1.2 g (33%) of methyl 2-chloro-3-aminobenzoate as a yellow oil, identical in all respects to the material derived via catalytic hydrogenation described above.

c) 3-(3-Carbomethoxy-2-chloroanilino)cyclohex-2-en-1-one

A mixture of methyl 2-chloro-3-aminobenzoate (11.11 g, 59.86 mM) and 1,3-cyclohexanedione (9.05 g, 80.8 mM) was heated at 120° C. under a stream of nitrogen for 4 hours. The resultant solid was triturated with hot ethyl acetate, then dried in vacuo to afford 14.05 g (84%) of 3-(3-carbomethoxy-2-chloroanilino)cyclohex-2-en-1-one as a yellow orange solid. $^1$H NMR (CDCl$_3$) δ7.6 (dt, 1H, J=1 and 8 Hz), 7.3 (t, 1H, J=8 Hz), 6.6 (br s, 1H), 5.62 (s, 1H), 3.95 (s, 3H), 2.6 (t, 2H, J=6 Hz), 2.4 (t, 2H, J=6 Hz), and 2.1 (m, 2H). IR (CHCl$_3$, cm$^{-1}$) 3050, 2950, 1729, 1536, 1351, 1299, 1290, 1267, and 1135. MS (ES) m/e 278, 280, 282.

Elemental Analyses for $C_{14}H_{14}NO_3Cl$: Calculated: C, 60.11; H, 5.04; N, 5.01. Found: C, 57.51; H, 4.99; N, 4.68.

d) 5-Carbomethoxy-1,2-dihydro-9H-carbazol-4(3H)-one

A suspension of 3-(3-carbomethoxy-2-chloroanilino)cyclohex-2-en-1-one (10.22 g, 36.67 mM), palladium acetate (0.82 g, 3.66 mM), tricyclohexylphosphine (4.10 g, 14.62 mM), and triethylamine (30.0 mL, 21.78 g, 215.2 mM) in 100 mL acetonitrile was heated at 130° C. in a sealed vessel for 14 days. The mixture was diluted with ethyl acetate, washed twice with 1 N HCl, twice with $H_2O$, once with saturated brine, dried over anhydrous magnesium sulfate, filtered, and concentrated to afford 9.9 g of a light brown gum. Purification by HPLC on silica gel (elution with gradient methylene chloride/ethyl acetate) afforded 4.68 g (52%) of the 5-carbomethoxy-1,2-dihydro-9H-carbazol-4(3H)-one as a yellow solid. $^1$H NMR (CDCl$_3$) δ9.15 (br s, 1H), 7.4 (dd, 1H, J=1 and 8 Hz), 7.35 (dd, 1H, J=1 and 8 Hz), 7.25 (t, 1H, J=8 Hz), 4.05 (s, 3H), 2.95 (t, 2H, J=6 Hz), 2.55 (t, 2H, J=6 Hz), and 2.2 (m, 2H). IR (CHCl$_3$, cm$^{-1}$) 3400, 3200 (br), 3000, 2950, 1721, 1646, 1466, 1439, 1427, 1299, 1284, 1165, and 1135. MS (ES) m/e 242, 244.

Elemental Analyses for $C_{14}H_{13}NO_3$: Calculated: C, 69.12; H, 5.39; N, 5.76. Found: C, 68.82; H, 5.67; N, 5.60.

Preparation 4

Preparation of 5-Carbomethoxy-1,2-dihydro-9H-carbazol-4(3H)-one from 2-bromo-3-nitrobenzoic acid

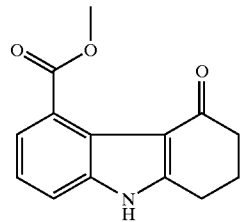

a) Methyl 2-bromo-3-nitrobenzoate

A solution of 2-bromo-3-nitrobenzoic acid (28.4 g, 115.0 mM), iodomethane (18.0 g, 127 mM), and potassium carbonate (19.0 g, 137.4 mM) in 100 mL DMF was stirred at room temperature for 72 hours. The mixture was poured into 1.5 liters of $H_2O$. The resultant precipitate was collected by filtration and dried in vacuo to afford 28.79 g (96%) of methyl 2-bromo-3-nitrobenzoate as a white solid. $^1$H NMR (DMSO-d6) δ8.3 (dd, 1H, J=1 and 8 Hz), 7.9 (dd, 1H, J=1 and 8 Hz), 7.7 (t, 1H, J=8 Hz), and 3.9 (s, 3H). IR (KBr, cm$^{-1}$) 2950, 1738, 1541, 1435, 1364, 1298, and 1142. MS (FD) m/e 259, 261.

Elemental Analyses for $C_8H_6NO_4Br$: Calculated: C, 36.95; H, 2.33; N, 5.39. Found: C, 37.14; H, 2.37; N, 5.45.

b) Methyl 2-bromo-3-aminobenzoate

Hydrogen gas was passed through a solution of methyl 2-bromo-3-nitrobenzoate (0.20 g, 0.77 mM) and 0.1 g of 3% sulfided platinum on carbon in 25 mL ethyl acetate for 24 hours at room temperature. The catalyst was removed by filtration through celite. Concentration of the filtrate afforded 0.175 g (99%) of methyl 2-bromo-3-aminobenzoate as a yellow oil. $^1$H NMR (CDCl$_3$) δ7.15 (t, 1H, J=8 Hz), 7.1 (dd, 1H, J=1 and 8 Hz), 6.8 (dd, 1H, J=1 and 8 Hz), and 3.95 (s, 3H). IR (CHCl$_3$, cm$^{-1}$) 3550, 3380, 2980, 2900, 1729, 1613, 1465, 1451, 1434, 1324, 1266, and 1025. MS (FD) m/e 230, 232.

Elemental Analyses for C$_8$H$_8$NO$_2$Br: Calculated: C, 41.77; H, 3.51; N, 6.09. Found: C, 42.01; H, 3.29; N, 6.00.
b) Methyl 2-bromo-3-aminobenzoate A solution of stannous chloride (15.0 g, 76.1 mM) in 30 mL of concentrated hydrochloric acid was slowly added to a solution of methyl 2-bromo-3-nitrobenzoate (4.0 g, 15.4 mM) in 90 mL ethanol at 15–30° C. over 1 hour. The mixture was then heated at 50–60° C. for 15 minutes. The mixture was cooled to room temperature and made alkaline by slow addition of solid sodium hydroxide maintaining a temperature of 30–35° C. The resultant mixture was extracted three times with chloroform. The extracts were washed with brine, dried over sodium sulfate, filtered and concentrated to afford 3.51 g (99%) of methyl 2-bromo-3-aminobenzoate as a yellow oil, identical in all respects to the material derived via catalytic hydrogenation described above.
c) 3-(3-Carbomethoxy-2-bromoanilino)cyclohex-2-en-1-one A mixture of methyl 2-bromo-3-aminobenzoate (13.2 g, 60.0 mM) and 1,3-cyclohexanedione (8.4 g, 75 mM) was heated at 125° C. under a stream of nitrogen for 4 h. The resultant solid was purified by HPLC on silica gel (elution with methylene chloride/ethyl acetate) to afford 17.2 g (88%) of 3-(3-carbomethoxy-2-bromoanilino)cyclohex-2-en-1-one as a tan foam. $^1$H NMR (DMSO-d6) δ8.75 (s, 1H), 7.6–7.4 (m, 3H), 4.65 (s, 1H), 3.85 (s, 3H), 2.6 (t, 2H, J=6 Hz), 2.15 (t, 2H, J=6 Hz), and 1.9 (m, 2H). IR (CHCl$_3$, cm$^{-1}$) 3400, 3004, 2954, 1732, 1607, 1588, 1573, 1513, 1464, 1436, 1412, 1308, 1249, 1177, and 1144. MS (ES) m/e 322, 324, 326.

Elemental Analyses for C$_{14}$H$_{14}$NO$_3$Br: Calculated: C, 51.85; H, 4.32; N, 4.32. Found: C, 53.60; H, 4.73; N, 4.09.
d) 5-Carbomethoxy-1,2-dihydro-9H-carbazol-4(3H)-one A suspension of 3-(3-carbomethoxy-2-bromoanilino)cyclohex-2-en-1-one (15.8 g, 48.8 mM), palladium acetate (1.12 g, 5.0 mnM), tri-o-tolylphosphine (3.1 g, 10.0 mM), and triethylamine (6.3 g, 62.0 mM) in 120 mL acetonitrile was heated at reflux for 8 hours. The solvent was removed in vacuo. The residue was dissolved in methylene chloride, washed twice with 1 N HCl, twice with H$_2$O, once with saturated brine, dried over anhydrous magnesium-sulfate, filtered, and concentrated to afford 17 g of a light brown foam. Purification by HPLC on silica gel (elution with gradient methylene chloride/ethyl acetate) afforded 9.2 g (78%) of the 5-carbomethoxy-1,2-dihydro-9H-carbazol-4(3H)-one as a yellow solid, identical with the material derived from 3-(3-carbomethoxy-2-chloroanilino)cyclohex-2-en-1-one, described above. $^1$H NMR (DMSO-d6) δ7.5 (d, 1H, J=8 Hz), 7.25–7.1 (m, 2H), 5.7 (s, 1H), 3.8 (s, 3H), 2.95 (t, 2H, J=6 Hz), 2.4 (t, 2H, J=6 Hz), and 2.1 (m , 2H). MS (ES) m/e 242, 244.

EXAMPLE 24

Preparation of {9-[(phenyl)methyl]-5-carbamoylcarbazol-4-yl}oxyacetic acid, sodium salt

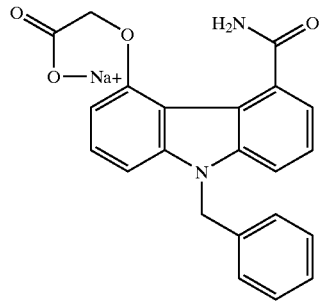

A. 9-[(Phenyl)methyl]-5-carbomethoxy-1,2-dihydrocarbazol-4(3H)-one

A suspension of 5-carbomethoxy-1,2-dihydro-9H-carbazol-4(3H)-one (300 mg, 1.23 mM), benzyl bromide (210 mg, 1.23 mM), and potassium carbonate (170 mg, 1.23 mM) in 15 mL DMF was stirred at room temperature for 6 hours. The mixture was diluted with 80 mL H$_2$O and chilled in the refrigerator. The resultant white precipitate was collected by filtration, washed with H$_2$O, and dried in vacuo to afford 325 mg (79%) of the 9-[(phenyl)methyl]-5-carbomethoxy-1,2-dihydrocarbazol-4(3H)-one as a white solid. $^1$H NMR (DMSO-d6) δ7.7 (dd, 1H, J=1 and 8 Hz), 7.45–7.0 (m, 7H), 5.6 (s, 2H), 3.8 (s, 3H), 3.05 (t, 2H, J=6 Hz), 2.5 (t, 2H, J=6 Hz), and 2.2 (m, 2H). IR (KBr, cm$^{-1}$) 3421, 1726, 1676, 1636, 1473, 1450, 1435, 1288, 1122, 764, 745, and 706. MS (ES) m/e 334.

Elemental Analyses for C$_{21}$H$_{19}$NO$_3$: Calculated: C, 75.68; H, 5.71; N, 4.20. Found: C, 70.85; H, 5.53; N, 4.49.
B. 9-[(Phenyl)methyl]-4-hydroxy-5-carbomethoxy carbazole (a) A solution of the 9-[(phenyl)methyl]-5-carbomethoxy-1,2-dihydrocarbazol-4(3H)-one (1.5 g, 4.5 mM) and 2,3-dichloro-5,6-dicyano-1,4-benzoquinone (1.12 g, 5.0 mM) in 25 mL of toluene was stirred between 80–90° C. for 6 h. The mixture was purified directly by column chromatography on silica gel (elution with methylene chloride/ethyl acetate) to afford 420 mg (28%) of the 9-[(phenyl)methyl]-4-hydroxy-5-carbomethoxy carbazole as a yellow solid. $^1$H NMR (DMSO-d6) δ10.25 (s, 1H), 7.7 (d, 1H, J=8 Hz), 7.4 (t, 1H, J=8 Hz), 7.4–7.0 (m, 8H), 6.6 (d, 1H, J=8 Hz), 5.6 (s, 2H), and 3.8 (s, 3H). IR (CHCl$_3$, cm$^{-1}$) 1723, 1685, 1621, 1597, 1568, 1496, 1453, 1442, 1392, 1286, 1267, 1156, and 1138. MS (ES) m/e 330, 332.

Elemental Analyses for C$_{21}$H$_{17}$NO$_3$: Calculated: C, 76.13; H, 5.14; N, 4.23. Found: C, 75.90; H, 5.20; N, 4.46.

(b) To a solution of the 9-[(phenyl)methyl]-5-carbomethoxy-1,2-dihydrocarbazol-4(3H)-one (2.87 g, 8.61 mM) in 29 ml dioxane was added 60% sodium hydride in mineral oil (0.79 g, 19.8 mM). The reaction was stirred 8 minutes, then methyl benzenesulfinate (1.80 ml, 13.8 mM) was added. The reaction was stirred an additional 1.5 h, then diluted with 43 ml dioxane and 1.13 ml acetic acid. The mixture was refluxed 1 h, diluted with ethyl acetate, and extracted with sat'd NaHCO$_3$ two times, then with brine. After drying (NaSO$_4$), evaporation in vacuo afforded 4.90 g. The mixture was purified by column chromatography on silica gel (elution with toluene/methylene chloride) to afford 2.31 g (81%) of the 9-[(phenyl)methyl]-4-hydroxy-5-carbomethoxy carbazole. $^1$H NMR (DMSO-d6) δ10.25 (s, 1H), 7.7 (d, 1H, J=8 Hz), 7.4 (t, 1H, J=8 Hz), 7.4–7.0 (m, 8H), 6.6 (d, 1H, J=8 Hz), 5.6 (s, 2H), and 3.8 (s, 3H). IR (CHCl₃, cm⁻¹) 1723, 1685, 1621, 1597, 1568, 1496, 1453, 1442, 1392, 1286, 1267, 1156, and 1138. MS (ES) m/e 330, 332.

Elemental Analyses for C$_{21}$H$_{17}$NO$_3$: Calculated: C, 76.13; H, 5.14; N, 4.23. Found: C, 75.90; H, 5.20; N, 4.46.

C. 9-[(Phenyl)methyl]-4-hydroxy-5-carbamoyl carbazole

A solution of the 9-[(phenyl)methyl]-4-hydroxy-5-carbomethoxy carbazole (200 mg, 0.6 mM) in 4 mL MeOH and 40 mL concentrated aqueous ammonium hydroxide was sonicated for 30 h at 40–50° C. The mixture was diluted with ethyl acetate and acidified to pH 1 with 5 N HCl. The aqueous layer was extracted three times with ethyl acetate. The combined organic extracts were washed with saturated brine, dried over magnesium sulfate, filtered, and concentrated. The residue was purified by column chromatography on silica gel (elution with gradient methylene chloride/ethyl acetate) to afford 50 mg (26%) of the 9-[(phenyl)methyl]-4-hydroxy-5-carbamoyl carbazole as a white solid. ¹H NMR (DMSO-d6) δ10.5 (s, 1H), 8.8 (br s, 1H), 8.4 (br s, 1H), 7.85 (dd, 1H, J=1 and 8 Hz), 7.5–7.1 (m, 9H), 6.6 (d, 1H, J=8 Hz), and 5.8 (s, 2H). IR (KBr, cm⁻¹) 3428, 3198, 3063, 1631, 1599, 1579, 1562, 1496, 1442, 1330, 1261, 1215, 775, and 697. MS (ES) m/e 315, 317.

Elemental Analyses for C$_{20}$H$_{16}$N$_2$O$_2$: Calculated: C, 75.95; H, 5.06; N, 8.86. Found: C, 74.88; H, 5.40; N, 7.78.

D. {9-[(Phenyl)methyl]-5-carbamoylcarbazol-4-yl}oxyacetic acid, methyl ester

40% Methanolic Triton B (0.11 mL, 0.24 mM) was added to a solution of the 9-[(phenyl)methyl]-4-hydroxy-5-carbamoyl carbazole (70 mg, 0.22 mM) in 20 mL DMF at 0° C. After 15 minutes, methyl bromoacetate (70 mg, 0.44 mM) was added and the resultant mixture stirred at room temperature for 5 h. The mixture was diluted with ethyl acetate, washed with 1 N HCl, H₂O, and saturated brine, dried over magnesium sulfate, filtered, and concentrated. The residue was combined with the crude material derived from a similar run utilizing 45 mg (0.14 mM [0.36 mM total]) of 9-[(phenyl)methyl]-4-hydroxy-5-carbamoyl carbazole. The combined residues were purified by column chromatography on silica gel (elution with ethyl acetate) to afford 76 mg (54%) of the {9-[(phenyl)methyl]-5-carbamoylcarbazol-4-yl}oxyacetic acid, methyl ester as a white solid. ¹H NMR (DMSO-d6) δ7.65 (d, 1H, J=8 Hz), 7.5 (br s, 1H), 7.4–7.15 (m, 9H), 7.1 (d, 1H, J=8 Hz), 6.6 (d, 1H, J=8 Hz), 5.7 (s, 2H), 4.9 (s, 2H), and 3.75 (s, 3H). IR (KBr, cm⁻¹) 3367, 3200, 1760, 1643, 1579, 1496, 1452, 1427, 1216, 1157, 772, and 716. MS (FD) m/e 388.

Elemental Analyses for C$_{23}$H$_{20}$N$_2$O$_4$: Calculated: C, 71.13; H, 5.15; N, 7.22. Found: C, 70.77; H, 5.49; N, 6.79.

E. {9-[(Phenyl)methyl]-5-carbamoylcarbazol-4-yl}oxyacetic acid, sodium salt

A solution of the {9-[(phenyl)methyl]-5-carbamoylcarbazol-4-yl}oxyacetic acid, methyl ester (10.1 mg, 0.025 mM) and 0.025 mL (0.025 mM) of 1 N NaOH in 3 mL of ethanol was stirred for 16 h at 25° C. The resultant white precipitate was collected by filtration, washed with a small amount of EtOH, then dried in vacuo to afford 7.1 mg (70%) of the {9-[(phenyl)methyl]-5-carbamoylcarbazol-4-yl}oxyacetic acid, sodium salt as a white powder. ¹H NMR (DMSO-d6) δ7.6 (d, 1H, J=8 Hz), 7.5–7.05 (m, 11H), 6.55 (d, 1H, J=8 Hz), 5.75 (s, 2H), and 4.3 (s, 2H). IR (KBr, cm⁻¹) 3471, 1657, 1615, 1591, 1496, 1453, 1412, 1330, 1272, and 1151. MS (ES) m/e 373, 375, 397. Elemental Analyses for C$_{22}$H$_{17}$N$_2$O$_4$Na: C, 66.67; H, 4.29; N, 7.07. Found C, 66.75; H, 4.55; N, 6.83.

EXAMPLE 25

Preparation of {9-[(3-fluorophenyl)methyl]-5-carbamoylcarbazol-4-yl}oxyacetic acid

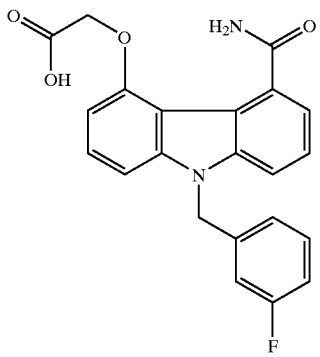

A. 9-[(3-Fluorophenyl)methyl]-5-carbomethoxy-1,2-dihydrocarbazol-4(3H)-one

40% Methanolic Triton B (2.06 mL, 4.53 mM) was slowly added dropwise to a solution of 5-carbomethoxy-1,2-dihydro-9H-carbazol-4(3H)-one (930.0 mg, 3.82 mM) in 5 mL of DMF at 0° C. After 5 minutes, 3-fluorobenzyl chloride (664.0 mg, 4.59 mM) was added and the resultant mixture stirred at 0° C. for 3 h, then at room temperature for 20 hours. The mixture was diluted with ethyl acetate, washed three times with 1 N HCl, three times with H₂O, once with saturated brine, dried over anhydrous magnesium sulfate, filtered, and concentrated. The residue was purified by column chromatography on silica gel (elution with gradient methylene chloride/ethyl acetate) to afford 502.3 mg (37%) of the 9-[(3-fluorophenyl)methyl]-5-carbomethoxy-1,2-dihydrocarbazol-4(3H)-one as a yellow foam. ¹H NMR (CDCl₃) δ7.4–7.2 (m, 4H), 6.9 (m, 1H), 6.7 (m, 2H), 5.35 (s, 2H), 4.05 (s, 3H), 2.9 (t, 2H, J=6 Hz), 2.65 (t, 2H, J=6 Hz), and 2.3 (m, 2H). IR (CDCl₃, cm⁻¹) 3050, 2950, 1725, 1654, 1464, 1451, 1440, 1288 and 1119. MS (ES) m/e 350, 352.

Elemental Analyses for C$_{21}$H$_{18}$NO$_3$F: Calculated: C, 71.78; H, 5.16; N, 3.99. Found: C, 72.00; H, 4.95; N, 4.11.

B. 9-[(3-Fluorophenyl)methyl]-4-hydroxy-5-carbomethoxy carbazole

A solution of the 9-[(3-fluorophenyl)methyl]-5-carbomethoxy-1,2-dihydrocarbazol-4(3H)-one (434.0 mg, 1.23 mM) and 2,3-dichloro-5,6-dicyano-1,4-benzoquinone (324.0 mg, 1.42 mM) in 20 mL of toluene was stirred between 70–80° C. for 5 h. The mixture was purified directly by column chromatography on silica gel (elution with methylene chloride) to afford 137.0 mg (32%) of the 9-[(3-fluorophenyl)methyl]-4-hydroxy-5-carbomethoxy carbazole as a yellow foam. ¹H NMR (DMSO-d6) δ10.2 (s, 1H), 7.7 (d, 1H, J=8 Hz), 7.4 (t, 1H, J=8 Hz), 7.3 (m, 2H), 7.2 (d, 1H, J=8 Hz), 7.1 (d, 1H, J=8 Hz), 7.05–6.85 (m, 3H), 6.6 (d, 1H, J=8 Hz), 5.65 (s, 2H), and 3.85 (s, 3H). IR (CHCl₃, cm⁻¹) 3200 (br), 1687, 1597, 1452, 1442, 1285, and 1267. MS (ES) m/e 348, 350.

Elemental Analyses for C$_{21}$H$_{16}$NO$_3$F: Calculated: C, 72.20; H, 4.62; N, 4.01. Found: C, 72.30; H, 4.66; N, 4.04.

C. 9-[(3-Fluorophenyl)methyl]-4-hydroxy-5-carbamoyl carbazole

A solution of the 9-[(3-fluorophenyl)methyl]-4-hydroxy-5-carbomethoxy carbazole (130.8 mg, 0.37 mM) in 5 mL THF and 20 mL concentrated aqueous ammonium hydroxide was sonicated for 5 h at 40–50° C. The mixture was diluted with ethyl acetate and acidified to pH 1 with 5 N HCl. The aqueous layer was extracted twice with ethyl acetate. The combined organic extracts were washed with saturated brine, dried over magnesium sulfate, filtered, and concentrated. The residue was purified by column chromatography on silica gel (elution with gradient methylene chloride/ethyl acetate) to afford 57.4 mg (45%) of the 9-[(3-fluorophenyl)methyl]-4-hydroxy-5-carbamoyl carbazole as a white solid. $^1$H NMR (DMSO-d6) δ10.5 (s, 1H), 8.8 (br s, 1H), 8.4 (br s, 1H), 7.8 (dd, 1H, J=1 and 8 Hz), 7.5 (m, 2H), 7.3 (m, 2H), 7.15–7.0 (m, 2H), 6.95 (d, 1H, J=8 Hz), 6.85 (d, 1H, J=8 Hz), 6.6 (d, 1H, J=8 Hz), and 5.7 (s, 2H). IR (CHCl$_3$, cm$^{-1}$) 3431, 3200 (br), 1628, 1614, 1600, 1580, 1546, 1488, 1448, 1329, 1261, and 776. MS (ES) m/e 333, 335.

Elemental Analyses for C$_{20}$H$_{15}$N$_2$O$_2$F: Calculated: C, 71.85; H, 4.52; N, 8.38. Found: C, 74.45; H, 6.01; N, 8.48.

D. {9-[(3-Fluorophenyl)methyl]-5-carbamoylcarbazol-4-yl}oxyacetic acid, tert-butyl ester 40% Methanolic Triton B (0.086 mL, 0.19 mM) was added to a solution of the 9-[(3-fluorophenyl)methyl]-4-hydroxy-5-carbamoyl carbazole (51.9 mg, 0.155 mM) in 3 mL DMF at room temperature. After 3 minutes, t-butyl bromoacetate (87.8 mg, 0.44 mM) Was added and the resultant mixture stirred at room temperature for 5 hours. The mixture was diluted with ethyl acetate, washed four times with H$_2$O, and saturated brine, dried over magnesium sulfate, filtered, and concentrated. The residue was purified by column chromatography on silica gel (elution with gradient methylene chloride/ethyl acetate) to afford 44.0 mg (63%) of the {9-[(3-fluorophenyl)methyl]-5-carbamoylcarbazol-4-yl}oxyacetic acid, tert-butyl ester as a white solid. $^1$H NMR (DMSO-d6) δ7.6 (d, 1H, J=8 Hz), 7.5–6.8 (m, 10H), 6.55 (d, 1H, J=8 Hz), 5.7 (s, 2H), 4.8 (s, 2H), and 1.45 (s, 9H). IR (CHCl$_3$, cm$^{-1}$) 3450, 3400, 1746, 1674, 1592, 1457, 1369, and 1151. MS (FD) m/e 448.

Elemental Analyses for C$_{26}$H$_{25}$N$_2$O$_4$F: Calculated: C, 69.63; H, 5.62; N, 6.25. Found: C, 69.35; H, 5.44; N, 6.23.

E. {9-[(3-Fluorophenyl)methyl]-5-carbamoylcarbazol-4-yl}oxyacetic acid

A solution of the {9-[(3-fluorophenyl)methyl]-5-carbamoylcarbazol-4-yl}oxyacetic acid, tert-butyl ester (40.0 mg, 0.089 mM) in 2 mL of trifluoroacetic acid was stirred at room temperature for 5 hours. The solvent was removed in vacuo. The residue was triturated with ethyl ether, then dried in vacuo to afford 35.0 mg (100%) of the {9-[(3-fluorophenyl)methyl]-5-carbamoylcarbazol-4-yl}oxyacetic acid as a white powder. $^1$H NMR (DMSO-d6) δ13.0 (br s, 1H), 7.75 (s, 1H), 7.6 (d, 1H, J=8 Hz), 7.5–7.25 (m, 5H), 7.2–6.8 (m, 4H), 6.6 (d, 1H, J=8 Hz), 5.7 (s, 2H), and 4.8 (s, 2H). IR (KBr, cm$^{-1}$) 3423, 3400, 1736, 1637, 1615, 1589, 1499, 1487, 1450, 1436, 1331, 1250, and 1156. MS (ES) m/e 391, 393.

Elemental Analyses for C$_{22}$H$_{17}$N$_2$O$_4$F: Calculated: C, 67.34; H, 4.37; N, 7.14. Found: C, 67.63; H, 4.22; N, 7.35.

EXAMPLE 26

Preparation of {9-[(3-Chlorophenyl)methyl]-5-carbamoylcarbazol-4-yl}oxyacetic acid

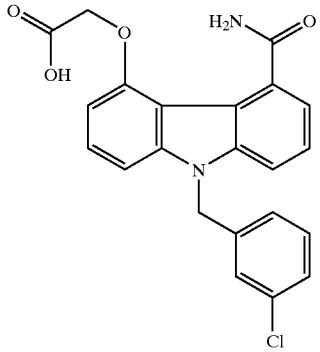

A. 9-[(3-Chlorophenyl)methyl]-5-carbomethoxy-1,2-dihydrocarbazol-4(3H)-one

A suspension of 5-carbomethoxy-1,2-dihydro-9H-carbazol-4(3H)-one (527.0 mg, 2.17 mM), 3-chlorobenzyl bromide (802.2 mg, 3.90 mM), a catalytic amount of sodium iodide (ca. 1 mg), and potassium carbonate (500.0 mg, 3.62 mM) was stirred at room temperature for 150 hours. The mixture was diluted with ethyl acetate, washed five times with H$_2$O, once with saturated brine, dried over anhydrous magnesium sulfate, filtered, and concentrated. The residue was purified by column chromatography on silica gel (elution with gradient methylene chloride/ethyl acetate) to afford 537.1 mg (67%) of the 9-[(3-chlorophenyl)methyl]-5-carbomethoxy-1,2-dihydrocarbazol-4(3H)-one as a yellow foam. $^1$H NMR (CDCl$_3$) δ7.5–7.2 (m, 5H), 7.1 (s, 1H), 6.85 (m, 1H), 5.35 (s, 2H), 4.05 (s, 3H), 2.9 (t, 2H, J=6 Hz), 2.65 (t, 2H, J=6 Hz), and 2.3 (m, 2H). IR (CDCl$_3$, cm$^{-1}$) 3050, 2950, 1725, 1654, 1464, 1444, 1432, 1288 and 1120. MS (ES) m/e 366, 368, 370.

Elemental Analyses for C$_{21}$H$_{18}$NO$_3$Cl: Calculated: C, 68.57; H, 4.93; N, 3.81. Found: C, 68.61; H, 4.92; N, 3.70.

B. 9-[(3-Chlorophenyl)methyl]-4-hydroxy-5-carbomethoxy carbazole

A solution of the 9-[(3-chlorophenyl)methyl]-5-carbomethoxy-1,2-dihydrocarbazol-4(3H)-one (480.5 mg, 1.31 mM) and 2,3-dichloro-5,6-dicyano-1,4-benzoquinone (325.7 mg, 1.43 mM) in 50 mL of toluene was stirred between 70–80° C. for 3 hours. The mixture was purified directly by column chromatography on silica gel (elution with methylene chloride) to afford 172.6 mg (36%) of the 9-[(3-chlorophenyl)methyl]-4-hydroxy-5-carbomethoxy carbazole as a yellow foam. $^1$H NMR (CDCl$_3$) δ10.4 (s, 1H), 8.05 (d, 1H, J=8 Hz), 7.6 (d, 1H, J=8 Hz), 7.4 (m, 2H), 7.3–7.1 (m, 3H), 6.9–6.7 (m, 3H), 5.55 (s, 2H), and 4.15 (s, 3H). IR (CDCl$_3$, cm$^{-1}$) 3200 (br), 1684, 1598, 1442, 1428, 1331, 1285, and 1267. MS (ES) m/e 364, 366, 368.

Elemental Analyses for C$_{21}$H$_{16}$NO$_3$Cl: Calculated: C, 68.95; H, 4.41; N, 3.83. Found: C, 69.23; H, 4.52; N, 3.88.

C. 9-[(3-Chlorophenyl)methyl]-4-hydroxy-5-carbamoyl carbazole

A solution of the 9-[(3-chlorophenyl)methyl]-4-hydroxy-5-carbomethoxy carbazole (156.2 mg, 0.43 mM) in 5 mL THF and 20 mL concentrated aqueous ammonium hydroxide was sonicated for 5 hours at 40–50° C. The mixture was diluted with ethyl acetate and acidified to pH 1 with 5 N HCl. The aqueous layer was extracted twice with ethyl acetate. The combined organic extracts were washed with saturated brine, dried over magnesium sulfate, filtered, and concentrated. The residue was purified by column chromatography on silica gel (elution with gradient methylene chloride/ethyl acetate) to afford 69.7 mg (47%) of the 9-[(3-chlorophenyl)methyl]-4-hydroxy-5-carbamoyl carbazole as a white solid. ¹H NMR (DMSO-d6) δ10.5 (s, 1H), 8.8 (br s, 1H), 8.4 (br s, 1H), 7.8 (dd, 1H, J=1 and 8 Hz), 7.45 (m, 2H), 7.3 (m, 3H), 7.2 (s, 1H), 7.1 (d, 1H, J=8 Hz), 6.95 (s, 1H), 6.6 (d, 1H, J=8 Hz), and 5.7 (s, 2H). IR (CHCl₃, cm⁻¹) 3433, 3202 (br), 1630, 1600, 1580, 1564, 1433, 1330, 1261, and 776. MS (ES) m/e 349, 351, 353.

Elemental Analyses for $C_{20}H_{15}N_2O_2Cl$: Calculated: C, 68.48; H, 4.31; N, 7.99. Found: C, 68.64; H, 4.55; N, 7.93.

D. {9-[(3-Chlorophenyl)methyl]-5-carbamoylcarbazol-4-yl}oxyacetic acid, tert-butyl ester 40% Methanolic Triton B (0.053 mL, 0.12 mM) was added to a solution of the 9-[(3-chlorophenyl)methyl]-4-hydroxy-5-carbamoyl carbazole (33.2 mg, 0.12 mM) in 2 mL DMF at room temperature. After 3 minutes, t-butyl bromoacetate (53.8 mg, 0.27 mM) was added and the resultant mixture stirred at room temperature for 20 h. The mixture was diluted with ethyl acetate, washed four times with H₂O, once with saturated brine, dried over magnesium sulfate, filtered, and concentrated. The residue was purified by column chromatography on silica gel (elution with gradient methylene chloride/ethyl acetate) to afford 42.1 mg (95%) of the {9-[(3-chlorophenyl)methyl]-5-carbamoylcarbazol-4-yl}oxyacetic acid, tert-butyl ester as a white solid. 1H NMR (DMSO-d6) δ7.6 (d, 1H, J=8 Hz), 7.5–6.8 (m, 10H), 6.55 (d, 1H, J=8 Hz), 5.7 (s, 2H), 4.8 (s, 2H), and 1.45 (s, 9H). IR (CDCl₃, cm⁻¹) 3450, 3400, 1744, 1676, 1591, 1457, 1369, and 1150. MS (FD) m/e 464, 466.

Elemental Analyses for $C_{26}H_{25}N_2O_4Cl$: Calculated: C, 67.17; H, 5.42; N, 6.03. Found: C, 67.17; H, 5.65; N, 5.97.

E. {9-[(3-Chlorophenyl)methyl]-5-carbamoylcarbazol-4-yl}oxyacetic acid

A solution of the {9-[(3-chlorophenyl)methyl]-5-carbamoylcarbazol-4-yl}oxyacetic acid, tert-butyl ester (35.6 mg, 0.077 mM) in 2 mL of trifluoroacetic acid was stirred at room temperature for 6 hours. The solvent was removed in vacuo. The residue was triturated with ethyl acetate, then dried in vacuo to afford 31.4 mg (100%) of the {9-[(3-chlorophenyl)methyl]-5-carbamoylcarbazol-4-yl}oxyacetic acid as a white powder. ¹H NMR (DMSO-d6) δ13.0 (br s, 1H), 7.75 (s, 1H), 7.6 (d, 1H, J=8 Hz), 7.4–7.25 (m, 7H), 7.2 (d, 1H, J=8 Hz), 7.0 (br t, 1H), 6.6 (d, 1H, J=8 Hz), 5.7 (s, 2H), and 4.8 (s, 2H). IR (KBr, cm⁻¹) 3456, 3416, 3335, 1735, 1638, 1617, 1580, 1499, 1452, 1431, 1431, 1329, 1255, 1157, 772, 764, and 717. MS (ES) m/e 407, 409, 411.

Elemental Analyses for $C_{22}H_{17}N_2O_4Cl$: Calculated: C, 64.63; H, 4.19; N, 6.85. Found: C, 64.55; H, 4.12; N, 6.74.

EXAMPLE 27

Preparation of {9-[(3-phenoxyphenyl)methyl]-5-carbamoylcarbazol-4-yl}oxyacetic acid

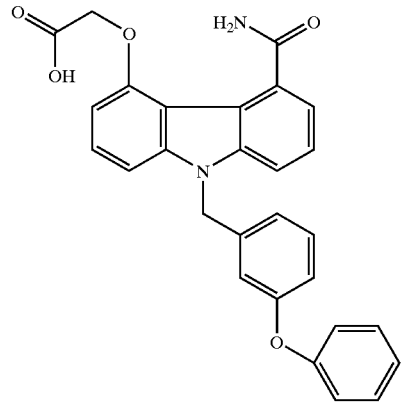

A. 9-[(3-Phenoxyphenyl)methyl]-5-carbomethoxy-1,2-dihydrocarbazol-4(3H)-one

40% Methanolic Triton B (1.53 mL, 3.4 mM) was slowly added dropwise to a solution of 5-carbomethoxy-1,2-dihydro-9H-carbazol-4(3H)-one (554.6 mg, 2.28 mM) in 5 mL of DMF at 25° C. After 5 minutes, 3-phenoxybenzyl chloride (748.0 mg, 3.42 mM) was added and the resultant mixture stirred at room temperature for 24 hours. The mixture was diluted with ethyl acetate, washed three times with 1N HCl, three times with H₂O, once with saturated brine, dried over anhydrous magnesium sulfate, filtered, and concentrated. The residue was purified by column chromatography on silica gel (elution with gradient methylene chloride/ethyl acetate) to afford 563.6 mg (58%) of 9-[(3-phenoxyphenyl)methyl]-5-carbomethoxy-1,2-dihydrocarbazol-4(3H)-one as a thick yellow oil. ¹H NMR (DMSO-d6) δ7.7 (dd, 1H, J=1 and 8 Hz), 7.4–7.2 (m, 6H), 7.1 (t, 1H, J=8 Hz), 6.95 (m, 2H), 6.8–6.7 (m, 2H), 5.55 (s, 2H), 3.75 (s, 3H), 3.0 (t, 2H, J=6 Hz), 2.45 (t, 2H, J=6 Hz), and 2.1 (m, 2H). IR (CDCl₃, cm⁻¹) 3050, 2950, 1725, 1653, 1585, 1487, 1465, 1288, 1252, and 1119. MS (ES) m/e 426.

Elemental Analyses for $C_{27}H_{23}NO_4$: Calculated: C, 76.22; H, 5.45; N, 3.29. Found: C, 76.21; H, 5.35; N, 3.36.

B. 9-[(3-Phenoxyphenyl)methyl]-4-hydroxy-5-carbomethoxy carbazole

A solution of the 9-[(3-phenoxyphenyl)methyl]-5-carbomethoxy-1,2-dihydrocarbazol-4(3H)-one (544.5 mg, 1.28 mM) and 2,3-dichloro-5,6-dicyano-1,4-benzoquinone (337.5 mg, 1.48 mM) in 20 mL of toluene was stirred between 70–80° C. for 4 hours. The mixture was purified directly by column chromatography on silica gel (elution with methylene chloride) to afford 107.0 mg (20%) of 9-[(3-phenoxyphenyl)methyl]-4-hydroxy-5-carbomethyoxy carbazole as a yellow powder. ¹H NMR (DMSO-d6) δ10.4 (s, 1H), 7.7 (d, 1H, J=8 Hz), 7.4–6.7 (m, 13H), 6.55 (d, 1H, J=8 Hz), 5.65 (s, 2H), and 3.85 (s, 3H). IR (CDCl₃, cm⁻¹) 3200 (br), 1687, 1597, 1584, 1487, 1441, 1332, 1284, 1267, and 1252. MS (ES) m/e 422, 424.

Elemental Analyses for $C_{27}H_{21}NO_4$: Calculated: C, 76.58; H, 5.00; N, 3.31. Found: C, 76.68; H, 5.20; N, 3.40.

c) 9-[(3-Phenoxyphenyl)methyl]-4-hydroxy-5-carbamoyl carbazole

A solution of the 9-[(3-phenoxyphenyl)methyl]-4-hydroxy-5-carbomethoxy carbazole (100.0 mg, 0.24 mM) in 5 mL THF and 20 mL concentrated aqueous ammonium hydroxide was sonicated for 24 hours at 40–50° C. The mixture was diluted with ethyl acetate and acidified to pH 1 with 5 N HCl. The aqueous layer was extracted twice with ethyl acetate. The combined organic extracts were washed with saturated brine, dried over magnesium sulfate, filtered, and concentrated. The residue was purified by column chromatography on silica gel (elution with gradient methylene chloride/ethyl acetate) to afford 41.0 mg (43%) of the 9-[(3-phenoxyphenyl)methyl]-4-hydroxy-5-carbamoyl carbazole as a white solid. $^1$H NMR (DMSO-d6) δ10.5 (s, 1H), 8.8 (br s, 1H), 8.4 (br s, 1H), 7.8 (dd, 1H, J=1 and 8 Hz), 7.5–6.7 (m, 13H), 6.6 (d, 1H, J=8 Hz), and 5.7 (s, 2H). MS (ES) m/e 407, 409.

Elemental Analyses for $C_{26}H_{20}N_2O_3$: Calculated: C, 76.46; H, 4.94; N, 6.86. Found: C, 75.66; H, 5.29; N, 6.58.

D. {9-[(3-Phenoxyphenyl)methyl]-5-carbamoylcarbazol-4-yl}oxyacetic acid, tert-butyl ester 40% Methanolic Triton B (0.054 mL, 0.12 mM) was added to a solution of the 9-[(3-phenoxyphenyl)methyl]-4-hydroxy-5-carbamoyl carbazole (39.5 mg, 0.10 mM) in 3 mL DMF at room temperature. After 3 minutes, t-butyl bromoacetate (54.8 mg, 0.27 mM) was added and the resultant mixture stirred at room temperature for 5 hours. The mixture was diluted with ethyl acetate, washed four times with H$_2$O, once with saturated brine, dried over magnesium sulfate, filtered, and concentrated. The residue was purified by column chromatography on silica gel (elution with gradient methylene chloride/ethyl acetate) to afford 33.0 mg (65%) of the {9-[(3-phenoxyphenyl)methyl]-5-carbamoylcarbazol-4-yl}oxyacetic acid, tert-butyl ester as a white solid. $^1$H NMR (DMSO-d6) δ7.6 (d, 1H, J=8 Hz), 7.5–6.8 (m, 15H), 6.55 (d, 1H, J=8 Hz), 5.7 (s, 2H), 4.8 (s, 2H), and 1.45 (s, 9H). IR (KBr, cm$^{-1}$) 3450, 1748, 1670, 1582, 1486, 1246, 1225, and 1151. MS (ES) m/e 523.

Elemental Analyses for $C_{32}H_{30}N_2O_5$: Calculated: C, 73.55; H, 5.79; N, 5.36. Found: C, 73.84; H, 5.83; N, 5.30.

E. {9-[(3-Phenoxyphenyl)methyl]-5-carbamoylcarbazol-4-yl}oxyacetic acid

A solution of the {9-[(3-phenoxyphenyl)methyl]-5-carbamoylcarbazol-4-yl}oxyacetic acid, tert-butyl ester (30.0 mg, 0.063 mM) in 2 mL of trifluoroacetic acid was stirred at room temperature for 6 hours. The solvent was removed in vacuo. The residue was dried in vacuo to afford 30.0 mg (100%) of the {9-[(3-phenoxyphenyl)methyl]-5-carbamoylcarbazol-4-yl}oxyacetic acid as a white powder. $^1$H NMR (DMSO-d6) δ13.0 (br s, 1H), 7.75 (s, 1H), 7.6 (d, 1H, J=8 Hz), 7.5–6.8 (m, 14H), 6.6 (d, 1H, J=8 Hz), 5.7 (s, 2H), and 4.8 (s, 2H). IR (KBr, cm$^{-1}$) 3450, 3400, 1740, 1651, 1592, 1585, 1487, 1457, 1441, 1329, 1250, and 1158. MS (ES) m/e 465, 467.

Elemental Analyses for $C_{28}H_{22}N_2O_5$: Calculated: C, 72.09; H, 4.75; N, 6.00. Found: C, 67.65; H, 4.64; N, 6.02.

EXAMPLE 28

Preparation of {9-[(2-Fluorophenyl)methyl]-5-carbamoylcarbazol-4-yl}oxyacetic acid

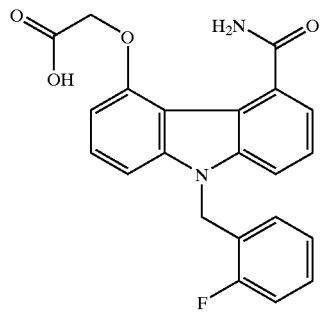

A. 9-[(2-Fluorophenyl)methyl]-5-carbomethoxy-1,2-dihydrocarbazol-4(3H)-one

40% Methanolic Triton B (2.82 mL, 6.2 mM) was slowly added dropwise to a solution of 5-carbomethoxy-1,2-dihydro-9H-carbazol-4(3H)-one (1.27 g, 5.22 mM) in 10 mL of DMF at 25° C. After 5 minutes, 2-fluorobenzyl bromide (1.19 g, 6.2 mM) was added and the resultant mixture stirred at room temperature for 17 days. The mixture was diluted with ethyl acetate, washed five times with H$_2$O, once with saturated brine, dried over anhydrous magnesium sulfate, filtered, and concentrated. The residue was purified by column chromatography on silica gel (elution with gradient methylene chloride/ethyl acetate) to afford 1.00 g (55%) of the 9-[(2-fluorophenyl)methyl]-5-carbomethoxy-1,2-dihydrocarbazol-4(3H)-one as a tan foam. $^1$H NMR (DMSO-d6) δ7.7 (dd, 1H, J=1 and 8 Hz), 7.4–7.2 (m, 4H), 7.1 (t, 1H, J=8 Hz), 6.7 (t, 1H, J=8 Hz), 5.65 (s, 2H), 3.8 (s, 3H), 3.0 (t, 2H, J=6 Hz), 2.45 (t, 2H, J=6 Hz), and 2.1 (m, 2H). IR (CDCl$_3$, cm$^{-1}$) 3050, 2950, 1725, 1652, 1464, 1441, 1288 and 1120. MS (ES) m/e 350, 352.

Elemental Analyses for $C_{21}H_{18}NO_3F$: Calculated: C, 71.78; H, 5.16; N, 3.99. Found: C, 71.51; H, 5.08; N, 3.85.

B. 9-[(2-Fluorophenyl)methyl]-4-hydroxy-5-carbomethoxy carbazole

A solution of the 9-[(2-fluorophenyl)methyl]-5-carbomethoxy-1,2-dihydrocarbazol-4(3H)-one (1.00 g, 2.85 mM) and 2,3-dichloro-5,6-dicyano-1,4-benzoquinone (800.0 mg, 3.51 mM) in 50 mL of toluene was stirred between 70–80° C. for 6 h. The mixture was purified directly by column chromatography on silica gel (elution with methylene chloride) to afford 250.0 mg (25%) of the 9-[(2-fluorophenyl)methyl]-4-hydroxy-5-carbomethyoxy carbazole as a dark solid. $^1$H NMR (DMSO-d6) δ10.2 (s, 1H), 7.7 (d, 1H, J=8 Hz), 7.4 (t, 1H, J=8 Hz), 7.3–6.85 (m, 6H), 6.75 (dt, 1H, J=0.5 and 8 Hz), 6.6 (d, 1H, J=8 Hz), 5.7 (s, 2H), and 3.85 (s, 3H). IR (CHCl$_3$, cm$^{-1}$) 3200 (br), 1686, 1598, 1490, 1442, 1285, 1268, 1230, and 1139. MS (ES) m/e 348, 350.

Elemental Analyses for $C_{21}H_{16}NO_3F$: Calculated: C, 72.20; H, 4.62; N, 4.01. Found: C, 71.32; H, 4.75; N, 4.11.

C. 9-[(2-Fluorophenyl)methyl]-4-hydroxy-5-carbamoyl carbazole

A solution of the 9-[(2-fluorophenyl)methyl]-4-hydroxy-5-carbomethoxy carbazole (237.5 mg, 0.68 mM) in 10 mL THF and 40 mL concentrated aqueous ammonium hydroxide was sonicated for 20 h at 40–50° C. The mixture was diluted with ethyl acetate and acidified to pH 1 with 5 N HCl. The aqueous layer was extracted twice with ethyl acetate. The combined organic extracts were washed with saturated brine, dried over magnesium sulfate, filtered, and concentrated. The residue was purified by column chromatography on silica gel (elution with gradient methylene chloride/ethyl acetate) to afford 89.7 mg (40%) of the 9-[(2-fluorophenyl)methyl]-4-hydroxy-5-carbamoyl carbazole as a white solid. $^1$H NMR (DMSO-d6) δ10.5 (s, 1H), 8.8 (br s, 1H), 8.4 (br s, 1H), 7.8 (dd, 1H, J=1 and 8 Hz), 7.5–6.9 (m, 7H), 6.65 (m, 2H), and 5.75 (s, 2H). IR (KBr, cm$^{-1}$) 3395, 3192 (br), 1621, 1599, 1580, 1564, 1491, 1455, 1334, 1261, and 774. MS (ES) m/e 333, 335.

Elemental Analyses for $C_{20}H_{15}N_2O_2F$: Calculated: C, 71.85; H, 4.52; N, 8.38. Found: C, 72.57; H, 4.88; N, 7.84.

D. {9-[(2-Fluorophenyl)methyl]-5-carbamoylcarbazol-4-yl}oxyacetic acid, methyl ester 40% Methanolic Triton B (0.14 mL, 0.31 mM) was added to a solution of the 9-[(2-fluorophenyl)methyl]-4-hydroxy-5-carbamoyl carbazole (51.9 mg, 0.155 mM) in 5 mL DMF at room temperature. After 3 minutes, methyl bromoacetate (110.5 mg, 0.72 mM) was added and the resultant mixture stirred at room temperature for 20 hours. The mixture was diluted with ethyl acetate, washed four times with $H_2O$, once with saturated brine, dried over magnesium sulfate, filtered, and concentrated. The residue was purified by column chromatography on silica gel (elution with gradient methylene chloride/ethyl acetate) to afford 72.8 mg (71%) of the {9-[(2-fluorophenyl)methyl]-5-carbamoylcarbazol-4-yl}oxyacetic acid, methyl ester as a white solid. $^1$H NMR (DMSO-d6) δ7.65 (d, 1H, J=8 Hz), 7.5 (s, 1H), 7.4–7.2 (m, 5H), 7.15 (s, 1H), 7.1 (d, 1H, J=8 Hz), 7.05 (t, 1H, J=8 Hz), 6.7 (t, 1H, J=8 Hz), 6.55 (d, 1H, J=8 Hz), 5.7 (s, 2H), 4.85 (s, 2H), and 3.7 (s, 3H). IR (CHCl$_3$, cm$^{-1}$) 3436, 1763, 1675, 1457, 1327, 1208, 1198, 1150, 1102, 772, 756, and 719. MS (FD) m/e 407.

Elemental Analyses for $C_{23}H_{19}N_2O_4F$: Calculated: C, 67.97; H, 4.71; N, 6.89. Found: C, 68.00; H, 4.92; N, 6.75.

E. {9-[(2-Fluorophenyl)methyl]-5-carbamoylcarbazol-4-yl}oxyacetic acid

A solution of the {9-[(2-fluorophenyl)methyl]-5-carbamoylcarbazol-4-yl}oxyacetic acid, methyl ester (47.9 mg, 0.118 mM) and 0.28 mL (0.28 mM) of 1 N NaOH in 10 mL of methanol was sonicated for 6 hours at 50–60° C., then stirred at room temperature for 16 hours. The mixture was diluted with ethyl acetate and acidified to pH 1 with 5 N HCl. The aqueous layer was extracted twice with ethyl acetate. The combined organic extracts were washed with saturated brine, dried over magnesium sulfate, filtered, and concentrated to afford 42.8 mg (92%) of the {9-[(2-fluorophenyl)methyl]-5-carbamoylcarbazol-4-yl}oxyacetic acid as a white powder. $^1$H NMR (DMSO-d6) δ7.75 (s, 1H), 7.6 (d, 1H, J=8 Hz), 7.5–7.25 (m, 6H), 7.15 (d, 1H, J=8 Hz), 7.05 (dt, 1H, J=1 and 8 Hz), 6.75 (dt, 1H, J=1 and 8 Hz), 6.65 (d, 1H, J=8 Hz), 5.7 (s, 2H), and 4.8 (s, 2H). IR (KBr, cm$^{-1}$) 3428, 3400, 1737, 1635, 1617, 1583, 1572, 1500, 1491, 1453, 1434, 1330, 1248, 1158, 1098, 760, and 714. MS (FD) m/e 392.

Elemental Analyses for $C_{22}H_{17}N_2O_4F$: Calculated: C, 67.34; H, 4.37; N, 7.14. Found: C, 66.65; H, 4.55; N, 6.92.

EXAMPLE 29

Preparation of {9-[(2-trifluoromethylphenyl)methyl]-5-carbamoylcarbazol-4-yl}oxyacetic acid

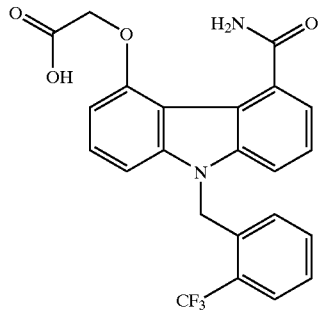

A. 9-[(2-Trifluoromethylphenyl)methyl]-5-carbomethoxy-1,2-dihydrocarbazol-4(3H)-one 40% Methanolic Triton B (2.18 mL, 4.8 mM) was slowly added dropwise to a solution of 5-carbomethoxy-1,2-dihydro-9H-carbazol-4(3H)-one (973 mg, 4.0 mM) in 10 mL of DMF at –10° C. After 30 minutes, 2-(trifluoromethyl)benzyl bromide (1.3 g, 5.2 mM) was added and the resultant mixture stirred at room temperature for 23 hours. The mixture was diluted with ethyl acetate, washed five times with $H_2O$, once with saturated brine, dried over anhydrous magnesium sulfate, filtered, concentrated, and dried in vacuo to afford 1.34 g (83%) of the 9-[(2-trifluoromethylphenyl)methyl]-5-carbomethoxy-1,2-dihydrocarbazol-4(3H)-one as a tan solid. $^1$H NMR (CDCl$_3$) δ7.7 (d, 1H, J=8 Hz), 7.4–7.1 (m, 5H), 6.4 (d, 1H, J=8 Hz), 5.5 (s, 2H), 4.05 (s, 3H), 2.8 (t, 2H, J=6 Hz), 2.6 (t, 2H, J=6 Hz), and 2.2 (m, 2H). IR (KBr, cm$^{-1}$) 1729 and 1656. MS (ES) m/e 402.

Elemental Analyses for $C_{22}H_{18}NO_3F_3$: Calculated: C, 65.83; H, 4.52; N, 3.49; F, 14.20. Found: C, 66.07; H, 4.59; N, 3.20; F, 13.95.

B. 9-[(2-Trifluoromethylphenyl)methyl]-4-hydroxy-5-carbomethoxy carbazole

A solution of the 9-[(2-trifluoromethylphenyl)methyl]-5-carbomethoxy-1,2-dihydrocarbazol-4(3H)-one (1.21 g, 3.00 mM) and 2,3-dichloro-5,6-dicyano-1,4-benzoquinone (764 mg, 3.3 mM) in 25 mL of toluene was stirred between 80–90° C. for 7 h. The mixture was purified directly by column chromatography on silica gel (elution with methylene chloride) to afford 340.0 mg (28%) of the 9-[(2-trifluoromethylphenyl)methyl]-4-hydroxy-5-carbomethyoxy carbazole as a brown powder. $^1$H NMR (CDCl$_3$) δ10.4 (s, 1H), 8.0 (d, 1H, J=8 Hz), 7.7 (d, 1H, J=8 Hz), 7.5–7.2 (m, 5H), 6.85 (m, 2H), 6.45 (d, 1H, J=8 Hz), 5.7 (s, 2H), and 4.1 (s, 3H). IR (CDCl$_3$, cm$^{-1}$) 3200 (br) and 1677. MS (ES) m/e 398, 400.

Elemental Analyses for $C_{22}H_{16}NO_3F_3$: Calculated: C, 66.17; H, 4.04; N, 3.51; F, 14.27. Found: C, 66.93; H, 4.06; N, 3.54; F, 14.00.

C. 9-[(2-Trifluoromethylphenyl)methyl]-4-hydroxy-5-carbamoyl carbazole

A solution of the 9-[(2-trifluoromethylphenyl)methyl]-4-hydroxy-5-carbomethoxy carbazole (310 mg, 0.77 mM) in 5 mL THF and 20 mL concentrated aqueous ammonium hydroxide was sonicated for 25 hours at 40–50° C. The mixture was diluted with ethyl acetate and acidified to pH 1 with 5 N HCl. The aqueous layer was extracted twice with ethyl acetate. The combined organic extracts were washed with saturated brine, dried over magnesium sulfate, filtered, and concentrated. The residue was purified by column chromatography on silica gel (elution with gradient methylene chloride/ethyl acetate) to afford 145 mg (49%) of the 9-[(2-trifluoromethylphenyl)methyl]-4-hydroxy-5-carbamoyl carbazole as a white solid. $^1$H NMR (DMSO-d6) δ10.5 (s, 1H), 8.8 (br s, 1H), 8.4 (br s, 1H), 7.8 (d, 1H, J=8 Hz), 7.6–7.2 (m, 6H), 6.85 (d, 1H, J=8 Hz), 6.6 (d, 1H, J=8 Hz), 6.25 (d, 1H, J=8 Hz), and 5.8 (s, 2H). IR (KBr, cm$^{-1}$) 3460, 3360, and 1589. MS (ES) m/e 383, 385.

Elemental Analyses for $C_{21}H_{15}N_2O_2F_3$: Calculated: C, 65.62; H, 3.93; N, 7.29; F, 14.83. Found: C, 65.65; H, 3.94; N, 7.51; F, 14.94.

D. {9-[(2-Trifluoromethylphenyl)methyl]-5-carbamoylcarbazol-4-yl}oxyacetic acid, methyl ester 40% Methanolic Triton B (0.18 mL, 0.4 mM) was added to a solution of the 9-[(2-trifluoromethylphenyl)methyl]-4-hydroxy-5-carbamoyl carbazole (120 mg, 0.31 mM) in 5 mL DMF at room temperature. After 15 minutes, methyl bromoacetate (98.5 mg, 0.62 mM) was added and the resultant mixture stirred at room temperature for 4.5 hours. The mixture was diluted with ethyl acetate, washed four times with $H_2O$, 1 N HCl, $H_2O$, sat. $NaHCO_3$, and saturated brine, dried over magnesium sulfate, filtered, and concentrated. The residue was purified by column chromatography on silica gel (elution with gradient methylene chloride/ethyl acetate/THF) to afford 95 mg (67%) of the {9-[(2-trifluoromethylphenyl)methyl]-5-carbamoylcarbazol-4-yl}oxyacetic acid, methyl ester as a white solid. $^1$H NMR (CDCl$_3$) δ7.7 (d, 1H, J=8 Hz), 7.5–7.2 (m, 6H), 6.95 (d, 1H, J=8 Hz), 6.6 (d, 1H, J=8 Hz), 6.45 (d, 1H, J=8 Hz), 6.3 (br s, 1H), 6.1 (br s, 1H), 5.7 (s, 2H), 4.9 (s, 2H), and 3.9 (s, 3H). IR (CHCl$_3$, cm$^{-1}$) 1763 and 1674. MS (ES) m/e 457.

Elemental Analyses for $C_{24}H_{19}N_2O_4F_3$: Calculated: C, 63.16; H, 4.20; N, 6.14. Found: C, 61.82; H, 4.31; N, 5.86.

E. {9-[(2-Trifluoromethylphenyl)methyl]-5-carbamoylcarbazol-4-yl}oxyacetic acid

A solution of the {9-[(2-trifluoromethylphenyl)methyl]-5-carbamoylcarbazol-4-yl}oxyacetic acid, methyl ester (70 mg, 0.153 mM) and 0.21 mL (0.21 mM) of 1 N NaOH in 5 mL of methanol was sonicated for 23 hours at 50–60° C. The methanol was removed in vacuo and the mixture acidified to pH 1.6 with 1 N HCl. The resultant white precipitate was collected by filtration, washed with $H_2O$, small amounts of MeOH and diethyl ether, then dried in vacuo to afford 59 mg (88%) of the {9-[(2-trifluoromethylphenyl)methyl]-5-carbamoylcarbazol-4-yl}oxyacetic acid as a white powder. $^1$H NMR (DMSO-d6) δ13.0 (br s, 1H), 7.8 (d, 1H, J=8 Hz), 7.75 (s, 1H), 7.5–7.3 (m, 6H), 7.1 (d, 1H, J=8 Hz), 7.05 (d, 1H, J=8 Hz), 6.6 (d, 1H, J=8 Hz), 6.3 (d, 1H, J=8 Hz), 5.8 (s, 2H), and 4.8 (s, 2H). IR (KBr, cm$^{-1}$) 1737 and 1635. MS (ES) m/e 441, 443.

Elemental Analyses for $C_{23}H_{17}N_2O_4F_3$: Calculated: C, 62.45; H, 3.87; N, 6.33; F, 12.88. Found: C, 60.86; H, 3.89; N, 6.08; F, 12.59.

EXAMPLE 30

Preparation of {9-[(2-benzylphenyl)methyl]-5-carbamoylcarbazol-4-yl}oxyacetic acid, sodium salt

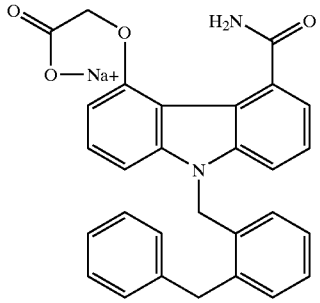

A. 2-Benzylbenzyl bromide

A solution of phosphorus tribromide (2.1 mL, 6.0 g, 22.1 mM) in 30 mL of carbon tetrachloride was slowly added dropwise to solution of 2-benzylbenzyl alcohol (1.98 g, 10 mM) in 70 mL of carbon tetrachloride at 0° C. The mixture was stirred at 0° C. for 2 hours, then at room temperature for 2 hours. The solvent was removed in vacuo and the residue diluted with ethyl acetate and saturated aqueous sodium bicarbonate. The organic layer was washed with brine, dried over magnesium sulfate, filtered, and concentrated to afford 2.6 g (99%) of 2-benzylbenzyl bromide as a yellow solid. $^1$H NMR (DMSO-d6) δ7.5–7.0 (m, 9H), 4.7 (s, 2H), and 4.15 (s, 2H). IR (CDCl$_3$, cm$^{-1}$) 3065, 1601, 1495, and 1453. MS (FD) m/e 260, 262.

Elemental Analyses for $C_{14}H_{13}Br$: Calculated: C, 64.37; H, 4.98; N, 0.00. Found: C, 65.26; H, 5.26; N, 0.00.

B. 9-[(2-Benzylphenyl)methyl]-5-carbomethoxy-1,2-dihydrocarbazol-4(3H)-one

40% Methanolic Triton B (0.95 mL, 2.1 mM) was slowly added dropwise to a solution of 5-carbomethoxy-1,2-dihydro-9H-carbazol-4(3H)-one (510 mg, 2.1 mM) in 30 mL of DMF at −10° C. After 3 minutes, 2-benzylbenzyl bromide (548 mg, 2.1 mM) was added and the resultant mixture stirred at room temperature for 6 hours. The mixture was diluted with ethyl acetate and 1 N HCl, washed twice with $H_2O$, once with saturated brine, dried over anhydrous magnesium sulfate, filtered, concentrated, and dried in vacuo. The reside was purified by column chromatography on silica gel (elution with ethyl acetate) to afford 324 mg (36%) of the 9-[(2-benzylphenyl)methyl]-5-carbomethoxy-1,2-dihydrocarbazol-4(3H)-one as a tan solid. $^1$H NMR (CDCl$_3$) δ7.45–7.0 (m, 10H), 6.9 (d, 1H, J=8 Hz), 6.3 (d, 1H, J=8 Hz), 5.2 (s, 2H), 4.15 (s, 2H), 4.05 (s, 3H), 2.5 (m, 4H), and 2.1 (m, 2H). IR (KBr, cm$^{-1}$) 1726, 1653, 1466, 1443, 1411, 1283, 1200, 1119, and 749. MS (ES) m/e 422, 424.

Elemental Analyses for $C_{28}H_{25}NO_3$: Calculated: C, 79.43; H, 5.91; N, 3.31. Found: C, 79.58; H, 5.94; N, 3.32.

C. 9-[(2-Benzylphenyl)methyl]-4-hydroxy-5-carbomethoxy carbazole

A solution of the 9-[(2-benzylphenyl)methyl]-5-carbomethoxy-1,2-dihydrocarbazol-4(3H)-one (480 mg, 1.14 mM) and 2,3-dichloro-5,6-dicyano-1,4-benzoquinone (250 mg, 5.0 mM) in 30 mL of toluene was stirred between 80–90° C. for 5 hours. The mixture was purified directly by column chromatography on silica gel (elution with methylene chloride/ethyl acetate) to afford 166 mg (35%) of the 9-[(2-benzylphenyl)methyl]-4-hydroxy-5-carbomethyoxy carbazole as a yellow solid. $^1$H NMR (CDCl$_3$) δ10.4 (s, 1H), 8.0 (d, 1H, J=8 Hz), 7.4–7.0 (m, 11H), 6.8 (d, 1H, J=8 Hz), 6.6 (d, 1H, J=8 Hz), 6.4 (d, 1H, J=8 Hz), 5.4 (s, 2H), 4.25 (s, 2H), and 4.1 (s, 3H). IR (CDCl₃, cm⁻¹) 1684, 1597, 1495, 1452, 1442, 1333, 1284, 1269, and 1140. MS (ES) m/e 420, 422.

D. 9-[(2-Benzylphenyl)methyl]-4-hydroxy-5-carbamoyl carbazole

A solution of the 9-[(2-benzylphenyl)methyl]-4-hydroxy-5-carbomethoxy carbazole (166 mg, 0.39 mM) in 8 mL THF and 30 mL concentrated aqueous ammonium hydroxide was sonicated for 30 hours at 40–50° C. The mixture was diluted with ethyl acetate and acidified to pH 1 with 5 N HCl. The aqueous layer was extracted twice with ethyl acetate. The combined organic extracts were washed with saturated brine, dried over magnesium sulfate, filtered, and concentrated. The residue was purified by column chromatography on silica gel (elution with ethyl acetate) to afford 70 mg (44%) of the 9-[(2-benzylphenyl)methyl]-4-hydroxy-5-carbamoyl carbazole as a white solid. ¹H NMR (CDCl₃) δ8.0 (d, 1H, J=8 Hz), 7.4–7.0 (m, 12H), 6.8 (d, 1H, J=8 Hz), 6.6 (d, 1H, J=8 Hz), 6.5 (m, 1H), 6.4 (m, 1H), 5.8 (s, 1H), 5.4 (s, 2H), and 4.2 (s, 2H). MS (ES) m/e 405, 407.

E. {9-[(2-Benzylphenyl)methyl]-5-carbamoylcarbazol-4-yl}oxyacetic acid, methyl ester 40% Methanolic Triton B (0.12 mL, 0.26 mM) was added to a solution of the 9-[(2-benzylphenyl)methyl]-4-hydroxy-5-carbamoyl carbazole (70 mg, 0.17 mM) in 10 mL DMF at 25° C. After 3 minutes, methyl bromoacetate (55 mg, 0.34 mM) was added and the resultant mixture stirred at room temperature for 25 hours. The mixture was diluted with ethyl acetate, washed with 1 N HCl, H₂O, and saturated brine, dried over magnesium sulfate, filtered, and concentrated. The residue was purified by column chromatography on silica gel (elution with ethyl acetate) to afford 60 mg (73%) of the {9-[(2-benzylphenyl)methyl]-5-carbamoylcarbazol-4-yl}oxyacetic acid, methyl ester as a white solid. ¹H NMR (CDCl₃) δ7.4–7.00 (m, 14H), 6.65 (d, 1H, J=8 Hz), 6.55 (d, 1H, J=8 Hz), 6.4 (d, 1H, J=8 Hz), 5.4 (s, 2H), 4.95 (s, 2H), 4.2 (s, 2H), and 3.80 (s, 3H). IR (KBr, cm⁻¹) 3414, 3186, 1759, 1625, 1583, 1500, 1452, 1424, 1340, 1325, 1213, 1199, and 1108. MS (ES) m/e 477, 479.

Elemental Analyses for C₃₀H₂₆N₂O₄: Calculated: C, 75.31; H, 5.44; N, 5.86. Found: C, 75.08; H, 5.61; N, 5.70.

F. {9-[(2-Benzylphenyl)methyl]-5-carbamoylcarbazol-4-yl}oxyacetic acid, sodium salt A solution of the {9-[(2-benzylphenyl)methyl]-5-carbamoylcarbazol-4-yl}oxyacetic acid, methyl ester (16.2 mg, 0.034 mM) and 0.034 mL (0.034 mM) of 1 N NaOH in 3 mL of ethanol was stirred for 16 hours at 25° C. The resultant white precipitate was collected by filtration, washed with a small amount of EtOH, then dried in vacuo to afford 7.1 mg (70%) of the {9-[(2-benzylphenyl)methyl]-5-carbamoylcarbazol-4-yl}oxyacetic acid, sodium salt as a white powder. ¹H NMR (DMSO-d6) δ7.5–6.8 (m, 14H), 6.65 (d, 1H, J=8 Hz), 6.55 (d, 1H, J=8 Hz), 6.05 (d, 1H, J=8 Hz), 5.55 (s, 2H), 4.35 (s, 2H), and 4.3 (s, 2H). IR (CDCl₃, cm⁻¹) 1666, 1616, 1495, 1452, and 1422. MS (ES) m/e 463, 465.

Elemental Analyses for C₂₉H₂₃N₂O₄Na: Calculated: C, 71.60; H, 4.73; N, 5.76. Found: C, 64.68; H, 4.79; N, 5.08.

EXAMPLE 31

Preparation of {9-[(3-trifluoromethylphenyl)methyl]-5-carbamoylcarbazol-4-yl}oxyacetic acid, sodium salt

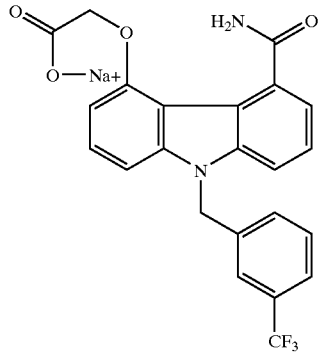

A. 9-[(3-Trifluoromethylphenyl)methyl]-5-carbomethoxy-1,2-dihydrocarbazol-4(3H)-one 40% Methanolic Triton B (2.18 mL, 4.8 mM) was slowly added dropwise to a solution of 5-carbomethoxy-1,2-dihydro-9H-carbazol-4(3H)-one (973 mg, 4.0 mM) in 10 mL of DMF at −10° C. After 30 minutes, 3-(trifluoromethyl) benzyl chloride (1.53 g, 6.0 mM) and sodium iodide (900 mg, 6.0 mM) were added and the resultant mixture stirred at room temperature for 25 hours. The mixture was diluted with ethyl acetate, washed five times with H₂O, 1 N HCl, H₂O, sat NaHCO₃, and saturated brine, dried over anhydrous magnesium sulfate, filtered, concentrated, and dried in vacuo. The residue was purified by column chromatography on silica gel (elution with gradient methylene chloride/ethyl acetate) to afford 1.02 g (63%) of the 9-[(3-trifluoromethylphenyl)methyl]-5-carbomethoxy-1,2-dihydrocarbazol-4(3H)-one as a tan solid. ¹H NMR (CDCl₃) δ7.6 (d, 1H, J=8 Hz), 7.45–7.2 (m, 5H), 7.0 (d, 1H, J=8 Hz), 5.4 (s, 2H), 4.05 (s, 3H), 2.85 (t, 2H, J=6 Hz), 2.6 (t, 2H, J=6 Hz), and 2.2 (m, 2H). IR (KBr, cm⁻¹) 1727 and 1652. MS (ES) m/e 400, 402.

Elemental Analyses for C₂₂H₁₈NO₃F₃: Calculated: C, 65.83; H, 4.52; N, 3.49; F, 14.20. Found: C, 65.63; H, 4.58; N, 3.39; F, 14.14.

B. 9-[(3-Trifluoromethylphenyl)methyl]-4-hydroxy-5-carbomethoxy carbazole

A solution of the 9-[(3-trifluoromethylphenyl)methyl]-5-carbomethoxy-1,2-dihydrocarbazol-4(3H)-one (1.21 g, 3.00 mM) and 2,3-dichloro-5,6-dicyano-1,4-benzoquinone (764 mg, 3.3 mM) in 25 mL of toluene was stirred between 80–90° C. for 7 hours. The mixture was purified directly by column chromatography on silica gel (elution with methylene chloride) to afford 340.0 mg (28%) of the 9-[(3-trifluoromethylphenyl)methyl]-4-hydroxy-5-carbomethyoxy carbazole as a yellow solid. ¹H NMR (CDCl₃) δ10.35 (s, 1H), 8.0 (d, 1H, J=8 Hz), 7.6–7.3 (m, 6H), 7.05 (d, 1H, J=8 Hz), 6.85 (m, 2H), 5.6 (s, 2H), and 4.1 (s, 3H). IR (CHCl₃, cm⁻¹) 3378 and 1712. MS (ES) m/e 398, 400.

Elemental Analyses for C₂₂H₁₆NO₃F₃: Calculated: C, 66.17; H, 4.04; N, 3.51. Found: C, 66.99; H, 4.12; N, 3.53; F.

C. 9-[(3-Trifluoromethylphenyl)methyl]-4-hydroxy-5-carbamoyl carbazole

A solution of the 9-[(3-trifluoromethylphenyl)methyl]-4-hydroxy-5-carbomethoxy carbazole (250 mg, 0.625 mM) in 5 mL THF and 20 mL concentrated aqueous ammonium hydroxide was sonicated for 30 h at 40–50° C. The mixture was diluted with ethyl acetate and acidified to pH 1 with 5 N HCl. The aqueous layer was extracted three times with ethyl acetate. The combined organic extracts were washed with saturated brine, dried over magnesium sulfate, filtered, and concentrated. The residue was purified by column chromatography on silica gel (elution with gradient methylene chloride/ethyl acetate) to afford 120 mg (50%) of the 9-[(3-trifluoromethylphenyl)methyl]-4-hydroxy-5-carbamoyl carbazole as a white solid. $^1$H NMR (DMSO-d6) δ10.5 (s, 1H), 8.8 (br s, 1H), 8.4 (br s, 1H), 7.8 (d, 1H, J=8 Hz), 7.6–7.5 (m, 5H), 7.3 (t, 1H, J=8 Hz), 7.15 (d, 1H, J=8 Hz), 7.1 (d, 1H, J=8 Hz), 6.6 (d, 1H, J=8 Hz), and 5.8 (s, 2H). IR (KBr, cm$^{-1}$) 3429, 3206, and 1630. MS (ES) m/e 383, 385.

Elemental Analyses for $C_{21}H_{15}N_2O_2F_3$: Calculated: C, 65.62; H, 3.93; N, 7.29. Found: C, 67.50; H, 4.00; N, 7.19.

D. {9-[(3-Trifluoromethylphenyl)methyl]-5-carbamoylcarbazol-4-yl}oxyacetic acid, methyl ester 40% Methanolic Triton B (0.18 mL, 0.4 mM) was added to a solution of the 9-[(3-trifluoromethylphenyl)methyl]-4-hydroxy-5-carbamoyl carbazole (115 mg, 0.3 mN) in 5 mL DMF at room temperature. After 15 minutes, methyl bromoacetate (95 mg, 0.6 mM) was added and the resultant mixture stirred at room temperature for 22 hours. The mixture was diluted with ethyl acetate, washed four times with H$_2$O, 1 N HCl, H$_2$O, sat. NaHCO$_3$, and saturated brine, dried over magnesium sulfate, filtered, and concentrated. The residue was purified by column chromatography on silica gel (elution with ethyl acetate) to afford 120 mg (88%) of the {9-[(3-trifluoromethylphenyl)methyl]-5-carbamoylcarbazol-4-yl}oxyacetic acid, methyl ester as a white solid. $^1$H NMR (CDCl$_3$) δ7.5–7.2 (m, 7H), 7.1 (d, 1H, J=8 Hz), 7.0 (d, 1H, J=8 Hz), 6.6 (d, 1H, J=8 Hz), 6.4 (br s, 1H), 6.0 (br s, 1H), 5.55 (s, 2H), 4.9 (s, 2H), and 3.9 (s, 3H). IR (KBr, cm$^{-1}$) 1763 and 1673. MS (ES) m/e 457.

Elemental Analyses for $C_{24}H_{19}N_2O_4F_3$: Calculated: C, 63.16; H, 4.20; N, 6.14. Found: C, 61.37; H, 4.19; N, 5.77.

E. {9-[(3-Trifluoromethylphenyl)methyl]-5-carbamoylcarbazol-4-yl}oxyacetic acid, sodium salt A solution of the {9-[(3-trifluoromethylphenyl)methyl]-5-carbamoylcarbazol-4-yl}oxyacetic acid, methyl ester (91 mg, 0.153 mM) and 0.22 mL (0.22 mM) of 1 N NaOH in 8 mL of ethanol was stirred for 17 h at 25° C. The ethanol was removed in vacuo. The resultant white precipitate was collected by filtration, washed with small amounts of EtOH and diethyl ether, then dried in vacuo to afford 75 mg (81%) of the {9-[(3-trifluoromethylphenyl)methyl]-5-carbamoylcarbazol-4-yl}oxyacetic acid, sodium salt as a white powder. $^1$H NMR (DMSO-d6) δ7.65 (s, 1H), 7.6 (m, 4H), 7.45 (t, 1H, J=8 Hz), 7.35 (t, 1H, J=8 Hz), 7.3 (t, 1H, J=8 Hz), 7.2 (d, 1H, J=8 Hz), 7.1 (d, 1H, J=8 Hz), 7.05 (d, 1H, J=8 Hz), 6.5 (d, 1H, J=8 Hz), 5.75 (s, 2H), and 4.3 (s, 2H). IR (KBr, cm$^{-1}$) 1665 and 1618. MS (ES) m/e 441, 443.

Elemental Analyses for $C_{23}H_{16}N_2O_4F_3Na$: Calculated: C, 59.49; H, 3.47; N, 6.03. Found: C, 60.69; H, 3.78; N, 5.75.

EXAMPLE 32

Preparation of {9-[(1-naphthyl)methyl]-5-carbamoylcarbazol-4-yl}oxyacetic acid, sodium salt

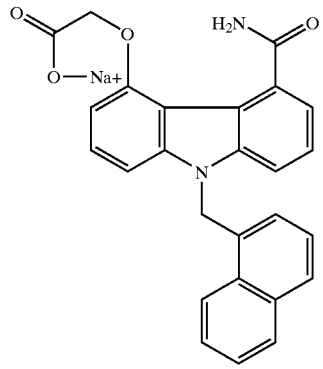

A. 9-[(1-Naphthyl)methyl]-5-carbomethoxy-1,2-dihydrocarbazol-4(3H)-one

40% Methanolic Triton B (1.6 mL, 3.6 mM) was slowly added dropwise to a solution of 5-carbomethoxy-1,2-dihydro-9H-carbazol-4(3H)-one (870 mg, 3.6 mM) in 30 mL of DMF at 25° C. After 5 minutes, 1-chloromethyl naphthylene (642 mg, 3.6 mM) and sodium iodide (450 mg, 3.0 mM) were added and the resultant mixture stirred at room temperature for 25 hours. The mixture was diluted with ethyl acetate, washed five times with H$_2$O, 1 N HCl, H$_2$O, sat NaHCO$_3$, and saturated brine, dried over anhydrous magnesium sulfate, filtered, concentrated, and dried in vacuo. The residue was purified by column chromatography on silica gel (elution with ethyl acetate) to afford 560 mg (41%) of the 9-[(1-naphthyl)methyl]-5-carbomethoxy-1,2-dihydrocarbazol-4(3H)-one as a yellow solid. $^1$H NMR (CDCl$_3$) δ8.0 (d, 1H, J=8 Hz), 7.9 (d, 1H, J=8 Hz), 7.7 (d, 1H, J=8 Hz), 7.6 (t, 1H, J=8 Hz), 7.55 (t, 1H, J=8 Hz), 7.35 (d, 1H, J=8 Hz), 7.15–7.05 (m, 3H), 6.4 (d, 1H, J=8 Hz), 5.8 (s, 2H), 4.05 (s, 3H), 2.8 (t, 2H, J=6 Hz), 2.55 (t, 2H, J=6 Hz), and 2.2 (m, 2H). IR (KBr, cm$^{-1}$) 1721, 1646, 1464, 1448, 1438, 1285, 1122, 796, and 761. MS (ES) m/e 382, 384.

Elemental Analyses for $C_{25}H_{21}NO_3$: Calculated: C, 78.33; H, 5.48; N, 3.66. Found: C, 76.28; H, 5.46; N, 3.93.
B. 9-[(1-Naphthyl)methyl]-4-hydroxy-5-carbomethoxy carbazole A solution of the 9-[(1-naphthyl)methyl]-5-carbomethoxy-1,2-dihydrocarbazol-4(3H)-one (540 mg, 1.4 mM) and 2,3-dichloro-5,6-dicyano-1,4-benzoquinone (304 mg, 1.33 mM) in 30 mL of toluene was stirred between 80–90° C. for 5 hours. The mixture was purified directly by column chromatography on silica gel (elution with ethyl acetate) to afford 240.0 mg (45%) of the 9-[(1-naphthyl)methyl]-4-hydroxy-5-carbomethyoxy carbazole as a yellow solid. $^1$H NMR (DMSO-d6) δ10.25 (s, 1H), 8.35 (d, 1H, J=8 Hz), 8.0 (d, 1H, J=8 Hz), 7.8 (d, 1H, J=8 Hz), 7.6–7.1 (m, 7H), 6.9 (d, 1H, J=8 Hz), 6.6 (d, 1H, J=8 Hz), 6.3 (d, 1H, J=8 Hz), 6.15 (s, 2H), and 3.8 (s, 3H). IR (CHCl$_3$, cm$^{-1}$) 1685, 1598, 1442, 1269, and 1140. MS (ES) m/e 380, 382.

Elemental Analyses for $C_{25}H_{19}NO_3$: Calculated: C, 78.74; H, 4.99; N, 3.67. Found C, 78.67; H, 5.14; N, 3.54.
C. 9-[(1-Naphthyl)methyl]-4-hydroxy-5-carbamoyl carbazole A solution of the 9-[(1-naphthyl)methyl]-4-hydroxy-5-carbomethoxy carbazole (210 mg, 0.55 mM) in 10 mL THF and 30 mL concentrated aqueous ammonium hydroxide was sonicated for 20 hours at 40–50° C. The mixture was diluted with ethyl acetate and acidified to pH 1 with 5 N HCl. The aqueous layer was extracted three times with ethyl acetate. The combined organic extracts were washed with saturated brine, dried over magnesium sulfate, filtered, and concentrated. The residue was purified by column chromatography on silica gel (elution with gradient hexanes/ethyl acetate) to afford 80 mg (40%) of the 9-[(1-naphthyl)methyl]-4-hydroxy-5-carbamoyl carbazole as a white solid. $^1$H NMR (DMSO-d6) δ10.55 (s, 1H), 8.8 (br s, 1H), 8.4 (br s, 1H), 8.35 (d, 1H, J=8 Hz), 7.95 (d, 1H, J=8 Hz), 7.8 (d, 1H, J=8 Hz), 7.65 (m, 4H), 7.45 (m, 2H), 7.25 (t, 1H, J=8 Hz), 7.15 (t, 1H, J=8 Hz), 6.9 (d, 1H, J=8 Hz), 6.6 (d, 1H, J=8 Hz), and 6.2 (s, 2H). MS (ES) m/e 365, 367.

D. {9-[(1-Naphthyl)methyl]-5-carbamoylcarbazol-4-yl}oxyacetic acid, methyl ester 40% Methanolic Triton B (0.2 mL, 0.26 mM) was added to a solution of the 9-[(1-naphthyl)methyl]-4-hydroxy-5-carbamoyl carbazole (80 mg, 0.22 mM) in 7 mL DMF at room temperature. After 15 minutes, methyl bromoacetate (40 mg, 0.3 mM) was added and the resultant mixture stirred at room temperature for 3 hours. The mixture was diluted with ethyl acetate, washed twice with H$_2$O, and once with saturated brine, dried over magnesium sulfate, filtered, and concentrated. The residue was purified by column chromatography on silica gel (elution with ethyl acetate) to afford 81 mg (85%) of the {9-[(1-naphthyl)methyl]-5-carbamoylcarbazol-4-yl}oxyacetic acid, methyl ester as a white solid. $^1$H NMR (CDCl$_3$) δ8.2 (d, 1H, J=8 Hz), 8.05 (d, 1H, J=8 Hz), 7.85–7.0 (m, 11H), 6.65 (d, 1H, J=8 Hz), 6.3 (d, 1H, J=8 Hz), 6.2 (s, 2H), 4.95 (s, 2H), and 3.8 (s, 3H). IR (KBr, cm$^{-1}$) 3364, 1739, 1630, 1582, 1500, 1455, 1285, 1232, 1153, and 774. MS (FD) m/e 438.

Elemental Analyses for C$_{27}$H$_{22}$N$_2$O$_4$: Calculated: C, 73.97; H, 5.02; N, 6.39. Found: C, 71.66; H, 5.14; N, 5.96.

E. {9-[(1-Naphthyl)methyl]-5-carbamoylcarbazol-4-yl}oxyacetic acid, sodium salt

A solution of the {9-[(1-naphthyl)methyl]-5-carbamoylcarbazol-4-yl}oxyacetic acid, methyl ester (21 mg, 0.048 mM) and 0.05 mL (0.05 mM) of 1 N NaOH in 5 mL of ethanol was stirred for 20 hours at 25° C. The resultant white precipitate was collected by filtration, washed with a small amount of EtOH, then dried in vacuo to afford 17 mg (80%) of the {9-[(1-naphthyl)methyl]-5-carbamoylcarbazol-4-yl}oxyacetic acid, sodium salt as a white powder. $^1$H NMR (DMSO-d6) δ8.4 (d, 1H, J=8 Hz), 8.05 (d, 1H, J=8 Hz), 7.8 (d, 1H, J=8 Hz), 7.75–7.2 (m, 8H), 7.1 (d, 1H, J=8 Hz), 6.95 (d, 1H, J=8 Hz), 6.55 (d, 1H, J=8 Hz), 6.3 (d, 1H, J=8 Hz), 6.15 (s, 2H), and 4.4 (s, 2H). IR (KBr, cm$^{-1}$) 1664, 1615, 1595, 1455, 1408, 1324, 1275, and 775. MS (ES) m/e 423, 425.

Elemental Analyses for C$_{26}$H$_{19}$N$_2$O$_4$Na: Calculated: C, 69.96; H, 4.26; N, 6.28. Found: C, 67.91; H, 4.24; N, 5.76.

EXAMPLE 33

Preparation of {9-[(2-cyanophenyl)methyl]-5-carbamoylcarbazol-4-yl}oxyacetic acid, sodium salt

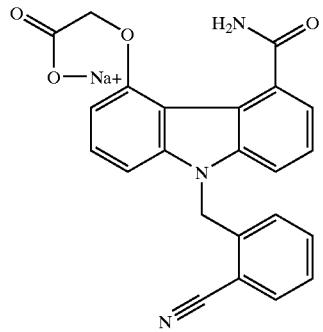

A. 9-[(2-Cyanophenyl)methyl]-5-carbomethoxy-1,2-dihydrocarbazol-4(3H)-one

40% Methanolic Triton B (2.18 mL, 4.8 mM) was slowly added dropwise to a solution of 5-carbomethoxy-1,2-dihydro-9H-carbazol-4(3H)-one (973 mg, 4.0 mM) in 10 mL of DMF at 25° C. After 10 minutes, a-bromo-o-tolunitrile (1.0 g, 5.0 mM) was added and the resultant mixture stirred at room temperature for 30 hours. The mixture was diluted with ethyl acetate, washed five times with H$_2$O, 1 N HCl, H$_2$O, sat NaHCO$_3$, H$_2$O, and saturated brine, dried over anhydrous magnesium sulfate, filtered, concentrated. The residue was triturated with diethyl ether and methylene chloride, then dried in vacuo to afford 1.31 g (91%) of the 9-[(2-cyanophenyl)methyl]-5-carbomethoxy-1,2-dihydrocarbazol-4(3H)-one as a tan solid. $^1$H NMR (CDCl$_3$) δ7.75 (dd, 1H, J=1 and 8 Hz), 7.5–7.2 (m, 5H), 6.6 (d, 1H, J=8 Hz), 5.55 (s, 2H), 4.05 (s, 3H), 2.85 (t, 2H, J=6 Hz), 2.6 (t, 2H, J=6 Hz), and 2.25 (m, 2H). IR (KBr, cm$^{-1}$) 2222, 1711, and 1650. MS (ES) m/e 357, 359.

Elemental Analyses for C$_{22}$H$_{18}$N$_2$O$_3$: Calculated: C, 73.73; H, 5.06; N, 7.82. Found: C, 73.62; H, 5.34; N, 7.59.

B. 9-[(2-Cyanophenyl)methyl]-4-hydroxy-5-carbomethoxy carbazole

A solution of the 9-[(2-cyanophenyl)methyl]-5-carbomethoxy-1,2-dihydrocarbazol-4(3H)-one (1.27 g, 3.5 mM) and 2,3-dichloro-5,6-dicyano-1,4-benzoquinone (892 mg, 3.85 mM) in 25 mL of toluene was stirred at reflux for 7 hours. The mixture was purified directly by column chromatography on silica gel (elution with methylene chloride) to afford 305 mg (24%) of the 9-[(2-cyanophenyl) methyl]-4-hydroxy-5-carbomethyoxy carbazole as a yellow solid. $^1$H NMR (CDCl$_3$) δ10.35 (s, 1H), 8.0 (d, 1H, J=8 Hz), 7.75 (d, 1H, J=8 Hz), 7.5–7.2 (m, 5H), 6.85 (m, 2H), 6.6 (d, 1H, J=8 Hz), 5.75 (s, 2H), and 4.1 (s, 3H). IR (CHCl$_3$, cm$^{-1}$) 3025, 2223, and 1686. MS (ES) m/e 355, 357.

Elemental Analyses for C$_{22}$H$_{16}$N$_2$O$_3$: Calculated: C, 74.15; H, 4.53; N, 7.86. Found: C, 72.99; H, 4.41; N, 7.65.

C. 9-[(2-Cyanophenyl)methyl]-4-hydroxy-5-carbamoyl carbazole

A solution of the 9-[(2-cyanophenyl)methyl]-4-hydroxy-5-carbomethoxy carbazole (295 mg, 0.83 mM) in 5 mL THF and 20 mL concentrated aqueous ammonium hydroxide was sonicated for 22 hours at 40–50° C. The mixture was diluted with ethyl acetate and acidified to pH 1 with 5 N HCl. The aqueous layer was extracted three times with ethyl acetate.

The combined organic extracts were washed with H$_2$O and saturated brine, dried over magnesium sulfate, filtered, and concentrated. The residue was purified by column chromatography on silica gel (elution with gradient hexanes/ethyl acetate) to afford 140 mg (49%) of the 9-[(2-cyanophenyl)methyl]-4-hydroxy-5-carbamoyl carbazole as a tan solid. $^1$H NMR (DMSO-d6) δ10.5 (s, 1H), 8.8 (br s, 1H), 8.4 (br s, 1H), 7.9 (d, 1H, J=8 Hz), 7.75 (d, 1H, J=8 Hz), 7.5–7.4 (m, 4H), 7.25 (t, 1H, J=8 Hz), 7.0 (d, 1H, J=8 Hz), 6.6 (d, 1H, J=8 Hz), 6.4 (m, 1H), and 5.85 (s, 2H). IR (KBr, cm$^{-1}$) 3448, 3356, 2225, 1628, and 1600. MS (ES) m/e 340, 342.

Elemental Analyses for C$_{21}$H$_{15}$N$_3$O$_2$: Calculated: C, 73.89; H, 4.43; N, 12.31. Found: C, 73.39; H, 4.56; N, 13.32.

D. {9-[(2-Cyanophenyl)methyl]-5-carbamoylcarbazol-4-yl}oxyacetic acid, methyl ester 40% Methanolic Triton B (0.24 mL, 0.53 mM) was added to a solution of the 9-[(2-cyanophenyl)methyl]-4-hydroxy-5-carbamoyl carbazole (140 mg, 0.41 mM) in 5 mL DMF at room temperature. After 15 minutes, methyl bromoacetate (130 mg, 0.82 mM) was added and the resultant mixture stirred at room temperature for 24 hours. The mixture was diluted with ethyl acetate, washed four times with H$_2$O, 1 N HCl, H$_2$O, sat. NaHCO$_3$, and saturated brine, dried over magnesium sulfate, filtered, and concentrated. The residue was purified by column chromatography on silica gel (elution with gradient methylene chloride/ethyl acetate/ THF) to afford 116 mg (68%) of the {9-[(2-cyanophenyl)methyl]-5-carbamoylcarbazol-4-yl}oxyacetic acid, methyl ester as a white solid. $^1$H NMR (CDCl$_3$) δ7.75 (d, 1H, J=8 Hz), 7.5–7.2 (m, 6H), 6.95 (d, 1H, J=8 Hz), 6.6 (d, 2H, J=8 Hz),), 6.3 (br s, 1H), 6.1 (br s, 1H), 5.75 (s, 2H), 4.9 (s, 2H), and 3.8 (s, 3H). IR (KBr, cm$^{-1}$) 2228, 1732, and 1675. MS (ES) m/e 412, 414.

Elemental Analyses for C$_{24}$H$_{19}$N$_3$O$_4$: Calculated: C, 69.72; H, 4.63; N, 10.16. Found: C, 70.00; H, 4.69; N, 10.32.

E. {9-[(2-Cyanophenyl)methyl]-5-carbamoylcarbazol-4-yl}oxyacetic acid, sodium salt A suspension of the {9-[(2-cyanophenyl)methyl]-5-carbamoylcarbazol-4-yl}oxyacetic acid, methyl ester (110 mg, 0.266 mM) and 0.29 mL (0.29 mM) of 1 N NaOH in 5 mL of ethanol was sonicated for 2 hours at 25° C. The resultant white precipitate was collected by filtration, washed with small amounts of EtOH, diethyl ether, and hexanes, then dried in vacuo to afford 107 mg (95%) of the {9-[(2-cyanophenyl)methyl]-5-carbamoylcarbazol-4-yl}oxyacetic acid, sodium salt as a white powder. $^1$H NMR (DMSO-d6) δ7.9 (d, 1H, J=8 Hz), 7.6 (br s, 1H), 7.5 (d, 1H, J=8 Hz), 7.45–7.4 (m, 3H), 7.35 (t, 1H, J=8 Hz), 7.25 (t, 1H, J=8 Hz), 7.1 (d, 1H, J=8 Hz), 7.05 (d, 1H, J=8 Hz), 6.55 (d, 1H, J=8 Hz), 6.4 (d, 1H, J=8 Hz), 5.8 (s, 2H), and 4.3 (s, 2H). IR (KBr, cm$^{-1}$) 2220, 1652, and 1613. MS (ES) m/e 398, 400.

Elemental Analyses for C$_{23}$H$_{16}$N$_3$O$_4$Na: Calculated: C, 65.56; H, 3.83; N, 9.97. Found: C, 65.61; H, 3.71; N, 9.89.

EXAMPLE 34

Preparation of {9-[(3-cyanophenyl)methyl]-5-carbamoylcarbazol-4-yl}oxyacetic acid

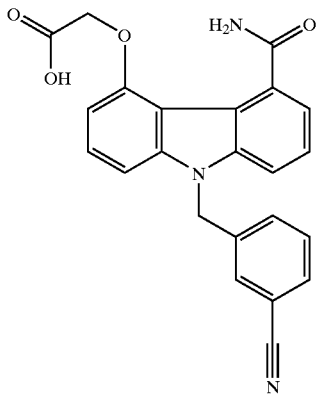

A. 9-[(3-Cyanophenyl)methyl]-5-carbomethoxy-1,2-dihydrocarbazol-4(3H)-one

A suspension of 5-carbomethoxy-1,2-dihydro-9H-carbazol-4(3H)-one (973 mg, 4.0 mM), a-bromo-m-tolunitrile (1.0 g, 4.9 mM), and potassium carbonate (553 mg, 4.0 mM) in 10 mL of DMF was stirred at 25° C. for 24 hours. The mixture was diluted with ethyl acetate, washed five times with H$_2$O, 1 N HCl, H$_2$O, sat NaHCO$_3$, H$_2$O, and saturated brine, dried over anhydrous magnesium sulfate, filtered, concentrated. The residue was dried in vacuo to afford 1.18 g (82%) of the 9-[(3-cyanophenyl)methyl]-5-carbomethoxy -1,2-dihydrocarbazol-4(3H)-one as a tan solid. $^1$H NMR (CDCl$_3$) δ7.65–7.2 (m, 6H), 7.15 (d, 1H, J=8 Hz), 5.4 (s, 2H), 4.05 (s, 3H), 2.85 (t, 2H, J=6 Hz), 2.6 (t, 2H, J=6 Hz), and 2.25 (m, 2H). IR (KBr, cm$^{-1}$) 2226, 1729, and 1646. MS (ES) m/e 357, 359.

Elemental Analyses for C$_{22}$H$_{18}$N$_2$O$_3$: Calculated: C, 73.73; H, 5.06; N, 7.82. Found: C, 70.18; H, 4.97; N, 7.07.

B. 9-[(3-Cyanophenyl)methyl]-4-hydroxy-5-carbomethoxy carbazole

A solution of the 9-[(3-cyanophenyl)methyl]-5-carbomethoxy-1,2-dihydrocarbazol-4(3H)-one (1.15 g, 3.2 mM) and 2,3-dichloro-5,6-dicyano-1,4-benzoquinone (815 mg, 3.52 mM) in 25 mL of toluene was stirred at reflux for 2 hours. The mixture was purified directly by column chromatography on silica gel (elution with methylene chloride) to afford 120 mg (10%) of the 9-[(3-cyanophenyl)methyl]-4-hydroxy-5-carbomethyoxy carbazole as a yellow solid. $^1$H NMR (CDCl$_3$) δ10.35 (s, 1H), 8.0 (d, 1H, J=8 Hz), 7.6–7.2 (m, 7H), 6.85 (m, 2H), 5.55 (s, 2H), and 4.1 (s, 3H). IR (KBr, cm$^{-1}$) 3063, 3025, 2234, and 1685. MS (ES) m/e 355, 357.

Elemental Analyses for C$_{22}$H$_{16}$N$_2$O$_3$: Calculated: C, 74.15; H, 4.53; N, 7.86. Found: C, 73.36; H, 4.51; N, 8.06.

C. 9-[(3-Cyanophenyl)methyl]-4-hydroxy-5-carbamoyl carbazole

A solution of the 9-[(3-cyanophenyl)methyl]-4-hydroxy-5-carbomethoxy carbazole (114 mg, 0.32 mM) in 5 mL THF and 20 mL concentrated aqueous ammonium hydroxide was sonicated for 7 hours at 40–50° C. The mixture was diluted with ethyl acetate and acidified to pH 1 with 5 N HCl. The aqueous layer was extracted three times with ethyl acetate. The combined organic extracts were washed with H$_2$O and saturated brine, dried over magnesium sulfate, filtered, and concentrated. The residue was purified by column chromatography on silica gel (elution with gradient hexanes/ethyl acetate) to afford 40 mg (49%) of the 9-[(3-cyanophenyl)methyl]-4-hydroxy-5-carbamoyl carbazole as a white solid. $^{1}$H NMR (DMSO-d6) δ10.5 (s, 1H), 8.8 (br s, 1H), 8.4 (br s, 1H), 7.8 (d, 1H, J=8 Hz), 7.7 (d, 1H, J=8 Hz), 7.6 (s, 1H), 7.5–7.4 (m, 3H), 7.3 (t, 1H, J=8 Hz), 7.25 (d, 1H, J=8 Hz), 7.1 (d, 1H, J=8 Hz), 6.6 (d, 1H, J=8 Hz), and 5.75 (s, 2H). IR (KBr, cm$^{-1}$) 3430, 3347, 2231, 1628, and 1601. MS (ES) m/e 340, 342.

Elemental Analyses for $C_{21}H_{15}N_3O_2$: Calculated: C, 73.89; H, 4.43; N, 12.31. Found: C, 75.20; H, 4.80; N, 12.15.

D. {9-[(3-Cyanophenyl)methyl]-5-carbamoylcarbazol-4-yl}oxyacetic acid, tert-butyl ester 40% Methanolic Triton B (0.06 mL, 0.13 mM) was added to a solution of the 9-[(3-cyanophenyl)methyl]-4-hydroxy-5-carbamoyl carbazole (34.1 mg, 0.1 mM) in 5 mL DMF at room temperature. After 1 minute, tert-butyl bromoacetate (40 mg, 0.2 mM) was added and the resultant mixture stirred at room temperature for 24 h. The mixture was diluted with ethyl. acetate, washed four times with H$_2$O, 1 N HCl, H$_2$O, sat. NaHCO$_3$, and saturated brine, dried over magnesium sulfate, filtered, and concentrated. The residue was triturated with hexane to afford 51 mg (100%) of the {9-[(3-cyanophenyl)methyl]-5-carbamoylcarbazol-4-yl}oxyacetic acid, tert-butyl ester as a white solid. $^{1}$H NMR (CDCl$_3$) δ7.55 (d, 1H, J=8 Hz), 7.5–7.2 (m, 7H), 6.95 (d, 1H, J=8 Hz), 6.6 (d, 1H, J=8 Hz), 6.3 (br s, 1H), 6.1 (br s, 1H), 5.5 (s, 2H), 4.8 (s, 2H), and 1.5 (s, 9H). IR (KBr, cm$^{-1}$) 2228, 1748, and 1669. MS (ES) m/e 455, 456.

Elemental Analyses for $C_{27}H_{25}N_3O_4$: Calculated: C, 71.19; H, 5.53; N, 9.22. Found: C, 70.24; H, 5.68; N, 8.96.

E. {9-[(3-Cyanophenyl)methyl]-5-carbamoylcarbazol-4-yl}oxyacetic acid

A solution of the {9-[(3-cyanophenyl)methyl]-5-carbamoylcarbazol-4-yl}oxyacetic acid, tert-butyl ester (45 mg, 0.1 mM) ) in 3 mL of trifluoroacetic acid was stirred at room temperature for 2 hours. The solvent was removed in vacuo. The residue was triturated with ethyl ether-hexanes, then dried in vacuo to afford 41 mg (100%) of the {9-[(2-cyanophenyl)methyl]-5-carbamoylcarbazol-4-yl}oxyacetic acid as a tan powder. $^{1}$H NMR (DMSO-d6) δ13.0 (br s, 1H), 7.6–7.3 (m, 10H), 7.1 (d, 1H, J=8 Hz), 6.65 (d, 1H, J=8 Hz), 5.8 (s, 2H), and 4.8 (s, 2H). IR (KBr, cm$^{-1}$) 2226, 1733, and 1640. MS (ES) m/e 398, 400.

Elemental Analyses for $C_{23}H_{17}N_3O_4$: Calculated: C, 69.17; H, 4.29; N, 10.52. Found: C, 66.96; H, 4.37; N, 10.03.

EXAMPLE 35

Preparation of {9-[(2-methylphenyl)methyl]-5-carbamoylcarbazol-4-yl}oxyacetic acid, sodium salt

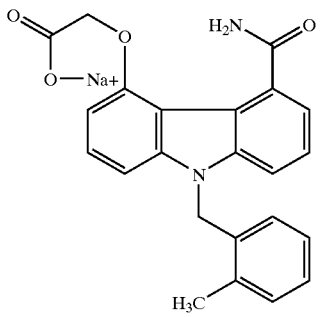

A. 9-[(2-Methylphenyl)methyl]-5-carbomethoxy-1,2-dihydrocarbazol-4(3H)-one

A suspension of 5-carbomethoxy-1,2-dihydro-9H-carbazol-4(3H)-one (870 mg, 3.58 mM), a-bromo-o-xylene (662 mg, 3.58 mM), and potassium carbonate (500 mg, 3.61 mM) in 20 mL DMF was stirred at room temperature for 20 hours. The mixture was diluted with ethyl acetate, washed with H$_2$O and saturated brine, dried over anhydrous magnesium sulfate, filtered, concentrated to afford 1.21 g (98%) of the 9-[(2-methylphenyl)methyl]-5-carbomethoxy-1,2-dihydrocarbazol-4(3H)-one as a dark oil. $^{1}$H NMR (DMSO-d6) δ7.5–7.2 (m, 4H), 7.15 (t, 1H, J=8 Hz), 7.0 (t, 1H, J=8 Hz), 6.15 (d, 1H, J=8 Hz), 5.55 (s, 2H), 3.85 (s, 3H), 2.6 (m, 2H), 2.4 (m, 2H), 2.4 (s, 3H), and 2.1 (m, 2H). IR (CHCl$_3$, cm$^{-1}$) 3010, 2952, 1724, 1671, 1653, 1604, 1460, 1444, 1290, 1174, and 1122. MS (ES) m/e 348.5.

Elemental Analyses for $C_{22}H_{21}NO_3$: Calculated: C, 76.08; H, 6.05; N, 4.03. Found C, 73.33; H, 6.36; N, 4.30.

B. 9-[(2-Methylphenyl)methyl]-4-hydroxy-5-carbomethoxy carbazole

A solution of the 9-[(2-methylphenyl)methyl]-5-carbomethoxy-1,2-dihydrocarbazol-4(3H)-one (1.2 g, 3.5 mM) and 2,3-dichloro-5,6-dicyano-1,4-benzoquinone (800 mg, 3.6 mM) in 70 mL of toluene was stirred at 80–90° C. for 5 hours. The mixture was purified directly by column chromatography on silica gel (elution with methylene chloride) to afford 260 mg (22%) of the 9-[(2-methylphenyl)methyl]-4-hydroxy-5-carbomethyoxy carbazole as a yellow solid. $^{1}$H NMR (DMSO-d6) δ10.25 (s, 1H), 7.5 (d, 1H, J=8 Hz), 7.4 (t, 1H, J=8 Hz), 7.3–7.1 (m, 4H), 6.9 (m, 2H), 6.6 (d, 1H, J=8 Hz), 6.1 (d, 1H, J=8 Hz), 5.65 (s, 2H), 3.8 (s, 3H), and 2.5 (s, 3H). IR (KBr, cm$^{-1}$) 3200, 1672, 1440, 1426, 1332, 1302, 1265, 1216, 1141, 761, 749, and 718. MS (ES) m/e 344, 346.

Elemental Analyses for $C_{22}H_{19}NO_3$: Calculated: C, 76.52; H, 5.51; N, 4.06. Found: C, 76.44; H, 5.66; N, 3.94.

C. 9-[(2-Methylphenyl)methyl]-4-hydroxy-5-carbamoyl carbazole

A solution of the 9-[(2-methylphenyl)methyl]-4-hydroxy-5-carbomethoxy carbazole (260 mg, 0.75 mM) in 10 mL THF and 30 mL concentrated aqueous ammonium hydroxide was sonicated for 5 hours at 40–50° C. The mixture was diluted with ethyl acetate and acidified to pH 1 with 5 N HCl. The aqueous layer was extracted three times with ethyl acetate. The combined organic extracts were washed with H$_2$O and saturated brine, dried over magnesium sulfate, filtered, and concentrated. The residue was purified by column chromatography on silica gel (elution with gradient hexanes/ethyl acetate) to afford 90 mg (36%) of the 9-[(2-methylphenyl)methyl]-4-hydroxy-5-carbamoyl carbazole as a tan solid. $^{1}$H NMR (DMSO-d6) δ10.5 (s, 1H), 8.8 (br s, 1H), 8.4 (br s, 1H), 7.7 (m, 1H), 7.5 (m, 2H), 7.3 (m, 2H), 7.1 (t, 1H, J=8 Hz), 6.95 (d, 1H, J=8 Hz), 6.85 (t, 1H, J=8 Hz), 6.6 (d, 1H, J=8 Hz), 5.95 (d, 1H, J=8 Hz), 5.7 (s, 2H), and 2.5 (s, 3H). IR (KBr, cm$^{-1}$) 3451, 3191, 1627, 1600, 1584, 1562, 1435, 1329, 1322, 1263, and 774. MS (ES) m/e 329, 331.

Elemental Analyses for $C_{21}H_{18}N_2O_2$: Calculated: C, 76.36; H, 5.45; N, 8.48. Found: C, 75.66; H, 5.79; N, 8.07.

D. {9-[(2-Methylphenyl)methyl]-5-carbamoylcarbazol-4-yl}oxyacetic acid, methyl ester 40% Methanolic Triton B (0.45 mL, 0.99 mM) was added to a solution of the 9-[(2-methylphenyl)methyl]-4-hydroxy-5-carbamoyl carbazole (80 mg, 0.24 mM) in 8 mL DMF at room temperature. After 3 minutes, methyl bromoacetate (115 mg, 0.72 mM) was added and the resultant mixture stirred at room temperature for 48 hours. The mixture was diluted with ethyl acetate, washed with $H_2O$, 1 N HCl, $H_2O$, and saturated brine, dried over magnesium sulfate, filtered, and concentrated. The residue was purified by column chromatography on silica gel (elution with ethyl acetate) to afford 80 mg (82%) of the {9-[(2-methylphenyl)methyl]-5-carbamoylcarbazol-4-yl}oxyacetic acid, methyl ester as a white solid. $^1$H NMR (DMSO-d6) δ7.56 (br s, 1H), 7.5–7.1 (m, 9H), 6.9 (t, 1H, J=8 Hz), 6.6 (d, 1H, J=8 Hz), 5.65 (s, 2H), 4.9 (s, 2H), 3.8 (s, 3H), and 2.5 (s, 3H). IR (KBr, cm$^{-1}$) 3367, 3153, 1760, 1740, 1672, 1644, 1619, 1591, 1578, 1498, 1456, 1425, 1327, 1200, 1153, 1109, 1100, and 777. MS (FD) m/e 402.

Elemental Analyses for $C_{24}H_{22}N_2O_4$: Calculated: C, 71.64; H, 5.47; N, 6.96. Found: C, 71.51; H, 5.56; N, 6.67.

E. {9-[(2-Methylphenyl)methyl]-5-carbamoylcarbazol-4-yl}oxyacetic acid, sodium salt A suspension of the {9-[(2-methylphenyl)methyl]-5-carbamoylcarbazol-4-yl}oxyacetic acid, methyl ester (15.5 mg, 0.039 mM) and 0.04 mL (0.04 mM) of 1 N NaOH in 5 mL of ethanol was stirred for 24 hours at 25° C. The resultant white precipitate was collected by filtration, washed with a small amount of EtOH, then dried in vacuo to afford 10 mg (63%) of the {9-[(2-methylphenyl)methyl]-5-carbamoylcarbazol-4-yl}oxyacetic acid, sodium salt as a whitw powder. $^1$H NMR (DMSO-d6) δ7.55 (br s, 1H), 7.5–7.0 (m, 7H), 6.9 (d, 1H, J=8 Hz), 6.85 (t, 1H, J=8 Hz), 6.6 (d, 1H, J=8 Hz), 6.2 (d, 1H, J=8 Hz), 5.6 (s, 2H), 4.35 (s, 2H), and 2.5 (s, 3H). IR (KBr, cm$^{-1}$) 3390, 1656, 1613, 1595, 1573, 1498, 1455, 1408, 1325, 1332, and 719. MS (ES) m/e 387, 389.

Elemental Analyses for $C_{23}H_{19}N_2O_4$: Calculated: C, 67.32; H, 4.63; N, 6.83. Found: C, 64.72; H, 4.44; N, 6.40.

EXAMPLE 36

Preparation of {9-[(3-methylphenyl)methyl]-5-carbamoylcarbazol-4-yl}oxyacetic acid, sodium salt

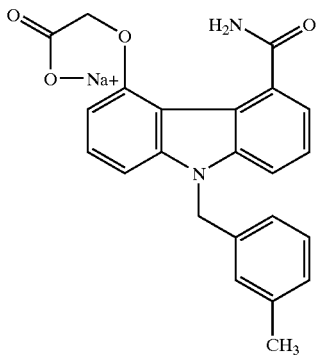

A. 9-[(3-Methylphenyl)methyl]-5-carbomethoxy-1,2-dihydrocarbazol-4(3H)-one

A suspension of 5-carbomethoxy-1,2-dihydro-9H-carbazol-4(3H)-one (870 mg, 3.58 mM), a-bromo-m-xylene (662 mg, 3.58 mM), and potassium carbonate (500 mg, 3.61 mM) in 20 mL DMF was stirred at room temperature for 16 hours. The mixture was diluted with ethyl acetate, washed with $H_2O$ and saturated brine, dried over anhydrous magnesium sulfate, filtered, concentrated to afford 1.18 g (95%) of the 9-[(3-methylphenyl)methyl]-5-carbomethoxy-1,2-dihydrocarbazol-4(3H)-one as a dark oil. $^1$H NMR (DMSO-d6) δ7.65 (dd, 1H, J=1 and 8 Hz), 7.3–7.1 (m, 3H), 7.05 (d, 1H, J=8 Hz), 7.0 (s, 1H), 6.85 (d, 1H, J=8 Hz), 5.5 (s, 2H), 3.8 (s, 3H), 3.0 (m, 2H), 2.45 (m, 2H), 2.3 (s, 3H), and 2.1 (m, 2H). IR (CHCl$_3$, cm$^{-1}$) 3010, 2953, 1724, 1652, 1605, 1465, 1442, 1288, 1174, and 1119. MS (ES) m/e 348.5.

Elemental Analyses for $C_{22}H_{21}NO_3$: Calculated: C, 76.08; H, 6.05; N, 4.03. Found: C, 74.53; H, 6.03; N, 3.68.

B. 9-[(3-Methylphenyl)methyl]-4-hydroxy-5-carbomethoxy carbazole

A solution of the 9-[(3-methylphenyl)methyl]-5-carbomethoxy-1,2-dihydrocarbazol-4(3H)-one (1.18 g, 3.4 mM) and 2,3-dichloro-5,6-dicyano-1,4-benzoquinone (800 mg, 3.6 mM) in 70 mL of toluene was stirred at 80–90° C. for 6 hours. The mixture was purified directly by column chromatography on silica gel (elution with methylene chloride) to afford 300 mg (26%) of the 9-[(3-methylphenyl)methyl]-4-hydroxy-5-carbomethyoxy carbazole as a yellow solid. $^1$H NMR (DMSO-d6) δ10.2 (s, 1H), 7.65 (d, 1H, J=8 Hz), 7.35 (t, 1H, J=8 Hz), 7.25 (t, 1H, J=8 Hz), 7.2–7.0 (m, 4H), 6.9 (m, 2H), 6.6 (d, 1H, J=8 Hz), 5.6 (s, 2H), 3.85 (s, 3H), and 2.2 (s, 3H). IR (KBr, cm$^{-1}$) 3200, 1673, 1596, 1440, 1426, 1394, 1265, 1216, 1152, 750, 711, and 694. MS (ES) m/e 344, 346.

Elemental Analyses for $C_{22}H_{19}NO_3$: Calculated: C, 76.52; H, 5.51; N, 4.06. Found: C, 76.22; H, 5.55; N, 3.97.

C. 9-[(3-Methylphenyl)methyl]-4-hydroxy-5-carbamoyl carbazole

A solution of the 9-[(3-methylphenyl)methyl]-4-hydroxy-5-carbomethoxy carbazole (300 mg, 0.87 mM) in 10 mL THF and 30 mL concentrated aqueous ammonium hydroxide was sonicated for 5 hours at 40–50° C. The mixture was diluted with ethyl acetate and acidified to pH 1 with 5 N HCl. The aqueous layer was extracted three times with ethyl acetate. The combined organic extracts were washed with $H_2O$ and saturated brine, dried over magnesium sulfate, filtered, and concentrated. The residue was purified by column chromatography on silica gel (elution with gradient hexanes/ethyl acetate) to afford 114 mg (40%) of the 9-[(3-methylphenyl)methyl]-4-hydroxy-5-carbamoyl carbazole as an off-white solid. $^1$H NMR (DMSO-d6) δ10.5 (s, 1H), 8.8 (br s, 1H), 8.4 (br s, 1H), 7.8 (dd, 1H, J=1 and 8 Hz), 7.4 (m, 2H), 7.3 (t, 1H, J=8 Hz), 7.15–7.0 (m, 3H), 6.85 (d, 1H, J=8 Hz), 6.6 (d, 1H, J=8 Hz), 5.95 (d, 1H, J=8 Hz), 5.65 (s, 2H), and 2.25 (s, 3H). IR (KBr, cm$^{-1}$) 3434, 3203, 1629, 1599, 1579, 1552, 1443, 1330, 1262, 1214, and 776. MS (ES) m/e 329, 331.

Elemental Analyses for $C_{21}H_{18}N_2O_2$: Calculated: C, 76.36; H, 5.45; N, 8.48. Found: C, 77.56; H, 5.67; N, 8.26.

D. {9-[(3-Methylphenyl)methyl]-5-carbamoylcarbazol-4-yl}oxyacetic acid, methyl ester 40% Methanolic Triton B (0.45 mL, 0.99 mM) was added to a solution of the 9-[(3-methylphenyl)methyl]-4-hydroxy-5-carbamoyl carbazole (100 mg, 0.30 mM) in 8 mL DMF at room temperature. After 3 minutes, methyl bromoacetate (115 mg, 0.72 mM) was added and the resultant mixture stirred at room temperature for 24 hours. The mixture was diluted with ethyl acetate, washed with $H_2O$, and saturated brine, dried over magnesium sulfate, filtered, and concentrated. The residue was purified by column chromatography on silica gel (elution with ethyl acetate) to afford 80 mg (66%) of the {9-[(3-methylphenyl)methyl]-5-carbamoylcarbazol-4-yl}oxyacetic acid, methyl ester as a white solid. $^1$H NMR (DMSO-d6) δ7.6 (d, 1H, J=8 Hz), 7.55 (br s, 1H), 7.45–7.0 (m, 8H), 6.9 (d, 1H, J=8 Hz), 6.6 (d, 1H, J=8 Hz), 5.65 (s, 2H), 4.9 (s, 2H), 3.75 (s, 3H), and 2.2 (s, 3H). IR (KBr, cm$^{-1}$) 3367, 3157, 1760, 1642, 1589, 1499, 1455, 1424, 1328, 1216, 1151, 1102, 772, and 714. MS (FD) m/e 402.

Elemental Analyses for $C_{24}H_{22}N_2O_4$: Calculated: C, 71.64; H, 5.47; N, 6.96. Found: C, 71.01; H, 5.60; N, 6.66.

E. {9-[(3-Methylphenyl)methyl]-5-carbamoylcarbazol-4-yl}oxyacetic acid, sodium salt A suspension of the {9-[(3-methylphenyl)methyl]-5-carbamoylcarbazol-4-yl}oxyacetic acid, methyl ester (15.8 mg, 0.039 mM) and 0.04 mL (0.04 mM) of 1 N NaOH in 5 mL of ethanol was stirred for 24 h at 25° C. The resultant white precipitate was collected by filtration, washed with a small amount of EtOH, then dried in vacuo to afford 10 mg (62%) of the {9-[(3-methylphenyl)methyl]-5-carbamoylcarbazol-4-yl}oxyacetic acid, sodium salt as a white powder. $^1$H NMR (DMSO-d6) δ7.55 (d, 1H, J=8 Hz), 7.5–7.0 (m, 9H), 6.85 (d, 1H, J=8 Hz), 6.55 (d, 1H, J=8 Hz), 5.6 (s, 2H), 4.35 (s, 2H), and 2.2 (s, 3H). IR (KBr, cm$^{-1}$) 3390, 1656, 1613, 1595, 1573, 1498, 1455, 1408, 1325, 1332, and 719. MS (ES) m/e 387, 389.

Elemental Analyses for $C_{23}H_{19}N_2O_4Na$: Calculated: C, 67.32; H, 4.63; N, 6.83. Found: C, 61.20; H, 4.64; N, 6.06.

EXAMPLE 37

Preparation of {9-[(3,5-dimethylphenyl)methyl]-5-carbamoylcarbazol-4-yl}oxyacetic acid, sodium salt

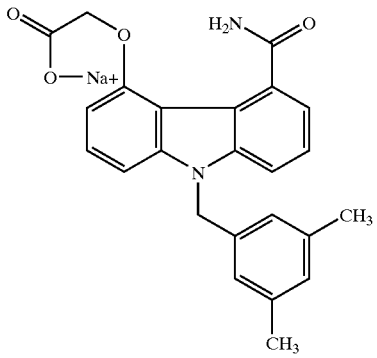

A. 9-[(3,5-Dimethylphenyl)methyl]-5-carbomethoxy-1,2-dihydrocarbazol-4(3H)-one

A suspension of 5-carbomethoxy-1,2-dihydro-9H-carbazol-4(3H)-one (850 mg, 3.5 mM), 3,5-dimethylbenzyl bromide (765 mg, 3.8 mM), and potassium carbonate (500 mg, 3.61 mM) in 25 mL DMF was stirred at room temperature for 19 hours. The mixture was diluted with ethyl acetate, washed with H$_2$O and saturated brine, dried over anhydrous magnesium sulfate, filtered, concentrated. The residue was purified by column chromatography on silica gel (elution with ethyl acetate) to afford 0.84 g (67%) of the 9-[(3,5-dimethylphenyl)methyl]-5-carbomethoxy-1,2-dihydrocarbazol-4(3H)-one as a foam. $^1$H NMR (DMSO-d6) δ7.7 (dd, 1H, J=1 and 8 Hz), 7.3–7.2 (m, 2H), 6.9 (s, 1H), 6.75 (s, 2H), 5.45 (s, 2H), 3.8 (s, 3H), 3.0 (m, 2H), 2.45 (m, 2H), 2.2 (s, 6H), and 2.1 (m, 2H). IR (KBr, cm$^{-1}$) 1726, 1653, 1602, 1465, 1442, 1282, 1172, and 1116. MS (ES) m/e 362.

Elemental Analyses for $C_{23}H_{23}NO_3$: Calculated: C, 76.45; H, 6.37; N, 3.88. Found: C, 76.82; H, 6.54; N, 3.91.

B. 9-[(3,5-Dimethylphenyl)methyl]-4-hydroxy-5-carbomethoxy carbazole

A solution of the 9-[(3,5-dimethylphenyl)methyl]-5-carbomethoxy-1,2-dihydrocarbazol-4(3H)-one (0.8 g, 2.2 mM) and 2,3-dichloro-5,6-dicyano-1,4-benzoquinone (550 mg, 2.43 mM) in 70 mL of toluene was stirred at 80–90° C. for 5 hours. The mixture was purified directly by column chromatography on silica gel (elution with methylene chloride) to afford 234 mg (29%) of the 9-[(3,5-dimethylphenyl)methyl]-4-hydroxy-5-carbomethyoxy carbazole as a yellow solid. $^1$H NMR (DMSO-d6) δ10.2 (s, 1H), 7.65 (d, 1H, J=8 Hz), 7.35 (t, =H, J=8 Hz), 7.25 (t, 1H, J=8 Hz), 7.15 (d, 1H, J=8 Hz), 7.05 (d, 1H, J=8 Hz), 6.9 (s, 1H), 6.7 (s, 2H), 6.6 (d, 1H, J=8 Hz), 5.6 (s, 2H), 3.85 (s, 3H), and 2.2 (s, 6H). IR (KBr, cm$^{-1}$) 3016, 1675, 1598, 1441, 1426, 1394, 1288, 1270, 1221, 1152, 754, and 713. MS (ES) m/e 358, 360.

Elemental Analyses for $C_{23}H_{21}NO_3$: Calculated: C, 76.88; H, 5.85; N, 3.90. Found: C, 76.94; H, 6.00; N, 3.93.

C. 9-[(3,5-Dimethylphenyl)methyl]-4-hydroxy-5-carbamoyl carbazole

A solution of the 9-[(3,5-dimethylphenyl)methyl]-4-hydroxy-5-carbomethoxy carbazole (200 mg, 0.55 mM) in 10 mL THF and 30 mL concentrated aqueous ammonium hydroxide was sonicated for 4 days at 40–50° C. The mixture was diluted with ethyl acetate and acidified to pH 2.5 with 5 N HCl. The aqueous layer was extracted three times with ethyl acetate. The combined organic extracts were washed with saturated brine, dried over magnesium sulfate, filtered, and concentrated. The residue was purified by column chromatography on silica gel (elution with gradient hexanes/ethyl acetate) to afford 90 mg (47%) of the 9-[(3,5-dimethylphenyl)methyl]-4-hydroxy-5-carbamoyl carbazole as an off-white solid. $^1$H NMR (DMSO-d6) δ10.5 (s, 1H), 8.6 (s, 1H), 8.4 (s, 1H), 7.75 (d, 1H, J=8 Hz), 7.45 (m, 2H), 7.3 (t, 1H, J=8 Hz), 7.1 (d, 1H, J=8 Hz), 6.85 (s, 1H), 6.7 (s, 2H), 6.6 (d, 1H, J=8 Hz), 5.6 (s, 2H), and 2.2 (s, 6H). IR (KBr, cm$^{-1}$) 3417, 3198, 3113, 3063, 1631, 1601, 1562, 1438, 1332, 1263, 1217, 781, and 773. MS (ES) m/e 343, 345.

Elemental Analyses for $C_{22}H_{20}N_2O_2$: Calculated: C, 76.74; H, 5.81; N, 8.14. Found: C, 76.97; H, 5.94; N, 7.95.

D. {9-[(3,5-Dimethylphenyl)methyl]-5-carbamoylcarbazol-4-yl}oxyacetic acid, methyl ester 40% Methanolic Triton B (0.13 mL, 0.28 mM) was added to a solution of the 9-[(3,5-dimethylphenyl)methyl]-4-hydroxy-5-carbamoyl carbazole (80 mg, 0.23 mM) in 8 mL DMF at room temperature. After 3 minutes, methyl bromoacetate (43 mg, 0.28 mM) was added and the resultant mixture stirred at room temperature for 17 hours. The mixture was diluted with ethyl acetate, washed with H$_2$O, and saturated brine, dried over magnesium sulfate, filtered, and concentrated. The residue was purified by column chromatography on silica gel (elution with ethyl acetate) to afford 70 mg (72%) of the {9-[(3,5-dimethylphenyl)methyl]-5-carbamoylcarbazol-4-yl}oxyacetic acid, methyl ester as a white solid. $^1$H NMR (DMSO-d6) δ7.6 (d, 1H, J=8 Hz), 7.55 (br s, 1H), 7.45–7.3 (m, 2H), 7.25 (d, 1H, J=8 Hz), 7.2 (br s, 1H), 7.1 (d, 1H, J=8 Hz), 6.9 (s, 1H), 6.8 (s, 2H), 6.6 (d, 1H, J=8 Hz), 5.65 (s, 2H), 4.9 (s, 2H), 3.75 (s, 3H), and 2.2 (s, 6H). IR (KBr, cm$^{-1}$) 3362, 3173, 1758, 1638, 1583, 1500, 1454, 1434, 1330, 1215, 1151, 1106, 772, 715, and 706. MS (FD) m/e 417.

Elemental Analyses for $C_{25}H_{24}N_2O_4$: Calculated: C, 72.12; H, 5.76; N, 6.73. Found: C, 71.80; H, 5.60; N, 6.73.

E. {9-[(3,5-Dimethylphenyl)methyl]-5-carbamoylcarbazol-4-yl}oxyacetic acid, sodium salt A suspension of the {9-[(3,5-dimethylphenyl)methyl]-5-carbamoylcarbazol-4-yl}oxyacetic acid, methyl ester (18 mg, 0.043 mM) and 0.043 mL (0.043 mM) of 1 N NaOH in 5 mL of ethanol was stirred for 42 hours at 25° C. The resultant white precipitate was collected by filtration, washed with a small amount of EtOH, then dried in vacuo to afford 12 mg (67%) of the {9-[(3,5-dimethylphenyl)methyl]-5-carbamoylcarbazol-4-yl}oxyacetic acid, sodium salt as a white powder. $^1$H NMR (DMSO-d6) δ7.6 (d, 1H, J=8 Hz), 7.5–7.3 (m, 4H), 7.1 (m, 2H), 6.9 (s, 1H), 6.8 (s, 2H), 6.6 (d, 1H, J=8 Hz), 5.65 (s, 2H), 4.35 (s, 2H), and 2.2 (s, 6H). IR (KBr, cm$^{-1}$) 3385, 1663, 1616, 1575, 1498, 1456, 1412, and 1330. MS (ES) m/e 401, 403.

Elemental Analyses for $C_{24}H_{21}N_2O_4Na$: Calculated: C, 67.92; H, 4.95; N, 6.60. Found: C, 66.53; H, 5.06; N, 6.37.

EXAMPLE 38

Preparation of {9-[(3-iodophenyl)methyl]-5-carbamoylcarbazol-4-yl}oxyacetic acid, sodium salt

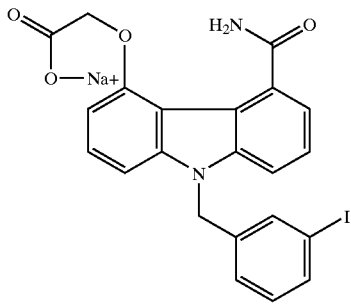

A. 9-[(3-Iodophenyl)methyl]-5-carbomethoxy-1,2-dihydrocarbazol-4(3H)-one

A suspension of 5-carbomethoxy-1,2-dihydro-9H-carbazol-4(3H)-one (680 mg, 3.5 mM), 3-iodobenzyl bromide (1.2 g, 4.7 mM), and potassium carbonate (500 mg, 3.61 mM) in 20 mL DMF was stirred at room temperature for 18 hours. The mixture was diluted with ethyl acetate, washed with H$_2$O and saturated brine, dried over anhydrous magnesium sulfate, filtered, concentrated. The residue was purified trituration with methylene chloride-diethyl ether) to afford 0.70 g (55%) of the 9-[(3-iodophenyl)methyl]-5-carbomethoxy-1,2-dihydrocarbazol-4(3H)-one as a white solid. $^1$H NMR (DMSO-d6) δ7.7–7.6 (m, 3H), 7.2 (m, 2H), 7.1 (t, 1H, J=8 Hz), 6.95 (d, 1H, J=8Hz), 5.6 (s, 2H), 3.8 (s, 3H), 3.0 (t, 2H, J=6 Hz), 2.5 (t, 2H, J=6 Hz), and 2.2 (m, 2H). IR (KBr, cm$^{-1}$) 1732, 1639, 1441, 1421, 1273, 1117, and 763. MS (ES) m/e 458, 460.

Elemental Analyses for $C_{21}H_{18}NO_3I$: Calculated: C, 54.90; H, 3.92; N, 3.05. Found: C, 54.92; H, 3.98; N, 2.97.

B. 9-[(3-Iodophenyl)methyl]-4-hydroxy-5-carbomethoxy carbazole

A solution of the 9-[(3-iodophenyl)methyl]-5-carbomethoxy-1,2-dihydrocarbazol-4(3H)-one (700 mg, 1.52 mM) and 2,3-dichloro-5,6-dicyano-1,4-benzoquinone (380 mg, 1.67 mM) in 70 mL of toluene was stirred between 70–80° C. for 5 hours. The mixture was purified directly by column chromatography on silica gel (elution with methylene chloride) to afford 220 mg (31%) of the 9-[(3-iodophenyl)methyl]-4-hydroxy-5-carbomethyoxy carbazole as a yellow foam. $^1$H NMR (DMSO-d6) δ10.25 (s, 1H), 7.7 (d, 1H, J=8 Hz), 7.6 (m, 2H), 7.4 (t, 1H, J=8 Hz), 7.25 (t, 1H, J=8 Hz), 7.2 (d, 1H, J=8 Hz), 7.1 (m, 3H), 6.65 (d, 1H, J=8 Hz), 5.65 (s, 2H), and 3.8 (s, 3H). IR (KBr, cm$^{-1}$) 3377 (br), 3028, 1711, 1672, 1621, 1580, 1565, 1495, 1459, 1439, 1423, 1332, 1287, 1267, 1135, 773, 752, 712, and 688. MS (ES) m/e 456, 458.

Elemental Analyses for $C_{21}H_{16}NO_3I$: Calculated: C, 55.14; H, 3.50; N, 3.06. Found: C, 56.18; H, 3.87; N, 3.32.

C. 9-[(3-Iodophenyl)methyl]-4-hydroxy-5-carbamoyl carbazole

A solution of the 9-[(3-iodophenyl)methyl]-4-hydroxy-5-carbomethoxy carbazole (170 mg, 0.37 mM) in 10 mL THF and 30 mL concentrated aqueous ammonium hydroxide was stirred vigorously at room temperature for 120 hours. The mixture was diluted with ethyl acetate and acidified to pH 2 with 5 N HCl. The aqueous layer was extracted twice with ethyl acetate. The combined organic extracts were washed with saturated brine, dried over magnesium sulfate, filtered, and concentrated. The residue was purified by column chromatography on silica gel (elution with gradient methylene chloride/ethyl acetate) to afford 61 mg (37%) of the 9-[(3-iodophenyl)methyl]-4-hydroxy-5-carbamoyl carbazole as a white solid. $^1$H NMR (DMSO-d6) δ10.5 (s, 1H), 8.8 (br s, 1H), 8.4 (br s, 1H), 7.8 (dd, 1H, J=1 and 8 Hz), 7.6–7.4 (m, 4H), 7.3 (t, 1H, J=8 Hz), 7.1–6.9 (m, 3H), 6.6 (d, 1H, J=8 Hz), and 5.7 (s, 2H). IR (CHCl$_3$, cm$^{-1}$) 3423, 3201 (br), 1630, 1600, 1579, 1564, 1445, 1330, 1261, and 775. MS (ES) m/e 441, 443.

Elemental Analyses for $C_{20}H_{15}N_2O_2I$: Calculated: C, 54.30; H, 3.39; N, 6.33. Found: C, 54.92; H, 3.81; N, 6.08.

D. {9-[(3-Iodophenyl)methyl]-5-carbamoylcarbazol-4-yl}oxyacetic acid, methyl ester 40% Methanolic Triton B (0.07 mL, 0.15 mM) was added to a solution of the 9-[(3-iodophenyl)methyl]-4-hydroxy-5-carbamoyl carbazole (60 mg, 0.13 mM) in 8 mL DMF at room temperature. After 3 minutes, methyl bromoacetate (30 mg, 0.19 mM) was added and the resultant mixture stirred at room temperature for 17 hours. The mixture was diluted with ethyl acetate, washed with H$_2$O and saturated brine, dried over magnesium sulfate, filtered, and concentrated. The residue was purified by column chromatography on silica gel (elution with ethyl acetate) to afford 60 mg (86%) of the {9-[(3-iodophenyl)methyl]-5-carbamoylcarbazol-4-yl}oxyacetic acid, methyl ester as a white solid. $^1$H NMR (DMSO-d6) δ7.6–7.0 (m, 11H), 6.6 (d, 1H, J=8 Hz), 5.7 (s, 2H), 4.9 (s, 2H), and 3.75 (s, 3H). IR (KBr, cm$^{-1}$) 3500, 3350, 1727, 1642, 1291, 1236, and 772. MS (ES) m/e 515.

Elemental Analyses for $C_{23}H_{19}N_2O_4I$: Calculated: C, 53.70; H, 3.70; N, 5.45. Found: C, 53.92; H, 3.72; N, 5.32.

E. {9-[(3-Iodophenyl)methyl]-5-carbamoylcarbazol-4-yl}oxyacetic acid

A suspension of the {9-[(3-iodophenyl)methyl]-5-carbamoylcarbazol-4-yl}oxyacetic acid, methyl ester (15 mg, 0.03 mM) and 0.03 mL (0.03 mM) of 1 N NaOH in 5 mL of ethanol was stirred for 43 hours at 25° C., then cooled in an ice-bath. The resultant white precipitate was collected by filtration, washed with a small amount of EtOH, then dried in vacuo to afford 6.5 mg (43%) of the {9-[(3-iodophenyl)methyl]-5-carbamoylcarbazol-4-yl}oxyacetic acid, sodium salt as a white powder. $^1$H NMR (DMSO-d6) δ7.6–7.0 (m, 11H), 6.6 (d, 1H, J=8 Hz), 5.7 (s, 2H), and 4.35 (s, 2H). IR (KBr, cm$^{-1}$) 3456, 3416, 3335, 1735, 1638, 1617, 1580, 1499, 1452, 1431, 1431, 1329, 1255, 1157, 772, 764, and 717. MS (ES) m/e 407, 409, 411.

Elemental Analyses for $C_{22}H_{16}N_2O_4INa$, Calculated: C, 50.57; H, 3.07; N, 5.36. Found: C, 49.57; H, 2.93; N, 5.06.

EXAMPLE 39

Preparation of {9-[(2-Chlorophenyl)methyl]-5-carbamoylcarbazol-4-yl}oxyacetic acid

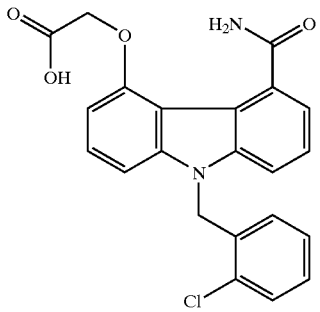

A. 9-[(2-Chlorophenyl)methyl]-5-carbomethoxy-1,2-dihydrocarbazol-4(3H)-one

40% Methanolic Triton B (2.42 mL, 5.3 mM) was slowly added dropwise to a solution of 5-carbomethoxy-1,2-dihydro-9H-carbazol-4(3H)-one (873.7 mg, 3.59 mM) in 10 mL of DMF at 25° C. After 5 minutes, 2-chlorobenzyl bromide (1.11 g, 5.39 mM) was added and the resultant mixture stirred at room temperature for 72 hours. The mixture was diluted with ethyl acetate, washed five times with $H_2O$, once with saturated brine, dried over anhydrous magnesium sulfate, filtered, and concentrated. The residue was purified by crystallization from ethyl acetate to afford 706.3 mg (53%) of the 9-[(2-chlorophenyl)methyl]-5-carbomethoxy-1,2-dihydrocarbazol-4(3H)-one as a yellow solid. $^1$H NMR (DMSO-d6) δ7.6 (m, 2H), 7.4–7.1 (m, 4H), 6.5 (d, 1H, J=8 Hz), 5.6 (s, 2H), 3.8 (s, 3H), 2.9 (t, 2H, J=6 Hz), 2.4 (t, 2H, J=6 Hz), and 2.1 (m, 2H). IR (CDCl$_3$, cm$^{-1}$) 3050, 2950, 1725, 1655, 1462, 1446, 1435, 1288 and 1120. MS (ES) m/e 368, 370.

Elemental Analyses for $C_{21}H_{18}NO_3Cl$: Calculated: C, 68.57; H, 4.93; N, 3.81. Found: C, 68.52; H, 5.18; N, 3.67.

B. 9-[(2-Chlorophenyl)methyl]-4-hydroxy-5-carbomethoxy carbazole

A solution of the 9-[(2-chlorophenyl)methyl]-5-carbomethoxy-1,2-dihydrocarbazol-4(3H)-one (692.2 mg, 1.88 mM) and 2,3-dichloro-5,6-dicyano-1,4-benzoquinone (529 mg, 2.32 mM) in 35 mL of toluene was stirred between 70–80° C. for 6 hours. The mixture was purified directly by column chromatography on silica gel (elution with methylene chloride) to afford 245 mg (35%) of the 9-[(2-chlorophenyl)methyl]-4-hydroxy-5-carbomethyoxy carbazole as a greenish solid. $^1$H NMR (DMSO-d6) δ10.3 (s, 1H), 7.6 (t, 2H, J=8 Hz), 7.4 (t, 1H, J=8 Hz), 7.3–7.1 (m, 4H), 6.9 (d, 1H, J=8 Hz), 6.6 (d, 1H, J=8 Hz), 6.3 (d, 1H, J=8 Hz), 5.65 (s, 2H), and 3.85 (s, 3H). IR (CHCl$_3$, cm$^{-1}$) 3200 (br), 1686, 1598, 1442, 1428, 1332, 1285, 1267, and 1141. MS (ES) m/e 364, 366, 368.

Elemental Analyses for $C_{21}H_{16}NO_3Cl$: Calculated: C, 68.95; H, 4.41; N, 3.83. Found: C, 67.88; H, 4.29; N, 3.67.

C. 9-[(2-Chlorophenyl)methyl]-4-hydroxy-5-carbamoyl carbazole

A solution of the 9-[(2-chlorophenyl)methyl]-4-hydroxy-5-carbomethoxy carbazole (238 mg, 0.43 mM) in 20 mL THF and 25 mL concentrated aqueous ammonium hydroxide was sonicated for 20 hours at 40–50° C. The mixture was diluted with ethyl acetate and acidified to pH 1 with 5 N HCl. The aqueous layer was extracted twice with ethyl acetate. The combined organic extracts were washed with saturated brine, dried over magnesium sulfate, filtered, and concentrated. The residue was purified by column chromatography on silica gel (elution with gradient methylene chloride/ethyl acetate) to afford 86.9 mg (38%) of the 9-[(2-chlorophenyl)methyl]-4-hydroxy-5-carbamoyl carbazole as a white solid. $^1$H NMR (DMSO-d6) δ10.5 (s, 1H), 8.8 (br s, 1H), 8.4 (br s, 1H), 7.7 (m, 1H), 7.55 (d, 1H, J=8 Hz), 7.45 (m, 2H), 7.3 (m, 2H), 7.15 (t, 1H, J=8 Hz), 6.95 (d, 1H, J=8 Hz), 6.6 (d, 1H, J=8 Hz), 6.2 (d, 1H, J=8 Hz), 5.75 (s, 2H). IR (CHCl$_3$, cm$^{-1}$) 3500, 3400, 3200 (br), 1649, 1597, 1585, 1446, 1431, 1331, and 1269. MS (ES) m/e 349, 351, 353.

Elemental Analyses for $C_{20}H_{15}N_2O_2Cl$: Calculated: C, 68.48; H, 4.31; N, 7.99. Found: C, 68.05; H, 4.33; N, 7.19.

D. {9-[(2-Chlorophenyl)methyl]-5-carbamoylcarbazol-4-yl}oxyacetic acid, tert-butyl ester 40% Methanolic Triton B (0.15 mL, 0.34 mM) was added to a solution of the 9-[(2-chlorophenyl)methyl]-4-hydroxy-5-carbamoyl carbazole (80 mg, 0.23 mM) in 5 mL DMF at room temperature. After 3 minutes, t-butyl bromoacetate (182 mg, 0.91 mM) was added and the resultant mixture stirred at room temperature for 72 hours. The mixture was diluted with ethyl acetate, washed five times with $H_2O$, and saturated brine, dried over magnesium sulfate, filtered, and concentrated. The residue was purified by column chromatography on silica gel (elution with ethyl acetate) to afford 57 mg (53%) of the {9-[(2-chlorophenyl)methyl]-5-carbamoylcarbazol-4-yl}oxyacetic acid, tert-butyl ester as a white solid. $^1$H NMR (DMSO-d6) δ7.6 (d, 1H, J=8 Hz), 7.5–6.9 (m, 9H), 6.55 (d, 1H, J=8 Hz), 6.35 (d, 1H, J=8 Hz), 5.7 (s, 2H), 4.75 (s, 2H), and 1.45 (s, 9H). IR (KBr, cm$^{-1}$) 1753 and 1678. MS (FD) m/e 464.

Elemental Analyses for $C_{26}H_{25}N_2O_4Cl$: Calculated: C, 67.17; H, 5.42; N, 6.03. Found: C, 64.02; H, 5.33; N, 5.77.

E. {9-[(2-Chlorophenyl)methyl]-5-carbamoylcarbazol-4-yl}oxyacetic acid

A solution of the {9-[(2-chlorophenyl)methyl]-5-carbamoylcarbazol-4-yl}oxyacetic acid, tert-butyl ester (46 mg, 0.1 mM) in 3 mL of trifluoroacetic acid was stirred at room temperature for 2 hours. The solvent was removed in vacuo. The residue was triturated with diethyl ether/hexanes, then dried in vacuo to afford 40 mg (98%) of the {9-[(2-chlorophenyl)methyl]-5-carbamoylcarbazol-4-yl}oxyacetic acid as a white powder. $^1$H NMR (DMSO-d6) δ12.9 (br s, 1H), 7.55 (s, 1H), 7.5 (d, 1H, J=8 Hz), 7.45 (s, 1H), 7.4–7.3 (m, 3H), 7.25 (t, 1H, J=8 Hz), 7.1–7.0 (m, 3H), 6.6 (d, 1H, J=8 Hz), 6.3 (d, 1H, J=8 Hz), 5.7 (s, 2H), and 4.8 (s, 2H). IR (KBr, cm$^{-1}$) 3430, 1735, and 1635. MS (ES) m/e 407, 409.

Elemental Analyses for $C_{22}H_{17}N_2O_4Cl$: Calculated: C, 64.63; H, 4.19; N, 6.85. Found: C, 64.60; H, 4.08; N, 6.70.

EXAMPLE 40

Preparation of {9-[(2,3-difluorophenyl)methyl]-5-carbamoylcarbazol-4-yl}oxyacetic acid, sodium salt

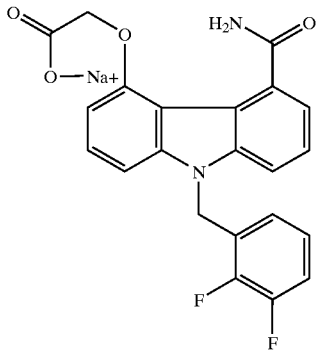

A. 9-[(2,3-Difluorophenyl)methyl]-5-carbomethoxy-1,2-dihydrocarbazol-4(3H)-one

A suspension of 5-carbomethoxy-1,2-dihydro-9H-carbazol-4(3H)-one (973 mg, 4.0 mM), a-bromo-2,3-difluorotoluene (1.01 g, 4.8 mM), and potassium carbonate (553 mg, 4.0 mM) in 10 mL DMF was stirred at room temperature for 73 hours. The mixture was diluted with ethyl acetate, washed with $H_2O$, 1 N HCl, $H_2O$, saturated $NaHCO_3$, $H_2O$, and saturated brine, dried over anhydrous magnesium sulfate, filtered, concentrated. The residue was purified by column chromatography on silica gel (elution with methylene chloride/ethyl acetate) to afford 1.04 g (70%) of the 9-[2,3-difluorophenyl)methyl]-5-carbomethoxy-1,2-dihydrocarbazol-4(3H)-one as a tan solid. $^1$H NMR (CDCl$_3$) δ7.4 (d, 1H, J=8 Hz), 7.35 (d, 1H, J=8 Hz), 7.15–6.9 (m, 5H), 6.35 (t, 1H, J=8 Hz), 5.4 (s, 2H), 4.05 (s, 3H), 2.9 (t, 2H, J=6 Hz), 2.6 (t, 2H, J=6 Hz), and 2.25 (m, 2H). IR (KBr, cm$^{-1}$) 1719 and 1650. MS (ES) m/e 368, 370.

Elemental Analyses for $C_{21}H_{17}NO_3F_2$: Calculated: C, 68.29; H, 4.64; N, 3.79. Found: C, 68.50; H, 4.62; N, 3.94.

B. 9-[(2,3-Difluorophenyl)methyl]-4-hydroxy-5-carbomethoxy carbazole

A solution of the 9-[(2,3-difluorophenyl)methyl]-5-carbomethoxy-1,2-dihydrocarbazol-4(3H)-one (490 mg, 1.32 mM) and 2,3-dichloro-5,6-dicyano-1,4-benzoquinone (336 mg, 1.45 mM) in 70 mL of toluene was stirred at 80–90° C. for 2.25 hours. The mixture was purified directly by column chromatography on silica gel (elution with methylene chloride) to afford 165 mg (34%) of the 9-[(2,3-difluorophenyl)methyl]-4-hydroxy-5-carbomethyoxy carbazole as a yellow solid. $^1$H NMR (CDCl$_3$) δ10.25 (s, 1H), 8.0 (d, 1H, J=8 Hz), 7.6 (d, 1H, J=8 Hz), 7.5–7.4 (m, 2H), 7.05 (m, 1H), 6.9 (d, 1H, J=8 Hz), 6.85 (d, 1H, J=8 Hz), 6.8 (m, 1H), 6.35 (t, 1H, J=8 Hz), 5.6 (s, 2H), and 4.1 (s, 3H). IR (KBr, cm$^{-1}$) 3025 and 1684. MS (ES) m/e 366, 368.

Elemental Analyses for $C_{21}H_{15}NO_3F_2$: Calculated: C, 68.66; H, 4.12; N, 3.81. Found: C, 69.54; H, 4.44; N, 3.81.

C. 9-[(2,3-Difluorophenyl)methyl]-4-hydroxy-5-carbamoyl carbazole

A solution of the 9-[(2,3-difluorophenyl)methyl]-4-hydroxy-5-carbomethoxy carbazole (514 mg, 1.4 mM) in 5 mL THF and 20 mL concentrated aqueous ammonium hydroxide was stirred at room temperature for 94 hours. The mixture was diluted with ethyl acetate and acidified to pH 1 with 5 N HCl. The aqueous layer was extracted three times with ethyl acetate. The combined organic extracts were washed with $H_2O$ and saturated brine, dried over magnesium sulfate, filtered, and concentrated. The residue was purified by column chromatography on silica gel (elution with gradient hexanes/ethyl acetate) to afford 320 mg (65%) of the 9-[(2,3-difluorophenyl)methyl]-4-hydroxy-5-carbamoyl carbazole as a yellow solid. $^1$H NMR (DMSO-d6) δ10.45 (s, 1H), 8.8 (br s, 1H), 8.4 (br s, 1H), 7.8 (d, 1H, J=8 Hz), 7.5–7.2 (m, 4H), 7.05 (d, 1H, J=8 Hz), 6.95 (m, 1H), 6.6 (d, 1H, J=8 Hz), 6.35 (t, 1H, J=8 Hz), and 5.9 (s, 2H). IR (KBr, cm$^{-1}$) 3350, 3125, 1628, 1598, and 1583. MS (ES) m/e 351, 353.

Elemental Analyses for $C_{20}H_{14}N_2O_2F_2$: Calculated: C, 68.18; H, 4.01; N, 7.95. Found: C, 68.15; H, 4.23; N, 8.01.

D. {9-[(2,3-Difluorophenyl)methyl]-5-carbamoylcarbazol-4-yl}oxyacetic acid, methyl ester 40% Methanolic Triton B (0.51 mL, 1.12 mM) was added to a solution of the 9-[(2,3-difluorophenyl)methyl]-4-hydroxy-5-carbamoyl carbazole (303 mg, 0.86 mM) in 5 mL DMF at room temperature. After 15 minutes, methyl bromoacetate (270 mg, 1.72 mM) was added and the resultant mixture stirred at room temperature for 18 hours. The mixture was diluted with ethyl acetate, washed with $H_2O$, 1 N HCl, $H_2O$, and saturated brine, dried over magnesium sulfate, filtered, and concentrated. The residue was purified by column chromatography on silica gel (elution with ethyl acetate) to afford 295 mg (80%) of the {9-[(2,3-difluorophenyl)methyl]-5-carbamoylcarbazol-4-yl}oxyacetic acid, methyl ester as a white solid. $^1$H NMR (CDCl$_3$) δ7.5–7.3 (m, 5H), 7.05 (d, 1H, J=8 Hz), 6.8 (m, 1H), 6.6 (d, 1H, J=8 Hz), 6.4 (t, 1H, J=8 Hz), 6.2 (br s, 1H), 6.0 (br s, 1H), 5.6 (s, 2H), 4.9 (s, 2H), and 3.8 (s, 3H). IR (KBr, cm$^{-1}$) 3432, 3180, 1774, 1766, and 1674. MS (ES) m/e 425.

Elemental Analyses for $C_{23}H_{18}N_2O_4F_2$: Calculated: C, 65.09; H, 4.28; N, 6.60. Found: C, 64.11; H, 4.12; N, 6.32.

E. {9-[(2,3-Difluorophenyl)methyl]-5-carbamoylcarbazol-4-yl}oxyacetic acid, sodium salt A suspension of the {9-[(2,3-difluorophenyl)methyl]-5-carbamoylcarbazol-4-yl}oxyacetic acid, methyl ester (85 mg, 0.2 mM) and 0.22 mL (0.22 mM) of 1 N NaOH in 5 mL of ethanol was stirred for 18 hours at 25° C. A small volume of diethyl ether/hexanes was added, then cooled in the refrigerator. The resultant white precipitate was collected by filtration, washed with a small amount of EtOH/diethyl ether/hexanes, then dried in vacuo to afford 77 mg (89%) of the {9-[(2,3-difluorophenyl)methyl]-5-carbamoylcarbazol-4-yl}oxyacetic acid, sodium salt as a white powder. $^1$H NMR (DMSO-d6) δ7.7–7.2 (m, 6H), 7.2–7.0 (m, 3H), 6.6 (d, 1H, J=8 Hz), 6.45 (t, 1H, J=8 Hz), 5.7 (s, 2H), and 4.35 (s, 2H). IR (KBr, cm$^{-1}$) 3467, 3390, 1662, and 1616. MS (ES) m/e 409, 411, 433.

Elemental Analyses for $C_{22}H_{15}N_2O_4F_2Na$: Calculated: C, 61.12; H, 3.50; N, 6.48. Found: C, 61.34; H, 3.38; N, 6.41.

EXAMPLE 41

Preparation of {9-[(2,6-difluorophenyl)methyl]-5-carbamoylcarbazol-4-yl}oxyacetic acid, sodium salt

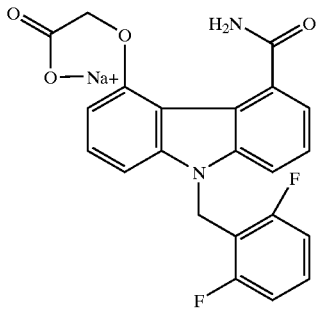

A. 9-[(2,6-Difluorophenyl)methyl]-5-carbomethoxy-1,2-dihydrocarbazol-4(3H)-one

A suspension of 5-carbomethoxy-1,2-dihydro-9H-carbazol-4(3H)-one (973 mg, 4.0 mM), a-bromo-2,6-difluorotoluene (1.01 g, 4.8 mM), and potassium carbonate (553 mg, 4.0 mM) in 10 mL DMF was stirred at room temperature for 74 hours. The mixture was diluted with ethyl acetate, washed with $H_2O$, 1 N HCl, $H_2O$, saturated $NaHCO_3$, $H_2O$, and saturated brine, dried over anhydrous magnesium sulfate, filtered, concentrated. The residue was purified by column chromatography on silica gel (elution with methylene chloride/ethyl acetate) to afford 1.04 g (70%) of the 9-[(2,6-difluorophenyl)methyl]-5-carbomethoxy-1,2-dihydrocarbazol-4(3H)-one as a tan solid. $^1$H NMR (CDCl$_3$) δ7.5 (d, 1H, J=8 Hz), 7.35–7.2 (m, 3H), 6.95 (t, 2H, J=8 Hz), 5.4 (s, 2H), 4.0 (s, 3H), 3.05 (t, 2H, J=6 Hz), 2.6 (t, 2H, J=6 Hz), and 2.25 (m, 2H). IR (KBr, cm$^{-1}$) 1728 and 1655. MS (ES) m/e 370.

Elemental Analyses for $C_{21}H_{17}NO_3F_2$: Calculated: C, 68.29; H, 4.64; N, 3.79. Found: C, 68.51; H, 4.82; N, 3.78.

B. 9-[(2,6-Difluorophenyl)methyl]-4-hydroxy-5-carbomethoxy carbazole

A 60% oil dispersion of sodium hydride (257 mg, 6.42 mM) was added to a solution of the 9-[(2,6-difluorophenyl)methyl]-5-carbomethoxy-1,2-dihydrocarbazol-4(3H)-one (1.03 g, 2.79 mM) in 7 mL of dioxane at room temperature. After 5 minutes methyl benzenesulfinate (0.6 mL, 4.46 mM) was added and the mixture stirred at room temperature for 1.75 hours. The mixture was diluted with 10 mL dioxane, then glacial acetic acid (0.37 mL, 6.42 mM) was added. The resultant mixture was refluxed for 45 min, cooled to room temperature, diluted with ethyl acetate, washed three times with saturated $NaHCO_3$, and saturated brine, dried over anhydrous magnesium sulfate, filtered and concentrated. The residue was purified by column chromatography on silica gel (elution with toluene) to afford 480 mg (47%) of the 9-[(2,6-difluorophenyl)methyl]-4-hydroxy-5-carbomethyoxy carbazole as a yellow solid. 1H NMR (CDCl$_3$) δ10.15 (s, 1H), 7.95 (d, 1H, J=8 Hz), 7.5 (d, 1H, J=8 Hz), 7.5–7.0 (m, 4H), 6.9–6.8 (m, 3H), 5.6 (s, 2H), and 4.1 (s, 3H). IR (KBr, cm$^{-1}$) 3040 and 1682. MS (ES) m/e 366, 368.

Elemental Analyses for $C_{21}H_{15}NO_3F_2$: Calculated: C, 68.66; H, 4.12; N, 3.81. Found: C, 69.48; H, 4.07; N, 4.11.

C. 9-[(2,6-Difluorophenyl)methyl]-4-hydroxy-5-carbamoyl carbazole

A solution of the 9-[(2,6-difluorophenyl)methyl]-4-hydroxy-5-carbomethoxy carbazole (514 mg, 1.4 mM) in 5 mL THF and 20 mL concentrated aqueous ammonium hydroxide was stirred at room temperature for 64 hours. The pH was adjusted to 10.5 with 5 N HCl. The resultant precipitate was collected by filtration, resuspended in $H_2O$, adjusted the pH to 11.7 with concentrated ammonium hydroxide. The resultant precipitate was collected by filtration. The precipitate was dissolved in ethyl acetate, washed three times with 5 N NaOH, $H_2O$, and saturated brine, dried over anhydrous magnesium sulfate, filtered, concentrated to afford 310 mg (70%) of the 9-[(2,6-difluorophenyl)methyl]-4-hydroxy-5-carbamoyl carbazole as a yellow solid. $^1$H NMR (DMSO-d6) δ10.4 (s, 1H), 8.8 (br s, 1H), 8.4 (br s, 1H), 7.8 (d, 1H, J=8 Hz), 7.6–7.0 (m, 7H), 6.6 (d, 1H, J=8 Hz), and 5.7 (s, 2H). IR (KBr, cm$^{-1}$) 3404, 3113, 1626, and 1587. MS (ES) m/e 351, 353.

Elemental Analyses for $C_{20}H_{14}N_2O_2F_2$: Calculated: C, 68.18; H, 4.01; N, 7.95. Found: C, 68.45; H, 4.01; N, 7.87.

D. {9-[(2,6-Difluorophenyl)methyl]-5-carbamoylcarbazol-4-yl}oxyacetic acid, methyl ester 40% Methanolic Triton B (0.49 mL, 1.07 mM) was added to a solution of the 9-[(2,6-difluorophenyl)methyl]-4-hydroxy-5-carbamoyl carbazole (290 mg, 0.82 mM) in 5 mL DMF at room temperature. After 15 minutes, methyl bromoacetate (259 mg, 1.65 mM) was added and the resultant mixture stirred at room temperature for 24 hours. The mixture was diluted with $H_2O$ and the resultant white precipitate collected by filtration, triturated with diethyl ether/hexanes, and dried in vacuo to afford 228 mg (65%) of the 19-[(2,6-difluorophenyl)methyl]-5-carbamoylcarbazol-4-yl}oxyacetic acid, methyl ester as a white solid. $^1$H NMR (CDCl$_3$) δ7.65 (d, 1H, J=8 Hz), 7.45–7.2 (m, 5H), 6.85 (t, 2H, J=8 Hz), 6.55 (d, 1H, J=8 Hz), 6.3 (br s, 1H), 6.0 (br s, 1H), 5.5 (s, 2H), 4.9 (s, 2H), and 3.8 (s, 3H). IR (KBr, cm$^{-1}$) 3432, 3170, 1762, and 1675. MS (ES) m/e 425.

Elemental Analyses for $C_{23}H_{18}N_2O_4F_2$: Calculated: C, 65.09; H, 4.28; N, 6.60. Found: C, 65.05; H, 4.40; N, 6.53.

E. {9-[(2,6-Difluorophenyl)methyl]-5-carbamoylcarbazol-4-yl}oxyacetic acid, sodium salt A suspension of the {9-[(2,6-difluorophenyl)methyl]-5-carbamoylcarbazol-4-yl}oxyacetic acid, methyl ester (85 mg, 0.2 mM) and 0.22 mL (0.22 mM) of 1 N NaOH in 5 mL of ethanol was stirred for 18 hours at 25° C. A small volume of diethyl ether/hexanes was added, then cooled in the refrigerator. The resultant white precipitate was collected by filtration, washed with a small amount of EtOH/diethyl ether/hexanes, then dried in vacuo to afford 82 mg (95%) of the {9-[(2,6-difluorophenyl)methyl]-5-carbamoylcarbazol-4-yl}oxyacetic acid, sodium salt as a white powder. $^1$H NMR (DMSO-d6) δ7.6 (d, 1H, J=8 Hz), 7.55 (br s, 1H), 7.45–7.3 (m, 3H), 7.25 (t, 1H, J=8 Hz), 7.1–7.0 (m, 4H), 6.5 (d, 1H, J=8 Hz), 5.65 (s, 2H), and 4.3 (s, 2H). IR (KBr, cm$^{-1}$) 3470, 3360, 1658, and 1606. MS (ES) m/e 409, 411, 433.

Elemental Analyses for $C_{22}H_{15}N_2O_4F_2Na$: Calculated: C, 61.12; H, 3.50; N, 6.48. Found: C, 59.18; H, 3.70; N, 6.19.

EXAMPLE 42

Preparation of {9-[(2,6-dichlorophenyl)methyl]-5-carbamoylcarbazol-4-yl}oxyacetic acid, sodium salt

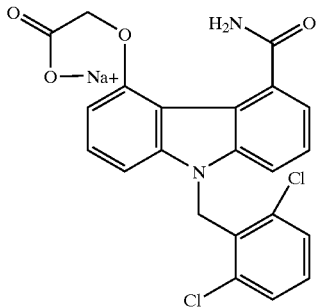

A. 9-[(2,6-Dichlorophenyl)methyl]-5-carbomethoxy-1,2-dihydrocarbazol-4(3H)-one

A suspension of 5-carbomethoxy-1,2-dihydro-9H-carbazol-4(3H)-one (973 mg, 4.0 mM), a-bromo-2,6-dichlorotoluene (1.19 g, 4.8 mM), and potassium carbonate (553 mg, 4.0 mM) in 10 mL DMF was stirred at room temperature for 24 hours. The mixture was diluted with ethyl acetate, washed with $H_2O$, 1 N HCl, $H_2O$, saturated $NaHCO_3$, $H_2O$, and saturated brine, dried over anhydrous magnesium sulfate, filtered, concentrated. The residue was purified by column chromatography on silica gel (elution with methylene chloride/ethyl acetate) to afford 900 mg (56%) of the 9-[(2,6-dichlorophenyl)methyl]-5-carbomethoxy-1,2-dihydrocarbazol-4(3H)-one as a white foam. $^1$H NMR ($CDCl_3$) δ7.4–7.2 (m, 6H), 5.6 (s, 2H), 4.0 (s, 3H), 2.9 (t, 2H, J=6 Hz), 2.55 (t, 2H, J=6 Hz), and 2.2 (m, 2H). IR (KBr, $cm^{-1}$) 1725 and 1652. MS (ES) m/e 400, 402, 404.

Elemental Analyses for $C_{21}H_{17}NO_3Cl_2$: Calculated: C, 62.70; H, 4.26; N, 3.48. Found: C, 62.98; H, 4.35; N, 3.35.

B. 9-[(2,6-Dichlorophenyl)methyl]-4-hydroxy-5-carbomethoxy carbazole

A solution of the 9-[(2,6-dichlorophenyl)methyl]-5-carbomethoxy-1,2-dihydrocarbazol-4(3H)-one (861 mg, 2.14 mM) and 2,3-dichloro-5,6-dicyano-1,4-benzoquinone (595 mg, 2.57 mM) in 60 mL of toluene was stirred at reflux for 3.5 hours. The mixture was purified directly by column chromatography on silica gel (elution with methylene chloride) to afford 255 mg (29%) of the 9-[(2,6-dichlorophenyl)methyl]-4-hydroxy-5-carbomethyoxy carbazole as a yellow solid. $^1$H NMR ($CDCl_3$) δ10.05 (s, 1H), 7.95 (d, 1H, J=8 Hz), 7.6 (d, 1H, J=8 Hz), 7.45–7.2 (m, 5H), 6.95 (d, 1H, J=8 Hz), 6.8 (d, 1H, J=8 Hz), 5.75 (s, 2H), and 4.1 (s, 3H). IR (KBr, $cm^{-1}$) 3430 and 1668. MS (ES) m/e 409, 411.

Elemental Analyses for $C_{21}H_{15}NO_3Cl_2$: Calculated: C, 63.02; H, 3.78; N, 3.50. Found: C, 63.78; H, 3.82; N, 3.59.

C. 9-[(2,6-Dichlorophenyl)methyl]-4-hydroxy-5-carbamoyl carbazole

A solution of the 9-[(2,6-dichlorophenyl)methyl]-4-hydroxy-5-carbomethoxy carbazole (240 mg, 0.6 mM) in 5 mL THF and 20 mL concentrated aqueous ammonium hydroxide was stirred at room temperature for 22 hours. The resultant precipitate was collected by filtration and dried in vacuo to afford 151 mg (65%) of the 9-[(2,6-dichlorophenyl)methyl]-4-hydroxy-5-carbamoyl carbazole as a yellow solid. $^1$H NMR (DMSO-d6) δ10.35 (s, 1H), 8.8 (br s, 1H), 8.4 (br s, 1H), 7.7 (d, 1H, J=8 Hz), 7.6–7.3 (m, 5H), 7.25 (t, 1H, J=8 Hz), 6.85 (d, 1H, J=8 Hz), 6.55 (d, 1H, J=8 Hz), and 5.85 (s, 2H). IR (KBr, $cm^{-1}$) 3429, 1631, and 1597. MS (ES) m/e 385, 387.

Elemental Analyses for $C_{20}H_{14}N_2O_2Cl_2$: Calculated: C, 62.35; H, 3.66; N, 7.27. Found: C, 62.87; H, 3.99; N, 6.00.

D. {9-[(2,6-Dichlorophenyl)methyl]-5-carbamoylcarbazol-4-yl}oxyacetic acid, methyl ester 40% Methanolic Triton B (0.23 mL, 0.49 mM) was added to a solution of the 9-[(2,6-dichlorophenyl)methyl]-4-hydroxy-5-carbamoyl carbazole (146 mg, 0.38 mM) in 5 mL DMF at room temperature. After 15 minutes, methyl bromoacetate (119 mg, 0.76 mM) was added and the resultant mixture stirred at room temperature for 17 hours. The mixture was diluted with ethyl acetate, washed with $H_2O$, 1 N HCl, $H_2O$, sat. $NaHCO_3$, and saturated brine, dried over magnesium sulfate, filtered, and concentrated. The residue was purified by column chromatography on silica gel (elution with ethyl acetate) to afford 83 mg (48%) of the {9-[(2,6-dichlorophenyl)methyl]-5-carbamoylcarbazol-4-yl}oxyacetic acid, methyl ester as a tan solid. $^1$H NMR (DMSO-d6) δ7.5–7.0 (m, 10H), 6.55 (d, 1H, J=8 Hz), 5.8 (s, 2H), 4.9 (s, 2H), and 3.75 (s, 3H). IR (KBr, $cm^{-1}$). MS (ES) m/e 457, 459.

E. {9-[(2,6-Dichlorophenyl)methyl]-5-carbamoylcarbazol-4-yl}oxyacetic acid, sodium salt A suspension of the {9-[(2,6-dichlorophenyl)methyl]-5-carbamoylcarbazol-4-yl}oxyacetic acid, methyl ester (45.7 mg, 0.1 mM) and 0.11 mL (0.11 mM) of 1 N NaOH in 5 mL of ethanol was stirred for 22 hours at 25° C. A small volume of diethyl ether/hexanes was added, then cooled in the refrigerator. The resultant white precipitate was collected by filtration, washed with a small amount of EtOH/diethyl ether/hexanes, then dried in vacuo to afford 40 mg (86%) of the {9-[(2,6-dichlorophenyl)methyl]-5-carbamoylcarbazol-4-yl}oxyacetic acid, sodium salt as a white powder. $^1$H NMR (DMSO-d6) δ7.6–7.4 (m, 6H), 7.3 (t, 1H, J=8 Hz), 7.2 (t, 1H, J=8 Hz), 7.0 (d, 1H, J=8 Hz), 6.9 (t, 1H, J=8 Hz), 6.5 (d, 1H, J=8 Hz), 5.8 (s, 2H), and 4.25 (s, 2H). MS (ES) m/e 441, 443, 445.

EXAMPLE 43

Preparation of {9-[(3-trifluoromethoxyphenyl)methyl]-5-carbamoylcarbazol-4-yl}oxyacetic acid, sodium salt

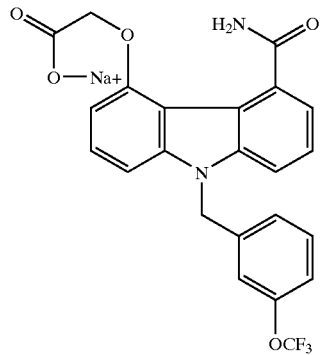

A. 9-[(3-Trifluoromethoxyphenyl)methyl]-5-carbomethoxy-1,2-dihydrocarbazol-4(3H)-one A suspension of 5-carbomethoxy-1,2-dihydro-9H-carbazol-4(3H)-one (935 mg, 3.85 mM), 3-trifluoromethoxybenzyl bromide (1.0 g, 3.93 mM), and potassium carbonate (531 mg, 3.85 mM) in 20 mL DMF was stirred at room temperature for 17 hours. The mixture was diluted with ethyl acetate, washed with $H_2O$ and saturated brine, dried over anhydrous magnesium sulfate, filtered, concentrated to afford 1.6 g (100%) of the 9-[(3- trifluoromethoxyphenyl)methyl]-5-carbomethoxy-1,2-dihydrocarbazol-4(3H)-one as a foam. $^1$H NMR (DMSO-d6) δ7.7 (dd, 1H, J=1 and 8 Hz), 7.45 (t, 1H, J=8 Hz), 7.3–7.1 (m, 4H), 7.05 (d, 1H, J=8 Hz), 5.6 (s, 2H), 3.8 (s, 3H), 3.0 (m, 2H), 2.45 (m, 2H), and 2.1 (m, 2H). IR (CDCl$_3$, cm$^{-1}$) 1729, 1647, 1439, 1259, 1176, and 1116. MS (ES) m/e 418.

Elemental Analyses for $C_{22}H_{18}NO_4F_3$: Calculated: C, 63.31; H, 4.32; N, 3.36. Found: C, 63.12; H, 4.35; N, 3.31.

B. 9-[(3-Trifluoromethoxyphenyl)methyl]-4-hydroxy-5-carbomethoxy carbazole

A solution of the 9-[(3-trifluoromethoxyphenyl)methyl]-5-carbomethoxy-1,2-dihydrocarbazol-4(3H)-one (0.75 g, 1.8 mM) and 2,3-dichloro-5,6-dicyano-1,4-benzoquinone (490 mg, 2.16 mM) in 70 mL of toluene was stirred at reflux for 6 hours. The mixture was purified directly by column chromatography on silica gel (elution with methylene chloride) to afford 300 mg (40%) of the 9-[(3-trifluoromethoxyphenyl)methyl]-4-hydroxy-5-carbomethyoxy carbazole as a yellow solid. $^1$H NMR (DMSO-d6) δ10.25 (s, 1H), 7.7 (d, 1H, J=8 Hz), 7.5–7.0 (m, 8H), 6.6 (d, 1H, J=8 Hz), 5.7 (s, 2H), and 3.85 (s, 3H). IR (KBr, cm$^{-1}$) 3200, 1673, 1441, 1268, 1217, 1173, and 753. MS (ES) m/e 414, 416.

Elemental Analyses for $C_{22}H_{16}NO_3F_3$ Calculated: C, 63.61; H, 3.86; N, 3.37. Found: C, 63.40; H, 3.99; N, 3.43.

C. 9-[(3-Trifluoromethoxyphenyl)methyl]-4-hydroxy-5-carbamoyl carbazole

A solution of the 9-[(3-trifluoromethoxyphenyl)methyl]-4-hydroxy-5-carbomethoxy carbazole (260 mg, 0.62 mM) in 10 mL THF and 30 mL concentrated aqueous ammonium hydroxide was stirred vigorously for 132 hours. The mixture was diluted with ethyl acetate and acidified to pH 1 with 5 N HCl. The aqueous layer was extracted three times with ethyl acetate. The combined organic extracts were washed with H$_2$O and saturated brine, dried over magnesium sulfate, filtered, and concentrated. The residue was purified by column chromatography on silica gel (elution with gradient hexanes/ethyl acetate) to afford 150 mg (60%) of the 9-[(3-trifluoromethoxyphenyl)methyl]-4-hydroxy-5-carbamoyl carbazole as an off-white solid. $^1$H NMR (DMSO-d6) δ10.5 (s, 1H), 8.8 (br s, 1H), 8.4 (br s, 1H), 7.85 (dd, 1H, J=1 and 8 Hz), 7.5–7.15 (m, 5H), 7.1 (d, 1H, J=8 Hz), 7.0 (d, 1H, J=8 Hz), 6.6 (d, 1H, J=8 Hz), 5.95 (d, 1H, J=8 Hz), and 5.65 (s, 2H). IR (KBr, cm$^{-1}$) 3431, 3203, 1629, 1601, 1580, 1548, 1446, 1330, 1261, 1215, and 777. MS (ES) m/e 399, 401.

Elemental Analyses for $C_{21}H_{15}N_2O_2F_3$: Calculated: C, 63.00; H, 3.75; N, 7.0. Found: C, 63.15; H, 4.07; N, 6.84.

D. {9-[(3-Trifluoromethoxyphenyl)methyl]-5-carbamoylcarbazol-4-yl}oxyacetic acid, methyl ester 40% Methanolic Triton B (0.15 mL, 0.34 mM) was added to a solution of the 9-[(3-trifluoromethoxyphenyl)methyl]-4-hydroxy-5-carbamoyl carbazole (115 mg, 0.28 mM) in 8 mL DMF at room temperature. After 3 minutes, methyl bromoacetate (65 mg, 0.41 mM) was added and the resultant mixture stirred at room temperature for 23 hours. The mixture was diluted with ethyl acetate, washed with H$_2$O, and saturated brine, dried over magnesium sulfate, filtered, and concentrated. The residue was purified by column chromatography on silica gel (elution with ethyl acetate) to afford 112 mg (83%) of the {9-[(3-trifluoromethoxyphenyl)methyl]-5-carbamoylcarbazol-4-yl}oxyacetic acid, methyl ester as a white solid. $^1$H NMR (DMSO-d6) δ7.6 (d, 1H, J=8 Hz), 7.55 (br s, 1H), 7.5–7.0 (m, 9H), 6.6 (d, 1H, J=8 Hz), 5.7 (s, 2H), 4.9 (s, 2H), and 3.75 (s, 3H). IR (KBr, cm$^{-1}$) 3488, 3141, 1763, 1674, 1501, 1444, 1269, 1215, 1178, 1102, 772, and 714. MS (FD) m/e 472.

Elemental Analyses for $C_{24}H_{19}N_2O_5F_3$: Calculated: C, 61.02; H, 4.03; N, 5.93. Found: C, 61.05; H, 4.17; N, 5.81.

E. {9-[(3-Trifluoromethoxyphenyl)methyl]-5-carbamoylcarbazol-4-yl}oxyacetic acid, sodium salt A suspension of the {9-[(3-trifluoromethoxyphenyl)methyl]-5-carbamoylcarbazol-4-yl}oxyacetic acid, methyl ester (22.4 mg, 0.047 mM) and 0.065 mL (0.065 mM) of 1 N NaOH in 5 mL of ethanol was stirred for 24 hours at 25° C. The solvent was removed in vacuo and the residue suspended in EtOH. The resultant white precipitate was collected by filtration, washed with a small amount of EtOH, then dried in vacuo to afford 9 mg (41%) of the {9-[(3-trifluoromethoxyphenyl)methyl]-5-carbamoylcarbazol-4-yl}oxyacetic acid, sodium salt as a white powder. MS (ES) m/e 457, 459.

EXAMPLE 44

Preparation of {9-[(2-biphenyl)methyl]-5-carbamoylcarbazol-4-yl}oxyacetic acid

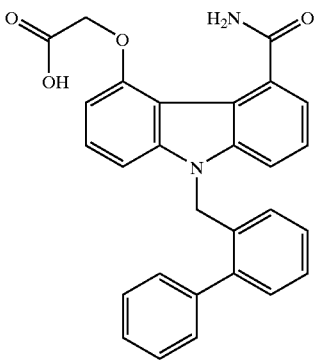

A. 2-Carbomethoxy-6-nitro-2'-methoxy-biphenyl

A solution of methyl 2-chloro-3-nitrobenzoate (2.16 g, 10.0 mM), 2-methoxybenzeneboronic acid (1.64 g, 10.5 mM), tetrakis(triphenylphosphine)palladium (0) (584 mg, 0.5 mM), and 2 M aqueous sodium carbonate (10.5 mL, 21.0 mM) in 50 mL of THF was wrapped in aluminum foil and stirred at reflux for 27 hours. The THF was removed in vacuo and the residue dissolved in ethyl acetate. The mixture was washed with with H$_2$O, 1 N HCl, H$_2$O, sat. NaHCO$_3$, and saturated brine, dried over magnesium sulfate, filtered, and concentrated. The resultant light brown oil was purified by column chromatography on silica (elution with gradient toluene/ethyl acetate) to afford 2.0 g (69%) of 2-carbomethoxy-6-nitro-2'-methoxy-biphenyl as a yellow-orange solid. $^1$H NMR (CDCl$_3$) δ8.05 (d, 1H, J=8 Hz), 7.95 (d, 1H, J=8 Hz), 7.55 (t, 1H, J=8 Hz), 7.35 (t, 1H, J=8 Hz), 7.05 (d, 1H, J=8 Hz), 7.0 (t, 1H, J=8 Hz), 6.9 (d, 1H, J=8 Hz), 3.7 (s, 3H), and 3.6 (s, 3H). IR (KBr, cm$^{-1}$) 1730, 1538, 1499, 1366, 1298, 1271, 1130, 774, 765, 759, 752, and 707. MS (ES) m/e 288.

Elemental Analyses for $C_{15}H_{13}NO_5$: Calculated: C, 62.72; H, 4.56; N, 4.88. Found: C, 62.65; H, 4.61; N, 4.72.

B. 9H-4-methoxy-5-carbomethoxy carbazole

A solution of the 2-carbomethoxy-6-nitro-2'-methoxy-biphenyl (144 mg, 0.5 mM) in triethylphosphite (339 mg, 0.35 mL, 2.0 mM) was heated at 150–160° C. in a sealed tube for 4 h then at room temperature for 15 hours. The mixture was dried in vacuo with toluene, then purified by preparative TLC on silica gel (elution with 4:1 toluene/ethyl acetate to afford 39.0 mg (30%) of the 9H-4-methoxy-5-carbomethoxy carbazole as a tan solid. $^1$H NMR (CDCl$_3$) δ8.25 (s, 1H), 7.4–7.2 (m, 4H), 7.05 (d, 1H, J=8 Hz), 6.65

(d, 1H, J=8 Hz), and 4.05 (s, 6H). IR (CHCl$_3$, cm$^{-1}$) 3274 (br), 1706, 1602, 1583, 1456, 1431, 1351, 1333, 1294, 1239, 1198, 1175, 1144, 1103, 781, and 724. MS (ES) m/e 256.

Elemental Analyses for C$_{15}$H$_{13}$NO$_3$: Calculated: C, 70.58; H, 5.13; N, 5.49. Found: C, 70.85; H, 5.29; N, 5.29.

C. 9-[(2-Biphenyl)methyl]-4-methoxy-5-carbomethoxy carbazole

A solution of the 9H-4-methoxy-5-carbomethoxy carbazole (727 mg, 2.85 mM) in 15 mL DMF was added to 60% NaH mineral oil dispersion (342 mg, 8.56 mM), washed twice with hexane) at room temperature. Following cessation of gas evolution, 2-(bromomethyl)biphenyl (0.79 mL, 4.19 mM) was added and the mixture stirred at room temperature for 19 hours. The mixture was diluted with ethyl acetate and H$_2$O. The ethyl acetate layer was washed with with H$_2$O, 1 N HCl, H$_2$O, sat. NaHCO$_3$, and saturated brine, dried over magnesium sulfate, filtered, and concentrated to afford 1.2 g (100%) of the 9-[(2-biphenyl)methyl]-4-methoxy-5-carbomethoxy carbazole as a yellow solid. $^1$H NMR (CDCl$_3$) δ7.6–7.2 (m, 11H), 7.05 (t, 1H, J=8 Hz), 6.8 (d, 1H, J=8 Hz), 6.65 (d, 1H, J=8 Hz), 6.6 (d, 1H, J=8 Hz), 5.4 (s, 2H) and 4.0 (s, 6H). IR (KBr, cm$^{-1}$) 1727. MS (ES) m/e 422.

Elemental Analyses for C$_{28}$H$_{23}$NO$_3$: Calculated: C, 79.79; H, 5.50; N, 3.32. Found: C, 79.53; H, 5.61; N, 3.15.

D. 9-[(2-Biphenyl)methyl]-4-hydroxy-5-carbomethoxy carbazole

Boron tribromide (1.0 M in methylene chloride, 1.69 mL, 1.69 mM) was slowly added to a solution of 9-[(2-biphenyl) methyl]-4-methoxy-5-carbomethoxy carbazole (547 mg, 1.3 mM) in 5 mL methylene chloride at –10° C. After 2 hours, the mixture was quenched with methanol (1.31 mL, 32.5 mM) and stirred at room temperature for 5 hours. The mixture was diluted with ethyl acetate, washed with H$_2$O, 1 N HCl, H$_2$O, sat. NaHCO$_3$, and saturated brine, dried over magnesium sulfate, filtered, and concentrated. The residue was purified by column chromatography on silica gel (elution with methylene chloride) to afford 445 mg (84%) of the 9-[(2-biphenyl)methyl]-4-hydroxy-5-carbomethoxy carbazole as a yellow foam. $^1$H NMR (CDCl$_3$) δ10.35 (s, 1H), 7.95 (d, 1H, J=8 Hz), 7.6–7.2 (m, 10fH), 7.05 (t, 1H, J=8 Hz), 6.8 (m, 2H), 6.6 (d, 1H, J=8 Hz), 5.4 (s, 2H), and 4.1 (s, 3H). IR (KBr, cm$^{-1}$) 3200 (br), 1680, 1596, 1451, 1439, 1427, 1333, 1262, 1217, 1137, 752, 713, 1763 and 703. MS (ES) m/e 406, 408.

Elemental Analyses for C$_{27}$H$_{21}$NO$_3$: Calculated: C, 79.59; H, 5.19; N, 3.44. Found: C, 80.62; H, 5.73; N, 3.44.

E. 9-[(2-Biphenyl)methyl]-4-hydroxy-5-carbamoyl carbazole

A solution of the 9-[(2-biphenyl)methyl]-4-hydroxy-5-carbomethoxy carbazole (407.5 mg, 1.0 mM) in 5 mL THF and 20 mL concentrated aqueous ammonium hydroxide was sonicated for 28.5 hours at 40–50° C. The mixture was diluted with ethyl acetate and acidified to pH 1 with 5 N HCl. The aqueous layer was extracted three times with ethyl acetate. The combined organic extracts were washed with H$_2$O and saturated brine, dried over magnesium sulfate, filtered, and concentrated. The residue was purified by column chromatography on silica gel (elution with gradient methylene chloride/ethyl acetate) to afford 165 mg (42%) of the 9-[(2-biphenyl)methyl]-4-hydroxy-5-carbamoyl carbazole as a yellow solid. $^1$H NMR (DMSO-d6) δ10.45 (s, 1H), 8.8 (br s, 1H), 8.4 (br s, 1H), 7.6–7.2 (m, 11H), 7.05 (t, 1H, J=8 Hz), 6.75 (d, 1H, J=8 Hz), 6.55 (d, 1H, J=8 Hz), 6.35 (d, 1H, J=8 Hz), and 5.55 (s, 2H). IR (KBr, cm$^{-1}$) 3451, 3331, and 1639. MS (ES) m/e 391, 393.

Elemental Analyses for C$_{26}$H$_{20}$N$_2$O$_2$: Calculated: C, 79.57; H, 5.14; N, 7.14. Found: C, 79.60; H, 5.37; N, 6.90.

F. {9-[(2-Biphenyl)methyl]-5-carbamoylcarbazol-4-yl}oxyacetic acid, tert-butyl ester 40% Methanolic Triton B (0.2 mL, 0.44 mM) was added to a solution of the 9-[(2-biphenyl)methyl]-4-hydroxy-5-carbamoyl carbazole (141 mg, 0.36 mM) in 5 mL DMF at room temperature. After 5 minutes, t-butyl bromoacetate (107 mg, 0.54 mM) was added and the resultant mixture stirred at room temperature for 6.5 hours. The mixture was diluted with ethyl acetate, washed with H$_2$O, 1 N HCl, H$_2$O, sat. NaHCO$_3$, and saturated brine, dried over magnesium sulfate, filtered, and concentrated. The residue was purified by column chromatography on silica gel (elution with gradient methylene chloride/ethyl acetate) to afford 140 mg (76%) of the {9-[(2-biphenyl)methyl]-5-carbamoylcarbazol-4-yl}oxyacetic acid, tert-butyl ester as a white foam. $^1$H NMR (CDCl$_3$) δ7.6–7.2 (m, 13H), 7.05 (t, 1H, J=8 Hz), 6.85 (d, 1H, J=8 Hz), 6.6 (d, 1H, J=8 Hz), 6.55 (d, 1H, J=8 Hz), 5.4 (s, 2H), 4.8 (s, 2H), and 1.45 (s, 9H). IR (CHCl$_3$, cm$^{-1}$) 1753 and 1674. MS (ES) m/e 507.

Elemental Analyses for C$_{32}$H$_{30}$N$_2$O$_4$: Calculated: C, 75.87; H, 5.97; N, 5.53. Found: C, 76.10; H, 6.12; N, 5.37.

G. {9-[(2-Biphenyl)methyl]-5-carbamoylcarbazol-4-yl}oxyacetic acid

A solution of the {9-[(2-biphenyl)methyl]-5-carbamoylcarbazol-4-yl}oxyacetic acid, tert-butyl ester (116 mg, 0.23 mM) in 3 mL of trifluoroacetic acid was stirred at room temperature for 2 hours. The solvent was removed in vacuo. The residue was triturated with ethyl ether/hexanes, then dried in vacuo to afford 103 mg (100%) of the {9-[(2-biphenyl)methyl]-5-carbamoylcarbazol-4-yl}oxyacetic acid as a white powder. $^1$H NMR (DMSO-d6) δ12.95 (br s, 1H), 7.75 (s, 1H), 7.65 (d, 2H, J=8 Hz), 7.55 (t, 2H, J=8 Hz), 7.4 (s, 1H), 7.35–7.2 (m, 6H), 7.05 (m, 2H), 6.9 (d, 1H, J=8 Hz), 6.6 (d, 1H, J=8 Hz), 6.4 (d, 1H, J=8 Hz), 5.55 (s, 2H), and 4.8 (s, 2H). IR (KBr, cm$^{-1}$) 3400, 3200, 1736, 1636, 1618, 1583, 1499, 1455, 1433, 1329, 1249, 1155, 753, and 713. MS (ES) m/e 449, 451.

Elemental Analyses for C$_{28}$H$_{22}$N$_2$O$_4$: Calculated: C, 74.65; H, 4.92; N, 6.22. Found: C, 75.47; H, 4.77; N, 6.24.

EXAMPLE 45

Esterification of {9-[(2-Biphenyl)methyl]-5-carbamoylcarbazol-4-yl}oxyacetic acid to the {9-[(2-Biphenyl)methyl]-5-carbamoylcarbazol-4-yl}oxyacetic acid, methyl ester

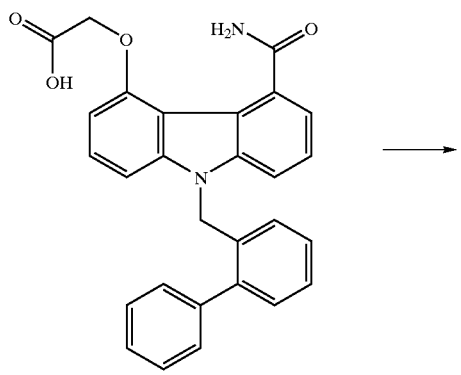

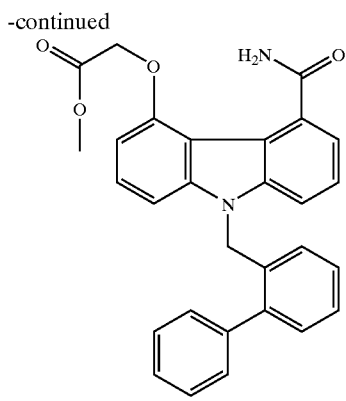

A suspension of the {9-[(2-biphenyl)methyl]-5-carbamoylcarbazol-4-yl}oxyacetic acid (35 mg, 0.08 mM), iodomethane (12 mg, 0.09 mM), and potassium carbonate (13 mg, 0.09 mM) in 2 mL DMF at room temperature for 4.5 hours. The mixture was diluted with ethyl acetate, washed with $H_2O$, sat. $NaHCO_3$, $H_2O$, and saturated brine, dried over magnesium sulfate, filtered, and concentrated to afford 36 mg (100%) of the {9-[(2-biphenyl)methyl]-5-carbamoylcarbazol-4-yl}oxyacetic acid, methyl ester as a white solid. $^1H$ NMR ($CDCl_3$) δ7.6–7.2 (m, 11H), 7.1 (t, 1H, J=8 Hz), 6.85 (d, 1H, J=8 Hz), 6.6 (d, 1H, J=8 Hz), 6.55 (d, 1H, J=8 Hz), 5.8 (br s, 2H), 5.4 (s, 2H), 4.8 (s, 2H), and 3.75 (s, 3H). IR (KBr, $cm^{-1}$) 1750 and 1666. MS (ES) m/e 465.

Elemental Analyses for $C_{29}H_{24}N_2O_4$: Calculated: C, 74.98; H, 5.21; N, 6.03. Found: C, 75.09; H, 5.57; N, 5.63.

EXAMPLE 46

Preparation of [9-Benzyl-4-carbamoyl-1,2,3,4-tetrahydrocarbaole-5-yl]oxyacetic acid

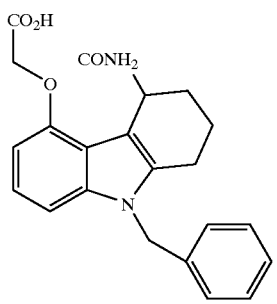

A. 9-Benzyl-4-carboxy-5-methoxy-1,2,3,4-tetrahydrocarbazole, Ethyl Ester

A solution of 1.50 g (4.02 mmol) of 9-Benzyl-4-carboxy-8-chloro-5-methoxy-1,2,3,4-tetrahydrocarbazole, ethyl ester and 0.45 g (4.40 mmol) of $Et_3N$ in 25 mL of EtOH was treated with 0.24 g of 5% Pd—C and the mixture hydrogenated at 60 pounds per square inch for 16 hours. The reaction was filtered and concentrated in vacuo to give 1.40 g of a tan solid. $^1H$ NMR ($CDCl_3$) δ7.30–7.19 (m, 3H), 7.03–6.95 (m, 3H), 6.80 (d, 1H, J=8.1 Hz), 6.44 (d, 1H, J=7.7 Hz), 5.22 (d, 2H, J=5.9 Hz), 4.22–4.11 (m, 3H), 3.82 (s, 3H), 2.75–2.64 (m, 1H), 2.59–2.48 (m, 1H), 2.11–1.64 (m, 4H), and 1.25 (t, 3H, J=7.0 Hz). IR ($CHCl_3$) 2959, 1725, 1499, 1453, 1260, 1178, 1128 cm–1;

Elemental Analyses for $C_{23}H_{25}NO_3$: Calculated: 363.1836. Found: 363.1834.

B. 9-Benzyl-4-carbamoyl-5-hydroxy-1,2,3,4-tetrahydrocarbazole

A 0° C. solution of 1.00 g (2.80 mmol) 9-benzyl-4-carboxy-5-methoxy-1,2,3,4-tetrahydrocarbazole, ethyl ester in 15 mL of $CH_2Cl_2$ was treated with 22.40 mL (22.40 mmol; 1M in $CH_2Cl_2$) of $BBr_3$. The cold bath was removed and the reaction stirred until tlc analysis (10% EtOAc in hexanes) indicated complete consumption of starting material (1.5 hours). The reaction was cooled to 0° C. and was quenched with 5.0 mL of MeOH. The mixture was stirred at ambient temperature for 18 hours and was concentrated in vacuo. The black oil was taken up in 200 mL of $CH_2Cl_2$ and the solution washed with $H_2O$ (100 mL) and saturated aqueous $NaHCO_3$ (100 mL). Evaporation of the solvent in vacuo afforded 700 mg of a black oil. Purification by radial chromatography (10% EtOAc in hexanes) afforded 400 mg of 9-benzyl-4-carboxy-5-hydroxy-1,2,3,4-tetrahydrocarbazole, ethyl ester which was taken on directly to the next reaction.

The phenol was taken up in 40 ml of THF and the solution treated with 10 mL of $NH_4OH$. The reaction vessel was capped and the mixture stirred vigorously for 13 days. The reaction was poured into $H_2O$ and the mixture extracted with EtOAc (3×150 mL). The combined organic layers were dried ($Na_2SO_4$), filtered and concentrated in vacuo to give 300 mg of a brown foam. Radial chromatography (3% MeOH in $CH_2Cl_2$) afforded 50 mg of starting phenol and 80 mg (0.03 mmol; 22%) of 9-benzyl-4-carbamoyl-5-hydroxy-1,2,3,4-tetrahydrocarbazole. $^1H$ NMR ($CDCl_3$) δ7.33–7.24 (m, 3H), 7.06–6.97 (m, 3H), 6.81 (d, 1H, J=8.1 Hz), 6.56 (d, 1H, J=7.5 Hz), 5.22 (d, 2H, J=2.2 Hz), 4.20–4.15 (m, 1H), 2.78–2.67 (m, 1H), 2.63–2.51 (m, 1H), 2.35–2.27 (m, 1H), and 2.09–1.91 (m, 3H), no phenol proton detected. IR (CHCl3) 3007, 1667, 1586, 1567, 1496, 1266 cm–1;

Elemental Analyses for $C_{20}H_{21}N_2O_2$: Calculated: 321.1603. Found: 321.1607.

C. [9-Benzyl-4-carbamoyl-1,2,3,4-tetrahydrocarbazole-5-yl]oxyacetic acid, Methyl Ester A solution of 80 mg (0.25 mmol) of 9-benzyl-4-carbamoyl-5-hydroxy-1,2,3,4-tetrahydrocarbazole in 2.5 mL of DMF was treated with 61 mg (0.30 mmol) of $Cs_2CO_3$ followed by 26 mg (0.30 mmol) of methyl bromoacetate. The mixture was stirred at room temperature until tlc indicated complete consumption of starting material (2 hours). The reaction was diluted with $H_2O$ (10 mL) and was extracted with EtOAc (3×10 mL). The combined organic layers were washed with $H_2O$ (3×20 mL), dried over $Na_2SO_4$, filtered, and concentrated in vacuo. The residue was purified by radial chromatography ($SiO_2$; 2.5% MeOH in $CH_2Cl_2$) to afford 50 mg (0.13 mmol; 51%) of [9-benzyl-4-carbamoyl-1,2,3,4-tetrahydrocarbazole-5-yl]oxyacetic acid, methyl ester as an oil. $^1H$ NMR ($CDCl_3$) δ7.33–7.21 (m, 3H), 7.05–6.98 (m, 3H), 6.98 (d, 1H, J=7.4 Hz), 6.46 (br s, 1H), 6.37 (d, 1H, J=7.7 Hz), 5.52 (br s, 1H), 5.23 (d, 1H, J=4.9 Hz) 4.79–4.70 (m, 2H), 4.20–4.15 (m, 1H), 3.81 (s, 3H), 2.79–2.69 (m, 1H), 2.63–2.49 (m, 1H), 2.43–2.35 (m, 1H), 2.25–2.09 (m, 1H), and 1.99–1.78 (m, 2H). IR ($CHCl_3$, $cm^{-1}$) 1759, 1670, 1497, 1453, 1440, and 1132. MS (ES) m/e 393 (M+1).

Elemental Analyses for $C_{23}H_{24}N_2O_4$: Calculated: C, 70.39; H, 6.16; N, 7.14. Found: C, 70.29; H, 6.31; N, 7.08.

D. [9-Benzyl-4-carbamoyl-1,2,3,4-tetrahydrocarbazole-5-yl]oxyacetic acid

A solution of 30 mg (0.076 mmol) of [9-benzyl-4-carbamoyl-1,2,3,4-tetrahydrocarbazole-5-yl]oxyacetic acid, methyl ester in 1.0 mL of THF and 1.0 mL of MeOH was treated with 0.2 mL of 1 N aqueous LiOH (0.2 mmol). The mixture was stirred for 18 hours. An additional 0.2 mL of 1 N aqueous LiOH (0.2 mmol) was added and stirring continued. After 1 hour, the mixture was concentrated in vacuo. The residue was dissolved in 2.0 mL of H$_2$O and the solution acidified with 0.2 N aqueous HCl. The solid was filtered and dried to afford 25 mg of [9-benzyl-4-carbamoyl-1,2,3,4-tetrahydrocarbazole-5-yl]oxyacetic acid as a white solid. $^1$H NMR (DMSO-d6) δ7.36–7.12 (m, 5H), 7.05–6.83 (m, 5H), 6.71 (br s, 1H), 6.35 (d, 1H, J=7.6 Hz), 5.27 (s, 2H), 4.64 (s, 2H), 3.93–3.84 (m, 2H), 2.75–2.64 (m, 1H), 2.16–1.95 (m, 2H), 1.81–1.64 (m, 2H) and 1 proton masked by H$_2$O peak between 2.58–2.40. IR (KBr, cm$^{-1}$) 3435, 2936, 1722, 1644, 1586, 1566, 1495, 1451, 1354, 1227, 1134, 730, 716, and 698. MS (ES) m/e 377 (M–1) and 379 (M+1).

Elemental Analyses for C$_{22}$H$_{22}$N$_2$O$_4$: Calculated: C, 69.83; H, 5.86; N, 7.40. Found: C, 70.11; H, 5.76; N, 7.12.

EXAMPLE 47

Preparation of {9-[(2-Pyridyl)methyl]-5-carbamoylcarbazol-4-yl}oxyacetic acid

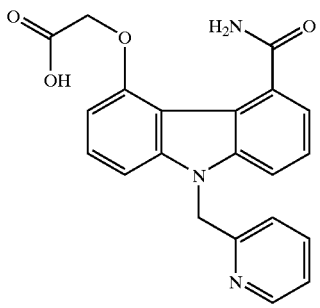

A. 9-[(2-Pyridyl)methyl]-5-carbomethoxy-1,2-dihydrocarbazol-4(3H)-one

A 0° C. suspension of 5-carbomethoxy-1,2-dihydro-9H-carbazol-4(3H)-one (1.50 g, 6.17 mmol), potassium carbonate (2.60 g, 18.8 mmol), and catalytic amount of sodium iodide (ca. 10 mg), was treated with 2-picolyl chloride hydrochloride (1.10 g, 6.70 mmol). The cold bath was removed and the reaction stirred at ambient temperature 72 hours. The reaction was poured into H$_2$O (100 mL) and the mixture extracted four times with ethyl acetate. The combined organic layers were washed four times with H$_2$O, once with saturated brine, dried over anhydrous sodium sulfate, filtered, and concentrated. The residue was purified by flash chromatography on silica gel (elution with 70% then 80% then 85% EtOAc in hexanes) to afford 1.70 g (82%) of the 9-[(2-pyridyl)methyl]-5-carbomethoxy-1,2-dihydrocarbazol-4(3H)-one as an oil which solidified on standing. $^1$H NMR (CDCl$_3$) δ8.52 (br s, 1H), 7.54–7.47 (m, 1H), 7.34–7.26 (m, 2H), 7.18–7.11 (m, 2H), 6.67 (d, J=7.8 Hz, 1H) 5.34 (s, 2H), 3.99 (s, 3H), 2.87 (t, 2H, J=6.0 Hz), 2.50 (t, 2H, J=6.3 Hz), and 2.20–2.13 (m, 2H). IR (CDCl$_3$, cm$^{-1}$) 3010, 2953, 1725, 1654, 1463, 1446, 1288 and 1121. MS (ES) m/e 335 (M+1).

Elemental Analyses for C$_{20}$H$_{18}$N$_2$O$_3$: Calculated: C, 71.84; H, 5.43; N, 8.38. Found: C, 71.70; H, 5.49; N, 8.37.
B. 9-[(2-Pyridyl)methyl]-4-hydroxy-5-carbomethoxy carbazole A solution of the 9-[(2-pyridyl)methyl]-5-carbomethoxy-1,2-dihydrocarbazol-4(3H)-one (500 mg, 1.50 mmol) in 2 mL of dioxane was treated with sodium hydride (140 mg; 3.50 mmol; 60% dispersion in mineral oil) and the mixture stirred for 15 minutes. Methyl benzenesulfinate (0.32 mL; 2.45 mmol) was added dropwise and the reaction stirred at room temperature. After 0.5 hours, gas evolution began and the reaction turned dark brown. The mixture was stirred until tlc indicated complete consumption of starting material (1 hour) at which time glacial acetic acid (0.20 mL; 3.50 mmol) was added. An additional 2 mL of dioxane was added to assist stirring and the mixture was heated to mild reflux for 1 hour. The reaction was cooled and diluted with EtOAc (50 mL). The organic layer was separated, washed once with saturated aqueous. NaHCO$_3$ and once with saturated brine, dried over anhydrous sodium sulfate, filtered, and concentrated. The residue was purified by radial chromatography on silica gel (elution with 20% ethyl acetate in hexanes) to afford 470.0 mg (94%) of the 9-[(2-pyridyl)methyl]-4-hydroxy-5-carbomethyoxy carbazole as a solid. $^1$H NMR (CDCl$_3$) δ10.37 (s, 1H), 8.61 (d, 1H, J=3.7 Hz), 8.01 (d, 1H, J=7.8 Hz), 7.63 (d, 1H, J=8.3 Hz), 7.47–7.39 (m, 3H), 7.19–7.14 (m, 1H), 6.94 (d, 1H, J=8.3 Hz), 6.84 (d, 1H, J=8.3 Hz), 6.59 (d, 1H, J=7.8 Hz), 5.66 (s, 2H), and 4.10 (s, 3H). IR (CHCl$_3$, cm$^{-1}$) 3200 (br), 1686, 1597, 1442, 1428, 1332, 1286, and 1268. MS (ES) m/e 333 (M+1).

Elemental Analyses for C$_{20}$H$_{16}$N$_2$O$_3$: Calculated: C, 72.28; H, 4.85; N, 8.43. Found: C, 72.44; H, 4.79; N, 8.44.
C. 9-[(2-Pyridyl)methyl]-$^4$-hydroxy-5-carbamoyl carbazole A solution of the 9-[(2-pyridyl)methyl]-4-hydroxy-5-carbomethoxy carbazole (480 mg, 1.43 mmol) in 10 mL THF and 40 mL concentrated aqueous ammonium hydroxide was treated with a stream of NH$_3$ gas to ensure saturation. The reaction vessel was capped and the mixture heated to 35° C. with stirring until tlc indicated complete consumption of starting material (20 hours). The THF was evaporated and the aqueous layer saturated with solid sodium chloride. The mixture was extracted three times with THF. The combined organic layers were dried over anhydrous sodium sulfate, filtered and concentrated. The foam was taken up in hot ethyl acetate and passed over a shoroom temperaturecolumn of silica gel using ethyl acetate as the eluent to afford 247 mg (54%) of the 9-[(2-pyridyl)methyl]-4-hydroxy-5-carbamoyl carbazole as a white solid. $^1$H NMR (DMSO-d6) δ10.46 (s, 1H), 8.81 (br s, 1H), 8.46 (d, 1H, J=5.8 Hz), 8.36 (br s, 1H), 7.8 (dd, 1H, J=2.9 and 6.4 Hz), 7.67–7.59 (m, 1H), 7.47–7.41 (m, 2H), 7.30–7.20 (m, 2H), 7.05 (d, 1H, J=7.9 Hz), 6.87 (d, 1H, J=8.3 Hz), 6.57 (d, 1H, J=7.8 Hz), and 5.73 (s, 2H). IR (KBr, cm$^{-1}$) 3404, 3051, 1652, 1618, 1595, 1582, 1567, 1559, 1450, 1436, 1334, 1266, 1226, 776, 763 and 647. MS (ES) m/e 318 (M+1).

Elemental Analyses for C$_{19}$H$_{15}$N$_3$O$_2$: Calculated: C, 71.91; H, 4.76; N, 13.24. Found: C, 72.11; H, 4.70; N, 12.95.
D. {9-[(2-Pyridyl)methyl]-5-carbamoylcarbazol-4-yl}oxyacetic acid, methyl ester A mixture of the 9-[(2-pyridyl)methyl]-4-hydroxy-5-carbamoyl carbazole (216 mg, 0.68 mmol) and Cs$_2$CO$_3$ (550 mg; 1.69 mmol) in 5 mL DMF was treated with methyl bromoacetate (0.08 mL; 0.85 mmol). The reaction was stirred until tlc analysis indicated complete consumption of starting material (2 hours). The mixture was concentrated and the residue taken up in H$_2$O (50 mL). The aqueous layer was saturated with solid NaCl and was extracted five times with THF. The combined organic layers were dried over anhydrous sodium sulfate, filtered and concentrated. The solid was triturated with EtOAc to afford 205 mg (77%) of the {9-[(2-pyridyl)methyl]-5-carbamoylcarbazol-4-yl}oxyacetic acid, methyl ester as an off white solid. $^1$H NMR (DMSO-d6) δ8.47 (d, 1H, J=4.9 Hz), 7.66–7.57 (m, 2H), 7.48 (br s, 1H), 7.38–7.27 (m, 2H), 7.24–7.19 (m, 2H), 7.19 (br s, 1H), 7.04 (d, 1H, J=7.3 Hz), 6.87 (d, 1H, J=7.8 Hz), 6.56 (d, 1H, J=7.8 Hz), 5.71 (s, 2H), 4.89 (s, 2H), and 3.69 (s, 3H). IR (CHCl$_3$, cm$^{-1}$) 3380, 3140, 1737, 1675, 1500, 1457, 1354, 1340, 1242, 1158, 772, and 715. MS (ES) m/e 390 (M+1).

Elemental Analyses for C$_{22}$H$_{19}$N$_3$O$_4$: Calculated: C, 67.86; H, 4.92; N, 10.79. Found: C, 67.75; H, 5.08; N, 10.66.

E. {9-[(2-Pyridyl)methyl]-5-carbamoylcarbazol-4-yl}oxyacetic acid, hydrochloride A slurry of the {9-[(2-pyridyl)methyl]-5-carbamoylcarbazol-4-yl}oxyacetic acid, methyl ester (75.0 mg, 0.19 mmol) in 1.3 mL of THF and 0.4 mL of MeOH was treated with 0.4 mL of 1 N aqueous LiOH (0.4 mmol) and the mixture stirred at room temperature for 16 hours. The reaction was concentrated and the residue purified by reverse phase chromatography (Vydac C18 column using a 5% to 40% gradient of 0.01% HCl in acetonitrile in 0.01% HCl in H$_2$O. The fractions containing product were lyopholized to afford 75 mg (96%) of {9-[(2-pyridyl)methyl]-5-carbamoylcarbazol-4-yl}oxyacetic acid hydrochloride as a white powder. $^1$H NMR (DMSO-d6) δ$^1$H NMR (DMSO-d6) δ8.50–8.46 (m, 1H), 7.71 (br s, 1H), 7.62–7.67 (m, 1H), 7.58 (d, 1H, J=8.3 Hz), 7.38 (br s, 1H), 7.42–7.29 (m, 3H), 7.26–7.19 (m, 2H), 7.06 (d, 1H, J=7.3 Hz), 6.87 (d, 1H, J=7.8 Hz), 6.58 (d, 1H, J=8.3 Hz) 5.73 (s, 2H) and 4.80 (s, 2H), no acid proton detected. IR (KBr, cm$^{-1}$) 3381, 1716, 1637, 1593, 1580, 1499, 1454, 1430, 1330, 1287, 1157, 1093, 776 and 720. MS (ES) m/e376 (M+1).

Elemental Analyses for C$_{21}$H$_{17}$N$_3$O$_4$.HCl: Calculated: C, 61.24; H, 4.41; N, 10.20. Found C, 61.11; H, 4.25; N, 10.23.

EXAMPLE 48

Preparation of {9-[(3-Pyridyl)methyl]-5-carbamoylcarbazol-4-yl}oxyacetic acid

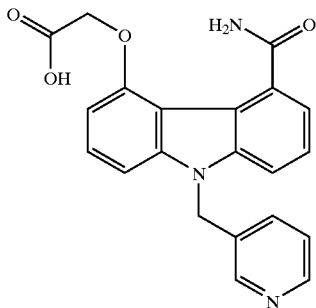

A. 9-[(3-Pyridyl)methyl]-5-carbomethoxy-1,2-dihydrocarbazol-4(3H)-one

A suspension of 5-carbomethoxy-1,2-dihydro-9H-carbazol-4(3H)-one (500 mg, 2.06 mmol), potassium carbonate (860 mg, 18.8 mmol), and catalytic amount of sodium iodide (ca. 10 mg), was treated with 3-picolyl chloride hydrochloride (500 mg, 3.05 mmol). The reaction was stirred at ambient temperature 19.5 hours. The mixture was poured into H$_2$O (100 mL) and the mixture extracted four times with ethyl acetate. The combined organic layers were washed four times with H$_2$O, once with saturated brine, dried over anhydrous sodium sulfate, filtered, and concentrated. The residue was purified by flash chromatography on silica gel (elution with 5% MeOH in EtOAc) to afford 550 mg (80%) of the 9-[(3-pyridyl)methyl]-5-carbomethoxy-1,2-dihydrocarbazol-4(3H)-one as a white solid. $^1$H NMR (CDCl$_3$) δ8.48 (d, 1H, J=2.9 Hz), 8.43 (br s, 1H), 7.31 (d, 1H, J=7.3 Hz), 7.25–7.09 (m, 5H), 5.29 (s, 2H), 3.97 (s, 3H), 2.80 (t, 2H, J=6.1 Hz), 2.49 (t, 2H, J=6.4 Hz), and 2.20–2.12 (m, 2H). IR (CDCl$_3$, cm$^{-1}$) 1726, 1656, 1464, 1444, 1434, 1289 and 1119. MS (ES) m/e 335 (M+1).

Elemental Analyses for C$_{20}$H$_{18}$N$_2$O$_3$: Calculated: C, 71.84; H, 5.43; N, 8.38. Found: C, 70.97; H, 5.89; N, 8.53.

B. 9-[(3-Pyridyl)methyl]-4-hydroxy-5-carbomethoxy carbazole

A solution of the 9-[(3-pyridyl)methyl]-5-carbomethoxy-1,2-dihydrocarbazol-4(3H)-one (456 mg, 1.31 mmol) in 3 mL of dioxane was treated with sodium hydride (128 mg; 3.20 mmol; 60% dispersion in mineral oil) and the mixture stirred for 15 minutes. Methyl benzenesulfinate (0.32 mL; 2.45 mmol) was added dropwise and the reaction heated to 70° C. until tlc analysis indicated complete consumption of starting material (2 hours). The reaction was cooled and diluted with EtOAc (50 mL). The organic layer was separated, washed once with saturated aqueous. NaHCO$_3$ and once with saturated brine, dried over anhydrous sodium sulfate, filtered, and concentrated. The residue was purified by radial chromatography on silica gel (elution with 20% then 30% then 50% then 75% ethyl acetate in hexanes) to afford 400 mg (92%) of the 9-[(3-pyridyl)methyl]-4-hydroxy-5-carbomethyoxy carbazole as a yellow solid. $^1$H NMR (DMSO-d6) δ10.20 (s, 1H), 8.46 (d, 1H, J=2.0 Hz), 8.39 (d, 1H, J=4.9 Hz), 7.73 (d, 1H, J=8.3 Hz), 7.43–7.37 (m, 2H), 7.28–7.21 (m, 2H), 7.15–7.08 (m, 2H), 6.56 (d, 1H, J=7.8 Hz), 5.67 (s, 2H), and 3.80 (s, 3H). IR (KBr, cm$^{-1}$) 1722, 1585, 1459, 1431, 1331, 1321, 1292, 1278, 1136, 781 and 763. MS (ES) m/e 333 (M+1).

Elemental Analyses for C$_{20}$H$_{16}$N$_2$O$_3$: Calculated: C, 72.28; H, 4.85; N, 8.43. Found: C, 72.37; H, 4.67; N, 8.71.

C. 9-[(3-Pyridyl)methyl]-4-hydroxy-5-carbamoyl carbazole

A solution of the 9-[(3-pyridyl)methyl]-4-hydroxy-5-carbomethoxy carbazole (362 mg, 1.09 mmol) in 15 mL THF and 60 mL concentrated aqueous ammonium hydroxide was treated with a stream of NH$_3$ gas to ensure saturation. The reaction vessel was capped and the mixture heated to 35° C. with stirring until tlc indicated complete consumption of starting material (48 hours). The mixture was neutralized to pH 8 with 5 N aqueous HCl, saturated with solid sodium chloride, and extracted twice with THF. The combined organic layers were concentrated. The resulting foam was taken up in a minimal amount of THF and loaded onto a silica gel column which had been pre equilibrated with EtOAc. Elution with EtOAc afforded 255 mg (74%) of the 9-[(3-pyridyl)methyl]-74-hydroxy-5-carbamoyl carbazole as a yellow solid. $^1$H NMR (DMSO-d6) δ10.46 (s, 1H), 8.79 (br s, 1H), 8.43 (d, 1H, J=1.5 Hz), 8.39 (dd, 1H, J=1.4 and 4.9 Hz), 8.35 (br s, 1H), 7.84 (d, 1H, J=7.8 Hz), 7.48–7.22 (m, 6H), 7.13 (d, 1H, J=8.3 Hz), 6.58 (d, 1H, J=7.8 Hz), and 5.73 (s, 2H). IR (KBr, cm$^{-1}$) 3436, 3198 (br), 1629, 1619, 1599, 1580, 1564, 1547, 1444, 1433, 1329, 1263, and 776. MS (ES) m/e 318 (M+1).

Elemental Analyses for C$_{19}$H$_{15}$N$_3$O$_2$: Calculated: C, 71.91; H, 4.76; N, 13.24. Found: C, 72.10; H, 4.66; N, 13.19.

D. {9-[(3-Pyridyl)methyl]-5-carbamoylcarbazol-4-yl}oxyacetic acid, methyl ester

A mixture of the 9-[(3-pyridyl)methyl]-4-hydroxy-5-carbamoyl carbazole (225 mg, 0.71 mmol) and Cs$_2$CO$_3$ (580 mg; 1.78 mmol) in 5 mL DMF was treated with methyl bromoacetate (0.09 mL; 0.95 mmol). The reaction was stirred until tlc analysis indicated complete consumption of starting material (2 hours). The mixture was concentrated and the residue taken up in H$_2$O (50 mL). The aqueous layer was saturated with solid NaCl and was extracted five times with THF. The combined organic layers were dried over anhydrous sodium sulfate, filtered and concentrated. The solid was triturated with THF then EtOAc to afford 85 mg of the {9-[(2-pyridyl)methyl]-5-carbamoylcarbazol-4-yl}oxyacetic acid, methyl ester as an off white solid. The mother liquors from the triturations were chromatographed over silica gel using radial chromatography (0.5% then 1% then 2% MeOH in CHCl$_3$) to afford an additional 80 mg of product (165 mg total; 60%). $^1$H NMR (CDCl$_3$) δ8.53 (br, 2H), 7.42–7.39 (m, 4H), 7.20 (d, 1H, J=7.8 Hz), 7.13 (br s, 1H), 6.98 (d, 1H, J=8.3 Hz), 6.56 (d, 1H, J=7.9 Hz), 6.17 (br s, 1H), 5.91 (br s, 1H), 5.49 (s, 2H), 4.88 (s, 2H), and 3.79 (s, 3H). IR (KBr, cm$^{-1}$) 3367, 3161, 1760, 1733, 1673, 1577, 1501, 1458, 1433, 1418, 1328, 1216, 1202, 1180, 1157, 771, and 714. MS (ES) m/e 373 (M+–NH$_2$) and 390 (M+1).

E. {9-[(3-Pyridyl)methyl]-5-carbamoylcarbazol-4-yl}oxyacetic acid, hydrochloride A slurry of the {9-[(3-pyridyl)methyl]-5-carbamoylcarbazol-4-yl}oxyacetic acid, methyl ester (85.0 mg, 0.22 mmol) in 1.5 mL of THF and 0.48 mL of MeOH was treated with 0.48 mL of 1 N aqueous LiOH (0.48 mmol) and the mixture stirred at room temperature for 16 hours. The reaction was concentrated and the residue purified by reverse phase chromatography (Vydac C18 column using a 5% to 40% gradient of 0.01% HCl in acetonitrile in 0.01% HCl in H$_2$O. The fractions containing product were lyopholized to afford 63 mg (70%) of {9-[(3-pyridyl)methyl]-5-carbamoylcarbazol-4-yl}oxyacetic acid hydrochloride as a white powder. $^1$H NMR (DMSO-d6) δ8.62–8.57 (m, 2H), 7.77–7.67 (m, 3H), 7.62–7.54 (m, 1H), 7.43–7.28 (m, 4H), 7.09 (d, 1H, J=6.3 Hz), 6.61 (d, 1H, J=7.8 Hz), 5.81 (s, 2H) and 4.80 (s, 2H), no acid proton detected. IR (KBr, cm$^{-1}$) 3424, 3324, 1728, 1671, 1655, 1616, 1595, 1579, 1500, 1456, 1421, 1328, 1203, 1156, and 772. MS (ES) m/e 374 (M–1), 376 (M+1).

Elemental Analyses for C$_{22}$H$_{17}$N$_3$O$_4$.HCl: Calculated: C, 61.24; H, 4.41; N, 10.20. Found: C, 61.28; H, 4.25; N, 10.28.

EXAMPLE 49

Preparation of [9-benzyl-4-carbamoyl-8-methyl-1,2,3,4-tetrahydrocarbazol-5-yl]oxyacetic acid A. Preparation of ethyl 5-methoxy-8-methyl-1,2,3,4-tetrahydrocarbazole-4-carboxylate A solution of 1.87 g (13.65 mmol) of 2-methyl-5-methoxyaniline and 3.40 g (13.65 mmol) of 2-carboethoxy-6-bromocyclohexanone (Sheehan and Mumaw, JACS, 72, 2127 (1950)) in 10 ml of anhydrous dimethylformamide was heated at 55° C. for 13 hours. The reaction mixture was cooled, poured into brine and extracted twice with diethyl ether. The extracts were washed twice with water and then with brine, dried over magnesium sulfate and concentrated. The residue was chromatographed on silica gel using a 10:1 hexane/ethyl acetate mixture to afford 2.88 g (69%) of a mixture of diastereomers of N-alkylated material. This mixture was refluxed in 90 ml of benzene with 4.69 g (34.4 mmol) of zinc chloride for 10 hours. The solvent was evaporated and the residue was partitioned between 80 ml of 1 N HCl and 80 ml of ethyl acetate and then extracted once more with ethyl acetate. The organic layers were washed with water and then brine, dried over magnesium sulfate and concentrated to afford 2.60 g (95%) of the subtitled compound. m.p. 119–122° C.

Elemental Analyses Calculated: C, 71.06; H, 7.37; N, 4.87. Found: C, 71.35; H, 7.25; N, 4.92.

B. Preparation of ethyl 9-benzyl-5-methoxy-8-methyl-1,2,3,4-tetrahydtocarbazole-4-carboxylate A solution of 1.58 g of ethyl 5-methoxy-8-methyl-1,2,3,4-tetrahydrocarbazole-4-carboxylate in 5 ml of dimethylformamide was added to 0.24 g of sodium hydride (60% in mineral oil) in 5 ml of dimethylformamide and stirred for 30 minutes at room temperature. Potassium iodide (90 mg) and 0.75 ml of benzyl bromide were then added and the reaction was stirred overnight. The reaction mixture was poured into 75 ml of saturated ammonium chloride solution and then extracted twice with ether. The extracts were washed with water and then with brine, dried over magnesium sulfate and concentrated. The residue was chromatographed on silica gel using hexane/ethyl acetate mixtures to afford 1.09 g (53%) of the subtitle compound. ESIMS m/e 378 (M$^+$+1) NMR (300 MHz, CDCl$_3$): δ7.28–7.19 (m, 3H); 6.84 (d, J=7.4, 2H); 6.67 (d, J=7.8, 1H); 6.33 (d, J=7.9, 1H); 5.55 and 5.39 (ABq, J=7.8, 2H); 4.17 (q+m, J=6.9, 3H); 3.80 (s, 3H); 2.64 (dt, J=16.1, 5.3, 1H); 2.48 (dt, J=16.6, 6.9,1H); 2.41 (s, 3H); 2.05 (m, 2H); 1.95 (m, 1H); 1.83 (m, 1H); 1.25 (t, J=7.3, 3H).

C. Preparation of 9-benzyl-5-methoxy-8-methyl-1,2,3,4-tetrahydrocarbazole-4-carboxamide A slurry of 0.38 g of ammonium chloride in 15 ml of dry toluene was cooled in an ice bath and treated with 3.5 ml of a 2.0 M solution of trimethylaluminum in toluene. This mixture was stirred for 1 hour at room temperature, whereupon 0.762 g (2.02 mmol) of ethyl 9-benzyl-5-methoxy-8-methyl-1,2,3,4-tetrahydrocarbazole-4-carboxylate in 10 ml of toluene and 1 ml of dichloromethane was added. The mixture was heated to 50° C. overnight, cooled and quenched with 20 ml of aqueous 5% HCl solution. Ethyl acetate extracts (3×100 ml) were washed with water and then with brine, dried over magnesium sulfate and concentrated to afford 0.693 g (98%) of the subtitle compound. ESIMS m/e 349 (M$^+$+1) NMR (300 MHz, CDCl$_3$): δ7.25 (m, 3H); 6.83 (d, J=7.2, 2H); 6.74 (d, J=7.8, 1H); 6.40 (d, J=7.8, 1H); 5.93 (br, 1H); 5.54 and 5.45 (ABq, J=17.7, 2H); 5.42 (br, 1H); 4.14 (br, 1H); 3.87 (s, 3H); 2.65 (dt, J=16.4, 4.1, 1H); 2.55–2.36 (m,2H); 2.45 (s, 3H); 1.97–1.86 (m, 3H).

D. Preparation of [9-benzyl-4-carbamoyl-8-methyl-1,2,3,4-tetrahydrocarbazol-5-yl[oxyacetic acid methyl ester A solution of 0.661 g of 9-benzyl-5-methoxy-8-methyl-1,2,3,4-tetrahydrocarbazole-4-carboxamide in 50 ml of dry dichloromethane was cooled to −40° C. and treated dropwise with 1.8 ml of neat boron tribromide. The reaction was stirred for 2 hours at room temperature and quenched by pouring into ice and adding 1 N HCl solution. This mixture was extracted twice with dichloromethane and the organic layers were dried over magnesium sulfate and concentrated to afford 0.625 g of the demethylated compound.

A solution of 0.55 g of this intermediate in 10 ml of dimethylformamide was cooled in an ice bath and treated with 1.61 g of cesium carbonate and 0.16 ml of methyl bromoacetate. After stirring for 1 hour at room temperature, the reaction mixture was poured into water and extracted twice with ethyl acetate. The extracts were washed with water and then with brine, dried over magnesium sulfate and concentrated. The residue was chromatographed on silica gel using methanol/0–2% in dichloromethane to afford 0.46 g (69%) of the subtitle compound. m.p. 209° C.

Elemental Analyses Calculated: C, 70.92; H, 6.45; N, 6.89. Found: C, 70.85; H, 6.19; N, 6.98.

E. Preparation of [9-benzyl-4-carbamoyl-8-methyl-1,2,3,4-tetrahydrocarbazol-5-yl]oxyacetic acid]

A slurry of 64 mg (0.157 mmol) of [9-benzyl-4-carbamoyl-8-methyl-1,2,3,4-tetrahydrocarbazol-5-yl]oxyacetic acid methyl ester in 2 ml of tetrahydrofuran and 7 ml of methanol was treated with 0.5 ml of an aqueous 2 N sodium hydroxide solution and stirred overnight at room temperature. The solvent was evaporated and the residue was partitioned between ethyl acetate and 1 N HCl solution. After another extraction with ethyl acetate, the extracts were washed with brine, dried over magnesium sulfate and concentrated to afford a quantitative yield (62 mg) of the title compound. ESIMS m/e 393 (M$^+$+1), 391 (M$^+$−1). NMR (300 MHz, d$^6$-DMSO): δ12.98 (br, 1H); 7.30–7.18 (m, 3H); 6.82 (d+br, J=7.0, 3H); 6.73 (br, 1H); 6.59 (d, J=7.9,1H);

6.26 (d, J=7.9, 1H); 5.53 and 5.45 (ABq, J=18.1, 2H); 4.62 (s, 2H); 3.96 (br, 1H); 2.63 (m, 1H); 2.43 (m, 1H); 2.34 (s, 3H); 2.04 (m, 2H); 1.78 (m, 2H).

Elemental Analyses Calculated: C, 70.39; H, 6.16; N, 7.14. Found: C, 70.41; H, 6.44; N, 6.88.

EXAMPLE 50

Preparation of [9-benzyl-5-carbamoyl-1-methylcarbazol-4-yl]oxyacetic acid

A. Preparation of 5-carbamoyl-4-methoxy-1-methylcarbazole

A solution of 0.805 g of 9-benzyl-5-methoxy-8-methyl-1,2,3,4-tetrahydrocarbazole-4-carboxamide in 24 ml of carbitol was treated with 1.1 g of 5% palladium on carbon and was refluxed for 6 hours open to the air. After cooling, the solution was filtered thourough a pad of celite and the pad was washed with ethyl acetate. The filtrates were diluted with ether and washed four times with water and dried over magnesium sulfate and concentrated. The residue was chromatographed on silica gel using methanol/0–4% in dichloromethane to afford 0.166 g (28%) of debenzylated carbazole. ESIMS m/e 255 ($M^++1$), 253 ($M^+-1$) NMR (300 MHz, CDCl$_3$): $\delta$8.13 (br, 1H); 7.51 (d, J=8.1, 1H); 7.40 (t, J=7.6, 1H); 7.32 (d, J=7.2, 1H); 7.18 (d, J=7.8, 1H); 6.60 (d, J=8.0, 1H); 5.68 (br, 2H); 3.99 (s, 3H); 2.50 (s 3H).

B. Preparation of 9-benzyl-5-carbamoyl-4-methoxy-1-methylcarbazole

A solution of 0.148 g of 5-carbamoyl-4-methoxy-1-methylcarbazole in 1.1 ml of dimethylformamide was added to 0.026 g of sodium hydride (60% in mineral oil) in 0.4 ml of dimethylformamide and stirred for 60 minutes at room temperature. Benzyl bromide (0.076 ml) was then added and the reaction was stirred overnight. The reaction mixture was poured into 20 ml of saturated ammonium chloride solution and then extracted twice with ethyl acetate. The extracts were washed with water and then with brine, dried over magnesium sulfate and concentrated. The residue was rinsed with hexane and dissolved in dichloromethane, filtered and concentrated to afford 0.21 g of the subtitle compound. FDMS m/e 344 ($M^+$).

Elemental Analyses Calculated: C, 76.72; H, 5.85; N, 8.13. Found: C, 75.20; H, 6.19; N, 7.54.

C. Preparation of [9-benzyl-5-carbamoyl-1-methylcarbazol-4-yl]oxyacetic acid methyl ester]

A solution of 0.23 g of 9-benzyl-5-carbamoyl-4-methoxy-1-methylcarbazole in 4 ml of dimethylformamide was added to a 1 ml solution of sodium ethane thiolate (prepared from 0.116 g of sodium hydride 60% dispersion and 0.22 ml of ethanethiol under nitrogen) and heated at 110° C. for 15 hours. The reaction mixture was cooled, poured into 20 ml of 1 N HCl and extracted twice with ethyl acetate. The extracts were washed twice with water and then with brine, dried over magnesium sulfate and concentrated. The residue was chromatographed on silica gel using methanol/0–1% in dichloromethane to afford 0.146 g (66%) of the demethylated intermediate. A solution of 0.146 g of this intermediate in 1.5 ml of dimethylformamide was added to 0.021 g of sodium hydride (60% in mineral oil) in 0.5 ml of dimethylformamide. After stirring for 10 minutes at room temperature, 0.054 ml of methyl bromoacetate was added. After stirring for 5 hours at room temperature, the reaction mixture was poured into water and extracted twice with ethyl acetate. The extracts were washed with water and then with brine, dried over magnesium sulfate and concentrated. The residue was chromatographed on silica gel using methanol/0–2% in dichloromethane to afford 0.10 g (56%) of the subtitle compound. mp. 228–230° C. ESIMS m/e 403 ($M^++1$)

Elemental Analyses Calculated: C, 71.63; H, 5.51; N, 6.96. Found: C, 71.34; H, 5.60; N, 6.70.

D. Preparation of [9-benzyl-5-carbamoyl-1-methylcarbazol-4-yl]oxyacetic acid

A slurry of 32 mg (0.0795 mmol) of [9-benzyl-5-carbamoyl-1-methylcarbazol-4-yl]oxyacetic acid methyl ester in 1 ml of tetrahydrofuran and 3.5 ml of methanol was treated with 0.3 ml of an aqueous 2 N sodium hydroxide solution and stirred overnight at room temperature. The solvent was evaporated and the residue was partitioned between 1:1 ethyl acetate/tetrahydrofuran and 0.2 N HCl solution. After another extraction with 1:1 ethyl acetate/tetrahydrofuran, the extracts were washed with brine, dried over magnesium sulfate and concentrated to afford (27 mg) of the title compound. mp. 253–254° C. ESIMS m/e 389 ($M^++1$), 387 ($M^+-1$) NMR (300 MHz, d$^6$-DMSO): $\delta$12.83 (br, 1H); 7.75 (br, 1H); 7.53 (d, J=8.2, 1H); 7.41–7.34 (m, 2H); 7.28–7.17 (m, 3H); 7.07 (m, 2H); 6.90 (d, J=7.2, 2H); 6.49 (d, J=8.1, 1H); 5.89 (s, 2H); 4.79 (s, 2H); 2.52 (s, 3H).

EXAMPLE 51

Preparation of [9-benzyl-4-carbamoyl-8-fluoro-1,2,3,4-tetrahydrocarbazol-5-yl]oxyacetic acid A. Preparation of (2-chloro-4-fluorophenyl)-ethyl carbonate A solution of 19.16 g of 2-chloro-4-fluorophenol in 65.4 ml of 2 N aqueous sodium hydroxide solution was cooled in an ice bath and treated dropwise with 16.3 ml of ethyl chloroformate. After stirring at room temperature overnight, the two-phase reaction mixture was diluted with 100 ml of water and extracted with 300 ml of a 1:1 pentane/ether mixture. The extract was washed three times with 0.02 N sodium hydroxide solution, water and then brine. After drying and evaporation, 27.63 g (97%) of the subtitle compound were obtained. NMR (300 MHz, CDCl$_3$): $\delta$7.23–7.18 (m, 2H); 7.00 (dt, J=8.4, 2.7, 1H); 4.35 (q, J=7.1, 2H); 1.40 (t, J=7.1, 3H).

B. Preparation of (2-chloro-4-fluoro-5-nitrophenyl)-ethyl carbonate

A solution of 27.63 g of (2-chloro-4-fluorophenyl)-ethyl carbonate in 60 ml of dichloromethane was cooled in an ice bath and treated dropwise with 31.86 g of a 1:2 mixture of fuming nitric acid (90%) and concentrated sulfuric acid. The reaction was stirred for 2 hours at room temperature and then cooled with ice and treated with another 4.5 g of the same nitrating mixture. The reaction was stirred overnight at room temperature, poured into 200 ml of ice and water, and extracted twice with dichloromethane. The extracts were washed with water and then with brine, dried over magnesium sulfate and concentrated to afford 33.01 g (99%) of the subtitle compound. mp. 50–51° C.

Elemental Analyses Calculated: C, 41.01; H, 2.68; N, 5.31; Cl, 13.45. Found: C, 41.03; H, 2.59; N, 5.38; Cl, 13.71.

C. Preparation of 2-chloro-4-fluoro-5-nitroanisole

A solution of 15.0 g of (2-chloro-4-fluoro-5-nitrophenyl)-ethyl carbonate in 100 ml of dimethyl formamide was treated with 18.6 g of cesium carbonate, 7.1 ml of iodomethane and 7 ml of methanol and stirred overnight at room temperature. The reaction mixture was poured into water and extracted twice with ether. The extracts were washed twice with water and then with brine, dried over magnesium sulfate and concentrated to afford 11.4 g of the subtitle compound. mp. 69–70° C. Ex. 57, C.

Elemental Analyses Calculated: C, 40.90; H, 2.45; N, 6.81; Cl, 17.25. Found: C, 41.20; H, 2.48; N, 6.70; Cl, 17.44.

D. Preparation of 2-fluoro-5-methoxyaniline

A solution of 5.63 g of 2-chloro-4-fluoro-5-nitroanisole in 90 ml of ethanol and 5 ml of triethylamine was hydrogenated at room temperature under 60 pounds per square inch with 1.0 g of 5% palladium on carbon for four hours. The catalyst was filtered off and the solvent was evaporated. The residue was slurried in chloroform and filtered thourough a plug of silica gel and then evaporated.

This residue was chromatographed on silica gel using hexane/chloroform mixtures to afford 2.77 g (72%) of the subtitle compound. mp. 253–254° C. NMR (300 MHz, CDCl$_3$): $\delta$6.88 (dd, J=10.6, 8.9, 1H); 6.32 (dd, J=7.4, 3.0, 1H); 6.20 (dt, J=8.9, 3.2,1H); 3.73 (s, 3H); 3.72 (br, 2H).

E. Preparation of N-benzyl-2-fluoro-5-methoxyaniline

This procedure was patterned after that of Tietze and Grote, Chem Ber. 126(12), 2733 (1993). A solution of 2.73 g of 2-fluoro-5-methoxyaniline and 2.67 g of benzaldehyde in 48 ml of methanol was treated with 3.43 g of zinc chloride and then cooled in an ice bath. Sodium cyanoborohydride (1.58 g) was added in small poroom temperature ions over 30 minutes and the reaction was stirred for five hours at room temperature. After evaporation of the solvent, the residue was slurried in 40 ml of 1 N sodium hydroxide solution and then extracted twice with ether. The extracts were washed with water and then with brine, dried over magnesium sulfate and concentrated. The residue was recrystallized from hexane to afford 2.61 g and the mother liquors were chromatographed on silica gel using 20:1 hexane/ether to afford another 1.4 g of the subtitle compound (90%). mp. 56–58° C.

Elemental Analyses Calculated: C, 72.71; H, 6.10; N, 6.06. Found: C, 72.51; H, 6.06; N, 5.99.

F. Preparation of ethyl 9-benzyl-5-methoxy-8-fluoro-1,2,3,4-tetrahydrocarbazole-4-carboxylate A solution of 0.62 g of N-benzyl-2-fluoro-5-methoxyaniline in 20 ml of dry tetrahydrofuran was cooled in an ice bath and treated with 11.3 ml of 0.5 M potassium bis(trimethylsilyl)amide in toluene. After stirring for 30 minutes, 0.74 g of 2-carboethoxy-6-bromocyclohexanone (Sheehan and Mumaw, JACS, 72, 2127 (1950)) in 4 ml of tetrahydrofuran was added and the reaction was allowed to warm slowly to room temperature over two hours. The reaction was quenched with saturated ammonium chloride solution and extracted twice with ether. The extracts were washed with water and then with brine, dried over magnesium sulfate and concentrated. This residue was chromatographed on silica gel using hexane/ether mixtures to afford 0.796 g (74%) of N-alkylated intermediate diastereomers. This mixture was refluxed in 20 ml of benzene with 0.99 g of zinc chloride overnight. The solvent was evaporated and the residue was partitioned between 25 ml of 1 N HCl and 25 ml of ethyl acetate and then extracted once more with ethyl acetate. The organic layers were washed with water and then brine, dried over magnesium sulfate and concentrated to afford 0.734 g (96%) of the subtitled compound. ESIMS m/e 382 (M$^+$+1)

Elemental Analyses Calculated: C, 72.42; H, 6.34; N, 3.67. Found: C, 72.20; H, 6.26; N, 3.70.

G. Preparation of 9-benzyl-5-methoxy-8-fluoro-1,2,3,4-tetrahydrocarbazole-4-carboxamide Ethyl 9-benzyl-5-methoxy-8-fluoro-1,2,3,4-tetrahydrocarbazole-4-carboxylate (0.722 g) was treated similarly as described in Example 49, Part C and chromatographed on silica gel using 1% methanol in dichloromethane to afford 0.482 g (72%) of the subtitle compound. ESIMS m/e 353 (M$^+$+1)

Elemental Analyses Calculated: C, 71.57; H, 6.01; N, 7.95. Found: C, 71.42; H, 5.83; N, 7.75.

H. Preparation of [9-benzyl-4-carbamoyl-8-fluoro-1,2,3,4-tetrahydrocarbazol-5-yl]oxyacetic acid methyl ester 9-Benzyl-5-methoxy-8-fluoro-1,2,3,4-tetrahydrocarbazole-4-carboxamide (0.170 g) was converted similarly as described in Example 49, Part D and chromatographed on silica gel using methanol/0–1% in dichloromethane to afford 85 mg (50%) of the subtitle compound. mp. 183–185° C.

Elemental Analyses Calculated: C, 67.31; H, 5.65; N, 6.82. Found: C, 67.58; H, 5.48; N, 6.95.

I. Preparation of [9-benzyl-4-carbamoyl-8-fluoro-1,2,3,4-tetrahydrocarbazol-5-yl]oxyacetic acid

[9-Benzyl-4-carbamoyl-8-fluoro-1,2,3,4-tetrahydrocarbazol-5-yl]oxyacetic acid methyl ester (71 mg) was hydrolyzed similarly as described in Example 50, Part D to afford 65 mg of the title compound. ESIMS m/e 397 (M$^+$+1), 395 (M$^+$−1) NMR (300 MHz, d$^6$-DMSO): $\delta$13.03 (br, 1H); 7.31–7.19 (m, 3H); 6.97 (d, J=7.4, 2H); 6.95 (br, 1H); 6.70 (d, J=3.8, 1H); 6.67 (dd, J=12.4, 3.9, 1H); 6.28 (dd, J=8.5, 2.6, 1H); 5.39 (ABq, 2H); 4.64 (s, 2H); 3.92 (br, 1H); 2.71 (m, 1H); 2.44 (m, 1H); 2.02 (m, 2H); 1.76 (m, 2H).

EXAMPLE 52

Preparation of [9-benzyl-5-carbamoyl-1-fluorocarbazol-4-yl]oxyacetic acid

A. Preparation of 9-benzyl-5-carbamoyl-4-methoxy-1-fluorocarbazole

A solution of 0.458 g of 9-benzyl-5-methoxy-8-fluoro-1,2,3,4-tetrahydrocarbazole-4-carboxamide in 13 ml of dry dioxane under nitrogen was treated with 0.59 g of 2,3-dichloro-5,6-dicyano-1,4-benzoquinone and refluxed for one hour. The reaction mixture was cooled and filtered and the precipitate was washed with 15 ml of dioxane. The filtrate and washing were poured into saturated sodium bicarbonate solution and extracted three times with ethyl acetate. The extracts were washed with saturated sodium bicarbonate, with water and then with brine; dried over magnesium sulfate and concentrated. This residue was chromatographed on silica gel using dichloromethane/0–2% methanol to afford 0.45 g of subtitle compound. ESIMS m/e 349 (M$^+$+1)

Elemental Analyses Calculated: C, 72.42; H, 4.92; N, 8.04. Found: C, 72.35; H, 4.81; N, 7.88.

B. Preparation of [9-benzyl-5-carbamoyl-1-fluorocarbazol-4-yl]oxyacetic acid methyl ester A solution of 0.45 g of 9-benzyl-5-carbamoyl-4-methoxy-1-fluorocarbazole in 25 ml of dichloromethane was cooled in an ice bath treated dropwise with 12 ml of 1.0 M boron tribromide solution in dichloromethane. The reaction was allowed to warm to room temperature slowly over 2 hours and then quenched by pouring into ice and then adding 50 ml of 1 N HCl. The mixture was extracted with dichloromethane (3×200 ml) and the extracts were dried over magnesium sulfate and concentrated to afford 0.35 g (78%) of the demethylated intermediate. This intermediate (0.215 g) was alkylated and purified similarly to Example GH1, Part D to afford 0.166 g (64%) of the subtitle compound. mp. 190–191° C.

Elemental Analyses Calculated: C, 67.97; H, 4.71; N, 6.89. Found: C, 67.81; H, 4.94; N, 6.96.

C. Preparation of [9-benzyl-5-carbamoyl-1-fluorocarbazol-4-yl]oxyacetic acid

[9-Benzyl-5-carbamoyl-1-fluorocarbazol-4-yl]oxyacetic acid methyl ester (56 mg) was hydrolyzed and isolated similarly as described in Example 50, Part D to afford 54 mg of the title compound. FDMS m/e 392 (M$^+$); ESIMS m/e 393 (M$^+$+1), 391 (M$^+$−1) NMR (300 MHz, d$^6$-DMSO): $\delta$12.92

(br, 1H); 7.70 (m, 2H); 7.45 (t, J=7.5, 1H); 7.39 (br, 1H); 7.28–7.17 (m, 4H); 7.12 (d, J=7.2, 1H); 7.07 (d, J=7.0, 2H); 6.51 (dd, J=8.8, 2.7, 1H); 5.77 (s, 2H); 4.80 (s, 2H).

Elemental Analyses Calculated: C, 67.34; H, 4.37; N, 7.14. Found: C, 66.92; H, 4.49; N, 6.77.

EXAMPLE 53

Preparation of [9-benzyl-4-carbamoyl-8-chloro-1,2, 3,4-tetrahydrocarbazol-5-yl]oxyacetic acid A. Preparation of ethyl 9-benzyl-5-methoxy-8-chloro-1,2,3, 4-tetrahydrocarbazole-4-carboxylate N-benzyl-2-chloro-5-methoxyaniline was prepared similarly to Example 51, Part E. A solution of 2.07 g of N-benzyl-2-chloro-5-methoxyaniline in 60 ml of dry tetrahydrofuran was converted similarly to Example GH3, Part F and chromatographed on silica gel using 15:1 hexane/ethyl acetate to afford 1.65 g (50%) of the subtitle compound. Ex. 59, A. ESIMS m/e 398 (M$^+$+1) NMR (300 MHz, CDCl$_3$): δ7.29–7.19 (m, 3H); 6.92 (m, 3H); 6.36 (d, J=8.4, 1H); 5.87 (d, J=17.4, 1H); 5.53 (d, J=17.3, 1H); 4.16 m, 3H); 3.81 (s, 3H); 2.66 (dt, J=16.3, 5.4, 1H); 2.49 (dt, J=16.6, 6.6, 1H); 2.05 (m, 2H); 1.98–1.79 (m, 2H); 1.25 (t, 3H).

B. Preparation of 9-benzyl-5-methoxy-8-chloro-1,2,3,4-tetrahydrocarbazole-4-carboxamide Ethyl 9-benzyl-5-methoxy-8-chloro-1,2,3,4-tetrahydrocarbazole-4-carboxylate (1.65 g) was converted similarly to Example 51, Part G to afford 1.54 g (100%) of the subtitle compound. Ex. 59, B. mp. 205–8° C. ESIMS m/e 369 (M$^+$+1).

C. Preparation of [9-benzyl-4-carbamoyl-8-chloro-1,2,3,4-tetrahydrocarbazol-5-yl]oxyacetic acid methyl ester 9-Benzyl-5-methoxy-8-chloro-1,2,3,4-tetrahydrocarbazole-4-carboxamide (0.405 g) was converted similarly to Example 51, Part H and chromatographed on silica gel using dichlormethane/0–1.5% methanol to afford 0.248 g (53%) of the subtitle compound. Ex. 59, C. m.p. 185–186° C.

Elemental Analyses Calculated: C, 64.71; H, 5.43; N, 6.56. Found: C, 64.98; H, 5.39; N, 6.67.

D. Preparation of [9-benzyl-4-carbamoyl-8-chloro-1,2,3,4-tetrahydrocarbazol-5-yl]oxyacetic acid

[9-Benzyl-4-carbamoyl-8-chloro-1,2,3,4-tetrahydrocarbazol-5-yl]oxyacetic acid methyl ester (58 mg) was hydrolyzed similarly as described in Example 49, Part E to afford 54 mg of the title compound. Ex. 59, D. ESIMS m/e 413 (M$^+$+1), 411 (M$^+$−1) NMR (300 MHz, d$^6$-DMSO): δ13.05 (br, 1H); 7.30–7.18 (m, 3H); 6.90 (d+m, J=7.6, 4H); 6.73 (br, 1H); 6.39 (d, J=8.3, 1H); 5.77 and 5.58 (ABq, J=17.5, 2H); 4.67 (s, 2H); 3.95 (br, 1H); 2.66 (m, 1H); 2.43 (m, 1H); 2.00 (m, 2H); 1.76 (m, 2H).

Elemental Analyses Calculated: C, 64.00; H, 5.13; N, 6.78; Cl, 8.59. Found: C, 62.82; H, 5.34; N, 6.22; Cl, 7.99.

EXAMPLE 54

Preparation of [9-benzyl-5-carbamoyl-1-chlorocarbazol-4-yl]oxyacetic acid

A. Preparation of 9-benzyl-5-carbamoyl-4-methoxy-1-chlorocarbazole

A solution of 1.0 g of 9-benzyl-5-methoxy-8-methyl-1,2, 3,4-tetrahydrocarbazole-4-carboxamide was oxidized similarly to Example 51, Part A and chromatographed on silica gel using dichloromethane/0–1% methanol to afford 0.66 g (67%) of the subtitle compound. FDMS m/e 364 (M$^+$)

Elemental Analyses Calculated: C, 69.14; H, 4.70; N, 7.68; Cl, 9.72. Found: C, 69.40; H, 4.64; N, 7.49; Cl, 9.98.

B. Preparation of 5-carbamoyl-4-hydroxy-1-chlorocarbazole

A solution of 0.66 g of 9-benzyl-5-carbamoyl-4-methoxy-1-chlorocarbazole in 40 ml of dichloromethane was cooled in an ice bath treated dropwise with 14 ml of 1.0 M boron tribromide solution in dichloromethane. The reaction was allowed to warm to room temperature slowly over 2 hours and then quenched by pouring into ice and then adding 50 ml of 1 N HCl. The mixture was extracted with dichloromethane (3×200 ml) and the extracts were washed with brine, dried with magnesium sulfate and concentrated. The aqueous layers exhibited a precipitate and was then extracted twice with ethyl acetate, washed with brine, dried with magnesium sulfate and concentrated to afford 0.287 g of the subtitle compound. The first residue was chromatographed on silica gel using 0.5% methanol in dichloromethane to afford another 93 mg of the subtitle compound. (total yield 80%) ESIMS m/e 259 (M$^+$−1) NMR (300 MHz, d$^6$-DMSO): δ11.79 (s, 1H); 10.76 (s, 1H); 8.87 (br s, 1H); 8.41 (br s, 1H); 7.77 (t, J=4.6, 1H); 7.48 (d, J=4.2, 2H); 7.34 (d, J=8.5, 1H); 6.54 (d, J=8.5, 1H).

C. Preparation of [5-carbamoyl-1-chlorocarbazol-4-yl]oxyacetic acid methyl ester A solution of 0.28 g of 5-carbamoyl-4-hydroxy-1-chlorocarbazole in 6 ml of tetrahydrofuran was added to 0.043 g of sodium hydride (60% in mineral oil) in 1 ml of tetrahydrofuran and stirred for 60 minutes at room temperature. Methyl bromoacetate (0.11 ml) was then added and the reaction was stirred overnight. The reaction mixture was poured into 20 ml of saturated ammonium chloride solution and then extracted twice with ethyl acetate. The extracts were washed with water and then with brine, dried over magnesium sulfate and concentrated. The residue was chromatographed on silica gel eluting with chloroform and then 2:1 chloroform/ethyl acetate to afford 0.16 g (45%) of the subtitle compound. ESIMS m/e 333 (M$^+$+1), 335 (M$^+$+3), 331 (M$^+$−1) NMR (300 MHz, d$^6$-DMSO): δ11.73 (s, 1H); 7.56 (d, J=8.1, 1H); 7.50 (br s, 1H); 7.43–7.35 (m, 2H); 7.18 (br s, 1H); 7.06 (d, J=7.8, 1H); 6.56 (d, J=8.6, 1H); 4.90 (s, 2H); 3.70 (s, 3H).

D. Preparation of [9-benzyl-5-carbamoyl-1-chlorocarbazol-4-yl]oxyacetic acid methyl ester A solution of 78 mg of [5-carbamoyl-1-chlorocarbazol-4-yl]oxyacetic acid methyl ester in 0.8 ml of dry dimethylformamide was added to 10 mg sodium hydride (60% in mineral oil) in 0.2 ml of dimethylformamide and stirred for 15 minutes. Benzyl bromide (0.031 ml) was then added and the reaction was stirred overnight. The reaction mixture was poured into water and acidified with 1 ml of 1 N HCl solution and extracted twice with ethyl acetate. The extracts were washed with water (3×) and then with brine, dried over magnesium sulfate and concentrated. The residue was chromatographed on silica gel eluting with methanol/0–2% in dichloromethane to afford 40 mg of the subtitle compound. ESIMS m/e 423 (M$^+$+1) 425 (M$^+$+3) NMR (300 MHz, CDCl$_3$): δ7.43–7.22 (m, 7H); 7.06 (d, J=7.3, 2H); 6.51 (d, J=8.6, 1H); 6.05 (s, 2H); 5.80 (br, 2H); 4.88 (s, 2H); 3.83 (s, 3H).

E. Preparation of [9-benzyl-5-carbamoyl-1-chlorocarbazol-4-yl]oxyacetic acid

[9-Benzyl-5-carbamoyl-1-chlorocarbazol-4-yl]oxyacetic acid methyl ester (15 mg) was hydrolyzed similarly as described in Example 50, Part D to afford 14 mg of the title compound. mp. 240–2° C. ESIMS m/e 409 (M$^+$+1), 411 (M$^+$+3), 407 (M$^+$−1) NMR (300 MHz, d$^6$-DMSO): δ12.94 (br, 1H); 7.70 (br, 1H); 7.61 (d, J=8.3, 1H); 7.43 (t, J=7.8, 1H); 7.36 (m, 2H); 7.28–7.19 (m, 3H); 7.13 (d, J=7.2, 1H); 6.99 (d, J=7.4, 2H); 6.63 (d, J=8.6, 1H); 6.08 (s, 2H); 4.83 (s, 2H).

EXAMPLE 55

Preparation of [9-[(Cyclohexyl)methyl]-5-carbamoylcarbazol-4-yl]oxyacetic acid

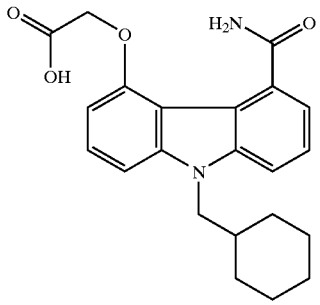

A. 9-[(Cyclohexyl)methyl]-5-carbomethoxy-1,2-dihydrocarbazol-4(3H)-one

A 0° C. suspension of 5-carbomethoxy-1,2-dihydro-9H-carbazol-4(3H)-one (1.0 g, 4.11 mmol), a catalytic amount of NaI (ca. 10 mg) and $K_2CO_3$ (1.1 g, 8.22 mmol) in 10 mL of DMF was treated with cyclohexylmethyl bromide (0.631 mL, 4.52 mmol). After stirring overnight at ambient temperature, an additional 0.63 mL cyclohexylmethylbromide was added, and the resulting mixture was heated at 60° C. for 3 hours. The mixture was poured into $H_2O$ (30 mL) and extracted with EtOAc (2×25 mL). The combined organic layers were washed with $H_2O$ (4×50 mL), dried over anhydrous $Na_2SO_4$, filtered and concentrated in vacuo. The residue was purified by radial chromatography on silica gel (elution with a gradient of 20% to 40% EtOAc/hexanes) to afford 1.36 g (4.01 mmol; 97%) of 9-[(cyclohexyl)methyl]-5-carbomethoxy-1,2-dihydrocarbazol-4(3H)-one as a white foam. IR ($CHCl_3$, $cm^{-1}$) 3011, 2932, 2857, 1725, 1649, 1469, 1446, 1288 and 1120. MS (ES) m/e 340 (M+1), 453 (M+AcO$^-$). FAB HRMS m/e, Calcd for $C_{21}H_{26}NO_3$: 340.1913. Found: 340.1916 (M+1).

Elemental Analyses for $C_{21}H_{25}NO_3$: Calculated: C, 74.31; H, 7.42; N, 4.13. Found: C, 72.65; H, 7.39; N, 4.70.

B. 9-[(Cyclohexyl)methyl]-4-hydroxy-5-carbomethoxy carbazole

A solution of 9-[(cyclohexyl)methyl]-5-carbomethoxy-1,2-dihydrocarbazol-4(3H)-one (1.16 g, 3.42 mmol) and 2,3-dichloro-5,6-dicyano-1,4-benzoquinone (853 mg, 3.76 mmol) in 20 mL of toluene was heated at 80° C. for 3 hours. The mixture was purified directly by column chromatography on silica gel (elution with $CH_2Cl_2$) to afford 259 mg (0.768 mmol; 22%) of 9-[(cyclohexyl)methyl]-4-hydroxy-5-carbomethoxy carbazole as a yellow oil which slowly solidified. MS (ES) m/e 338 (M+1), 336 (M-1).

Elemental Analyses for $C_{21}H_{23}NO_3$: Calculated: C, 74.75; H, 6.87; N, 4.15. Found: C, 74.95; H, 6.99; N, 4.42.

C. 9-[(Cyclohexyl)methyl]-4-hydroxy-5-carbamoyl carbazole

A solution of 9-[(cyclohexyl)methyl]-4-hydroxy-5-carbomethoxy carbazole (205 mg, 0.608 mmol) in 5 mL of THF and 20 mL of concentrated aqueous ammonium hydroxide was treated with a stream of $NH_3$ gas to ensure saturation. The reaction vessel was capped, and the mixture was heated at 35° C. with stirring until tlc indicated complete consumption of starting material (20 hrs). The THF was evaporated, and the aqueous layer was filtered. The green solid precipitate was dissolved in THF and purified by radial chromatography on silica gel (elution with $CH_2Cl_2$). The resultant foam was triturated with ether to afford 138 mg (70%) of the title compound as an off-white solid. IR (KBr, $cm^{-1}$) 3418, 3200, 3131, 1629, 1600, 1443, 1261, 778. 'FAB HRMS m/e, Calcd for $C_{20}H_{23}N_2O_2$: 323.1760. Found: 323.1760 (M+1).

D. [9-[(Cyclohexyl)methyl]-5-carbamoylcarbazol-4-yl]oxyacetic acid, methyl ester A mixture of 9-[(cyclohexyl)methyl]-4-hydroxy-5-carbamoyl carbazole (60 mg, 0.186 mmol) and $Cs_2CO_3$ (150 mg; 0.460 mmol) in 2 mL of DMF was treated with methyl bromoacetate (0.023 mL; 0.242 mmol). The reaction was stirred for 2 hours at ambient temperature, then it was diluted with EtOAc and $H_2O$ (10 mL each). The aqueous layer was saturated with solid NaCl and extracted with EtOAc (2×10 mL). The combined organic layers were washed with $H_2O$ (2×25 mL), dried over anhydrous $Na_2SO_4$, filtered and concentrated in vacuo. Purification of the crude residue by flash chromatography on silica gel (elution with a gradient of 0% to 90% EtOAc/hexanes) followed by trituration with $Et_2O$/EtOAc afforded 45 mg (0.114 mmol; 61%) of title compound as an off-white solid. MS (ES) m/e 395 (M+1), 378 (M+H—$NH_3$), 453 (M+AcO$^-$).

Elemental Analyses for $C_{23}H_{26}N_2O_4$·0.3$H_2O$: Calculated: C, 69.08; H, 6.71; N, 7.01. Found: C, 69.13; H, 6.71; N, 7.09.

E. [9-[(Cyclohexyl)methyl]-5-carbamoylcarbazol-4-yl]oxyacetic acid

A slurry of [9-[(cyclohexyl)methyl]-5-carbamoylcarbazol-4-yl]oxyacetic acid, methyl ester (20 mg, 0.051 mmol) in 0.3 mL of THF and 0.1 mL of MeOH was treated with 0.1 mL of 1 N aq LiOH (0.1 mmol), and the mixture stirred at room temperature for 2 h. The reaction was acidified with 0.2 N HCl, and the organics were removed in vacuo. The white precipitate was filtered away from the aqueous layer and rinsed with $Et_2O$ to afford 16 mg (0.042 mmol; 83%) the title acid as a white powder. MS (ES) m/e 381 (M+1), 364 (M+H—$NH_3$), 379 (M-1).

Elemental Analyses for $C_{22}H_{24}N_2O_4$: Calculated: C, 69.46; H, 6.36; N, 7.36. Found: C, 69.34; H, 6.35; N, 7.29.

EXAMPLE 56

Preparation of [9-[(Cyclopentyl)methyl]-5-carbamoylcarbazol-4-yl]oxyacetic acid

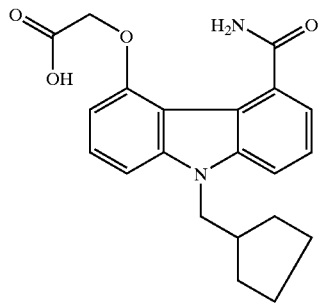

A. 9-[(Cyclopentyl)methyl]-5-carbomethoxy-1,2-dihydrocarbazol-4(3H)-one

A suspension of 5-carbomethoxy-1,2-dihydro-9H-carbazol-4(3H)-one (820 g, 3.37 mmol), a catalytic amount of NaI (ca. 10 mg) and $K_2CO_3$ (930 mg, 6.74 mmol) in 6 mL of DMF was treated with cyclopentylmethyl chloride (*JOC*, 1964, 29, 421–423; 400 mg, 3.37 mmol). After stirring overnight at ambient temperature, an additional 800 mg of cyclopentylmethyl chloride and 1 g of NaI were added, and the resulting mixture was heated at 80° C. overnight. An additional 800 mg of cyclopentylmethyl chloride and 2.2 g of $Cs_2CO_3$ were added, and the reaction mixture was heated at 80° C. for 24 h. An additional 1.6 g of cyclopentylmethyl chloride was added, and the reaction mixture was heated at 80° C. for 3 d The mixture was poured into $H_2O$ (30 mL) and extracted with EtOAc (3×10 mL). The combined organic layers were dried over anhydrous $Na_2SO_4$, filtered, and concentrated in vacuo. The residue was purified by radial chromatography on silica gel (elution with gradient of 10% to 40% EtOAc/hexanes) to afford 775 mg (2.38 mmol; 71%) of 9-[(cyclopentyl)methyl]-5-carbomethoxy-1,2-dihydrocarbazol-4(3H)-one as a brown foam. MS (ES) m/e 326 (M+1), 384 (M+AcO⁻).

Elemental Analyses for $C_{20}H_{23}NO_3$: Calculated: C, 73.82; H, 7.12; N, 4.30. Found: C, 74.12; H, 7.21; N, 4.45.

B. 9-[(Cyclopentyl)methyl]-4-hydroxy-5-carbomethoxy carbazole

A solution of 9-[(cyclopentyl)methyl]-5-carbomethoxy-1,2-dihydrocarbazol-4(3H)-one (730 mg, 2.24 mmol) and 2,3-dichloro-5,6-dicyano-1,4-benzoquinone (560 mg, 2.47 mmol) in 20 mL of toluene was heated at 80° C. for 3 hours. The mixture was purified directly by column chromatography on silica gel (elution with $CH_2Cl_2$) to afford 140 mg (0.433 mmol; 19%) of 9-[(cyclopentyl)methyl]-4-hydroxy-5-carbomethoxy carbazole as a yellow oil which slowly solidified. MS (ES) m/e 324 (M+1), 322 (M−1).

Elemental Analyses for $C_{20}H_{21}NO_3 \cdot 0.3H_2O$: Calculated: C, 73.06; H, 6.62; N, 4.26. Found: C, 73.19; H, 6.44; N, 4.40.

C. 9-[(Cyclopentyl)methyl]-4-hydroxy-5-carbamoyl carbazole

A solution of 9-[(cyclopentyl)methyl]-4-hydroxy-5-carbomethoxy carbazole (110 mg, 0.34 mmol) in 3 mL of THF and 20 mL of concentrated aqueous ammonium hydroxide was treated with a stream of $NH_3$ gas to ensure saturation. The reaction vessel was capped, and the mixture heated to 35° C. with stirring until tlc indicated complete consumption of starting material (20 h). The THF was evaporated, and the aqueous layer was filtered. The resultant solid was triturated with ether to afford 50 mg (0.162; 48%) of the title compound as a greenish-white solid. IR (KBr, cm⁻¹) 3416, 3199, 3126, 1630, 1599. 1442, 1262, 778. 'FAB HRMS m/e, Calcd for $C_{20}H_{21}N_2O_2$: 309.1603. Found: 309.1607 (M+1).

D. [9-[(Cyclopentyl)methyl]-5-carbamoylcarbazol-4-yl] oxyacetic acid, methyl ester A mixture of 9-[(cyclopentyl)methyl]-4-hydroxy-5-carbamoyl carbazole (45 mg, 0.146 mmol) and $Cs_2CO_3$ (120 mg; 0.365 mmol) in 2 mL of DMF was treated with methyl bromoacetate (0.018 mL; 0.19 mmol). The reaction was stirred for 2 hours at ambient temperature, then it was diluted with EtOAc and $H_2O$ (10 mL each). The aqueous layer was saturated with solid NaCl extracted with EtOAc (2×10 mL). The combined organic layers were washed with $H_2O$ (2×25 mL), dried over anhydrous $Na_2SO_4$, filtered and concentrated in vacuo. Purification of the crude residue by flash chromatography on silica gel (elution with a gradient of 0% to 100% EtOAc/hexanes) followed by trituration with $Et_2O$/EtOAc afforded 26 mg (0.0683 mmol; 47%) of title compound as a tan solid. MS (ES) m/e 381 (M+1), 364 (M+H—$NH_3$), 439 (M+AcO⁻).

Elemental Analyses for $C_{23}H_{26}N_2O_4 \cdot 0.1H_2O$: Calculated: C, 69.13; H, 6.38; N, 7.33. Found: C, 68.99; H, 6.39; N, 7.41.

E. [9-[(Cyclopentyl)methyl]-5-carbamoylcarbazol-4-yl] oxyacetic acid

A slurry of [9-[(cyclopentyl)methyl]-5-carbamoylcarbazol-4-yl}oxyacetic acid, methyl ester (20 mg, 0.065 mmol) in 0.3 mL of THF and 0.1 mL of MeOH was treated with 0.1 mL of 1 N aq LiOH (0.1 mmol), and the mixture stirred at room temperature for 2 hours. The reaction was acidified with 0.2 N HCl, and the organics were removed in vacuo. The white precipitate was filtered away from the aqueous layer and rinsed with $Et_2O$ to afford 15 mg (0.0409 mmol; 63%) the title acid as a white powder. MS (ES) m/e 367 (M+1), 350 (M+H—$NH_3$), 365 (M−1).

Elemental Analyses for $C_{21}H_{22}N_2O_4 \cdot 0.3H_2O$: Calculated: C, 67.84; H, 6.13; N, 7.53. Found: C, 67.73; H, 5.97; N, 7.70.

EXAMPLE 57

[5-carbamoyl-9-(phenylmethyl)-2-(2-thienyl) carbazol-4-yl]oxyacetic acid

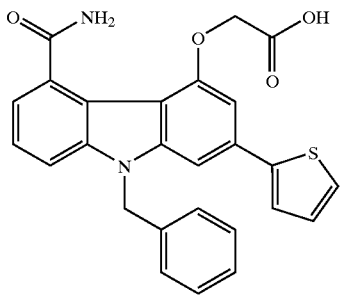

A. Preparation of 3-(2-bromo-3-carbomethoxyanilino)-5-(2-thienyl)cyclohex-2-en-1-one

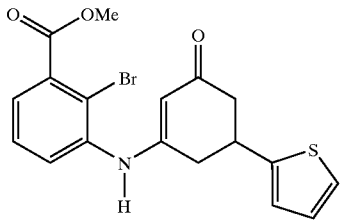

Prepared in 59% yield by the method of Example 17C. ¹H-NMR (CDCl₃): δ2.63 (dd, J=16.5, 118. Hz, 1H), 2.78–2.96 (m, 3H), 3.71–3.80 (m, 1H), 3.94 (s, 3H), 5.61 (s, 1H), 6.23 (br s, 1H), 6.93 (d, J=3.5 Hz, 1H), 6.97–6.99 (m, 1H), 7.21 (d, J=5.2 Hz, 1H), 7.34 (br t, J=7.8 Hz, 1H), 7.55 (d, J=7.8 Hz, 2H).

B. Preparation of 5-carbomethoxy-1,2-dihydro-2-(2-thienyl)-9H-carbazol-4(3H)-one

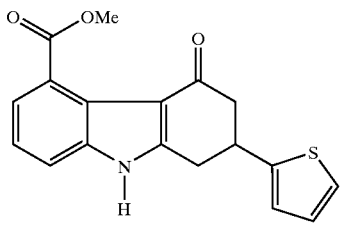

Prepared in 85% yield by the method of Example 17D. ¹H-NMR CDCl₃): δ2.73 (dd, J=16.3, 11.8 Hz, 1H), 2.91 (dd, J=16.4, 4.0 Hz, 1H), 3.03 (dd, J=16.6, 10.8 Hz, 1H), 3.24 (dd, J=16.6, 4.5 Hz, 1H), 3.75–3.78 (m, 1H), 4.03 (s, 3H), 6.88 (br s, 1H), 6.93–6.96 (m, 1H), 7.17 (d, J=5.0 Hz, 1H), 7.22–7.26 (m, 1H), 7.36 (d, J=7.4 Hz, 1H), 7.40 (d, J=8.0 Hz, 1H), 9.17 (br s, 1H).

C. Preparation of 5-carbomethoxy-1,2-dihydro-9-(phenylmethyl)-2-(2-thienyl)carbazol-4(3H)-one

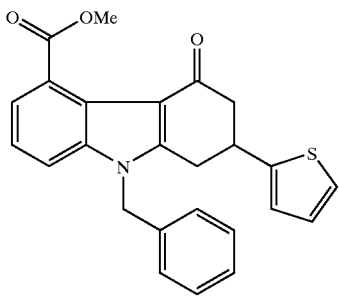

Prepared in 88% yield by the method of Example 17E. $^1$H-NMR (CDCl$_3$): δ2.84 (dd, J=16.5, 11.6 Hz, 1H), 2.97–3.10 (m, 2H), 3.34 (dd, J=16.5, 4.5 Hz, 1H), 3.89–3.96 (m, 1H), 4.06 (s, 3H), 5.38 (s, 2H), 6.89–7.00 (m, 4H), 7.18 (d, J=5.3 Hz, 1H), 7.25–7.41 (m, 6H).

D. Preparation of 5-carbomethoxy-4-hydroxy-9-(phenylmethyl)-2-(2-thienyl)carbazole

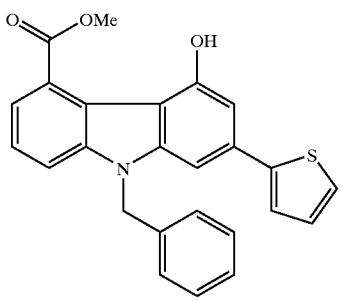

Prepared in 76% yield by the method (b) of Example 17F. $^1$H-NMR (CDCl$_3$): δ4.11 (s, 3H), 5.55 (s, 2H), 7.07–7.12 (m, 3H), 7.16 (s, 2H), 7.24–7.30 (m, 4H), 7.37–7.42 (m, 2H), 7.56 (d, J=8.1 Hz, 1H), 8.01 (d, J=7.6 Hz, 1H).

E. Preparation of 5-carbamoyl-4-hydroxy-9-(phenylmethyl)-2-(2-thienyl)carbazole

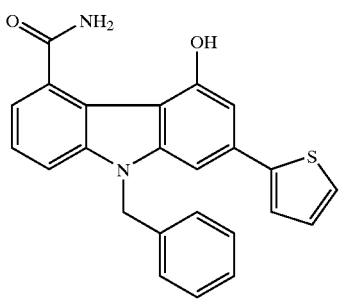

Prepared in 85% yield by the method of Example 17G. $^1$H-NMR (DMSO-d$_6$): δ5.73 (s, 2H), 6.87 (s, 1H), 7.08–7.26 (m, 6H), 7.41–7.56 (m, 5H), 7.76 (br t, J=4.5 Hz, 1H), 8.39 (s, 1H), 8.83 (s, 1H), 10.76 (s, 1H).

F. Preparation of [5-carbamoyl-9-(phenylmethyl)-2-(2-thienyl)carbazol-4-yl]oxyacetic acid, methyl ester

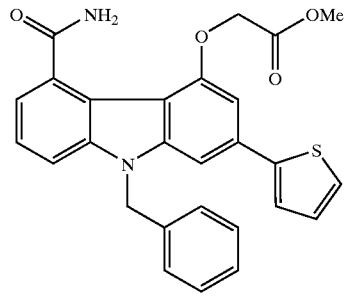

Prepared in 92% yield by the method of Example 17H. $^1$H-NMR (DMSO-d$_6$): δ3.70 (s, 3H), 4.99 (s, 2H), 5.71 (s, 2H), 6.85 (s, 1H), 7.04 (d, J=7.2 Hz, 1H), 7.11–7.26 (m, 7H), 7.35 (br t, J=7.7 Hz, 1H), 7.50–7.57 (m, 5H).

G. Preparation of [5-carbamoyl-9-(phenylmethyl)-2-(2-thienyl)carbazol-4-yl]oxyacetic acid

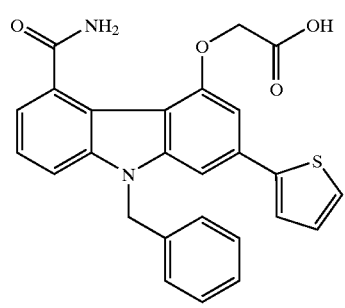

Prepared in 98% yield by the method of Example 17I. $^1$H-NMR (DMSO-d$_6$): δ4.90 (s, 2H), 5.72 (s, 2H), 6.85 (s, 1H), 7.04–7.26 (m, 7H), 7.33–7.38 (m, 2H), 7.50–7.59 (m, 4H), 7.71 (s, 1H), 12.99 (br s, 1H).

EXAMPLE 58

[5-carbamoyl-9-(phenylmethyl)-2-[[(propen-3-yl)oxy]methyl]carbazol-4-yl]oxyacetic acid

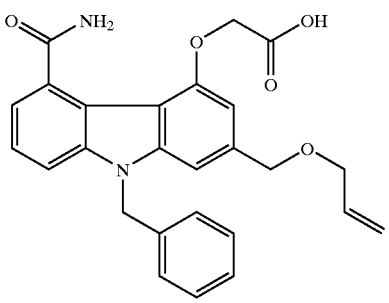

A. Preparation of 5-carbomethoxy-1,2-dihydro-9-(phenylmethyl)-2-[[(propen-3-yl)oxy]methyl]carbazol-4(3H)-one

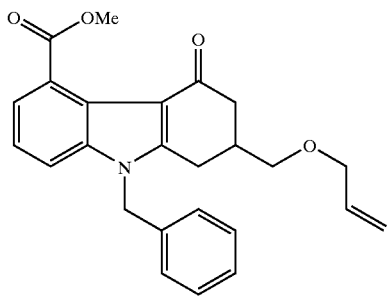

Sodium hydride (63.4 mg, 1.58 mmol) was added to a stirred anhydrous DMF (7 mL) solution containing the compound of Example 19C (480 mg, 1.32 mmol) and allyl bromide (0.172 mL, 1.98 mmol) under a nitrogen atmosphere. The resultant solution was stirred at ambient temperature for 2 hours. Then the mixture was treated with two drops of acetic acid before it was concentrated in vacuo. The residue was subject to chromatography on silica (gradient 30–70% ethyl acetate in hexane) to provide the subtitled compound (395 mg, 74%) as a white solid. IR (KBr) 1726, 1654 cm$^{-1}$; $^1$H-NMR (CDCl$_3$): δ2.40 (dd, J=16.5, 11.1 Hz, 1H), 2.57–2.78 (m, 3H), 3.01–3.08 (m, 1H), 3.41 (dd, J=9.2, 6.9 Hz, 1H), 3.49 (dd, J=9.2, 4.3 Hz, 1H), 3.95 (d, J=5.4 Hz, 2H, —CH$_2$O—), 4.04 (s, 3H, —OCH$_3$), 5.14–5.27 (m, 2H, =CH$_2$), 5.32 (s, 2H, —NCH$_2$—), 5.80–5.92 (m, 1H, —CH=), 6.97–7.02 (m, 2H), 7.20–7.39 (m, 6H); ESIMS m/e 404 (M$^+$+1);

Elemental Analyses for C$_{25}$H$_{25}$NO$_4$: Calculated: C, 74.42; H, 6.25. Found: C, 74.59; H, 6.07.

B. Preparation of 5-carbomethoxy-4-hydroxy-9-(phenylmethyl)-2-[[(propen-3-yl)oxy]methyl]carbazole

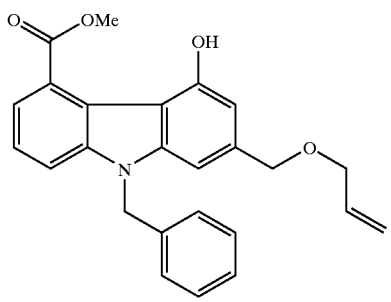

Prepared in a 78% yield by the method (b) of Example 17F. IR (CHCl$_3$) 3200 (br), 1687 cm$^{-1}$; $^1$H-NMR (CDCl$_3$): δ4.04 (d, J=5.7 Hz, 2H, —CH$_2$O—), 4.11 (s, 3H, —OCH$_3$), 4.63 (s, 2H, —OCH$_2$—), 5.15–5.31 (m, 2H, =CH$_2$), 5.55 (s, 2H, —NCH$_2$—), 5.88–6.02 (m, 1H, —CH=), 6.81 (s, 1H), 6.99 (s, 1H), 7.05–7.09 (m, 2H), 7.22–7.30 (m, 3H), 7.40 (br t, J=8.0 Hz, 1H), 7.58 (d, J=8.0 Hz, 1H), 8.00 (d, J=8.0 Hz, 1H), 10.48 (s, 1H, —OH); ESIMS m/e 402 (M$^+$+1);

Elemental Analyses for C$_{25}$H$_{23}$NO$_4$: Calculated: C, 74.80; H, 5.77. Found: C, 75.08; H, 5.78.

C. Preparation of 5-carbamoyl-4-hydroxy-9-(phenylmethyl)-2-[[(propen-3-yl)oxy]methyl]carbazole

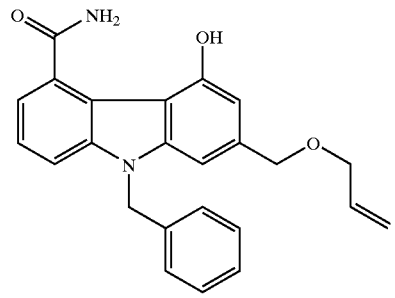

Prepared in a 75% yield by the method of Example 17G. IR (KBr) 3420, 3203 (br), 3121, 1632, 1601 cm$^{-1}$; $^1$H-NMR (DMSO-d$_6$): δ3.95 (d, J=5.3 Hz, 2H, —CH$_2$O—), 4.50 (s, 2H, —OCH$_2$—), 5.08–5.25 (m, 2H, =CH$_2$), 5.65 (s, 2H, —NCH$_2$—), 5.83–5.93 (m, 1H, —CH=), 6.54 (s, 1H), 7.02–7.05 (m, 3H), 7.14–7.25 (m, 3H), 7.39–7.45 (m, 2H), 7.73–7.77 (m, 1H), 8.34 (s, 1H, —NH), 8.79 (s, 1H, —NH), 10.53 (s, 1H, —OH); ESIMS m/e 387 (M$^+$+1);

Elemental Analyses for C$_{24}$H$_{22}$N$_2$O$_3$: Calculated: C, 74.59; H, 5.74. Found: C, 74.85; H, 5.93.

D. Preparation of [5-carbamoyl-9-(phenylmethyl)-2-[[(propen-3-yl)oxy]methyl]carbazol-4-yl]oxyacetic acid, methyl ester

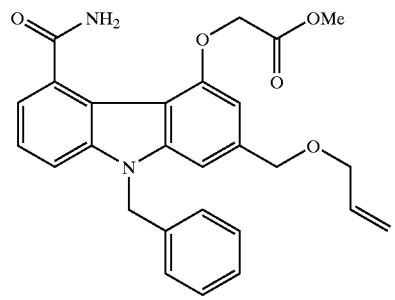

Prepared in a 90% yield by the method of Example 17H. IR (KBr) 3360, 3167, 1758, 1639 cm$^{-1}$; $^1$H-NMR (CDCl$_3$): δ3.83 (s, 3H, —OCH$_3$), 4.00 (d, J=5.7 Hz, 2H, —CH$_2$O—), 4.62 (s, 2H, —OCH$_2$—), 4.91 (s, 2H, —OCH$_2$—), 5.16–5.30 (m, 2H, =CH$_2$), 5.52 (s, 2H, —NCH$_2$—), 5.88–6.00 (m, 1H, —CH=), 6.05 (br s, 2H, —NH$_2$), 6.59 (s, 1H), 7.05 (s, 1H), 7.06–7.10 (m, 2H), 7.22–7.41 (m, 6H); ESIMS m/e 459 (M$^+$+1).

E. Preparation of [5-carbamoyl-9-(phenylmethyl)-2-[[(propen-3-yl)oxy]methyl]carbazol-4-yl]oxyacetic acid

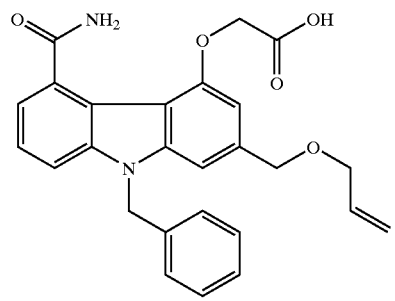

Prepared in a 89% yield by the method of Example 17I. IR (KBr) 3453, 3421, 3332, 3220, 2580 (br), 1740, 1724, 1631 cm$^{-1}$; $^1$H-NMR (DMSO-d$_6$): δ3.95 (d, J=4.7 Hz, 2H, —CH$_2$O—), 4.53 (s, 2H, —OCH$_2$—), 4.79 (s, 2H, —OCH$_2$—), 5.10–5.26 (m, 2H, =CH$_2$), 5.64 (s, 2H, —NCH$_2$—), 5.80–6.00 (m, 1H, —CH=), 6.56 (s, 1H), 7.04–7.40 (m, 9H), 7.57 (d, J=8.1 Hz, 1H), 7.70 (s, 1H, —NH), 12.94 (br s, 1H, —CO$_2$H); ESIMS m/e 445 (M$^+$+1);

Elemental Analyses for C$_{26}$H$_{24}$N$_2$O$_5$: Calculated: C, 70.26; H, 5.44. Found: C, 70.00; H, 5.42.

EXAMPLE 59

[5-carbamoyl-9-(phenylmethyl)-2-[(propyloxy)methyl]carbazol-4-yl]oxyacetic acid

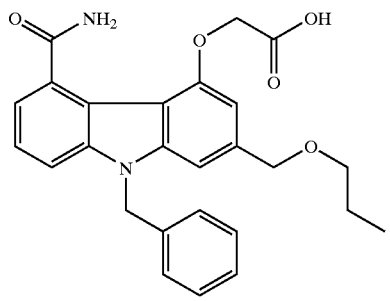

A. Preparation of [5-carbamoyl-9-(phenylmethyl)-2-[(propyloxy)methyl]carbazol-4-yl]oxyacetic acid, methyl ester

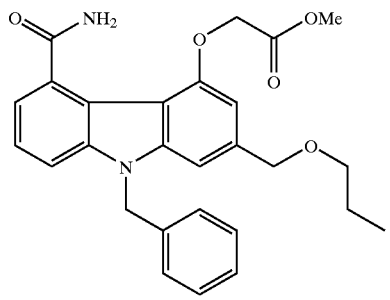

Platinum oxide (30 mg) was added to a stirred THF (30 mL) solution containing the compound of Example IID (120 mg, 0.262 mmol) under a nitrogen atmosphere. The mixture was then stirred under a hydrogen atmosphere for 30 minutes. After filtration and concentration, the residue was chromatographed on silica (gradient 0–6% methanol in methylene chloride) to afford the subtitled compound (117 mg, 97%) as a white solid. IR (KBr) 3364, 3166, 1758, 1742, 1642 cm$^{-1}$; $^1$H-NMR (CDCl$_3$): δ0.91 (t, J=7.4 Hz, 3H, —CH$_3$), 1.57–1.65 (m, 2H), 3.40 (t, J=6.6 Hz, 2H, —OCH$_2$—), 3.83 (s, 3H, —OCH$_3$), 4.60 (s, 2H, —OCH$_2$—), 4.91 (s, 2H, —OCH$_2$—), 5.52 (s, 2H, —NCH$_2$—), 5.95 (br s, 1H, —NH), 6.06 (br s, 1H, —NH), 6.58 (s, 1H), 7.04 (s, 1H), 7.07–7.10 (m, 2H), 7.20–7.41 (m, 6H); ESIMS m/e 461 (M$^+$+1).

B. Preparation of [5-carbamoyl-9-(phenylmethyl)-2-[(propyloxy)methyl]carbazol-4-yl]oxyacetic acid

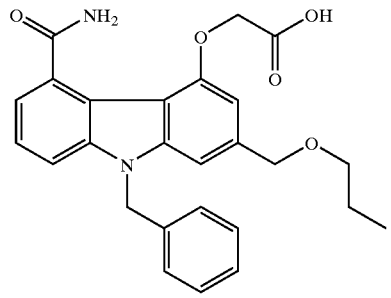

Prepared in a 99% yield by the method of Example 17I. IR (KBr) 3458, 3413, 3332, 3232, 2500 (br), 1716, 1627 cm$^{-1}$; $^1$H-NMR (DMSO-d$_6$): δ0.82 (t, J=7.3 Hz, 3H, —CH$_3$), 1.45–1.53 (m, 2H), 3.33 (t, J=6.3 Hz, 2H, —OCH$_2$—), 4.51 (s, 2H, —CH$_2$O—), 4.78 (s, 2H, —OCH$_2$—), 5.64 (s, 2H, —NCH$_2$—), 6.54 (s, 1H), 7.03–7.39 (m, 9H), 7.57 (d, J=8.2 Hz, 1H), 7.70 (s, 1H, —NH), 12.93 (s, 1H, —CO$_2$H); ESIMS m/e 447 (M$^+$+1);

Elemental Analyses for C$_{26}$H$_{26}$N$_2$O$_5$: Calculated: C, 69.94; H, 5.87. Found: C, 70.00; H, 5.88.

EXAMPLE 60

Preparation of 9-benzyl-7-methoxy-5-((carboxamidomethyl)oxy)-1,2,3,4-tetrahydrocarbazole-4-carboxamide To 195 mg (0.5 mmol) of 9-benzyl-7-methoxy-5-cyanomethyloxy-1,2,3,4-tetrahydrocarbazole-4-carboxamide in 3 ml CH$_2$Cl$_2$ was added 34 mg (0.1 mmol) tetrabutylammonium sulfate. After cooling to 0° C., 0.25 ml 30% H$_2$O$_2$ and 3 ml 20% NaOH were added. The reaction was allowed to warm to room temperature and stirred for 18 h. The mixture was diluted with CH$_2$Cl$_2$, washed with water, washed with brine, dried over sodium sulfate, and evaporated in vacuo. The residue was chromatographed on silica gel eluting with a gradient of 2 to 10% isopropanol in methylene chloride to give the titled product (36.7 mg 19%). An analytical sample was crystallized from methanol. MS (ES+) 408

Elemental analysis for C$_{23}$H$_{25}$N$_3$O$_4$: Calculated: C, 67.80; H, 6.18; N, 10.31. Theory: C, 67.91; H, 6.17; N, 10.44.

EXAMPLE 61

Preparation of 9-benzyl-7-methoxy-5-cyanomethyloxy-carbazole-4-carboxamide

To a stirred solution of 9-benzyl-5-hydroxy-7-methoxycarbazole-4-carboxamide (0.75 g, 2.17 mmol) in DMF (76 ml) and THF (16 ml) and added 60% NaH (0.11 g, 2.71 mmol). After 15 min bromoacetonitrile (0.20 ml, 2.93 mmol) was added and the reaction was allowed to stir for 4 h. The reaction was diluted with EtOAc, extracted with water, then brine, dried (Na$_2$SO$_4$), and chromatographed on silica gel using a CH$_2$Cl$_2$-EtOAc-methanol gradient to give the titled compound (0.52 g, 63%). MS (ES+) 386

Elemental analysis for C$_{23}$H$_{19}$N$_3$O$_3$: Calculated: C, 71.68; H, 4.97; N, 10.90. Theory: C, 71.67; H, 4.72; N, 10.65.

EXAMPLE 62 424805

Preparation of 9-benzyl-7-methoxy-5-((1H-tetrazol-5-yl-methyl)oxy)-carbazole-4-carboxamide 0.20 gram (0.52 mmol) of 9-benzyl-7-methoxy-5-cyanomethyloxy-carbazole-4-carboxamide was heated with 2.2 ml tri-n-butyl tin hydride at 95° C. for 3.5 h. The reaction was then added to a mixture of 56 ml acetonitrile, 11 ml tetrahydrofuran, and 22 ml acetic acid and stirred for 2 h. The mixture was extracted 4 times with hexane and the residue evaporated in vacuo. The residue was chromatographed on silica gel using a $CH_2Cl_2$-methanol gradient, then 1% HOAc in EtOAc. Crystallization from acetone and hexane afforded the titled compound (0.047 g, 21%). MS (ES+) 412, 429

Elemental analysis for $C_{23}H_{24}N_6O_3$: Calculated: C, 64.48; H, 4.71; N, 19.61. Theory: C, 64.58; H, 4.67; N, 19.68.

EXAMPLE 63

Preparation of 9-benzyl-7-methoxy-5-((carboxamidomethyl)oxy)-carbazole-4-carboxamide To 200 mg (0.52 mmol) of 9-benzyl-7-methoxy-5-cyanomethyloxy-carbazole-4-carboxamide in 6 ml $CH_2Cl_2$ was added 35 mg (0.1 mmol) tetrabutylammonium sulfate. After cooling to 0° C., 0.26 ml 30% $H_2O_2$ and 6 ml 20% NaOH, were added. The reaction was allowed to warm to room temperature and stirred for 18 h. The mixture was diluted with $CH_2Cl_2$ and methanol, washed with water, washed with brine, dried over sodium sulfate, and evaporated in vacuo. The residue was chromatographed on silica gel using a $CH_2Cl_2$-ethanol gradient. Crystallization from methanol afforded the titled compound (22.5 mg, 11%). MS (FD) 403

Elemental analysis for $C_{23}H_{21}N_3O_4$: Calculated: C, 68.47; H, 5.25; N, 10.42. Theory: C, 68.65; H, 4.99; N, 10.40.

EXAMPLE 64

Preparation of [9-Benzyl-4-carbamoyl-1,2,3,4-tetrahydrocarbaole-5-yl]oxyacetic acid

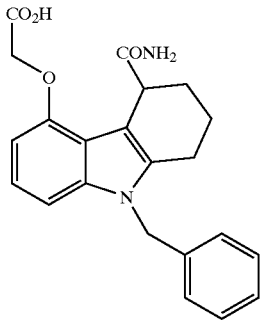

A. 9-Benzyl-4-carboxy-5-methoxy-1,2,3,4-tetrahydrocarbazole, Ethyl Ester

A solution of 1.50 g (4.02 mmol) of 9-Benzyl-4-carboxy-8-chloro-5-methoxy-1,2,3,4-tetrahydrocarbazole, ethyl ester and 0.45 g (4.40 mmol) of $Et_3N$ in 25 mL of EtOH was treated with 0.24 g of 5% Pd—C and the mixture hydrogenated at 60 psi for 16 hrs. The reaction was filtered and concentrated in vacuo to give 1.40 g of a tan solid. $^1$H NMR (CDCl$_3$): δ7.30–7.19 (m, 3H), 7.03–6.95 (m, 3H), 6.80 (d, 1H, J=8.1 Hz), 6.44 (d, 1H, J=7.7 Hz), 5.22 (d, 2H, J=5.9 Hz), 4.22–4.11 (m, 3H), 3.82 (s, 3H), 2.75–2.64 (m, 1H), 2.59–2.48 (m, 1H), 2.11–1.64 (m, 4H), and 1.25 (t, 3H, J=7.0 Hz). IR (CHCl$_3$) 2959, 1725, 1499, 1453, 1260, 1178, 1128 cm–1;

Elemental Analysis for $C_{23}H_{25}NO_3$: Calculated: 363.1836. Found: 363.1834.

B. 9-Benzyl-4-carbamoyl-5-hydroxy-1,2,3,4-tetrahydrocarbazole

A 0° C. solution of 1.00 g (2.80 mmol) 9-benzyl-4-carboxy-5-methoxy-1,2,3,4-tetrahydrocarbazole, ethyl ester in 15 mL of $CH_2Cl_2$ was treated with 22.40 mL (22.40 mmol; 1M in $CH_2Cl_2$) of BBr$_3$. The cold bath was removed and the reaction stirred until tlc analysis (10% EtOAc in hexanes) indicated complete consumption of starting material (1.5 hrs). The reaction was cooled to 0° C. and quenched with 5.0 mL of MeOH. The mixture was stirred at ambient temperature for 18 hrs and was concentrated in vacuo. The black oil was taken up in 200 mL of $CH_2Cl_2$ and the solution washed with H2O (100 mL) and sat'd aq NaHCO$_3$ (100 mL). Evaporation of the solvent in vacuo afforded 700 mg of a black oil. Purification by radial chromatography (10% EtOAc in hexanes) afforded 400 mg of 9-benzyl-4-carboxy-5-hydroxy-1,2,3,4-tetrahydrocarbazole, ethyl ester which was taken on directly to the next reaction.

The phenol was taken up in 40 ml of THF and the solution treated with 10 mL of NH$_4$OH. The reaction vessel was capped and the mixture stirred vigorously for 13 days. The reaction was poured into H$_2$O and the mixture extracted with EtOAc (3×150 mL). The combined organic layers were dried (Na$_2$SO$_4$), filtered and concentrated in vacuo to give 300 mg of a brown foam. Radial chromatography (3% MeOH in $CH_2Cl_2$) afforded 50 mg of starting phenol and 80 mg (0.03 mmol; 22%) of 9-benzyl-4-carbamoyl-5-hydroxy-1,2,3,4-tetrahydrocarbazole. $^1$H NMR (CDCl$_3$): δ7.33–7.24 (m, 3H), 7.06–6.97 (m, 3H), 6.81 (d, 1H, J=8.1 Hz), 6.56 (d, 1H, J=7.5 Hz), 5.22 (d, 2H, J=2.2 Hz), 4.20–4.15 (m, 1H), 2.78–2.67 (m, 1H), 2.63–2.51 (m, 1H), 2.35–2.27 (m, 1H), and 2.09–1.91 (m, 3H), no phenol proton detected. IR (CHCl3) 3007, 1667, 1586, 1567, 1496, 1266 cm–1;

Elemental Analysis for $C_{20}H_{21}N_2O_2$: Calculated: 321.1603. Found: 321.1607.

C. [9-Benzyl-4-carbamoyl-1,2,3,4-tetrahydrocarbaole-5-yl] oxyacetic acid, Methyl Ester A solution of 80 mg (0.25 mmol) of 9-benzyl-4-carbamoyl-5-hydroxy-1,2,3,4-tetrahydrocarbazole in 2.5 mL of DMF was treated with 61 mg (0.30 mmol) of $Cs_2CO_3$ followed by 26 mg (0.30 mmol) of methyl bromoacetate. The mixture was stirred at room temperature until tlc indicated complete consumption of starting material (2 hrs). The reaction was diluted with H$_2$O (10 mL) and was extracted with EtOAc (3×10 mL). The combined organic layers were washed with H$_2$O (3×20 mL), dried over Na$_2$SO$_4$, filtered, and concentrated in vacuo. The residue was purified by radial chromatography (SiO$_2$; 2.5% MeOH in $CH_2Cl_2$) to afford 50 mg (0.13 mmol; 51%) of [9-benzyl-4-carbamoyl-1,2,3,4-tetrahydrocarbaole-5-yl]oxyacetic acid, methyl ester as an oil. $^1$H NMR (CDCl$_3$): δ7.33–7.21 (m, 3H), 7.05–6.98 (m, 3H), 6.98 (d, 1H, J=7.4 Hz), 6.46 (br s, 1H), 6.37 (d, 1H, J=7.7 Hz), 5.52 (br s, 1H), 5.23 (d, 1H, J=4.9 Hz) 4.79–4.70 (m, 2H), 4.20–4.15 (m, 1H), 3.81 (s, 3H), 2.79–2.69 (m, 1H), 2.63–2.49 (m, 1H), 2.43–2.35 (m, 1H), 2.25–2.09 (m, 1H), and 1.99–1.78 (m, 2H). IR (CHCl$_3$, cm$^{-1}$) 1759, 1670, 1497, 1453, 1440, and 1132. MS (ES) m/e 393 (M+1).

Elemental Analysis for $C_{23}H_{24}N_2O_4$: Calculated: C, 70.39; H, 6.16; N, 7.14. Found: C, 70.29; H, 6.31; N, 7.08.

D. [9-Benzyl-4-carbamoyl-1,2,3,4-tetrahydrocarbaole-5-yl] oxyacetic acid

A solution of 30 mg (0.076 mmol) of [9-benzyl-4-carbamoyl-1,2,3,4-tetrahydrocarbaole-5-yl]oxyacetic acid, methyl ester in 1.0 mL of THF and 1.0 mL of MeOH was treated with 0.2 mL of 1 N aq LiOH (0.2 mmol). The mixture was stirred for 18 hrs. An additional 0.2 mL of 1 N aq LiOH (0.2 mmol) was added and stirring continued. After 1 hr, the mixture was concentrated in vacuo. The residue was dissolved in 2.0 mL of $H_2O$ and the solution acidified with 0.2 N aq HCl. The solid was filtered and dried to afford 25 mg of [9-benzyl-4-carbamoyl-1,2,3,4-tetrahydrocarbaole-5-yl]oxyacetic acid as a white solid. $^1$H NMR (DMSO-$d_6$) δ7.36–7.12 (m, 5H), 7.05–6.83 (m, 5H), 6.71 (br s, 1H), 6.35 (d, 1H, J=7.6 Hz), 5.27 (s, 2H), 4.64 (s, 2H), 3.93–3.84 (m, 2H), 2.75–2.64 (m, 1H), 2.16–1.95 (m, 2H), 1.81–1.64 (m, 2H) and 1 proton masked by $H_2O$ peak between 2.58–2.40. IR (KBr, cm$^{-1}$) 3435, 2936, 1722, 1644, 1586, 1566, 1495, 1451, 1354, 1227, 1134, 730, 716, and 698. MS (ES) m/e 377 (M−1) and 379 (M+1).

Elemental Analysis for $C_{22}H_{22}N_2O_4$: Calculated: C, 69.83; H, 5.86; N, 7.40. Found: C, 70.11; H, 5.76; N, 7.12.

EXAMPLE 65

Preparation of (R,S)-(9-Benzyl-4-carbamoyl-1-oxo-3-thia-1,2,3,4-tetrahydrocarbazol-5-yl)oxyacetic Acid

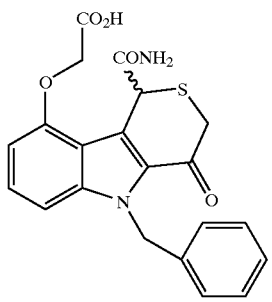

A. 1-Benzyl-4-methoxyindole

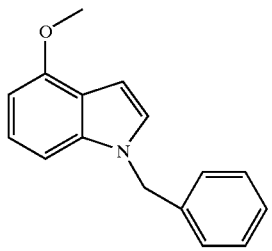

NaH (7.7 g, 191.7 mmol) was added portionwise to a 0° C. solution of 4-methoxyindole (21.7 g, 147 mmol) in 750 mL of anhydrous DMF. After 15 min, the slurry was treated with benzyl bromide (17.5 mL, 147 mmol). The reaction mixture was allowed to warm to ambient temperature and stir overnight. The reaction mixture was poured into 1 L of $H_2O$. The layers were separated, and the aqueous phase was extracted with EtOAc (2×200 mL). The combined organic layers were washed with $H_2O$ (4×500 mL), dried over $Na_2SO_4$, filtered and concentrated in vacuo. The crude residue was purified by flash chromatography ($SiO_2$; hexanes) to give 32.9 g (138.6 mmol; 94%) of the title compound as a white solid. Electrospray MS 238 (M+1);

Elemental Analysis for $C_{16}H_{15}NO$: Calculated: C, 80.98; H, 6.37; N, 5.90. Found: C, 81.20; H, 6.09; N, 5.83.

B. Methyl (1-Benzyl-4-methoxyindol-3-yl)oxoacetate

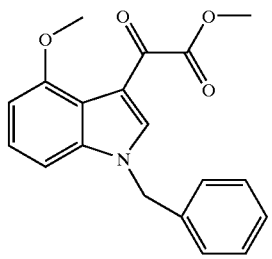

A 0° C. solution of 1-benzyl-4-methoxyindole (31.9 g, 134.4 mmol) in 500 mL of $CH_2Cl_2$ and pyridine (21.7 mL, 268.8 mmol) was treated with methyl oxalyl chloride (13.6 mL, 147.9 mmol). After 1.5 h at 0° C., 500 mL of saturated $NaHCO_3$ solution was added. The aqueous layer was extracted with $CHCl_3$ (1×200 mL, 2×50 mL). The combined organic layers were concentrated in vacuo to a tan solid, which was triturated with EtOAc/hexanes to give 29.8 g (92.1 mmol; 69%) of the title compound as an off-white powder. Electrospray MS 324 (M+1);

Elemental Analysis for $C_{19}H_{17}NO_4$: Calculated: C, 70.58; H, 5.30; N, 4.33. Found: C, 70.86; H, 5.42; N, 4.49.

C. Methyl (R,S)-(1-Benzyl-4-methoxyindol-3-yl)hydroxyacetate

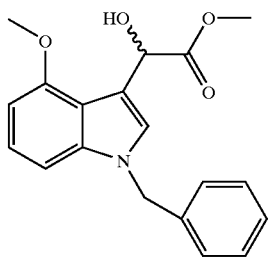

A solution of methyl (1-benzyl-4-methoxyindol-3-yl)oxoacetate (10 g, 30.9 mmol) in 300 mL of MEOH was treated with $NaBH_4$ (1.46 g, 38.6 mmol). After stirring overnight, EtOAc and $H_2O$ (20 mL each) were added. The aqueous layer was extracted with EtOAc (2×25 mL). The combined organic layers were dried over $Na_2SO_4$, filtered and concentrated in vacuo. The crude residue was recrystallized with EtOAc/hexanes to give 9.1 g (28.0 mmol; 91%) of the title compound as a white powder. FDMS 325 (M+);

Elemental Analysis for $C_{19}H_{19}NO_4$: Calculated: C, 70.14; H, 5.89; N, 4.30. Found: C, 70.42; H, 5.93; N, 4.41.

D. (R,S)-[(1-Benzyl-4-methoxyindol-3-yl)(carbomethoxy)methyl]thioacetic Acid

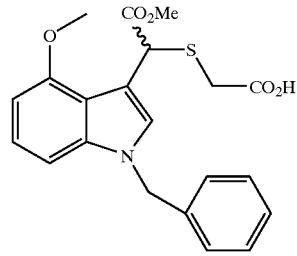

A 0° C. slurry of methyl (R,S)-(1-benzyl-4-methoxyindol-3-yl)hydroxyacetate (3.5 g, 10.8 mmol) and $K_2CO_3$ (2.2 g, 16.1 mmol) in 50 mL of $CH_2Cl_2$ was treated with TEA (0.075 mL, 0.54 mmol). After 15 min, MsCl (1.25 mL, 16.1 mmol) was added. After stirring for 2 h at 0° C., mercaptoacetic acid (3 mL, 43 mmol) was added, and the reaction was heated at reflux overnight. The reaction mixture was poured into 25 mL of saturated NaHCO$_3$ solution. The aqueous layer was extracted with 25 mL of CHCl$_3$, acidified with 1 N HCl and extracted again with CHCl$_3$ (3×25 mL). The acidified extracts were combined, dried over Na$_2$SO$_4$, filtered and concentrated in vacuo. The oily residue was purified by flash chromatography (SiO$_2$; gradient of 0% to 2% glacial acetic acid in 1:1 EtOAc/hexanes) to give 2.58 g (6.46 mmol; 60%) of the title compound as a clear oil which solidified on standing. FDMS 399 (M+);

Elemental Analysis for C$_{21}$H$_{21}$NO$_5$S.0.2H$_2$O: Calculated: C, 62.58; H, 5.35; N, 3.48. Found: C, 62.57; H, 5.26; N, 3.55.

E. Methyl (R,S)-(9-Benzyl-5-methoxy-1-oxo-3-thia-1,2,3,4-tetrahydrocarbazol-5-yl)carboxylate

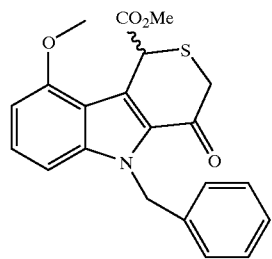

A solution of the carboxylic acid from Part D above (2.32 g, 5.81 mmol) in 50 mL of 1,2-dichloroethane was treated with oxalyl chloride (2.0 mL, 22.9 mmol) and 1 drop of DMF. The resulting mixture was allowed to stir at ambient temperature for 3 h, then it was concentrated in vacuo. The crude residue was purified by flash chromatography (SiO$_2$; gradient of 0% to 5% to 10% EtOAc/hexanes) to give 1.39 g (3.64 mmol; 63%) of the title compound as a pale yellow powder. FDMS 381 (M+);

Elemental Analysis for C$_{21}$H$_{19}$NO$_4$S: Calculated: C, 66.12; H, 5.02; N, 3.67. Found: C, 66.00; H, 5.26; N, 3.63.

F. Methyl (R,S)-(9-Benzyl-5-methoxy-1-oxo-3-thia-1,2,3,4-tetrahydrocarbazol-5-yl)carboxamide

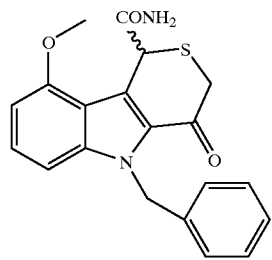

A solution of methyl (R,S)-(9-benzyl-5-methoxy-1-oxo-3-thia-1,2,3,4-tetrahydrocarbazol-5yl)carboxylate (1.1 g, 2.88 mmol) in 25 mL of THF/MeOH/H$_2$O (3:1:1) was treated with LiOH (83 mg, 3.46 mmol) and allowed to stir at ambient temperature overnight. The aqueous layer was extracted with 25 mL of CH$_2$Cl$_2$, acidified with 1 N HCl and extracted again with CH$_2$Cl$_2$ (2×25 mL). The acidified extracts were combined, dried over Na$_2$SO$_4$, filtered and concentrated in vacuo. The crude intermediate acid was dissolved in 20 mL of 1,2 dichloroethane and treated with (COCl)$_2$ (0.77 mL, 8.82 mmol). After 4 h, the reaction mixture was concentrated in vacuo and resuspended in 20 mL of 1,2 dichloroethane. Ammonia was bubbled through the solution for ca. 10 min, then the reaction mixture was capped and allowed to stand for 1.5 h. The crude amide was concentrated in vacuo and recrystallized from EtOAc/hexanes to give 780 mg (2.13 mmol; 74%) of the title compound as a light tan solid. FDMS 366 (M+);

Elemental Analysis for C$_{20}$H$_{18}$N$_2$O$_4$S.0.2H$_2$O: Calculated: C, 64.92; H, 5.01; N, 7.57. Found: C, 64.95; H, 5.04; N, 7.78.

G. (R,S)-(9-Benzyl-5-hydroxy-1-oxo-3-thia-1,2,3,4-tetrahydrocarbazol-5-yl)carboxamide

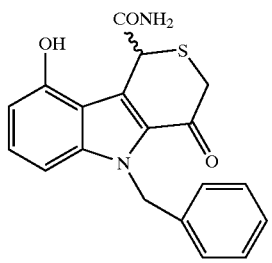

A 0° C. solution of methyl (R, S)-(9-benzyl-5-methoxy-1-oxo-3-thia-1,2,3,4-tetrahydrocarbazol-5-yl)carboxamide in 10 mL of 1,2 dichloroethane was treated with BBr$_3$ (2.4 mL, 24.9 mmol). After 3 h, the reaction mixture was quenched cold with MeOH and poured into 20 mL of saturated NaHCO$_3$ solution. The aqueous layer was extracted with CHCl$_3$ (4×50 mL). The combined organic layers were dried over Na$_2$SO$_4$, filtered and concentrated in vacuo. Purification of the crude residue by radial chromatography (SiO$_2$; gradient of 0% to 2% MeOH/CHCl$_3$) to give 162 mg (0.46 mmol; 28%) of the title compound as brown foam. FDMS 352 (M+);

Elemental Analysis for C$_{19}$H$_{16}$N$_2$O$_3$S.0.8H$_2$O: Calculated: C, 62.21; H, 4.84; N, 7.64. Found: C, 62.57; H, 4.50; N, 7.27.

H. Ethyl (R,S)-(9-Benzyl-4-carbamoyl-1-oxo-3-thia-1,2,3,4-tetrahydrocarbazol-5-yl)oxyacetate

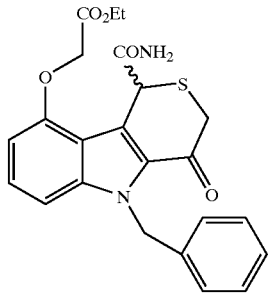

A slurry of (R,S)-(9-benzyl-5-hydroxy-1-oxo-3-thia-1,2,3,4-tetrahydrocarbazol-5-yl)carboxamide (145 mg, 0.411 mmol) and Cs$_2$CO$_3$ (400 mg, 1.23 mmol) in 5 mL of DMF was treated with ethyl bromoacetate (0.046 mL, 0.411 mmol). After stirring overnight, the reaction mixture was poured into 20 mL of H$_2$O. The aqueous layer was extracted with EtOAc (4×50 mL). The combined organic layers were washed with H$_2$O (3×100 mL), dried over Na$_2$SO$_4$, filtered and concentrated in vacuo. Purification of the crude residue by radial chromatography (SiO$_2$; gradient of 0% to 0.5% MeOH/CHCl$_3$) afforded 120 mg (0.274 mmol; 67%) of the title compound as light tan foam. FDMS 438 (M+);

Elemental Analysis for C$_{23}$H$_{22}$N$_2$O$_5$S.0.3H$_2$O.0.4CHCl$_3$: Calculated: C, 57.16; H, 4.72; N, 5.70. Found: C, 57.18; H, 4.61; N, 5.68.

I. (R, S)-(9-Benzyl-4-carbamoyl-1-oxo-3-thia-1,2,3,4-tetrahydrocarbazol-5-yl)oxyacetic Acid A solution of ethyl (R,S)-(9-benzyl-4-carbamoyl-1-oxo-3-thia-1,2,3,4-tetrahydrocarbazol-5-yl)oxyacetate (20 mg, 0.0456 mmol) in 0.5 mL of THF/MeOH/H$_2$O (3:1:1) was treated with LiOH (1.3 mg, 0.0547 mmol). The solution quickly turned clear orange, and after 45 min, the aqueous layer was extracted with 10 mL of CHCl$_3$, acidified with 1 N HCl and extracted again with CHCl$_3$ (3×20 mL). The acidified extracts were combined, dried over Na$_2$SO$_4$, filtered and concentrated in vacuo to an orange solid. The crude acid was purified on a pipet column (SiO$_2$; gradient of 0 to 2% MeOH/CHCl$_3$, trace glacial acetic acid) to afford 10 mg (0.0244 mmol; 53%) of the title compound as a light tan solid. FAB HRMS: m/e for C$_{21}$H$_{19}$N$_2$O$_5$S: 411.1015. Found: 411.1010 (M+1).

EXAMPLE 66

Preparation of (R,S)-(9-Benzyl-4-carbamoyl-1-oxo-3-thia-1,2,3,4-tetrahydrocarbazol-5-yl)oxyacetic Acid

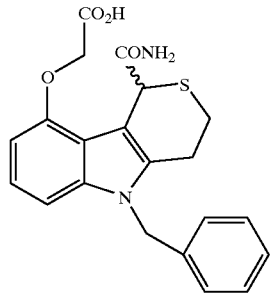

A. Ethyl (R,S)-(9-Benzyl-4-carbamoyl-3-thia-1,2,3,4-tetrahydrocarbazol-5-yl)oxyacetate

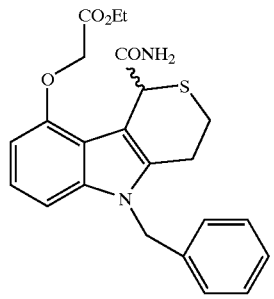

A slurry of ethyl (R,S)-(9-benzyl-4-carbamoyl-1-oxo-3-thia-1,2,3,4-tetrahydrocarbazol-5-yl)oxyacetate (75 mg, 0.171 mmol) in 1 mL of MeOH and 1.5 mL of THF (for solubility) was treated with NaBH$_4$ (8 mg, 0.214 mmol). After 20 min, the reaction mixture was quenched with 10 mL of H$_2$O. The layers were separated, and the aqueous layer was extracted with EtOAc (3×20 mL). The combined organic layers were dried over K$_2$CO$_3$, filtered and concentrated in vacuo. The crude intermediate alcohol was immediately dissolved in 2 mL of 1,2-dichloroethane. The resulting solution was treated with Et$_3$SiH (0.19 mL, 1.2 mmol). Upon cooling to 0° C., TFA (0.13 mL, 1.7 mmol) was added dropwise. After 1 h, the reaction mixture was poured into 25 mL of saturated aqueous NaHCO$_3$. The layers were separated, and the aqueous layer was extracted with EtOAc (3×25 mL). The combined organic layers were dried over Na$_2$SO$_4$, filtered and concentrated in vacuo. Purification of the crude residue by flash chromatography (SiO$_2$; gradient of 0% to 0.5% MeOH/CHCl$_3$) afforded 38 mg (0.0895 mmol, 52%) of the title compound as an off-white solid. FDMS 424 (M+);

Elemental Analysis for C$_{23}$H$_{24}$N$_2$O$_4$S.0.3H$_2$O.0.6CHCl$_3$: Calculated: C, 56.51; H, 5.06; N, 5.59. Found: C, 56.61; H, 4.87; N, 5.60.

B. (R,S)-(9-Benzyl-4-carbamoyl-1-oxo-3-thia-1,2,3,4-tetrahydrocarbazol-5-yl)oxyacetic Acid)

A solution of ethyl (R,S)-(9-benzyl-4-carbamoyl-3-thia-1,2,3,4-tetrahydrocarbazol-5-yl)oxyacetate (28 mg, 0.066 mmol) in 0.5 mL of THF/MeOH/H$_2$O (3:1:1) was treated with LiOH (1.9 mg, 0.079 mmol). After 1 h, the aqueous layer was extracted with 10 mL of CHCl$_3$, acidified with 1 N HCl and extracted again with CHCl$_3$ (3×20 mL). The organics were combined, dried over Na$_2$SO$_4$, filtered and concentrated in vacuo. The crude acid was purified on a pipet column (SiO$_2$; gradient of 0 to 1% MeOH/CHCl$_3$, trace glacial acetic acid) to afford 18 mg (0.045 mmol; 69%) of the title compound as an off-white solid. FAB HRMS: m/e, calcd for C$_{21}$H$_{21}$N$_2$O$_4$S: 397.1222., Found: 397.1216 (m+1).

EXAMPLE 67

Preparation of 2-(4-oxo-5-carboxamido-9-benzyl-9H-pyrido[3,4-b]indolyl)acetic acid hydrochloride

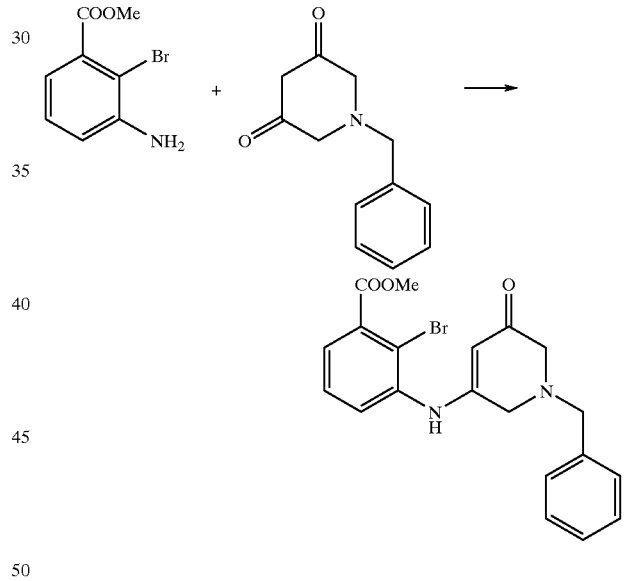

A. Preparation of N-[5-(1-benzyl-3-oxo-1,2,3,6-tetrahydropyridinyl)]-2-bromo-3-carbomethoxyaniline To a mixture of 2-bromo-3-carbomethoxyaniline (12.0 g, 52.2 mmol) and pyridinium p-toluenesulfonate (13.8 g, 54.9 mmol) in 2:1 toluene/dioxane (300 mL) was added 1-benzyl-3,5-piperidinedione (13.0 g, 70.2 mmol, Chen, L.-C.; Yang, S.-C. *Heterocycles* 1990, 31, 911–916). The apparatus was fitted with a Dean-Starke trap and the mixture refluxed for 10 h. The mixture was concentrated in vacuo and the residue dissolved in chloroform. This solution was washed three times with water, once with saturated sodium chloride solution, dried (sodium sulfate), filtered, and concentrated in vacuo to provide a dark oil. Chromatography (silica gel, chloroform to 4% methanol/96% chloroform) provided 2.0 g (9%) of the title product as a foam which could be crystallized form acetonitrile: mp 156–158° C. $^1$H NMR (CDCl$_3$) d 7.55 (m, 2 H), 7.40 (m, 6 H), 5.55 (s, 1 H), 3.94 (s, 3 H), 3.85 (m, 2 H), 3.56 (m, 2 H), 3.30 (bs, 2 H); MS ES+ m/e 414.9 (p), 416.9 (p); IR (KBr, cm$^{-1}$) 3185, 2944, 1728, 1603, 1544, 1306.

Elemental Analysis for $C_{20}H_{19}BrN_2O_3$: Calculated: C, 57.84; H, 4.61; N, 6.75. Found: C, 58.13; H, 4.49; N, 6.91.

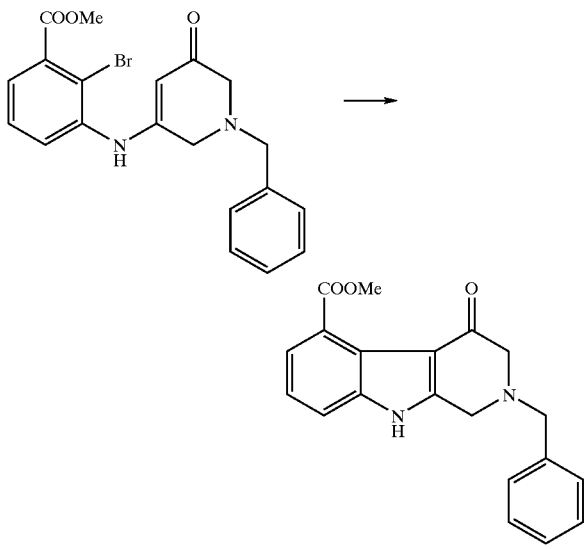

B. Preparation of 2-benzyl-4-oxo-5-carbomethoxy-1,2,3,4-tetrahydro-9H-pyrido[3,4-b]indole A mixture of N-[5-(1-benzyl-3-oxo-1,2,3,6-tetrahydropyridinyl)]-2-bromo-3-carbomethoxyaniline (2.07 g, 4.98 mmol), palladium(II) acetate (0.112 g, 0.499 mmol), tri-o-tolylphosphine (0.304 g, 0.999 mmol), triethylamine (1.3 mL, 9.3 mmol), and N,N-dimethylformamide (3 mL) in acetonitrile (12 mL) was placed in a tube and purged with argon. The tube was sealed and heated at 100° C. for 16 h. The mixture was cooled to room temperature, diluted with ethyl acetate, filtered, and the filtrate concentrated in vacuo to give a dark oil. Chromatography (silica gel, chloroform to 4% methanol/96% chloroform) provided 1.28 g (77%) of an oil which crystallized upon storing at 10° C.: recrystallized fro EtoAc/hexane mp 174–176° C. $^1$H NMR (CDCl$_3$) d 9.25 (bs, 1 H), 7.38 (d, J=9 Hz, 2 H), 7.30 (m, 5 H), 7.23 (t, J=8 Hz, 1 H), 3.97 (s, 3 H), 3.75 (s, 2 H), 3.72 (s, 2 H), 3.61 (s, 2 H); MS ES+ m/e 335 (p+1); IR (KBr, cm$^{-1}$) 3080, 1721, 1628, 1476, 1294, 1138.

Elemental Analysis for $C_{20}H_{18}N_2O_3$: Calculated: C, 71.84; H, 5.43; N, 8.38. Found: C, 72.06; H, 5.31; N, 8.31.

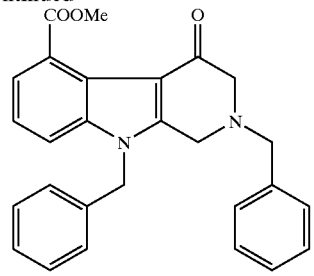

C. Preparation of 2,9-dibenzyl-4-oxo-5-carbomethoxy-1,2,3,4-tetrahydro-9H-pyrido[3,4-b]indole To a solution of 2-benzyl-4-oxo-5-carbomethoxy-1,2,3,4-tetrahydro-9H-pyrido[3,4-b]indole (0.928 g, 2.78 mmol) in dry tetrahydrofuran (5 mL) was added 60% sodium hydride in oil (111 mg). The resulting mixture was stirred at room temperature until gas evolution ceased. A solution of benzyl iodide (0.606. g, 2.78 mmol) in dry tetrahydrofuran (5 mL) was added to the reaction mixture and the resulting solution stirred at room temperature for 60 h. The mixture was diluted with methylene chloride and washed twice with saturated sodium chloride solution. The organic layer was dried (magnesium sulfate), filtered, and concentrated in vacuo. The residue was triturated with ethyl acetate resulting in a yellow precipitate (163 mg). The filtrate was concentrated in vacuo and chromatographed (silica gel, 5% methanol/95% methylene chloride) to provide an additional 580 mg of the title compound (743 mg total, 63%) as a crystalline solid: mp 198–199° C. $^1$H NMR (CDCl$_3$) d 7.43 (d, J=7 Hz, 1 H), 7.36 (d, J=8 Hz, 1 H), 7.25 (m, 9 H), 6.95 (m, 2 H), 5.24 (s, 2 H), 4.01 (s, 3 H), 3.78 (m, 4 H), 3.40 (bs, 2 H); MS EI+ m/e 425 (p+1); IR (KBr, cm$^{-1}$) 1726, 1648, 1449, 1291, 1134, 1107.

Elemental Analysis for $C_{27}H_{24}N_2O_3$: Calculated: C, 76.40; H, 5.70; N, 6.60. Found: C, 76.11; H, 5.45; N, 6.54.

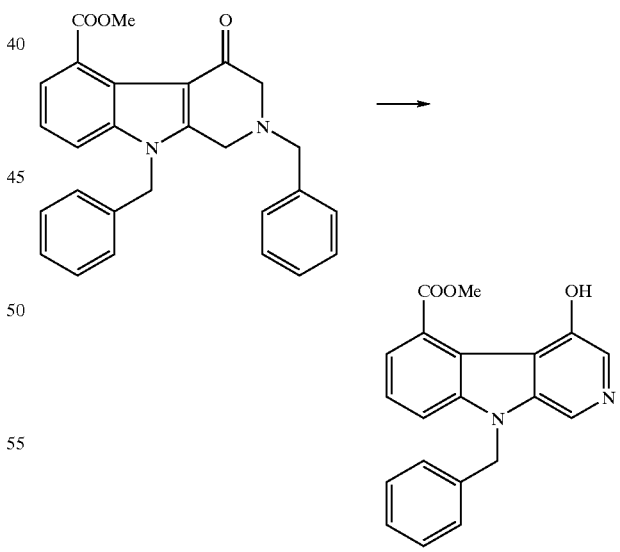

D. Preparation 4-hydroxy-5-carbomethoxy-9-benzyl-9H-pyrido[3,4-b]indole

A mixture of of 2,9-dibenzyl-4-oxo-5-carbomethoxy-1,2,3,4-tetrahydro-9H-pyrido[3,4-b]indole (521 mg, 1.23 mmol) and 10% palladium-on-carbon (250 mg) in acetic acid (15 mL) was refluxed for 4 h. The reaction flask was cooled to room temperature and purged with nitrogen. The flask was placed under a positive pressure of hydrogen and heated at 75° C. for 16 h. The mixture was cooled to room temperature, filtered, and concentrated in vacuo to provide an orange solid. Chromatography (silica gel, 4% methanol/ 96% methylene chloride) provided 271 mg (60%) of the title compound as a mono-hydrated yellow powder: mp>250° C. ¹H NMR (CDCl₃) d 8.46 (s, 1 H), 8.22 (s, 1 H), 8.09 (d, J=8 Hz, 1 H), 7.70 (d, J=8 Hz, 1 H), 7.56 (t, J=8 Hz, 1 H), 7.23 (m, 3 H), 7.08 (m, 2 H), 5.60 (s, 2 H), 4.11 (s, 3 H); MS ES+ m/e 333 (p+1).

Elemental Analysis for C₂₀H₁₆N₂O₃.H₂O: Calculated: C, 68.60; H, 4.98; N, 7.91. Found: C, 68.56; H, 5.18; N, 8.00.

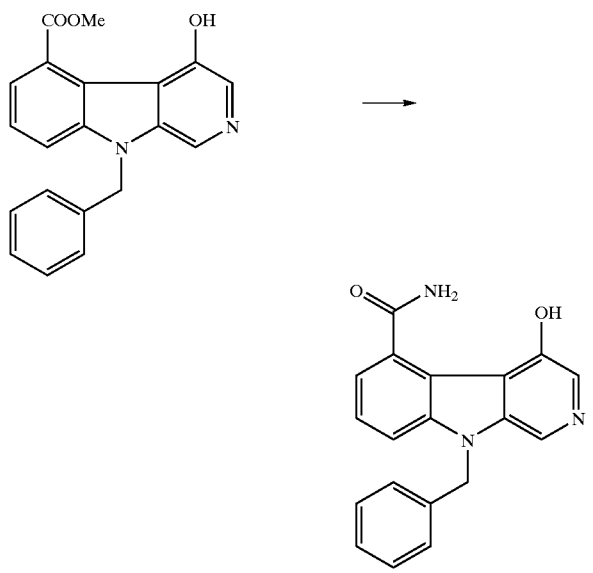

E. Preparation of 4-hydroxy-5-carboxamido-9-benzyl-9H-pyrido[3,4-b]indole

4-Hydroxy-5-carbomethoxy-9-benzyl-9H-pyrido[3,4-b] indole (200 mg, 0.618 mmol) was dissolved in a solution of 2M methanolic ammonia (10 mL) and placed in an open tube. The solution was saturated with gaseous ammonia for 10 min. The tube was sealed and heated at 60–65° C. for 8 h. The reaction mixture was cooled to room temperature and the resulting precipitate was collected in vacuo to provide 0.12 g (61%) of the title compound as a yellow solid: mp>250° C. ¹H NMR (DMSO-d₆) d 10.99 (s, 1 H, —OH), 8.99 (bs, 1 H, —NH), 8.59 (s, 1 H), 8.55 (bs, 1 H, —NH), 7.96 (d, J=7 Hz, 1 H), 7.94 (s, 1 H), 7.64 (t, J=8 Hz, 1 H), 7.57 (d, J=7 Hz, 1 H), 7.22 (m, 3 H), 7.12 (d, J=7 Hz, 2 H), 5.80 (s, 2 H); MS ES+ m/e 318 (p+1).

Elemental Analysis for C₁₉H₁₅N₃O₂: Calculated: C, 71.91; H, 4.76; N, 13.24. Found: C, 72.20; H, 4.57; N, 13.48.

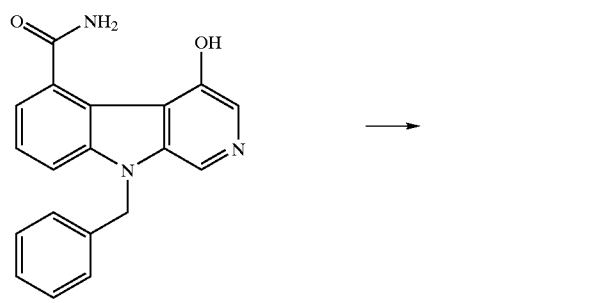

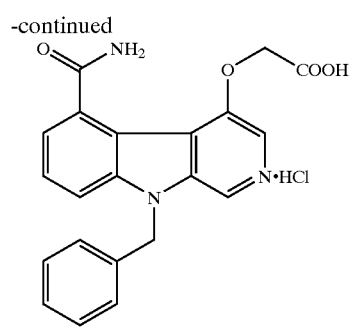

F. Preparation of 2-(4-oxo-5-carboxamido-9-benzyl-9H-pyrido[3,4-b]indolyl)acetic acid hydrochloride A mixture of 4-hydroxy-5-carboxamido-9-benzyl-9H-pyrido[3,4-b]indole (57 mg, 0.18 mmol), methyl bromoacetate (51 mL, 0.54 mmol), and cesium carbonate (114 mg, 0.349 mmol) in N,N-dimethylformamide (2 mL) was stirred at room temperature for 45 min. The mixture was treated with a minimum of water and methanol and concentrated in vacuo. The residue was dissolved in 1M aqueous lithium hydroxide (0.5 mL) and stirred at room temperature for 1 h. The mixture was concentrated in vacuo. The residue was dissolved in dilute aqueous hydrochloric acid and purified via reverse-phase HPLC, followed by lyophilization, to provide 28.5 mg (38%) of the title product. ¹H NMR (DMSO-d₆) d 12.85 (bs, 1 H), 9.41 (s, 1 H), 9.11 (s, 1 H), 8.66 (s, 1 H), 8.30 (s, 1 H), 8.10 (d, J=8 Hz, 1 H), 7.85 (t, J=8 Hz, 1 H), 7.76 (d, J=7 Hz, 1 H), 7.27 (m, 3 H), 7.19 (m, 2 H), 5.88 (s, 2 H), 5.37 (s, 2 H); MS ES+ m/e 375 (p+1).

Elemental Analysis for C₂₁H₁₇N₃O₄.HCl.0.5H₂O: Calculated: C, 60.58; H, 4.47; N, 10.09. Found: C, 60.39; H, 4.35; N, 9.69.

EXAMPLE 68

Preparation of [N-benzyl-1-carbamoyl-1-aza-1,2,3, 4-tetrahydrocarbazol-8-yl]oxyacetic acid A. Preparation of methyl N-benzyl-4-methoxyindole-2-carboxylate 6.15 g of methyl 4-methoxy indole-2-carboxylate were dissolved in 30 ml of dimethylformamide, added to a slurry of 12 g of cesium carbonate in 20 ml of dimethyl formamide and warmed to 45–50° C. for 1 hour. After cooling, benzyl bromide was added in the same solvent and stirred over night at r.t. The work up was done by adding ice-water and extracting twice with ether. The ether layer was washed with water, brine, dried over magnesium sulfate, filtered and concentrated to dryness. 8.6 g (97%). Mass Spec.: M⁺+1 (296) mp. 104–5° C.

B. Preparation of N-benzyl-2-hydroxymethyl-4-methoxyindole

To a slurry of 0.31 g of lithium aluminum hydride (8.2 mmol) in 25 ml of ether at 0–10° C. was added the methyl N-benzyl-4-methoxy indole-2-carboxylate (2.95 g) dissolved in 10 ml of the same solvent. The mixture was stirred at r.t. for 2 hours, quenched under the standard Fieser and Fieser procedure, filtered through a pad of celite and concentrated to dryness to give 2.8 g of alcohol. Mass spec.: M⁺+1 (268) mp.142–3° C.

C. Preparation of N-benzyl-4-methoxyindole-2-carboxaldehyde

A mixture of 3.2 g of N-benzyl-2-hydroxymethyl-4-methoxyindole (12 mmol) and 15 g of manganese dioxide (172 mmol) in 50 cc of dry dichloromethane was heated at reflux for 6 hours, cooled down to r.t. and filtered through celite. Concentration to dryness afford 3.6 g of a yellow solid. mp.130–31° C.

D. Preparation of methyl N-benzyl-4-methoxyindole-2-propionate 3.1 g (11.7 mmol) of N-benzyl-4-methoxyindole-2-carboxaldehyde were combined in 20 ml of pyridine with 3.65 g (35.1 mmol) of malonic acid and 0.4 g of piperidine; the mixture was heated at 100° C. for 2 hours, concentrated under vacuum to one third of volume and acidified with 1N HCl. The solid was filtered off, washed with water and vacuum dried to give 3.0 g of product.(85%). Mass Spec.:M$^+$+1(308) mp.208–10° C. This material was dissolved in 30 ml of methanol and 1 ml of sulfuric acid, heated to reflux for 2 hours, cooled to r.t. and concentrated to a small volume. The resultant solid was isolated by filtration. This material was hydrogenated in methanol-tetrahydrofuran with 5% Pd on carbon to afford the title compound (2.5 g) in 66% yield overall. Mass Spec.: M$^{30}$+1(324) mp.195–6° C.

E. Preparation of N-benzyl-1-aza-(3,4-dihydro)-8-methoxycarbazol-2-one 2.5 g of methyl N-benzyl-4-methoxyindole-2-propionate (7.7 mmol) were dissolved in 25 ml of ether and 2 equivalents (5.86 g ) of bis(2,2,2-trichloroethyl)azodicarboxylate were added portionwise over half hour, stirred at r.t. over night, filtered and concentrated to dryness. This compound was dissolved in a small amount of ether and filtered to give 3.2 g of a green solid. 1 g of this complex was reduced in 5 ml of acetic acid with 1 g of activated Zn. The temperature was kept at 10° C. for 1 hour, allowed to warmed up to r.t. and stirred overnight. Water was added and basified with 1N sodium hydroxide. Extraction with tetrahydrofuran and ethyl acetate, washing, drying and concentration gave a brown oil that crystallized from isopropyl alcohol.300 mg of crude and 130 mg after crystallization. Mass Spec.: M$^+$+1 (307) mp.206–8° C.

F. Preparation of N-benzyl-1-carbamoyl-1-aza-8-methoxy-1,2,3,4-tetrahydrocarbazole 500 mg of N-benzyl-1-aza-(3,4-dihydro)-8-methoxycarbazol-2-one in tetrahydrofuran were treated with 82 mg of lithium aluminum hydride at r.t. then warmed to 50° C. Work up was done according to the Fieser and Fieser procedure, The Agents for Organic Synthesis, Fieser, L. et al., John Wiley and Sons, NY 1967, p583), filtered through celite and concentrated to dryness. 420 mg of crude product. This product without further purification was treated with trimethylsilyl isocyanate in tetrahydrofuran for two hours and then concentrated to dryness. Ether was added and the amorphous solid isolated by filtration. 360 mg. Mass Spec.: M$^+$+1(336)

G. Preparation of [N-benzyl-1-carbamoyl-1-aza-1,2,3,4-tetrahydrocarbazol-8-yl]oxyacetic acid methyl ester 300 mg of N-benzyl-1-carbamoyl-1-aza-8-methoxy-1,2,3,4-tetrahydrocarbazole were dissolved in 10 ml of dichloromethane and cooled down to −20° C. 10 ml of a 1M solution of Boron tribromide in the same solvent were added dropwise. It was stirred at r.t. for three hours and poured over 1 N HCl-ice. This material was extracted in ethyl acetate, washed with water, brine, dried over magnesium sulfate, filtered and concentrated to dryness to give 190 mg. This material was dissolved in 5 ml of dimethylformamide and a slight excess of cesium carbonate was added. After warming to 35° C. for 10 minutes the methyl bromoacetate added and stirred at r.t. over night. Water was added, extracted with ethyl acetate, washed, dried over magnesium sulfate, filtered, and concentrated to dryness. Flash purification using 3:1 chloroform-ethyl acetate afforded 45 mg of product. Mass Spec.: M$^+$+1(394) NMR(CDCl$_3$): 7.3 (m,5 H), 7.0 (m,1 H), 6.95 (d, 1H) 6.4(d,1H) 5.25 (s,2H) 5.2 (b,2H) 4.8 (s,2H), 3.8 (s,3H), 2.75 (b,2H), 2.1 (b,2H), 1.25 (2,2H).

H. Preparation of [N-benzyl-1-carbamoyl-1-aza-1,2,3,4-tetrahydrocarbazol-8-yl]oxyacetic acid 15 mg of [N-benzyl-1-carbamoyl-1-aza-1,2,3,4-tetrahydrocarbazol-8-yl]oxyacetic acid methyl ester were dissolved in 10 ml of 7:1 tetrahydrofuran:methanol and 0.5 ml of 1N sodium hydroxide was added. After stirring at r.t. overnight, the solvents were stripped off, the residue acidified with 1N HCl and the solid filtered. This was washed with water and vacuum dried. Mass Spec.: M$^+$+1(380)

EXAMPLE 69

Preparation of 4-methoxy-6-methoxycarbonyl-10-phenylmethyl-6,7,8,9-tetrahydropyrido[1,2-a]indole

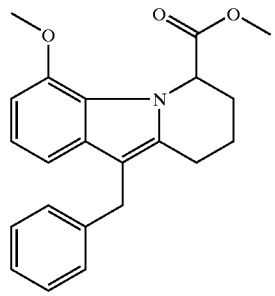

A. Preparation of 3-phenylmethyl-7-methoxyindole

A mixture of 15 gm (0.086 mol) of 2-methoxyphenylhydrazine hydrochloride and 12 mL (0.09 mol) of 3-phenylpropionaldehyde in 300 mL of toluene was refluxed for 1.5 hours with azeotropic removal of water. The suspension was cooled, evaporated in vacuo and the residue dissolved in 500 mL of dichloromethane and stirred with 9 mL (0.09 mol) of phosphorous trichloride for 18 hours. The solution was poured into ice-water, stirred well, and made basic with sodium bicarbonate. The organic phase was washed with saturated sodium chloride, dried over sodium sulfate, and evaporated in vacuo. The residue was chromatographed on silica gel eluting with a gradient hexane/5–15% ethyl ether to give product, 8.0 gm, 40%, as a viscous oil. $^1$H NMR (CDCl$_3$) δ: 3.95 (s, 3H), 4.10 (s, 2H), 6.65 (d, 1H), 6.90 (s, 1H), 7.00 (t, 1H), 7.10 (d, 1H), 7.20 (m, 1H), 7.30 (m, 4H), 8.20 (br s, 1H)

B. Preparation of methyl 2-[3-phenylmethyl-7-methoxyindol-1-yl]-5-chloropentanoate A solution of 2.7 gm (11 mmol) of the product from Part A in 75 mL of dimethylsulfoxide and a few mL's of tetrahydrofuran was treated in portions with 480 mg of sodium hydride (60% in mineral oil, 12 mmol), stirred for 10 minutes, and then for 16.5 hours after the addition of 0.3 gm of 18-crown-6 and and 1.7 gm (13 mmol) of methyl 2-bromo-5-chloropentanoate. The solution was diluted with ethyl acetate and water. The organic phase was washed with water, washed with saturated sodium chloride, dried over sodium sulfate, and evaporated in vacuo. The residue was chromatograhed on silica gel eluting with a gradient hexane/10–25% ethyl ether to give product, 1.7 gm, 40%, as an oil. $^1$H NMR (DMSOd$_6$) δ: 1.35 (m, 1H), 1.60 (m, 1H), 2.10 (m, 1H), 2.20 (m, 1H), 3.55 (t, 2H), 3.60 (s, 3H), 3.80 (s, 3H), 4.00 (s, 2H), 6.60 (d, 1H), 6.85 (t, 1H), 7.00 (d, 1H), 7.10 (m, 1H), 7.15 (s, 1H), 7.20 (m, 4H).

C. Preparation of 4-methoxy-6-methoxycarbonyl-10-phenylmethyl-6,7,8,9-tetrahydropyrido[1,2-a]indole A solution of 1.8 gm (4.7 mmol) of the product from Part B and 4 mL (15 mmol) of tri-n-butyltin hydride in 50 mL of toluene was heated to reflux and treated dropwise with a solution of 85 mg (0.5 mmol) of 2,2'-azobis(2-methylpropionitrile). The solution was refluxed 1 hour after the addition, cooled, evaporated in vacuo, taken up in ethyl acetate, shaken with aqueous potassium floride, and filtered. The organic phase was washed with saturated sodium chloride, dried over sodium sulfate, and evaporated in vacuo to give a mixture of 4-methoxy-6-methoxycarbonyl-10-phenylmethyl-6,7,8,9,9a,10-hexahydropyrido[1,2-a]indole and methyl 2-[3-phenylmethyl-7-methoxyindol-1-yl] pentanoate which was dissolved in 25 mL of dioxane and stirred with 450 mg (2 mmol) of dichlorodicyanoquinone for 30 minutes. The solution was evaporated in vacuo, taken up in dichloromethane, filtered through florisil, and evaporated in vacuo. The residue was chromatographed on silica gel eluting with a gradient hexane/10–20% ethyl ether to give the title compound, 75 mg, 5%, as an amorphous solid. $^1$H NMR (CDCl$_3$) δ: 1.70 (m, 1H), 1.85 (m, 1H), 2.20 (m, 1H), 2.35 (m, 1H), 2.70 (m, 1H), 3.00 (m, 1H), 3.70 (s, 3H), 3.80 (s, 3H), 4.00 (q, 2H), 5.65 (m, 1H), 6.50 (d, 1H), 6.90 (t, 1H), 7.00 (d, 1H), 7.10 (m, 1H), 7.20 (m, 4H).

EXAMPLE 70

Preparation of (4-carboxamido-9-phenylmethyl-4,5-dihydrothiopyrano[3,4-b]indol-5-yl)oxyacetic acid

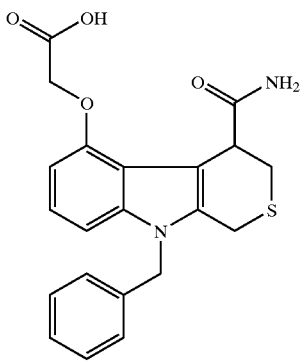

A. Preparation of methyl 3-(4-methoxyindol-3-yl)lactate

To a solution of 4-methoxyindole (200 mg, 1.36 mmol) and methyl 2,3-epoxypropionate (258 mg, 2.22 mmol) in 40 ml of carbon tetrachloride was added stannic chloride (0.16 ml, 1.39 mmol) dropwise at −5 to −10° C. The reaction mixture was stirred at that temperature for 1 hour and warmed up to room temperature slowly and with continous stirring. The reaction mixture was diluted with ethyl acetate and sodium bicarbonate solution, washed with brine, dried over sodium sulfate, and evaporated in vacuo to give 210 mg a yellow oil which was subjected to flash column chromatography (2:1 to 1:1 hexanes:ethyl acetate) to give product, 157 mg, 44%, as a yellow foam. $^1$H NMR (CDCl$_3$) d: 1.20 (t, 3H), 3.15(dd, 1H), 3.49 (dd, 1H), 3.95(s, 3H), 4.12 (q, 2H), 4.49(dd, 1H), 5.27 (s, 2H), 6.50(d, 1H), 6.83 (d, 1H), 7.08 (m, 2H), 7.31(m, 5H).

B. Preparation of a mixture of methyl 2-bromo-3-(4-methoxyindol-3-yl)propionate and methyl 2-bromomethyl-3-(4-methoxyindol-3-yl)acetate To a solution of the product from Part A (29 mg, 0.11 mmol) and triphenylphosphine (57.7 mg, 0.22 mmol) in 2 ml of 1,2-dichloroethane was added a solution of 1,2-dibromotetrachloroethane (71.6 mg, 0.22 mmol) in 1 mL of 1,2-dichloroethane at −10° C. The reaction mixture was warmed up to room temperature and stirred for an additional 10–15 minutes. It was then concentrated in vacuo and subjected to flash column chromatography (2:1 hexanes:ethyl ether) to give 31 mg,86%, of a mixture of methyl 2-bromo-3-(4-methoxyindol-3-yl)propionate and methyl 2-bromomethyl-3-(4-methoxyindol-3-yl)acetate as a yellow oil. $^1$H NMR (CDCl$_3$) d: 1.20 (t, 3H), 3.15(dd, 1H), 3.49 (dd, 1H), 3.95(s, 3H), 4.12 (q, 2H), 4.49(dd, 1H), 5.27 (s, 2H), 6.50(d, 1H), 6.83 (d, 1H), 7.08 (m, 2H), 7.31(m, 5H).

C. Preparation of a mixture of methyl 2-bromo-3-(1-phenylmethyl-4-methoxyindol-3-yl)propionate and methyl 2-bromomethyl-3-(1-phenylmethyl-4-methoxyindol-3-yl)acetate The product mixture from Part B was dissolved in 5 ml of acetonitrile and ~1 equivalent of potassium carbonate was added. This was heated to reflux overnight to form methyl 2-[4-methoxyindol-3,3-yl]spirocyclopropane carboxylate. To this reaction mixture was added 2 equivalents of benzyl bromide and the mixture refluxed overnight. The mix was filtered and concentrated. The residue was purified by flash column chromatography (97:1 hexanes:ether) to give 29 mg, 66%, of a ca. 1:9 mixture of methyl 2-bromo-3-(1-phenylmethyl-4-methoxyindol-3-yl)propionate and methyl 2-bromomethyl-3-(1-phenylmethyl-4-methoxyindol-3-yl)acetate. $^1$H NMR (CDCl$_3$) d: 1.28 (t, 3H), 3.82 (d, 2H), 3.96 (5, 3H), 4.26 (q, 2H), 4.81 (t, 1H), 5.25 (s, 2H), 6.53 (d, 1H), 6.89 (d, 1H), 7.02–7.18 (m, 7H).

D. Preparation of methyl 2-acetylthiomethyl-3-(1-phenylmethyl-4-methoxyindol-3-yl)acetate To a solution of the product mixture from Part C (2.87 g, 7.0 mmol) in 15 ml of tetrahydrofuran and 40 ml of dimethylformamide was added 18-crown-6 (0.31 gm) and potassium thioacetate (12.2 g, 0.11 mol) and then stirred at 50° C. for 2 hours. The mixture was diluted with ethyl acetate and brine. The organic phase was washed, dried and concentrated. The residue was purified by HPLC and afforded 1.8 g, 64.2%, of product. $^1$H NMR (CDCl$_3$) d: 1.19 (t, 3H), 2.28 (s, 3H), 3.54 (dd, 2H), 3.91 (s, 3H), 4.52 (t, 1H), 5.22 (s, 2H), 6.53 (d, 1H), 6.82 (d, 1H), 7.00 (s, 1H), 7.11 (m, 3H), 7.28 (m, 3H).

E. Preparation of methyl 2-mercaptomethyl-3-(1-phenylmethyl-4-methoxyindol-3-yl)acetate To a solution of the product from Part D (0.84 g, 2.0 mmol) in ethanol (70 ml) was added potassium carbonate (4.1 g, 30 mmol). The reaction mixture was stirred at room temperature for 1.5 hours. It was quenched with hydrochloric acid solution and extracted with ethyl acetate, dried, concentrated to give the product, 0.74 gm, 98%. $^1$H NMR (CDCl$_3$) d: 1.21 (t, 3H), 1.55 (t, 1H), 3.03 (m, 2H), 3.91 (s, 1H), 4.19 (q, 2H), 4.50 (t, 1H), 5.22 (s, 3H), 6.48 (d, 1H), 6.83 (d, 1H), 6.98 (s, 1H), 7.10 (m, 3H), 7.27 (m, 3H).

F. Preparation of methyl 2-methoxymethylmercaptomethyl-3-(1-phenylmethyl-4-methoxyindol-3-yl)acetate To a solution of the product from Part E (0.71 g, 1.92 mmol) in tetrahydrofuran (45 ml) was added a few mgs of 18-crown-6 and potassium hexamethyldisilazide (4.54 ml, 0.5M in toluene) at −75° C. The solution was stirred at −75° C. for 3 minutes and then iodomethyl methyl ether (0.28 ml, mmol) was added and stirred for 20 minutes at −7.5° C. The reaction mixture was poured into a mixture of ethyl acetate and brine. The organic layer was washed with brine, dried over sodium sulfate, and concentrated in vacuo. The residue was purified by column chromatography (3:1 hexanes:ethyl acetate) to give product, 650 mg, 82%, as a light yellow oil. $^1$H NMR (CDCl$_3$) d: 1.23 (t, 3H), 3.14 (m, 2H), 3.35 (s, 3H), 3.91 (s, 3H), 4.22 (q, 2H), 4.65 (d, 1H), 4.66 (t, 1H), 4.75 (d, 1H), 5.22 (s,2H), 6.51 (d, 1H), 6.90 (d, 1H), 7.00 (s, 1H), 7.07 (m, 3H), 7.28 (m, 3H).

G. Preparation of 4-methoxycarbonyl-5-methoxy-9-phenylmethyl-4,5-dihydrothiopyrano[3,4-b]indole To a solution of the product from Part F (518 mg, 1.25 mmol) in dichloromethane (10 ml) was quickly added one spatula of zinc bromide. The mixture was stirred at room temperature for 4.5 hours. The mix was poured into ethyl acetate and sodium bicarbonate solution. The organic layer was washed with brine, dried over sodium sulfate, and concentrated in vacuo. The residue was purified by column chromatography (3:1 hexanes:ethyl acetate) to give 269 mg, 56.4%, of the product as a yellow oil. $^1$H NMR (CDCl$_3$) d: 1.22 (t, 3H), 3.20 (dd, 1H), 3.59 (d, 1H), 3.72 (d, 1H), 3.83 (s, 3H), 4.21 (m 3H), 4.53 (t, 1H), 5.18 (d, 1H), 5.24 (d, 1H), 6.43 (d, 1H), 6.82 (d, 1H), 6.98 (d, 1H), 7.09 (t, 1H), 7.22 (m 4H).

H. Preparation of 4-carboxamido-5-methoxy-9-phenylmethyl-4,5-dihydrothiopyrano[3,4-b]indole To a solution of the product from Part G (120 mg, 0.31 mmol) in benzene (15 ml) was added freshly prepared methylchloroaluminum amide (0.67M, 9.3 ml). The mixture was stirred at 50° C. overnight. It was cooled, added to 1N hydrochloric acid, and diluted with ethyl acetate and brine. The organic layer was washed with brine, dried over sodium sulfate, and concentrated. The residue was purified by column chromatography (3:1 hexanes:ethyl acetate to ethyl acetate to 1% methanol in dichloromethane) to give product, 49.3 mg, 45%. MS FIA 353.4 (M+1)

Elemental Analyses for C$_{20}$H$_{20}$N$_{20}$O$_2$S: Calculated: C, 68.16; H, 5.72; N, 7.95. Found C, 68.31; H, 5.83; N, 8.05.

I. Preparation of ethyl [4-carboxamido-9-phenylmethyl-4,5-dihydrothiopyrano[3,4-b]indol-5-yl]oxyacetate To a solution of the product from Part H (210 mg, 0.60 mmol) in dichloromethane (30 ml) was added boron tribromide (10 ml, 1M in dichloromethane). The mixture was stirred for 0.5 hour. The reaction mixture was poured into ice-water, extracted with 1% methanol in dichloromethane, washed with brine, dried, and concentrated. The crude 4-carboxamido-5-hydroxy-9-phenylmethyl-4,5-dihydrothiopyrano[3,4-b]indole was dissolved in 13 ml DMF and the resulting solution was treated with sodium hydride (50 mg, 60% in mineral oil, 1.25 mmol) for 5 minutes and then with ethyl bromoacetate (0.09 ml, 1.2 mmol.) for 1.5 hours. The reaction mixture was diluted with ethyl acetate and brine. The organic layer was washed, dried, and concentrated. The residue was purified by column chromatography (1%–2% methanol in dichloromethane) to give product 79 mg, 31%, as a yellow foam. MS FIA 425.2 (M+1)

Elemental Analyses for C$_{23}$H$_{24}$N$_2$O$_4$S: Calculated: C, 65.07; H, 5.57; N, 6.47. Found: C, 65.88; H, 5.57; N, 6.47.

J. Preparation of (4-carboxamido-9-phenylmethyl-4,5-dihydrothiopyrano[3,4-b]indol-5-yl)oxyacetic acid To a solution of the product from Part I (53.7 mg, 0.13 mmol) in a mixture solvent (5 ml, tetrahydrofuran:methanol:water, 3:1:1) was added lithium hydroxide (~2.5 equiv). The solution was stirred overnight, acidified to PH ~2, and extracted with ethyl acetate. The organic solution was dried over sodium sulfate and evaporated in vacuo to give the title compound, 37 mg, 74%, as a yellow solid. MS FIA 397.1 (M+1).

Elemental Analyses for C$_{21}$H$_{20}$N$_2$O$_4$S: Calculated: C, 63.62; H, 5.08; N, 7.07. Found: C, 63.83; H, 5.33; N, 6.87.

EXAMPLE 71

Preparation of 3,4-dihydro-4-carboxamidol-5-methoxy-9-phenylmethylpyrano[3,4-b]indole

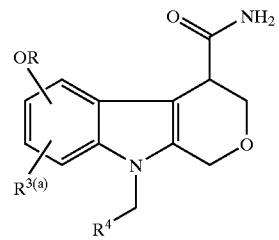

A. Preparation of ethyl [4-methoxyindol-3-yl]acetate

To a solution of 2.94 gm (20 mmol) of 4-methoxyindole in 150 ml of tetrahydrofuran was added slowly 13 ml of n-butyl lithium (1.6M in hexane; 20 mmol) followed by the slow addition of 20 ml of zinc chloride (1.0M in ethyl ether; 20 mmol) at 0–5° C. The cooling bath was removed and the solution stirred for 2 hours and then treated with 2.1 ml (25 mmol) of ethyl bromoacetate for 19 hours, diluted with ethyl acetate, washed with water, washed with brine, dried over sodium sulfate, and evaporated in vacuo. The residue was chromatographed on silica gel eluting with a gradient hexane/10–50% ethyl ether to give starting material (40%) and then product, 2.3 gm, 50%, as an oil. $^1$H NMR (CDCl$_3$) δ: 1.25 (t, 3H), 3.85 (s, 3H), 3.90 (s, 2H), 4.10 (q, 2H), 6.45 (d, 1H), 6.90 (d, 1H), 6.95 (s, 1H), 7.05 (t, 1H), 8.00 (br s, 1H).

B. Preparation of ethyl [4-methoxy-1-phenylmethylindol-3-yl]acetate

A solution of 1.6 gm (6.9 mmol) of the product from Part A in 75 ml of dimethylformamide and 10 ml of tetrahydrofuran was treated in portions with 300 mg of sodium hydride (60% in mineral oil; 7.5 mmol) and then with 1.0 ml (8.4 mmol) of benzyl bromide for 4 hours, and then diluted with ethyl acetate and water. The organic phase was washed with water, washed with brine, dried over sodium sulfate, and evaporated in vacuo. The residue was chromatographed on silica gel eluting with a gradient hexane/10–20% ethyl ether to give product, 1.0 gm, 45%, as an oil. $^1$H NMR (CDCl$_3$) δ: 1.25 (t, 3H), 3.85 (s, 3H), 3.90 (s, 2H), 4.10 (q, 2H), 5.25 (s, 2H), 6.50 (d, 1H), 6.85 (d, 1H), 6.95 (s, 1H), 7.05 (t, 1H), 7.10 (d, 2H), 7.25 (m, 3H). MS ES+ 324.0 (M+1).

C. Preparation of ethyl 2-[4-methoxy-1-phenylmethylindol-3-yl]-3-phenylmethoxypropionate To a stirred solution of the product from Part B (1.4 g, 4.3 mmol) in 50 mL of tetrahydrofuran was added potassium hexamethydisilazide (9.54 mL, 0.5M in toluene; 4.77 mmol) slowly at −75° C. under nitrogen. The resulting reaction mixture was stirred for a couple minutes and treated with chloromethyl benzyl ether (1.7 g, 8.6 mmol) at −75° C. The reaction mixture was stirred at −75° C. for 0.5 hour and poured into a mixture of brine and ethyl acetate. The organic layer was washed with brine, dried and concentrated in vacuo. The residue was purified by flash column chromatography (3:1 hexanes:ethyl acetate) to give product as a yellow oil, 1.34 g, 70.3%. $^1$H NMR (CDCl$_3$) δ: 1.22 (t, 3H), 3.88 (s, 3H), 3.94 (dd, 1H), 4.21 (m, 3H), 4.56 (s, 2H), 4.75 (dd, 1H), 5.20 (s, 2H), 6.40 (d, 1H), 6.81 (d, 1H), 7.02–7.34 (m, 7H).

D. Preparation of ethyl 2-[4-methoxy-1-phenylmethylindol-3-yl]-3-hydroxypropionate To a stirred solution of the product from Part C (0.33 g) in ethyl acetate (50 mL) was added 5% Pd/C (0.17 g) and 1 mL of 1N hydrochloric acid. The reaction mixture was stirred under ca. 1 atmosphere of hydrogen at room temperature overnight. The reaction mixture was filtered, neutralized with sodium bicarbonate solution, and washed with brine. The organic layer was dried over sodium sulfate and concentrated in vacuo to give product, 0.23 g, 89%, as a yellow oil. $^1$H NMR (CDCl$_3$) δ: 1.21(t, 3H), 3.87 (s, 3H), 3.92 (dd, 1H), 4.20 (m, 3H), 4.44 (dd, 1H), 5.21 (s, 2H), 6.43 (d, 1H), 6.84 (d, 1H), 6.98 (s, 1H), 7.00 (m, 3H), 7.30 (m, 3H).

E. Preparation of ethyl 2-[4-methoxy-1-phenylmethylindol-3-yl]-3-methoxypropionate To a stirred solution of the product from Part D (0.26 g, 0.74 mmol) in 18 mL of tetrahydrofuran was added potassium hexamethyldisilazide (1.63 mL, 0.5M in toluene, 0.815 mmol) slowly at −75° C. To the reaction mixture was added iodomethyl methyl ether (0.13 mL, 1.48 mmol) at −75° C. after 2 minutes stirring at the same temperature. The mixture was diluted with brine and ethyl acetate after 15 minutes at −75° C. The organic layer was washed with brine, dried over sodium sulfate, and concentrated in vacuo. The residue was purified by column chromatography (4:1 to 3:1 hexanes-:ethyl acetate) to give product, 0.23 g, 79.3%, as a yellow oil. $^1$H NMR (CDCl$_3$) δ: 1.21 (t, 3H), 3.35 (s, 3H), 3.91 (s, 3H), 9.95 (m, 2H), 4.22 (q, 2H), 4.65 (s, 2H), 4.72 (dd, 1H), 5.21 (s, 2H), 6.41 (d, 1H), 6.82 (d, 1H), 7.04 (m, 4H), 7.24 (m, 3H).

F. Preparation of 3,4-dihydro-4-ethoxycarbonyl-5-methoxy-9-phenylmethylpyrano[3,4-b]indole To a stirred solution of boron trifluoride etherate (0.071 mL, 0.55 mmol) in dichloromethane (6 mL) was added a solution of the product from Part E (148 mg, 0.37 mmol) in dichloromethane (4 mL) at 0–5° C. slowly. The reaction mixture was warmed up to room temperature and stirred for 0.5 hour to complete the reaction. The reaction mixture was diluted with ethyl acetate and brine. The organic layer was washed with brine, dried over sodium sulfate, and concentrated in vacuo. The residue was chromatographed on silica gel (1:1 hexanes:ethyl ether) to give product, 49.3 mg, 36.2%, as a white solid. $^1$H NMR (CDCl$_3$) δ: 1.21 (t, 3H), 3.88(s, 3H), 4.05 (dd, 1H), 4.15 (m, 1H), 4.24 (m, 3H), 4.60 (d, 1H), 4.78 (d, 1H), 5.04 (d, 1H), 5.18 (d, 1H), 6.44 (d, 1H), 6.82 (d, 1H), 7.01 (m, 3H), 7.22 (m, 3H).

G. Preparation of 3,4-dihydro-4-carboxamidol-5-methoxy-9-phenylmethylpyrano[3,4-b]indole To a solution of the product from Part F (490 mg, 1.34 mmol) in benzene (60–80 mL) was added freshly prepared methylchloroaluminum amide (0.67M, 60 ml, 40 mmol). The reaction mixture was stirred at 50° C. for 24 hours, cooled, decomposed by the addition of 1N hydrochloric acid, and diluted with ethyl acetate and brine. The organic layer was washed with brine, dried over sodium sulfate, and concentrated. The residue was purified by column chromatography on silica gel eluting with a gradient dichloromethane/1–2% methanol to give product, 335 mg, 74.6%. MS FIA 337.2 (M+1)

Analyses for C$_{20}$H$_{20}$N$_2$O$_3$: Calculated: C, 71.41; H, 5.99; N, 8.33. Found: C, 71.51; H, 6.19; N, 8.26.

EXAMPLE 72

Preparation of 2-[(2,9 bis-benzyl-4-carbamoyl-1,2,3,4-tetrahydro-beta-carbolin-5-yl)oxy]acetic acid A. Preparation of 4-(tertbutyldimethylsilyl)oxyindole Imidazole (15.3 g, 225 mmol) was added to a solution of 4-hydroxyindole (20 g, 150 mmol) in 300 mL of anhydrous methylene chloride at ambient temperature. The resulting mixture was treated with tert-butyldimethylsilyl chloride (25 g, 165 mmol). After stirring overnight at ambient temperature, the reaction mixture was poured into 300 mL of water. The layers were separated, and the aqueous phase was extracted with methylene (2×100 mL). The combined organic layers were dried over sodium sulfate, filtered and concentrated in vacuo to a black oil. The crude residue was purified on a Prep 500 (silica gel; 0% to 5% ethyl acetate/hexanes) to give the title compound as a light purple waxy solid in quantitative yield. MS (ion spray, NH$_4$OAc) m/e [M+1]$^+$ 248, [M−1]$^-$ 246.

Elemental Analysis for C$_{14}$H$_{21}$NOSi: Calculated: C, 67.96; H, 8.55; N, 5.66. Found: C, 69.10; H, 8.79; N, 5.70.

B. Preparation of Ethyl [4-(tert-H-butyldimethylsilyl)oxyindole]-3-acetic acid

A solution of indole (78) (247 mg, 1.00 mmol) in dry tetrahydrofuran (2 mL) under a nitrogen atmosphere was cooled to −10° C. then n-butyllithium (0.625 mL, 1.00 mmol), 1.6 M in hexanes, was added dropwise over 30 sec by syringe. The resultant solution was stirred 15 minutes zinc chloride (1.0 mL, 1.0 mmol), 1 M in ether, was added all at once. The solution was stirred 2 hours while warming to ambient temperature. To this solution was added ethyl iodoacetate (0.118 mL, 1.00 mmol) all at once. The reaction mixture darkened but remained clear. The mixture was stirred 3 hours at ambient temperature concentrated in vacuo. The residue was purified directly on silica gel (30×35 mm column) eluting with methylene chloride. Concentration of the appropriate fractions yielded 192 mg (57.8%) of the titled product as a white solid. MS (ion spray, NH$_4$OAc) m/e [M+1]$^+$ 334, [M−1]$^-$ 332.

Elemental Analyses for C$_{18}$H$_{27}$NO$_3$Si: Calculated: C, 64.86; H, 8.11; N, 4.20. Found: C, 65.11; H, 8.02; N, 4.24.

C. Preparation of Ethyl [2,9-bis-benzyl-5-(tert-butyldimethylsilyl)oxy-1,2,3,4-tetrahydro-beta-carboline]-4-acetic acid A solution of the ester (79) (5.08 g, 15.2 mmol) in dry tetrahydrofuran (100 mL) was cooled to −78° C. then treated dropwise with 0.5 M potassium bis(trimethylsilyl)amide in toluene (32 mL, 16 mmol). The resultant solution was stirred 10 min then benzyl iodide (3.32 g, 15.2 mmol) was added all at once. The cooling bath was removed, the mixture warmed quickly to 0° C., then slowly to ambient temperature. After stirring 75 minutes at ambient temperature the mixture was concentrated in vacuo. The residue was taken up in ether and washed successively with 10% aqueous citric acid, water and saturated sodium bicarbonate solution. The ethereal solution was dried over magnesium sulfate and concentrated in vacuo. The residue was purified on silica gel (70×130 mm column) eluting with 500 mL 1:1 methylene chloride/hexanes then 500 mL methylene chloride. The appropriate fractions were combined and concentrated in vacuo to yield 5.90 g (91%) of ethyl [1-benzyl-4-(tert-butyldimethylsilyl)oxyindole]-3-acetic acid as a brown oil. Benzyl amine (2.14 g, 20.0 mmol) and paraformaldehyde (1.80 g, 120 mmol) were combined and warmed to reflux in anhydrous methanol (10 mL) for 2 hours. The mixture was concentrated in vacuo and dried under vacuum for 30 minutes to yield crude benzyl bis(methoxymethyl)amine as a water white oil. This material was used immediately without purification. To a cooled solution of ethyl [1-benzyl-4-(tert-butyldimethylsilyl)oxyindole]-3-acetic acid (190 mg, 0.45 mmol) in dry tetrahydrofuran (2 mL) was added potassium bis(trimethylsilyl)amide (0.98 mL, 0.49 mmol), 0.5 M in toluene, dropwise by syringe. After stirring the mixture 10 minutes, trimethylsilylchloride (0.057 mL, 0.45 mmol) was added all at once. The mixture was allowed to warm to ambient temperature then concentrated in vacuo. The residue was dried 30 minutes under vacuum to yield the trimethylsilylketene acetal (81). The residual ketene acetal (81) was immediately dissolved in methylene chloride (30 mL) to which was added freshly prepared benzyl bis(methoxymethyl)amine (175 mg, 0.90 mmol). The mixture was cooled to −78° C. and treated with 1 M zinc chloride in ether(0.9 mL, 0.9 mmol). The mixture was allowed to warm to ambient temperature and stirred for an additional 45 minutes. The mixture was washed with saturated sodium bicarbonate solution then passed thourough a silica gel plug eluting with 1:4 ethyl acetate/hexane. The desired fractions were combined and concentrated in vacuo then further purified on an SCX cartridge (1 g, Varian) with methanol and ammonia. The desired fractions were combined, concentrated and purified on silica gel eluting with methylene chloride to yield 34 mg (14%) of the titled tricyclic indole. MS (ion spray, $NH_4OAc$) m/e $[M+1]^+$ 555.

Elemental Analyses for $C_{34}H_{42}N_2O_3Si$: Calculated: C, 73.64; H, 7.58; N, 5.05. Found: C, 73.42; H, 7.61; N, 5.15.

D. Preparation of ethyl 2-[(2,9-bis-benzyl-4-carbamoyl-1,2,3,4-tetrahydro-beta-carbolin-5-yl)oxy]acetic acid A solution of 565 mg (1.02 mmol) of the compound of Part C in 10 mL 1:1 methanol/tetrahydrofuran was treated with 5 mL (5 mmol) 1 N lithium hydroxide under an atmosphere of nitrogen. The mixture was warmed briefly, allowed to stir at ambient temperature for 2 hours then concentrated in vacua to about 5 mL. The pH of the solution was adjusted to ~5 to 6 with 1 N hydrochloric acid. The resultant precipitate was collected and dried to yield 430 mg (102%) of hydroxy acid. This product was suspended with hydroxybenzotriazole (160 mg, 1.19 mmol) and 1-(3-dimethylaminopropyl)-3-ethylcarbodiimide hydrochloride (940 mg, 2.30 mmol) in 30 mL of 1:1 tetrahydrofuran/methylene chloride. The mixture was stirred vigorously for 10 minutes, saturated with ammonia gas, stirred vigorously for 1 hour, then concentrated in vacuo. The residue was partitioned between ethyl acetate and saturated sodium bicarbonate solution. The ethyl acetate solution was dried over anhydrous magnesium sulfate, filtered and concentrated in vacuo. The residue was passed thourough a plug of silica gel with ethyl acetate. The eluant was evaporated to yield 175 mg (43%) of the carboxamide.

This compound was dissolved in 3 mL dry tetrahydrofuran, cooled to −70° C. and treated with 0.5 M potassium bis(trimethylsilyl)amide in toluene (0.85 mL, 0.425 mmol). The solution was stirred 10 min then ethyl bromoacetate was added all at once. The reaction was stirred 6 hours while warming to ambient temperature. The mixture was concentrated in vacuo and the residue purified on silica gel eluting with ethyl acetate to yield 86 mg (41%) of the title compound. MS (ion spray, $NH_4OAc$) m/e $[M+1]^+$ 498.

Elemental Analyses for $C_{30}H_{31}N_3O_4$: Calculated: C, 72.43; H, 6.24; N, 8.45. Found: C, 72.54; H, 6.36; N, 8.64.

E. Preparation of 2-[(2,9-bis-benzyl-4-carbamoyl-1,2,3,4-tetrahydro-beta-carbol-5-yl)oxy]acetic acid A solution of the compound from Part D (78 mg, 0.16 mmol) in 2 mL 1:1 tetrahydrofuran/methanol was stirred with 1 M lithium hydroxide (0.63 mL, 0.63 mmol) for 3 hours. The mixture was concentrated in vacuo to give a white solid. The solid was suspended in 2 mL water and the pH adjusted to ~5 to 6 with 1 N hydrochloric acid forming a somewhat different white solid. The new solid was collected by filtration and dried under vacuum to yield 68 mg (93%) of the title compound. MS (ion spray, $NH_4OAc$) m/e $[M+1]^+$ 470.

Elemental Analyses for $C_{28}H_{27}N_3O_4 \cdot 0.8\ H_2O$: Calculated: C, 69.49; H, 5.96; N, 8.68. Found: C, 69.50; H, 5.64; N, 8.54.

F. Preparation of 2-[(9-benzyl-4-carbamoyl-1,2,3,4-tetrahydro-beta-carbolin-5-yl)oxy]acetic acid hydrochloride A suspension of the compound from part E (68 mg, 0.14 mmol) was treated with 3–4 drops of 1N HCl to effect solution. To the solution was added 10% palladium on carbon (70 mg). The flask was appropriately purged with nitrogen and hydrogen then stirred under a hydrogen atmosphere for 18 h. The mixture was filtered and the solids thoroughly washed with methanol. The filtrate was concentrated in vacuo to yield a mixture of acid and methyl ester. The mixture was treated with aqueous 1N LiOH (0.3 mL) in about 2 mL methanol over 2 h. The mixture was concentrated in vacuo and the residue acidified to pH=5 with 1 N HCl causing a precipitate to form. The precipitate was collected by filtration. The filtrate was concentrated in vacuo to leave a residue. The collected solid and the residue were purified by reverse phase chromatography to yield 31 mg (68%) of the title compound as the HCl salt. MS (ion spray) m/e $[M+1]^+$ 380. IR (KBr, $cm^{-1}$) 3393(br), 3100–2500 (COOH), 1735, 1671, 1638, 1615, 1445, 1263, 1133, 731, 722.

Therapeutic Use of Tricyclic Compounds

The compounds described herein are believed to achieve their beneficial therapeutic action principally by direct inhibition of human $sPLA_2$, and not by acting as antagonists for arachidonic acid, nor other active agents below arachidonic acid in the arachidonic acid cascade, such as 5-lipoxygenases, cyclooxygenases, etc.

The method of the invention for inhibiting $sPLA_2$ mediated release of fatty acids comprises contacting $sPLA_2$ with an therapeutically effective amount of the compound of Formula (I) or its salt.

The compounds of the invention may be used in a method of treating a mammal (e.g., a human) to alleviate the pathological effects of septic shock, adult respiratory distress syndrome, pancreatitus, trauma, bronchial asthma, allergic rhinitis, and rheumatoid arthritis; wherein the method comprises administering to the mammal a compound of formula (I) in a therapeutically effective amount. A "therapeutically effective" amount is an amount sufficient to inhibit $sPLA_2$ mediated release of fatty acid and to thereby inhibit or prevent the arachidonic acid cascade and its deleterious products. The therapeutic amount of compound of the invention needed to inhibit $sPLA_2$ may be readily determined by taking a sample of body fluid and assaying it for $sPLA_2$ content by conventional methods.

Throughout this document, the person or animal to be treated will be described as a "mammal", and it will be understood that the most preferred subject is a human. However it must be noted that the study of adverse conditions of the central nervous system in non-human animals is only now beginning, an that some instances of such treatments are coming into use. Accordingly, use of the present compounds in non-human animals is contemplated. It will be understood that the dosage ranges for other animals will necessarily be quite different from the doses administered to humans, and accordingly that the dosage ranges described be recalculated. For example, a small dog may be only $\frac{1}{10}^{th}$ of a typical human's size, and it will therefore be necessary for a much smaller dose to be used. The determination of an effective amount for a certain non-human animal is carried out in the same manner described below in the case of humans, and veterinarians are well accustomed to such determinations.

Pharmaceutical Formulations of the Invention

As previously noted the compounds of this invention are useful for inhibiting $sPLA_2$ mediated release of fatty acids such as arachidonic acid. By the term, "inhibiting" is meant the prevention or therapeutically significant reduction in release of sPLA$_2$ initiated fatty acids by the compounds of the invention. By "pharmaceutically acceptable" it is meant the carrier, diluent or excipient must be compatible with the other ingredients of the formulation and not deleterious to the recipient thereof.

In general, the compounds of the invention are most desirably administered at a dose that will generally afford effective results without causing any serious side effects and can be administered either as a single unit dose, or if desired, the dosage may be divided into convenient subunits administered at suitable times throughout the day.

The specific dose of a compound administered according to this invention to obtain therapeutic or prophylactic effects will, of course, be determined by the particular circumstances surrounding the case, including, for example, the route of administration, the age, weight and response of the individual patient, the condition being treated and the severity of the patient's symptoms. Typical daily doses will contain a non-toxic dosage level of from about 0.01 mg/kg to about 50 mg/kg of body weight of an active compound of this invention.

Preferably the pharmaceutical formulation is in unit dosage form. The unit dosage form can be a capsule or tablet itself, or the appropriate number of any of these. The quantity of active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

A "chronic" condition means a deteriorating condition of slow progress and long continuance. As such, it is treated when it is diagnosed and continued throughout the course of the disease. An "acute" condition is an exacerbation of short course followed by a period of remission. In an acute event, compound is administered at the onset of symptoms and discontinued when the symptoms disappear.

Pancreatitis, trauma-induced shock, bronchial asthma, allergic rhinitis and rheumatoid arthritis may occur as an acute event or a chronic event. Thus, the treatment of these conditions contemplates both acute and chronic forms. Septic shock and adult respiratory distress, on the other hand, are acute conditions treated when diagnosed.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the compounds of the invention together with a pharmaceutically acceptable carrier or diluent therefor. The present pharmaceutical formulations are prepared by known procedures using well known and readily available ingredients.

In making the compositions of the present a invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from about 1 to about 99 weight percent of the active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol. Other compositions can be made by dispersing the finely divided active ingredient in aqueous starch or sodium carboxymethyl cellulose solution or in a suitable oil.

The following pharmaceutical formulations 1 through 8 are illustrative only and are not intended to limit the scope of the invention in any way. "Active ingredient", refers to a compound according to Formula (III) or a pharmaceutically acceptable salt, solvate, or prodrug thereof.

Formulation 1
Hard gelatin capsules are prepared using the following ingredients:

|  | Quantity (mg/capsule) |
|---|---|
| Compound of Example 5 | 250 |
| Starch, dried | 200 |
| Magnesium stearate | 10 |
| Total | 460 mg |

| Formulation 2 | |
|---|---|
| A tablet is prepared using the ingredients below: | |
| | Quantity (mg/tablet) |
| Compound of Example 10 | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

| Formulation 3 | |
|---|---|
| An aerosol solution is prepared containing the following components: | |
| | Weight |
| Compound of Example 15 | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

| Formulation 4 | |
|---|---|
| Tablets, each containing 60 mg of active ingredient, are made as follows: | |
| Compound of Example 25 | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

| Formulation 5 | |
|---|---|
| Capsules, each containing 80 mg of active ingredient, are made as follows: | |
| Compound of Example 30 | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

| Formulation 6 | |
|---|---|
| Suppositories, each containing 225 mg of active ingredient, are made as follows: | |
| Compound of Example 35 | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

| Formulation 7 | |
|---|---|
| Suspensions, each containing 50 mg of active ingredient per 5 ml dose, are made as follows: | |
| Compound of Example 40 | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

| Formulation 8 | |
|---|---|
| An intravenous formulation may be prepared as follows: | |
| Compound of Example 45 | 100 mg |
| Isotonic saline | 1,000 ml |

The solution of the above ingredients generally is administered intravenously to a subject at a rate of 1 ml per minute.

Assay Experiments

Assay Example 1

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992 (the disclosure of which is incorporated herein by reference):

Reagents

REACTION BUFFER $CaCl_2.2H_2O$ (1.47 g/L)

KCl (7.455 g/L)

Bovine Serum Albumin (fatty acid free) (1 g/L)

(Sigma A-7030, product of Sigma Chemical Co. St. Louis Mo., USA)

TRIS HCl (3.94 g/L)

pH 7.5 (adjust with NaOH)

ENZYME BUFFER 0.05 $NaOAc.3H_2O$, pH 4.5

0.2 NaCl

Adjust pH to 4.5 with acetic acid

DTNB 5,5'-dithiobis-2-nitrobenzoic acid

RACEMIC DIHEPTANOYL THIO—PC racemic 1,2-bis(heptanoylthio)-1,2-dideoxy-sn-glycero-3-phosphorylcholine TRITON X-100™ prepare at 6.249 mg/ml in reaction buffer to equal 10 uM TRITON X-100™ is a polyoxy ethylene non-ionic detergent supplied by Pierce Chemical Company, 3747 N. Meridian Road, Rockford, Ill. 61101.

REACTION MIXTURE

A measured volume of racemic diheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains 1 mM diheptanoly thio-PC substrate, 0.29 mm Triton X-100™ detergent, and 0.12 mm DTMB in a buffered aqueous solution at pH 7.5.

Assay Procedure

1. Add 0.2 ml reaction mixture to all wells;
2. Add 10 ul test compound (or solvent blank) to appropriate wells, mix 20 seconds;
3. Add 50 nanograms of $sPLA_2$ (10 microliters) to appropriate wells;
4. Incubate plate at 40° C. for 30 minutes;
5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, $IC_{50}$ values were determined. Typically, the $IC_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of $IC_{50}$ values. $IC_{50}$ were determined by plotting log concentration versus inhibition values in the range from 10–90% inhibition.

Compounds of the instant invention were tested in Assay Example 1 and were found to be effective at concentrations of less than 100 µM.

Assay Example 2

Method

Male Hartley strain guinea pigs (500–700 g) were killed by cervical dislocation and their heart and lungs removed intact and placed in aerated (95% $O_2$:5% $CO_2$) Krebs buffer. Dorsal pleural strips (4×1×25 mm) were dissected from intact parenchymal segments (8×4×25 mm) cut parallel to the outer edge of the lower lung lobes. Two adjacent pleural strips, obtained from a single lobe and representing a single tissue sample, were tied at either end and independently attached to a metal support rod. One rod was attached to a Grass force-displacement transducer Model FTO3C, product of Grass Medical Instruments Co., Quincy, Mass., USA). Changes in isometric tension were displayed on a monitor and thermal recorder (product of Modular Instruments, Malvern, Pa.). All tissues were placed in 10 ml jacketed tissue baths maintained at 37° C. The tissue baths were continuously aerated and contained a modified Krebs solution of the following composition (millimolar) NaCl, 118.2; KCl, 4.6; $CaCl_2.2H_2O$, 2.5; $MgSO_4.7H_2O$, 1.2; $NaHCO_3$, 24.8; $KH_2PO_4$, 1.0; and dextrose, 10.0. Pleural strips from the opposite lobes of the lung were used for paired experiments. Preliminary data generated from tension/response curves demonstrated that resting tension of 800 mg was optimal. The tissues were allowed to equilibrate for 45 min. as the bath fluid was changed periodically.

Cumulative Concentration-response Curves

Initially tissues were challenged 3 times with KCl (40 mM) to test tissue viability and to obtain a consistent response. After recording the maximal response to KCl, the tissues were washed and allowed to return to baseline before the next challenge. Cumulative concentration-response curves were obtained from pleural strips by increasing the agonist concentration ($sPLA_2$) in the tissue bath by half-$log_{10}$ increments while the previous concentration remained in contact with the tissues (Ref.1, supra.). Agonist concentration was increased after reaching the plateau of the contraction elicited by the preceding concentration. One concentration-response curve was obtained from each tissue. To minimize variability between tissues obtained from different animals, contractile responses were expressed as a percentage of the maximal response obtained with the final KCl challenge. When studying the effects of various drugs on the contractile effects of $sPLA_2$, the compounds and their respective vehicles were added to the tissues 30 minutes prior to starting the $sPLA_2$ concentration-response curves.

Statistical Analysis

Data from different experiments were pooled and presented as a percentage of the maximal KCl responses (mean±S.E.). To estimate the drug induced rightward shifts in the concentration response curves, the curves were analyzed simultaneously using statistical nonlinear modeling methods similar to those described by Waud (1976), Equation 26, p. 163, (Ref.2). The model includes four parameters: the maximum tissue response which was assumed the same for each curve, the $ED_{50}$ for the control curve, the steepness of the curves, and the $pA_2$, the concentration of antagonist that requires a two-fold increase in agonist to achieve an equivalent response. The Schild slope was determined to be 1, using statistical nonlinear modeling methods similar to those described by Waud (1976), Equation 27, p. 164 (Ref. 2). The Schild slope equal to 1 indicates the model is consistent with the assumptions of a competitive antagonist; therefore, the pA2 may be interpreted as the apparent $K_B$, the dissociation constant of the inhibitor.

To estimate the drug-induced suppression of the maximal responses, $sPLA_2$ responses (10 ug/ml) were determined in the absence and presence of drug, and percent suppression was calculated for each pair of tissues. Representative examples of inhibitory activities are presented in Table 2, below.

Ref. 1—Van, J. M.: Cumulative dose-response curves. II. Technique for the making of dose-response curves in isolated organs and the evaluation of drug parameters. *Arch. Int. Pharmacodyn. Ther.*, 143: 299–330, 1963.

Ref. 2—Waud, D.: Analysis of dose-response relationships, in *Advances in General and Cellular Pharmacology* eds Narahashi, Bianchi 1:145–178, 1976.

Compounds of the instant invention were tested in Assay Example 2 and were found to be effective at concentrations below 20 μM.

Assay Example 3

$sPLA_2$ Transgenic Mice Assay

Materials & Methods

The mice utilized in these studies were mature, 6–8 month old, $ZnSO_4$-stimulated, hemizygous line 2608[a] transgenic mice (Fox et. al. 1996). Transgenic mice from this line express human $sPLA_2$ in the liver and other tissues and typically achieve levels of human $sPLA_2$ in their circulation of approximately 173±10 ng/ml when maximally stimulated with $ZnSO_4$ (Fox, et al. 1996). The mice were housed under constant humidity and temperature and received food and water ad libitum. Animal room lighting was maintained on a 12-hour light/dark cycle and all experiments were performed at the same time of the day during the early morning light period.

For intravenous testing, compounds or vehicle were administered as an IV bolus via the tail vein in a volume of 0.15 ml. Vehicle consisted of 1–5% dimethylsulfoxide, 1–5% ethanol and 10–30% polyethylene glycol 300 in $H_2O$; the concentrations of these ingredients were adjusted according to the solubility of the compound. Mice were bled retro-orbitally prior to drug or vehicle administration and 30 minutes, 2 and 4 hours thereafter. Three to six mice were used for each dose. $PLA_2$ catalytic activity in the serum was assayed with a modified phosphatidylcholine/deoxycholine mixed micelle assay (Fox, et al. 1996, Schadlich, et al., 1987) utilizing 3 mM sodium deoxycholate and 1 mM 1-palmitoyl-2-oleoyl-sn-glycero-3-phosphocholine.

For oral testing, compounds were dissolved in 1–5% ethanol/10–30% polyethylene glycol 300 in $H_2O$ or were suspended in 5% dextrose in $H_2O$ and administered by oral gavage. Serum was prepared from retro-orbital blood and assayed for $PLA_2$ catalytic activity as above.

References

Fox, N., M. Song, J. Schrementi, J. D. Sharp, D. L. White, D. W. Snyder, L. W. Hartley, D. G. Carlson, N. J. Bach, R. D. Dillard, S. E. Draheim, J. L. Bobbitt, L. Fisher and E. D. Mihelich. 1996. Eur. J. Pharmacol. 308: 195.

Schadlich, H. R., M. Buchler, and H. G. Beger, 1987, J. Clin. Chem. Clin. Biochem. 25, 505.

Compounds of the instant invention were tested in Assay Example 3 and were found to be effective.

While the present invention has been illustrated above by certain specific embodiments, it is not intended that these specific examples should limit the scope of the invention as described in the appended claims.

We claim:

1. A compound of the formula

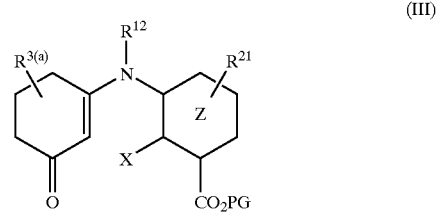

(III)

wherein

PG is an acid protecting group;

$R^{21}$ is a non-interfering substituent;

$R^{12}$ is H or $CH_2R^4$ where $R^4$ is H, —($C_5$–$C_{14}$)alkyl, —($C_3$–$C_{14}$)cycloalkyl; pyridyl, phenyl or phenyl substituted with from 1–5 substituents selected from the group consisting of —($C_1$–$C_6$)alkyl, halo, —$CF_3$, —$OCF_3$, —($C_1$–$C_4$)alkoxy, —CN, —($C_1$–$C_4$)alkylthio, phenyl ($C_1$–$C_4$)alkyl, —($C_1$–$C_4$)alkylphenyl, phenyl, phenoxy, —$OR^9$; where $R^9$ and $R^{10}$ are independently hydrogen, —$CF_3$, phenyl, —($C_1$–$C_4$)alkyl, —($C_1$–$C_4$)alkylphenyl or —phenyl($C_1$–$C_4$)alkyl; tetrazole; tetrazole substituted with —($C_1$–$C_4$)alkyl or —($C_1$–$C_4$)alkylphenyl: or naphthyl;

$R^3$(a) is H, —O($C_1$–$C_4$)alkyl, halo, —($C_1$–$C_6$)alkyl, phenyl, —($C_1$–$C_4$)alkylphenyl; phenyl substituted with —($C_1$–$C_6$)alkyl, halo or —$CF_3$; —$CH_2OSi(C_1$–$C_6)$ alkyl, furyl, thiophenyl, —($C_1$–$C_6$)hydroxyalkyl, —($C_1$–$C_6$)alkoxy($C_1$–$C_6$)alkyl, —($C_1$–$C_6$)alkoxy ($C_1$–$C_6$)alkenyl; or —$(CH_2)_nR^8$ where $R^8$ is H, —$NR^9R^{10}$, —CN or phenyl where $R^9$ and $R^{10}$ are independently hydrogen, —$CF_3$, phenyl, —($C_1$–$C_4$) alkyl, —($C_1$–$C_4$)alkylphenyl or -phenyl($C_1$–$C_4$)alkyl and n is 1 to 8:

Z is cyclohexenyl or phenyl; and

X is halo.

2. A compound which is selected from the group consisting of:

(3-Carbomethoxy-2-bromoanilino)-5-methyl-cyclohex-2-en-1-one;

5-Carbomethoxy-1,2-dihydro-2-methyl-9H-carbazol-4 (3H)-one;

(3-Carbomethoxy-2-bromoanilino)-5-methyl-cyclohex-2-en-1-one;

5-Carbomethoxy-1,2-dihydro-2-methyl-9H-carbazol-4 (3H)-one;

[(Phenyl)methyl]-5-carbomethoxy-2-methyl-1,2-dihydrocarbazol-4(3H)-one;

[(3-Fluorophenyl)methyl]-5-carbomethoxy-2-methyl-1,2-dihydrocarbazol-4(3H)-one;

[(3-Methylphenyl)methyl]-5-carbomethoxy-2-methyl-1,2-dihydrocarbazol-4(3H)-one;

(3-Carbomethoxy-2-bromoanilino)-5-(4-trifluoromethylphenyl-cyclohex-2-en-1-one;

5-Carbomethoxy-1,2-dihydro-2-(4-trifluoromethylphenyl)-9H-carbazol-4(3H)-one;
[(Phenyl)methyl]-5-carbomethoxy-2-(4-trifluoromethylphenyl)-1,2-dihydrocarbozol-4(3H)-one;
(2-Bromo-3-carbomethoxyanilino)-5-pentylcyclohex-2-en-1-one;
5-Carbomethoxy-1,2-dihydro-2-pentyl-9H-carbazol-4(3H)-one;
5-Carbomethoxy-1,2-dihydro-2-pentyl-9-(phenylmethyl)carbazol-4(3H)-one;
(2-Bromo-3-carbomethoxyanilino)-5-[(1-methyl)ethyl]cyclohex-2-en-1-one;
5-Carbomethoxy-1,2-dihydro-2-(1-methylethyl)-9H-carbazol-4(3H)-one;
5-Carbomethoxy-1,2-dihydro-2-(1-methylethyl)-9-(phenylmethyl)carbazol-4(3H)-one;
(2-Bromo-3-carbomethoxyanilino)-5-(hydroxymethyl)cyclohex-2-en-1-one;
5-Carbomethoxy-1,2-dihydro-2-(hydroxymethyl)-9H-carbazol-4(3H)-one;
5-Carbomethoxy-1,2-dihydro-2-(hydroxymethyl)-9-(phenylmethyl)carbazol-4(3H)-one;
(2-Bromo-3-carbomethoxyanilino)-5-phenylcyclohex-2-en-1-one;
5-Carbomethoxy-1,2-dihydro-2-phenyl-9H-carbazol-4(3H)-one;
5-Carbomethoxy-1,2-dihydro-2-phenyl-9-(phenylmethyl)carbazol-4(3H)-one;
(2-Bromo-3-carbomethoxyanilino)-5-(4-chlorophenyl)cyclohex-2-en-1-one;
5-Carbomethoxy-1,2-dihydro-2-(4-chlorophenyl)-9H-carbazol-4(3H)-one;
5-Carbomethoxy-1,2-dihydro-2-(4-chlorophenyl)-9-(phenylmethyl)carbozol-4(3H)-one;
(2-Bromo-3-carbomethoxyanilino)-5-(2-furyl)cyclohex-2-en-1-one;
5-Carbomethoxy-1,2-dihydro-2-(2-furyl)-9H-carbazol-4(3H)-one;
5-Carbomethoxy-1,2-dihydro-2-(2-furyl)-9-(phenylmethyl)carbazol-4(3H)-one;
5-Carbomethoxy-1,2-dihydro-9-(phenylmethyl)-2-[(tri(-1-methylethyl)silyl)oxymethyl]carbazol-4(3H)-one;
(3-Carbomethoxy-2-chloroanilino)cyclohex-2-en-1-one;
5-Carbomethoxy-1,2-dihydro-9H-carbazol-4(3H)-one;
(3-Carbomethoxy-2-bromoanilino)cyclohex-2-en-1-one;
[(Phenyl)methyl]-5-carbomethoxy-1,2-dihydrocarbazol-4(3H)-one;
[(3-Fluorophenyl)methyl]-5-carbomethoxy-1,2-dihydrocarbazol-4(3H)-one;
[(3-Chlorophenyl)methyl]-5-carbomethoxy-1,2-dihydrocarbazol-4(3H)-one;
[(3-Phenoxyphenyl)methyl-5-carbomethoxy-1,2-dihydrocarbazol-4(3H)-one;
[(2-Fluorophenyl)methyl]-5-carbomethoxy-1,2-dihydrocarbazol-4(3H)-one;
[(2-Trifluoromethylphenyl)methyl]-5-carbomethoxy-1,2-dihydrocarbazol-4(3H)-one;
[(2-Benzylphenyl)methyl]-5-carbomethoxy-1,2-dihydrocarbazol-4(3H)-one;
[(3-Trifluoromethylphenyl)methyl]-5-carbomethoxy-1,2-dihydrocarbazol-4(3H)-one;
[(1-Naphthyl)methyl]-5-carbomethoxy-1,2-dihydrocarbazol-4(3H)-one;
[(2-Cyanophenyl)methyl]-5-carbomethoxy-1,2-dihydrocarbazol-4(3H)-one;
[(3-Cyanophenyl)methyl]-5-carbomethoxy-1,2-dihydrocarbazol-4(3H)-one;
[(2-Methylphenyl)methyl]-5-carbomethoxy-1,2-dihydrocarbazol-4(3H)-one;
[(3-Methylphenyl)methyl]-5-carbomethoxy-1,2-dihydrocarbazol-4(3H)-one;
[(3,5-Dimethylphenyl)methyl]-5-carbomethoxy-1,2-dihydrocarbazol-4(3H)-one;
[(3-Iodophenyl)methyl]-5-carbomethoxy-1,2-dihydrocarbazol-4(3H)-one;
[(2-Chlorophenyl)methyl-5-carbomethoxy-1,2-dihydrocarbozol-4(3H)-one;
[(2,3-Difluorophenyl)methyl]-5-carbomethoxy-1,2-dihydrocarbazol-4(3H)-one;
[(2,6-Difluorophenyl)methyl]-5-carbomethoxy-1,2-dihydrocarbazol-4(3H)-one;
[(2,6-Dichlorophenyl)methyl]-5-carbomethoxy-1,2-dihydrocarbazol-4(3H)-one;
[(3-Trifluoromethoxyphenyl)methyl]-5-carbomethoxy-1,2-dihydrocarbazol-4(3H)-one;
[(2-Pyridyl)methyl]-5-carbomethoxy-1,2-dihydrocarbazol-4(3H)-one;
[(3-Pyridyl)methyl]-5-carbomethoxy-1,2-dihydrocarbazol-4(3H)-one;
[(Cyclohexyl)methyl]-5-carbomethoxy-1,2-dihydrocarbazol-4(3H)-one;
[(Cyclopentyl)-methyl]-5-carbomethoxy-1,2-dihydrocarbazol-4(3H)-one;

or a pharmaceutically acceptable racemate, solvate, tautomer, optical isomer, prodrug derivative or salt thereof.

* * * * *